US008703914B2

(12) United States Patent
Arico et al.

(10) Patent No.: US 8,703,914 B2
(45) Date of Patent: Apr. 22, 2014

(54) HETEROLOGOUS EXPRESSION OF NEISSERIAL PROTEINS

(75) Inventors: Maria Beatrice Arico, Siena (IT); Maurizio Comanducci, Siena (IT); Cesira Galeotti, Montegriggioni (IT); Vega Masignani, Siena (IT); Marizia Monica Guiliani, Siena (IT); Mariagrazia Pizza, Siena (IT)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/340,549

(22) Filed: Dec. 29, 2011

(65) Prior Publication Data

US 2013/0005667 A1 Jan. 3, 2013

Related U.S. Application Data

(62) Division of application No. 12/825,210, filed on Jun. 28, 2010, now Pat. No. 8,114,960, which is a division of application No. 10/220,481, filed as application No. PCT/IB01/00452 on Feb. 28, 2001, now Pat. No. 7,803,387.

(30) Foreign Application Priority Data

Feb. 28, 2000 (GB) .................................. 0004695.3
Nov. 13, 2000 (GB) .................................. 0027675.8

(51) Int. Cl.
*C07K 1/00* (2006.01)

(52) U.S. Cl.
USPC .......................... 530/350; 530/402; 530/403

(58) Field of Classification Search
None
See application file for complete search history.

(56) References Cited

U.S. PATENT DOCUMENTS

| 4,239,749 | A | 12/1980 | Buchanan |
| 5,547,670 | A | 8/1996 | Goldstein et al. |
| 5,914,254 | A | 6/1999 | Mascarenhas et al. |
| 6,013,267 | A | 1/2000 | Blake et al. |
| 6,028,049 | A | 2/2000 | Jacobs et al. |
| 6,197,312 | B1 | 3/2001 | Peak et al. |
| 6,248,329 | B1 | 6/2001 | Chandrashekar et al. |
| 6,709,660 | B1 | 3/2004 | Scarlato et al. |
| 6,914,131 | B1 | 7/2005 | Scarlato et al. |
| 7,348,006 | B2 | 3/2008 | Contorni et al. |
| 7,368,261 | B1 | 5/2008 | Rappuoli |
| 7,504,111 | B2 | 3/2009 | Fontana et al. |
| 7,576,176 | B1 | 8/2009 | Fraser et al. |
| 7,604,810 | B2 | 10/2009 | Rappuoli |
| 7,862,827 | B2 | 1/2011 | Giuliani et al. |
| 8,383,790 | B2 * | 2/2013 | Peak et al. .................. 536/23.1 |
| 2001/0031268 | A1 * | 10/2001 | Baldwin et al. ............ 424/249.1 |
| 2002/0160016 | A1 | 10/2002 | Peak et al. |
| 2004/0092711 | A1 | 5/2004 | Arico |
| 2004/0110670 | A1 | 6/2004 | Arico et al. |
| 2005/0222385 | A1 | 10/2005 | Pizza |
| 2006/0051840 | A1 | 3/2006 | Arico et al. |
| 2006/0171957 | A1 | 8/2006 | Pizza |
| 2006/0240045 | A1 | 10/2006 | Berthet et al. |
| 2007/0082014 | A1 | 4/2007 | Costantino |
| 2008/0241180 | A1 | 10/2008 | Contorni |
| 2009/0232820 | A1 | 9/2009 | Fraser et al. |
| 2009/0285845 | A1 | 11/2009 | Masignani et al. |
| 2010/0267931 | A1 | 10/2010 | Arico et al. |

FOREIGN PATENT DOCUMENTS

| EP | 0273116 | A2 | 7/1988 |
| EP | 0467714 | | 1/1992 |
| EP | 1790660 | | 5/2007 |
| JP | 2003-525050 | A2 | 8/2003 |
| NL | 8901612 | A | 7/1990 |
| WO | WO-90/06696 | | 6/1990 |
| WO | WO-92/16643 | A1 | 10/1992 |
| WO | WO-95/33049 | A2 | 12/1995 |
| WO | WO-96/29412 | A1 | 9/1996 |
| WO | WO-97/10844 | A1 | 3/1997 |
| WO | WO-97/13860 | A1 | 4/1997 |
| WO | WO-97/28273 | A2 | 8/1997 |
| WO | WO-99/24578 | A2 | 5/1999 |
| WO | WO-99/36544 | A2 | 7/1999 |
| WO | WO 99/41230 | * | 8/1999 |
| WO | WO-99/57280 | A | 11/1999 |
| WO | WO-00/22430 | A2 | 4/2000 |
| WO | WO-00/050075 | | 8/2000 |
| WO | WO-00/66741 | A2 | 11/2000 |
| WO | WO-00/66791 | | 11/2000 |
| WO | WO-00/71725 | | 11/2000 |
| WO | WO-01/31019 | | 5/2001 |
| WO | WO-01/40473 | | 6/2001 |
| WO | WO-01/52885 | | 7/2001 |
| WO | WO-01/64920 | A | 9/2001 |
| WO | WO-01/64922 | A2 | 9/2001 |
| WO | WO-01/81581 | | 11/2001 |
| WO | WO-02/02606 | A2 | 1/2002 |
| WO | WO-02/07763 | A2 | 1/2002 |

(Continued)

OTHER PUBLICATIONS

Abad et al. (2008). "PorB2/3 Protein Hybrid in *Neisseria meningitidis*," Emerging Infectious Diseases, 14(4):688-689.
Bartsevich et al. (Mar. 7, 1997). "Molecular Identification of a Novel Protein That Regulates Biogenesis of Photosystem I, a Membrane Protein Complex," *The Journal of Biological Chemistry* 272(10):6382-6387.
Bethell et al. (2002). "Meningococcal vaccines," Expert Review of Vaccines 1(1):75-84.
Blythe et al. (2005). "Benchmarking B cell epitope prediction: underperformance of existing methods," Protein Sci. 14:246-248.
Boslego et al. (1991). "Gonorrhea Vaccines," Chapter 17 *In Vaccines and Immunotherapy*, Cryz S.J. (Ed.), Pergamon Press: New York, NY, pp. 211-223.

(Continued)

*Primary Examiner* — Shulamith H Shafer
(74) *Attorney, Agent, or Firm* — Morrison & Foerster LLP

(57) ABSTRACT

Alternative and improved approaches to the heterologous expression of the proteins of *Neisseria meningitidis* and *Neisseria gonorrhoeae*. These approaches typically affect the level of expression, the ease of purification, the cellular localization, and/or the immunological properties of the expressed protein.

5 Claims, 13 Drawing Sheets

(56) References Cited

FOREIGN PATENT DOCUMENTS

| WO | WO-02/09746 A2 | 2/2002 |
|---|---|---|
| WO | WO-03/009869 A1 | 2/2003 |
| WO | WO-03/010194 A | 2/2003 |
| WO | WO-03/020756 A | 3/2003 |
| WO | WO-2004/032958 A1 | 4/2004 |
| WO | WO-2004/048404 | 6/2004 |
| WO | WO-2004/067030 A2 | 8/2004 |
| WO | WO-2004/112832 | 12/2004 |
| WO | WO-2005/032583 A2 | 4/2005 |
| WO | WO-2005/033148 A1 | 4/2005 |
| WO | WO-2005/102384 A2 | 11/2005 |
| WO | WO-2005/106009 | 11/2005 |
| WO | WO-2008/001224 A2 | 1/2008 |

OTHER PUBLICATIONS

Bowie, J. (1990). "Deciphering the Message in Protein Sequences: Tolerance to Amino Acid Substitutions," Science 247: 1306-1310.
Brandhorst et al. (1995). "Effects of leader Sequences upon the Heterologous Expression of Restriction in Aspergillus nidulans and Aspergillus niger," CJM 41(7):601-611.
Bygraves et al. (1992). "Analysis of the Clonal Relationships Between Strains of Neisseria meningitidis by Pulsed Field Gel Electrophoresis," Journal of General Microbiology 138:523-531.
Cann et al. (1989). "Detection of Antibodies to Common Antigens of Pathogenic and Commensal Neisseria Species," Journal of Medical Microbiology 30:23-30.
Caugant et al. (1987). "Genetic Structure of Neisseria meningitidis Populations in Relation to Serogroup, Serotype, and Outer Membrane Protein Pattern," Journal of Bacteriology 169(6):2781-2792.
Christodoulides et al. (1994). "Immunization with a Multiple Antigen Peptide Containing Defined B- and T-Cell Epitopes: Production of Bacterial Antibodies Group B Neisseria meningitidis," Microbiology 140:2951-2960.
Cooney et al. (1993). "Three Contiguous Lipoprotein Genes in Pasteurella haemolytica A1 which are Homologous to a Lipoprotein Gene in Haemophilus influenza Type B," Infection and Immunity 61(11):4682-4688.
Cruse et al. (2003). Illustrated Dictionary of Immunology, $2^{nd}$ Ed. CRC Press, pp. 46, 166, and 382.
Dempsey et al. (1991). "Physical Map of the Chromosome of Neisseria gonorrhoeae FA1090 with Locations of Genetic Markers, including Opa and Pil Genes," Journal of Bacteriology 173(17):5476-5486.
Devries et al. (Aug. 1996). "Invasion of Primary Nasopharyngeal Epithelial Cells by Neisseria meningitidis is Controlled by Phase Variation of Multiple Surface Antigens," Infection and Immunity 64(8):2998-3006.
Ellis (1988). Chapter 29 in Vaccines, Plotkin, S.A. et al. eds., W. B. Saunders Company: Philadelphia, PA. pp. 568-574.
Feng et al. (1996). "P55, an Immunogenic but Nonprotective 55-Kilodalton Borrelia burgdorferi Protein in Murine Lyme Disease," Infection and Immunity. 64(1):363-365.
Gervais et al. (1992). "Putative Lipoprotein Yaec Precursor," Database Swissport Acc No. p28635.
Greenspan et al. (1999). "Defining Epitopes: It's Not as Easy as It Seems," Nature Biotechnology 17:936-937.
Grifantini, R. et al. (2002). "Previously Unrecognized Vaccine Candidates against Group B Meningococcus Identified by DNA Microarrays," Nature Biotechnology 20(9): 914-921.
Guillen et al. (1996). "Expression in Escherichia coli and Immunological Characterization of a Hybrid Class I-P64K Protein from Neisseria meningitidis," Biotecnologia Aplicada 13(4):271-275.
Herbert et al. (Eds.) The Dictionary of Immunology, 1995, one page.
Herbert, W. et al. (1985). The Dictionary of Immunology. Academic Press: London $3^{rd}$ edition, pp. 58-59.
Holmes, E. (2001). "PSMA Specific Antibodies and their Diagnostic and Therapeutic Use," Expert Opinion on Investigational Drugs 10(3): 511-519.

Jacobsson et al. (2009). "Prevalence and sequence variations of the genes encoding the five antigens included in the novel 5CVMB vaccine covering group B meningococcal disease" Vaccine. 27:1579-1584.
Jolley et al. (2007). "Molecular typing of meningococci: recommendations for target choice and nomenclature," FEMS Microbiol. Rev. 31:89-96.
Legrain et al. (1995). "Production of Lipidated Meningococcal Transferrin Binding Protein 2 in Escherichia coli," Protein Expression and Purification 6:570-578.
Lucidarme et al., (Sep. 16, 2009) "Characterization of fHbp, nhba (gna2132), nadA, porA, sequence type (ST), and genomic presence of IS1301 in group B meningococcal ST269 clonal complex isolates from England and Wales" Journal of Clinical Microbiology, 47(11):3577-85.
Lucidarme et al., 2010 "Characterization of fHbp, nhba (gna2132), nadA, porA, and sequence type in group B meningococcal case isolates collected in England and Wales during Jan. 2008 and potential coverage of an investigational group B meningococcal vaccine" Clinical and Vaccine Immunology 17(6):919-929.
Maiden et al. (1998). "Multilocus Sequence Typing: a Portable Approach to the Identification of Clones within Populations of Pathogenic Microorganisms," Proceedings of the National Academy of Sciences USA 95:3140-3145.
Morley, S. et al. (Dec. 12, 2001). "Vaccine prevention of meningococcal disease, coming soon?" Vaccine 20(5-6):666-687.
Moudallal et al. (1982). "Monoclonal anti bodies as probes of the antigenic structure of tobacco mosaic virus," EMBO Journal 1:1005-1010.
Ni et al. (1992). "Phylogenetic and Epidemiological Analysis of Neisseria meningitidis Using DNA Probes," Epidemiology and Infection 109:227-239.
Nosoh et al. (1991). Protein Stability and Stabilization through Protein Engineering. Chapter 7, p. 197, second paragraph.
Parkhill, J. et al. (Mar. 2000). "Complete DNA Sequence of a Serogroup A Strain of Neisseria meningitides Z2491," Nature 404(6777):502-506.
Perrett et al. (2005). "Towards an improved serogroup B Neisseria meningitidis vaccine," Expert Opinion on Biological Therapy 5(12):1611-1625.
Pettersson et al. (1999). "Sequence Variability of the Meningococcal Lactoferrin-binding Protein LbpB," Gene 231:105-110.
Pizza et al. (2000). "Identification of Vaccine Candidates Against Serogroup B Meningococcus by Whole-Genome Sequencing," Science 287(5459):1816-1820.
Poolman et al. (1985). "Colony Variants of Neisseria meningitidis Strain 2996 (B:2b:P1.2): Influence of Class-5 Out Membrane Proteins and Lipolysaccharides," J. Med. Microbiol 19:203-209.
Poolman et al. (1988). "Outer membrane protein sero-subtyping of Neisseria meningitidis," European Journal of Clinical Microbiology and Infectious Diseases 7:291-292.
Renauld-Mongenie et al. (1997). "Identification of Human Transferrin-Binding Sites Within Meningococcal Transferrin-Binding Protein B," J. Bacteriology 197(20):6400-6407.
Roitt, I. et al. (1993). Immunology. Mosby: St. Louis, pp. 7,7-7,8.
Seiler et al. (1996). "Allelic Polymorphism and Site-specific Recombination in the Opc Locus of Neisseria meningitidis," Molecular Microbiology 19(4):841-856.
Serruto et al. (2010). "Neisseria meningitidis GNA2132, a heparin-binding protein that induces protective immunity in humans," PNAS 107(8):3770-3775.
Telford (Jun. 2008). "Bacterial Genome Variability and Its Impact on Vaccine Design," Cell Host & Microbe 3(6):408-416.
Tettelin et al. (2006). "Towards a universal group B Streptococcus vaccine using multistrain genome analysis," Expert Rev Vaccines 25:687-694.
Tettelin et al. (Mar. 10, 2000). "Complete Genome Sequence of Neisseria meningitidis Serogroup B Strain MC58," Science 287(5459):1809-1815.
Thomas E. Creighton (1984). Proteins: Structures and Molecular Properties. pp. 314-315.

(56) References Cited

OTHER PUBLICATIONS

Thomas E. Creighton (1989). Protein Structure: A Practical Approach. pp. 184-186.

Thompson et al. (1994). "Clustal W: Improving the Sensitivity of Progressive Multiple Sequence Alignment through Sequence Weighting, Position-specific Gap Penalties and Weight Matrix Choice," *Nucleic Acids Research* 22(22):4673-4680.

Thompson et al. (1998). "Multiple Sequence Alignment with Clustal X," *Trends in Biochemical Sciences* 23:403-405.

Van der Lay et al. (1995). "Construction of *Neisseria meningitidis* Strains Carrying Multiple Chromosomal Copies of the PorA Gene for Use in Production of a Multivalent Outer Membrane Vesicle Vaccine," *Vaccine* 13(4): 401-407.

Virji et al. (1992). "Variations in the Expression of Pili: the Effect on Adherence of *Neisseria meningitidis* to Human Epithelial and Endothelial Cells," Molecular Microbiology 6:1271-1279.

Welsch et al., 2003 "Antibody to genome-derived neisserial antigen 2132, a *Neisseria meningitidis* candidate vaccine, confers protection against bacteremia in the absence of complement-mediated bactericidal activity" Journal of Infectious Diseases 188 (11):1730-1740.

Wolff et al. (1992). "Phylogeny and Nucleotide Sequence of a 23S rRNA Gene from *Neisseria gonorrhea* and *Neisseria meningitidis*," Nucleic Acids Research 20(17):4657.

\* cited by examiner

FIGURE 3
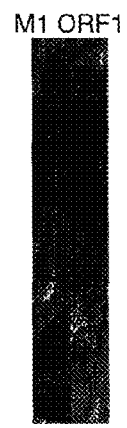
PURIFICATION
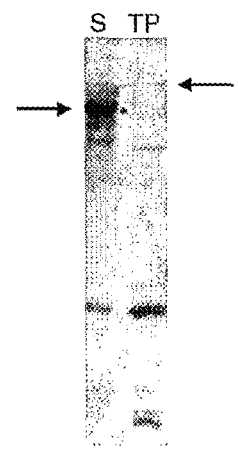
WESTERN BLOT
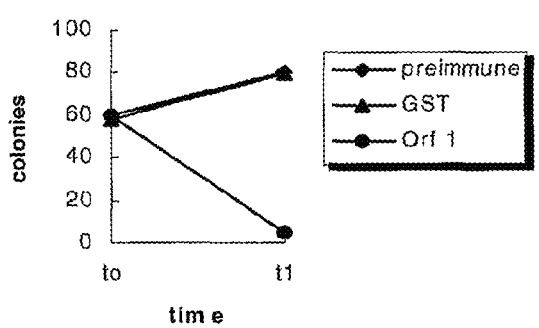
BACTERICIDAL ASSAY
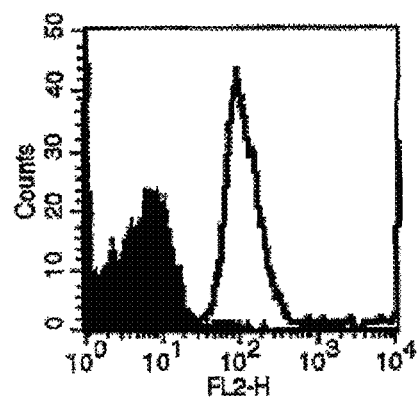
FACS
ELISA: POSITIVE

FIGURE 4
PURIFICATION       WESTERN BLOT
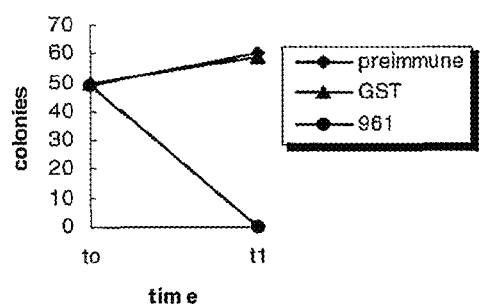 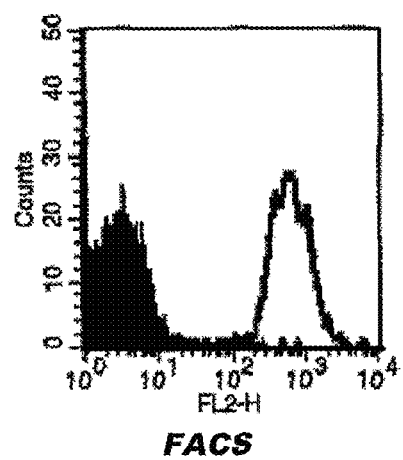
BACTERICIDAL ASSAY      FACS
ELISA: POSITIVE

FIGURE 7

```
              <A------------------------<Δ1---------------------------------------
MC58    1   MDERSVIAMACIFALSACGGGGGSPDVKSADTLSKPAAPVVSEKETEAKEDAPQAGSQG
2996    1   MDERSVIAMACIFALSACGGGGGSPDVKSADTLSKPAAPVVAEKETEVKEDAPQAGSQG

-----------<Δ2----------
MC58   61   QGAPSAQGSQDMAAVSEENTGNGGAVTADNPKNEDEVAQNDMPQNAAGTDSSTPNHTPDP
2996   61   QGAPSTQGSQDMAAVSAENTGNGGAATTEKPKNEDEGPQNDMPQN...............

<Δ3----------
MC58  121   NMLAGNMENQATDAGESSQPANQPDMANAADGMQGDDPSAGGQNAGNTAAQGANQAGNNQ
2996  106   ............................................SAESANQTGNNQ

--------------------------A><B-------------------------------
MC58  181   AAGSSDPIPASNPAPANGGSNFGRVDLANGVLIDGPSQNITLTHCKGDSCSGNNFLDEEV
2996  118   PADSSDSARASNPAPANGGSNFGRVDLANGVLIDGPSQNITLTHCKGDSCGDNLLDEEA

------------------------------------------------B>-----------
MC58  241   QLKSEFEKLSDADKISNYKKDGKNDKFVGLVADSVQMKGINQYIIFYKPK..PTSFARFR
2996  178   PSKSEFENLNESERIEKYKKDGKSDKFTNLVATAVQANGTNKYVIIYKDKSASSSSARFR

<C-----------------------------------------------------------
MC58  299   RSARSRRSLPAEMPLIPVNQADTLIVDGEAVSLTGHSGNIFAPEGNYRYLTYGAEKLPGG
2996  238   RSARSRRSLPAEMPLIPVNQADTLIVDGEAVSLTGHSGNIFAPEGNYRYLTYGAEKLPGG

MC58  359   SYALRVQGEPAKGEMLAGAAVYNGEVLHFHTENGRPYPTRGRFAAKVDFGSKSVDGIIDS
2996  298   SYALRVQGEPAKGEMLAGTAVYNGEVLHFHTENGRPYPTRGRFAAKVDFGSKSVDGIIDS

MC58  419   GDDLHMGTQKFKAAIDGNGFKGTWTENGSGDVSCKFYGPAGEEVAGKYSYRPTDAEKGGF
2996  358   GDDLHMGTQKFKAAIDGNGFKGTWTENGGGDVSGRFYGPAGEEVAGKYSYRPTDAEKGGF

--------C>
MC58  479   GVFAGKKEQD*
2996  418   GVFAGKKEQD*
```

FIGURE 11A      FIGURE 11B
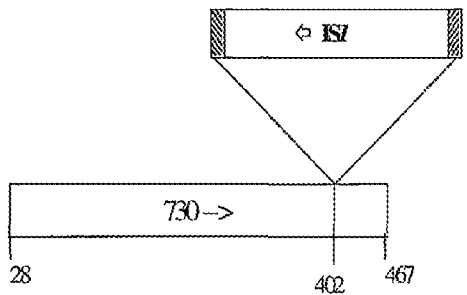
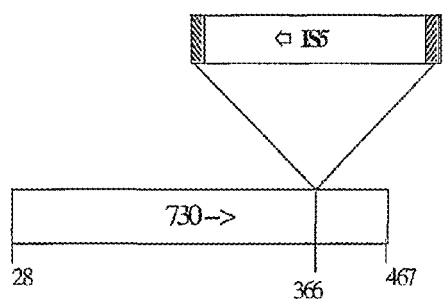
FIGURE 12
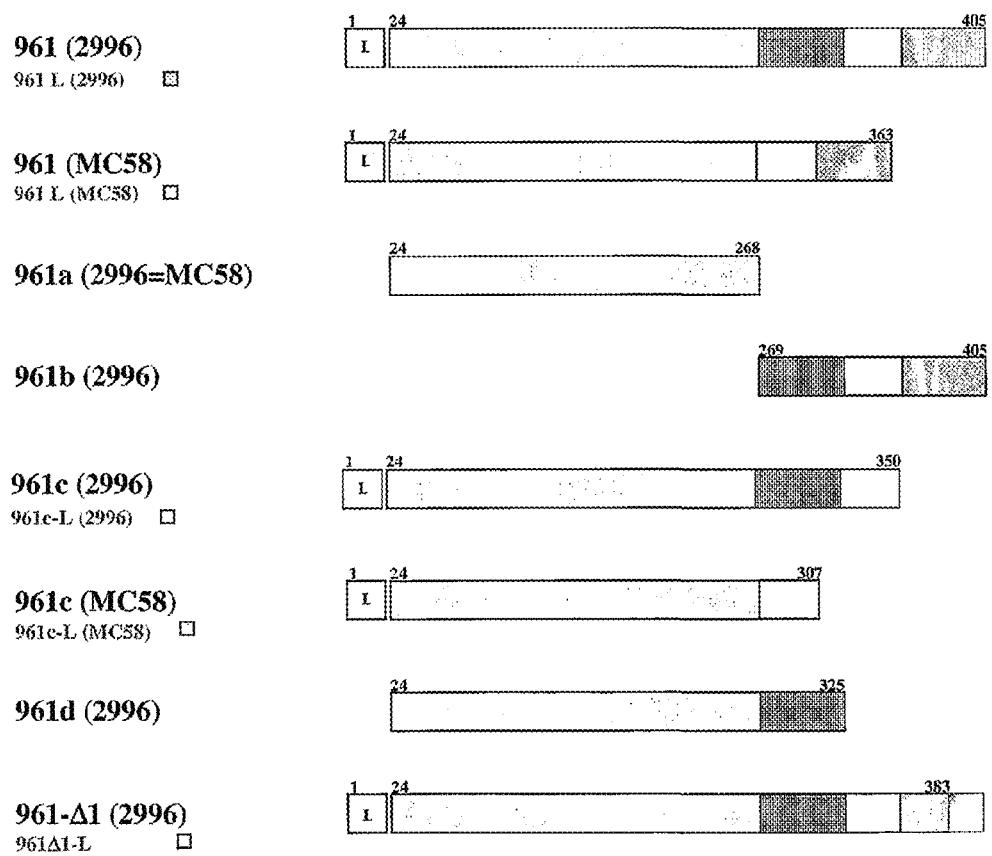
☐ Leader Peptide    ▨ Region present in 2996, not in MC58    ☐ Coil-coiled segment    ▨ Membrane anchor

FIGURE 13
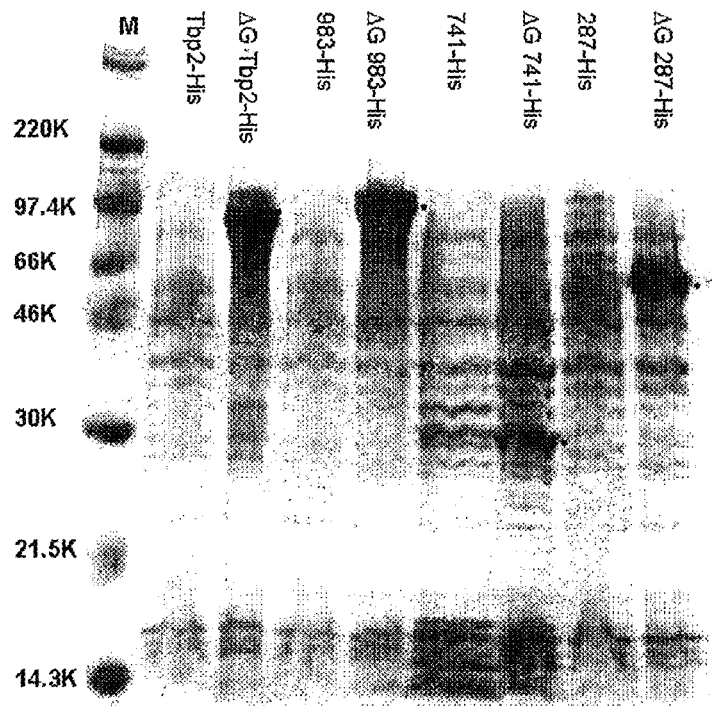
FIGURE 14
FIGURE 14A — ΔG287—919
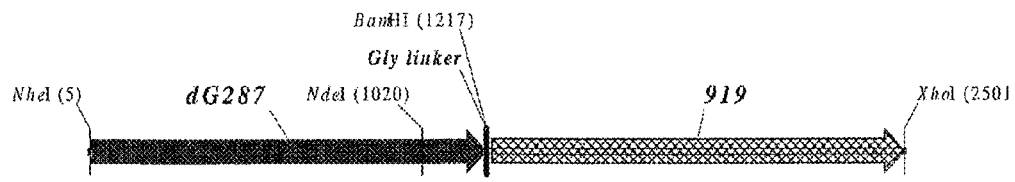
FIGURE 14B — ΔG287—953
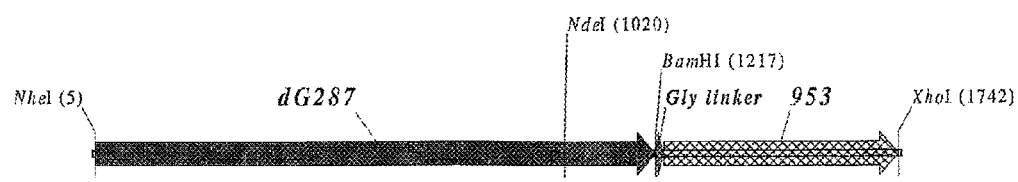

FIGURE 14C — ΔG287—961
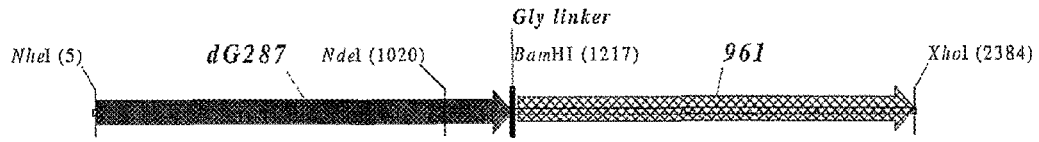
FIGURE 14D — ΔG287NZ—919
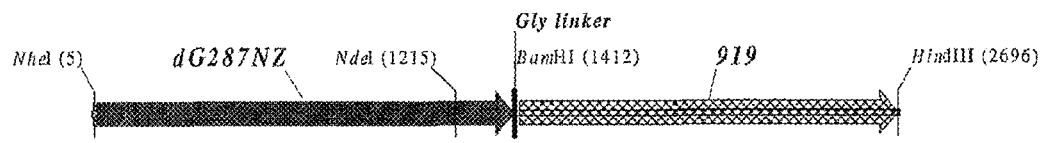
FIGURE 14E — ΔG287NZ—953
FIGURE 14F — ΔG287NZ—961
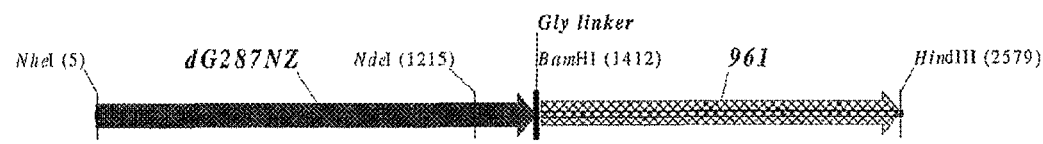
FIGURE 14G — ΔG983-ORF46.1
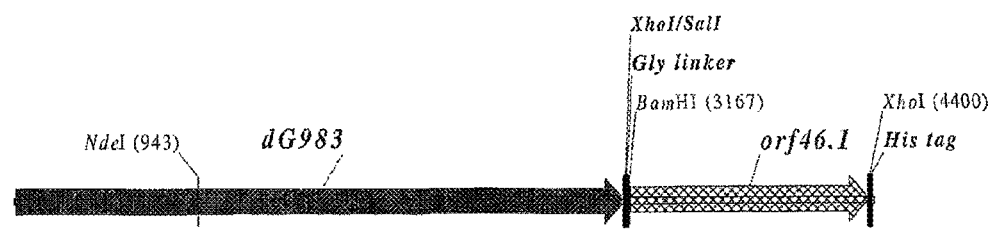

FIGURE 14H — ΔG983-741
FIGURE 14I — ΔG983-961
FIGURE 14J — ΔG983-961c
FIGURE 14K — ΔG741-961
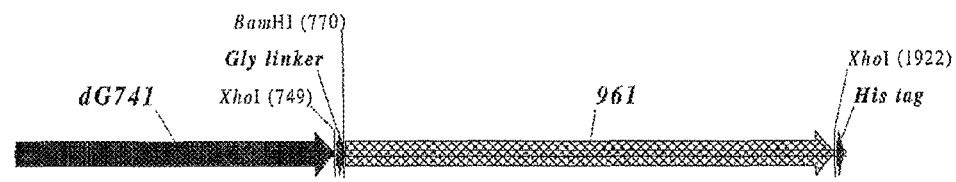
FIGURE 14L — ΔG741-961c
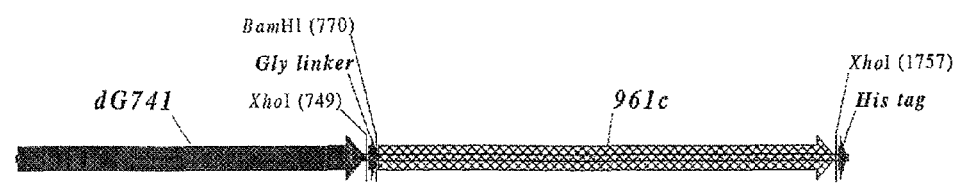

FIGURE 14M — ΔG741-983
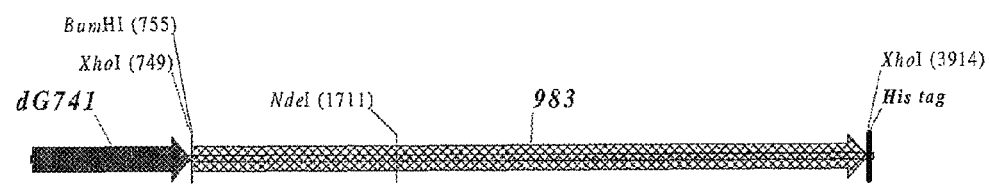
FIGURE 14N — ΔG741-ORF46.1
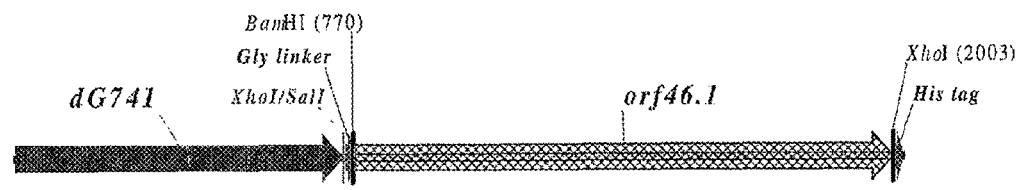
FIGURE 14O — ORF46.1-741
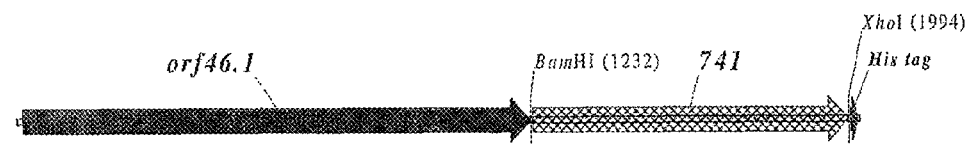
FIGURE 14P — ORF46.1-961
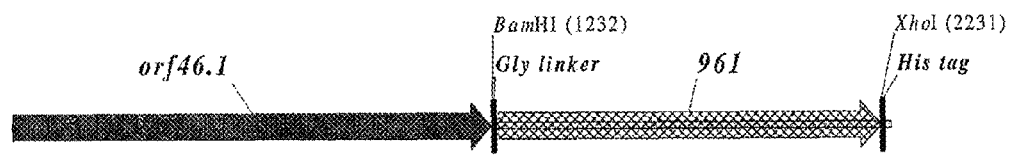
FIGURE 14Q — ORF46.1—961c
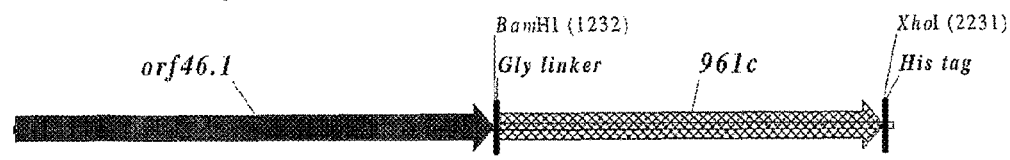

FIGURE 14R — 961-ORF46.1
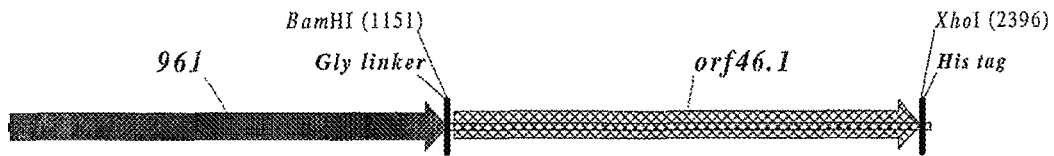
FIGURE 14S — 961-741
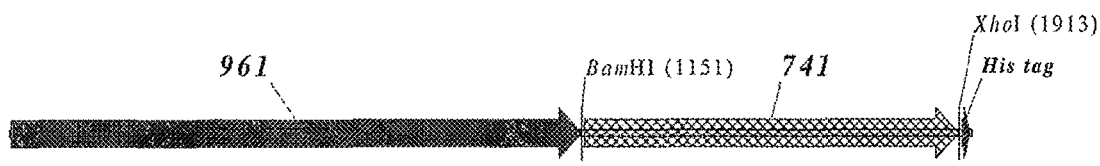
FIGURE 14T — 961-983
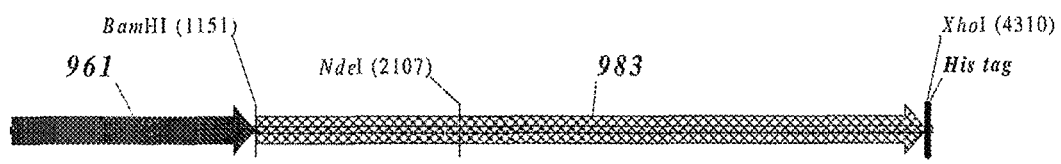
FIGURE 14U — 961c-ORF46.1
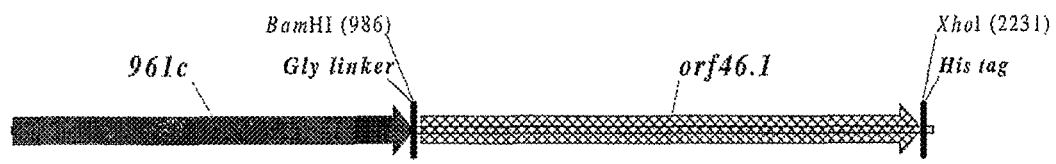
FIGURE 14V — 961c-741
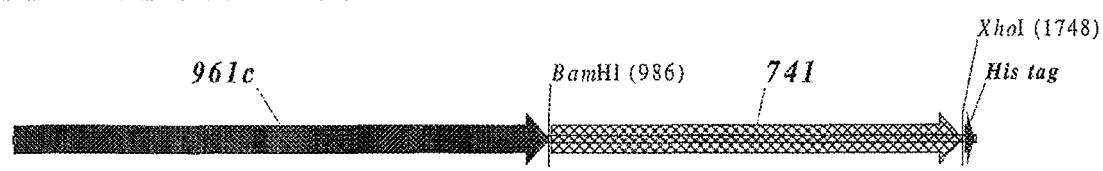

FIGURE 14W — 961c-983
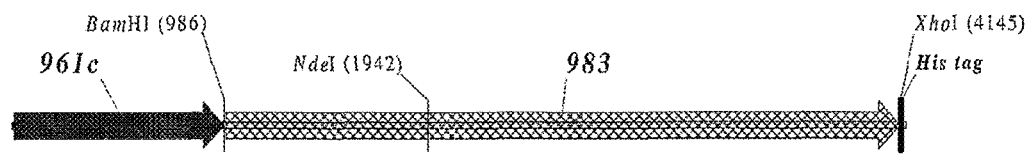
FIGURE 14X — 961cL-ORF46.1
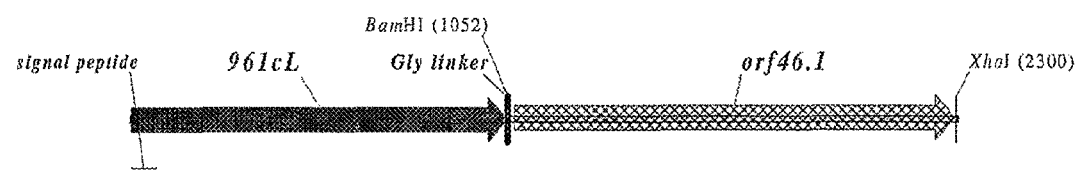
FIGURE 14Y — 961cL-741
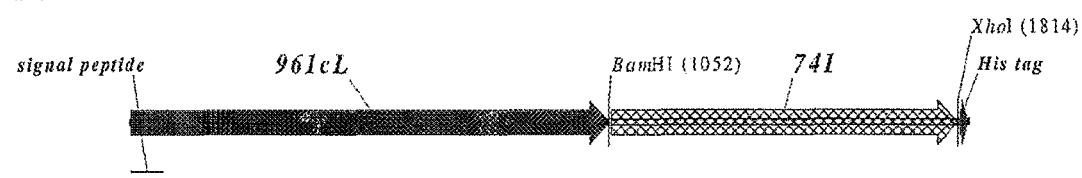
FIGURE 14Z — 961cL-983
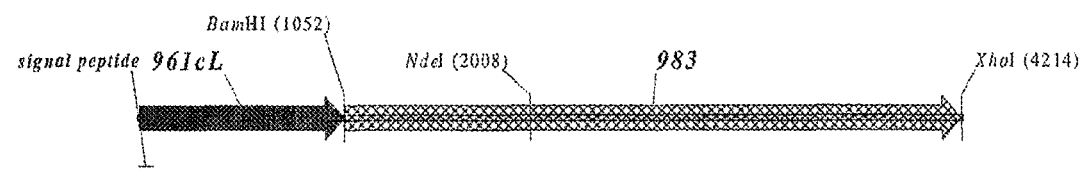

HETEROLOGOUS EXPRESSION OF NEISSERIAL PROTEINS

CROSS-REFERENCE TO RELATED APPLICATION

This application is a divisional patent application of U.S. Ser. No. 12/825,210, filed Jun. 28, 2010, now issued as U.S. Pat. No. 8,114,960, which is a divisional of U.S. Ser. No. 10/220,481, filed Aug. 13, 2003, now issued as U.S. Pat. No. 7,803,387, which is the National Stage filing of International Patent Application No. PCT/IB2001/000452, filed Feb. 28, 2001, which claims the benefit of two Great Britain patent applications GB0004695.3, filed Feb. 28, 2000, and GB0027675.8, filed Nov. 13, 2000, all of which are hereby incorporated by reference in their entireties for all purposes.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 223002099811SubSeqList.txt, date recorded: Mar. 6, 2012, size: 503 KB).

TECHNICAL FIELD

This invention is in the field of protein expression. In particular, it relates to the heterologous expression of proteins from *Neisseria* (e.g. *N. gonorrhoeae* or, preferably, *N. meningitidis*).

BACKGROUND ART

International patent applications WO99/24578, WO99/36544, WO99/57280 and WO00/22430 disclose proteins from *Neisseria meningitidis* and *Neisseria gonorrhoeae*. These proteins are typically described as being expressed in *E. coli* (i.e. heterologous expression) as either N-terminal GST-fusions or C-terminal His-tag fusions, although other expression systems, including expression in native *Neisseria*, are also disclosed.

It is an object of the present invention to provide alternative and improved approaches for the heterologous expression of these proteins. These approaches will typically affect the level of expression, the ease of purification, the cellular localisation of expression, and/or the immunological properties of the expressed protein.

DISCLOSURE OF THE INVENTION

Nomenclature Herein

The 2166 protein sequences disclosed in WO99/24578, WO99/36544 and WO99/57280 are referred to herein by the following SEQ# numbers:

| Application | Protein sequences | SEQ# herein |
|---|---|---|
| WO99/24578 | Even SEQ IDs 2-892 | SEQ#s 1-446 |
| WO99/36544 | Even SEQ IDs 2-90 | SEQ#s 447-491 |
| WO99/57280 | Even SEQ IDs 2-3020 | SEQ#s 492-2001 |
|  | Even SEQ IDs 3040-3114 | SEQ#s 2002-2039 |
|  | SEQ IDs 3115-3241 | SEQ#s 2040-2166 |

In addition to this SEQ# numbering, the naming conventions used in WO99/24578, WO99/36544 and WO99/57280 are also used (e.g. 'ORF4', 'ORF40', 'ORF40-1' etc. as used in WO99/24578 and WO99/36544; 'm919', 'g919' and 'a919' etc. as used in WO99/57280).

The 2160 proteins NMB0001 to NMB2160 from Tettelin et al. [*Science* (2000) 287:1809-1815] are referred to herein as SEQ#s 2167-4326 [see also WO00/66791].

The term 'protein of the invention' as used herein refers to a protein comprising:
 (a) one of sequences SEQ#s 1-4326; or
 (b) a sequence having sequence identity to one of SEQ#s 1-4326; or
 (c) a fragment of one of SEQ#s 1-4326.

The degree of 'sequence identity' referred to in (b) is preferably greater than 50% (e.g. 60%, 70%, 80%, 90%, 95%, 99% or more). This includes mutants and allelic variants [e.g. see WO00/66741]. Identity is preferably determined by the Smith-Waterman homology search algorithm as implemented in the MPSRCH program (Oxford Molecular), using an affine gap search with parameters gap open penalty=12 and gap extension penalty=1. Typically, 50% identity or more between two proteins is considered to be an indication of functional equivalence.

The 'fragment' referred to in (c) should comprise at least n consecutive amino acids from one of SEQ#s 1-4326 and, depending on the particular sequence, n is 7 or more (e.g. 8, 10, 12, 14, 16, 18, 20, 25, 30, 35, 40, 50, 60, 70, 80, 90, 100 or more). Preferably the fragment comprises an epitope from one of SEQ#s 1-4326. Preferred fragments are those disclosed in WO00/71574 and WO01/04316.

Preferred proteins of the invention are found in *N. meningitidis* serogroup B.

Preferred proteins for use according to the invention are those of serogroup B *N. meningitidis* strain 2996 or strain 394/98 (a New Zealand strain). Unless otherwise stated, proteins mentioned herein are from *N. meningitidis* strain 2996. It will be appreciated, however, that the invention is not in general limited by strain. References to a particular protein (e.g. '287', '919' etc.) may be taken to include that protein from any strain.

Non-Fusion Expression

In a first approach to heterologous expression, no fusion partner is used, and the native leader peptide (if present) is used. This will typically prevent any 'interference' from fusion partners and may alter cellular localisation and/or post-translational modification and/or folding in the heterologous host.

Thus the invention provides a method for the heterologous expression of a protein of the invention, in which (a) no fusion partner is used, and (b) the protein's native leader peptide (if present) is used.

The method will typically involve the step of preparing an vector for expressing a protein of the invention, such that the first expressed amino acid is the first amino acid (methionine) of said protein, and last expressed amino acid is the last amino acid of said protein (i.e. the codon preceding the native STOP codon).

This approach is preferably used for the expression of the following proteins using the native leader peptide: 111, 149, 206, 225-1, 235, 247-1, 274, 283, 286, 292, 401, 406, 502-1, 503, 519-1, 525-1, 552, 556, 557, 570, 576-1, 580, 583, 664, 759, 907, 913, 920-1, 936-1, 953, 961, 983, 989, Orf4, Orf7-1, Orf9-1, Orf23, Orf25, Orf37, Orf38, Orf40, Orf40.1, Orf40.2, Orf72-1, Orf76-1, Orf85-2, Orf91, Orf97-1, Orf119, Orf143.1, NMB0109 and NMB2050. The suffix 1' used herein in the name of a protein indicates expression in this manner using the native leader peptide.

Proteins which are preferably expressed using this approach using no fusion partner and which have no native leader peptide include: 008, 105, 117-1, 121-1, 122-1, 128-1, 148, 216, 243, 308, 593, 652, 726, 926, 982, Orf83-1 and Orf143-1.

Advantageously, it is used for the expression of ORF25 or ORF40, resulting in a protein which induces better anti-bactericidal antibodies than GST- or His-fusions.

This approach is particularly suited for expressing lipoproteins.

Leader-Peptide Substitution

In a second approach to heterologous expression, the native leader peptide of a protein of the invention is replaced by that of a different protein. In addition, it is preferred that no fusion partner is used. Whilst using a protein's own leader peptide in heterologous hosts can often localise the protein to its 'natural' cellular location, in some cases the leader sequence is not efficiently recognised by the heterologous host. In such cases, a leader peptide known to drive protein targeting efficiently can be used instead.

Thus the invention provides a method for the heterologous expression of a protein of the invention, in which (a) the protein's leader peptide is replaced by the leader peptide from a different protein and, optionally, (b) no fusion partner is used.

The method will typically involve the steps of: obtaining nucleic acid encoding a protein of the invention; manipulating said nucleic acid to remove nucleotides that encode the protein's leader peptide and to introduce nucleotides that encode a different protein's leader peptide. The resulting nucleic acid may be inserted into an expression vector, or may already be part of an expression vector. The expressed protein will consist of the replacement leader peptide at the N-terminus, followed by the protein of the invention minus its leader peptide.

The leader peptide is preferably from another protein of the invention (e.g. one of SEQ#s 1-4326), but may also be from an *E. coli* protein (e.g. the OmpA leader peptide) or an *Erwinia carotovora* protein (e.g. the PelB leader peptide), for instance.

A particularly useful replacement leader peptide is that of ORF4. This leader is able to direct lipidation in *E. coli*, improving cellular localisation, and is particularly useful for the expression of proteins 287, 919 and ΔG287. The leader peptide and N-terminal domains of 961 are also particularly useful.

Another useful replacement leader peptide is that of *E. coli* OmpA. This leader is able to direct membrane localisation of *E. coli*. It is particularly advantageous for the expression of ORF1, resulting in a protein which induces better anti-bactericidal antibodies than both fusions and protein expressed from its own leader peptide.

Another useful replacement leader peptide is MKKYLFSAA (SEQ ID NO:621). This can direct secretion into culture medium, and is extremely short and active. The use of this leader peptide is not restricted to the expression of Neisserial proteins—it may be used to direct the expression of any protein (particularly bacterial proteins).

Leader-Peptide Deletion

In a third approach to heterologous expression, the native leader peptide of a protein of the invention is deleted. In addition, it is preferred that no fusion partner is used.

Thus the invention provides a method for the heterologous expression of a protein of the invention, in which (a) the protein's leader peptide is deleted and, optionally, (b) no fusion partner is used.

The method will typically involve the steps of: obtaining nucleic acid encoding a protein of the invention; manipulating said nucleic acid to remove nucleotides that encode the protein's leader peptide. The resulting nucleic acid may be inserted into an expression vector, or may already be part of an expression vector. The first amino acid of the expressed protein will be that of the mature native protein.

This method can increase the levels of expression. For protein 919, for example, expression levels in *E. coli* are much higher when the leader peptide is deleted. Increased expression may be due to altered localisation in the absence of the leader peptide.

The method is preferably used for the expression of 919, ORF46, 961, 050-1, 760 and 287.

Domain-Based Expression

In a fourth approach to heterologous expression, the protein is expressed as domains. This may be used in association with fusion systems (e.g. GST or His-tag fusions).

Thus the invention provides a method for the heterologous expression of a protein of the invention, in which (a) at least one domain in the protein is deleted and, optionally, (b) no fusion partner is used.

The method will typically involve the steps of: obtaining nucleic acid encoding a protein of the invention; manipulating said nucleic acid to remove at least one domain from within the protein. The resulting nucleic acid may be inserted into an expression vector, or may already be part of an expression vector. Where no fusion partners are used, the first amino acid of the expressed protein will be that of a domain of the protein.

A protein is typically divided into notional domains by aligning it with known sequences in databases and then determining regions of the protein which show different alignment patterns from each other.

The method is preferably used for the expression of protein 287. This protein can be notionally split into three domains, referred to as A B & C (see FIG. 5). Domain B aligns strongly with IgA proteases, domain C aligns strongly with transferrin-binding proteins, and domain A shows no strong alignment with database sequences. An alignment of polymorphic forms of 287 is disclosed in WO00/66741.

Once a protein has been divided into domains, these can be (a) expressed singly (b) deleted from with the protein e.g. protein ABCD→ABD, ACD, BCD etc. or (c) rearranged e.g. protein ABC→ACB, CAB etc. These three strategies can be combined with fusion partners is desired.

ORF46 has also been notionally split into two domains—a first domain (amino acids 1-433) which is well-conserved between species and serogroups, and a second domain (amino acids 433-608) which is not well-conserved. The second domain is preferably deleted. An alignment of polymorphic forms of ORF46 is disclosed in WO00/66741.

Protein 564 has also been split into domains (FIG. 8), as have protein 961 (FIG. 12) and protein 502 (amino acids 28-167 of the MC58 protein).

Hybrid Proteins

In a fifth approach to heterologous expression, two or more (e.g. 3, 4, 5, 6 or more) proteins of the invention are expressed as a single hybrid protein. It is preferred that no non-Neisserial fusion partner (e.g. GST or poly-His) is used.

This offers two advantages. Firstly, a protein that may be unstable or poorly expressed on its own can be assisted by adding a suitable hybrid partner that overcomes the problem. Secondly, commercial manufacture is simplified—only one expression and purification need be employed in order to produce two separately-useful proteins.

Thus the invention provides a method for the simultaneous heterologous expression of two or more proteins of the invention, in which said two or more proteins of the invention are fused (i.e. they are translated as a single polypeptide chain).

The method will typically involve the steps of: obtaining a first nucleic acid encoding a first protein of the invention; obtaining a second nucleic acid encoding a second protein of the invention; ligating the first and second nucleic acids. The resulting nucleic acid may be inserted into an expression vector, or may already be part of an expression vector.

Preferably, the constituent proteins in a hybrid protein according to the invention will be from the same strain.

The fused proteins in the hybrid may be joined directly, or may be joined via a linker peptide e.g. via a poly-glycine linker (i.e. $G_n$ where n=3, 4, 5, 6, 7, 8, 9, 10 or more) or via a short peptide sequence which facilitates cloning. It is evidently preferred not to join a ΔG protein to the C-terminus of a poly-glycine linker.

The fused proteins may lack native leader peptides or may include the leader peptide sequence of the N-terminal fusion partner.

The method is well suited to the expression of proteins orf1, orf4, orf25, orf40, Orf46/46.1, orf83, 233, 287, 292L, 564, 687, 741, 907, 919, 953, 961 and 983.

The 42 hybrids indicated by 'X' in the following table of form $NH_2$-A-B—COOH are preferred:

| | | | | B | | | |
|---|---|---|---|---|---|---|---|
| A | ORF46.1 | 287 | 741 | 919 | 953 | 961 | 983 |
| ORF46.1 | | X | X | X | X | X | X |
| 287 | X | | X | X | X | X | X |
| 741 | X | X | | X | X | X | X |
| 919 | X | X | X | | X | X | X |
| 953 | X | X | X | X | | X | X |
| 961 | X | X | X | X | X | | X |
| 983 | X | X | X | X | X | X | |

Preferred proteins to be expressed as hybrids are thus ORF46.1, 287, 741, 919, 953, 961 and 983. These may be used in their essentially full-length form, or poly-glycine deletions (ΔG) forms may be used (e.g. ΔG-287, ΔGTbp2, ΔG741, ΔG983 etc.), or truncated forms may be used (e.g. Δ1-287, Δ2-287 etc.), or domain-deleted versions may be used (e.g. 287B, 287C, 287BC, $ORF46_{1-433}$, $ORF46_{433-608}$, ORF46, 961c etc.).

Particularly preferred are: (a) a hybrid protein comprising 919 and 287; (b) a hybrid protein comprising 953 and 287; (c) a hybrid protein comprising 287 and ORF46.1; (d) a hybrid protein comprising ORF1 and ORF46.1; (e) a hybrid protein comprising 919 and ORF46.1; (f) a hybrid protein comprising ORF46.1 and 919; (g) a hybrid protein comprising ORF46.1, 287 and 919; (h) a hybrid protein comprising 919 and 519; and (i) a hybrid protein comprising ORF97 and 225. Further embodiments are shown in FIG. 14.

Where 287 is used, it is preferably at the C-terminal end of a hybrid; if it is to be used at the N-terminus, if is preferred to use a ΔG form of 287 is used (e.g. as the N-terminus of a hybrid with ORF46.1, 919, 953 or 961).

Where 287 is used, this is preferably from strain 2996 or from strain 394/98.

Where 961 is used, this is preferably at the N-terminus. Domain forms of 961 may be used.

Alignments of polymorphic forms of ORF46, 287, 919 and 953 are disclosed in WO00/66741. Any of these polymorphs can be used according to the present invention.

Temperature

In a sixth approach to heterologous expression, proteins of the invention are expressed at a low temperature.

Expressed Neisserial proteins (e.g. 919) may be toxic to *E. coli*, which can be avoided by expressing the toxic protein at a temperature at which its toxic activity is not manifested.

Thus the present invention provides a method for the heterologous expression of a protein of the invention, in which expression of a protein of the invention is carried out at a temperature at which a toxic activity of the protein is not manifested.

A preferred temperature is around 30° C. This is particularly suited to the expression of 919.

Mutations

As discussed above, expressed Neisserial proteins may be toxic to *E. coli*. This toxicity can be avoided by mutating the protein to reduce or eliminate the toxic activity. In particular, mutations to reduce or eliminate toxic enzymatic activity can be used, preferably using site-directed mutagenesis.

In a seventh approach to heterologous expression, therefore, an expressed protein is mutated to reduce or eliminate toxic activity.

Thus the invention provides a method for the heterologous expression of a protein of the invention, in which protein is mutated to reduce or eliminate toxic activity.

The method is preferably used for the expression of protein 907, 919 or 922. A preferred mutation in 907 is at Glu-117 (e.g. Glu→Gly); preferred mutations in 919 are at Glu-255 (e.g. Glu→Gly) and/or Glu-323 (e.g. Glu→Gly); preferred mutations in 922 are at Glu-164 (e.g. Glu→Gly), Ser-213 (e.g. Ser→Gly) and/or Asn-348 (e.g. Asn→Gly).

Alternative Vectors

In a eighth approach to heterologous expression, an alternative vector used to express the protein. This may be to improve expression yields, for instance, or to utilise plasmids that are already approved for GMP use.

Thus the invention provides a method for the heterologous expression of a protein of the invention, in which an alternative vector is used. The alternative vector is preferably pSM214, with no fusion partners. Leader peptides may or may not be included.

This approach is particularly useful for protein 953. Expression and localisation of 953 with its native leader peptide expressed from pSM214 is much better than from the pET vector.

pSM214 may also be used with: ΔG287, Δ2-287, Δ3-287, Δ4-287, Orf46.1, 961L, 961, 961(MC58), 961c, 961c-L, 919, 953 and ΔG287-Orf46.1.

Another suitable vector is pET-24b (Novagen; uses kanamycin resistance), again using no fusion partners. pET-24b is preferred for use with: ΔG287K, Δ2-287K, Δ3-287K, Δ4-287K, Orf46.1-K, Orf46A-K, 961-K (MC58), 961a-K, 961b-K, 961c-K, 961c-L-K, 961d-K, ΔG287-9,9-K, ΔG287-Orf46.1-K and ΔG287-961-K.

Multimeric Form

In a ninth approach to heterologous expression, a protein is expressed or purified such that it adopts a particular multimeric form.

This approach is particularly suited to protein 953. Purification of one particular multimeric form of 953 (the monomeric form) gives a protein with greater bactericidal activity than other forms (the dimeric form).

Proteins 287 and 919 may be purified in dimeric forms.

Protein 961 may be purified in a 180 kDa oligomeric form (e.g. a tetramer).

Lipidation

In a tenth approach to heterologous expression, a protein is expressed as a lipidated protein.

Thus the invention provides a method for the heterologous expression of a protein of the invention, in which the protein is expressed as a lipidated protein.

This is particularly useful for the expression of 919, 287, ORF4, 406, 576-1, and ORF25. Polymorphic forms of 919, 287 and ORF4 are disclosed in WO00/66741.

The method will typically involve the use of an appropriate leader peptide without using an N-terminal fusion partner.

C-Terminal Deletions

In an eleventh approach to heterologous expression, the C-terminus of a protein of the invention is mutated. In addition, it is preferred that no fusion partner is used.

Thus the invention provides a method for the heterologous expression of a protein of the invention, in which (a) the protein's C-terminus region is mutated and, optionally, (b) no fusion partner is used.

The method will typically involve the steps of: obtaining nucleic acid encoding a protein of the invention; manipulating said nucleic acid to mutate nucleotides that encode the protein's C-terminus portion. The resulting nucleic acid may be inserted into an expression vector, or may already be part of an expression vector. The first amino acid of the expressed protein will be that of the mature native protein.

The mutation may be a substitution, insertion or, preferably, a deletion.

This method can increase the levels of expression, particularly for proteins 730, ORF29 and ORF46. For protein 730, a C-terminus region of around 65 to around 214 amino acids may be deleted; for ORF46, the C-terminus region of around 175 amino acids may be deleted; for ORF29, the C-terminus may be deleted to leave around 230-370 N-terminal amino acids.

Leader Peptide Mutation

In a twelfth approach to heterologous expression, the leader peptide of the protein is mutated. This is particularly useful for the expression of protein 919.

Thus the invention provides a method for the heterologous expression of a protein of the invention, in which the protein's leader peptide is mutated.

The method will typically involve the steps of: obtaining nucleic acid encoding a protein of the invention; and manipulating said nucleic acid to mutate nucleotides within the leader peptide. The resulting nucleic acid may be inserted into an expression vector, or may already be part of an expression vector.

Poly-Glycine Deletion

In a thirteenth approach to heterologous expression, polyglycine stretches in wild-type sequences are mutated. This enhances protein expression.

The poly-glycine stretch has the sequence $(Gly)_n$, where $n \geq 4$ (e.g. 5, 6, 7, 8, 9 or more). This stretch is mutated to disrupt or remove the $(Gly)_n$. This may be by deletion (e.g. CGGGGS (SEQ ID NO:622)→CGGGS (SEQ ID NO:623), CGGS (SEQ ID NO:624), CGS or CS), by substitution (e.g. CGGGGS (SEQ ID NO:622)→CGXGGS (SEQ ID NO:625), CGXXGS (SEQ ID NO:626), CGXGXS (SEQ ID NO:627) etc.), and/or by insertion (e.g. CGGGGS (SEQ ID NO:622)→CGGXGGS (SEQ ID NO:628), CGXGGGS (SEQ ID NO:629), etc.).

This approach is not restricted to Neisserial proteins—it may be used for any protein (particularly bacterial proteins) to enhance heterologous expression. For Neisserial proteins, however, it is particularly suitable for expressing 287, 741, 983 and Tbp2. An alignment of polymorphic forms of 287 is disclosed in WO00/66741.

Thus the invention provides a method for the heterologous expression of a protein of the invention, in which (a) a polyglycine stretch within the protein is mutated.

The method will typically involve the steps of: obtaining nucleic acid encoding a protein of the invention; and manipulating said nucleic acid to mutate nucleotides that encode a poly-glycine stretch within the protein sequence. The resulting nucleic acid may be inserted into an expression vector, or may already be part of an expression vector.

Conversely, the opposite approach (i.e. introduction of poly-glycine stretches) can be used to suppress or diminish expression of a given heterologous protein.

Heterologous Host

Whilst expression of the proteins of the invention may take place in the native host (i.e. the organism in which the protein is expressed in nature), the present invention utilises a heterologous host. The heterologous host may be prokaryotic or eukaryotic. It is preferably *E. coli*, but other suitable hosts include *Bacillus subtilis*, *Vibrio cholerae*, *Salmonella typhi*, *Salmonenna typhimurium*, *Neisseria meningitidis*, *Neisseria gonorrhoeae*, *Neisseria lactamica*, *Neisseria cinerea*, *Mycobateria* (e.g. *M. tuberculosis*), yeast etc.

Vectors Etc.

As well as the methods described above, the invention provides (a) nucleic acid and vectors useful in these methods (b) host cells containing said vectors (c) proteins expressed or expressable by the methods (d) compositions comprising these proteins, which may be suitable as vaccines, for instance, or as diagnostic reagents, or as immunogenic compositions (e) these compositions for use as medicaments (e.g. as vaccines) or as diagnostic reagents (f) the use of these compositions in the manufacture of (1) a medicament for treating or preventing infection due to Neisserial bacteria (2) a diagnostic reagent for detecting the presence of Neisserial bacteria or of antibodies raised against Neisserial bacteria, and/or (3) a reagent which can raise antibodies against Neisserial bacteria and (g) a method of treating a patient, comprising administering to the patient a therapeutically effective amount of these compositions.

Sequences

The invention also provides a protein or a nucleic acid having any of the sequences set out in the following examples. It also provides proteins and nucleic acid having sequence identity to these. As described above, the degree of 'sequence identity' is preferably greater than 50% (e.g. 60%, 70%, 80%, 90%, 95%, 99% or more).

Furthermore, the invention provides nucleic acid which can hybridise to the nucleic acid disclosed in the examples, preferably under "high stringency" conditions (e.g. 65° C. in a 0.1×SSC, 0.5% SDS solution).

The invention also provides nucleic acid encoding proteins according to the invention.

It should also be appreciated that the invention provides nucleic acid comprising sequences complementary to those described above (e.g. for antisense or probing purposes).

Nucleic acid according to the invention can, of course, be prepared in many ways (e.g. by chemical synthesis, from genomic or cDNA libraries, from the organism itself etc.) and can take various forms (e.g. single stranded, double stranded, vectors, probes etc.).

In addition, the term "nucleic acid" includes DNA and RNA, and also their analogues, such as those containing modified backbones, and also peptide nucleic acids (PNA) etc.

BRIEF DESCRIPTION OF DRAWINGS

FIG. 3 shows expression data for ORF1, and

FIG. 4 shows similar data for protein 961.

FIGS. 6 & 7 (SEQ ID NO:619 and 620) show deletions within domain A.

FIG. 11 shows insertion mutants of protein 730 (A: 730-C1; B: 730-C2).

FIG. 12 shows domains of protein 961.

FIG. 13 shows SDS-PAGE of ΔG proteins. Dots show the main recombinant product.

FIG. 14 shows 26 hybrid proteins according to the invention.

MODES FOR CARRYING OUT THE INVENTION

Example 1-919

And its Leader Peptide

Figure 1:
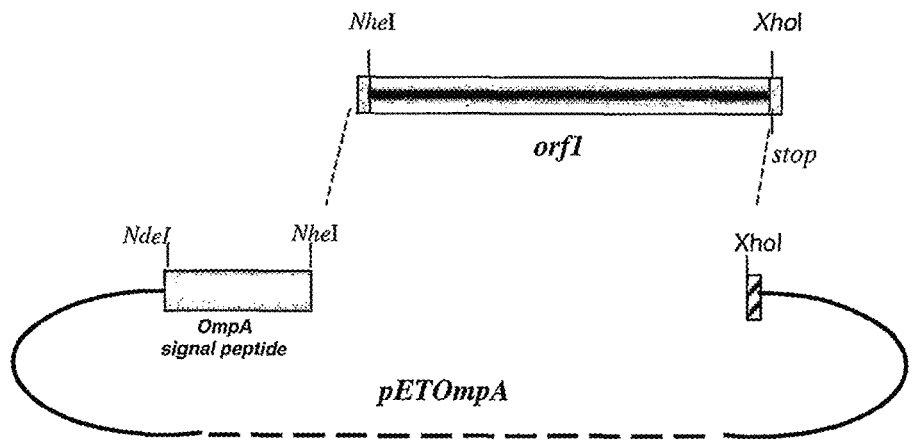
FIGS. 1 and 2 show constructs used to express proteins using heterologous leader peptides.

Protein 919 from *N. meningitidis* (serogroup B, strain 2996) has the following sequence (SEQ ID NO:1):

```
  1 MKKYLFRAAL YGIAAAILAA CQSKSIQTFP QPDTSVINGP
    DRPVGIPDPA

51 GTTVGGGGAV YTVVPHLSLP HWAAQDFAKS LQSFRLGCAN
    LKNRQGWQDV

101 CAQAFQTPVH SFQAKQFFER YFTPWQVAGN GSLAGTVTGY
    YEPVLKGDDR

151 RTAQARFPIY GIPDDFISVP LPAGLRSGKA LVRIRQTGKN
    SGTIDNTGGT

201 HTADLSRFPI TARTTAIKGR FEGSRFLPYH TRNQINGGAL
    DGKAPILGYA

251 EDPVELFFMH IQGSGRLKTP SGKYIRIGYA DKNEHPYVSI
    GRYMADKGYL

301 KLGQTSMQGI KAYMRQNPQR LAEVLGQNPS YIFFRELAGS
    SNDGPVGALG

351 TPLMGEYAGA VDRHYITLGA PLFVATAHPV TRKALNRLIM
    AQDTGSAIKG

401 AVRVDYFWGY GDEAGELAGK QKTTGYVWQL LPNGMKPEYR P*
```

The leader peptide is underlined.

The sequences of 919 from other strains can be found in FIGS. 7 and 18 of WO00/66741.

Example 2 of WO99/57280 discloses the expression of protein 919 as a His-fusion in *E. coli*. The protein is a good surface-exposed immunogen.

Three alternative expression strategies were used for 919:

1) 919 without its leader peptide (and without the mature N-terminal cysteine) and without any fusion partner ('919$^{untagged}$') (SEQ ID NO:2):

```
  1 QSKSIQTFP QPDTSVINGP DRPVGIPDPA GTTVGGGGAV
    YTVVPHLSLP

50 HWAAQDFAKS LQSFRLGCAN LKNRQGWQDV CAQAFQTPVH
    SFQAKQFFER

100 YFTPWQVAGN GSLAGTVTGY YEPVLKGDDR RTAQARFPIY
    GIPDDFISVP

150 LPAGLRSGKA LVRIRQTGKN SGTIDNTGGT HTADLSRFPI
    TARTTAIKGR

200 FEGSRFLPYH TRNQINGGAL DGKAPILGYA EDPVELFFMH
    IQGSGRLKTP

250 SGKYIRIGYA DKNEHPYVSI GRYMADKGYL KLGQTSMQGI
    KAYMRQNPQR

300 LAEVLGQNPS YIFFRELAGS SNDGPVGALG TPLMGEYAGA
    VDRHYITLGA

350 PLFVATAHPV TRKALNRLIM AQDTGSAIKG AVRVDYFWGY
    GDEAGELAGK

400 QKTTGYVWQL LPNGMKPEYR P*
```

The leader peptide and cysteine were omitted by designing the 5'-end amplification primer downstream from the predicted leader sequence.

2) 919 with its own leader peptide but without any fusion partner ('919L'); and 3) 919 with the leader peptide (MKTFFKTLSAAALALILAA (SEQ ID NO:630)) from ORF4 ('919LOrf4') (SEQ ID NO:3).

```
  1 MKTFFKTLS AAALALILAA CQSKSIQTFP QPDTSVINGP
    DRPVGIPDPA

50 GTTVGGGGAV YTVVPHLSLP HWAAQDFAKS LQSFRLGCAN
    LKNRQGWQDV

100 CAQAFQTPVH SFQAKQFFER YFTPWQVAGN GSLAGTVTGY
    YEPVLKGDDR

150 RTAQARFPIY GIPDDFISVP LPAGLRSGKA LVRIRQTGKN
    SGTIDNTGGT

200 HTADLSRFPI TARTTAIKGR FEGSRFLPYH TRNQINGGAL
    DGKAPILGYA

250 EDPVELFFMH IQGSGRLKTP SGKYIRIGYA DKNEHPYVSI
    GRYMADKGYL

300 KLGQTSMQGI KSYMRQNPQR LAEVLGQNPS YIFFRELAGS
    SNDGPVGALG

350 TPLMGEYAGA VDRHYITLGA PLFVATAHPV TRKALNRLIM
    AQDTGSAIKG

400 AVRVDYFWGY GDEAGELAGK QKTTGYVWQL LPNGMKPEYR P*
```

To make this construct, the entire sequence encoding the ORF4 leader peptide was included in the 5'-primer as a tail (primer 919Lorf4 For). A NheI restriction site was generated by a double nucleotide change in the sequence coding for the ORF4 leader (no amino acid changes), to allow different genes to be fused to the ORF4 leader peptide sequence. A stop codon was included in all the 3'-end primer sequences.

All three forms of the protein were expressed and could be purified.

The '919L' and '919LOrf4' expression products were both lipidated, as shown by the incorporation of [$^3$H]-palmitate label. 919$^{untagged}$ did not incorporate the $^3$H label and was located intracellularly.

919LOrf4 could be purified more easily than 919L. It was purified and used to immunise mice. The resulting sera gave excellent results in FACS and ELISA tests, and also in the bactericidal assay. The lipoprotein was shown to be localised in the outer membrane.

919$^{untagged}$ gave excellent ELISA titres and high serum bactericidal activity. FACS confirmed its cell surface location.

Example 2

919 and Expression Temperature

Growth of *E. coli* expressing the 919LOrf4 protein at 37° C. resulted in lysis of the bacteria. In order to overcome this problem, the recombinant bacteria were grown at 30° C. Lysis was prevented without preventing expression.

Example 3

Mutation of 907, 919 and 922

It was hypothesised that proteins 907, 919 and 922 are murein hydrolases, and more particularly lytic transglycosylases. Murein hydrolases are located on the outer membrane and participate in the degradation of peptidoglycan.

The purified proteins 919$^{untagged}$, 919Lorf4, 919-His (i.e. with a C-terminus His-tag) and 922-His were thus tested for murein hydrolase activity [Ursinus & Holtje (1994) *J. Bact.* 176:338-343]. Two different assays were used, one determining the degradation of insoluble murein sacculus into soluble muropeptides and the other measuring breakdown of poly (MurNAc-GlcNAc)$_{n>30}$ glycan strands.

The first assay uses murein sacculi radiolabelled with meso-2,6-diamino-3,4,5-[$^3$H]pimelic acid as substrate. Enzyme (3-10 µg total) was incubated for 45 minutes at 37° C. in a total volume of 100 µl comprising 10 mM Tris-maleate (pH 5.5), 10 mM MgCl$_2$, 0.2% v/v Triton X-100 and [$^3$H]A$_2$pm labelled murein sacculi (about 10000 cpm). The assay mixture was placed on ice for 15 minutes with 100 µl of 1% w/v N-acetyl-N,N,N-trimethylammonium for 15 minutes and precipitated material pelleted by centrifugation at 10000 g for 15 minutes. The radioactivity in the supernatant was measured by liquid scintillation counting. *E. coli* soluble lytic transglycosylase Slt70 was used as a positive control for the assay; the negative control comprised the above assay solution without enzyme.

All proteins except 919-His gave positive results in the first assay.

The second assay monitors the hydrolysis of poly(MurNAc-GlcNAc)glycan strands. Purified strands, poly(MurNAc-GlcNAc)$_{n>30}$ labelled with N-acetyl-D-1-[$^3$H]glucosamine were incubated with 3 µg of 919 L in 10 mM Tris-maleate (pH 5.5), 10 mM MgCl$_2$ and 0.2% v/v Triton X-100 for 30 min at 37° C. The reaction was stopped by boiling for 5 minutes and the pH of the sample adjusted to about 3.5 by addition of 10 µl of 20% v/v phosphoric acid. Substrate and product were separated by reversed phase HPLC on a NUCLEOSIL® 300 C$_{18}$ column (an octadecyl modified silica phase for HPLC) as described by Harz et. al. [*Anal. Biochem.* (1990) 190:120-128]. The *E. coli* lytic transglycosylase Mlt A was used as a positive control in the assay. The negative control was performed in the absence of enzyme.

By this assay, the ability of 919LOrf4 to hydrolyse isolated glycan strands was demonstrated when anhydrodisaccharide subunits were separated from the oligosaccharide by HPLC.

Protein 919Lorf4 was chosen for kinetic analyses. The activity of 919Lorf4 was enhanced 3.7-fold by the addition of 0.2% v/v Triton X-100 in the assay buffer. The presence of Triton X-100 had no effect on the activity of 919$^{untagged}$. The effect of pH on enzyme activity was determined in Tris-Maleate buffer over a range of 5.0 to 8.0. The optimal pH for the reaction was determined to be 5.5. Over the temperature range 18° C. to 42° C., maximum activity was observed at 37° C. The effect of various ions on murein hydrolase activity was determined by performing the reaction in the presence of a variety of ions at a final concentration of 10 mM. Maximum activity was found with Mg$^{2+}$, which stimulated activity 2.1-fold. Mn$^{2+}$ and Ca$^{2+}$ also stimulated enzyme activity to a similar extent while the addition Ni$^{2+}$ and EDTA had no significant effect. In contrast, both Fe$^{2+}$ and Zn$^{2+}$ significantly inhibited enzyme activity.

The structures of the reaction products resulting from the digestion of unlabelled *E. coli* murein sacculus were analysed by reversed-phase HPLC as described by Glauner [*Anal. Biochem.* (1988) 172:451-464]. Murein sacculi digested with the muramidase Cellosyl were used to calibrate and standardise the Hypersil ODS column. The major reaction products were 1,6 anhydrodisaccharide tetra and tri peptides, demonstrating the formation of 1,6 anhydromuraminic acid intramolecular bond.

These results demonstrate experimentally that 919 is a murein hydrolase and in particular a member of the lytic transglycosylase family of enzymes. Furthermore the ability of 922-His to hydrolyse murein sacculi suggests this protein is also a lytic transglycosylase.

This activity may help to explain the toxic effects of 919 when expressed in *E. coli*.

In order to eliminate the enzymatic activity, rational mutagenesis was used. 907, 919 and 922 show fairly low homology to three membrane-bound lipidated murein lytic transglycosylases from *E. coli*:

919 (441aa) is 27.3% identical over 440aa overlap to *E. coli* MLTA (P46885);

922 (369aa) is 38.7% identical over 310aa overlap to *E. coli* MLTB (P41052); and 907-2 (207aa) is 26.8% identical over 149aa overlap to *E. coli* MLTC (P52066).

907-2 also shares homology with *E. coli* MLTD (P23931) and Slt70 (PO$_{3810}$), a soluble lytic transglycosylase that is located in the periplasmic space. No significant sequence homology can be detected among 919, 922 and 907-2, and the same is true among the corresponding MLTA, MLTB and MLTC proteins.

Crystal structures are available for Slt70 [1 QTEA; 1QTEB; Thunnissen et al. (1995) *Biochemistry* 34:12729-12737] and for Slt35 [1LTM; 1QUS; 1QUT; van Asselt et al. (1999) *Structure Fold Des* 7:1167-80] which is a soluble form of the 40 kDa MLTB.

The catalytic residue (a glutamic acid) has been identified for both Slt70 and MLTB.

In the case of Slt70, mutagenesis studies have demonstrated that even a conservative substitution of the catalytic Glu505 with a glutamine (Gln) causes the complete loss of enzymatic activity. Although Slt35 has no obvious sequence similarity to Slt70, their catalytic domains shows a surprising similarity. The corresponding catalytic residue in MLTB is Glu162.

Another residue which is believed to play an important role in the correct folding of the enzymatic cleft is a well-conserved glycine (Gly) downstream of the glutamic acid. Recently, Terrak et al. [*Mol. Microbiol.* (1999) 34:350-64] have suggested the presence of another important residue which is an aromatic amino acid located around 70-75 residues downstream of the catalytic glutamic acid.

Sequence alignment of Slt70 (SEQ ID NO:5) with 907-2 (SEQ ID NO:4) and of MLTB (SEQ ID NO:7) with 922 (SEQ ID NO:6) were performed in order to identify the corresponding catalytic residues in the MenB antigens.

The two alignments in the region of the catalytic domain are reported below:

aromatic residues located approximately 75-77 residues downstream. These downstream residues are shown by □.

```
907-2/Slt70:

90        100       110     ▼120      130       140
907-2.pep    ERRRLLVNIQYESSRAG--LDTQIVLGLIEVESAFRQYAISGVGARGLMQVMPFWKNYIG
             ||   |    ::    :|  :  : ::::  : |||:    : | ||| ||||::||  ::
slty_ecoli   ERFPLAYNDLFKRYTSGKEIPQSYAMAIARQESAWNPKVKSPVGASGLMQIMPGTATHTV
                480       490       500    ▲ 510       520       530
                                             GLU505

922/MLTB 150       160     ▼  170       180       190       200
922.pep      VAQKYGVPAELIVAVIGIETNYGKNTGSFRVADALATLGFDYPRRAGFFQKELVELLKLA
             : | ||||  :||::||:|| :|:    |: |: ||||||:|:|||||  :|:  ||  :| :|
mltb_ecoli   AWQVYGVPPEIIVGIIGVETRWGRVMGKTRILDALATLSFNYPRRAEYFSGELETFLLMA
                150       160 ▲    170       180       190       200
                                  GLU162
                210       220       230       240       250       260
922.pep      KEEGGDVFAFKGSYAGAMGMPQFMPSSYRKWAVDYDGDGHRDIWGNVGDVAASVANYMKQ
             ::|   |  : :|||:||||:   ||||||||:::|||::||||   ::|    |  |: :|||||:|
mltb_ecoli   RDEQDDPLNLKGSFAGAMGYGQFMPSSYKQYAVDFSGDGHINLWDPV-DAIGSVANYFKA
                210       220       230       240       250       260
```

From these alignments, it results that the corresponding catalytic glutamate in 907-2 is Glu117, whereas in 922 is Glu164. Both antigens also share downstream glycines that could have a structural role in the folding of the enzymatic cleft (in bold), and 922 has a conserved aromatic residue around 70aa downstream (in bold).

In the case of protein 919, no 3D structure is available for its *E. coli* homologue MLTA, and nothing is known about a possible catalytic residue. Nevertheless, three amino acids in 919 (SEQ ID NO:8) are predicted as catalytic residues by alignment with MLTA (SEQ ID NO:9):

2) Glu323 (conserved in MLTA), followed by 2 conserved glycines (Gly347 and Gly355) and two conserved aromatic residues located 84-85 residues downstream (Tyr406 or Phe407). These downstream residues are shown by ◇.
3) Asp362 (instead of the expected Glu), followed by one glycine (Gly 369) and a conserved aromatic residue (Trp428). These downstream residues are shown by ○.

Alignments of polymorphic forms of 919 are disclosed in WO00/66741.

Based on the prediction of catalytic residues, three mutants of the 919 and one mutant of 907, containing each a single

```
919/MLTA 240       250    ▼  260 □ □ 270 □     280       290
919.pep      ALDGKAPILGYAEDPVELFFMHIQGSGRLKTPSGKYIRI-GYADKNEHPYVSIGRYMADK
             ||: |   ||:|:::  ::  :|: |||| :    :|: :  :|| ||  |   ||| : |:
mlta_ecoli.p ALSDKY-ILAYSNSLMDNFIMDVQGSGYIDFGDGSPLNFFSYAGKNGHAYRSIGKVLIDR
                170       180       190       200       210

300       310       320   ▼    330□  □□ 340     ◇350    ◇
919.pep      GYLKLGQTSMQGIKSYMRQNPQ-RLAEVLGQNPSYIFFRELAGSSNDGPV-GALGTPLMG
             |  :|   ||||:|| ||  |:|   :|   |  :| ||||::||:     |||  :: ||
mlta_ecoli.p GEVKKEDMSMQAIRHWGETHSEAEVRELLEQNPSFVFFKPQSFA----PVKGASAVPLVG
                220       230       240       250       260       270

360 ▼        ○   380         390       400  ◇ ◇410
919.pep      EYAGAVDRHYITLGAPLFVATAHPVTRKALN-----RLIMAQDTGSAIKGAVRVDYFWGY
             : : |||   | |:  |:: :    :|    ||::| |:|||||  : |:|
mlta_ecoli.p RASVASDRSIIPPGTTLLAEVPLLDNNGKFNGQYELRLMVALDVGGAIKGQ-HFDIYQGI
                280       290       300       310       320       330

420        ○
919.pep      GDEAGELAGKQKTTGYVWQLLP
             | |||:||  :   ||| |
mlta_ecoli.p GPEAGHRAGWYNHYGRVWVLKT
                340       350
```

The three possible catalytic residues are shown by the symbol ▼:

1) Glu255 (Asp in MLTA), followed by three conserved glycines (Gly263, Gly265 and Gly272) and three conserved amino acid substitution, have been generated. The glutamic acids in position 255 and 323 and the aspartic acids in position 362 of the 919 protein and the glutamic acid in position 117 of the 907 protein, were replaced with glycine residues using PCR-based SDM. To do this, internal primers containing a codon change from Glu or Asp to Gly were designed:

| Primers | SEQ ID NO | Sequences | Codon change |
|---|---|---|---|
| 919-E255 for | 10 | CGAAGACCCCGTCGgtCTTTTTTTTATG | GAA → Ggt |
| 919-E255 rev | 11 | GTGCATAAAAAAAAGacCGACGGGGTCT | |
| 919-E323 for | 12 | AACGCCTCGCCGgtGTTTTGGGTCA | GAA → Ggt |
| 919-E323 rev | 13 | TTTGACCCAAAACacCGGCGAGGCG | |
| 919-D362 for | 14 | TGCCGGCGCAGTCGgtCGGCACTACA | GAC → Ggt |
| 919-D362 rev | 15 | TAATGTAGTGCCGacCGACTGCGCCG | |
| 907-E117 for | 16 | TGATTGAGGTGGgtAGCGCGTTCCG | GAA → Ggt |
| 907-E117 rev | 17 | GGCGGAACGCGCTacCCACCTCAAT | |

Underlined nucleotides code for glycine; the mutated nucleotides are in lower case.

To generate the 919-E255, 919-E323 and 919-E362 mutants, PCR was performed using 20 ng of the pET 919-LOrf4 DNA as template, and the following primer pairs:
1) Orf4L for/919-E255 rev
2) 919-E255 for/919L rev
3) Orf4L for/919-E323 rev
4) 919-E323 for/919L rev
5) Orf4L for/919-D362 rev
6) 919-D362 for/919L rev The second round of PCR was performed using the product of PCR 1-2, 3-4 or 5-6 as template, and as forward and reverse primers the "Orf4L for" and "919L rev" respectively.

For the mutant 907-E117, PCR have been performed using 200 ng of chromosomal DNA of the 2996 strain as template and the following primer pairs:
7) 907L for/907-E117 rev
8) 907-E117 for/907L rev The second round of PCR was performed using the products of PCR 7 and 8 as templates and the oligos "907L for" and "907L rev" as primers.

The PCR fragments containing each mutation were processed following the standard procedure, digested with NdeI and XhoI restriction enzymes and cloned into pET-21b+vector. The presence of each mutation was confirmed by sequence analysis.

Mutation of Glu117 to Gly in 907 is carried out similarly, as is mutation of residues Glu164, Ser213 and Asn348 in 922.

The E255G mutant of 919 shows a 50% reduction in activity; the E323G mutant shows a 70% reduction in activity; the E362G mutant shows no reduction in activity.

Example 4

Multimeric Form

287-GST, 919$^{untagged}$ and 953-His were subjected to gel filtration for analysis of quaternary structure or preparative purposes. The molecular weight of the native proteins was estimated using either FPLC Superose 12 (H/R 10/30) or Superdex™ 75 gel filtration columns (prepacked columns, Pharmacia). The buffers used for chromatography for 287, 919 and 953 were 50 mM Tris-HCl (pH 8.0), 20 mM Bicine (pH 8.5) and 50 mM Bicine (pH 8.0), respectively.

Additionally each buffer contained 150-200 mM NaCl and 10% v/v glycerol. Proteins were dialysed against the appropriate buffer and applied in a volume of 200 µl. Gel filtration was performed with a flow rate of 0.5-2.0 ml/min and the eluate monitored at 280 nm. Fractions were collected and analysed by SDS-PAGE. Blue dextran 2000 and the molecular weight standards ribonuclease A, chymotrypsin A ovalbumin, albumin (Pharmacia) were used to calibrate the column The molecular weight of the sample was estimated from a calibration curve of $K_{av}$ vs. log $M_r$ of the standards. Before gel filtration, 287-GST was digested with thrombin to cleave the GST moiety.

The estimated molecular weights for 287, 919 and 953-His were 73 kDa, 47 kDa and 43 kDa respectively. These results suggest 919 is monomeric while both 287 and 953 are principally dimeric in their nature. In the case of 953-His, two peaks were observed during gel filtration. The major peak (80%) represented a dimeric conformation of 953 while the minor peak (20%) had the expected size of a monomer. The monomeric form of 953 was found to have greater bactericidal activity than the dimer.

Example 5 pSM214 and pET-24b Vectors 953 protein with its native leader peptide and no fusion partners was expressed from the pET vector and also from pSM214 [Velati Bellini et al. (1991) *J. Biotechnol.* 18, 177-192].

The 953 sequence was cloned as a full-length gene into pSM214 using the *E. coli* MM294-1 strain as a host. To do this, the entire DNA sequence of the 953 gene (from ATG to the STOP codon) was amplified by PCR using the following primers:

953L for/2
(SEQ ID NO: 18)
CCGGAATTCTTATGAAAAAAATCATCTTCGCCGC Eco RI 953L rev/2
(SEQ ID NO: 19)
GCCCAAGCTTTTATTGTTTGGCTGCCTCGATT Hind III which contain EcoRI and HindIII restriction sites, respectively. The amplified fragment was digested with EcoRI and HindIII and ligated with the pSM214 vector digested with the same two enzymes. The ligated plasmid was transformed into *E. coli* MM294-1 cells (by incubation in ice for 65 minutes at 37° C.) and bacterial cells plated on LB agar containing 20 µg/ml of chloramphenicol.

Recombinant colonies were grown over-night at 37° C. in 4 ml of LB broth containing 20 µg/ml of chloramphenicol; bacterial cells were centrifuged and plasmid DNA extracted as and analysed by restriction with EcoRI and HindIII. To analyse the ability of the recombinant colonies to express the protein, they were inoculated in LB broth containing 20 µg/ml of chloramphenicol and let to grown for 16 hours at 37° C. Bacterial cells were centrifuged and resuspended in PBS. Expression of the protein was analysed by SDS-PAGE and Coomassie Blue staining.

Expression levels were unexpectedly high from the pSM214 plasmid.

Oligos used to clone sequences into pSM-214 vectors were as follows:

| | | | |
|---|---|---|---|
| ΔG287 (pSM-214) | Fwd | CCGGAATTCTTATG-TCGCCCGATGTTAAATCGGCGGA | SEQ ID NO: 20 EcoRI |
| | Rev | GCCCAAGCTT-TCAATCCTGCTCTTTTTTGCCG | SEQ ID NO: 21 HindIII |
| Δ2 287 (pSM-214) | Fwd | CCGGAATTCTTATG-AGCCAAGATATGGCGGCAGT | SEQ ID NO: 22 EcoRI |
| | Rev | GCCCAAGCTT-TCAATCCTGCTCTTTTTTGCCG | SEQ ID NO: 23 HindIII |
| Δ3 287 (pSM-214) | Fwd | CCGGAATTCTTATG-TCCGCCGAATCCGCAAATCA | SEQ ID NO: 24 EcoRI |
| | Rev | GCCCAAGCTT-TCAATCCTGCTCTTTTTTGCCG | SEQ ID NO: 25 HindIII |
| Δ4 287 (pSM-214) | Fwd | CCGGAATTCTTATG-GGAAGGGTTGATTTGGCTAATG | SEQ ID NO: 26 EcoRI |
| | Rev | GCCCAAGCTT-TCAATCCTGCTCTTTTTTGCCG | SEQ ID NO: 27 HindIII |
| Orf46.1 (pSM-214) | Fwd | CCGGAATTCTTATG-TCAGATTTGGCAAACGATTCTT | SEQ ID NO: 28 EcoRI |
| | Rev | GCCCAAGCTT-TTACGTATCATATTTCACGTGCTTC | SEQ ID NO: 29 HindIII |
| ΔG287-Orf46.1 (pSM-214) | Fwd | CCGGAATTCTTATG-TCGCCCGATGTTAAATCGGCGGA | SEQ ID NO: 30 EcoRI |
| | Rev | GCCCAAGCTT-TTACGTATCATATTTCACGTGCTTC | SEQ ID NO: 31 HindIII |
| 919 (pSM-214) | Fwd | CCGGAATTCTTATG-CAAAGCAAGAGCATCCAAACCT | SEQ ID NO: 32 EcoRI |
| | Rev | GCCCAAGCTT-TTACGGGCGGTATTCGGGCT | SEQ ID NO: 33 HindIII |
| 961L (pSM-214) | Fwd | CCGGAATTCATATG-AAACACTTTCCATCC | SEQ ID NO: 34 EcoRI |
| | Rev | GCCCAAGCTT-TTACCACTCGTAATTGAC | SEQ ID NO: 35 HindIII |
| 961 (pSM-214) | Fwd | CCGGAATTCATATG-GCCACAAGCGACGAC | SEQ ID NO: 36 EcoRI |
| | Rev | GCCCAAGCTT-TTACCACTCGTAATTGAC | SEQ ID NO: 37 HindIII |
| 961c L pSM-214 | Fwd | CCGGAATTCTTATG-AAACACTTTCCATCC | SEQ ID NO: 38 EcoRI |
| | Rev | GCCCAAGCTT-TCAACCCACGTTGTAAGGTTG | SEQ ID NO: 39 HindIII |
| 961c pSM-214 | Fwd | CCGGAATTCTTATG-GCCACAAACGACGACG | SEQ ID NO: 40 EcoRI |
| | Rev | GCCCAAGCTT-TCAACCCACGTTGTAAGGTTG | SEQ ID NO: 41 HindIII |
| 953 (pSM-214) | Fwd | CCGGAATTCTTATG-GCCACCTACAAAGTGGACGA | SEQ ID NO: 42 EcoRI |
| | Rev | GCCCAAGCTT-TTATTGTTTGGCTGCCTCGATT | SEQ ID NO: 43 HindIII |

These sequences were manipulated, cloned and expressed as described for 953L.

For the pET-24 vector, sequences were cloned and the proteins expressed in pET-24 as described below for pET21.

pET2 has the same sequence as pET-21, but with the kanamycin resistance cassette instead of ampicillin cassette.

Oligonucleotides used to clone sequences into pET-24b vector were:

| | | | |
|---|---|---|---|
| ΔG 287 K | Fwd | CGCGGATCC<u>GCTAGC</u>-CCCGATGTTAAATCGGC§ | SEQ ID NO: 44 NheI |
| | Rev | CCCG<u>CTCGAG</u>-TCAATCCTGCTCTTTTTTGCC* | SEQ ID NO: 45 XhoI |
| Δ2 287 K | Fwd | CGCGGATCC<u>GCTAGC</u>-CAAGATATGGCGGCAGT§ | SEQ ID NO: 46 NheI |
| Δ3 287 K | Fwd | CGCGGATCC<u>GCTAGC</u>-GCCGAATCCGCAAATCA§ | SEQ ID NO: 47 NheI |
| Δ4 287 K | Fwd | CGC<u>GCTAGC</u>-GGAAGGGTTGATTTGGCTAATGG§ | SEQ ID NO: 48 NheI |
| Orf46.1 K | Fwd | GGGAATTC<u>CATATG</u>-GGCATTTCCCGCAAAATATC | SEQ ID NO: 49 NdeI |
| | Rev | CCCG<u>CTCGAG</u>-TTACGTATCATATTTCACGTGC | SEQ ID NO: 50 XhoI |
| Orf46A K | Fwd | GGGAATTC<u>CATATG</u>-GGCATTTCCCGCAAAATATC | SEQ ID NO: 51 NdeI |
| | Rev | CCCG<u>CTCGAG</u>-TTATTCTATGCCTTGTGCGGCAT | SEQ ID NO: 52 XhoI |
| 961 K (MC58) | Fwd | CGCGGATCC<u>CATATG</u>-GCCACAAGCGACGACGA | SEQ ID NO: 53 NdeI |
| | Rev | CCCG<u>CTCGAG</u>-TTACCACTCGTAATTGAC | SEQ ID NO: 54 XhoI |

| | | | |
|---|---|---|---|
| 961a K | Fwd CGCGGATCC<u>CATATG</u>-GCCACAAACGACG | SEQ ID NO: 55 | NdeI |
| | Rev CCCG<u>CTCGAG</u>-TCATTTAGCAATATTATCTTTGTTC | SEQ ID NO: 56 | XhoI |
| 961b K | Fwd CGCGGATCC<u>CATATG</u>-AAAGCAAACAGTGCCGAC | SEQ ID NO: 57 | NdeI |
| | Rev CCCG<u>CTCGAG</u>-TTACCACTCGTAATTGAC | SEQ ID NO: 58 | XhoI |
| 961c K | Fwd CGCGGATCC<u>CATATG</u>-GCCACAAACGACG | SEQ ID NO: 59 | NdeI |
| | Rev CCCG<u>CTCGAG</u>-TTAACCCACGTTGTAAGGT | SEQ ID NO: 60 | XhoI |
| 961cL K | Fwd CGCGGATCC<u>CATATG</u>-ATGAAACACTTTCCATCC | SEQ ID NO: 61 | NdeI |
| | Rev CCCG<u>CTCGAG</u>-TTAACCCACGTTGTAAGGT | SEQ ID NO: 62 | XhoI |
| 961d K | Fwd CGCGGATCC<u>CATATG</u>-GCCACAAACGACG | SEQ ID NO: 63 | NdeI |
| | Rev CCCG<u>CTCGAG</u>-TCAGTCTGACACTGTTTTATCC | SEQ ID NO: 64 | XhoI |
| ΔG 287-919 K | Fwd CGCGGATCC<u>GCTAGC</u>-CCCGATGTTAAATCGGC | SEQ ID NO: 65 | NheI |
| | Rev CCCG<u>CTCGAG</u>-TTACGGGCGGTATTCGG | SEQ ID NO: 66 | XhoI |
| ΔG 287-Orf46.1 K | Fwd CGCGGATCC<u>GCTAGC</u>-CCCGATGTTAAATCGGC | SEQ ID NO: 67 | NheI |
| | Rev CCCG<u>CTCGAG</u>-TTACGTATCATATTTCACGTGC | SEQ ID NO: 68 | XhoI |
| ΔG 287-961 K | Fwd CGCGGATCC<u>GCTAGC</u>-CCCGATGTTAAATCGGC | SEQ ID NO: 69 | NheI |
| | Rev CCCG<u>CTCGAG</u>-TTACCACTCGTAATTGAC | SEQ ID NO: 70 | XhoI |

*This primer was used as a Reverse primer for all the 287 forms.
$Forward primers used in combination with the ΔG278 K reverse primer.

Example 6

ORF1 and its Leader Peptide

ORF1 from *N. meningitidis* (serogroup B, strain MC58) is predicted to be an outer membrane or secreted protein. It has the following sequence:

```
   1 MKTTDKRTTEP THRKAPKTGR IRFSPAYLAI CLSFGILPQA
     WAGHTYFGIN

51 YQYYRDFAEN KGKFAVGAKD IEVYNKKGEL VGKSMTKAPM
     IDFSVVSRNG

101 VAALVGDQYI VSVAHNGGYN NVDFGAEGRN PDQHRFTYKI
     VKRNNYKAGT

151 KGHPYGGDYH MPRLHKFVTD AEPVEMTSYM DGRKYIDQNN
     YPDRVRIGAG

201 RQYWRSDEDE PNNRESSYHI ASAYSWLVGG NTFAQNGSGG
     GTVNLGSEKI

251 KHSPYGFLPT GGSFGDSGSP MFIYDAQKQK WLINGVLQTG
     NPYIGKSNGF

301 QLVRKDWFYD EIFAGDTHSV FYEPRQNGKY SFNDDNNGTG
     KINAKHEHNS

351 LPNRLKTRTV QLFNVSLSET AREPVYHAAG GVNSYRPRLN
     NGENISFIDE

401 GKGELILTSN INQGAGGLYF QGDFTVSPEN NETWQGAGVH
     ISEDSTVTWK

451 VNGVANDRLS KIGKGTLHVQ AKGENQGSIS VGDGTVILDQ
     QADDKGKKQA

501 FSEIGLVSGR GTVQLNADNQ FNPDKLYFGF RGGRLDLNGH
     SLSFHRIQNT

551 DEGAMIVNHN QDKESTVTIT GNKDIATTGN NNSLDSKKEI
     AYNGWFGEKD

601 TTKTNGRLNL VYQPAAEDRT LLLSGGTNLN GNITQTNGKL
     FFSGRPTPHA

651 YNHLNDHWSQ KEGIPRGEIV WDNDWINRTF KAENFQIKGG
     QAVVSRNVAK

701 VKGDWHLSNH AQAVFGVAPH QSHTICTRSD WTGLTNCVEK
     TITDDKVIAS

751 LTKTDISGNV DLADHAHLNL TGLATLNGNL SANGDTRYTV
     SHNATQNGNL

801 SLVGNAQATF NQATLNGNTS ASGNASFNLS DHAVQNGSLT
     LSGNAKANVS

851 HSALNGNVSL ADKAVFHFES SRFTGQISGG KDTALHLKDS
     EWTLPSGTEL

901 GNLNLDNATI TLNSAYRHDA AGAQTGSATD APRRRSRRSR
     RSLLSVTPPT

951 SVESRFNTLT VNGKLNGQGT FRFMSELFGY RSDKLKLAES
     SEGTYTLAVN

1001 NTGNEPASLE QLTVVEGKDN KPLSENLNFT LQNEHVDAGA
     WRYQLIRKDG

1051 EFRLHNPVKE QELSDKLGKA EAKKQAEKDN AQSLDALIAA
     GRDAVEKTES

1101 VAEPARQAGG ENVGIMQAEE EKKRVQADKD TALAKQREAE
     TRPATTAFPR

1151 ARRARRDLPQ LQPQPQPQPQ RDLISRYANS GLSEFSATLN
     SVFAVQDELD

1201 RVFAEDRRNA VWTSGIRDTK HYRSQDFRAY RQQTDLRQIG
     MQKNLGSGRV

1251 GILFSHNRTE NTFDDGIGNS ARLAHGAVFG QYGIDRFYIG
     ISAGAGFSSG

1301 SLSDGIGGKI RRRVLHYGIQ ARYRAGFGGF GIEPHIGATR
     YFVQKADYRY

1351 ENVNIATPGL AFNRYRAGIK ADYSFKPAQH ISITPYLSLS
     YTDAASGKVR

1401 TRVNTAVLAQ DFGKTRSAEW GVNAEIKGFT LSLHAAAAKG
     PQLEAQHSAG

1451 IKLGYRW*
```

The leader peptide is underlined.

A polymorphic form of ORF1 is disclosed in WO99/55873.

Three expression strategies have been used for ORF1:
1) ORF1 using a His tag, following WO99/24578 (ORF1-His);
2) ORF1 with its own leader peptide but without any fusion partner ('ORF1L'); and
3) ORF1 with the leader peptide (MKKTAIAIAVALAGFATVAQA (SEQ ID NO:72)) from *E. coli* OmpA ('Orf1LOmpA') (SEQ ID NO:73):

MKKTAIAIAVALAGFATVAQAASAGHTYFGINYQYYRDFAENKGKFAVGA

KDIEVYNKKGELVGKSMTKAPMIDFSVVSRNGVAALVGDQYIVSVAHNGG

YNNVDFGAEGRNPDQHRFTYKIVKRNNYKAGTKGHPYGGDYHMPRLHKFV

TDAEPVEMTSYMDGRKYIDQNNYPDRVRIGAGRQYWRSDEDEPNNRESSY

HIASAYSWLVGGNTFAQNGSGGGTVNLGSEKIKHSPYGFLPTGGSFGDSG

SPMFIYDAQKQKWLINGVLQTGNPYIGKSNGFQLVRKDWFYDEIFAGDTH

SVFYEPRQNGKYSFNDDNNGTGKINAKHEHNSLPNRLKTRTVQLFNVSLS

ETAREPVYHAAGGVNSYRPRLNNGENISFIDEGKGELILTSNINQGAGGL

YFQGDFTVSPENNETWQGAGVHISEDSTVTWKVNGVANDRLSKIGKGTLH

VQAKGENQGSISVGDGTVILDQQADDKGKKQAFSEIGLVSGRGTVQLNAD

NQFNPDKLYFGFRGGRLDLNGHSLSFHRIQNTDEGAMIVNHNQDKESTVT

ITGNKDIATTGNNNSLDSKKEIAYNGWFGEKDTTKTNGRLNLVYQPAAED

RTLLLSGGTNLNGNITQTNGKLFFSGRPTPHAYNHLNDHWSQKEGIPRGE

IVWDNDWINRTFKAENFQIKGGQAVVSRNVAKVKGDWHLSNHAQAVFGVA

PHQSHTICTRSDWTGLTNCVEKTITDDKVIASLTKTDISGNVDLADHAHL

NLTGLATLNGNLSANGDTRYTVSHNATQNGNLSLVGNAQATFNQATLNGN

TSASGNASFNLSDHAVQNGSLTLSGNAKANVSHSALNGNVSLADKAVFHF

ESSRFTGQISGGKDTALHLKDSEWTLPSGTELGNLNLDNATITLNSAYRH

DAAGAQTGSATDAPRRRSRRSRRSLLSVTPPTSVESRFNTLTVNGKLNGQ

GTFRFMSELFGYRSDKLKLAESSEGTYTLAVNNTGNEPASLEQLTVVEGK

DNKPLSENLNFTLQNEHVDAGAWRYQLIRKDGEFRLHNPVKEQELSDKLG

KAEAKKQAEKDNAQSLDALIAAGRDAVEKTESVAEPARQAGGENVGIMQA

EEEKKRVQADKDTALAKQREAETRPATTAFPRARRARRDLPQLQPQPQPQ

PQRDLISRYANSGLSEFSATLNSVFAVQDELDRVFAEDRRNAVWTSGIRD

TKHYRSQDFRAYRQQTDLRQIGMQKNLGSGRVGILFSHNRTENTFDDGIG

NSARLAHGAVFGQYGIDRFYIGISAGAGFSSGSLSDGIGGKIRRRVLHYG

IQARYRAGFGGFGIEPHIGATRYFVQKADYRYENVNIATPGLAFNRYRAG

IKADYSFKPAQHISITPYLSLSYTDAASGKVRTRVNTAVLAQDFGKTRSA

EWGVNAEIKGFTLSLHAAAAKGPQLEAQHSAGIKLGYRW*

To make this construct, the clone pET911LOmpA (see below) was digested with the NheI and XhoI restriction enzymes and the fragment corresponding to the vector carrying the OmpA leader sequence was purified (pET-LOmpA). The ORF1 gene coding for the mature protein was amplified using the oligonucleotides ORF1-For and ORF1-Rev (including the NheI and XhoI restriction sites, respectively), digested with NheI and XhoI and ligated to the purified pETOmpA fragment (see FIG. 1). An additional AS dipeptide was introduced by the NheI site.

All three forms of the protein were expressed. The His-tagged protein could be purified and was confirmed as surface exposed, and possibly secreted (see FIG. 3). The protein was used to immunise mice, and the resulting sera gave excellent results in the bactericidal assay.

ORF1LOmpA was purified as total membranes, and was localised in both the inner and outer membranes. Unexpectedly, sera raised against ORF1LOmpA show even better ELISA and anti-bactericidal properties than those raised against the His-tagged protein.

ORF1L was purified as outer membranes, where it is localised.

Example 7

Protein 911 and its Leader Peptide

Protein 911 from *N. meningitidis* (serogroup B, strain MC58) has the following sequence (SEQ ID NO:74):

```
  1 MKKNILEFWV GLFVLIGAAA VAFLAFRVAG GAAFGGSDKT
    YAVYADFGDI

51 GGLKVNAPVK SAGVLVGRVG AIGLDPKSYQ ARVRLDLDGK
    YQFSSDVSAQ

101 ILTSGLLGEQ YIGLQQGGDT ENLAAGDTIS VTSSAMVLEN
    LIGKFMTSFA

151 EKNADGGNAE KAAE*
```

The leader peptide is underlined.
Three expression strategies have been used for 911:
1) 911 with its own leader peptide but without any fusion partner ('911L');
2) 911 with the leader peptide from *E. coli* OmpA ('911LOmpA').
   To make this construct, the entire sequence encoding the OmpA leader peptide was included in the 5'-primer as a tail (primer 911LOmpA Forward). A NheI restriction site was inserted between the sequence coding for the OmpA leader peptide and the 911 gene encoding the predicted mature protein (insertion of one amino acid, a serine), to allow the use of this construct to clone different genes downstream the OmpA leader peptide sequence.
3) 911 with the leader peptide (MKYLLPTAAAGLLLAAQPAMA (SEQ ID NO:75)) from *Erwinia carotovora* PelB ('911LpelB').
   To make this construct, the 5'-end PCR primer was designed downstream from the leader sequence and included the NcoI restriction site in order to have the 911 fused directly to the PelB leader sequence; the 3'-end primer included the STOP codon. The expression vector used was pET22b+ (Novagen), which carries the coding sequence for the PelB leader peptide. The NcoI site introduces an additional methionine after the PelB sequence.

All three forms of the protein were expressed. ELISA titres were highest using 911L, with 919LOmpA also giving good results.

Example 8

ORF46

The complete ORF46 protein from *N. meningitidis* (serogroup B, strain 2996) has the following sequence (SEQ ID NO:76):

1 LGISRKISLI LSILAVCLPM HAHASDLAND SFIRQVLDRQ HFEPDGKYHL

51 FGSRGELAER SGHIGLGKIQ SHQLGNLMIQ QAAIKGNIGY IVRFSDHGHE

101 VHSPFDNHAS HSDSDEAGSP VDGFSLYRIH WDGYEHHPAD GYDGPQGGGY

151 PAPKGARDIY SYDIKGVAQN IRLNLTDNRS TGQRLADRFH NAGSMLTQGV

201 GDGFKRATRY SPELDRSGNA AEAFNGTADI VKNIIGAAGE IVGAGDAVQG

251 ISEGSNIAVM HGLGLLSTEN KMARINDLAD MAQLKDYAAA AIRDWAVQNP

301 NAAQGIEAVS NIFMAAIPIK GIGAVRGKYG LGGITAHPIK RSQMGAIALP

351 KGKSAVSDNF ADAAYAKYPS PYHSRNIRSN LEQRYGKENI TSSTVPPSNG

401 KNVKLADQRH PKTGVPFDGK GFPNFEKHVK YDTKLDIQEL SGGGIPKAKP

451 VSDAKPRWEV DRKLNKLTTR EQVEKNVQEI RNGNKNSNFS QHAQLEREIN

501 KLKSADEINF ADGMGKFTDS MNDKAFSRLV KSVKENGFTN PVVEYVEING

551 KAYIVRGNNR VFAAEYLGRI HELKFKKVDF PVPNTSWKNP TDVLNESGNV

601 KRPRYRSK*

The leader peptide is underlined.

The sequences of ORF46 from other strains can be found in WO00/66741.

Three expression strategies have been used for ORF46:

1) ORF46 with its own leader peptide but without any fusion partner ('ORF46-2L');
2) ORF46 without its leader peptide and without any fusion partner ('ORF46-2'), with the leader peptide omitted by designing the 5'-end amplification primer downstream from the predicted leader sequence (SEQ ID NO:77):

1 SDLANDSFIR QVLDRQHFEP DGKYHLFGSR GELAERSGHI GLGKIQSHQL

51 GNLMIQQAAI KGNIGYIVRF SDHGHEVHSP FDNHASHSDS DEAGSPVDGF

101 SLYRIHWDGY EHHPADGYDG PQGGGYPAPK GARDIYSYDI KGVAQNIRLN

151 LTDNRSTGQR LADRFHNAGS MLTQGVGDGF KRATRYSPEL DRSGNAAEAF

201 NGTADIVKNI IGAAGEIVGA GDAVQGISEG SNIAVMHGLG LLSTENKMAR

251 INDLADMAQL KDYAAAAIRD WAVQNPNAAQ GIEAVSNIFM AAIPIKGIGA

301 VRGKYGLGGI TAHPIKRSQM GAIALPKGKS AVSDNFADAA YAKYPSPYHS

351 RNIRSNLEQR YGKENITSST VPPSNGKNVK LADQRHPKTG VPFDGKGFPN

401 FEKHVKYDTK LDIQELSGGG IPKAKPVSDA KPRWEVDRKL NKLTTREQVE

-continued

451 KNVQEIRNGN KNSNFSQHAQ LEREINKLKS ADEINFADGM GKFTDSMNDK

501 AFSRLVKSVK ENGFTNPVVE YVEINGKAYI VRGNNRVFAA EYLGRIHELK

551 FKKVDFPVPN TSWKNPTDVL NESGNVKRPR YRSK*

3) ORF46 as a truncated protein, consisting of the first 433 amino acids ('ORF46.1L'), constructed by designing PCR primers to amplify a partial sequence corresponding to aa 1-433.

A STOP codon was included in the 3'-end primer sequences.

ORF46-2L is expressed at a very low level to *E. coli*. Removal of its leader peptide (ORF46-2) does not solve this problem. The truncated ORF46.1L form (first 433 amino acids, which are well conserved between serogroups and species), however, is well-expressed and gives excellent results in ELISA test and in the bactericidal assay.

ORF46.1 has also been used as the basis of hybrid proteins. It has been fused with 287, 919, and ORF1. The hybrid proteins were generally insoluble, but gave some good ELISA and bactericidal results (against the homologous 2996 strain):

| Protein | ELISA | Bactericidal Ab |
|---|---|---|
| Orf1-Orf46.1-His | 850 | 256 |
| 919-Orf46.1-His | 12900 | 512 |
| 919-287-Orf46-His | n.d. | n.d. |
| Orf46.1-287His | 150 | 8192 |
| Orf46.1-919His | 2800 | 2048 |
| Orf46.1-287-919His | 3200 | 16384 |

For comparison, 'triple' hybrids of ORF46.1, 287 (either as a GST fusion, or in ΔG287 form) and 919 were constructed and tested against various strains (including the homologous 2996 strain) versus a simple mixture of the three antigens. FCA was used as adjuvant:

| | 2996 | BZ232 | MC58 | NGH38 | F6124 | BZ133 |
|---|---|---|---|---|---|---|
| Mixture | 8192 | 256 | 512 | 1024 | >2048 | >2048 |
| ORF46.1-287-919his | 16384 | 256 | 4096 | 8192 | 8192 | 8192 |
| ΔG287-919-ORF46.1his | 8192 | 64 | 4096 | 8192 | 8192 | 16384 |
| ΔG287-ORF46.1-919his | 4096 | 128 | 256 | 8192 | 512 | 1024 |

Again, the hybrids show equivalent or superior immunological activity.

Hybrids of two proteins (strain 2996) were compared to the individual proteins against various heterologous strains:

| | 1000 | MC58 | F6124 (MenA) |
|---|---|---|---|
| ORF46.1-His | <4 | 4096 | <4 |
| ORF1-His | 8 | 256 | 128 |
| ORF1-ORF46.1-His | 1024 | 512 | 1024 |

Again, the hybrid shows equivalent or superior immunological activity.

Example 9

Protein 961

The complete 961 protein from *N. meningitidis* (serogroup B, strain MC58) has the following sequence (SEQ ID NO:78):

```
  1 MSMKHFPAKV LTTAILATFC SGALAATSDD DVKKAATVAI
    VAAYNNGQEI

51 NGFKAGETIY DIGEDGTITQ KDATAADVEA DDFKGLGLKK
    VVTNLTKTVN

101 ENKQNVDAKV KAAESEIEKL TTKLADTDAA LADTDAALDE
    TTNALNKLGE

151 NITTFAEETK TNIVKIDEKL EAVADTVDKH AEAFNDIADS
    LDETNTKADE

201 AVKTANEAKQ TAEETKQNVD AKVKAAETAA GKAEAAAGTA
    NTAADKAEAV

251 AAKVTDIKAD IATNKADIAK NSARIDSLDK NVANLRKETR
    QGLAEQAALS

301 GLFQPYNVGR FNVTAAVGGY KSESAVAIGT GFRFTENFAA
    KAGVAVGTSS

351 GSSAAYHVGV NYEW*
```

The leader peptide is underlined.

Three approaches to 961 expression were used:
1) 961 using a GST fusion, following WO99/57280 ('GST961');
2) 961 with its own leader peptide but without any fusion partner ('961L'); and
3) 961 without its leader peptide and without any fusion partner ('961$^{untagged}$'), with the leader peptide omitted by designing the 5'-end PCR primer downstream from the predicted leader sequence.

All three forms of the protein were expressed. The GST-fusion protein could be purified and antibodies against it confirmed that 961 is surface exposed (FIG. 4). The protein was used to immunise mice, and the resulting sera gave excellent results in the bactericidal assay. 961L could also be purified and gave very high ELISA titres.

Protein 961 appears to be phase variable. Furthermore, it is not found in all strains of *N. meningitidis*.

Example 10

Protein 287

Protein 287 from *N. meningitidis* (serogroup B, strain 2996) has the following sequence (SEQ ID NO:79):

```
  1 MFERSVIAMA CIFALSACGG GGGGSPDVKS ADTLSKPAAP
    VVAEKETEVK

51 EDAPQAGSQG QGAPSTQGSQ DMAAVSAENT GNGGAATTDK
    PKNEDEGPQN

101 DMPQNSAESA NQTGNNQPAD SSDSAPASNP APANGGSNFG
    RVDLANGVLI

151 DGPSQNITLT HCKGDSCNGD NLLDEEAPSK SEFENLNESE
    RIEKYKKDGK

201 SDKFTNLVAT AVQANGTNKY VIIYKDKSAS SSSARFRRSA
    RSRRSLPAEM

251 PLIPVNQADT LIVDGEAVSL TGHSGNIFAP EGNYRYLTYG
    AEKLPGGSYA

301 LRVQGEPAKG EMLAGTAVYN GEVLHFHTEN GRPYPTRGRF
    AAKVDFGSKS

351 VDGIIDSGDD LHMGTQKFKA AIDGNGFKGT WTENGGGDVS
    GRFYGPAGEE

401 VAGKYSYRPT DAEKGGFGVF AGKKEQD*
```

The leader peptide is shown underlined.

Figure 5:
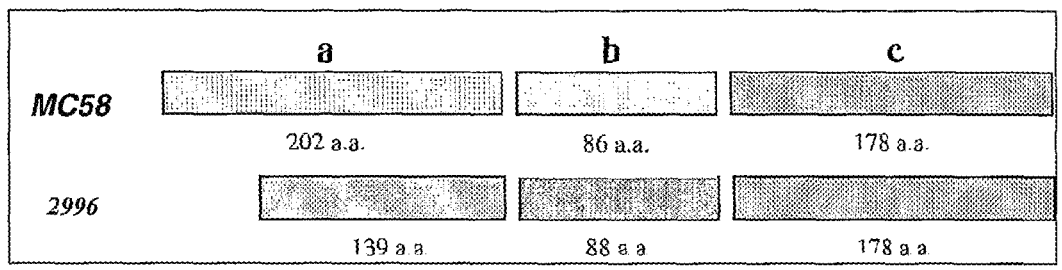
FIG. 5 shows domains of protein 287.

The sequences of 287 from other strains can be found in FIGS. 5 and 15 of WO00/66741.

Example 9 of WO99/57280 discloses the expression of 287 as a GST-fusion in *E. coli*.

A number of further approaches to expressing 287 in *E. coli* have been used, including:
1) 287 as a His-tagged fusion ('287-His');
2) 287 with its own leader peptide but without any fusion partner ('287L');
3) 287 with the ORF4 leader peptide and without any fusion partner ('287LOrf4'); and
4) 287 without its leader peptide and without any fusion partner ('287$^{untagged}$') (SEQ ID NO:80):

```
  1 CGGGGGGSPD VKSADTLSKP AAPVVAEKET EVKEDAPQAG
    SQGQGAPSTQ

51 GSQDMAAVSA ENTGNGGAAT TDKPKNEDEG PQNDMPQNSA
    ESANQTGNNQ

101 PADSSDSAPA SNPAPANGGS NFGRVDLANG VLIDGPSQNI
    TLTHCKGDSC

151 NGDNLLDEEA PSKSEFENLN ESERIEKYKK DGKSDKFTNL
    VATAVQANGT

201 NKYVIIYKDK SASSSSARFR RSARSRRSLP AEMPLIPVNQ
    ADTLIVDGEA

251 VSLTGHSGNI FAPEGNYRYL TYGAEKLPGG SYALRVQGEP
    AKGEMLAGTA

301 VYNGEVLHFH TENGRPYPTR GRFAAKVDFG SKSVDGIIDS
    GDDLHMGTQK

351 FKAAIDGNGF KGTWTENGGG DVSGRFYGPA GEEVAGKYSY
    RPTDAEKGGF

401 GVFAGKKEQD *
```

All these proteins could be expressed and purified.

'287L' and '287LOrf4' were confirmed as lipoproteins.

Figure 2:
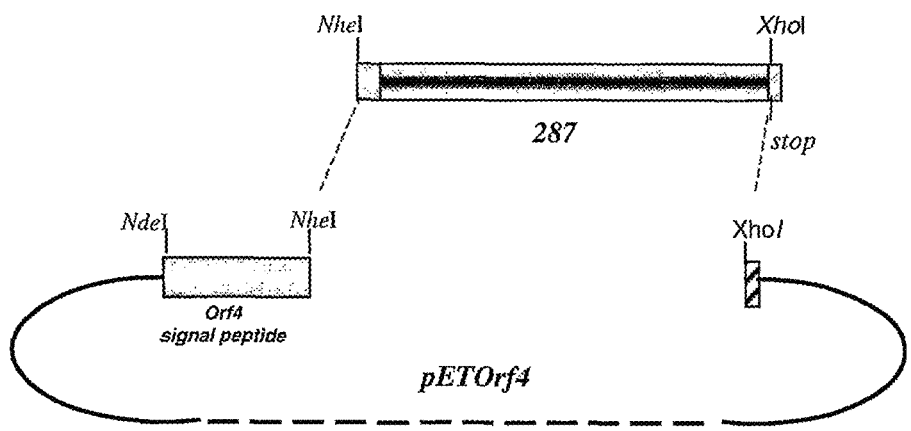

As shown in FIG. 2, '287LOrf4' was constructed by digesting 919LOrf4 with NheI and XhoI. The entire ORF4 leader peptide was restored by the addition of a DNA sequence coding for the missing amino acids, as a tail, in the 5'-end primer (287LOrf4 for), fused to 287 coding sequence. The 287 gene coding for the mature protein was amplified using the oligonucleotides 287LOrf4 For and Rev (including the NheI and XhoI sites, respectively), digested with NheI and XhoI and ligated to the purified pETOrf4 fragment.

Example 11

Further Non-Fusion Proteins with/without Native Leader Peptides

A similar approach was adopted for *E. coli* expression of further proteins from WO99/24578, WO99/36544 and WO99/57280.

The following were expressed without a fusion partner: 008, 105, 117-1, 121-1, 122-1, 128-1, 148, 216, 243, 308, 593, 652, 726, 982, and Orf143-1. Protein 117-1 was confirmed as surface-exposed by FACS and gave high ELISA titres.

The following were expressed with the native leader peptide but without a fusion partner: 111, 149, 206, 225-1, 235, 247-1, 274, 283, 286, 292, 401, 406, 502-1, 503, 519-1, 525-1, 552, 556, 557, 570, 576-1, 580, 583, 664, 759, 907, 913, 920-1, 926, 936-1, 953, 961, 983, 989, Orf4, Orf7-1, Orf9-1, Orf23, Orf25, Orf37, Orf38, Orf40, Orf40.1, Orf40.2, Orf72-1, Orf76-1, Orf85-2, Orf91, Orf97-1, Orf119, Orf143.1. These proteins are given the suffix 'L'.

His-tagged protein 760 was expressed with and without its leader peptide. The deletion of the signal peptide greatly increased expression levels. The protein could be purified most easily using 2M urea for solubilisation.

His-tagged protein 264 was well-expressed using its own signal peptide, and the 30 kDa protein gave positive Western blot results.

All proteins were successfully expressed.

The localisation of 593, 121-1, 128-1, 593, 726, and 982 in the cytoplasm was confirmed.

The localisation of 920-1L, 953L, ORF9-1L, ORF85-2L, ORF97-1L, 570L, 580L and 664L in the periplasm was confirmed.

The localisation of ORF40L in the outer membrane, and 008 and 519-1L in the inner membrane was confirmed. ORF25L, ORF4L, 406L, 576-1L were all confirmed as being localised in the membrane.

Protein 206 was found not to be a lipoprotein.

ORF25 and ORF40 expressed with their native leader peptides but without fusion partners, and protein 593 expressed without its native leader peptide and without a fusion partner, raised good anti-bactericidal sera. Surprisingly, the forms of ORF25 and ORF40 expressed without fusion partners and using their own leader peptides (i.e. 'ORF25L' and 'ORF40L') give better results in the bactericidal assay than the fusion proteins.

Proteins 920L and 953L were subjected to N-terminal sequencing, giving HRVWVETAH (SEQ ID NO:81) and ATYKVDEYHANARFAF (SEQ ID NO:82), respectively. This sequencing confirms that the predicted leader peptides were cleaved and, when combined with the periplasmic location, confirms that the proteins are correctly processed and localised by *E. coli* when expressed from their native leader peptides.

The N-terminal sequence of protein 519.1L localised in the inner membrane was MEFFIILLA (SEQ ID NO:83), indicating that the leader sequence is not cleaved. It may therefore function as both an uncleaved leader sequence and a transmembrane anchor in a manner similar to the leader peptide of PBP1 from *N. gonorrhoeae* [Ropp & Nicholas (1997) *J. Bact.* 179:2783-2787.]. Indeed the N-terminal region exhibits strong hydrophobic character and is predicted by the Tmpred. program to be transmembrane.

Example 12

Lipoproteins

The incorporation of palmitate in recombinant lipoproteins was demonstrated by the method of Kraft et. al. [*J. Bact.* (1998) 180:3441-3447.]. Single colonies harbouring the plasmid of interest were grown overnight at 37° C. in 20 ml of LB/Amp (100 μg/ml) liquid culture. The culture was diluted to an $OD_{550}$ of 0.1 in 5.0 ml of fresh medium LB/Amp medium containing 5 μC/ml [$^3$H] palmitate (Amersham). When the $OD_{550}$ of the culture reached 0.4-0.8, recombinant lipoprotein was induced for 1 hour with IPTG (final concentration 1.0 mM). Bacteria were harvested by centrifugation in a bench top centrifuge at 2700 g for 15 mM and washed twice with 1.0 ml cold PBS. Cells were resuspended in 120 μl of 20 mM Tris-HCl (pH 8.0), 1 mM EDTA, 1.0% w/v SDS and lysed by boiling for 10 mM After centrifugation at 13000 g for 10 min the supernatant was collected and proteins precipitated by the addition of 1.2 ml cold acetone and left for 1 hour at −20° C. Protein was pelleted by centrifugation at 13000 g for 10 min and resuspended in 20-50 μl (calculated to standardise loading with respect to the final O.D of the culture) of 1.0% w/v SDS. An aliquot of 15 μl was boiled with 5 μl of SDS-PAGE sample buffer and analysed by SDS-PAGE. After electrophoresis gels were fixed for 1 hour in 10% v/v acetic acid and soaked for 30 minutes in Amplify solution (Amersham). The gel was vacuum-dried under heat and exposed to Hyperfilm (Kodak) overnight −80° C.

Incorporation of the [$^3$H] palmitate label, confirming lipidation, was found for the following proteins: Orf4L, Orf25L, 287L, 287LOrf4, 406.L, 576L, 926L, 919L and 919LOrf4.

Example 13

Domains in 287

Based on homology of different regions of 287 to proteins that belong to different functional classes, it was split into three 'domains', as shown in FIG. 5. The second domain shows homology to IgA proteases, and the third domain shows homology to transferrin-binding proteins.

Each of the three 'domains' shows a different degree of sequence conservation between *N. meningitidis* strains—domain C is 98% identical, domain A is 83% identical, whilst domain B is only 71% identical. Note that protein 287 in strain MC58 is 61 amino acids longer than that of strain 2996. An alignment of the two sequences is shown in FIG. 7, and alignments for various strains are disclosed in WO00/66741 (see FIGS. 5 and 15 therein).

The three domains were expressed individually as C-terminal His-tagged proteins. This was done for the MC58 and 2996 strains, using the following constructs:
287a-MC58 (aa 1-202), 287b-MC58 (aa 203-288), 287c-MC58 (aa 311-488).
287a-2996 (aa 1-139), 287b-2996 (aa 140-225), 287c-2996 (aa 250-427).

To make these constructs, the stop codon sequence was omitted in the 3'-end primer sequence. The 5' primers included the NheI restriction site, and the 3' primers included a XhoI as a tail, in order to direct the cloning of each amplified fragment into the expression vector pET21b+ using NdeI-XhoI, NheI-XhoI or NdeI-HindIII restriction sites.

All six constructs could be expressed, but 287b-MC8 required denaturation and refolding for solubilisation.

Deletion of domain A is described below ('Δ4 287-His').

Immunological data (serum bactericidal assay) were also obtained using the various domains from strain 2996, against the homologous and heterologous MenB strains, as well as MenA (F6124 strain) and MenC (BZ133 strain):

|  | 2996 | BZ232 | MC58 | NGH38 | 394/98 | MenA | MenC |
|---|---|---|---|---|---|---|---|
| 287-His | 32000 | 16 | 4096 | 4096 | 512 | 8000 | 16000 |
| 287(B)-His | 256 | — | — | — | — | 16 | — |

-continued

|  | 2996 | BZ232 | MC58 | NGH38 | 394/98 | MenA | MenC |
|---|---|---|---|---|---|---|---|
| 287 (C)-His | 256 | — | 32 | 512 | 32 | 2048 | >2048 |
| 287 (B-C)-His | 64000 | 128 | 4096 | 64000 | 1024 | 64000 | 32000 |

Using the domains of strain MC58, the following results were obtained:

|  | MC58 | 2996 | BZ232 | NGH38 | 394/98 | MenA | MenC |
|---|---|---|---|---|---|---|---|
| 287-His | 4096 | 32000 | 16 | 4096 | 512 | 8000 | 16000 |
| 287 (B)-His | 128 | 128 | — | — | — | — | 128 |
| 287 (C)-His | — | 16 | — | 1024 | — | 512 | — |
| 287 (B-C)-His | 16000 | 64000 | 128 | 64000 | 512 | 64000 | >8000 |

Example 14

Deletions in 287

Figure 6:
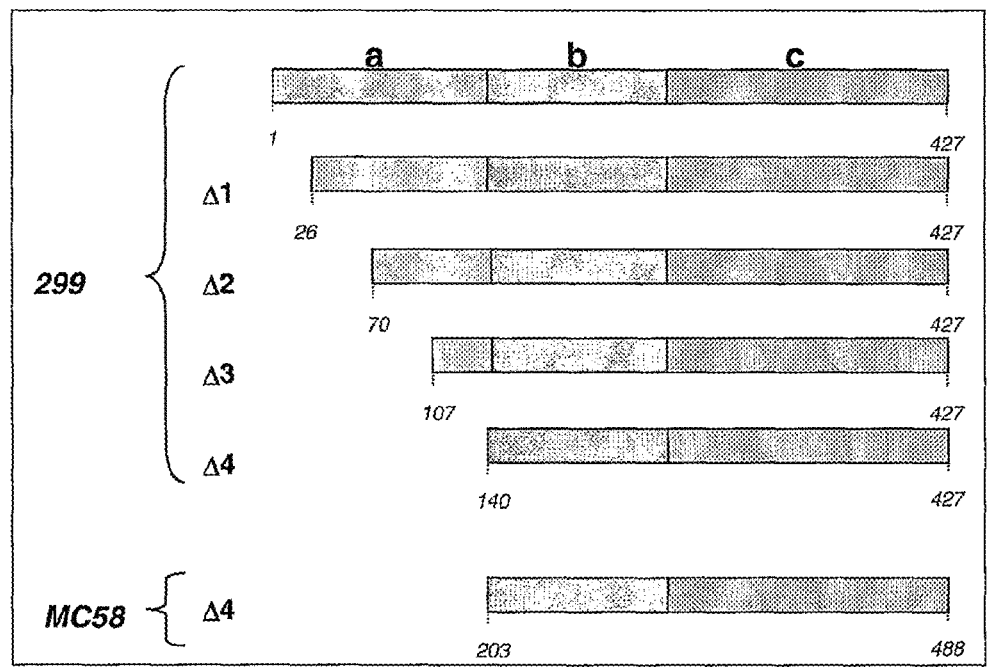
Figure 9:
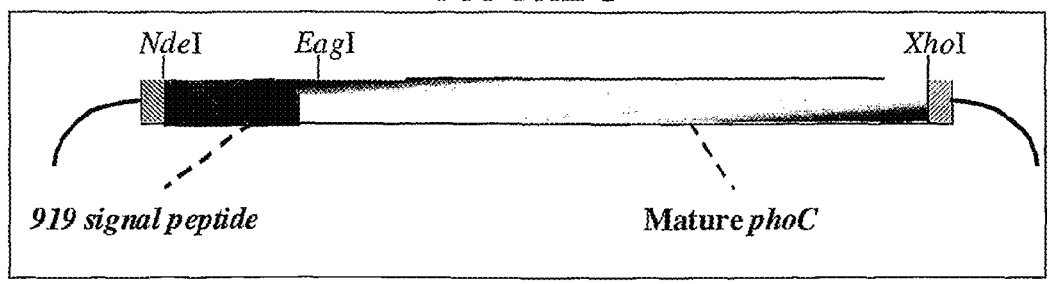
FIG. 9 shows the PhoC reporter gene driven by the 919 leader peptide.
Figure 8:
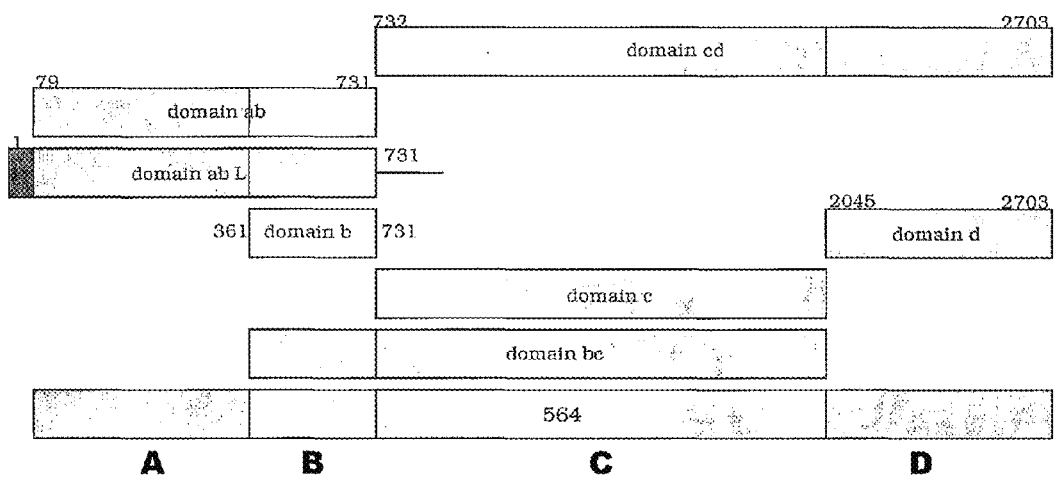
FIG. 8 shows domains of protein 564.

As well as expressing individual domains, 287 was also expressed (as a C-terminal His-tagged protein) by making progressive deletions within the first domain. These Four deletion mutants of protein 287 from strain 2996 were used (FIG. 6):

1) '287-His', consisting of amino acids 18-427 (i.e. leader peptide deleted);
2) 'Δ1287-His', consisting of amino acids 26-427;
3) 'Δ2 287-His', consisting of amino acids 70-427;
4) 'Δ3 287-His', consisting of amino acids 107-427; and
5) 'Δ4 287-His', consisting of amino acids 140-427 (=287-bc).

The 'Δ4' protein was also made for strain MC58 ('Δ4 287MC58-His'; aa 203-488).

The constructs were made in the same way as 287a/b/c, as described above.

All six constructs could be expressed and protein could be purified. Expression of 287-His was, however, quite poor.

Expression was also high when the C-terminal His-tags were omitted.

Immunological data (serum bactericidal assay) were also obtained using the deletion mutants, against the homologous (2996) and heterologous MenB strains, as well as MenA (F6124 strain) and MenC (BZ133 strain):

|  | 2996 | BZ232 | MC58 | NGH38 | 394/98 | MenA | MenC |
|---|---|---|---|---|---|---|---|
| 287-his | 32000 | 16 | 4096 | 4096 | 512 | 8000 | 16000 |
| Δ1 287-His | 16000 | 128 | 4096 | 4096 | 1024 | 8000 | 16000 |
| Δ2 287-His | 16000 | 128 | 4096 | >2048 | 512 | 16000 | >8000 |
| Δ3 287-His | 16000 | 128 | 4096 | >2048 | 512 | 16000 | >8000 |
| Δ4 287-His | 64000 | 128 | 4096 | 64000 | 1024 | 64000 | 32000 |

The same high activity for the Δ4 deletion was seen using the sequence from strain MC58.

As well as showing superior expression characteristics, therefore, the mutants are immunologically equivalent or superior.

Example 15

Poly-Glycine Deletions

The 'Δ1 287-His' construct of the previous example differs from 287-His and from '287$^{untagged}$' only by a short N-terminal deletion (GGGGGGS (SEQ ID NO:631)). Using an expression vector which replaces the deleted serine with a codon present in the Nhe cloning site, however, this amounts to a deletion only of $(Gly)_6$ (SEQ ID NO:632). Thus, the deletion of this $(Gly)_6$ sequence (SEQ ID NO:632) has been shown to have a dramatic effect on protein expression.

The protein lacking the N-terminal amino acids up to GGGGGG (SEQ ID NO:632) is called 'ΔG 287'. In strain MC58, its sequence (leader peptide underlined) is (SEQ ID NO:84):

```
                                    ➡ ΔG287
  1 MFKRSVIAMA CIFALSACGG GGGGSPDVKS ADTLSKPAAP
    VVSEKETEAK

51 EDAPQAGSQG QGAPSAQGSQ DMAAVSEENT GNGGAVTADN
    PKNEDEVAQN

101 DMPQNAAGTD SSTPNHTPDP NMLAGNMENQ ATDAGESSQP
    ANQPDMANAA

151 DGMQGDDPSA GGQNAGNTAA QGANQAGNNQ AAGSSDPIPA
    SNPAPANGGS

201 NFGRVDLANG VLIDGPSQNI TLTHCKGDSC SGNNFLDEEV
    QLKSEFEKLS

251 DADKISNYKK DGKNDKFVGL VADSVQMKGI NQYIIFYKPK
    PTSFARFRRS

301 ARSRRSLPAE MPLIPVNQAD TLIVDGEAVS LTGHSGNIFA
    PEGNYRYLTY

351 GAEKLPGGSY ALRVQGEPAK GEMLAGAAVY NGEVLHFHTE
    NGRPYPTRGR

401 FAAKVDFGSK SVDGIIDSGD DLHMGTQKFK AAIDGNGFKG
    TWTENGSGDV

451 SGKFYGPAGE EVAGKYSYRP TDAEKGGFGV FAGKKEQD*
```

ΔG287, with or without His-tag ('ΔG287-His' and 'ΔG287K', respectively), are expressed at very good levels in comparison with the '287-His' or '287$^{tagged}$'.

On the basis of gene variability data, variants of ΔG287-His were expressed in *E. coli* from a number of MenB strains, in particular from strains 2996, MC58, 1000, and BZ232. The results were also good.

It was hypothesised that poly-Gly deletion might be a general strategy to improve expression. Other MenB lipoproteins containing similar (Gly)$_n$ motifs (near the N-terminus, downstream of a cysteine) were therefore identified, namely Tbp2 (NMB0460) (SEQ ID NO:85), 741 (NMB 1870) (SEQ ID NO:86) and 983 (NMB 1969) (SEQ ID NO:87):

```
TBP2                           → ΔGTbp2
   1 MNNPLVNQAA MVLPVFLLSA CLGGGGSFDL DSVDTEAPRP
     APKYQDVFSE

51 KPQAQKDQGG YGFAMRLKRR NWYPQAKEDE VKLDESDWEA
     TGLPDEPKEL

101 PKRQKSVIEK VETDSDNNIY SSPYLKPSNH QNGNTGNGIN
     QPKNQAKDYE

151 NFKYVYSGWF YKHAKREFNL KVEPKSAKNG DDGYIFYHGK
     EPSRQLPASG

201 KITYKGVWHF ATDTKKGQKF REIIQPSKSQ GDRYSGFSGD
     DGEEYSNKNK

251 STLTDGQEGY GFTSNLEVDF HNKKLTGKLI RNNANTDNNQ
     ATTTQYYSLE

301 AQVTGNRFNG KATATDKPQQ NSETKEHPFV SDSSSLSGGF
     FGPQGEELGF

351 RFLSDDQKVA VVGSAKTKDK PANGNTAAAS GGTDAAASNG
     AAGTSSENGK

401 LTTVLDAVEL KLGDKEVQKL DNFSNAAQLV VDGIMIPLLP
     EASESGNNQA

451 NQGTNGGTAF TRKFDHTPES DKKDAQAGTQ TNGAQTASNT
     AGDTNGKTKT

501 YEVEVCCSNL NYLKYGMLTR KNSKSAMQAG ESSSQADAKT
     EQVEQSMFLQ

551 GERTDEKEIP SEQNIVYRGS WYGYIANDKS TSWSGNASNA
     TSGNRAEFTV

601 NFADKKITGT LTADNRQEAT FTIDGNIKDN GFEGTAKTAE
     SGFDLDQSNT

651 TRTPKAYITD AKVQGGFYGP KAEELGGWFA YPGDKQTKNA
     TNASGNSSAT

701 VVFGAKRQQP VR*

741                            → ΔG741
   1 VNRTAFCCLS LTTALILTAC SSGGGGVAAD IGAGLADALT
     APLDHKDKGL

51 QSLTDQSVR KNEKLKLAAQ GAEKTYGNGD SLNTGKLKND
     KVSRFDFIRQ

101 IEVDGQLITL ESGEFQVYKQ SHSALTAFQT EQIQDSEHSG
     KMVAKRQFRI

151 GDIAGEHTSF DKLPEGGRAT YRGTAFGSDD AGGKLTYTID
     FAAKQGNGKI

201 EHLKSPELNV DLAAADIKPD GKRHAVISGS VLYNQAEKGS
     YSLGIFGGKA

251 QEVAGSAEVK TVNGIRHIGL AAKQ*

983                            → ΔG983
   1 MRTTPTFPTK TFKPTAMALA VATTLSACLG GGGGGTSAPD
     FNAGGTGIGS

51 NSRATTAKSA AVSYAGIKNE MCKDRSMLCA GRDDVAVTDR
     DAKINAPPPN

101 LHTGDFPNPN DAYKNLINLK PAIEAGYTGR GVEVGIVDTG
     ESVGSISFPE

151 LYGRKEHGYN ENYKNYTAYM RKEAPEDGGG KDIEASFDDE
     AVIETEAKPT

201 DIRHVKEIGH IDLVSHIIGG RSVDGRPAGG IAPDATLHIM
     NTNDETKNEM

251 MVAAIRNAWV KLGERGVRIV NNSFGTTSRA GTADLFQIAN
     SEEQYRQALL

301 DYSGGDKTDE GIRLMQQSDY GNLSYHIRNK NMLFIFSTGN
     DAQAQPNTYA

351 LLPFYEKDAQ KGIITVAGVD RSGEKFKREM YGEPGTEPLE
     YGSNHCGITA

401 MWCLSAPYEA SVRFTRTNPI QIAGTSFSAP IVTGTAALLL
     QKYPWMSNDN

451 LRTTLLTTAQ DIGAVGVDSK FGWGLLDAGK AMNGPASFPF
     GDFTADTKGT

501 SDIAYSFRND ISGTGGLIKK GGSQLQLHGN NTYTGKTIIE
     GGSLVLYGNN

551 KSDMRVETKG ALIYNGAASG GSLNSDGIVY LADTDQSGAN
     ETVHIKGSLQ

601 LDGKGTLYTR LGKLLKVDGT AIIGGKLYMS ARGKGAGYLN
     STGRRVPFLS

651 AAKIGQDYSF FTNIETDGGL LASLDSVEKT AGSEGDTLSY
     YVRRGNAART

701 ASAAAHSAPA GLKHAVEQGG SNLENLMVEL DASESSATPE
     TVETAAADRT

751 DMPGIRPYGA TFRAAAAVQH ANAADGVRIF NSLAATVYAD
     STAAHADMQG

801 RRLKAVSDGL DHNGTGLRVI AQTQQDGGTW EQGGVEGKMR
     GSTQTVGIAA

851 KTGENTTAAA TLGMGRSTWS ENSANAKTDS ISLFAGIRHD
     AGDIGYLKGL

901 FSYGRYKNSI SRSTGADEHA EGSVNGTLMQ LGALGGVNVP
     FAATGDLTVE

951 GGLRYDLLKQ DAFAEKGSAL GWSGNSLTEG TLVGLAGLKL
     SQPLSDKAVL

1001 FATAGVERDL NGRDYTVTGG FTGATAATGK TGARNMPHTR
     LVAGLGADVE

1051 FGNGWNGLAR YSYAGSKQYG NHSGRVGVGY RF*
```

Tbp2 and 741 genes were from strain MC58; 983 and 287 genes were from strain 2996. These were cloned in pET vector and expressed in *E. coli* without the sequence coding for their leader peptides or as "ΔG forms", both fused to a C-terminal His-tag. In each case, the same effect was seen—expression was good in the clones carrying the deletion of the poly-glycine stretch, and poor or absent if the glycines were present in the expressed protein:

| ORF | Express. | Purification | Bact. Activity |
|---|---|---|---|
| 287-His(2996) | +/− | + | + |
| '287$^{untagged}$'(2996) | +/− | nd | nd |
| ΔG287-His(2996) | + | + | + |
| ΔG287K(2996) | + | + | + |
| ΔG287-His(MC58) | + | + | + |
| ΔG287-His(1000) | + | + | + |
| ΔG287-His(BZ232) | + | + | + |
| Tbp2-His(MC58) | +/− | nd | nd |

| ORF | Express. | Purification | Bact. Activity |
|---|---|---|---|
| ΔGTbp2-His(MC58) | + | + | |
| 741-His(MC58) | +/− | nd | nd |
| ΔG741-His(MC58) | + | + | |
| 983-His (2996) | | | |
| ΔG983-His (2996) | + | + | |

SDS-PAGE of the proteins is shown in FIG. 13.

ΔG287 and Hybrids

ΔG287 proteins were made and purified for strains MC58, 1000 and BZ232. Each of these gave high ELISA titres and also serum bactericidal titres of >8192. ΔG287K, expressed from pET-24b, gave excellent titres in ELISA and the serum bactericidal assay. ΔG287-ORF46.1K may also be expressed in pET-24b.

ΔG287 was also fused directly in-frame upstream of 919 (SEQ ID NOS:88 and 89), 953 (SEQ ID NOS:90 and 91), 961 (SEQ ID NOS:92 and 93) (sequences shown below) and ORF46.1:

```
ΔG287-919
   1 ATGGCTAGCC CCGATGTTAA ATCGGCGGAC ACGCTGTCAA
     AACCGGCCGC

51 TCCTGTTGTT GCTGAAAAAG AGACAGAGGT AAAAGAAGAT
     GCGCCACAGG

101 CAGGTTCTCA AGGACAGGGC GCGCCATCCA CACAAGGCAG
     CCAAGATATG

151 GCGGCAGTTT CGGCAGAAAA TACAGGCAAT GGCGGTGCGG
     CAACAACGGA

201 CAAACCCAAA AATGAAGACG AGGGACCGCA AAATGATATG
     CCGCAAAATT

251 CCGCCGAATC CGCAAATCAA ACAGGGAACA ACCAACCCGC
     CGATTCTTCA

301 GATTCCGCCC CCGCGTCAAA CCCTGCACCT GCGAATGGCG
     GTAGCAATTT

351 TGGAAGGGTT GATTTGGCTA ATGGCGTTTT GATTGATGGG
     CCGTCGCAAA

401 ATATAACGTT GACCCACTGT AAAGGCGATT CTTGTAATGG
     TGATAATTTA

451 TTGGATGAAG AAGCACCGTC AAAATCAGAA TTTGAAAATT
     TAAATGAGTC

501 TGAACGAATT GAGAAATATA AGAAAGATGG GAAAAGCGAT
     AAATTTACTA

551 ATTTGGTTGC GACAGCAGTT CAAGCTAATG GAACTAACAA
     ATATGTCATC

601 ATTTATAAAG ACAAGTCCGC TTCATCTTCA TCTGCGCGAT
     TCAGGCGTTC

651 TGCACGGTCG AGGAGGTCGC TTCCTGCCGA GATGCCGCTA
     ATCCCCGTCA

701 ATCAGGCGGA TACGCTGATT GTCGATGGGG AAGCGGTCAG
     CCTGACGGGG

751 CATTCCGGCA ATATCTTCGC GCCCGAAGGG AATTACCGGT
     ATCTGACTTA

801 CGGGGCGGAA AAATTGCCCG GCGGATCGTA TGCCCTCCGT
     GTGCAAGGCG

851 AACCGGCAAA AGGCGAAATG CTTGCTGGCA CGGCCGTGTA
     CAACGGCGAA

901 GTGCTGCATT TTCATACGGA AAACGGCCGT CCGTACCCGA
     CTAGAGGCAG

951 GTTTGCCGCA AAAGTCGATT TCGGCAGCAA ATCTGTGGAC
     GGCATTATCG

1001 ACAGCGGCGA TGATTTGCAT ATGGGTACGC AAAAATTCAA
     AGCCGCCATC

1051 GATGGAAACG GCTTTAAGGG GACTTGGACG GAAAATGGCG
     GCGGGGATGT

1101 TTCCGGAAGG TTTTACGGCC CGGCCGGCGA GGAAGTGGCG
     GGAAAATACA

1151 GCTATCGCCC GACAGATGCG GAAAAGGGCG GATTCGGCGT
     GTTTGCCGGC

1201 AAAAAGAGC AGGATGGATC CGGAGGAGGA GGATGCCAAA
     GCAAGAGCAT

1251 CCAAACCTTT CCGCAACCCG ACACATCCGT CATCAACGGC
     CCGGACCGGC

1301 CGGTCGGCAT CCCCGACCCC GCCGGAACGA CGGTCGGCGG
     CGGCGGGGCC

1351 GTCTATACCG TTGTACCGCA CCTGTCCCTG CCCCACTGGG
     CGGCGCAGGA

1401 TTTCGCCAAA AGCCTGCAAT CCTTCCGCCT CGGCTGCGCC
     AATTTGAAAA

1451 ACCGCCAAGG CTGGCAGGAT GTGTGCGCCC AAGCCTTTCA
     ACCCCCGTC

1501 CATTCCTTTC AGGCAAAACA GTTTTTTGAA CGCTATTTCA
     CGCCGTGGCA

1551 GGTTGCAGGC AACGGAAGCC TTGCCGGTAC GGTTACCGGC
     TATTACGAGC

1601 CGGTGCTGAA GGGCGACGAC AGGCGGACGG CACAAGCCCG
     CTTCCCGATT

1651 TACGGTATTC CCGACGATTT TATCTCCGTC CCCCTGCCTG
     CCGGTTTGCG

1701 GAGCGGAAAA GCCCTTGTCC GCATCAGGCA GACGGGAAAA
     AACAGCGGCA

1751 CAATCGACAA TACCGGCGGC ACACATACCG CCGACCTCTC
     CCGATTCCCC

1801 ATCACCGCGC GCACAACGGC AATCAAAGGC AGGTTTGAAG
     GAAGCCGCTT

1851 CCTCCCCTAC CACACGCGCA ACCAAATCAA CGGCGGCGCG
     CTTGACGGCA

1901 AAGCCCCGAT ACTCGGTTAC GCCGAAGACC CCGTCGAACT
     TTTTTTTATG

1951 CACATCCAAG GCTCGGGCCG TCTGAAAACC CCGTCCGGCA
     AATACATCCG

2001 CATCGGCTAT GCCGACAAAA ACGAACATCC CTACGTTTCC
     ATCGGACGCT

2051 ATATGGCGGA CAAAGGCTAC CTCAAGCTCG GGCAGACCTC
     GATGCAGGGC

2101 ATCAAAGCCT ATATGCGGCA AAATCCGCAA CGCCTCGCCG
     AAGTTTTGGG

2151 TCAAAACCCC AGCTATATCT TTTTCCGCGA GCTTGCCGGA
     AGCAGCAATG
```

```
2201 ACGGTCCCGT CGGCGCACTG GGCACGCCGT TGATGGGGGA
     ATATGCCGGC

2251 GCAGTCGACC GGCACTACAT TACCTTGGGC GCGCCCTTAT
     TTGTCGCCAC

2301 CGCCCATCCG GTTACCCGCA AAGCCCTCAA CCGCCTGATT
     ATGGCGCAGG

2351 ATACCGGCAG CGCGATTAAA GGCGCGGTGC GCGTGGATTA
     TTTTTGGGGA

2401 TACGGCGACG AAGCCGGCGA ACTTGCCGGC AAACAGAAAA
     CCACGGGTTA

2451 CGTCTGGCAG CTCCTACCCA ACGGTATGAA GCCCGAATAC
     CGCCCGTAAC

2501 TCGAG

1 MASPDVKSAD TLSKPAAPVV AEKETEVKED APQAGSQGQG
     APSTQGSQDM

51 AAVSAENTGN GGAATTDKPK NEDEGPQNDM PQNSAESANQ
     TGNNQPADSS

101 DSAPASNPAP ANGGSNFGRV DLANGVLIDG PSQNITLTHC
     KGDSCNGDNL

151 LDEEAPSKSE FENLNESERI EKYKKDGKSD KFTNLVATAV
     QANGTNKYVI

201 IYKDKSASSS SARFRRSARS RRSLPAEMPL IPVNQADTLI
     VDGEAVSLTG

251 HSGNIFAPEG NYRYLTYGAE KLPGGSYALR VQGEPAKGEM
     LAGTAVYNGE

301 VLHFHTENGR PYPTRGRFAA KVDFGSKSVD GIIDSGDDLH
     MGTQKFKAAI

351 DGNGFKGTWT ENGGGDVSGR FYGPAGEEVA GKYSYRPTDA
     EKGGFGVFAG

401 KKEQDGSGGG GCQSKSIQTF PQPDTSVING PDRPVGIPDP
     AGTTVGGGGA

451 VYTVVPHLSL PHWAAQDFAK SLQSFRLGCA NLKNRQGWQD
     VCAQAFQTPV

501 HSFQAKQFFE RYFTPWQVAG NGSLAGTVTG YYEPVLKGDD
     RRTAQARFPI

551 YGIPDDFISV PLPAGLRSGK ALVRIRQTGK NSGTIDNTGG
     THTADLSRFP

601 ITARTTAIKG RFEGSRFLPY HTRNQINGGA LDGKAPILGY
     AEDPVELFFM

651 HIQGSGRLKT PSGKYIRIGY ADKNEHPYVS IGRYMADKGY
     LKLGQTSMQG

701 IKAYMRQNPQ RLAEVLGQNP SYIFFRELAG SSNDGPVGAL
     GTPLMGEYAG

751 AVDRHYITLG APLFVATAHP VTRKALNRLI MAQDTGSAIK
     GAVRVDYFWG

801 YGDEAGELAG KQKTTGYVWQ LLPNGMKPEY RP*

ΔG287-953
   1 ATGGCTAGCC CCGATGTTAA ATCGGCGGAC ACGCTGTCAA
     AACCGGCCGC

51 TCCTGTTGTT GCTGAAAAAG AGACAGAGGT AAAAGAAGAT
     GCGCCACAGG

101 CAGGTTCTCA AGGACAGGGC GCGCCATCCA CACAAGGCAG
     CCAAGATATG

151 GCGGCAGTTT CGGCAGAAAA TACAGGCAAT GGCGGTGCGG
     CAACAACGGA

201 CAAACCCAAA AATGAAGACG AGGGACCGCA AAATGATATG
     CCGCAAAATT

251 CCGCCGAATC CGCAAATCAA ACAGGGAACA ACCAACCCGC
     CGATTCTTCA

301 GATTCCGCCC CCGCGTCAAA CCCTGCACCT GCGAATGGCG
     GTAGCAATTT

351 TGGAAGGGTT GATTTGGCTA ATGGCGTTTT GATTGATGGG
     CCGTCGCAAA

401 ATATAACGTT GACCCACTGT AAAGGCGATT CTTGTAATGG
     TGATAATTTA

451 TTGGATGAAG AAGCACCGTC AAAATCAGAA TTTGAAAATT
     TAAATGAGTC

501 TGAACGAATT GAGAAATATA AGAAAGATGG GAAAAGCGAT
     AAATTTACTA

551 ATTTGGTTGC GACAGCAGTT CAAGCTAATG GAACTAACAA
     ATATGTCATC

601 ATTTATAAAG ACAAGTCCGC TTCATCTTCA TCTGCGCGAT
     TCAGGCGTTC

651 TGCACGGTCG AGGAGGTCGC TTCCTGCCGA GATGCCGCTA
     ATCCCCGTCA

701 ATCAGGCGGA TACGCTGATT GTCGATGGGG AAGCGGTCAG
     CCTGACGGGG

751 CATTCCGGCA ATATCTTCGC GCCCGAAGGG AATTACCGGT
     ATCTGACTTA

801 CGGGGCGGAA AAATTGCCCG GCGGATCGTA TGCCCTCCGT
     GTGCAAGGCG

851 AACCGGCAAA AGGCGAAATG CTTGCTGGCA CGGCCGTGTA
     CAACGGCGAA

901 GTGCTGCATT TCATACGGA AAACGGCCGT CCGTACCCGA
     CTAGAGGCAG

951 GTTTGCCGCA AAAGTCGATT TCGGCAGCAA ATCTGTGGAC
     GGCATTATCG

1001 ACAGCGGCGA TGATTTGCAT ATGGGTACGC AAAAATTCAA
     AGCCGCCATC

1051 GATGGAAACG GCTTTAAGGG ACTTGGACG GAAAATGGCG
     GCGGGGATGT

1101 TTCCGGAAGG TTTTACGGCC CGGCCGGCGA GGAAGTGGCG
     GGAAAATACA

1151 GCTATCGCCC GACAGATGCG GAAAAGGGCG GATTCGGCGT
     GTTTGCCGGC

1201 AAAAAAGAGC AGGATGGATC CGGAGGAGGA GGAGCCACCT
     ACAAAGTGGA

1251 CGAATATCAC GCCAACGCCC GTTTCGCCAT CGACCATTTC
     AACACCAGCA

1301 CCAACGTCGG CGGTTTTTAC GGTCTGACCG GTTCCGTCGA
     GTTCGACCAA

1351 GCAAACGCG ACGGTAAAAT CGACATCACC ATCCCCGTTG
     CCAACCTGCA

1401 AAGCGGTTCG CAACACTTTA CCGACCACCT GAAATCAGCC
     GACATCTTCG

1451 ATGCCGCCCA ATATCCGGAC ATCCGCTTTG TTTCCACCAA
     ATTCAACTTC
```

-continued

```
1501 AACGGCAAAA AACTGGTTTC CGTTGACGGC AACCTGACCA
     TGCACGGCAA

1551 AACCGCCCCC GTCAAACTCA AAGCCGAAAA ATTCAACTGC
     TACCAAAGCC

1601 CGATGGCGAA AACCGAAGTT TGCGGCGGCG ACTTCAGCAC
     CACCATCGAC

1651 CGCACCAAAT GGGGCGTGGA CTACCTCGTT AACGTTGGTA
     TGACCAAAAG

1701 CGTCCGCATC GACATCCAAA TCGAGGCAGC CAAACAATAA
     CTCGAG

1 MASPDVKSAD TLSKPAAPVV AEKETEVKED APQAGSQGQG
     APSTQGSQDM

51 AAVSAENTGN GGAATTDKPK NEDEGPQNDM PQNSAESANQ
     TGNNQPADSS

101 DSAPASNPAP ANGGSNFGRV DLANGVLIDG PSQNITLTHC
     KGDSCNGDNL

151 LDEEAPSKSE FENLNESERI EKYKKDGKSD KFTNLVATAV
     QANGTNKYVI

201 IYKDKSASSS SARFRRSARS RRSLPAEMPL IPVNQADTLI
     VDGEAVSLTG

251 HSGNIFAPEG NYRYLTYGAE KLPGGSYALR VQGEPAKGEM
     LAGTAVYNGE

301 VLHFHTENGR PYPTRGRFAA KVDFGSKSVD GIIDSGDDLH
     MGTQKFKAAI

351 DGNGFKGTWT ENGGGDVSGR FYGPAGEEVA GKYSRPTDA
     EKGGFGVFAG

401 KKEQDGSGGG GATYKVDEYH ANARFAIDHF NTSTNVGGFY
     GLTGSVEFDQ

451 AKRDGKIDIT IPVANLQSGS QHFTDHLKSA DIFDAAQYPD
     IRFVSTKFNF

501 NGKKLVSVDG NLTMHGKTAP VKLKAEKFNC YQSPMAKTEV
     CGGDFSTTID

551 RTKWGVDYLV NVGMTKSVRI DIQIEAAKQ*

ΔG287-961
   1 ATGGCTAGCC CCGATGTTAA ATCGGCGGAC ACGCTGTCAA
     AACCGGCCGC

51 TCCTGTTGTT GCTGAAAAAG AGACAGAGGT AAAAGAAGAT
     GCGCCACAGG

101 CAGGTTCTCA AGGACAGGGC GCGCCATCCA CACAAGGCAG
     CCAAGATATG

151 GCGGCAGTTT CGGCAGAAAA TACAGGCAAT GGCGGTGCGG
     CAACAACGGA

201 CAAACCCAAA AATGAAGACG AGGGACCGCA AAATGATATG
     CCGCAAAATT

251 CCGCCGAATC CGCAAATCAA CAGGGAACA ACCAACCCGC
     CGATTCTTCA

301 GATTCCGCCC CCGCGTCAAA CCCTGCACCT GCGAATGGCG
     GTAGCAATTT

351 TGGAAGGGTT GATTTGGCTA ATGGCGTTTT GATTGATGGG
     CCGTCGCAAA

401 ATATAACGTT GACCCACTGT AAAGGCGATT CTTGTAATGG
     TGATAATTTA

451 TTGGATGAAG AAGCACCGTC AAAATCAGAA TTTGAAAATT
     TAAATGAGTC

501 TGAACGAATT GAGAAATATA AGAAAGATGG GAAAAGCGAT
     AAATTTACTA

551 ATTTGGTTGC GACAGCAGTT CAAGCTAATG GAACTAACAA
     ATATGTCATC

601 ATTTATAAAG ACAAGTCCGC TTCATCTTCA TCTGCGCGAT
     TCAGGCGTTC

651 TGCACGGTCG AGGAGGTCGC TTCCTGCCGA GATGCCGCTA
     ATCCCCGTCA

701 ATCAGGCGGA TACGCTGATT GTCGATGGGG AAGCGGTCAG
     CCTGACGGGG

751 CATTCCGGCA ATATCTTCGC GCCCGAAGGG AATTACCGGT
     ATCTGACTTA

801 CGGGGCGGAA AAATTGCCCG GCGGATCGTA TGCCCTCCGT
     GTGCAAGGCG

851 AACCGGCAAA AGGCGAAATG CTTGCTGGCA CGGCCGTGTA
     CAACGGCGAA

901 GTGCTGCATT TTCATACGGA AAACGGCCGT CCGTACCCGA
     CTAGAGGCAG

951 GTTTGCCGCA AAAGTCGATT TCGGCAGCAA ATCTGTGGAC
     GGCATTATCG

1001 ACAGCGGCGA TGATTTGCAT ATGGGTACGC AAAAATTCAA
     AGCCGCCATC

1051 GATGGAAACG GCTTTAAGGG GACTTGGACG GAAAATGGCG
     GCGGGGATGT

1101 TTCCGGAAGG TTTTACGGCC CGGCCGGCGA GGAAGTGGCG
     GGAAAATACA

1151 GCTATCGCCC GACAGATGCG GAAAAGGGCG GATTCGGCGT
     GTTTGCCGGC

1201 AAAAAAGAGC AGGATGGATC CGGAGGAGGA GGAGCCACAA
     ACGACGACGA

1251 TGTTAAAAAA GCTGCCACTG TGGCCATTGC TGCTGCCTAC
     AACAATGGCC

1301 AAGAAATCAA CGGTTTCAAA GCTGGAGAGA CCATCTACGA
     CATTGATGAA

1351 GACGGCACAA TTACCAAAAA GACGCAACT GCAGCCGATG
     TTGAAGCCGA

1401 CGACTTTAAA GGTCTGGGTC TGAAAAAAGT CGTGACTAAC
     CTGACCAAAA

1451 CCGTCAATGA AACAAACAA AACGTCGATG CCAAAGTAAA
     AGCTGCAGAA

1501 TCTGAAATAG AAAAGTTAAC AACCAAGTTA GCAGACACTG
     ATGCCGCTTT

1551 AGCAGATACT GATGCCGCTC TGGATGCAAC CACCAACGCC
     TTGAATAAAT

1601 TGGGAGAAAA TATAACGACA TTTGCTGAAG AGACTAAGAC
     AAATATCGTA

1651 AAATTGATG AAAAATTAGA AGCCGTGGCT GATACCGTCG
     ACAAGCATGC

1701 CGAAGCATTC AACGATATCG CCGATTCATT GGATGAAACC
     AACACTAAGG

1751 CAGACGAAGC CGTCAAAACC GCCAATGAAG CCAAACAGAC
     GGCCGAAGAA

1801 ACCAAACAAA ACGTCGATGC CAAAGTAAAA GCTGCAGAAA
     CTGCAGCAGG
```

```
1851 CAAAGCCGAA GCTGCCGCTG GCACAGCTAA TACTGCAGCC
     GACAAGGCCG

1901 AAGCTGTCGC TGCAAAAGTT ACCGACATCA AAGCTGATAT
     CGCTACGAAC

1951 AAAGATAATA TTGCTAAAAA AGCAAACAGT GCCGACGTGT
     ACACCAGAGA

2001 AGAGTCTGAC AGCAAATTTG TCAGAATTGA TGGTCTGAAC
     GCTACTACCG

2051 AAAAATTGGA CACACGCTTG GCTTCTGCTG AAAAATCCAT
     TGCCGATCAC

2101 GATACTCGCC TGAACGGTTT GGATAAAACA GTGTCAGACC
     TGCGCAAAGA

2151 AACCCGCCAA GGCCTTGCAG AACAAGCCGC GCTCTCCGGT
     CTGTTCCAAC

2201 CTTACAACGT GGGTCGGTTC AATGTAACGG CTGCAGTCGG
     CGGCTACAAA

2251 TCCGAATCGG CAGTCGCCAT CGGTACCGGC TTCCGCTTTA
     CCGAAAACTT

2301 TGCCGCCAAA GCAGGCGTGG CAGTCGGCAC TTCGTCCGGT
     TCTTCCGCAG

2351 CCTACCATGT CGGCGTCAAT TACGAGTGGT AACTCGAG

1 MASPDVKSAD TLSKPAAPVV AEKETEVKED APQAGSQGQG
    APSTQGSQDM

51 AAVSAENTGN GGAATTDKPK NEDEGPQNDM PQNSAESANQ
    TGNNQPADSS

101 DSAPASNPAP ANGGSNFGRV DLANGVLIDG PSQNITLTHC
    KGDSCNGDNL

151 LDEEAPSKSE FENLNESERI EKYKKDGKSD KFTNLVATAV
    QANGTNKYVI

201 IYKDKSASSS SARFRRSARS RRSLPAEMPL IPVNQADTLI
    VDGEAVSLTG

251 HSGNIFAPEG NYRYLTYGAE KLPGGSYALR VQGEPAKGEM
    LAGTAVYNGE

301 VLHFHTENGR PYPTRGRFAA KVDFGSKSVD GIIDSGDDLH
    MGTQKFKAAI

351 DGNGFKGTWT ENGGGDVSGR FYGPAGEEVA GKYSYRPTDA
    EKGGFGVFAG

401 KKEQDGSGGG GATNDDDVKK AATVAIAAAY NNGQEINGFK
    AGETIYDIDE

451 DGTITKKDAT AADVEADDFK GLGLKKVVTN LTKTVNENKQ
    NVDAKVKAAE

501 SEIEKLTTKL ADTDAALADT DAALDATTNA LNKLGENITT
    FAEETKTNIV

551 KIDEKLEAVA DTVDKHAEAF NDIADSLDET NTKADEAVKT
    ANEAKQTAEE

601 TKQNVDAKVK AAETAAGKAE AAAGTANTAA DKAEAVAAKV
    TDIKADIATN

651 KDNIAKKANS ADVYTREESD SKFVRIDGLN ATTEKLDTRL
    ASAEKSIADH

701 DTRLNGLDKT VSDLRKETRQ GLAEQAALSG LFQPYNVGRF
    NVTAAVGGYK

751 SESAVAIGTG FRFTENFAAK AGVAVGTSSG SSAAYHVGVN
    YEW*
```

|              | ELISA  | Bactericidal |
|--------------|--------|--------------|
| ΔG287-953-His | 3834   | 65536        |
| ΔG287-961-His | 108627 | 65536        |

The bactericidal efficacy (homologous strain) of antibodies raised against the hybrid proteins was compared with antibodies raised against simple mixtures of the component antigens (using 287-GST) for 919 and ORF46.1:

|        | Mixture with 287 | Hybrid with ΔG287 |
|--------|------------------|-------------------|
| 919    | 32000            | 128000            |
| ORF46.1| 128              | 16000             |

Data for bactericidal activity against heterologous MenB strains and against serotypes A and C were also obtained:

|            | 919 |  | ORF46.1 |  |
|------------|---------|--------|---------|--------|
| Strain     | Mixture | Hybrid | Mixture | Hybrid |
| NGH38      | 1024    | 32000  | —       | 16384  |
| MC58       | 512     | 8192   | —       | 512    |
| BZ232      | 512     | 512    | —       | —      |
| MenA (F6124)| 512    | 32000  | —       | 8192   |
| MenC (C11) | >2048   | >2048  | —       | —      |
| MenC (BZ133)| >4096  | 64000  | —       | 8192   |

The hybrid proteins with ΔG287 at the N-terminus are therefore immunologically superior to simple mixtures, with ΔG287-ORF46.1 being particularly effective, even against heterologous strains. ΔG287-ORF46.1K may be expressed in pET-24b.

The same hybrid proteins were made using New Zealand strain 394/98 rather than 2996:

ΔG287NZ-919
```
                              (SEQ ID NOS: 94 and 95)
  1 ATGGCTAGCC CCGATGTCAA GTCGGCGGAC ACGCTGTCAA
    AACCTGCCGC

51 CCCTGTTGTT TCTGAAAAAG AGACAGAGGC AAAGGAAGAT
    GCGCCACAGG

101 CAGGTTCTCA AGGACAGGGC GCGCCATCCG CACAAGGCGG
    TCAAGATATG

151 GCGGCGGTTT CGGAAGAAAA TACAGGCAAT GGCGGTGCGG
    CAGCAACGGA

201 CAAACCCAAA AATGAAGACG AGGGGGCGCA AAATGATATG
    CCGCAAAATG

251 CCGCCGATAC AGATAGTTTG ACACCGAATC ACACCCCGGC
    TTCGAATATG

301 CCGGCCGGAA ATATGGAAAA CCAAGCACCG GATGCCGGGG
    AATCGGAGCA

351 GCCGGCAAAC CAACCGGATA TGGCAAATAC GGCGGACGGA
    ATGCAGGGTG

401 ACGATCCGTC GGCAGGCGGG GAAAATGCCG GCAATACGGC
    TGCCCAAGGT

451 ACAAATCAAG CCGAAAACAA TCAAACCGCC GGTTCTCAAA
    ATCCTGCCTC
```

-continued

```
 501 TTCAACCAAT CCTAGCGCCA CGAATAGCGG TGGTGATTTT
     GGAAGGACGA

551 ACGTGGGCAA TTCTGTTGTG ATTGACGGGC CGTCGCAAAA
     TATAACGTTG

601 ACCCACTGTA AAGGCGATTC TTGTAGTGGC AATAATTTCT
     TGGATGAAGA

651 AGTACAGCTA AAATCAGAAT TTGAAAAATT AAGTGATGCA
     GACAAAATAA

701 GTAATTACAA GAAAGATGGG AAGAATGACG GGAAGAATGA
     TAAATTTGTC

751 GGTTTGGTTG CCGATAGTGT GCAGATGAAG GGAATCAATC
     AATATATTAT

801 CTTTTATAAA CCTAAACCCA CTTCATTTGC GCGATTTAGG
     CGTTCTGCAC

851 GGTCGAGGCG GTCGCTTCCG GCCGAGATGC CGCTGATTCC
     CGTCAATCAG

901 GCGGATACGC TGATTGTCGA TGGGGAAGCG GTCAGCCTGA
     CGGGGCATTC

951 CGGCAATATC TTCGCGCCCG AAGGGAATTA CCGGTATCTG
     ACTTACGGGG

1001 CGGAAAAATT GCCCGGCGGA TCGTATGCCC TCCGTGTTCA
     AGGCGAACCT

1051 TCAAAAGGCG AAATGCTCGC GGGCACGGCA GTGTACAACG
     GCGAAGTGCT

1101 GCATTTTCAT ACGGAAAACG GCCGTCCGTC CCCGTCCAGA
     GGCAGGTTTG

1151 CCGCAAAAGT CGATTTCGGC AGCAAATCTG TGGACGGCAT
     TATCGACAGC

1201 GGCGATGGTT TGCATATGGG TACGCAAAAA TTCAAAGCCG
     CCATCGATGG

1251 AAACGGCTTT AAGGGGACTT GGACGGAAAA TGGCGGCGGG
     GATGTTTCCG

1301 GAAAGTTTTA CGGCCCGGCC GGCGAGGAAG TGGCGGGAAA
     ATACAGCTAT

1351 CGCCCAACAG ATGCGGAAAA GGGCGGATTC GGCGTGTTTG
     CCGGCAAAAA

1401 AGAGCAGGAT GGATCCGGAG GAGGAGGATG CCAAAGCAAG
     AGCATCCAAA

1451 CCTTTCCGCA ACCCGACACA TCCGTCATCA ACGGCCCGGA
     CCGGCCGGTC

1501 GGCATCCCCG ACCCCGCCGG AACGACGGTC GGCGGCGGCG
     GGGCCGTCTA

1551 TACCGTTGTA CCGCACCTGT CCCTGCCCCA CTGGGCGGCG
     CAGGATTTCG

1601 CCAAAAGCCT GCAATCCTTC CGCCTCGGCT GCGCCAATTT
     GAAAAACCGC

1651 CAAGGCTGGC AGGATGTGTG CGCCCAAGCC TTTCAAACCC
     CCGTCCATTC

1701 CTTTCAGGCA AAACAGTTTT TTGAACGCTA TTTCACGCCG
     TGGCAGGTTG

1751 CAGGCAACGG AAGCCTTGCC GGTACGGTTA CCGGCTATTA
     CGAGCCGGTG

1801 CTGAAGGGCG ACGACAGGCG GACGGCACAA GCCCGCTTCC
     CGATTTACGG
```

```
1851 TATTCCCGAC GATTTTATCT CCGTCCCCCT GCCTGCCGGT
     TTGCGGAGCG

1901 GAAAAGCCCT TGTCCGCATC AGGCAGACGG GAAAAAACAG
     CGGCACAATC

1951 GACAATACCG GCGGCACACA TACCGCCGAC CTCTCCCGAT
     TCCCCATCAC

2001 CGCGCGCACA ACGGCAATCA AAGGCAGGTT TGAAGGAAGC
     CGCTTCCTCC

2051 CCTACCACAC GCGCAACCAA ATCAACGGCG GCGCGCTTGA
     CGGCAAAGCC

2101 CCGATACTCG GTTACGCCGA AGACCCCGTC GAACTTTTTT
     TTATGCACAT

2151 CCAAGGCTCG GGCCGTCTGA AAACCCCGTC CGGCAAATAC
     ATCCGCATCG

2201 GCTATGCCGA CAAAAACGAA CATCCCTACG TTTCCATCGG
     ACGCTATATG

2251 GCGGACAAAG GCTACCTCAA GCTCGGGCAG ACCTCGATGC
     AGGGCATCAA

2301 AGCCTATATG CGGCAAAATC CGCAACGCCT CGCCGAAGTT
     TTGGGTCAAA

2351 ACCCCAGCTA TATCTTTTTC CGCGAGCTTG CCGGAAGCAG
     CAATGACGGT

2401 CCCGTCGGCG CACTGGGCAC GCCGTTGATG GGGGAATATG
     CCGGCGCAGT

2451 CGACCGGCAC TACATTACCT TGGGCGCGCC CTTATTTGTC
     GCCACCGCCC

2501 ATCCGGTTAC CCGCAAAGCC CTCAACCGCC TGATTATGGC
     GCAGGATACC

2551 GGCAGCGCGA TTAAAGGCGC GGTGCGCGTG GATTATTTTT
     GGGGATACGG

2601 CGACGAAGCC GGCGAACTTG CCGGCAAACA GAAACCACG
     GGTTACGTCT

2651 GGCAGCTCCT ACCCAACGGT ATGAAGCCCG AATACCGCCC
     GTAAAAGCTT
```

```
   1 MASPDVKSAD TLSKPAAPVV SEKETEAKED APQAGSQGQG
     APSAQGGQDM

51 AAVSEENTGN GGAAATDKPK NEDEGAQNDM PQNAADTDSL
     TPNHTPASNM

101 PAGNMENQAP DAGESEQPAN QPDMANTADG MQGDDPSAGG
     ENAGNTAAQG

151 TNQAENNQTA GSQNPASSTN PSATNSGGDF GRTNVGNSVV
     IDGPSQNITL

201 THCKGDSCSG NNFLDEEVQL KSEFEKLSDA DKISNYKKDG
     KNDGKNDKFV

251 GLVADSVQMK GINQYIIFYK PKPTSFARFR RSARSRRSLP
     AEMPLIPVNQ

301 ADTLIVDGEA VSLTGHSGNI FAPEGNYRYL TYGAEKLPGG
     SYALRVQGEP

351 SKGEMLAGTA VYNGEVLHFH TENGRPSPSR GRFAAKVDFG
     SKSVDGIIDS

401 GDGLHMGTQK FKAAIDGNGF KGTWTENGGG DVSGKFYGPA
     GEEVAGKYSY

451 RPTDAEKGGF GVFAGKKEQD GSGGGGCQSK SIQTFPQPDT
     SVINGPDRPV
```

```
501 GIPDPAGTTV GGGGAVYTVV PHLSLPHWAA QDFAKSLQSF
    RLGCANLKNR

551 QGWQDVCAQA FQTPVHSFQA KQFFERYFTP WQVAGNGSLA
    GTVTGYYEPV

601 LKGDDRRTAQ ARFPIYGIPD DFISVPLPAG LRSGKALVRI
    RQTGKNSGTI

651 DNTGGTHTAD LSRFPITART TAIKGRFEGS RFLPYHTRNQ
    INGGALDGKA

701 PILGYAEDPV ELFFMHIQGS GRLKTPSGKY IRIGYADKNE
    HPYVSIGRYM

751 ADKGYLKLGQ TSMQGIKAYM RQNPQRLAEV LGQNPSYIFF
    RELAGSSNDG

801 PVGALGTPLM GEYAGAVDRH YITLGAPLFV ATAHPVTRKA
    LNRLIMAQDT

851 GSAIKGAVRV DYFWGYGDEA GELAGKQKTT GYVWQLLPNG
    MKPEYRP*

ΔG287NZ-953
                         (SEQ ID NOS: 96 and 97)
  1 ATGGCTAGCC CCGATGTCAA GTCGGCGGAC ACGCTGTCAA
    AACCTGCCGC

51 CCCTGTTGTT TCTGAAAAAG AGACAGAGGC AAAGGAAGAT
    GCGCCACAGG

101 CAGGTTCTCA AGGACAGGGC GCGCCATCCG CACAAGGCGG
    TCAAGATATG

151 GCGGCGGTTT CGGAAGAAAA TACAGGCAAT GGCGGTGCGG
    CAGCAACGGA

201 CAAACCCAAA AATGAAGACG AGGGGGCGCA AAATGATATG
    CCGCAAAATG

251 CCGCCGATAC AGATAGTTTG ACACCGAATC ACACCCCGGC
    TTCGAATATG

301 CCGGCCGGAA ATATGGAAAA CCAAGCACCG GATGCCGGGG
    AATCGGAGCA

351 GCCGGCAAAC CAACCGGATA TGGCAAATAC GGCGGACGGA
    ATGCAGGGTG

401 ACGATCCGTC GGCAGGCGGG GAAAATGCCG GCAATACGGC
    TGCCCAAGGT

451 ACAAATCAAG CCGAAAACAA TCAAACCGCC GGTTCTCAAA
    ATCCTGCCTC

501 TTCAACCAAT CCTAGCGCCA CGAATAGCGG TGGTGATTTT
    GGAAGGACGA

551 ACGTGGGCAA TTCTGTTGTG ATTGACGGGC CGTCGCAAAA
    TATAACGTTG

601 ACCCACTGTA AAGGCGATTC TTGTAGTGGC AATAATTTCT
    TGGATGAAGA

651 AGTACAGCTA AAATCAGAAT TTGAAAAATT AAGTGATGCA
    GACAAAATAA

701 GTAATTACAA GAAAGATGGG AAGAATGACG GAAGAATGA
    TAAATTTGTC

751 GGTTTGGTTG CCGATAGTGT GCAGATGAAG GAATCAATC
    AATATATTAT

801 CTTTTATAAA CCTAAACCCA CTTCATTTGC GCGATTTAGG
    CGTTCTGCAC

851 GGTCGAGGCG GTCGCTTCCG GCCGAGATGC CGCTGATTCC
    CGTCAATCAG
```

```
901 GCGGATACGC TGATTGTCGA TGGGGAAGCG GTCAGCCTGA
    CGGGGCATTC

951 CGGCAATATC TTCGCGCCCG AAGGGAATTA CCGGTATCTG
    ACTTACGGGG

1001 CGGAAAAATT GCCCGGCGGA TCGTATGCCC TCCGTGTTCA
     AGGCGAACCT

1051 TCAAAAGGCG AAATGCTCGC GGGCACGGCA GTGTACAACG
     GCGAAGTGCT

1101 GCATTTTCAT ACGGAAAACG GCCGTCCGTC CCGTCCAGA
     GGCAGGTTTG

1151 CCGCAAAAGT CGATTTCGGC AGCAAATCTG TGGACGGCAT
     TATCGACAGC

1201 GGCGATGGTT TGCATATGGG TACGCAAAAA TTCAAAGCCG
     CCATCGATGG

1251 AAACGGCTTT AAGGGGACTT GGACGGAAAA TGGCGGCGGG
     GATGTTTCCG

1301 GAAAGTTTTA CGGCCCGGCC GGCGAGGAAG TGGCGGGAAA
     ATACAGCTAT

1351 CGCCCAACAG ATGCGGAAAA GGGCGGATTC GGCGTGTTTG
     CCGGCAAAAA

1401 AGAGCAGGAT GGATCCGGAG GAGGAGGAGC CACCTACAAA
     GTGGACGAAT

1451 ATCACGCCAA CGCCCGTTTC GCCATCGACC ATTTCAACAC
     CAGCACCAAC

1501 GTCGGCGGTT TTTACGGTCT GACCGGTTCC GTCGAGTTCG
     ACCAAGCAAA

1551 ACGCGACGGT AAAATCGACA TCACCATCCC CGTTGCCAAC
     CTGCAAAGCG

1601 GTTCGCAACA CTTTACCGAC CACCTGAAAT CAGCCGACAT
     CTTCGATGCC

1651 GCCCAATATC CGGACATCCG CTTTGTTTCC ACCAAATTCA
     ACTTCAACGG

1701 CAAAAAACTG GTTTCCGTTG ACGGCAACCT GACCATGCAC
     GGCAAAACCG

1751 CCCCCGTCAA ACTCAAAGCC GAAAAATTCA ACTGCTACCA
     AAGCCCGATG

1801 GCGAAAACCG AAGTTTGCGG CGGCGACTTC AGCACCACCA
     TCGACCGCAC

1851 CAAATGGGGC GTGGACTACC TCGTTAACGT TGGTATGACC
     AAAAGCGTCC

1901 GCATCGACAT CCAAATCGAG GCAGCCAACA ATAAAAAGCT T

1 MASPDVKSAD TLSKPAAPVV SEKETEAKED APQAGSQGQG
    APSAQGGQDM

51 AAVSEENTGN GGAAATDKPK NEDEGAQNDM PQNAADTDSL
    TPNHTPASNM

101 PAGNMENQAP DAGESEQPAN QPDMANTADG MQGDDPSAGG
    ENAGNTAAQG

151 TNQAENNQTA GSQNPASSTN PSATNSGGDF GRTNVGNSVV
    IDGPSQNITL

201 THCKGDSCSG NNFLDEEVQL KSEFEKLSDA DKISNYKKDG
    KNDGKNDKFV

251 GLVADSVQMK GINQYIIFYK PKPTSFARFR RSARSRRSLP
    AEMPLIPVNQ
```

```
301 ADTLIVDGEA VSLTGHSGNI FAPEGNYRYL TYGAEKLPGG
    SYALRVQGEP

351 SKGEMLAGTA VYNGEVLHFH TENGRPSPSR GRFAAKVDFG
    SKSVDGIIDS

401 GDGLHMGTQK FKAAIDGNGF KGTWTENGGG DVSGKFYGPA
    GEEVAGKYSY

451 RPTDAEKGGF GVFAGKKEQD GSGGGGATYK VDEYHANARF
    AIDHFNTSTN

501 VGGFYGLTGS VEFDQAKRDG KIDITIPVAN LQSGSQHFTD
    HLKSADIFDA

551 AQYPDIRFVS TKFNFNGKKL VSVDGNLTMH GKTAPVKLKA
    EKFNCYQSPM

601 AKTEVCGGDF STTIDRTKWG VDYLVNVGMT KSVRIDIQIE
    AAKQ*

ΔG287NZ-961
                              (SEQ ID NOS: 98 and 99)
  1 ATGGCTAGCC CCGATGTCAA GTCGGCGGAC ACGCTGTCAA
    AACCTGCCGC

51 CCCTGTTGTT TCTGAAAAAG AGACAGAGGC AAAGGAAGAT
    GCGCCACAGG

101 CAGGTTCTCA AGGACAGGGC GCGCCATCCG CACAAGGCGG
    TCAAGATATG

151 GCGGCGGTTT CGGAAGAAAA TACAGGCAAT GGCGGTGCGG
    CAGCAACGGA

201 CAAACCCAAA AATGAAGACG AGGGGCGCA AAATGATATG
    CCGCAAAATG

251 CCGCCGATAC AGATAGTTTG ACACCGAATC ACACCCCGGC
    TTCGAATATG

301 CCGGCCGGAA ATATGGAAAA CCAAGCACCG GATGCCGGGG
    AATCGGAGCA

351 GCCGGCAAAC CAACCGGATA TGGCAAATAC GGCGGACGGA
    ATGCAGGGTG

401 ACGATCCGTC GGCAGGCGGG GAAAATGCCG GCAATACGGC
    TGCCCAAGGT

451 ACAAATCAAG CCGAAAACAA TCAAACCGCC GGTTCTCAAA
    ATCCTGCCTC

501 TTCAACCAAT CCTAGCGCCA CGAATAGCGG TGGTGATTTT
    GGAAGGACGA

551 ACGTGGGCAA TTCTGTTGTG ATTGACGGGC CGTCGCAAAA
    TATAACGTTG

601 ACCCACTGTA AAGGCGATTC TTGTAGTGGC AATAATTTCT
    TGGATGAAGA

651 AGTACAGCTA AAATCAGAAT TTGAAAAATT AAGTGATGCA
    GACAAAATAA

701 GTAATTACAA GAAAGATGGG AAGAATGACG GAAGAATGA
    TAAATTTGTC

751 GGTTTGGTTG CCGATAGTGT GCAGATGAAG GGAATCAATC
    AATATATTAT

801 CTTTTATAAA CCTAAACCCA CTTCATTTGC GCGATTTAGG
    CGTTCTGCAC

851 GGTCGAGGCG GTCGCTTCCG GCCGAGATGC CGCTGATTCC
    CGTCAATCAG

901 GCGGATACGC TGATTGTCGA TGGGGAAGCG GTCAGCCTGA
    CGGGGCATTC
```

```
951 CGGCAATATC TTCGCGCCCG AAGGGAATTA CCGGTATCTG
    ACTTACGGGG

1001 CGGAAAAATT GCCCGGCGGA TCGTATGCCC TCCGTGTTCA
     AGGCGAACCT

1051 TCAAAAGGCG AAATGCTCGC GGGCACGGCA GTGTACAACG
     GCGAAGTGCT

1101 GCATTTTCAT ACGGAAAACG GCCGTCCGTC CCCGTCCAGA
     GGCAGGTTTG

1151 CCGCAAAAGT CGATTTCGGC AGCAAATCTG TGGACGGCAT
     TATCGACAGC

1201 GGCGATGGTT TGCATATGGG TACGCAAAAA TTCAAAGCCG
     CCATCGATGG

1251 AAACGGCTTT AAGGGGACTT GGACGGAAAA TGGCGGCGGG
     GATGTTTCCG

1301 GAAAGTTTTA CGGCCCGGCC GGCGAGGAAG TGGCGGGAAA
     ATACAGCTAT

1351 CGCCCAACAG ATGCGGAAAA GGGCGGATTC GGCGTGTTTG
     CCGGCAAAAA

1401 AGAGCAGGAT GGATCCGGAG GAGGAGGAGC CACAAACGAC
     GACGATGTTA

1451 AAAAAGCTGC CACTGTGGCC ATTGCTGCTG CCTACAACAA
     TGGCCAAGAA

1501 ATCAACGGTT TCAAAGCTGG AGAGACCATC TACGACATTG
     ATGAAGACGG

1551 CACAATTACC AAAAAAGACG CAACTGCAGC CGATGTTGAA
     GCCGACGACT

1601 TTAAAGGTCT GGGTCTGAAA AAGTCGTGA CTAACCTGAC
     CAAAACCGTC

1651 AATGAAAACA AACAAAACGT CGATGCCAAA GTAAAAGCTG
     CAGAATCTGA

1701 AATAGAAAAG TTAACAACCA AGTTAGCAGA CACTGATGCC
     GCTTTAGCAG

1751 ATACTGATGC CGCTCTGGAT GCAACCACCA ACGCCTTGAA
     TAAATTGGGA

1801 GAAAATATAA CGACATTTGC TGAAGAGACT AAGACAAATA
     TCGTAAAAAT

1851 TGATGAAAAA TTAGAAGCCG TGGCTGATAC CGTCGACAAG
     CATGCCGAAG

1901 CATTCAACGA TATCGCCGAT TCATTGGATG AAACCAACAC
     TAAGGCAGAC

1951 GAAGCCGTCA AAACCGCCAA TGAAGCCAAA CAGACGGCCG
     AAGAAACCAA

2001 ACAAAACGTC GATGCCAAAG TAAAAGCTGC AGAAACTGCA
     GCAGGCAAAG

2051 CCGAAGCTGC CGCTGGCACA GCTAATACTG CAGCCGACAA
     GGCCGAAGCT

2101 GTCGCTGCAA AAGTTACCGA CATCAAAGCT GATATCGCTA
     CGAACAAAGA

2151 TAATATTGCT AAAAAAGCAA ACAGTGCCGA CGTGTACACC
     AGAGAAGAGT

2201 CTGACAGCAA ATTTGTCAGA ATTGATGGTC TGAACGCTAC
     TACCGAAAAA
```

```
2251 TTGGACACAC GCTTGGCTTC TGCTGAAAAA TCCATTGCCG
     ATCACGATAC

2301 TCGCCTGAAC GGTTTGGATA AACAGTGTC AGACCTGCGC
     AAAGAAACCC

2351 GCCAAGGCCT TGCAGAACAA GCCGCGCTCT CCGGTCTGTT
     CCAACCTTAC

2401 AACGTGGGTC GGTTCAATGT AACGGCTGCA GTCGGCGGCT
     ACAAATCCGA

2451 ATCGGCAGTC GCCATCGGTA CCGGCTTCCG CTTTACCGAA
     AACTTTGCCG

2501 CCAAAGCAGG CGTGGCAGTC GGCACTTCGT CCGGTTCTTC
     CGCAGCCTAC

2551 CATGTCGGCG TCAATTACGA GTGGTAAAAG CTT

1 MASPDVKSAD TLSKPAAPVV SEKETEAKED APQAGSQGQG
     APSAQGGQDM

51 AAVSEENTGN GGAAATDKPK NEDEGAQNDM PQNAADTDSL
     TPNHTPASNM

101 PAGNMENQAP DAGESEQPAN QPDMANTADG MQGDDPSAGG
     ENAGNTAAQG

151 TNQAENNQTA GSQNPASSTN PSATNSGGDF GRTNVGNSVV
     IDGPSQNITL

201 THCKGDSCSG NNFLDEEVQL KSEFEKLSDA DKISNYKKDG
     KNDGKNDKFV

251 GLVADSVQMK GINQYIIFYK PKPTSFARFR RSARSRRSLP
     AEMPLIPVNQ

301 ADTLIVDGEA VSLTGHSGNI FAPEGNYRYL TYGAEKLPGG
     SYALRVQGEP

351 SKGEMLAGTA VYNGEVLHFH TENGRPSPSR GRFAAKVDFG
     SKSVDGIIDS

401 GDGLHMGTQK FKAAIDGNGF KGTWTENGGG DVSGKFYGPA
     GEEVAGKYSY

451 RPTDAEKGGF GVFAGKKEQD GSGGGGATND DDVKKAATVA
     IAAAYNNGQE

501 INGFKAGETI YDIDEDGTIT KKDATAADVE ADDFKGLGLK
     KVVTNLTKTV

551 NENKQNVDAK VKAAESEIEK LTTKLADTDA ALADTDAALD
     ATTNALNKLG

601 ENITTFAEET KTNIVKIDEK LEAVADTVDK HAEAFNDIAD
     SLDETNTKAD

651 EAVKTANEAK QTAEETKQNV DAKVKAAETA AGKAEAAAGT
     ANTAADKAEA

701 VAAKVTDIKA DIATNKDNIA KKANSADVYT REESDSKFVR
     IDGLNATTEK

751 LDTRLASAEK SIADHDTRLN GLDKTVSDLR KETRQGLAEQ
     AALSGLFQPY

801 NVGRFNVTAA VGGYKSESAV AIGTGFRFTE NFAAKAGVAV
     GTSSGSSAAY

851 HVGVNYEW*
```

ΔG983 and Hybrids

Bactericidal titres generated in response to ΔG983 (His-fusion) were measured against various strains, including the homologous 2996 strain:

|  | 2996 | NGH38 | BZ133 |
|---|---|---|---|
| ΔG983 | 512 | 128 | 128 |

ΔG983 was also expressed as a hybrid, with ORF46.1 (SEQ ID NOS:100 and 101), 741 (SEQ ID NOS:102 and 103), 961 (SEQ ID NOS:104 and 105) or 961c (SEQ ID NOS:106 and 107) at its C-terminus:

```
ΔG983-ORF46.1
   1 ATGACTTCTG CGCCCGACTT CAATGCAGGC GGTACCGGTA
     TCGGCAGCAA

51 CAGCAGAGCA ACAACAGCGA AATCAGCAGC AGTATCTTAC
     GCCGGTATCA

101 AGAACGAAAT GTGCAAAGAC AGAAGCATGC TCTGTGCCGG
     TCGGGATGAC

151 GTTGCGGTTA CAGACAGGGA TGCCAAAATC AATGCCCCCC
     CCCCGAATCT

201 GCATACCGGA GACTTTCCAA ACCCAAATGA CGCATACAAG
     AATTTGATCA

251 ACCTCAAACC TGCAATTGAA GCAGGCTATA CAGGACGCGG
     GGTAGAGGTA

301 GGTATCGTCG ACACAGGCGA ATCCGTCGGC AGCATATCCT
     TTCCCGAACT

351 GTATGGCAGA AAAGAACACG GCTATAACGA AAATTACAAA
     AACTATACGG

401 CGTATATGCG GAAGGAAGCG CCTGAAGACG GAGGCGGTAA
     AGACATTGAA

451 GCTTCTTTCG ACGATGAGGC CGTTATAGAG ACTGAAGCAA
     AGCCGACGGA

501 TATCCGCCAC GTAAAAGAAA TCGGACACAT CGATTTGGTC
     TCCCATATTA

551 TTGGCGGGCG TTCCGTGGAC GGCAGACCTG CAGGCGGTAT
     TGCGCCCGAT

601 GCGACGCTAC ACATAATGAA TACGAATGAT GAAACCAAGA
     ACGAAATGAT

651 GGTTGCAGCC ATCCGCAATG CATGGGTCAA GCTGGGCGAA
     CGTGGCGTGC

701 GCATCGTCAA TAACAGTTTT GGAACAACAT CGAGGGCAGG
     CACTGCCGAC

751 CTTTTCCAAA TAGCCAATTC GGAGGAGCAG TACCGCCAAG
     CGTTGCTCGA

801 CTATTCCGGC GGTGATAAAA CAGACGAGGG TATCCGCCTG
     ATGCAACAGA

851 GCGATTACGG CAACCTGTCC TACCACATCC GTAATAAAAA
     CATGCTTTTC

901 ATCTTTTCGA CAGGCAATGA CGCACAAGCT CAGCCCAACA
     CATATGCCCT

951 ATTGCCATTT TATGAAAAAG ACGCTCAAAA AGGCATTATC
     ACAGTCGCAG

1001 GCGTAGACCG CAGTGGAGAA AAGTTCAAAC GGGAAATGTA
     TGGAGAACCG

1051 GGTACAGAAC CGCTTGAGTA TGGCTCCAAC CATTGCGGAA
     TTACTGCCAT
```

-continued

```
1101  GTGGTGCCTG TCGGCACCCT ATGAAGCAAG CGTCCGTTTC
      ACCCGTACAA
1151  ACCCGATTCA AATTGCCGGA ACATCCTTTT CCGCACCCAT
      CGTAACCGGC
1201  ACGGCGGCTC TGCTGCTGCA GAAATACCCG TGGATGAGCA
      ACGACAACCT
1251  GCGTACCACG TTGCTGACGA CGGCTCAGGA CATCGGTGCA
      GTCGGCGTGG
1301  ACAGCAAGTT CGGCTGGGGA CTGCTGGATG CGGGTAAGGC
      CATGAACGGA
1351  CCCGCGTCCT TTCCGTTCGG CGACTTTACC GCCGATACGA
      AAGGTACATC
1401  CGATATTGCC TACTCCTTCC GTAACGACAT TTCAGGCACG
      GGCGGCCTGA
1451  TCAAAAAGG CGGCAGCCAA CTGCAACTGC ACGGCAACAA
      CACCTATACG
1501  GGCAAAACCA TTATCGAAGG CGGTTCGCTG GTGTTGTACG
      GCAACAACAA
1551  ATCGGATATG CGCGTCGAAA CCAAAGGTGC GCTGATTTAT
      AACGGGGCGG
1601  CATCCGGCGG CAGCCTGAAC AGCGACGGCA TTGTCTATCT
      GGCAGATACC
1651  GACCAATCCG GCGCAAACGA AACCGTACAC ATCAAAGGCA
      GTCTGCAGCT
1701  GGACGGCAAA GGTACGCTGT ACACACGTTT GGGCAAACTG
      CTGAAAGTGG
1751  ACGGTACGGC GATTATCGGC GGCAAGCTGT ACATGTCGGC
      ACGCGGCAAG
1801  GGGGCAGGCT ATCTCAACAG TACCGGACGA CGTGTTCCCT
      TCCTGAGTGC
1851  CGCCAAAATC GGGCAGGATT ATTCTTTCTT CACAAACATC
      GAAACCGACG
1901  GCGGCCTGCT GGCTTCCCTC GACAGCGTCG AAAAAACAGC
      GGGCAGTGAA
1951  GGCGACACGC TGTCCTATTA TGTCCGTCGC GGCAATGCGG
      CACGGACTGC
2001  TTCGGCAGCG GCACATTCCG CGCCCGCCGG TCTGAAACAC
      GCCGTAGAAC
2051  AGGGCGGCAG CAATCTGGAA AACCTGATGG TCGAACTGGA
      TGCCTCCGAA
2101  TCATCCGCAA CACCCGAGAC GGTTGAAACT GCGGCAGCCG
      ACCGCACAGA
2151  TATGCCGGGC ATCCGCCCCT ACGGCGCAAC TTTCCGCGCA
      GCGGCAGCCG
2201  TACAGCATGC GAATGCCGCC GACGGTGTAC GCATCTTCAA
      CAGTCTCGCC
2251  GCTACCGTCT ATGCCGACAG TACCGCCGCC CATGCCGATA
      TGCAGGGACG
2301  CCGCCTGAAA GCCGTATCGG ACGGGTTGGA CCACAACGGC
      ACGGGTCTGC
2351  GCGTCATCGC GCAAACCCAA CAGGACGGTG AACGTGGGA
      ACAGGGCGGT
2401  GTTGAAGGCA AAATGCGCGG CAGTACCCAA ACCGTCGGCA
      TTGCCGCGAA
2451  AACCGGCGAA AATACGACAG CAGCCGCCAC ACTGGGCATG
      GGACGCAGCA
2501  CATGGAGCGA AACAGTGCA AATGCAAAAA CCGACAGCAT
      TAGTCTGTTT
2551  GCAGGCATAC GGCACGATGC GGGCGATATC GGCTATCTCA
      AAGGCCTGTT
2601  CTCCTACGGA CGCTACAAAA ACAGCATCAG CCGCAGCACC
      GGTGCGGACG
2651  AACATGCGGA AGGCAGCGTC AACGGCACGC TGATGCAGCT
      GGGCGCACTG
2701  GGCGGTGTCA ACGTTCCGTT TGCCGCAACG GGAGATTTGA
      CGGTCGAAGG
2751  CGGTCTGCGC TACGACCTGC TCAAACAGGA TGCATTCGCC
      GAAAAAGGCA
2801  GTGCTTTGGG CTGGAGCGGC AACAGCCTCA CTGAAGGCAC
      GCTGGTCGGA
2851  CTCGCGGGTC TGAAGCTGTC GCAACCCTTG AGCGATAAAG
      CCGTCCTGTT
2901  TGCAACGGCG GCGTGGAAC GCGACCTGAA CGGACGCGAC
      TACACGGTAA
2951  CGGGCGGCTT TACCGGCGCG ACTGCAGCAA CCGGCAAGAC
      GGGGGCACGC
3001  AATATGCCGC ACACCCGTCT GGTTGCCGGC CTGGGCGCGG
      ATGTCGAATT
3051  CGGCAACGGC TGGAACGGCT TGGCACGTTA CAGCTACGCC
      GGTTCCAAAC
3101  AGTACGGCAA CCACAGCGGA CGAGTCGGCG TAGGCTACCG
      GTTCCTCGAC
3151  GGTGGCGGAG GCACTGGATC CTCAGATTTG GCAAACGATT
      CTTTTATCCG
3201  GCAGGTTCTC GACCGTCAGC ATTTCGAACC CGACGGGAAA
      TACCACCTAT
3251  TCGGCAGCAG GGGGGAACTT GCCGAGCGCA GCGGCCATAT
      CGGATTGGGA
3301  AAAATACAAA GCCATCAGTT GGGCAACCTG ATGATTCAAC
      AGGCGGCCAT
3351  TAAAGGAAAT ATCGGCTACA TTGTCCGCTT TTCCGATCAC
      GGGCACGAAG
3401  TCCATTCCCC CTTCGACAAC CATGCCTCAC ATTCCGATTC
      TGATGAAGCC
3451  GGTAGTCCCG TTGACGGATT TAGCCTTTAC CGCATCCATT
      GGGACGGATA
3501  CGAACACCAT CCCGCCGACG GCTATGACGG GCCACAGGGC
      GGCGGCTATC
3551  CCGCTCCCAA AGGCGCGAGG GATATATACA GCTACGACAT
      AAAAGGCGTT
3601  GCCCAAAATA TCCGCCTCAA CCTGACCGAC AACCGCAGCA
      CCGGACAACG
3651  GCTTGCCGAC CGTTTCCACA ATGCCGGTAG TATGCTGACG
      CAAGGAGTAG
3701  GCGACGGATT CAAACGCGCC ACCCGATACA GCCCCGAGCT
      GGACAGATCG
3751  GGCAATGCCG CCGAAGCCTT CAACGGCACT GCAGATATCG
      TTAAAAACAT
```

-continued

```
3801 CATCGGCGCG GCAGGAGAAA TTGTCGGCGC AGGCGATGCC
     GTGCAGGGCA

3851 TAAGCGAAGG CTCAAACATT GCTGTCATGC ACGGCTTGGG
     TCTGCTTTCC

3901 ACCGAAAACA AGATGGCGCG CATCAACGAT TTGGCAGATA
     TGGCGCAACT

3951 CAAAGACTAT GCCGCAGCAG CCATCCGCGA TTGGGCAGTC
     CAAAACCCCA

4001 ATGCCGCACA AGGCATAGAA GCCGTCAGCA ATATCTTTAT
     GGCAGCCATC

4051 CCCATCAAAG GGATTGGAGC TGTTCGGGGA AAATACGGCT
     TGGGCGGCAT

4101 CACGGCACAT CCTATCAAGC GGTCGCAGAT GGGCGCGATC
     GCATTGCCGA

4151 AAGGGAAATC CGCCGTCAGC GACAATTTTG CCGATGCGGC
     ATACGCCAAA

4201 TACCCGTCCC CTTACCATTC CCGAAATATC CGTTCAAACT
     TGGAGCAGCG

4251 TTACGGCAAA GAAAACATCA CCTCCTCAAC CGTGCCGCCG
     TCAAACGGCA

4301 AAAATGTCAA ACTGGCAGAC CAACGCCACC CGAAGACAGG
     CGTACCGTTT

4351 GACGGTAAAG GGTTTCCGAA TTTTGAGAAG CACGTGAAAT
     ATGATACGCT

4401 CGAGCACCAC CACCACCACC ACTGA

1 MTSAPDFNAG GTGIGSNSRA TTAKSAAVSY AGIKNEMCKD
     RSMLCAGRDD

51 VAVTDRDAKI NAPPPNLHTG DFPNPNDAYK NLINLKPAIE
     AGYTGRGVEV

101 GIVDTGESVG SISFPELYGR KEHGYNENYK NYTAYMRKEA
     PEDGGGKDIE

151 ASFDDEAVIE TEAKPTDIRH VKEIGHIDLV SHIIGGRSVD
     GRPAGGIAPD

201 ATLHIMNTND ETKNEMMVAA IRNAWVKLGE RGVRIVNNSF
     GTTSRAGTAD

251 LFQIANSEEQ YRQALLDYSG GDKTDEGIRL MQQSDYGNLS
     YHIRNKNMLF

301 IFSTGNDAQA QPNTYALLPF YEKDAQKGII TVAGVDRSGE
     KFKREMYGEP

351 GTEPLEYGSN HCGITAMWCL SAPYEASVRF TRTNPIQIAG
     TSFSAPIVTG

401 TAALLLQKYP WMSNDNLRTT LLTTAQDIGA VGVDSKFGWG
     LLDAGKAMNG

451 PASFPFGDFT ADTKGTSDIA YSFRNDISGT GGLIKKGGSQ
     LQLHGNNTYT

501 GKTIIEGGSL VLYGNNKSDM RVETKGALIY NGAASGGSLN
     SDGIVYLADT

551 DQSGANETVH IKGSLQLDGK GTLYTRLGKL LKVDGTAIIG
     GKLYMSARGK

601 GAGYLNSTGR RVPFLSAAKI GQDYSFFTNI ETDGGLLASL
     DSVEKTAGSE

651 GDTLSYYVRR GNAARTASAA AHSAPAGLKH AVEQGGSNLE
     NLMVELDASE
```

```
 701 SSATPETVET AAADRTDMPG IRPYGATFRA AAAVQHANAA
     DGVRIFNSLA

751 ATVYADSTAA HADMQGRRLK AVSDGLDHNG TGLRVIAQTQ
     QDGGTWEQGG

801 VEGKMRGSTQ TVGIAAKTGE NTTAAATLGM GRSTWSENSA
     NAKTDSISLF

851 AGIRHDAGDI GYLKGLFSYG RYKNSISRST GADEHAEGSV
     NGTLMQLGAL

901 GGVNVPFAAT GDLTVEGGLR YDLLKQDAFA EKGSALGWSG
     NSLTEGTLVG

951 LAGLKLSQPL SDKAVLFATA GVERDLNGRD YTVTGGFTGA
     TAATGKTGAR

1001 NMPHTRLVAG LGADVEFGNG WNGLARYSYA GSKQYGNHSG
     RVGVGYRFLD

1051 GGGGTGSSDL ANDSFIRQVL DRQHFEPDGK YHLFGSRGEL
     AERSGHIGLG

1101 KIQSHQLGNL MIQQAAIKGN IGYIVRFSDH GHEVHSPFDN
     HASHSDSDEA

1151 GSPVDGFSLY RIHWDGYEHH PADGYDGPQG GGYPAPKGAR
     DIYSYDIKGV

1201 AQNIRLNLTD NRSTGQRLAD RFHNAGSMLT QGVGDGFKRA
     TRYSPELDRS

1251 GNAAEAFNGT ADIVKNIIGA AGEIVGAGDA VQGISEGSNI
     AVMHGLGLLS

1301 TENKMARIND LADMAQLKDY AAAAIRDWAV QNPNAAQGIE
     AVSNIFMAAI

1351 PIKGIGAVRG KYGLGGITAH PIKRSQMGAI ALPKGKSAVS
     DNFADAAYAK

1401 YPSPYHSRNI RSNLEQRYGK ENITSSTVPP SNGKNVKLAD
     QRHPKTGVPF

1451 DGKGFPNFEK HVKYDTLEHH HHH*

ΔG983-741
   1 ATGACTTCTG CGCCCGACTT CAATGCAGGC GGTACCGGTA
     TCGGCAGCAA

51 CAGCAGAGCA ACAACAGCGA AATCAGCAGC AGTATCTTAC
     GCCGGTATCA

101 AGAACGAAAT GTGCAAAGAC AGAAGCATGC TCTGTGCCGG
     TCGGGATGAC

151 GTTGCGGTTA CAGACAGGGA TGCCAAAATC AATGCCCCCC
     CCCCGAATCT

201 GCATACCGGA GACTTTCCAA ACCCAAATGA CGCATACAAG
     AATTTGATCA

251 ACCTCAAACC TGCAATTGAA GCAGGCTATA CAGGACGCGG
     GGTAGAGGTA

301 GGTATCGTCG ACACAGGCGA ATCCGTCGGC AGCATATCCT
     TTCCCGAACT

351 GTATGGCAGA AAAGAACACG GCTATAACGA AAATTACAAA
     AACTATACGG

401 CGTATATGCG GAAGGAAGCA CCTGAAGACG GAGGCGGTAA
     AGACATTGAA

451 GCTTCTTTCG ACGATGAGGC CGTTATAGAG ACTGAAGCAA
     AGCCGACGGA
```

```
-continued
 501 TATCCGCCAC GTAAAAGAAA TCGGACACAT CGATTTGGTC
     TCCCATATTA

551 TTGGCGGGCG TTCCGTGGAC GGCAGACCTG CAGGCGGTAT
     TGCGCCCGAT

601 GCGACGCTAC ACATAATGAA TACGAATGAT GAAACCAAGA
     ACGAAATGAT

651 GGTTGCAGCC ATCCGCAATG CATGGGTCAA GCTGGGCGAA
     CGTGGCGTGC

701 GCATCGTCAA TAACAGTTTT GGAACAACAT CGAGGGCAGG
     CACTGCCGAC

751 CTTTTCCAAA TAGCCAATTC GGAGGAGCAG TACCGCCAAG
     CGTTGCTCGA

801 CTATTCCGGC GGTGATAAAA CAGACGAGGG TATCCGCCTG
     ATGCAACAGA

851 GCGATTACGG CAACCTGTCC TACCACATCC GTAATAAAAA
     CATGCTTTTC

901 ATCTTTTCGA CAGGCAATGA CGCACAAGCT CAGCCCAACA
     CATATGCCCT

951 ATTGCCATTT TATGAAAAAG ACGCTCAAAA AGGCATTATC
     ACAGTCGCAG

1001 GCGTAGACCG CAGTGGAGAA AAGTTCAAAC GGGAAATGTA
     TGGAGAACCG

1051 GGTACAGAAC CGCTTGAGTA TGGCTCCAAC CATTGCGGAA
     TTACTGCCAT

1101 GTGGTGCCTG TCGGCACCCT ATGAAGCAAG CGTCCGTTTC
     ACCCGTACAA

1151 ACCCGATTCA AATTGCCGGA ACATCCTTTT CCGCACCCAT
     CGTAACCGGC

1201 ACGGCGGCTC TGCTGCTGCA GAAATACCCG TGGATGAGCA
     ACGACAACCT

1251 GCGTACCACG TTGCTGACGA CGGCTCAGGA CATCGGTGCA
     GTCGGCGTGG

1301 ACAGCAAGTT CGGCTGGGGA CTGCTGGATG CGGGTAAGGC
     CATGAACGGA

1351 CCCGCGTCCT TTCCGTTCGG CGACTTTACC GCCGATACGA
     AAGGTACATC

1401 CGATATTGCC TACTCCTTCC GTAACGACAT TTCAGGCACG
     GGCGGCCTGA

1451 TCAAAAAAGG CGGCAGCCAA CTGCAACTGC ACGGCAACAA
     CACCTATACG

1501 GGCAAAACCA TTATCGAAGG CGGTTCGCTG GTGTTGTACG
     GCAACAACAA

1551 ATCGGATATG CGCGTCGAAA CCAAAGGTGC GCTGATTTAT
     AACGGGGCGG

1601 CATCCGGCGG CAGCCTGAAC AGCGACGGCA TTGTCTATCT
     GGCAGATACC

1651 GACCAATCCG GCGCAAACGA AACCGTACAC ATCAAAGGCA
     GTCTGCAGCT

1701 GGACGGCAAA GGTACGCTGT ACACACGTTT GGGCAAACTG
     CTGAAAGTGG

1751 ACGGTACGGC GATTATCGGC GGCAAGCTGT ACATGTCGGC
     ACGCGGCAAG

1801 GGGGCAGGCT ATCTCAACAG TACCGGACGA CGTGTTCCCT
     TCCTGAGTGC

1851 CGCCAAAATC GGGCAGGATT ATTCTTTCTT CACAAACATC
     GAAACCGACG

1901 GCGGCCTGCT GGCTTCCCTC GACAGCGTCG AAAAAACAGC
     GGGCAGTGAA

1951 GGCGACACGC TGTCCTATTA TGTCCGTCGC GGCAATGCGG
     CACGGACTGC

2001 TTCGGCAGCG GCACATTCCG CGCCCGCCGG TCTGAAACAC
     GCCGTAGAAC

2051 AGGGCGGCAG CAATCTGGAA AACCTGATGG TCGAACTGGA
     TGCCTCCGAA

2101 TCATCCGCAA CACCCGAGAC GGTTGAAACT GCGGCAGCCG
     ACCGCACAGA

2151 TATGCCGGGC ATCCGCCCCT ACGGCGCAAC TTTCCGCGCA
     GCGGCAGCCG

2201 TACAGCATGC GAATGCCGCC GACGGTGTAC GCATCTTCAA
     CAGTCTCGCC

2251 GCTACCGTCT ATGCCGACAG TACCGCCGCC CATGCCGATA
     TGCAGGGACG

2301 CCGCCTGAAA GCCGTATCGG ACGGGTTGGA CCACAACGGC
     ACGGGTCTGC

2351 GCGTCATCGC GCAAACCCAA CAGGACGGTG AACGTGGGA
     ACAGGGCGGT

2401 GTTGAAGGCA AAATGCGCGG CAGTACCCAA ACCGTCGGCA
     TTGCCGCGAA

2451 AACCGGCGAA AATACGACAG CAGCCGCCAC ACTGGGCATG
     GGACGCAGCA

2501 CATGGAGCGA AAACAGTGCA AATGCAAAAA CCGACAGCAT
     TAGTCTGTTT

2551 GCAGGCATAC GGCACGATGC GGGCGATATC GGCTATCTCA
     AAGGCCTGTT

2601 CTCCTACGGA CGCTACAAAA ACAGCATCAG CCGCAGCACC
     GGTGCGGACG

2651 AACATGCGAA AGGCAGCGTC AACGGCACGC TGATGCAGCT
     GGGCGCACTG

2701 GGCGGTGTCA ACGTTCCGTT TGCCGCAACG GGAGATTTGA
     CGGTCGAAGG

2751 CGGTCTGCGC TACGACCTGC TCAAACAGGA TGCATTCGCC
     GAAAAAGGCA

2801 GTGCTTTGGG CTGGAGCGGC AACAGCCTCA CTGAAGGCAC
     GCTGGTCGGA

2851 CTCGCGGGTC TGAAGCTGTC GCAACCCTTG AGCGATAAAG
     CCGTCCTGTT

2901 TGCAACGGCG GCGTGGAAC GCGACCTGAA CGGACGCGAC
     TACACGGTAA

2951 CGGGCGGCTT TACCGGCGCG ACTGCAGCAA CCGGCAAGAC
     GGGGGCACGC

3001 AATATGCCGC ACACCCGTCT GGTTGCCGGC CTGGGCGCGG
     ATGTCGAATT

3051 CGGCAACGGC TGGAACGGCT TGGCACGTTA CAGCTACGCC
     GGTTCCAAAC

3101 AGTACGGCAA CCACAGCGGA CGAGTCGGCG TAGGCTACCG
     GTTCCTCGAG

3151 GGATCCGGAG GGGGTGGTGT CGCCGCCGAC ATCGGTGCGG
     GGCTTGCCGA
```

```
3201 TGCACTAACC GCACCGCTCG ACCATAAAGA CAAAGGTTTG
     CAGTCTTTGA

3251 CGCTGGATCA GTCCGTCAGG AAAAACGAGA AACTGAAGCT
     GGCGGCACAA

3301 GGTGCGGAAA AAACTTATGG AAACGGTGAC AGCCTCAATA
     CGGGCAAATT

3351 GAAGAACGAC AAGGTCAGCC GTTTCGACTT TATCCGCCAA
     ATCGAAGTGG

3401 ACGGGCAGCT CATTACCTTG GAGAGTGGAG AGTTCCAAGT
     ATACAAACAA

3451 AGCCATTCCG CCTTAACCGC CTTTCAGACC GAGCAAATAC
     AAGATTCGGA

3501 GCATTCCGGG AAGATGGTTG CGAAACGCCA GTTCAGAATC
     GGCGACATAG

3551 CGGGCGAACA TACATCTTTT GACAAGCTTC CCGAAGGCGG
     CAGGGCGACA

3601 TATCGCGGGA CGGCGTTCGG TTCAGACGAT GCCGGCGGAA
     AACTGACCTA

3651 CACCATAGAT TTCGCCGCCA AGCAGGGAAA CGGCAAAATC
     GAACATTTGA

3701 AATCGCCAGA ACTCAATGTC GACCTGGCCG CCGCCGATAT
     CAAGCCGGAT

3751 GGAAAACGCC ATGCCGTCAT CAGCGGTTCC GTCCTTTACA
     ACCAAGCCGA

3801 GAAAGGCAGT TACTCCCTCG GTATCTTTGG CGGAAAAGCC
     CAGGAAGTTG

3851 CCGGCAGCGC GGAAGTGAAA ACCGTAAACG GCATACGCCA
     TATCGGCCTT

3901 GCCGCCAAGC AACTCGAGCA CCACCACCAC CACCACTGA

1 MTSAPDFNAG GTGIGSNSRA TTAKSAAVSY AGIKNEMCKD
     RSMLCAGRDD

51 VAVTDRDAKI NAPPPNLHTG DFPNPNDAYK NLINLKPAIE
     AGYTGRGVEV

101 GIVDTGESVG SISFPELYGR KEHGYNENYK NYTAYMRKEA
     PEDGGGKDIE

151 ASFDDEAVIE TEAKPTDIRH VKEIGHIDLV SHIIGGRSVD
     GRPAGGIAPD

201 ATLHIMNTND ETKNEMMVAA IRNAWVKLGE RGVRIVNNSF
     GTTSRAGTAD

251 LFQIANSEEQ YRQALLDYSG GDKTDEGIRL MQQSDYGNLS
     YHIRNKNMLF

301 IFSTGNDAQA QPNTYALLPF YEKDAQKGII TVAGVDRSGE
     KFKREMYGEP

351 GTEPLEYGSN HCGITAMWCL SAPYEASVRF TRTNPIQIAG
     TSFSAPIVTG

401 TAALLLQKYP WMSNDNLRTT LLTTAQDIGA VGVDSKFGWG
     LLDAGKAMNG

451 PASFPFGDFT ADTKGTSDIA YSFRNDISGT GGLIKKGGSQ
     LQLHGNNTYT

501 GKTIIEGGSL VLYGNNKSDM RVETKGALIY NGAASGGSLN
     SDGIVYLADT

551 DQSGANETVH IKGSLQLDGK GTLYTRLGKL LKVDGTAIIG
     GKLYMSARGK

601 GAGYLNSTGR RVPFLSAAKI GQDYSFFTNI ETDGGLLASL
     DSVEKTAGSE

651 GDTLSYYVRR GNAARTASAA AHSAPAGLKH AVEQGGSNLE
     NLMVELDASE

701 SSATPETVET AAADRTDMPG IRPYGATFRA AAAVQHANAA
     DGVRIFNSLA

751 ATVYADSTAA HADMQGRRLK AVSDGLDHNG TGLRVIAQTQ
     QDGGTWEQGG

801 VEGKMRGSTQ TVGIAAKTGE NTTAAATLGM GRSTWSENSA
     NAKTDSISLF

851 AGIRHDAGDI GYLKGLFSYG RYKNSISRST GADEHAEGSV
     NGTLMQLGAL

901 GGVNVPFAAT GDLTVEGGLR YDLLKQDAFA EKGSALGWSG
     NSLTEGTLVG

951 LAGLKLSQPL SDKAVLFATA GVERDLNGRD YTVTGGFTGA
     TAATGKTGAR

1001 NMPHTRLVAG LGADVEFGNG WNGLARYSYA GSKQYGNHSG
     RVGVGYRFLE

1051 GSGGGGVAAD IGAGLADALT APLDHKDKGL QSLTLDQSVR
     KNEKLKLAAQ

1101 GAEKTYGNGD SLNTGKLKND KVSRFDFIRQ IEVDGQLITL
     ESGEFQVYKQ

1151 SHSALTAFQT EQIQDSEHSG KMVAKRQFRI GDIAGEHTSF
     DKLPEGGRAT

1201 YRGTAFGSDD AGGKLTYTID FAAKQGNGKI EHLKSPELNV
     DLAAADIKPD

1251 GKRHAVISGS VLYNQAEKGS YSLGIFGGKA QEVAGSAEVK
     TVNGIRHIGL

1301 AAKQLEHHHH HH*

ΔG983-961
   1 ATGACTTCTG CGCCCGACTT CAATGCAGGC GGTACCGGTA
     TCGGCAGCAA

51 CAGCAGAGCA ACAACAGCGA AATCAGCAGC AGTATCTTAC
     GCCGGTATCA

101 AGAACGAAAT GTGCAAAGAC AGAAGCATGC TCTGTGCCGG
     TCGGGATGAC

151 GTTGCGGTTA CAGACAGGGA TGCCAAAATC AATGCCCCCC
     CCCCGAATCT

201 GCATACCGGA GACTTTCCAA ACCCAAATGA CGCATACAAG
     AATTTGATCA

251 ACCTCAAACC TGCAATTGAA GCAGGCTATA CAGGACGCGG
     GGTAGAGGTA

301 GGTATCGTCG ACACAGGCGA ATCCGTCGGC AGCATATCCT
     TTCCCGAACT

351 GTATGGCAGA AAAGAACACG GCTATAACGA AAATTACAAA
     AACTATACGG

401 CGTATATGCG GAAGGAAGCG CCTGAAGACG GAGGCGGTAA
     AGACATTGAA

451 GCTTCTTTCG ACGATGAGGC CGTTATAGAG ACTGAAGCAA
     AGCCGACGGA

501 TATCCGCCAC GTAAAAGAAA TCGGACACAT CGATTTGGTC
     TCCCATATTA
```

```
 551 TTGGCGGGCG TTCCGTGGAC GGCAGACCTG CAGGCGGTAT
     TGCGCCCGAT
 601 GCGACGCTAC ACATAATGAA TACGAATGAT GAAACCAAGA
     ACGAAATGAT
 651 GGTTGCAGCC ATCCGCAATG CATGGGTCAA GCTGGGCGAA
     CGTGGCGTGC
 701 GCATCGTCAA TAACAGTTTT GGAACAACAT CGAGGGCAGG
     CACTGCCGAC
 751 CTTTTCCAAA TAGCCAATTC GGAGGAGCAG TACCGCCAAG
     CGTTGCTCGA
 801 CTATTCCGGC GGTGATAAAA CAGACGAGGG TATCCGCCTG
     ATGCAACAGA
 851 GCGATTACGG CAACCTGTCC TACCACATCC GTAATAAAAA
     CATGCTTTTC
 901 ATCTTTTCGA CAGGCAATGA CGCACAAGCT CAGCCCAACA
     CATATGCCCT
 951 ATTGCCATTT TATGAAAAAG ACGCTCAAAA AGGCATTATC
     ACAGTCGCAG
1001 GCGTAGACCG CAGTGGAGAA AAGTTCAAAC GGGAAATGTA
     TGGAGAACCG
1051 GGTACAGAAC CGCTTGAGTA TGGCTCCAAC CATTGCGGAA
     TTACTGCCAT
1101 GTGGTGCCTG TCGGCACCCT ATGAAGCAAG CGTCCGTTTC
     ACCCGTACAA
1151 ACCCGATTCA AATTGCCGGA ACATCCTTTT CCGCACCCAT
     CGTAACCGGC
1201 ACGGCGGCTC TGCTGCTGCA GAAATACCCG TGGATGAGCA
     ACGACAACCT
1251 GCGTACCACG TTGCTGACGA CGGCTCAGGA CATCGGTGCA
     GTCGGCGTGG
1301 ACAGCAAGTT CGGCTGGGGA CTGCTGGATG CGGGTAAGGC
     CATGAACGGA
1351 CCCGCGTCCT TTCCGTTCGG CGACTTTACC GCCGATACGA
     AAGGTACATC
1401 CGATATTGCC TACTCCTTCC GTAACGACAT TTCAGGCACG
     GGCGGCCTGA
1451 TCAAAAAAGG CGGCAGCCAA CTGCAACTGC ACGGCAACAA
     CACCTATACG
1501 GGCAAAACCA TTATCGAAGG CGGTTCGCTG GTGTTGTACG
     GCAACAACAA
1551 ATCGGATATG CGCGTCGAAA CCAAAGGTGC GCTGATTTAT
     AACGGGGCGG
1601 CATCCGGCGG CAGCCTGAAC AGCGACGGCA TTGTCTATCT
     GGCAGATACC
1651 GACCAATCCG GCGCAAACGA AACCGTACAC ATCAAAGGCA
     GTCTGCAGCT
1701 GGACGGCAAA GGTACGCTGT ACACACGTTT GGGCAAACTG
     CTGAAAGTGG
1751 ACGGTACGGC GATTATCGGC GGCAAGCTGT ACATGTCGGC
     ACGCGGCAAG
1801 GGGGCAGGCT ATCTCAACAG TACCGGACGA CGTGTTCCCT
     TCCTGAGTGC
1851 CGCCAAAATC GGGCAGGATT ATTCTTTCTT CACAAACATC
     GAAACCGACG
1901 GCGGCCTGCT GGCTTCCCTC GACAGCGTCG AAAAAACAGC
     GGGCAGTGAA
1951 GGCGACACGC TGTCCTATTA TGTCCGTCGC GGCAATGCGG
     CACGGACTGC
2001 TTCGGCAGCG GCACATTCCG CGCCCGCCGG TCTGAAACAC
     GCCGTAGAAC
2051 AGGGCGGCAG CAATCTGGAA AACCTGATGG TCGAACTGGA
     TGCCTCCGAA
2101 TCATCCGCAA CACCCGAGAC GGTTGAAACT GCGGCAGCCG
     ACCGCACAGA
2151 TATGCCGGGC ATCCGCCCCT ACGGCGCAAC TTTCCGCGCA
     GCGGCAGCCG
2201 TACAGCATGC GAATGCCGCC GACGGTGTAC GCATCTTCAA
     CAGTCTCGCC
2251 GCTACCGTCT ATGCCGACAG TACCGCCGCC CATGCCGATA
     TGCAGGGACG
2301 CCGCCTGAAA GCCGTATCGG ACGGGTTGGA CCACAACGGC
     ACGGGTCTGC
2351 GCGTCATCGC GCAAACCCAA CAGGACGGTG AACGTGGGA
     ACAGGGCGGT
2401 GTTGAAGGCA AAATGCGCGG CAGTACCCAA ACCGTCGGCA
     TTGCCGCGAA
2451 AACCGGCGAA AATACGACAG CAGCCGCCAC ACTGGGCATG
     GGACGCAGCA
2501 CATGGAGCGA AACAGTGCA AATGCAAAAA CCGACAGCAT
     TAGTCTGTTT
2551 GCAGGCATAC GGCACGATGC GGGCGATATC GGCTATCTCA
     AAGGCCTGTT
2601 CTCCTACGGA CGCTACAAAA ACAGCATCAG CCGCAGCACC
     GGTGCGGACG
2651 AACATGCGGA AGGCAGCGTC AACGGCACGC TGATGCAGCT
     GGGCGCACTG
2701 GGCGGTGTCA ACGTTCCGTT TGCCGCAACG GGAGATTTGA
     CGGTCGAAGG
2751 CGGTCTGCGC TACGACCTGC TCAAACAGGA TGCATTCGCC
     GAAAAAGGCA
2801 GTGCTTTGGG CTGGAGCGGC AACAGCCTCA CTGAAGGCAC
     GCTGGTCGGA
2851 CTCGCGGGTC TGAAGCTGTC GCAACCCTTG AGCGATAAAG
     CCGTCCTGTT
2901 TGCAACGGCG GCGTGGAAC GCGACCTGAA CGGACGCGAC
     TACACGGTAA
2951 CGGGCGGCTT TACCGGCGCG ACTGCAGCAA CCGGCAAGAC
     GGGGGCACGC
3001 AATATGCCGC ACACCCGTCT GGTTGCCGGC CTGGGCGCGG
     ATGTCGAATT
3051 CGGCAACGGC TGGAACGGCT TGGCACGTTA CAGCTACGCC
     GGTTCCAAAC
3101 AGTACGGCAA CCACAGCGGA CGAGTCGGCG TAGGCTACCG
     GTTCCTCGAG
3151 GGTGGCGGAG GCACTGGATC CGCCACAAAC GACGACGATG
     TTAAAAAAGC
3201 TGCCACTGTG GCCATTGCTG CTGCCTACAA CAATGGCCAA
     GAAATCAACG
```

```
3251 GTTTCAAAGC TGGAGAGACC ATCTACGACA TTGATGAAGA
     CGGCACAATT
3301 ACCAAAAAAG ACGCAACTGC AGCCGATGTT GAAGCCGACG
     ACTTTAAAGG
3351 TCTGGGTCTG AAAAAAGTCG TGACTAACCT GACCAAAACC
     GTCAATGAAA
3401 ACAAACAAAA CGTCGATGCC AAAGTAAAAG CTGCAGAATC
     TGAAATAGAA
3451 AAGTTAACAA CCAAGTTAGC AGACACTGAT GCCGCTTTAG
     CAGATACTGA
3501 TGCCGCTCTG GATGCAACCA CCAACGCCTT GAATAAATTG
     GGAGAAAATA
3551 TAACGACATT TGCTGAAGAG ACTAAGACAA ATATCGTAAA
     AATTGATGAA
3601 AAATTAGAAG CCGTGGCTGA TACCGTCGAC AAGCATGCCG
     AAGCATTCAA
3651 CGATATCGCC GATTCATTGG ATGAAACCAA CACTAAGGCA
     GACGAAGCCG
3701 TCAAACCGC CAATGAAGCC AAACAGACGG CCGAAGAAAC
     CAAACAAAAC
3751 GTCGATGCCA AAGTAAAAGC TGCAGAAACT GCAGCAGGCA
     AAGCCGAAGC
3801 TGCCGCTGGC ACAGCTAATA CTGCAGCCGA CAAGGCCGAA
     GCTGTCGCTG
3851 CAAAAGTTAC CGACATCAAA GCTGATATCG CTACGAACAA
     AGATAATATT
3901 GCTAAAAAG CAAACAGTGC CGACGTGTAC ACCAGAGAAG
     AGTCTGACAG
3951 CAAATTTGTC AGAATTGATG GTCTGAACGC TACTACCGAA
     AAATTGGACA
4001 CACGCTTGGC TTCTGCTGAA AAATCCATTG CCGATCACGA
     TACTCGCCTG
4051 AACGGTTTGG ATAAAACAGT GTCAGACCTG CGCAAAGAAA
     CCCGCCAAGG
4101 CCTTGCAGAA CAAGCCGCGC TCTCCGGTCT GTTCCAACCT
     TACAACGTGG
4151 GTCGGTTCAA TGTAACGGCT GCAGTCGGCG GCTACAAATC
     CGAATCGGCA
4201 GTCGCCATCG GTACCGGCTT CCGCTTTACC GAAAACTTTG
     CCGCCAAAGC
4251 AGGCGTGGCA GTCGGCACTT CGTCCGGTTC TTCCGCAGCC
     TACCATGTCG
4301 GCGTCAATTA CGAGTGGCTC GAGCACCACC ACCACCACCA
     CTGA

1 MTSAPDFNAG GTGIGSNSRA TTAKSAAVSY AGIKNEMCKD
     RSMLCAGRDD
  51 VAVTDRDAKI NAPPPNLHTG DFPNPNDAYK NLINLKPAIE
     AGYTGRGVEV
 101 GIVDTGESVG SISFPELYGR KEHGYNENYK NYTAYMRKEA
     PEDGGGKDIE
 151 ASFDDEAVIE TEAKPTDIRH VKEIGHIDLV SHIIGGRSVD
     GRPAGGIAPD
 201 ATLHIMNTND ETKNEMMVAA IRNAWVKLGE RGVRIVNNSF
     GTTSRAGTAD
 251 LFQIANSEEQ YRQALLDYSG GDKTDEGIRL MQQSDYGNLS
     YHIRNKNMLF
 301 IFSTGNDAQA QPNTYALLPF YEKDAQKGII TVAGVDRSGE
     KFKREMYGEP
 351 GTEPLEYGSN HCGITAMWCL SAPYEASVRF TRTNPIQIAG
     TSFSAPIVTG
 401 TAALLLQKYP WMSNDNLRTT LLTTAQDIGA VGVDSKFGWG
     LLDAGKAMNG
 451 PASFPFGDFT ADTKGTSDIA YSFRNDISGT GGLIKKGGSQ
     LQLHGNNTYT
 501 GKTIIEGGSL VLYGNNKSDM RVETKGALIY NGAASGGSLN
     SDGIVYLADT
 551 DQSGANETVH IKGSLQLDGK GTLYTRLGKL LKVDGTAIIG
     GKLYMSARGK
 601 GAGYLNSTGR RVPFLSAAKI GQDYSFFTNI ETDGGLLASL
     DSVEKTAGSE
 651 GDTLSYYVRR GNAARTASAA AHSAPAGLKH AVEQGGSNLE
     NLMVELDASE
 701 SSATPETVET AAADRTDMPG IRPYGATFRA AAAVQHANAA
     DGVRIFNSLA
 751 ATVYADSTAA HADMQGRRLK AVSDGLDHNG TGLRVIAQTQ
     QDGGTWEQGG
 801 VEGKMRGSTQ TVGIAAKTGE NTTAAATLGM GRSTWSENSA
     NAKTDSISLF
 851 AGIRHDAGDI GYLKGLFSYG RYKNSISRST GADEHAEGSV
     NGTLMQLGAL
 901 GGVNVPFAAT GDLTVEGGLR YDLLKQDAFA EKGSALGWSG
     NSLTEGTLVG
 951 LAGLKLSQPL SDKAVLFATA GVERDLNGRD YTVTGGFTGA
     TAATGKTGAR
1001 NMPHTRLVAG LGADVEFGNG WNGLARYSYA GSKQYGNHSG
     RVGVGYRFLE
1051 GGGGTGSATN DDDVKKAATV AIAAAYNNGQ EINGFKAGET
     IYDIDEDGTI
1101 TKKDATAADV EADDFKGLGL KKVVTNLTKT VNENKQNVDA
     KVKAAESEIE
1151 KLTTKLADTD AALADTDAAL DATTNALNKL GENITTFAEE
     TKTNIVKIDE
1201 KLEAVADTVD KHAEAFNDIA DSLDETNTKA DEAVKTANEA
     KQTAEETKQN
1251 VDAKVKAAET AAGKAEAAAG TANTAADKAE AVAAKVTDIK
     ADIATNKDNI
1301 AKKANSADVY TREESDSKFV RIDGLNATTE KLDTRLASAE
     KSIADHDTRL
1351 NGLDKTVSDL RKETRQGLAE QAALSGLFQP YNVGRFNVTA
     AVGGYKSESA
1401 VAIGTGFRFT ENFAAKAGVA VGTSSGSSAA YHVGVNYEWL
     EHHHHHH*

ΔG983-961c
   1 ATGACTTCTG CGCCCGACTT CAATGCAGGC GGTACCGGTA
     TCGGCAGCAA
  51 CAGCAGAGCA ACAACAGCGA AATCAGCAGC AGTATCTTAC
     GCCGGTATCA
 101 AGAACGAAAT GTGCAAAGAC AGAAGCATGC TCTGTGCCGG
     TCGGGATGAC
```

```
 151 GTTGCGGTTA CAGACAGGGA TGCCAAAATC AATGCCCCCC
     CCCCGAATCT

201 GCATACCGGA GACTTTCCAA ACCCAAATGA CGCATACAAG
     AATTTGATCA

251 ACCTCAAACC TGCAATTGAA GCAGGCTATA CAGGACGCGG
     GGTAGAGGTA

301 GGTATCGTCG ACACAGGCGA ATCCGTCGGC AGCATATCCT
     TTCCCGAACT

351 GTATGGCAGA AAAGAACACG GCTATAACGA AAATTACAAA
     AACTATACGG

401 CGTATATGCG GAAGGAAGCG CCTGAAGACG GAGGCGGTAA
     AGACATTGAA

451 GCTTCTTTCG ACGATGAGGC CGTTATAGAG ACTGAAGCAA
     AGCCGACGGA

501 TATCCGCCAC GTAAAAGAAA TCGGACACAT CGATTTGGTC
     TCCCATATTA

551 TTGGCGGGCG TTCCGTGGAC GGCAGACCTG CAGGCGGTAT
     TGCGCCCGAT

601 GCGACGCTAC ACATAATGAA TACGAATGAT GAAACCAAGA
     ACGAAATGAT

651 GGTTGCAGCC ATCCGCAATG CATGGGTCAA GCTGGGCGAA
     CGTGGCGTGC

701 GCATCGTCAA TAACAGTTTT GGAACAACAT CGAGGGCAGG
     CACTGCCGAC

751 CTTTTCCAAA TAGCCAATTC GGAGGAGCAG TACCGCCAAG
     CGTTGCTCGA

801 CTATTCCGGC GGTGATAAAA CAGACGAGGG TATCCGCCTG
     ATGCAACAGA

851 GCGATTACGG CAACCTGTCC TACCACATCC GTAATAAAAA
     CATGCTTTTC

901 ATCTTTTCGA CAGGCAATGA CGCACAAGCT CAGCCCAACA
     CATATGCCCT

951 ATTGCCATTT TATGAAAAAG ACGCTCAAAA AGGCATTATC
     ACAGTCGCAG

1001 GCGTAGACCG CAGTGGAGAA AAGTTCAAAC GGGAAATGTA
     TGGAGAACCG

1051 GGTACAGAAC CGCTTGAGTA TGGCTCCAAC CATTGCGGAA
     TTACTGCCAT

1101 GTGGTGCCTG TCGGCACCCT ATGAAGCAAG CGTCCGTTTC
     ACCCGTACAA

1151 ACCCGATTCA AATTGCCGGA ACATCCTTTT CCGCACCCAT
     CGTAACCGGC

1201 ACGGCGGCTC TGCTGCTGCA GAAATACCCG TGGATGAGCA
     ACGACAACCT

1251 GCGTACCACG TTGCTGACGA CGGCTCAGGA CATCGGTGCA
     GTCGGCGTGG

1301 ACAGCAAGTT CGGCTGGGGA CTGCTGGATG CGGGTAAGGC
     CATGAACGGA

1351 CCCGCGTCCT TTCCGTTCGG CGACTTTACC GCCGATACGA
     AAGGTACATC

1401 CGATATTGCC TACTCCTTCC GTAACGACAT TTCAGGCACG
     GGCGGCCTGA

1451 TCAAAAAAGG CGGCAGCCAA CTGCAACTGC ACGGCAACAA
     CACCTATACG

1501 GGCAAAACCA TTATCGAAGG CGGTTCGCTG GTGTTGTACG
     GCAACAACAA

1551 ATCGGATATG CGCGTCGAAA CCAAAGGTGC GCTGATTTAT
     AACGGGGCGG

1601 CATCCGGCGG CAGCCTGAAC AGCGACGGCA TTGTCTATCT
     GGCAGATACC

1651 GACCAATCCG GCGCAAACGA AACCGTACAC ATCAAAGGCA
     GTCTGCAGCT

1701 GGACGGCAAA GGTACGCTGT ACACACGTTT GGGCAAACTG
     CTGAAAGTGG

1751 ACGGTACGGC GATTATCGGC GGCAAGCTGT ACATGTCGGC
     ACGCGGCAAG

1801 GGGGCAGGCT ATCTCAACAG TACCGGACGA CGTGTTCCCT
     TCCTGAGTGC

1851 CGCCAAAATC GGGCAGGATT ATTCTTTCTT CACAAACATC
     GAAACCGACG

1901 GCGGCCTGCT GGCTTCCCTC GACAGCGTCG AAAAAACAGC
     GGGCAGTGAA

1951 GGCGACACGG TGTCCTATTA TGTCCGTCGC GGCAATGCGG
     CACGGACTGC

2001 TTCGGCAGCG GCACATTCCG CGCCCGCCGG TCTGAAACAC
     GCCGTAGAAC

2051 AGGGCGGCAG CAATCTGGAA AACCTGATGG TCGAACTGGA
     TGCCTCCGAA

2101 TCATCCGCAA CACCCGAGAC GGTTGAAACT GCGGCAGCCG
     ACCGCACAGA

2151 TATGCCGGGC ATCCGCCCCT ACGGCGCAAC TTTCCGCGCA
     GCGGCAGCCG

2201 TACAGCATGC GAATGCCGCC GACGGTGTAC GCATCTTCAA
     CAGTCTCGCC

2251 GCTACCGTCT ATGCCGACAG TACCGCCGCC CATGCCGATA
     TGCAGGGACG

2301 CCGCCTGAAA GCCGTATCGG ACGGGTTGGA CCACAACGGC
     ACGGGTCTGC

2351 GCGTCATCGC GCAAACCCAA CAGGACGGTG AACGTGGGA
     ACAGGGCGGT

2401 GTTGAAGGCA AAATGCGCGG CAGTACCCAA ACCGTCGGCA
     TTGCCGCGAA

2451 AACCGGCGAA AATACGACAG CAGCCGCCAC ACTGGGCATG
     GGACGCAGCA

2501 CATGGAGCGA AACAGTGCA AATGCAAAAA CCGACAGCAT
     TAGTCTGTTT

2551 GCAGGCATAC GGCACGATGC GGGCGATATC GGCTATCTCA
     AAGGCCTGTT

2601 CTCCTACGGA CGCTACAAAA ACAGCATCAG CCGCAGCACC
     GGTGCGGACG

2651 AACATGCGGA AGGCAGCGTC AACGGCACGC TGATGCAGCT
     GGGCGCACTG

2701 GGCGGTGTCA ACGTTCCGTT TGCCGCAACG GGAGATTTGA
     CGGTCGAAGG

2751 CGGTCTGCGC TACGACCTGC TCAAACAGGA TGCATTCGCC
     GAAAAAGGCA

2801 GTGCTTTGGG CTGGAGCGGC AACAGCCTCA CTGAAGGCAC
     GCTGGTCGGA
```

```
2851  CTCGCGGGTC TGAAGCTGTC GCAACCCTTG AGCGATAAAG
      CCGTCCTGTT

2901  TGCAACGGCG GGCGTGGAAC GCGACCTGAA CGGACGCGAC
      TACACGGTAA

2951  CGGGCGGCTT TACCGGCGCG ACTGCAGCAA CCGGCAAGAC
      GGGGGCACGC

3001  AATATGCCGC ACACCCGTCT GGTTGCCGGC CTGGGCGCGG
      ATGTCGAATT

3051  CGGCAACGGC TGGAACGGCT TGGCACGTTA CAGCTACGCC
      GGTTCCAAAC

3101  AGTACGGCAA CCACAGCGGA CGAGTCGGCG TAGGCTACCG
      GTTCCTCGAG

3151  GGTGGCGGAG GCACTGGATC CGCCACAAAC GACGACGATG
      TTAAAAAAGC

3201  TGCCACTGTG GCCATTGCTG CTGCCTACAA CAATGGCCAA
      GAAATCAACG

3251  GTTTCAAAGC TGGAGAGACC ATCTACGACA TTGATGAAGA
      CGGCACAATT

3301  ACCAAAAAAG ACGCAACTGC AGCCGATGTT GAAGCCGACG
      ACTTTAAAGG

3351  TCTGGGTCTG AAAAAAGTCG TGACTAACCT GACCAAAACC
      GTCAATGAAA

3401  ACAAACAAAA CGTCGATGCC AAAGTAAAAG CTGCAGAATC
      TGAAATAGAA

3451  AAGTTAACAA CCAAGTTAGC AGACACTGAT GCCGCTTTAG
      CAGATACTGA

3501  TGCCGCTCTG GATGCAACCA CCAACGCCTT GAATAAATTG
      GGAGAAAATA

3551  TAACGACATT TGCTGAAGAG ACTAAGACAA ATATCGTAAA
      AATTGATGAA

3601  AAATTAGAAG CCGTGGCTGA TACCGTCGAC AAGCATGCCG
      AAGCATTCAA

3651  CGATATCGCC GATTCATTGG ATGAAACCAA CACTAAGGCA
      GACGAAGCCG

3701  TCAAAACCGC CAATGAAGCC AAACAGACGG CCGAAGAAAC
      CAAACAAAAC

3751  GTCGATGCCA AAGTAAAAGC TGCAGAAACT GCAGCAGGCA
      AAGCCGAAGC

3801  TGCCGCTGGC ACAGCTAATA CTGCAGCCGA CAAGGCCGAA
      GCTGTCGCTG

3851  CAAAAGTTAC CGACATCAAA GCTGATATCG CTACGAACAA
      AGATAATATT

3901  GCTAAAAAAG CAAACAGTGC CGACGTGTAC ACCAGAGAAG
      AGTCTGACAG

3951  CAAATTTGTC AGAATTGATG GTCTGAACGC TACTACCGAA
      AAATTGGACA

4001  CACGCTTGGC TTCTGCTGAA AAATCCATTG CCGATCACGA
      TACTCGCCTG

4051  AACGTTTGG ATAAAACAGT GTCAGACCTG CGCAAAGAAA
      CCCGCCAAGG

4101  CCTTGCGAA CAAGCCGCGC TCTCCGGTCT GTTCCAACCT
      TACAACGTGG

4151  GTCTCGAGCA CCACCACCAC CACCACTGA
```

```
   1  MTSAPDFNAG GTGIGSNSRA TTAKSAAVSY AGIKNEMCKD
      RSMLCAGRDD

51  VAVTDRDAKI NAPPPNLHTG DFPNPNDAYK NLINLKPAIE
      AGYTGRGVEV

101  GIVDTGESVG SISFPELYGR KEHGYNENYK NYTAYMRKEA
      PEDGGGKDIE

151  ASFDDEAVIE TEAKPTDIRH VKEIGHIDLV SHIIGGRSVD
      GRPAGGIAPD

201  ATLHIMNTND ETKNEMMVAA IRNAWVKLGE RGVRIVNNSF
      GTTSRAGTAD

251  LFQIANSEEQ YRQALLDYSG GDKTDEGIRL MQQSDYGNLS
      YHIRNKNMLF

301  IFSTGNDAQA QPNTYALLPF YEKDAQKGII TVAGVDRSGE
      KFKREMYGEP

351  GTEPLEYGSN HCGITAMWCL SAPYEASVRF TRTNPIQIAG
      TSFSAPIVTG

401  TAALLLQKYP WMSNDNLRTT LLTTAQDIGA VGVDSKFGWG
      LLDAGKAMNG

451  PASFPFGDFT ADTKGTSDIA YSFRNDISGT GGLIKKGGSQ
      LQLHGNNTYT

501  GKTIIEGGSL VLYGNNKSDM RVETKGALIY NGAASGGSLN
      SDGIVYLADT

551  DQSGANETVH IKGSLQLDGK GTLYTRLGKL LKVDGTAIIG
      GKLYMSARGK

601  GAGYLNSTGR RVPFLSAAKI GQDYSFFTNI ETDGGLLASL
      DSVEKTAGSE

651  GDTLSYYVRR GNAARTASAA AHSAPAGLKH AVEQGGSNLE
      NLMVELDASE

701  SSATPETVET AAADRTDMPG IRPYGATFRA AAAVQHANAA
      DGVRIFNSLA

751  ATVYADSTAA HADMQGRRLK AVSDGLDHNG TGLRVIAQTQ
      QDGGTWEQGG

801  VEGKMRGSTQ TVGIAAKTGE NTTAAATLGM GRSTWSENSA
      NAKTDSISLF

851  AGIRHDAGDI GYLKGLFSYG RYKNSISRST GADEHAEGSV
      NGTLMQLGAL

901  GGVNVPFAAT GDLTVEGGLR YDLLKQDAFA EKGSALGWSG
      NSLTEGTLVG

951  LAGLKLSQPL SDKAVLFATA GVERDLNGRD YTVTGGFTGA
      TAATGKTGAR

1001  NMPHTRLVAG LGADVEFGNG WNGLARYSYA GSKQYGNHSG
      RVGVGYRFLE

1051  GGGGTGSATN DDDVKKAATV AIAAAYNNGQ EINGFKAGET
      IYDIDEDGTI

1101  TKKDATAADV EADDFKGLGL KKVVTNLTKT VNENKQNVDA
      KVKAAESEIE

1151  KLTTKLADTD AALADTDAAL DATTNALNKL GENITTFAEE
      TKTNIVKIDE

1201  KLEAVADTVD KHAEAFNDIA DSLDETNTKA DEAVKTANEA
      KQTAEEETKQN

1251  VDAKVKAAET AAGKAEAAAG TANTAADKAE AVAAKVTDIK
      ADIATNKDNI
```

```
1301 AKKANSADVY TREESDSKFV RIDGLNATTE KLDTRLASAE
     KSIADHDTRL

1351 NGLDKTVSDL RKETRQGLAE QAALSGLFQP YNVGLEHHHH
     HH*
```

ΔG741 and Hybrids

Bactericidal titres generated in response to ΔG741 (His-fusion) were measured against various strains, including the homologous 2996 strain:

|  | 2996 | MC58 | NGH38 | F6124 | BZ133 |
|---|---|---|---|---|---|
| ΔG741 | 512 | 131072 | >2048 | 16384 | >2048 |

As can be seen, the ΔG741-induced anti-bactericidal titre is particularly high against heterologous strain MC58.

ΔG741 was also fused directly in-frame upstream of proteins 961 (SEQ ID NOS:108 and 109), 961c (SEQ ID NOS: 110 and 111), 983 (SEQ ID NOS:112 and 113) and ORF46.1 (SEQ ID NOS:114 and 115):

```
ΔG741-961
   1 ATGGTCGCCG CCGACATCGG TGCGGGGCTT GCCGATGCAC
     TAACCGCACC

51 GCTCGACCAT AAAGACAAAG GTTTGCAGTC TTTGACGCTG
     GATCAGTCCG

101 TCAGGAAAAA CGAGAAACTG AAGCTGGCGG CACAAGGTGC
     GGAAAAAACT

151 TATGGAAACG GTGACAGCCT CAATACGGGC AAATTGAAGA
     ACGACAAGGT

201 CAGCCGTTTC GACTTTATCC GCCAAATCGA AGTGGACGGG
     CAGCTCATTA

251 CCTTGGAGAG TGGAGAGTTC CAAGTATACA AACAAAGCCA
     TTCCGCCTTA

301 ACCGCCTTTC AGACCGAGCA AATACAAGAT TCGGAGCATT
     CCGGGAAGAT

351 GGTTGCGAAA CGCCAGTTCA GAATCGGCGA CATAGCGGGC
     GAACATACAT

401 CTTTTGACAA GCTTCCCGAA GGCGGCAGGG CGACATATCG
     CGGGACGGCG

451 TTCGGTTCAG ACGATGCCGG CGGAAAACTG ACCTACACCA
     TAGATTTCGC

501 CGCCAAGCAG GGAAACGGCA AAATCGAACA TTTGAAATCG
     CCAGAACTCA

551 ATGTCGACCT GGCCGCCGCC GATATCAAGC CGGATGGAAA
     ACGCCATGCC

601 GTCATCAGCG GTTCCGTCCT TTACAACCAA GCCGAGAAAG
     GCAGTTACTC

651 CCTCGGTATC TTTGGCGGAA AAGCCCAGGA AGTTGCCGGC
     AGCGCGGAAG

701 TGAAAACCGT AAACGGCATA CGCCATATCG GCCTTGCCGC
     CAAGCAACTC

751 GAGGGTGGCG GAGGCACTGG ATCCGCCACA AACGACGACG
     ATGTTAAAAA

801 AGCTGCCACT GTGGCCATTG CTGCTGCCTA CAACAATGGC
     CAAGAAATCA

851 ACGGTTTCAA AGCTGGAGAG ACCATCTACG ACATTGATGA
     AGACGGCACA

901 ATTACCAAAA AAGACGCAAC TGCAGCCGAT GTTGAAGCCG
     ACGACTTTAA

951 AGGTCTGGGT CTGAAAAAAG TCGTGACTAA CCTGACCAAA
     ACCGTCAATG

1001 AAAACAAACA AAACGTCGAT GCCAAAGTAA AAGCTGCAGA
     ATCTGAAATA

1051 GAAAAGTTAA CAACCAAGTT AGCAGACACT GATGCCGCTT
     TAGCAGATAC

1101 TGATGCCGCT CTGGATGCAA CCACCAACGC CTTGAATAAA
     TTGGGAGAAA

1151 ATATAACGAC ATTTGCTGAA GAGACTAAGA CAAATATCGT
     AAAAATTGAT

1201 GAAAAATTAG AAGCCGTGGC TGATACCGTC GACAAGCATG
     CCGAAGCATT

1251 CAACGATATC GCCGATTCAT TGGATGAAAC CAACACTAAG
     GCAGACGAAG

1301 CCGTCAAAAC CGCCAATGAA GCCAAACAGA CGGCCGAAGA
     AACCAAACAA

1351 AACGTCGATG CCAAAGTAAA AGCTGCAGAA ACTGCAGCAG
     GCAAAGCCGA

1401 AGCTGCCGCT GGCACAGCTA ATACTGCAGC CGACAAGGCC
     GAAGCTGTCG

1451 CTGCAAAAGT TACCGACATC AAAGCTGATA TCGCTACGAA
     CAAAGATAAT

1501 ATTGCTAAAA AAGCAAACAG TGCCGACGTG TACACCAGAG
     AAGAGTCTGA

1551 CAGCAAATTT GTCAGAATTG ATGGTCTGAA CGCTACTACC
     GAAAAATTGG

1601 ACACACGCTT GGCTTCTGCT GAAAAATCCA TTGCCGATCA
     CGATACTCGC

1651 CTGAACGGTT TGGATAAAAC AGTGTCAGAC TGCGCAAAG
     AAACCCGCCA

1701 AGGCCTTGCA GAACAAGCCG CGCTCTCCGG TCTGTTCCAA
     CCTTACAACG

1751 TGGGTCGGTT CAATGTAACG GCTGCAGTCG GCGGCTACAA
     ATCCGAATCG

1801 GCAGTCGCCA TCGGTACCGG CTTCCGCTTT ACCGAAAACT
     TTGCCGCCAA

1851 AGCAGGCGTG GCAGTCGGCA CTTCGTCCGG TTCTTCCGCA
     GCCTACCATG

1901 TCGGCGTCAA TTACGAGTGG CTCGAGCACC ACCACCACCA
     CCACTGA

1 MVAADIGAGL ADALTAPLDH KDKGLQSLTL DQSVRKNEKL
     KLAAQGAEKT

51 YGNGDSLNTG KLKNDKVSRF DFIRQIEVDG QLITLESGEF
     QVYKQSHSAL

101 TAFQTEQIQD SEHSGKMVAK RQFRIGDIAG EHTSFDKLPE
     GGRATYRGTA

151 FGSDDAGGKL TYTIDFAAKQ GNGKIEHLKS PELNVDLAAA
     DIKPDGKRHA

201 VISGSVLYNQ AEKGSYSLGI FGGKAQEVAG SAEVKTVNGI
     RHIGLAAKQL
```

-continued

```
251 EGGGGTGSAT NDDDVKKAAT VAIAAAYNNG QEINGFKAGE
    TIYDIDEDGT

301 ITKKDATAAD VEADDFKGLG LKKVVTNLTK TVNENKQNVD
    AKVKAAESEI

351 EKLTTKLADT DAALADTDAA LDATTNALNK LGENITTFAE
    ETKTNIVKID

401 EKLEAVADTV DKHAEAFNDI ADSLDETNTK ADEAVKTANE
    AKQTAEETKQ

451 NVDAKVKAAE TAAGKAEAAA GTANTAADKA EAVAAKVTDI
    KADIATNKDN

501 IAKKANSADV YTREESDSKF VRIDGLNATT EKLDTRLASA
    EKSIADHDTR

551 LNGLDKTVSD LRKETRQGLA EQAALSGLFQ PYNVGRFNVT
    AAVGGYKSES

601 AVAIGTGFRF TENFAAKAGV AVGTSSGSSA AYHVGVNYEW
    LEHHHHHH*
```

ΔG741-961c
```
  1 ATGGTCGCCG CCGACATCGG TGCGGGGCTT GCCGATGCAC
    TAACCGCACC

51 GCTCGACCAT AAAGACAAAG GTTTGCAGTC TTTGACGCTG
    GATCAGTCCG

101 TCAGGAAAAA CGAGAAACTG AAGCTGGCGG CACAAGGTGC
    GGAAAAAACT

151 TATGGAAACG GTGACAGCCT CAATACGGGC AAATTGAAGA
    ACGACAAGGT

201 CAGCCGTTTC GACTTTATCC GCCAAATCGA AGTGGACGGG
    CAGCTCATTA

251 CCTTGGAGAG TGGAGAGTTC CAAGTATACA AACAAGCCA
    TTCCGCCTTA

301 ACCGCCTTTC AGACCGAGCA AATACAAGAT TCGGAGCATT
    CCGGGAAGAT

351 GGTTGCGAAA CGCCAGTTCA GAATCGGCGA CATAGCGGGC
    GAACATACAT

401 CTTTTGACAA GCTTCCCGAA GGCGGCAGGG CGACATATCG
    CGGGACGGCG

451 TTCGGTTCAG ACGATGCCGG CGGAAAACTG ACCTACACCA
    TAGATTTCGC

501 CGCCAAGCAG GGAAACGGCA AAATCGAACA TTTGAAATCG
    CCAGAACTCA

551 ATGTCGACCT GGCCGCCGCC GATATCAAGC CGGATGGAAA
    ACGCCATGCC

601 GTCATCAGCG GTTCCGTCCT TTACAACCAA GCCGAGAAAG
    GCAGTTACTC

651 CCTCGGTATC TTTGGCGGAA AAGCCCAGGA AGTTGCCGGC
    AGCGCGGAAG

701 TGAAAACCGT AAACGGCATA CGCCATATCG GCCTTGCCGC
    CAAGCAACTC

751 GAGGGTGGCG GAGGCACTGG ATCCGCCACA AACGACGACG
    ATGTTAAAAA

801 AGCTGCCACT GTGGCCATTG CTGCTGCCTA CAACAATGGC
    CAAGAAATCA

851 ACGGTTTCAA AGCTGGAGAG ACCATCTACG ACATTGATGA
    AGACGGCACA

901 ATTACCAAAA AAGACGCAAC TGCAGCCGAT GTTGAAGCCG
    ACGACTTTAA
```

-continued

```
 951 AGGTCTGGGT CTGAAAAAAG TCGTGACTAA CCTGACCAAA
     ACCGTCAATG

1001 AAAACAAACA AAACGTCGAT GCCAAAGTAA AAGCTGCAGA
     AATCTGAAATA

1051 GAAAAGTTAA CAACCAAGTT AGCAGACACT GATGCCGCTT
     TAGCAGATAC

1101 TGATGCCGCT CTGGATGCAA CCACCAACGC CTTGAATAAA
     TTGGGAGAAA

1151 ATATAACGAC ATTTGCTGAA GAGACTAAGA CAAATATCGT
     AAAAATTGAT

1201 GAAAAATTAG AAGCCGTGGC TGATACCGTC GACAAGCATG
     CCGAAGCATT

1251 CAACGATATC GCCGATTCAT TGGATGAAAC CAACACTAAG
     GCAGACGAAG

1301 CCGTCAAAAC CGCCAATGAA GCCAAACAGA CGGCCGAAGA
     AACCAAACAA

1351 AACGTCGATG CCAAAGTAAA AGCTGCAGAA ACTGCAGCAG
     GCAAAGCCGA

1401 AGCTGCCGCT GGCACAGCTA ATACTGCAGC CGACAAGGCC
     GAAGCTGTCG

1451 CTGCAAAAGT TACCGACATC AAAGCTGATA TCGCTACGAA
     CAAAGATAAT

1501 ATTGCTAAAA AAGCAAACAG TGCCGACGTG TACACCAGAG
     AAGAGTCTGA

1551 CAGCAAATTT GTCAGAATTG ATGGTCTGAA CGCTACTACC
     GAAAAATTGG

1601 ACACACGCTT GGCTTCTGCT GAAAAATCCA TTGCCGATCA
     CGATACTCGC

1651 CTGAACGGTT TGGATAAAAC AGTGTCAGAC CTGCGCAAAG
     AAACCCGCCA

1701 AGGCCTTGCA GAACAAGCCG CGCTCTCCGG TCTGTTCCAA
     CCTTACAACG

1751 TGGGTCTCGA GCACCACCAC CACCACCACT GA
```

```
  1 MVAADIGAGL ADALTAPLDH KDKGLQSLTL DQSVRKNEKL
    KLAAQGAEKT

51 YGNGDSLNTG KLKNDKVSRF DFIRQIEVDG QLITLESGEF
    QVYKQSHSAL

101 TAFQTEQIQD SEHSGKMVAK RQFRIGDIAG EHTSFDKLPE
    GGRATYRGTA

151 FGSDDAGGKL TYTIDFAAKQ GNGKIEHLKS PELNVDLAAA
    DIKPDGKRHA

201 VISGSVLYNQ AEKGSYSLGI FGGKAQEVAG SAEVKTVNGI
    RHIGLAAKQL

251 EGGGGTGSAT NDDDVKKAAT VAIAAAYNNG QEINGFKAGE
    TIYDIDEDGT

301 ITKKDATAAD VEADDFKGLG LKKVVTNLTK TVNENKQNVD
    AKVKAAESEI

351 EKLTTKLADT DAALADTDAA LDATTNALNK LGENITTFAE
    ETKTNIVKID

401 EKLEAVADTV DKHAEAFNDI ADSLDETNTK ADEAVKTANE
    AKQTAEETKQ

451 NVDAKVKAAE TAAGKAEAAA GTANTAADKA EAVAAKVTDI
    KADIATNKDN
```

```
501 IAKKANSADV YTREESDSKF VRIDGLNATT EKLDTRLASA
    EKSIADHDTR
551 LNGLDKTVSD LRKETRQGLA EQAALSGLFQ PYNVGLEHHH
    HHH*

ΔG741-983
  1 ATGGTCGCCG CCGACATCGG TGCGGGGCTT GCCGATGCAC
    TAACCGCACC

51 GCTCGACCAT AAAGACAAAG GTTTGCAGTC TTTGACGCTG
    GATCAGTCCG

101 TCAGGAAAAA CGAGAAACTG AAGCTGGCGG CACAAGGTGC
    GGAAAAAACT

151 TATGGAAACG GTGACAGCCT CAATACGGGC AAATTGAAGA
    ACGACAAGGT

201 CAGCCGTTTC GACTTTATCC GCCAAATCGA AGTGGACGGG
    CAGCTCATTA

251 CCTTGGAGAG TGGAGAGTTC CAAGTATACA AACAAAGCCA
    TTCCGCCTTA

301 ACCGCCTTTC AGACCGAGCA AATACAAGAT TCGGAGCATT
    CCGGGAAGAT

351 GGTTGCGAAA CGCCAGTTCA GAATCGGCGA CATAGCGGGC
    GAACATACAT

401 CTTTTGCAAA GCTTCCCGAA GGCGGCAGGG CGACATATCG
    CGGGACGGCG

451 TTCGGTTCAG ACGATGCCGG CGGAAAACTG ACCTACACCA
    TAGATTTCGC

501 CGCCAAGCAG GGAAACGGCA AAATCGAACA TTTGAAATCG
    CCAGAACTCA

551 ATGTCGACCT GGCCGCCGCC GATATCAAGC CGGATGGAAA
    ACGCCATGCC

601 GTCATCAGCG GTTCCGTCCT TTACAACCAA GCCGAGAAAG
    GCAGTTACTC

651 CCTCGGTATC TTTGGCGGAA AAGCCCAGGA AGTTGCCGGC
    AGCGCGGAAG

701 TGAAAACCGT AAACGGCATA CGCCATATCG GCCTTGCCGC
    CAAGCAACTC

751 GAGGGATCCG GCGGAGGCGG CACTTCTGCG CCCGACTTCA
    ATGCAGGCGG

801 TACCGGTATC GGCAGCAACA GCAGAGCAAC AACAGCGAAA
    TCAGCAGCAG

851 TATCTTACGC CGGTATCAAG AACGAAATGT GCAAAGACAG
    AAGCATGCTC

901 TGTGCCGGTC GGGATGACGT TGCGGTTACA GACAGGGATG
    CCAAAATCAA

951 TGCCCCCCCC CCGAATCTGC ATACCGGAGA CTTTCCAAAC
    CCAAATGACG

1001 CATACAAGAA TTTGATCAAC CTCAAACCTG CAATTGAAGC
     AGGCTATACA

1051 GGACGCGGGG TAGAGGTAGG TATCGTCGAC ACAGGCGAAT
     CCGTCGGCAG

1101 CATATCCTTT CCCGAACTGT ATGGCAGAAA AGAACACGGC
     TATAACGAAA

1151 ATTACAAAAA CTATACGGCG TATATGCGGA AGGAAGCGCC
     TGAAGACGGA

1201 GGCGGTAAAG ACATTGAAGC TTCTTTCGAC GATGAGGCCG
     TTATAGAGAC

1251 TGAAGCAAAG CCGACGGATA TCCGCCACGT AAAAGAAATC
     GGACACATCG

1301 ATTTGGTCTC CCATATTATT GGCGGGCGTT CCGTGGACGG
     CAGACCTGCA

1351 GGCGGTATTG CGCCCGATGC GACGCTACAC ATAATGAATA
     CGAATGATGA

1401 AACCAAGAAC GAAATGATGG TTGCAGCCAT CCGCAATGCA
     TGGGTCAAGC

1451 TGGGCGAACG TGGCGTGCGC ATCGTCAATA ACAGTTTTGG
     AACAACATCG

1501 AGGGCAGGCA CTGCCGACCT TTTCCAAATA GCCAATTCGG
     AGGAGCAGTA

1551 CCGCCAAGCG TTGCTCGACT ATTCCGGCGG TGATAAAACA
     GACGAGGGTA

1601 TCCGCCTGAT GCAACAGAGC GATTACGGCA ACCTGTCCTA
     CCACATCCGT

1651 AATAAAAACA TGCTTTTCAT CTTTTCGACA GGCAATGACG
     CACAAGCTCA

1701 GCCCAACACA TATGCCCTAT TGCCATTTTA TGAAAAAGAC
     GCTCAAAAAG

1751 GCATTATCAC AGTCGCAGGC GTAGACCGCA GTGGAGAAAA
     GTTCAAACGG

1801 GAAATGTATG GAGAACCGGG TACAGAACCG CTTGAGTATG
     GCTCCAACCA

1851 TTGCGGAATT ACTGCCATGT GGTGCCTGTC GGCACCCTAT
     GAAGCAAGCG

1901 TCCGTTTCAC CCGTACAAAC CCGATTCAAA TTGCCGGAAC
     ATCCTTTTCC

1951 GCACCCATCG TAACCGGCAC GGCGGCTCTG CTGCTGCAGA
     AATACCCGTG

2001 GATGAGCAAC GACAACCTGC GTACCACGTT GCTGACGACG
     GCTCAGGACA

2051 TCGGTGCAGT CGGCGTGGAC AGCAAGTTCG CTGGGGACT
     GCTGGATGCG

2101 GGTAAGGCCA TGAACGGACC CGCGTCCTTT CCGTTCGGCG
     ACTTTACCGC

2151 CGATACGAAA GGTACATCCG ATATTGCCTA CTCCTTCCGT
     AACGACATTT

2201 CAGGCACGGG CGGCCTGATC AAAAAAGGCG GCAGCCAACT
     GCAACTGCAC

2251 GGCAACAACA CCTATACGGG CAAACCCATT ATCGAAGGCG
     GTTCGCTGGT

2301 GTTGTACGGC AACAACAAAT CGGATATGCG CGTCGAAACC
     AAAGGTGCGC

2351 TGATTTATAA CGGGGCGGCA TCCGGCGGCA GCCTGAACAG
     CGACGGCATT

2401 GTCTATCTGG CAGATACCGA CCAATCCGGC GCAAACGAAA
     CCGTACACAT

2451 CAAAGGCAGT CTGCAGCTGG ACGGCAAAGG TACGCTGTAC
     ACACGTTTGG

2501 GCAAACTGCT GAAAGTGGAC GGTACGGCGA TTATCGGCGG
     CAAGCTGTAC

2551 ATGTCGGCAC GCGGCAAGGG GGCAGGCTAT CTCAACAGTA
     CCGGACGACG
```

-continued

```
2601  TGTTCCCTTC CTGAGTGCCG CCAAAATCGG GCAGGATTAT
      TCTTTCTTCA

2651  CAAACATCGA AACCGACGGC GGCCTGCTGG CTTCCCTCGA
      CAGCGTCGAA

2701  AAAACAGCGG GCAGTGAAGG CGACACGCTG TCCTATTATG
      TCCGTCGCGG

2751  CAATGCGGCA CGGACTGCTT CGGCAGCGGC ACATTCCGCG
      CCCGCCGGTC

2801  TGAAACACGC CGTAGAACAG GCGGCAGCA ATCTGGAAAA
      CCTGATGGTC

2851  GAACTGGATG CCTCCGAATC ATCCGAACA CCCGAGACGG
      TTGAAACTGC

2901  GGCAGCCGAC CGCACAGATA TGCCGGGCAT CCGCCCCTAC
      GGCGCAACTT

2951  TCCGCGCAGC GGCAGCCGTA CAGCATGCGA ATGCCGCCGA
      CGGTGTACGC

3001  ATCTTCAACA GTCTCGCCGC TACCGTCTAT GCCGACAGTA
      CCGCCGCCCA

3051  TGCCGATATG CAGGGACGCC GCCTGAAAGC CGTATCGGAC
      GGGTTGGACC

3101  ACAACGGCAC GGGTCTGCGC GTCATCGCGC AAACCCAACA
      GGACGGTGGA

3151  ACGTGGGAAC AGGGCGGTGT TGAAGGCAAA ATGCGCGGCA
      GTACCCAAAC

3201  CGTCGGCATT GCCGCGAAAA CCGGCGAAAA TACGACAGCA
      GCCGCCACAC

3251  TGGGCATGGG ACGCAGCACA TGGAGCGAAA ACAGTGCAAA
      TGCAAAAACC

3301  GACAGCATTA GTCTGTTTGC AGGCATACGG CACGATGCGG
      GCGATATCGG

3351  CTATCTCAAA GGCCTGTTCT CCTACGGACG CTACAAAAAC
      AGCATCAGCC

3401  GCAGCACCGG TGCGGACGAA CATGCGGAAG CAGCGTCAA
      CGGCACGCTG

3451  ATGCAGCTGG GCGCACTGGG CGGTGTCAAC GTTCCGTTTG
      CCGCAACGGG

3501  AGATTTGACG GTCGAAGGCG GTCTGCGCTA CGACCTGCTC
      AAACAGGATG

3551  CATTCGCCGA AAAAGGCAGT GCTTTGGGCT GGAGCGGCAA
      CAGCCTCACT

3601  GAAGGCACGC TGGTCGGACT CGCGGGTCTG AAGCTGTCGC
      AACCCTTGAG

3651  CGATAAAGCC GTCCTGTTTG CAACGGCGGG CGTGGAACGC
      GACCTGAACG

3701  GACGCGACTA CACGGTAACG GGCGGCTTTA CCGGCGCGAC
      TGCAGCAACC

3751  GGCAAGACGG GGGCACGCAA TATGCCGCAC ACCCGTCTGG
      TTGCCGGCCT

3801  GGGCGCGGAT GTCGAATTCG GCAACGGCTG GAACGGCTTG
      GCACGTTACA

3851  GCTACGCCGG TTCCAAACAG TACGGCAACC ACAGCGGACG
      AGTCGGCGTA

3901  GGCTACCGGT TCCTCGAGCA CCACCACCAC CACCACTGA
```

```
   1  MVAADIGAGL ADALTAPLDH KDKGLQSLTL DQSVRKNEKL
      KLAAQGAEKT

51  YGNGDSLNTG KLKNDKVSRF DFIRQIEVDG QLITLESGEF
      QVYKQSHSAL

101  TAFQTEQIQD SEHSGKMVAK RQFRIGDIAG EHTSFDKLPE
      GGRATYRGTA

151  FGSDDAGGKL TYTIDFAAKQ GNGKIEHLKS PELNVDLAAA
      DIKPDGKRHA

201  VISGSVLYNQ AEKGSYSLGI FGGKAQEVAG SAEVKTVNGI
      RHIGLAAKQL

251  EGSGGGGTSA PDFNAGGTGI GSNSRATTAK SAAVSYAGIK
      NEMCKDRSML

301  CAGRDDVAVT DRDAKINAPP PNLHTGDFPN PNDAYKNLIN
      LKPAIEAGYT

351  GRGVEVGIVD TGESVGSISF PELYGRKEHG YNENYKNYTA
      YMRKEAPEDG

401  GGKDIEASFD DEAVIETEAK PTDIRHVKEI GHIDLVSHII
      GGRSVDGRPA

451  GGIAPDATLH IMNTNDETKN EMMVAAIRNA WVKLGERGVR
      IVNNSFGTTS

501  RAGTADLFQI ANSEEQYRQA LLDYSGGDKT DEGIRLMQQS
      DYGNLSYHIR

551  NKNMLFIFST GNDAQAQPNT YALLPFYEKD AQKGIITVAG
      VDRSGEKFKR

601  EMYGEPGTEP LEYGSNHCGI TAMWCLSAPY EASVRFTRTN
      PIQIAGTSFS

651  APIVTGTAAL LLQKYPWMSN DNLRTTLLTT AQDIGAVGVD
      SKFGWGLLDA

701  GKAMNGPASF PFGDFTADTK GTSDIAYSFR NDISGTGGLI
      KKGGSQLQLH

751  GNNTYTGKTI IEGGSLVLYG NNKSDMRVET KGALIYNGAA
      SGGGSLNSDGI

801  VYLADTDQSG ANETVHIKGS LQLDGKGTLY TRLGKLLKVD
      GTAIIGGKLY

851  MSARGKGAGY LNSTGRRVPF LSAAKIGQDY SFFTNIETDG
      GLLASLDSVE

901  KTAGSEGDTL SYYVRRGNAA RTASAAAHSA PAGLKHAVEQ
      GGSNLENLMV

951  ELDASESSAT PETVETAAAD RTDMPGIRPY GATFRAAAAV
      QHANAADGVR

1001  IFNSLAATVY ADSTAAHADM QGRRLKAVSD GLDHNGTGLR
      VIAQTQQDGG

1051  TWEQGGVEGK MRGSTQTVGI AAKTGENTTA AATLGMGRST
      WSENSANAKT

1101  DSISLFAGIR HDAGDIGYLK GLFSYGRYKN SISRSTGADE
      HAEGSVNGTL

1151  MQLGALGGVN VPFAATGDLT VEGGLRYDLL KQDAFAEKGS
      ALGWSGNSLT

1201  EGTLVGLAGL KLSQPLSDKA VLFATAGVER DLNGRDYTVT
      GGFTGATAAT

1251  GKTGARNMPH TRLVAGLGAD VEFGNGWNGL ARYSYAGSKQ
      YGNHSGRVGV

1301  GYRFLEHHHH HH*
```

-continued

```
ΔG741-ORF46.1
   1 ATGGTCGCCG CCGACATCGG TGCGGGGCTT GCCGATGCAC
     TAACCGCACC

51 GCTCGACCAT AAAGACAAAG GTTTGCAGTC TTTGACGCTG
     GATCAGTCCG

101 TCAGGAAAAA CGAGAAACTG AAGCTGGCGG CACAAGGTGC
     GGAAAAAACT

151 TATGGAAACG GTGACAGCCT CAATACGGGC AAATTGAAGA
     ACGACAAGGT

201 CAGCCGTTTC GACTTTATCC GCCAAATCGA AGTGGACGGG
     CAGCTCATTA

251 CCTTGGAGAG TGGAGAGTTC CAAGTATACA AACAAAGCCA
     TTCCGCCTTA

301 ACCGCCTTTC AGACCGAGCA AATACAAGAT TCGGAGCATT
     CCGGGAAGAT

351 GGTTGCGAAA CGCCAGTTCA GAATCGGCGA CATAGCGGGC
     GAACATACAT

401 CTTTTGACAA GCTTCCCGAA GGCGGCAGGG CGACATATCG
     CGGGACGGCG

451 TTCGGTTCAG ACGATGCCGG CGGAAAACTG ACCTACACCA
     TAGATTTCGC

501 CGCCAAGCAG GGAAACGGCA AAATCGAACA TTTGAAATCG
     CCAGAACTCA

551 ATGTCGACCT GGCCGCCGCC GATATCAAGC CGGATGGAAA
     ACGCCATGCC

601 GTCATCAGCG GTTCCGTCCT TTACAACCAA GCCGAGAAAG
     GCAGTTACTC

651 CCTCGGTATC TTTGGCGGAA AAGCCCAGGA AGTTGCCGGC
     AGCGCGGAAG

701 TGAAAACCGT AAACGGCATA CGCCATATCG GCCTTGCCGC
     CAAGCAACTC

751 GACGGTGGCG GAGGCACTGG ATCCTCAGAT TTGGCAAACG
     ATTCTTTTAT

801 CCGGCAGGTT CTCGACCGTC AGCATTTCGA ACCCGACGGG
     AAATACCACC

851 TATTCGGCAG CAGGGGGGAA CTTGCCGAGC GCAGCGGCCA
     TATCGGATTG

901 GGAAAAATAC AAAGCCATCA GTTGGGCAAC CTGATGATTC
     AACAGGCGGC

951 CATTAAAGGA AATATCGGCT ACATTGTCCG CTTTTCCGAT
     CACGGGCACG

1001 AAGTCCATTC CCCCTTCGAC AACCATGCCT CACATTCCGA
     TTCTGATGAA

1051 GCCGGTAGTC CCGTTGACGG ATTTAGCCTT TACCGCATCC
     ATTGGGACGG

1101 ATACGAACAC CATCCCGCCG ACGGCTATGA CGGGCCACAG
     GGCGGCGGCT

1151 ATCCCGCTCC CAAAGGCGCG AGGGATATAT ACAGCTACGA
     CATAAAAGGC

1201 GTTGCCCAAA ATATCCGCCT CAACCTGACC GACAACCGCA
     GCACCGGACA

1251 ACGGCTTGCC GACCGTTTCC ACAATGCCGG TAGTATGCTG
     ACGCAAGGAG

1301 TAGGCGACGG ATTCAAACGC GCCACCCGAT ACAGCCCCGA
     GCTGGACAGA

1351 TCGGGCAATG CCGCCGAAGC CTTCAACGGC ACTGCAGATA
     TCGTTAAAAA

1401 CATCATCGGC GCGGCAGGAG AAATTGTCGG CGCAGGCGAT
     GCCGTGCAGG

1451 GCATAAGCGA AGGCTCAAAC ATTGCTGTCA TGCACGGCTT
     GGGTCTGCTT

1501 TCCACCGAAA ACAAGATGGC GCGCATCAAC GATTTGGCAG
     ATATGGCGCA

1551 ACTCAAAGAC TATGCCGCAG CAGCCATCCG CGATTGGGCA
     GTCCAAAACC

1601 CCAATGCCGC ACAAGGCATA GAAGCCGTCA GCAATATCTT
     TATGGCAGCC

1651 ATCCCCATCA AAGGGATTGG AGCTGTTCGG GGAAAATACG
     GCTTGGGCGG

1701 CATCACGGCA CATCCTATCA AGCGGTCGCA GATGGGCGCG
     ATCGCATTGC

1751 CGAAAGGGAA ATCCGCCGTC AGCGACAATT TGCCGATGC
     GGCATACGCC

1801 AAATACCCGT CCCCTTACCA TTCCCGAAAT ATCCGTTCAA
     ACTTGGAGCA

1851 GCGTTACGGC AAAGAAAACA TCACCTCCTC AACCGTGCCG
     CCGTCAAACG

1901 GCAAAAATGT CAAACTGGCA GACCAACGCC ACCCGAAGAC
     AGGCGTACCG

1951 TTTGACGGTA AAGGGTTTCC GAATTTTGAG AAGCACGTGA
     AATATGATAC

2001 GCTCGAGCAC CACCACCACC ACCACTGA

1 MVAADIGAGL ADALTAPLDH KDKGLQSLTL DQSVRKNEKL
     KLAAQGAEKT

51 YGNGDSLNTG KLKNDKVSRF DFIRQIEVDG QLITLESGEF
     QVYKQSHSAL

101 TAFQTEQIQD SEHSGKMVAK RQFRIGDIAG EHTSFDKLPE
     GGRATYRGTA

151 FGSDDAGGKL TYTIDFAAKQ GNGKIEHLKS PELNVDLAAA
     DIKPDGKRHA

201 VISGSVLYNQ AEKGSYSLGI FGGKAQEVAG SAEVKTVNGI
     RHIGLAAKQL

251 DGGGGTGSSD LANDSFIRQV LDRQHFEPDG KYHLFGSRGE
     LAERSGHIGL

301 GKIQSHQLGN LMIQQAAIKG NIGYIVRFSD HGHEVHSPFD
     NHASHSDSDE

351 AGSPVDGFSL YRIHWDGYEH HPADGYDGPQ GGGYPAPKGA
     RDIYSYDIKG

401 VAQNIRLNLT DNRSTGQRLA DRFHNAGSML TQGVGDGFKR
     ATRYSPELDR

451 SGNAAEAFNG TADIVKNIIG AAGEIVGAGD AVQGISEGSN
     IAVMHGLGLL

501 STENKMARIN DLADMAQLKD YAAAAIRDWA VQNPNAAQGI
     EAVSNIFMAA

551 IPIKGIGAVR GKYGLGGITA HPIKRSQMGA IALPKGKSAV
     SDNFADAAYA
```

-continued

```
601 KYPSPYHSRN IRSNLEQRYG KENITSSTVP PSNGKNVKLA
    DQRHPKTGVP

651 FDGKGFPNFE KHVKYDTLEH HHHHH*
```

Example 16

C-Terminal Fusions ('Hybrids') with 287/ΔG287

According to the invention, hybrids of two proteins A & B may be either NH₂-A-B—COOH or NH₂—B-A-COOH. The effect of this difference was investigated using protein 287 either C-terminal (in '287-His' form) or N-terminal (in ΔG287 form—sequences shown above) to 919, 953 and ORF46.1. A panel of strains was used, including homologous strain 2996. FCA was used as adjuvant:

|  | 287 & 919 | | 287 & 953 | | 287 & ORF46.1 | |
| --- | --- | --- | --- | --- | --- | --- |
| Strain | ΔG287-919 | 919-287 | ΔG287-953 | 953-287 | ΔG287-46.1 | 46.1-287 |
| 2996 | 128000 | 16000 | 65536 | 8192 | 16384 | 8192 |
| BZ232 | 256 | 128 | 128 | <4 | <4 | <4 |
| 1000 | 2048 | <4 | <4 | <4 | <4 | <4 |
| MC58 | 8192 | 1024 | 16384 | 1024 | 512 | 128 |
| NGH38 | 32000 | 2048 | >2048 | 4096 | 16384 | 4096 |
| 394/98 | 4096 | 32 | 256 | 128 | 128 | 16 |
| MenA (F6124) | 32000 | 2048 | >2048 | 32 | 8192 | 1024 |
| MenC (BZ133) | 64000 | >8192 | >8192 | <16 | 8192 | 2048 |

Better bactericidal titres are generally seen with 287 at the N-terminus (in the ΔG form)

When fused to protein 961 [NH₂-ΔG287-961-COOH—sequence shown above], the resulting protein is insoluble and must be denatured and renatured for purification. Following renaturation, around 50% of the protein was found to remain insoluble. The soluble and insoluble proteins were compared, and much better bactericidal titres were obtained with the soluble protein (FCA as adjuvant):

|  | 2996 | BZ232 | MC58 | NGH38 | F6124 | BZ133 |
| --- | --- | --- | --- | --- | --- | --- |
| Soluble | 65536 | 128 | 4096 | >2048 | >2048 | 4096 |
| Insoluble | 8192 | <4 | <4 | 16 | n.d. | n.d. |

Titres with the insoluble form were, however, improved by using alum adjuvant instead:

| Insoluble | 32768 | 128 | 4096 | >2048 | >2048 | 2048 |
| --- | --- | --- | --- | --- | --- | --- |

Example 17

N-Terminal Fusions ('Hybrids') to 287

Expression of protein 287 as full-length with a C-terminal His-tag, or without its leader peptide but with a C-terminal His-tag, gives fairly low expression levels. Better expression is achieved using a N-terminal GST-fusion.

As an alternative to using GST as an N-terminal fusion partner, 287 was placed at the C-terminus of protein 919 ('919-287'), of protein 953 ('953-287'), and of proteins ORF46.1 ('ORF46.1-287'). In both cases, the leader peptides were deleted, and the hybrids were direct in-frame fusions.

To generate the 953-287 hybrid, the leader peptides of the two proteins were omitted by designing the forward primer downstream from the leader of each sequence; the stop codon sequence was omitted in the 953 reverse primer but included in the 287 reverse primer. For the 953 gene, the 5' and the 3' primers used for amplification included a NdeI and a BamHI restriction sites respectively, whereas for the amplification of the 287 gene the 5' and the 3' primers included a BamHI and a XhoI restriction sites respectively. In this way a sequential directional cloning of the two genes in pET21b+, using NdeI-BamHI (to clone the first gene) and subsequently BamHI-XhoI (to clone the second gene) could be achieved.

The 919-287 hybrid was obtained by cloning the sequence coding for the mature portion of 287 into the XhoI site at the 3'-end of the 919-His clone in pET21b+. The primers used for amplification of the 287 gene were designed for introducing a SalI restriction site at the 5'- and a XhoI site at the 3'- of the PCR fragment. Since the cohesive ends produced by the SalI and XhoI restriction enzymes are compatible, the 287 PCR product digested with SalI-XhoI could be inserted in the pET21b-919 clone cleaved with XhoI.

The ORF46.1-287 hybrid was obtained similarly.

The bactericidal efficacy (homologous strain) of antibodies raised against the hybrid proteins was compared with antibodies raised against simple mixtures of the component antigens:

|  | Mixture with 287 | Hybrid with 287 |
| --- | --- | --- |
| 919 | 32000 | 16000 |
| 953 | 8192 | 8192 |
| ORF46.1 | 128 | 8192 |

Data for bactericidal activity against heterologous MenB strains and against serotypes A and C were also obtained for 919-287 and 953-287:

|  | 919 | | 953 | | ORF46.1 | |
| --- | --- | --- | --- | --- | --- | --- |
| Strain | Mixture | Hybrid | Mixture | Hybrid | Mixture | Hybrid |
| MC58 | 512 | 1024 | 512 | 1024 | — | 1024 |
| NGH38 | 1024 | 2048 | 2048 | 4096 | — | 4096 |
| BZ232 | 512 | 128 | 1024 | 16 | — | — |
| MenA (F6124) | 512 | 2048 | 2048 | 32 | — | 1024 |
| MenC (C11) | >2048 | n.d. | >2048 | n.d. | — | n.d. |
| MenC (BZ133) | >4096 | >8192 | >4096 | <16 | — | 2048 |

Hybrids of ORF46.1 and 919 were also constructed. Best results (four-fold higher titre) were achieved with 919 at the N-terminus.

Hybrids 919-519H is, ORF97-225His and 225-ORF97H is were also tested. These gave moderate ELISA titres and bactericidal antibody responses.

Example 18

The Leader Peptide from ORF4

As shown above, the leader peptide of ORF4 can be fused to the mature sequence of other proteins (e.g. proteins 287 and 919). It is able to direct lipidation in *E. coli*.

Example 19

Domains in 564

The protein '564' is very large (2073aa), and it is difficult to clone and express it in complete form. To facilitate expression, the protein has been divided into four domains, as shown in FIG. 8 (according to the MC58 sequence):

| Domain | A | B | C | D |
|---|---|---|---|---|
| Amino Acids | 79-360 | 361-731 | 732-2044 | 2045-2073 |

These domains show the following homologies:

Domain A shows homology to other bacterial toxins:
- gb|AAG03431.1|AE004443_9 probable hemagglutinin [*Pseudomonas aeruginosa*] (38%)
- gb|AAC31981.1|(139897) HecA [*Pectobacterium chrysanthemi]* (45%)
- emb|CAA36409.1|(X52156) filamentous hemagglutinin [*Bordetella pertussis*] (31%)
- gb|AAC79757.1|(AF057695) large supernatant protein1 [*Haemophilus ducreyi*] (26%)
- gb|AAA25657.1|(M30186) HpmA precursor [*Proteus mirabilis*] (29%)

Domain B shows no homology, and is specific to 564.

Domain C shows homology to:
- gb|AAF84995.1|AE004032 HA-like secreted protein [*Xylella fastidiosa*] (33%)
- gb|AAG05850.1|AE004673 hypothetical protein [*Pseudomonas aeruginosa*] (27%)
- gb|AAF68414.1AF237928 putative FHA [*Pasteurella multocisida*] (23%)
- gb|AAC79757.1|(AF057695) large supernatant protein1 [*Haemophilus ducreyi*] (23%)
- pir||S21010 FHA B precursor [*Bordetella pertussis*] (20%)

Domain D shows homology to other bacterial toxins:
- gb|AAF84995.1|AE004032_14 HA-like secreted protein [*Xylella fastidiosa]* (29%)

Using the MC58 strain sequence, good intracellular expression of 564ab was obtained in the form of GST-fusions (no purification) and his-tagged protein; this domain-pair was also expressed as a lipoprotein, which showed moderate expression in the outer membrane/supernatant fraction.

The b domain showed moderate intracellular expression when expressed as a his-tagged product (no purification), and good expression as a GST-fusion.

The c domain showed good intracellular expression as a GST-fusion, but was insoluble. The d domain showed moderate intracellular expression as a his-tagged product (no purification).

The cd protein domain-pair showed moderate intracellular expression (no purification) as a GST-fusion.

Good bactericidal assay titres were observed using the c domain and the be pair.

Example 20

The 919 Leader Peptide

The 20mer leader peptide from 919 (SEQ ID NO:633) is discussed in example 1 above:

```
MKKYLFRAAL YGIAAAILAA
```

As shown in example 1, deletion of this leader improves heterologous expression, as does substitution with the ORF4 leader peptide. The influence of the 919 leader on expression was investigated by fusing the coding sequence to the PhoC reporter gene from *Morganella morganii* [Thaller et al. (1994) *Microbiology* 140:1341-1350]. The construct (SEQ ID NO:116) was cloned in the pET21-b plasmid between the NdeI and XhoI sites (FIG. 9):

```
  1 MKKYLFRAAL YGIAAAILAA AIPAGNDATT KPDLYYLKNE
    QAIDSLKLLP

51 PPPEVGSIQF LNDQAMYEKG RMLRNTERGK QAQADADLAA
    GGVATAFSGA

101 FGYPITEKDS PELYKLLTNM IEDAGDLATR SAKEHYMRIR
    PFAFYGTETC

151 NTKDQKKLST NGSYPSGHTS IGWATALVLA EVNPANQDAI
    LERGYQLGQS

201 RVICGYHWQS DVDAARIVGS AAVATLHSDP AFQAQLAKAK
    QEFAQKSQK*
```

The level of expression of PhoC from this plasmid is >200-fold lower than that found for the same construct but containing the native PhoC signal peptide. The same result was obtained even after substitution of the T7 promoter with the *E. coli* Plac promoter. This means that the influence of the 919 leader sequence on expression does not depend on the promoter used.

In order to investigate if the results observed were due to some peculiarity of the 919 signal peptide nucleotide sequence (secondary structure formation, sensitivity to RNAases, etc.) or to protein instability induced by the presence of this signal peptide, a number of mutants were generated. The approach used was a substitution of nucleotides of the 919 signal peptide sequence by cloning synthetic linkers containing degenerate codons. In this way, mutants were obtained with nucleotide and/or amino acid substitutions.

Two different linkers were used, designed to produce mutations in two different regions of the 919 signal peptide sequence, in the first 19 base pairs (L1) (SEQ ID NO:117) and between bases 20-36 (51) (SEQ ID NO:118).

```
L1:
5' T ATG AAa/g TAc/t c/tTN TTt/c a/cGC GCC GCC CTG
TAC GGC ATC GCC GCC GCC ATC CTC GCC GCC GCG ATC
CC 3'
```

-continued

S1:
5' T ATG AAA AAA TAC CTA TTC CGa/g GCN GCN c/tTa/g
TAc/t GGc/g ATC GCC GCC GCC ATC CTC GCC GCC GCG
ATC CC 3'

The alignment of some of the mutants obtained is given below.

L1 mutants:
9L1-a
(SEQ ID NO: 119)
ATGAAGAAGTACCTTTTCAGCGCCGCC~~~~~~~~~~~~~~~~~~~~~~
~~~~~~~~~~

9L1-e
(SEQ ID NO: 120)
ATGAAAAAATACTTTTTCCGCGCCGCC~~~~~~~~~~~~~~~~~~~~~~
~~~~~~~~~~

9L1-d
(SEQ ID NO: 121)
ATGAAAAAATACTTTTTCCGCGCCGCC~~~~~~~~~~~~~~~~~~~~~~
~~~~~~~~~~

9L1-f
(SEQ ID NO: 122)
ATGAAAAAATATCTCTTTAGCGCCGCCCTGTACGGCATCGCCGCCGCCAT
CCTCGCCGCC

919sp
(SEQ ID NO: 123)
ATGAAAAAATACCTATTCCGCGCCGCCCTGTACGGCATCGCCGCCGCCAT
CCTCGCCGCC

9L1a
(SEQ ID NO: 124)
MKKYLFSAA~~~~~~~~~~~

9L1e
(SEQ ID NO: 125)
MKKYFFRAA~~~~~~~~~~~

9L1d
(SEQ ID NO: 126)
MKKYFFRAA~~~~~~~~~~~

9L1f
(SEQ ID NO: 127)
MKKYLFSAALYGIAAAILAA

919sp
(SEQ ID NO: 128)
MKKYLFRAALYGIAAAILAA (i.e. native signal peptide)

S1 mutants:
9S1-e
(SEQ ID NO: 129)
ATGAAAAAATACCTATTC..................ATCGCCGCCGCC
CCTCGCCGCC 9S1-c
(SEQ ID NO: 130)
ATGAAAAAATACCTATTCCGAGCTGCCCAATACGGCATCGCCGCCGCCAT
CCTCGCCGCC 9S1-b
(SEQ ID NO: 131)
ATGAAAAAATACCTATTCCGGGCCGCCCAATACGGCATCGCCGCCGCCAT
CCTCGCCGCC 9S1-i
(SEQ ID NO: 132)
ATGAAAAAATACCTATTCCGGGCGGCTTTGTACGGGATCGCCGCCGCCAT
CCTCGCCGCC 919sp
(SEQ ID NO: 133)
ATGAAAAAATACCTATTCCGCGCCGCCCTGTACGGCATCGCCGCCGCCAT
CCTCGCCGCC 9S1e
(SEQ ID NO: 134)
MKKYLF......IAAAILAA 9S1c
(SEQ ID NO: 135)
MKKYLFRAAQYGIAAAILAA 9S1b
(SEQ ID NO: 136)
MKKYLFRAAQYGIAAAILAA 9S1i
(SEQ ID NO: 137)
MKKYLFRAALYGIAAAILAA 919sp
(SEQ ID NO: 128)
MKKYLFRAALYGIAAAILAA As shown in the sequences alignments, most of the mutants analysed contain in-frame deletions which were unexpectedly produced by the host cells.

Figure 10:
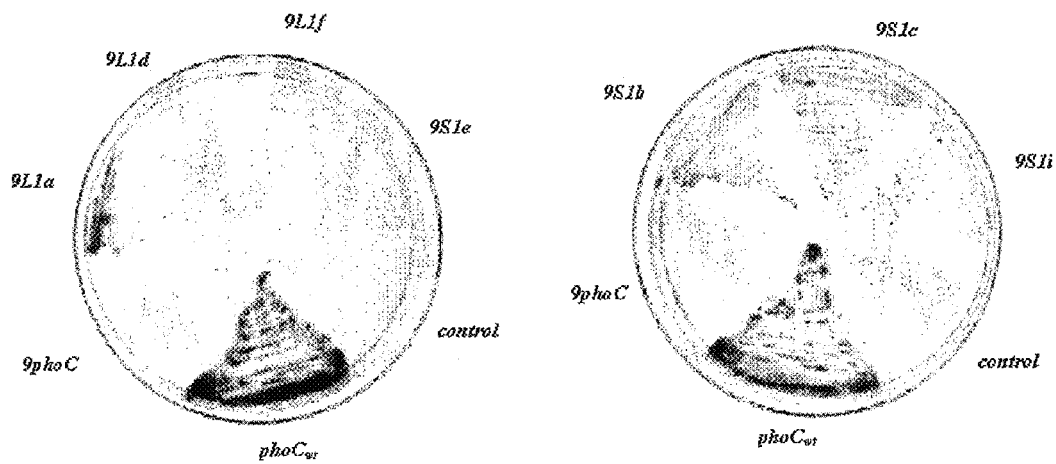
FIG. 10 shows the results obtained using mutants of the leader peptide.

Selection of the mutants was performed by transforming *E. coli* BL21(DE3) cells with DNA prepared from a mixture of L1 and S1 mutated clones. Single transformants were screened for high PhoC activity by streaking them onto LB plates containing 100 µg/ml ampicillin, 50 µg/ml methyl green, 1 mg/ml PDP (phenolphthaleindiphosphate). On this medium PhoC-producing cells become green (FIG. 10).

A quantitative analysis of PhoC produced by these mutants was carried out in liquid medium using pNPP as a substrate for PhoC activity. The specific activities measured in cell extracts and supernatants of mutants grown in liquid medium for 0, 30, 90, 180 min were:

Cell Extracts

|  | 0 | 30 | 90 | 180 |
| --- | --- | --- | --- | --- |
| control | 0.00 | 0.00 | 0.00 | 0.00 |
| 9phoC | 1.11 | 1.11 | 3.33 | 4.44 |
| 9S1e | 102.12 | 111.00 | 149.85 | 172.05 |
| 9L1a | 206.46 | 111.00 | 94.35 | 83.25 |
| 9L1d | 5.11 | 4.77 | 4.00 | 3.11 |
| 9L1f | 27.75 | 94.35 | 82.14 | 36.63 |
| 9S1b | 156.51 | 111.00 | 72.15 | 28.86 |
| 9S1c | 72.15 | 33.30 | 21.09 | 14.43 |
| 9S1i | 156.51 | 83.25 | 55.50 | 26.64 |
| phoCwt | 194.25 | 180.93 | 149.85 | 142.08 |

Supernatants

|  | 0 | 30 | 90 | 180 |
| --- | --- | --- | --- | --- |
| control | 0.00 | 0.00 | 0.00 | 0.00 |
| 9phoC | 0.33 | 0.00 | 0.00 | 0.00 |
| 9S1e | 0.11 | 0.22 | 0.44 | 0.89 |
| 9L1a | 4.88 | 5.99 | 5.99 | 7.22 |
| 9L1d | 0.11 | 0.11 | 0.11 | 0.11 |
| 9L1f | 0.11 | 0.22 | 0.11 | 0.11 |
| 9S1b | 1.44 | 1.44 | 1.44 | 1.67 |
| 9S1c | 0.44 | 0.78 | 0.56 | 0.67 |
| 9S1i | 0.22 | 0.44 | 0.22 | 0.78 |
| phoCwt | 34.41 | 43.29 | 87.69 | 177.60 |

Some of the mutants produce high amounts of PhoC and in particular, mutant 9L1a can secrete PhoC in the culture medium. This is noteworthy since the signal peptide sequence of this mutant is only 9 amino acids long. This is the shortest signal peptide described to date.

Example 21

C-Terminal Deletions of Maf-Related Proteins

MafB-related proteins include 730, ORF46 and ORF29.
The 730 protein from MC58 has the following sequence (SEQ ID NO:137):

```
  1 VKPLRRLTNL LAACAVAAAA LIQPALAADL AQDPFITDNA
    QRQHYEPGGK

51 YHLFGDPRGS VSDRTGKINV IQDYTHQMGN LLIQQANING
    TIGYHTRFSG

101 HGHEEHAPFD NHAADSASEE KGNVDEGFTV YRLNWEGHEH
    HPADAYDGPK

151 GGNYPKPTGA RDEYTYHVNG TARSIKLNPT DTRSIRQRIS
    DNYSNLGSNF

201 SDRADEANRK MFEHNAKLDR WGNSMEFING VAAGALNPFI
    SAGEALGIGD

251 ILYGTRYAID KAAMRNIAPL PAEGKFAVIG GLGSVAGFEK
    NTREAVDRWI

301 QENPNAAETV EAVFNVAAAA KVAKLAKAAK PGKAAVSGDF
    ADSYKKKLAL

351 SDSARQLYQN AKYREALDIH YEDLIRRKTD GSSKFINGRE
    IDAVTNDALI

401 QAKRTISAID KPKNFLNQKN RKQIKATIEA ANQQGKRAEF
    WFKYGVHSQV

451 KSYIESKGGI VKTGLGD*
```

The leader peptide is underlined.
730 shows similar features to ORF46 (see example 8 above):
- as for Orf46, the conservation of the 730 sequence among MenB, MenA and gonococcus is high (>80%) only for the N-terminal portion. The C-terminus, from ~340, is highly divergent.
- its predicted secondary structure contains a hydrophobic segment spanning the central region of the molecule (aa. 227-247).
- expression of the full-length gene in *E. coli* gives very low yields of protein. Expression from tagged or untagged constructs where the signal peptide sequence has been omitted has a toxic effect on the host cells. In other words, the presence of the full-length mature protein in the cytoplasm is highly toxic for the host cell while its translocation to the periplasm (mediated by the signal peptide) has no detectable effect on cell viability. This "intracellular toxicity" of 730 is particularly high since clones for expression of the leaderless 730 can only be obtained at very low frequency using a recA genetic background (*E. coli* strains: HB101 for cloning; HMS174(DE3) for expression).

To overcome this toxicity, a similar approach was used for 730 as described in example 8 for ORF46. Four C-terminal truncated forms were obtained, each of which is well expressed. All were obtained from intracellular expression of His-tagged leaderless 730.

Form A consists of the N-terminal hydrophilic region of the mature protein (aa. 28-226). This was purified as a soluble His-tagged product, having a higher-than-expected MW.

Form B extends to the end of the region conserved between serogroups (aa. 28-340). This was purified as an insoluble His-tagged product.

The C-terminal truncated forms named C1 and C2 were obtained after screening for clones expressing high levels of 730-His clones in strain HMS174(DE3). Briefly, the pET21b plasmid containing the His-tagged sequence coding for the full-length mature 730 protein was used to transform the recA strain HMS174(DE3). Transformants were obtained at low frequency which showed two phenotypes: large colonies and very small colonies. Several large and small colonies were analysed for expression of the 730-His clone. Only cells from large colonies over-expressed a protein recognised by anti-730A antibodies. However the protein over-expressed in different clones showed differences in molecular mass. Sequencing of two of the clones revealed that in both cases integration of an *E. coli* IS sequence had occurred within the sequence coding for the C terminal region of 730. The two integration events have produced in-frame fusion with 1 additional codon in the case of C1, and 12 additional codons in the case of C2 (FIG. 11). The resulting "mutant" forms of 730 have the following sequences:

```
730-C1 (due to an IS1 insertion - FIG. 11A)
                              (SEQ ID NO: 138)
  1 MADLAQDPFI TDNAQRQHYE PGGKYHLFGD PRGSVSDRTG
    KINVIQDYTH

51 QMGNLLIQQA NINGTIGYHT RFSGHGHEEH APFDNHAADS
    ASEEKGNVDE

101 GFTVYRLNWE GHEHHPADAY DGPKGGNYPK PTGARDEYTY
    HVNGTARSIK

151 LNPTDTRSIR QRISDNYSNL GSNFSDRADE ANRKMFEHNA
    KLDRWGNSME

201 FINGVAAGAL NPFISAGEAL GIGDILYGTR YAIDKAAMRN
    IAPLPAEGKF

251 AVIGGLGSVA GFEKNTREAV DRWIQENPNA AETVEAVFNV
    AAAAKVAKLA

301 KAAKPGKAAV SGDFADSYKK KLALSDSARQ LYQNAKYREA
    LDIHYEDLIR

351 RKTDGSSKFI NGREIDAVTN DALIQAR*
```

The additional amino acid produced by the insertion is underlined.

```
730-C2 (due to an IS5 insertion - FIG. 11B)
                              (SEQ ID NO: 139)
  1 MADLAQDPFI TDNAQRQHYE PGGKYHLFGD PRGSVSDRTG
    KINVIQDYTH

51 QMGNLLIQQA NINGTIGYHT RFSGHGHEEH APFDNHAADS
    ASEEKGNVDE

101 GFTVYRLNWE GHEHHPADAY DGPKGGNYPK PTGARDEYTY
    HVNGTARSIK

151 LNPTDTRSIR QRISDNYSNL GSNFSDRADE ANRKMFEHNA
    KLDRWGNSME

201 FINGVAAGAL NPFISAGEAL GIGDILYGTR YAIDKAAMRN
    IAPLPAEGKF
```

-continued

```
251 AVIGGLGSVA GFEKNTREAV DRWIQENPNA AETVEAVFNV
    AAAAKVAKLA

301 KAAKPGKAAV SGDFADSYKK KLALSDSARQ LYQNAKYREA
    LGKVRISGEI

351 LLG*
```

The additional amino acids produced by the insertion are underlined.

In conclusion, intracellular expression of the 730-C1 form gives very high level of protein and has no toxic effect on the host cells, whereas the presence of the native C-terminus is toxic. These data suggest that the "intracellular toxicity" of 730 is associated with the C-terminal 65 amino acids of the protein.

Equivalent truncation of ORF29 to the first 231 or 368 amino acids has been performed, using expression with or without the leader peptide (amino acids 1-26; deletion gives cytoplasmic expression) and with or without a His-tag.

Example 22

Domains in 961

As described in example 9 above, the GST-fusion of 961 was the best-expressed in *E. coli*. To improve expression, the protein was divided into domains (FIG. 12).

The domains of 961 were designed on the basis of YadA (an adhesin produced by *Yersinia* which has been demonstrated to be an adhesin localized on the bacterial surface that forms oligomers that generate surface projection 1Hoiczyk et al. (2000) *EMBO J* 19:5989-991) and are: leader peptide, head domain, coiled-coil region (stalk), and membrane anchor domain.

These domains were expressed with or without the leader peptide, and optionally fused either to C-terminal His-tag or to N-terminal GST. *E. coli* clones expressing different domains of 961 were analyzed by SDS-PAGE and western blot for the production and localization of the expressed protein, from over-night (o/n) culture or after 3 hours induction with IPTG. The results were:

| | Total lysate (Western Blot) | Periplasm (Western Blot) | Supernatant (Western Blot) | OMV SDS-PAGE |
|---|---|---|---|---|
| 961 (o/n) | − | − | − | |
| 961 (IPTG) | +/− | − | − | |
| 961-L (o/n) | + | − | − | + |
| 961-L (IPTG) | + | − | − | + |
| 961c-L (o/n) | − | − | − | |
| 961c-L (IPTG) | + | + | + | |
| 961Δ₁-L (o/n) | − | − | − | |
| 961Δ₁-L (IPTG) | + | − | − | + |

The results show that in *E. coli*:

961-L is highly expressed and localized on the outer membrane. By western blot analysis two specific bands have been detected: one at ~45 kDa (the predicted molecular weight) and one at ~180 kDa, indicating that 961-L can form oligomers. Additionally, these aggregates are more expressed in the over-night culture (without IPTG induction). OMV preparations of this clone were used to immunize mice and serum was obtained. Using overnight culture (predominantly by oligomeric form) the serum was bactericidal; the IPTG-induced culture (predominantly monomeric) was not bactericidal.

961Δ₁-L (with a partial deletion in the anchor region) is highly expressed and localized on the outer membrane, but does not form oligomers;

the 961c-L (without the anchor region) is produced in soluble form and exported in the supernatant.

Titres in ELISA and in the serum bactericidal assay using His-fusions were as follows:

| | ELISA | Bactericidal |
|---|---|---|
| 961a (aa 24-268) | 24397 | 4096 |
| 961b (aa 269-405) | 7763 | 64 |
| 961c-L | 29770 | 8192 |
| 961c (2996) | 30774 | >65536 |
| 961c (MC58) | 33437 | 16384 |
| 961d | 26069 | >65536 |

*E. coli* clones expressing different forms of 961 (961, 961-L, 961Δ₁-L and 961c-L) were used to investigate if the 961 is an adhesin (c.f. YadA). An adhesion assay was performed using (a) the human epithelial cells and (b) *E. coli* clones after either over-night culture or three hours IPTG induction. 961-L grown over-night (961Δ₁-L) and IPTG-induced 961c-L (the clones expressing protein on surface) adhere to human epithelial cells.

961c was also used in hybrid proteins (see above). As 961 and its domain variants direct efficient expression, they are ideally suited as the N-terminal portion of a hybrid protein.

Example 23

Further Hybrids

Further hybrid proteins of the invention are shown below (see also FIG. 14). These are advantageous when compared to the individual proteins:

```
ORF46.1-741
                               (SEQ ID NOS: 140 and 141)
  1 ATGTCAGATT TGGCAAACGA TTCTTTTATC CGGCAGGTTC
    TCGACCGTCA

51 GCATTTCGAA CCCGACGGGA AATACCACCT ATTCGGCAGC
    AGGGGGGAAC

101 TTGCCGAGCG CAGCGGCCAT ATCGGATTGG GAAAAATACA
    AAGCCATCAG

151 TTGGGCAACC TGATGATTCA ACAGGCGGCC ATTAAAGGAA
    ATATCGGCTA

201 CATTGTCCGC TTTTCCGATC ACGGGCACGA AGTCCATTCC
    CCCTTCGACA

251 ACCATGCCTC ACATTCCGAT TCTGATGAAG CCGGTAGTCC
    CGTTGACGGA

301 TTTAGCCTTT ACCGCATCCA TTGGGACGGA TACGAACACC
    ATCCCGCCGA

351 CGGCTATGAC GGGCCACAGG GCGGCGGCTA TCCCGCTCCC
    AAAGGCGCGA

401 GGGATATATA CAGCTACGAC ATAAAAGGCG TTGCCCAAAA
    TATCCGCCTC

451 AACCTGACCG ACAACCGCAG CACCGGACAA CGGCTTGCCG
    ACCGTTTCCA

501 CAATGCCGGT AGTATGCTGA CGCAAGGAGT AGGCGACGGA
    TTCAAACGCG
```

```
551 CCACCCGATA CAGCCCCGAG CTGGACAGAT CGGGCAATGC
    CGCCGAAGCC

601 TTCAACGGCA CTGCAGATAT CGTTAAAAAC ATCATCGGCG
    CGGCAGGAGA

651 AATTGTCGGC GCAGGCGATG CCGTGCAGGG CATAAGCGAA
    GGCTCAAACA

701 TTGCTGTCAT GCACGGCTTG GGTCTGCTTT CCACCGAAAA
    CAAGATGGCG

751 CGCATCAACG ATTTGGCAGA TATGGCGCAA CTCAAAGACT
    ATGCCGCAGC

801 AGCCATCCGC GATTGGGCAG TCCAAAACCC CAATGCCGCA
    CAAGGCATAG

851 AAGCCGTCAG CAATATCTTT ATGGCAGCCA TCCCCATCAA
    AGGGATTGGA

901 GCTGTTCGGG GAAAATACGG CTTGGGCGGC ATCACGGCAC
    ATCCTATCAA

951 GCGGTCGCAG ATGGGCGCGA TCGCATTGCC GAAAGGGAAA
    TCCGCCGTCA

1001 GCGACAATTT TGCCGATGCG GCATACGCCA ATACCCGTC
     CCCTTACCAT

1051 TCCCGAAATA TCCGTTCAAA CTTGGAGCAG CGTTACGGCA
     AAGAAAACAT

1101 CACCTCCTCA ACCGTGCCGC CGTCAAACGG CAAAAATGTC
     AAACTGGCAG

1151 ACCAACGCCA CCCGAAGACA GGCGTACCGT TTGACGGTAA
     AGGGTTTCCG

1201 AATTTTGAGA AGCACGTGAA ATATGATACG GGATCCGGAG
     GGGGTGGTGT

1251 CGCCGCCGAC ATCGGTGCGG GGCTTGCCGA TGCACTAACC
     GCACCGCTCG

1301 ACCATAAAGA CAAAGGTTTG CAGTCTTTGA CGCTGGATCA
     GTCCGTCAGG

1351 AAAAACGAGA AACTGAAGCT GGCGGCACAA GGTGCGGAAA
     AAACTTATGG

1401 AAACGGTGAC AGCCTCAATA CGGGCAAATT GAAGAACGAC
     AAGGTCAGCC

1451 GTTTCGACTT TATCCGCCAA ATCGAAGTGG ACGGGCAGCT
     CATTACCTTG

1501 GAGAGTGGAG AGTTCCAAGT ATACAAACAA AGCCATTCCG
     CCTTAACCGC

1551 CTTTCAGACC GAGCAAATAC AAGATTCGGA GCATTCCGGG
     AAGATGGTTG

1601 CGAAACGCCA GTTCAGAATC GGCGACATAG CGGGCGAACA
     TACATCTTTT

1651 GACAAGCTTC CGAAGGCGG CAGGGCGACA TATCGCGGGA
     CGGCGTTCGG

1701 TTCAGACGAT GCCGGCGAA AACTGACCTA CACCATAGAT
     TTCGCCGCCA

1751 AGCAGGGAAA CGGCAAAATC GAACATTTGA ATCGCCAGA
     ACTCAATGTC

1801 GACCTGGCCG CCGCCGATAT CAAGCCGGAT GGAAAACGCC
     ATGCCGTCAT

1851 CAGCGGTTCC GTCCTTTACA ACCAAGCCGA GAAAGGCAGT
     TACTCCCTCG

1901 GTATCTTTGG CGGAAAAGCC CAGGAAGTTG CCGGCAGCGC
     GGAAGTGAAA

1951 ACCGTAAACG GCATACGCCA TATCGGCCTT GCCGCCAAGC
     AACTCGAGCA

2001 CCACCACCAC CACCACTGA

1 MSDLANDSFI RQVLDRQHFE PDGKYHLFGS RGELAERSGH
     IGLGKIQSHQ

51 LGNLMIQQAA IKGNIGYIVR FSDHGHEVHS PFDNHASHSD
     SDEAGSPVDG

101 FSLYRIHWDG YEHHPADGYD GPQGGGYPAP KGARDIYSYD
     IKGVAQNIRL

151 NLTDNRSTGQ RLADRFHNAG SMLTQGVGDG FKRATRYSPE
     LDRSGNAAEA

201 FNGTADIVKN IIGAAGEIVG AGDAVQGISE GSNIAVMHGL
     GLLSTENKMA

251 RINDLADMAQ LKDYAAAAIR DWAVQNPNAA QGIEAVSNIF
     MAAIPIKGIG

301 AVRGKYGLGG ITAHPIKRSQ MGAIALPKGK SAVSDNFADA
     AYAKYPSPYH

351 SRNIRSNLEQ RYGKENITSS TVPPSNGKNV KLADQRHPKT
     GVPFDGKGFP

401 NFEKHVKYDT GSGGGGVAAD IGAGLADALT APLDHKDKGL
     QSLTLDQSVR

451 KNEKLKLAAQ GAEKTYGNGD SLNTGKLKND KVSRFDFIRQ
     IEVDGQLITL

501 ESGEFQVYKQ SHSALTAFQT EQIQDSEHSG KMVAKRQFRI
     GDIAGEHTSF

551 DKLPEGGRAT YRGTAFGSDD AGGKLTYTID FAAKQGNGKI
     EHLKSPELNV

601 DLAAADIKPD GKRHAVISGS VLYNQAEKGS YSLGIFGGKA
     QEVAGSAEVK

651 TVNGIRHIGL AAKQLEHHHH HH*

ORF46.1-961
                              (SEQ ID NOS: 142 and 143)
   1 ATGTCAGATT TGGCAAACGA TTCTTTTATC CGGCAGGTTC
     TCGACCGTCA

51 GCATTTCGAA CCCGACGGGA AATACCACCT ATTCGGCAGC
     AGGGGGGAAC

101 TTGCCGAGCG CAGCGGCCAT ATCGGATTGG GAAAAATACA
     AAGCCATCAG

151 TTGGGCAACC TGATGATTCA ACAGGCGGCC ATTAAAGGAA
     ATATCGGCTA

201 CATTGTCCGC TTTTCCGATC ACGGGCACGA AGTCCATTCC
     CCCTTCGACA

251 ACCATGCCTC ACATTCCGAT TCTGATGAAG CCGGTAGTCC
     CGTTGACGGA

301 TTTAGCCTTT ACCGCATCCA TTGGGACGGA TACGAACACC
     ATCCCGCCGA

351 CGGCTATGAC GGGCCACAGG GCGGCGGCTA TCCCGCTCCC
     AAAGGCGCGA

401 GGGATATATA CAGCTACGAC ATAAAAGGCG TTGCCCAAAA
     TATCCGCCTC

451 AACCTGACCG ACAACCGCAG CACCGGACAA CGGCTTGCCG
     ACCGTTTCCA
```

```
 501 CAATGCCGGT AGTATGCTGA CGCAAGGAGT AGGCGACGGA
     TTCAAACGCG

551 CCACCCGATA CAGCCCCGAG CTGGACAGAT CGGGCAATGC
     CGCCGAAGCC

601 TTCAACGGCA CTGCAGATAT CGTTAAAAAC ATCATCGGCG
     CGGCAGGAGA

651 AATTGTCGGC GCAGGCGATG CCGTGCAGGG CATAAGCGAA
     GGCTCAAACA

701 TTGCTGTCAT GCACGGCTTG GGTCTGCTTT CCACCGAAAA
     CAAGATGGCG

751 CGCATCAACG ATTTGGCAGA TATGGCGCAA CTCAAAGACT
     ATGCCGCAGC

801 AGCCATCCGC GATTGGGCAG TCCAAAACCC CAATGCCGCA
     CAAGGCATAG

851 AAGCCGTCAG CAATATCTTT ATGGCAGCCA TCCCCATCAA
     AGGGATTGGA

901 GCTGTTCGGG GAAAATACGG CTTGGGCGGC ATCACGGCAC
     ATCCTATCAA

951 GCGGTCGCAG ATGGGCGCGA TCGCATTGCC GAAAGGGAAA
     TCCGCCGTCA

1001 GCGACAATTT TGCCGATGCG GCATACGCCA ATACCCGTC
     CCCTTACCAT

1051 TCCCGAAATA TCCGTTCAAA CTTGGAGCAG CGTTACGGCA
     AAGAAAACAT

1101 CACCTCCTCA ACCGTGCCGC CGTCAAACGG CAAAAATGTC
     AAACTGGCAG

1151 ACCAACGCCA CCCGAAGACA GGCGTACCGT TTGACGGTAA
     AGGGTTTCCG

1201 AATTTTGAGA AGCACGTGAA ATATGATACG GGATCCGGAG
     GAGGAGGAGC

1251 CACAAACGAC GACGATGTTA AAAAAGCTGC CACTGTGGCC
     ATTGCTGCTG

1301 CCTACAACAA TGGCCAAGAA ATCAACGGTT TCAAAGCTGG
     AGAGACCATC

1351 TACGACATTG ATGAAGACGG CACAATTACC AAAAAAGACG
     CAACTGCAGC

1401 CGATGTTGAA GCCGACGACT TTAAAGGTCT GGGTCTGAAA
     AAAGTCGTGA

1451 CTAACCTGAC CAAAACCGTC AATGAAAACA AACAAAACGT
     CGATGCCAAA

1501 GTAAAAGCTG CAGAATCTGA AATAGAAAAG TTAACAACCA
     AGTTAGCAGA

1551 CACTGATGCC GCTTTAGCAG ATACTGATGC CGCTCTGGAT
     GCAACCACCA

1601 ACGCCTTGAA TAAATTGGGA GAAAATATAA CGACATTTGC
     TGAAGAGACT

1651 AAGACAAATA TCGTAAAAAT TGATGAAAAA TTAGAAGCCG
     TGGCTGATAC

1701 CGTCGACAAG CATGCCGAAG CATTCAACGA TATCGCCGAT
     TCATTGGATG

1751 AAACCAACAC TAAGGCAGAC GAAGCCGTCA AAACCGCCAA
     TGAAGCCAAA

1801 CAGACGGCCG AAGAAACCAA ACAAAACGTC GATGCCAAAG
     TAAAAGCTGC

1851 AGAAACTGCA GCAGGCAAAG CCGAAGCTGC CGCTGGCACA
     GCTAATACTG

1901 CAGCCGACAA GGCCGAAGCT GTCGCTGCAA AAGTTACCGA
     CATCAAAGCT

1951 GATATCGCTA CGAACAAAGA TAATATTGCT AAAAAAGCAA
     ACAGTGCCGA

2001 CGTGTACACC AGAGAAGAGT CTGACAGCAA ATTTGTCAGA
     ATTGATGGTC

2051 TGAACGCTAC TACCGAAAAA TTGGACACAC GCTTGGCTTC
     TGCTGAAAAA

2101 TCCATTGCCG ATCACGATAC TCGCCTGAAC GGTTTGGATA
     AAACAGTGTC

2151 AGACCTGCGC AAAGAAACCC GCCAAGGCCT TGCAGAACAA
     GCCGCGCTCT

2201 CCGGTCTGTT CCAACCTTAC AACGTGGGTC GGTTCAATGT
     AACGGCTGCA

2251 GTCGGCGGCT ACAAATCCGA ATCGGCAGTC GCCATCGGTA
     CCGGCTTCCG

2301 CTTTACCGAA AACTTTGCCG CCAAAGCAGG CGTGGCAGTC
     GGCACTTCGT

2351 CCGGTTCTTC CGCAGCCTAC CATGTCGGCG TCAATTACGA
     GTGGCTCGAG

2401 CACCACCACC ACCACCACTG A

1 MSDLANDSFI RQVLDRQHFE PDGKYHLFGS RGELAERSGH
     IGLGKIQSHQ

51 LGNLMIQQAA IKGNIGYIVR FSDHGHEVHS PFDNHASHSD
     SDEAGSPVDG

101 FSLYRIHWDG YEHHPADGYD GPQGGGYPAP KGARDIYSYD
     IKGVAQNIRL

151 NLTDNRSTGQ RLADRFHNAG SMLTQGVGDG FKRATRYSPE
     LDRSGNAAEA

201 FNGTADIVKN IIGAAGEIVG AGDAVQGISE GSNIAVMHGL
     GLLSTENKMA

251 RINDLADMAQ LKDYAAAAIR DWAVQNPNAA QGIEAVSNIF
     MAAIPIKGIG

301 AVRGKYGLGG ITAHPIKRSQ MGAIALPKGK SAVSDNFADA
     AYAKYPSPYH

351 SRNIRSNLEQ RYGKENITSS TVPPSNGKNV KLADQRHPKT
     GVPFDGKGFP

401 NFEKHVKYDT GSGGGGATND DDVKKAATVA IAAAYNNGQE
     INGFKAGETI

451 YDIDEDGTIT KKDATAADVE ADDFKGLGLK KVVTNLTKTV
     NENKQNVDAK

501 VKAAESEIEK LTTKLADTDA ALADTDAALD ATTNALNKLG
     ENITTFAEET

551 KTNIVKIDEK LEAVADTVDK HAEAFNDIAD SLDETNTKAD
     EAVKTANEAK

601 QTAEETKQNV DAKVKAAETA AGKAEAAAGT ANTAADKAEA
     VAAKVTDIKA

651 DIATNKDNIA KKANSADVYT REESDSKFVR IDGLNATTEK
     LDTRLASAEK

701 SIADHDTRLN GLDKTVSDLR KETRQGLAEQ AALSGLFQPY
     NVGRFNVTAA
```

```
751 VGGYKSESAV AIGTGFRFTE NFAAKAGVAV GTSSGSSAAY
    HVGVNYEWLE

801 HHHHHH*

ORF46.1-961c
                    (SEQ ID NOS: 144 and 145)
  1 ATGTCAGATT TGGCAAACGA TTCTTTTATC CGGCAGGTTC
    TCGACCGTCA

51 GCATTTCGAA CCCGACGGGA AATACCACCT ATTCGGCAGC
    AGGGGGGAAC

101 TTGCCGAGCG CAGCGGCCAT ATCGGATTGG GAAAAATACA
    AAGCCATCAG

151 TTGGGCAACC TGATGATTCA ACAGGCGGCC ATTAAGGAA
    ATATCGGCTA

201 CATTGTCCGC TTTTCCGATC ACGGGCACGA AGTCCATTCC
    CCCTTCGACA

251 ACCATGCCTC ACATTCCGAT TCTGATGAAG CCGGTAGTCC
    CGTTGACGGA

301 TTTAGCCTTT ACCGCATCCA TTGGGACGGA TACGAACACC
    ATCCCGCCGA

351 CGGCTATGAC GGGCCACAGG GCGGCGGCTA TCCCGCTCCC
    AAAGGCGCGA

401 GGGATATATA CAGCTACGAC ATAAAAGGCG TTGCCCAAAA
    TATCCGCCTC

451 AACCTGACCG ACAACCGCAG CACCGGACAA CGGCTTGCCG
    ACCGTTTCCA

501 CAATGCCGGT AGTATGCTGA CGCAAGGAGT AGGCGACGGA
    TTCAAACGCG

551 CCACCCGATA CAGCCCCGAG CTGGACAGAT CGGGCAATGC
    CGCCGAAGCC

601 TTCAACGGCA CTGCAGATAT CGTTAAAAAC ATCATCGGCG
    CGGCAGGAGA

651 AATTGTCGGC GCAGGCGATG CCGTGCAGGG CATAAGCGAA
    GGCTCAAACA

701 TTGCTGTCAT GCACGGCTTG GGTCTGCTTT CCACCGAAAA
    CAAGATGGCG

751 CGCATCAACG ATTTGGCAGA TATGGCGCAA CTCAAAGACT
    ATGCCGCAGC

801 AGCCATCCGC GATTGGGCAG TCCAAAACCC CAATGCCGCA
    CAAGGCATAG

851 AAGCCGTCAG CAATATCTTT ATGGCAGCCA TCCCCATCAA
    AGGGATTGGA

901 GCTGTTCGGG GAAAATACGC TTGGGCGGC ATCACGGCAC
    ATCCTATCAA

951 GCGGTCGCAG ATGGGCGCGA TCGCATTGCC GAAAGGGAAA
    TCCGCCGTCA

1001 GCGACAATTT TGCCGATGCG GCATACGCCA AATACCCGTC
     CCCTTACCAT

1051 TCCCGAAATA TCCGTTCAAA CTTGGAGCAG CGTTACGGCA
     AAGAAAACAT

1101 CACCTCCTCA ACCGTGCCGC CGTCAAACGG CAAAAATGTC
     AAACTGGCAG

1151 ACCAACGCCA CCCGAAGACA GGCGTACCGT TTGACGGTAA
     AGGGTTTCCG

1201 AATTTTGAGA AGCACGTGAA ATATGATACG GGATCCGGAG
     GAGGAGGAGC

1251 CACAAACGAC GACGATGTTA AAAAGCTGC CACTGTGGCC
     ATTGCTGCTG

1301 CCTACAACAA TGGCCAAGAA ATCAACGGTT TCAAAGCTGG
     AGAGACCATC

1351 TACGACATTG ATGAAGACGG CACAATTACC AAAAAAGACG
     CAACTGCAGC

1401 CGATGTTGAA GCCGACGACT TTAAAGGTCT GGGTCTGAAA
     AAAGTCGTGA

1451 CTAACCTGAC CAAAACCGTC AATGAAAACA AACAAAACGT
     CGATGCCAAA

1501 GTAAAAGCTG CAGAATCTGA AATAGAAAAG TTAACAACCA
     AGTTAGCAGA

1551 CACTGATGCC GCTTTAGCAG ATACTGATGC CGCTCTGGAT
     GCAACCACCA

1601 ACGCCTTGAA TAAATTGGGA GAAAATATAA CGACATTTGC
     TGAAGAGACT

1651 AAGACAAATA TCGTAAAAAT TGATGAAAAA TTAGAAGCCG
     TGGCTGATAC

1701 CGTCGACAAG CATGCCGAAG CATTCAACGA TATCGCCGAT
     TCATTGGATG

1751 AAACCAACAC TAAGGCAGAC GAAGCCGTCA AAACCGCCAA
     TGAAGCCAAA

1801 CAGACGGCCG AAGAAACCAA ACAAAACGTC GATGCCAAAG
     TAAAAGCTGC

1851 AGAAACTGCA GCAGGCAAAG CCGAAGCTGC CGCTGGCACA
     GCTAATACTG

1901 CAGCCGACAA GGCCGAAGCT GTCGCTGCAA AAGTTACCGA
     CATCAAAGCT

1951 GATATCGCTA CGAACAAAGA TAATATTGCT AAAAAAGCAA
     ACAGTGCCGA

2001 CGTGTACACC AGAGAAGAGT CTGACAGCAA ATTTGTCAGA
     ATTGATGGTC

2051 TGAACGCTAC TACCGAAAAA TTGGACACAC GCTTGGCTTC
     TGCTGAAAAA

2101 TCCATTGCCG ATCACGATAC TCGCCTGAAC GGTTTGGATA
     AAACAGTGTC

2151 AGACCTGCGC AAAGAAACCC GCCAAGGCCT TGCAGAACAA
     GCCGCGCTCT

2201 CCGGTCTGTT CCAACCTTAC AACGTGGGTC TCGAGCACCA
     CCACCACCAC

2251 CACTGA

1 MSDLANDSFI RQVLDRQHFE PDGKYHLFGS RGELAERSGH
    IGLGKIQSHQ

51 LGNLMIQQAA IKGNIGYIVR FSDHGHEVHS PFDNHASHSD
    SDEAGSPVDG

101 FSLYRIHWDG YEHHPADGYD GPQGGGYPAP KGARDIYSYD
    IKGVAQNIRL

151 NLTDNRSTGQ RLADRFHNAG SMLTQGVGDG FKRATRYSPE
    LDRSGNAAEA

201 FNGTADIVKN IIGAAGEIVG AGDAVQGISE GSNIAVMHGL
    GLLSTENKMA

251 RINDLADMAQ LKDYAAAAIR DWAVQNPNAA QGIEAVSNIF
    MAAIPIKGIG
```

-continued

```
301 AVRGKYGLGG ITAHPIKRSQ MGAIALPKGK SAVSDNFADA
    AYAKYPSPYH

351 SRNIRSNLEQ RYGKENITSS TVPPSNGKNV KLADQRHPKT
    GVPFDGKGFP

401 NFEKHVKYDT GSGGGGATND DDVKKAATVA IAAAYNNGQE
    INGFKAGETI

451 YDIDEDGTIT KKDATAADVE ADDFKGLGLK KVVTNLTKTV
    NENKQNVDAK

501 VKAAESEIEK LTTKLADTDA ALADTDAALD ATTNALNKLG
    ENITTFAEET

551 KTNIVKIDEK LEAVADTVDK HAEAFNDIAD SLDETNTKAD
    EAVKTANEAK

601 QTAEETKQNV DAKVKAAETA AGKAEAAAGT ANTAADKAEA
    VAAKVTDIKA

651 DIATNKDNIA KKANSADVYT REESDSKFVR IDGLNATTEK
    LDTRLASAEK

701 SIADHDTRLN GLDKTVSDLR KETRQGLAEQ AALSGLFQPY
    NVGLEHHHHH

751 H*
```

961-ORF46.1
(SEQ ID NOS: 146 and 147)

```
   1 ATGGCCACAA ACGACGACGA TGTTAAAAAA GCTGCCACTG
     TGGCCATTGC

51 TGCTGCCTAC AACAATGGCC AAGAAATCAA CGGTTTCAAA
     GCTGGAGAGA

101 CCATCTACGA CATTGATGAA GACGGCACAA TTACCAAAAA
     AGACGCAACT

151 GCAGCCGATG TTGAAGCCGA CGACTTTAAA GGTCTGGGTC
     TGAAAAAAGT

201 CGTGACTAAC CTGACCAAAA CCGTCAATGA AAACAAACAA
     AACGTCGATG

251 CCAAAGTAAA AGCTGCAGAA TCTGAAATAG AAAAGTTAAC
     AACCAAGTTA

301 GCAGACACTG ATGCCGCTTT AGCAGATACT GATGCCGCTC
     TGGATGCAAC

351 CACCAACGCC TTGAATAAAT TGGGAGAAAA TATAACGACA
     TTTGCTGAAG

401 AGACTAAGAC AAATATCGTA AAAATTGATG AAAAATTAGA
     AGCCGTGGCT

451 GATACCGTCG ACAAGCATGC CGAAGCATTC AACGATATCG
     CCGATTCATT

501 GGATGAAACC AACACTAAGG CAGACGAAGC CGTCAAAACC
     GCCAATGAAG

551 CCAAACAGAC GGCCGAAGAA ACCAAACAAA ACGTCGATGC
     CAAAGTAAAA

601 GCTGCAGAAA CTGCAGCAGG CAAAGCCGAA GCTGCCGCTG
     GCACAGCTAA

651 TACTGCAGCC GACAAGGCCG AAGCTGTCGC TGCAAAAGTT
     ACCGACATCA

701 AAGCTGATAT CGCTACGAAC AAAGATAATA TTGCTAAAAA
     AGCAAACAGT

751 GCCGACGTGT ACACCAGAGA AGAGTCTGAC AGCAAATTTG
     TCAGAATTGA

801 TGGTCTGAAC GCTACTACCG AAAAATTGGA CACACGCTTG
     GCTTCTGCTG

851 AAAAATCCAT TGCCGATCAC GATACTCGCC TGAACGGTTT
     GGATAAAACA

901 GTGTCAGACC TGCGCAAAGA AACCCGCCAA GGCCTTGCAG
     AACAAGCCGC

951 GCTCTCCGGT CTGTTCCAAC CTTACAACGT GGGTCGGTTC
     AATGTAACGG

1001 CTGCAGTCGG CGGCTACAAA TCCGAATCGG CAGTCGCCAT
     CGGTACCGGC

1051 TTCCGCTTTA CCGAAAACTT TGCCGCCAAA GCAGGCGTGG
     CAGTCGGCAC

1101 TTCGTCCGGT TCTTCCGCAG CCTACCATGT CGGCGTCAAT
     TACGAGTGGG

1151 GATCCGGAGG AGGAGGATCA GATTTGGCAA ACGATTCTTT
     TATCCGGCAG

1201 GTTCTCGACC GTCAGCATTT CGAACCCGAC GGGAAATACC
     ACCTATTCGG

1251 CAGCAGGGGG GAACTTGCCG AGCGCAGCGG CCATATCGGA
     TTGGGAAAAA

1301 TACAAAGCCA TCAGTTGGGC AACCTGATGA TTCAACAGGC
     GGCCATTAAA

1351 GGAAATATCG GCTACATTGT CCGCTTTTCC GATCACGGGC
     ACGAAGTCCA

1401 TTCCCCCTTC GACAACCATG CCTCACATTC CGATTCTGAT
     GAAGCCGGTA

1451 GTCCCGTTGA CGGATTTAGC CTTTACCGCA TCCATTGGGA
     CGGATACGAA

1501 CACCATCCCG CCGACGGCTA TGACGGGCCA CAGGGCGGCG
     GCTATCCCGC

1551 TCCCAAAGGC GCGAGGGATA TATACAGCTA CGACATAAAA
     GGCGTTGCCC

1601 AAAATATCCG CCCTCAACCTG ACCGACAACC GCAGCACCGG
     ACAACGGCTT

1651 GCCGACCGTT TCCACAATGC CGGTAGTATG CTGACGCAAG
     GAGTAGGCGA

1701 CGGATTCAAA CGCGCCACCC GATACAGCCC CGAGCTGGAC
     AGATCGGGCA

1751 ATGCCGCCGA AGCCTTCAAC GGCACTGCAG ATATCGTTAA
     AAACATCATC

1801 GGCGCGGCAG GAGAAATTGT CGGCGCAGGC GATGCCGTGC
     AGGGCATAAG

1851 CGAAGGCTCA ACATTGCTG TCATGCACGG CTTGGGTCTG
     CTTTCCACCG

1901 AAAACAAGAT GGCGCGCATC AACGATTTGG CAGATATGGC
     GCAACTCAAA

1951 GACTATGCCG CAGCAGCCAT CCGCGATTGG GCAGTCCAAA
     ACCCCAATGC

2001 CGCACAAGGC ATAGAAGCCG TCAGCAATAT CTTTATGGCA
     GCCATCCCCA

2051 TCAAAGGGAT TGGAGCTGTT CGGGGAAAAT ACGGCTTGGG
     CGGCATCACG

2101 GCACATCCTA TCAAGCGGTC GCAGATGGGC GCGATCGCAT
     TGCCGAAAGG

2151 GAAATCCGCC GTCAGCGACA ATTTTGCCGA TGCGGCATAC
     GCCAAATACC
```

-continued

```
2201  CGTCCCCTTA CCATTCCCGA ATATCCGTT CAAACTTGGA
      GCAGCGTTAC

2251  GGCAAAGAAA ACATCACCTC CTCAACCGTG CCGCCGTCAA
      ACGGCAAAAA

2301  TGTCAAACTG GCAGACCAAC GCCACCCGAA GACAGGCGTA
      CCGTTTGACG

2351  GTAAAGGGTT TCCGAATTTT GAGAAGCACG TGAAATATGA
      TACGCTCGAG

2401  CACCACCACC ACCACCACTG A
```

```
  1  MATNDDDVKK AATVAIAAAY NNGQEINGFK AGETIYDIDE
     DGTITKKDAT

51  AADVEADDFK GLGLKKVVTN LTKTVNENKQ NVDAKVKAAE
     SEIEKLTTKL

101  ADTDAALADT DAALDATTNA LNKLGENITT FAEETKTNIV
     KIDEKLEAVA

151  DTVDKHAEAF NDIADSLDET NTKADEAVKT ANEAKQTAEE
     TKQNVDAKVK

201  AAETAAGKAE AAAGTANTAA DKAEAVAAKV TDIKADIATN
     KDNIAKKANS

251  ADVYTREESD SKFVRIDGLN ATTEKLDTRL ASAEKSIADH
     DTRLNGLDKT

301  VSDLRKETRQ GLAEQAALSG LFQPYNVGRF NVTAAVGGYK
     SESAVAIGTG

351  FRFTENFAAK AGVAVGTSSG SSAAYHVGVN YEWGSGGGGS
     DLANDSFIRQ

401  VLDRQHFEPD GKYHLFGSRG ELAERSGHIG LGKIQSHQLG
     NLMIQQAAIK

451  GNIGYIVRFS DHGHEVHSPF DNHASHSDSD EAGSPVDGFS
     LYRIHWDGYE

501  HHPADGYDGP QGGGYPAPKG ARDIYSYDIK GVAQNIRLNL
     TDNRSTGQRL

551  ADRFHNAGSM LTQGVGDGFK RATRYSPELD RSGNAAEAFN
     GTADIVKNII

601  GAAGEIVGAG DAVQGISEGS NIAVMHGLGL LSTENKMARI
     NDLADMAQLK

651  DYAAAAIRDW AVQNPNAAQG IEAVSNIFMA AIPIKGIGAV
     RGKYGLGGIT

701  AHPIKRSQMG AIALPKGKSA VSDNFADAAY AKYPSPYHSR
     NIRSNLEQRY

751  GKENITSSTV PPSNGKNVKL ADQRHPKTGV PFDGKGFPNF
     EKHVKYDTLE

801  HHHHHH*
```

961-741

(SEQ ID NOS: 148 and 149)

```
  1  ATGGCCACAA ACGACGACGA TGTTAAAAAA GCTGCCACTG
     TGGCCATTGC

51  TGCTGCCTAC AACAATGGCC AAGAAATCAA CGGTTTCAAA
     GCTGGAGAGA

101  CCATCTACGA CATTGATGAA GACGGCACAA TTACCAAAAA
     AGACGCAACT

151  GCAGCCGATG TTGAAGCCGA CGACTTTAAA GGTCTGGGTC
     TGAAAAAAGT

201  CGTGACTAAC CTGACCAAAA CCGTCAATGA AAACAAACAA
     AACGTCGATG
```

```
 251  CCAAAGTAAA AGCTGCAGAA TCTGAAATAG AAAAGTTAAC
      AACCAAGTTA

301  GCAGACACTG ATGCCGCTTT AGCAGATACT GATGCCGCTC
      TGGATGCAAC

351  CACCAACGCC TTGAATAAAT TGGGAGAAAA TATAACGACA
      TTTGCTGAAG

401  AGACTAAGAC AAATATCGTA AAAATTGATG AAAAATTAGA
      AGCCGTGGCT

451  GATACCGTCG ACAAGCATGC CGAAGCATTC AACGATATCG
      CCGATTCATT

501  GGATGAAACC AACACTAAGG CAGACGAAGC CGTCAAAACC
      GCCAATGAAG

551  CCAAACAGAC GGCCGAAGAA ACCAAACAAA ACGTCGATGC
      CAAAGTAAAA

601  GCTGCAGAAA CTGCAGCAGG CAAAGCCGAA GCTGCCGCTG
      GCACAGCTAA

651  TACTGCAGCC GACAAGGCCG AAGCTGTCGC TGCAAAAGTT
      ACCGACATCA

701  AAGCTGATAT CGCTACGAAC AAAGATAATA TTGCTAAAAA
      AGCAAACAGT

751  GCCGACGTGT ACACCAGAGA AGAGTCTGAC AGCAAATTTG
      TCAGAATTGA

801  TGGTCTGAAC GCTACTACCG AAAAATTGGA CACACGCTTG
      GCTTCTGCTG

851  AAAAATCCAT TGCCGATCAC GATACTCGCC TGAACGGTTT
      GGATAAAACA

901  GTGTCAGACC TGCGCAAAGA AACCCGCCAA GGCCTTGCAG
      AACAAGCCGC

951  GCTCTCCGGT CTGTTCCAAC CTTACAACGT GGGTCGGTTC
      AATGTAACGG

1001  CTGCAGTCGG CGGCTACAAA TCCGAATCGG CAGTCGCCAT
      CGGTACCGGC

1051  TTCCGCTTTA CCGAAAACTT TGCCGCCAAA GCAGGCGTGG
      CAGTCGGCAC

1101  TTCGTCCGGT TCTTCCGCAG CCTACCATGT CGGCGTCAAT
      TACGAGTGGG

1151  GATCCGGAGG GGGTGGTGTC GCCGCCGACA TCGGTGCGGG
      GCTTGCCGAT

1201  GCACTAACCG CACCGCTCGA CCATAAAGAC AAAGGTTTGC
      AGTCTTTGAC

1251  GCTGGATCAG TCCGTCAGGA AAAACGAGAA ACTGAAGCTG
      GCGGCACAAG

1301  GTGCGGAAAA AACTTATGGA AACGGTGACA GCCTCAATAC
      GGGCAAATTG

1351  AAGAACGACA AGGTCAGCCG TTTCGACTTT ATCCGCCAAA
      TCGAAGTGGA

1401  CGGGCAGCTC ATTACCTTGG AGAGTGGAGA GTTCCAAGTA
      TACAAACAAA

1451  GCCATTCCGC CTTAACCGCC TTTCAGACCG AGCAAATACA
      AGATTCGGAG

1501  CATTCCGGGA AGATGGTTGC GAAACGCCAG TTCAGAATCG
      GCGACATAGC

1551  GGGCGAACAT ACATCTTTTG ACAAGCTTCC CGAAGGCGGC
      AGGGCGACAT
```

-continued

```
1601 ATCGCGGGAC GGCGTTCGGT TCAGACGATG CCGGCGGAAA
     ACTGACCTAC

1651 ACCATAGATT TCGCCGCCAA GCAGGGAAAC GGCAAAATCG
     AACATTTGAA

1701 ATCGCCAGAA CTCAATGTCG ACCTGGCCGC CGCCGATATC
     AAGCCGGATG

1751 GAAAACGCCA TGCCGTCATC AGCGGTTCCG TCCTTTACAA
     CCAAGCCGAG

1801 AAAGGCAGTT ACTCCCTCGG TATCTTTGGC GGAAAAGCCC
     AGGAAGTTGC

1851 CGGCAGCGCG GAAGTGAAAA CCGTAAACGG CATACGCCAT
     ATCGGCCTTG

1901 CCGCCAAGCA ACTCGAGCAC CACCACCACC ACCACTGA

1 MATNDDDVKK AATVAIAAAY NNGQEINGFK AGETIYDIDE
     DGTITKKDAT

51 AADVEADDFK GLGLKKVVTN LTKTVNENKQ NVDAKVKAAE
     SEIEKLTTKL

101 ADTDAALADT DAALDATTNA LNKLGENITT FAEETKTNIV
     KIDEKLEAVA

151 DTVDKHAEAF NDIADSLDET NTKADEAVKT ANEAKQTAEE
     TKQNVDAKVK

201 AAETAAGKAE AAAGTANTAA DKAEAVAAKV TDIKADIATN
     KDNIAKKANS

251 ADVYTREESD SKFVRIDGLN ATTEKLDTRL ASAEKSIADH
     DTRLNGLDKT

301 VSDLRKETRQ GLAEQAALSG LFQPYNVGRF NVTAAVGGYK
     SESAVAIGTG

351 FRFTENFAAK AGVAVGTSSG SSAAYHVGVN YEWGSGGGGV
     AADIGAGLAD

401 ALTAPLDHKD KGLQSLTLDQ SVRKNEKLKL AAQGAEKTYG
     NGDSLNTGKL

451 KNDKVSRFDF IRQIEVDGQL ITLESGEFQV YKQSHSALTA
     FQTEQIQDSE

501 HSGKMVAKRQ FRIGDIAGEH TSFDKLPEGG RATYRGTAFG
     SDDAGGKLTY

551 TIDFAAKQGN GKIEHLKSPE LNVDLAAADI KPDGKRHAVI
     SGSVLYNQAE

601 KGSYSLGIFG GKAQEVAGSA EVKTVNGIRH IGLAAKQLEH
     HHHHH*

961-983
                    (SEQ ID NOS: 150 and 151)
   1 ATGGCCACAA ACGACGACGA TGTTAAAAAA GCTGCCACTG
     TGGCCATTGC

51 TGCTGCCTAC AACAATGGCC AAGAAATCAA CGGTTTCAAA
     GCTGGAGAGA

101 CCATCTACGA CATTGATGAA GACGGCACAA TTACCAAAAA
     AGACGCAACT

151 GCAGCCGATG TTGAAGCCGA CGACTTTAAA GGTCTGGGTC
     TGAAAAAAGT

201 CGTGACTAAC CTGACCAAAA CCGTCAATGA AAACAAACAA
     AACGTCGATG

251 CCAAAGTAAA AGCTGCAGAA TCTGAAATAG AAAAGTTAAC
     AACCAAGTTA

301 GCAGACACTG ATGCCGCTTT AGCAGATACT GATGCCGCTC
     TGGATGCAAC

351 CACCAACGCC TTGAATAAAT TGGGAGAAAA TATAACGACA
     TTTGCTGAAG

401 AGACTAAGAC AAATATCGTA AAAATTGATG AAAAATTAGA
     AGCCGTGGCT

451 GATACCGTCG ACAAGCATGC CGAAGCATTC AACGATATCG
     CCGATTCATT

501 GGATGAAACC AACACTAAGG CAGACGAAGC CGTCAAAACC
     GCCAATGAAG

551 CCAAACAGAC GGCCGAAGAA ACCAAACAAA ACGTCGATGC
     CAAAGTAAAA

601 GCTGCAGAAA CTGCAGCAGG CAAAGCCGAA GCTGCCGCTG
     GCACAGCTAA

651 TACTGCAGCC GACAAGGCCG AAGCTGTCGC TGCAAAAGTT
     ACCGACATCA

701 AAGCTGATAT CGCTACGAAC AAAGATAATA TTGCTAAAAA
     AGCAAACAGT

751 GCCGACGTGT ACACCAGAGA AGAGTCTGAC AGCAAATTTG
     TCAGAATTGA

801 TGGTCTGAAC GCTACTACCG AAAAATTGGA CACACGCTTG
     GCTTCTGCTG

851 AAAAATCCAT TGCCGATCAC GATACTCGCC TGAACGGTTT
     GGATAAAACA

901 GTGTCAGACC TGCGCAAAGA AACCCGCCAA GGCCTTGCAG
     AACAAGCCGC

951 GCTCTCCGGT CTGTTCCAAC CTTACAACGT GGGTCGGTTC
     AATGTAACGG

1001 CTGCAGTCGG CGGCTACAAA TCCGAATCGG CAGTCGCCAT
     CGGTACCGGC

1051 TTCCGCTTTA CCGAAAACTT TGCCGCCAAA GCAGGCGTGG
     CAGTCGGCAC

1101 TTCGTCCGGT TCTTCCGCAG CCTACCATGT CGGCGTCAAT
     TACGAGTGGG

1151 GATCCGGCGG AGGCGGCACT TCTGCGCCCG ACTTCAATGC
     AGGCGGTACC

1201 GGTATCGGCA GCAACAGCAG AGCAACAACA GCGAAATCAG
     CAGCAGTATC

1251 TTACGCCGGT ATCAAGAACG AAATGTGCAA AGACAGAAGC
     ATGCTCTGTG

1301 CCGGTCGGGA TGACGTTGCG GTTACAGACA GGGATGCCAA
     AATCAATGCC

1351 CCCCCCCCGA ATCTGCATAC CGGAGACTTT CCAAACCCAA
     ATGACGCATA

1401 CAAGAATTTG ATCAACCTCA AACCTGCAAT TGAAGCAGGC
     TATACAGGAC

1451 GCGGGGTAGA GGTAGGTATC GTCGACACAG GCGAATCCGT
     CGGCAGCATA

1501 TCCTTTCCCG AACTGTATGG CAGAAAAGAA CACGGCTATA
     ACGAAAATTA

1551 CAAAAACTAT ACGGCGTATA TGCGGAAGGA AGCGCCTGAA
     GACGGAGGCG

1601 GTAAAGACAT TGAAGCTTCT TTCGACGATG AGGCCGTTAT
     AGAGACTGAA
```

-continued

1651 GCAAAGCCGA CGGATATCCG CCACGTAAAA GAAATCGGAC
     ACATCGATTT

1701 GGTCTCCCAT ATTATTGGCG GGCGTTCCGT GGACGGCAGA
     CCTGCAGGCG

1751 GTATTGCGCC CGATGCGACG CTACACATAA TGAATACGAA
     TGATGAAACC

1801 AAGAACGAAA TGATGGTTGC AGCCATCCGC AATGCATGGG
     TCAAGCTGGG

1851 CGAACGTGGC GTGCGCATCG TCAATAACAG TTTTGGAACA
     ACATCGAGGG

1901 CAGGCACTGC CGACCTTTTC CAAATAGCCA ATTCGGAGGA
     GCAGTACCGC

1951 CAAGCGTTGC TCGACTATTC CGGCGGTGAT AAAACAGACG
     AGGGTATCCG

2001 CCTGATGCAA CAGAGCGATT ACGGCAACCT GTCCTACCAC
     ATCCGTAATA

2051 AAAACATGCT TTTCATCTTT TCGACAGGCA ATGACGCACA
     AGCTCAGCCC

2101 AACACATATG CCCTATTGCC ATTTTATGAA AAAGACGCTC
     AAAAAGGCAT

2151 TATCACAGTC GCAGGCGTAG ACCGCAGTGG AGAAAAGTTC
     AAACGGGAAA

2201 TGTATGGAGA ACCGGGTACA GAACCGCTTG AGTATGGCTC
     CAACCATTGC

2251 GGAATTACTG CCATGTGGTG CCTGTCGGCA CCCTATGAAG
     CAAGCGTCCG

2301 TTTCACCCGT ACAAACCCGA TTCAAATTGC CGGAACATCC
     TTTTCCGCAC

2351 CCATCGTAAC CGGCACGGCG GCTCTGCTGC TGCAGAAATA
     CCCGTGGATG

2401 AGCAACGACA ACCTGCGTAC CACGTTGCTG ACGACGGCTC
     AGGACATCGG

2451 TGCAGTCGGC GTGGACAGCA AGTTCGGCTG GGGACTGCTG
     GATGCGGGTA

2501 AGGCCATGAA CGGACCCGCG TCCTTTCCGT TCGGCGACTT
     TACCGCCGAT

2551 ACGAAAGGTA CATCCGATAT TGCCTACTCC TTCCGTAACG
     ACATTTCAGG

2601 CACGGCCGGC CTGATCAAAA AAGGCGGCAG CCAACTGCAA
     CTGCACGGCA

2651 ACAACACCTA TACGGGCAAA ACCATTATCG AAGGCGGTTC
     GCTGGTGTTG

2701 TACGGCAACA ACAAATCGGA TATGCGCGTC GAAACCAAAG
     GTGCGCTGAT

2751 TTATAACGGG GCGGCATCCG GCGGCAGCCT GAACAGCGAC
     GGCATTGTCT

2801 ATCTGGCAGA TACCGACCAA TCCGGCGCAA ACGAAACCGT
     ACACATCAAA

2851 GGCAGTCTGC AGCTGGACGG CAAAGGTACG CTGTACACAC
     GTTTGGGCAA

2901 ACTGCTGAAA GTGGACGGTA CGGCGATTAT CGGCGGCAAG
     CTGTACATGT

2951 CGGCACGCGG CAAGGGGGCA GGCTATCTCA ACAGTACCGG
     ACGACGTGTT

3001 CCCTTCCTGA GTGCCGCCAA AATCGGGCAG GATTATTCTT
     TCTTCACAAA

3051 CATCGAAACC GACGGCGGCC TGCTGGCTTC CCTCGACAGC
     GTCGAAAAAA

3101 CAGCGGGCAG TGAAGGCGAC ACGCTGTCCT ATTATGTCCG
     TCGCGGCAAT

3151 GCGGCACGGA CTGCTTCGGC AGCGGCACAT TCCGCGCCCG
     CCGGTCTGAA

3201 ACACGCCGTA GAACAGGGCG GCAGCAATCT GGAAAACCTG
     ATGGTCGAAC

3251 TGGATGCCTC CGAATCATCC GCAACACCCG AGACGGTTGA
     AACTGCGGCA

3301 GCCGACCGCA CAGATATGCC GGGCATCCGC CCCTACGGCG
     CAACTTTCCG

3351 CGCAGCGGCA GCCGTACAGC ATGCGAATGC CGCCGACGGT
     GTACGCATCT

3401 TCAACAGTCT CGCCGCTACC GTCTATGCCG ACAGTACCGC
     CGCCCATGCC

3451 GATATGCAGG GACGCCGCCT GAAAGCCGTA TCGGACGGGT
     TGGACCACAA

3501 CGGCACGGGT CTGCGCGTCA TCGCGCAAAC CCAACAGGAC
     GGTGGAACGT

3551 GGGAACAGGG CGGTGTTGAA GGCAAAATGC GCGGCAGTAC
     CCAAACCGTC

3601 GGCATTGCCG CGAAAACCGG CGAAAATACG ACAGCAGCCG
     CCACACTGGG

3651 CATGGGACGC AGCACATGGA GCGAAAACAG TGCAAATGCA
     AAAACCGACA

3701 GCATTAGTCT GTTTGCAGGC ATACGGCACG ATGCGGGCGA
     TATCGGCTAT

3751 CTCAAAGGCC TGTTCTCCTA CGGACGCTAC AAAAACAGCA
     TCAGCCGCAG

3801 CACCGGTGCG GACGAACATG CGGAAGGCAG CGTCAACGGC
     ACGCTGATGC

3851 AGCTGGGCGC ACTGGGCGGT GTCAACGTTC CGTTTGCCGC
     AACGGGAGAT

3901 TTGACGGTCG AAGGCGGTCT GCGCTACGAC CTGCTCAAAC
     AGGATGCATT

3951 CGCCGAAAAA GGCAGTGCTT TGGGCTGGAG CGGCAACAGC
     CTCACTGAAG

4001 GCACGCTGGT CGGACTCGCG GGTCTGAAGC TGTCGCAACC
     CTTGAGCGAT

4051 AAAGCCGTCC TGTTTGCAAC GGCGGGCGTG AACGCGACC
     TGAACGGACG

4101 CGACTACACG GTAACGGGCG GCTTTACCGG CGCGACTGCA
     GCAACCGGCA

4151 AGACGGGGGC ACGCAATATG CCGCACACCC GTCTGGTTGC
     CGGCCTGGGC

4201 GCGGATGTCG AATTCGGCAA CGGCTGGAAC GGCTTGGCAC
     GTTACAGCTA

```
   1 MATNDDDVKK AATVAIAAAY NNGQEINGFK AGETIYDIDE
     DGTITKKDAT

51 AADVEADDFK GLGLKKVVTN LTKTVNENKQ NVDAKVKAAE
     SEIEKLTTKL

101 ADTDAALADT DAALDATTNA LNKLGENITT FAEETKTNIV
     KIDEKLEAVA

151 DTVDKHAEAF NDIADSLDET NTKADEAVKT ANEAKQTAEE
     TKQNVDAKVK

201 AAETAAGKAE AAAGTANTAA DKAEAVAAKV TDIKADIATN
     KDNIAKKANS

251 ADVYTREESD SKFVRIDGLN ATTEKLDTRL ASAEKSIADH
     DTRLNGLDKT

301 VSDLRKETRQ GLAEQAALSG LFQPYNVGRF NVTAAVGGYK
     SESAVAIGTG

351 FRFTENFAAK AGVAVGTSSG SSAAYHVGVN YEWGSGGGGT
     SAPDFNAGGT

401 GIGSNSRATT AKSAAVSYAG IKNEMCKDRS MLCAGRDDVA
     VTDRDAKINA

451 PPPNLHTGDF PNPNDAYKNL INLKPAIEAG YTGRGVEVGI
     VDTGESVGSI

501 SFPELYGRKE HGYNENYKNY TAYMRKEAPE DGGGKDIEAS
     FDDEAVIETE

551 AKPTDIRHVK EIGHIDLVSH IIGGRSVDGR PAGGIAPDAT
     LHIMNTNDET

601 KNEMMVAAIR NAWVKLGERG VRIVNNSFGT TSRAGTADLF
     QIANSEEQYR

651 QALLDYSGGD KTDEGIRLMQ QSDYGNLSYH IRNKNMLFIF
     STGNDAQAQP

701 NTYALLPFYE KDAQKGIIIV AGVDRSGEKF KREMYGEPGT
     EPLEYGSNHC

751 GITAMWCLSA PYEASVRFTR TNPIQIAGTS FSAPIVTGTA
     ALLLQKYPWM

801 SNDNLRTTLL TTAQDIGAVG VDSKFGWGLL DAGKAMNGPA
     SFPFGDFTAD

851 TKGTSDIAYS FRNDISGTGG LIKKGGSQLQ LHGNNTYTGK
     TIIEGGSLVL

901 YGNNKSDMRV ETKGALIYNG AASGGSLNSD GIVYLADTDQ
     SGANETVHIK

951 GSLQLDGKGT LYTRLGKLLK VDGTAIIGGK LYMSARGKGA
     GYLNSTGRRV

1001 PFLSAAKIGQ DYSFFTNIET DGGLLASLDS VEKTAGSEGD
     TLSYYVRRGN

1051 AARTASAAAH SAPAGLKHAV EQGGSNLENL MVELDASESS
     ATPETVETAA

1101 ADRTDMPGIR PYGATFRAAA AVQHANAADG VRIFNSLAAT
     VYADSTAAHA

1151 DMQGRRLKAV SDGLDHNGTG LRVIAQTQQD GGTWEQGGVE
     GKMRGSTQTV

1201 GIAAKTGENT TAAATLGMGR STWSENSANA KTDSISLFAG
     IRHDAGDIGY

1251 LKGLFSYGRY KNSISRSTGA DEHAEGSVNG TLMQLGALGG
     VNVPFAATGD

1301 LTVEGGLRYD LLKQDAFAEK GSALGWSGNS LTEGTLVGLA
     GLKLSQPLSD

1351 KAVLFATAGV ERDLNGRDYT VTGGFTGATA ATGKTGARNM
     PHTRLVAGLG

1401 ADVEFGNGWN GLARYSYAGS KQYGNHSGRV GVGYRFLEHH
     HHHH*

961c-ORF46.1
                         (SEQ ID NOS: 152 and 153)
   1 ATGGCCACAA ACGACGACGA TGTTAAAAAA GCTGCCACTG
     TGGCCATTGC

51 TGCTGCCTAC AACAATGGCC AAGAAATCAA CGGTTTCAAA
     GCTGGAGAGA

101 CCATCTACGA CATTGATGAA GACGGCACAA TTACCAAAAA
     AGACGCAACT

151 GCAGCCGATG TTGAAGCCGA CGACTTTAAA GGTCTGGGTC
     TGAAAAAAGT

201 CGTGACTAAC CTGACCAAAA CCGTCAATGA AAACAAACAA
     AACGTCGATG

251 CCAAAGTAAA AGCTGCAGAA TCTGAAATAG AAAAGTTAAC
     AACCAAGTTA

301 GCAGACACTG ATGCCGCTTT AGCAGATACT GATGCCGCTC
     TGGATGCAAC

351 CACCAACGCC TTGAATAAAT TGGGAGAAAA TATAACGACA
     TTTGCTGAAG

401 AGACTAAGAC AAATATCGTA AAATTGATG  AAAAATTAGA
     AGCCGTGGCT

451 GATACCGTCG ACAAGCATGC CGAAGCATTC AACGATATCG
     CCGATTCATT

501 GGATGAAACC AACACTAAGG CAGACGAAGC CGTCAAAACC
     GCCAATGAAG

551 CCAAACAGAC GGCCGAAGAA ACCAAACAAA ACGTCGATGC
     CAAAGTAAAA

601 GCTGCAGAAA CTGCAGCAGG CAAAGCCGAA GCTGCCGCTG
     GCACAGCTAA

651 TACTGCAGCC GACAAGGCCG AAGCTGTCGC TGCAAAAGTT
     ACCGACATCA

701 AAGCTGATAT CGCTACGAAC AAAGATAATA TTGCTAAAAA
     AGCAAACAGT

751 GCCGACGTGT ACACCAGAGA AGAGTCTGAC AGCAAATTTG
     TCAGAATTGA

801 TGGTCTGAAC GCTACTACCG AAAAATTGGA CACACGCTTG
     GCTTCTGCTG

851 AAAAATCCAT TGCCGATCAC GATACTCGCC TGAACGGTTT
     GGATAAAACA

901 GTGTCAGACC TGCGCAAAGA AACCCGCCAA GGCCTTGCAG
     AACAAGCCGC

951 GCTCTCCGGT CTGTTCCAAC CTTACAACGT GGGTGGATCC
     GGAGGAGGAG
```

```
                                -continued                                                          -continued
1001  GATCAGATTT GGCAAACGAT TCTTTTATCC GGCAGGTTCT         51  AADVEADDFK GLGLKKVVTN LTKTVNENKQ NVDAKVKAAE
      CGACCGTCAG                                              SEIEKLTTKL 1051  CATTTCGAAC CCGACGGGAA ATACCACCTA TTCGGCAGCA        101  ADTDAALADT DAALDATTNA LNKLGENITT FAEETKTNIV
      GGGGGGAACT                                              KIDEKLEAVA 1101  TGCCGAGCGC AGCGGCCATA TCGGATTGGG AAAAATACAA        151  DTVDKHAEAF NDIADSLDET NTKADEAVKT ANEAKQTAEE
      AGCCATCAGT                                              TKQNVDAKVK 1151  TGGGCAACCT GATGATTCAA CAGGCGGCCA TTAAAGGAAA        201  AAETAAGKAE AAAGTANTAA DKAEAVAAKV TDIKADIATN
      TATCGGCTAC                                              KDNIAKKANS 1201  ATTGTCCGCT TTTCCGATCA CGGGCACGAA GTCCATTCCC        251  ADVYTREESD SKFVRIDGLN ATTEKLDTRL ASAEKSIADH
      CCTTCGACAA                                              DTRLNGLDKT 1251  CCATGCCTCA CATTCCGATT CTGATGAAGC CGGTAGTCCC        301  VSDLRKETRQ GLAEQAALSG LFQPYNVGGS GGGGSDLAND
      GTTGACGGAT                                              SFIRQVLDRQ 1301  TTAGCCTTTA CCGCATCCAT TGGGACGGAT ACGAACACCA        351  HFEPDGKYHL FGSRGELAER SGHIGLGKIQ SHQLGNLMIQ
      TCCCGCCGAC                                              QAAIKGNIGY 1351  GGCTATGACG GCCACAGGG CGGCGGCTAT CCCGCTCCCA         401  IVRFSDHGHE VHSPFDNHAS HSDSDEAGSP VDGFSLYRIH
      AAGGCGCGAG                                              WDGYEHHPAD 1401  GGATATATAC AGCTACGACA TAAAAGGCGT TGCCCAAAAT        451  GYDGPQGGGY PAPKGARDIY SYDIKGVAQN IRLNLTDNRS
      ATCCGCCTCA                                              TGQRLADRFH 1451  ACCTGACCGA CAACCGCAGC ACCGGACAAC GGCTTGCCGA        501  NAGSMLTQGV GDGFKRATRY SPELDRSGNA AEAFNGTADI
      CCGTTTCCAC                                              VKNIIGAAGE 1501  AATGCCGGTA GTATGCTGAC GCAAGGAGTA GGCGACGGAT        551  IVGAGDAVQG ISEGSNIAVM HGLGLLSTEN KMARINDLAD
      TCAAACGCGC                                              MAQLKDYAAA 1551  CACCCGATAC AGCCCCGAGC TGGACAGATC GGGCAATGCC        601  AIRDWAVQNP NAAQGIEAVS NIFMAAIPIK GIGAVRGKYG
      GCCGAAGCCT                                              LGGITAHPIK 1601  TCAACGGCAC TGCAGATATC GTTAAAAACA TCATCGGCGC        651  RSQMGAIALP KGKSAVSDNF ADAAYAKYPS PYHSRNIRSN
      GGCAGGAGAA                                              LEQRYGKENI 1651  ATTGTCGGCG CAGGCGATGC CGTGCAGGGC ATAAGCGAAG        701  TSSTVPPSNG KNVKLADQRH PKTGVPFDGK GFPNFEKHVK
      GCTCAAACAT                                              YDTLEHHHHH 1701  TGCTGTCATG CACGGCTTGG GTCTGCTTTC CACCGAAAAC        751  H*
      AAGATGGCGC
                                                        961c-741
1751  GCATCAACGA TTTGGCAGAT ATGGCGCAAC TCAAAGACTA                              (SEQ ID NOS: 154 and 155)
      TGCCGCAGCA                                           1  ATGGCCACAA ACGACGACGA TGTTAAAAAA GCTGCCACTG
                                                              TGGCCATTGC
1801  GCCATCCGCG ATTGGGCAGT CCAAAACCCC AATGCCGCAC
      AAGGCATAGA                                          51  TGCTGCCTAC AACAATGGCC AAGAAATCAA CGGTTTCAAA
                                                              GCTGGAGAGA
1851  AGCCGTCAGC AATATCTTTA TGGCAGCCAT CCCCATCAAA
      GGGATTGGAG                                         101  CCATCTACGA CATTGATGAA GACGGCACAA TTACCAAAAA
                                                              AGACGCAACT
1901  CTGTTCGGGG AAAATACGGC TTGGGCGGCA TCACGGCACA
      TCCTATCAAG                                         151  GCAGCCGATG TTGAAGCCGA CGACTTTAAA GGTCTGGGTC
                                                              TGAAAAAAGT
1951  CGGTCGCAGA TGGGCGCGAT CGCATTGCCG AAAGGGAAAT
      CCGCCGTCAG                                         201  CGTGACTAAC CTGACCAAAA CCGTCAATGA AAACAAACAA
                                                              AACGTCGATG
2001  CGACAATTTT GCCGATGCGG CATACGCCAA ATACCCGTCC
      CCTTACCATT                                         251  CCAAAGTAAA AGCTGCAGAA TCTGAAATAG AAAAGTTAAC
                                                              AACCAAGTTA
2051  CCCGAAATAT CCGTTCAAAC TTGGAGCAGC GTTACGGCAA
      AGAAAACATC                                         301  GCAGACACTG ATGCCGCTTT AGCAGATACT GATGCCGCTC
                                                              TGGATGCAAC
2101  ACCTCCTCAA CCGTGCCGCC GTCAAACGGC AAAAATGTCA
      AACTGGCAGA                                         351  CACCAACGCC TTGAATAAAT TGGGAGAAAA TATAACGACA
                                                              TTTGCTGAAG
2151  CCAACGCCAC CCGAAGACAG GCGTACCGTT TGACGGTAAA
      GGGTTTCCGA                                         401  AGACTAAGAC AAATATCGTA AAATTGATG AAAAATTAGA
                                                              AGCCGTGGCT
2201  ATTTTGAGAA GCACGTGAAA TATGATACGC TCGAGCACCA
      CCACCACCAC                                         451  GATACCGTCG ACAAGCATGC CGAAGCATTC AACGATATCG
                                                              CCGATTCATT
2251  CACTGA
                                                        501  GGATGAAACC AACACTAAGG CAGACGAAGC CGTCAAAACC
   1  MATNDDDVKK AATVAIAAAY NNGQEINGFK AGETIYDIDE              GCCAATGAAG
      DGTITKKDAT
                                                        551  CCAAACAGAC GGCCGAAGAA ACCAAACAAA CGTCGATGC
                                                              CAAAGTAAAA
```

-continued

```
 601 GCTGCAGAAA CTGCAGCAGG CAAAGCCGAA GCTGCCGCTG
     GCACAGCTAA
 651 TACTGCAGCC GACAAGGCCG AAGCTGTCGC TGCAAAAGTT
     ACCGACATCA
 701 AAGCTGATAT CGCTACGAAC AAAGATAATA TTGCTAAAAA
     AGCAAACAGT
 751 GCCGACGTGT ACACCAGAGA AGAGTCTGAC AGCAAATTTG
     TCAGAATTGA
 801 TGGTCTGAAC GCTACTACCG AAAAATTGGA CACACGCTTG
     GCTTCTGCTG
 851 AAAAATCCAT TGCCGATCAC GATACTCGCC TGAACGGTTT
     GGATAAAACA
 901 GTGTCAGACC TGCGCAAAGA AACCCGCCAA GGCCTTGCAG
     AACAAGCCGC
 951 GCTCTCCGGT CTGTTCCAAC CTTACAACGT GGGTGGATCC
     GGAGGGGGTG
1001 GTGTCGCCGC CGACATCGGT GCGGGCTTG CCGATGCACT
     AACCGCACCG
1051 CTCGACCATA AAGACAAAGG TTTGCAGTCT TTGACGCTGG
     ATCAGTCCGT
1101 CAGGAAAAAC GAGAAACTGA AGCTGGCGGC ACAAGGTGCG
     GAAAAAACTT
1151 ATGGAAACGG TGACAGCCTC AATACGGGCA AATTGAAGAA
     CGACAAGGTC
1201 AGCCGTTTCG ACTTTATCCG CCAAATCGAA GTGGACGGGC
     AGCTCATTAC
1251 CTTGGAGAGT GGAGAGTTCC AAGTATACAA ACAAAGCCAT
     TCCGCCTTAA
1301 CCGCCTTTCA GACCGAGCAA ATACAAGATT CGGAGCATTC
     CGGGAAGATG
1351 GTTGCGAAAC GCCAGTTCAG AATCGGCGAC ATAGCGGGCG
     AACATACATC
1401 TTTTGACAAG CTTCCCGAAG GCGGCAGGGC GACATATCGC
     GGGACGGCGT
1451 TCGGTTCAGA CGATGCCGGC GGAAAACTGA CCTACACCAT
     AGATTTCGCC
1501 GCCAAGCAGG GAAACGGCAA AATCGAACAT TTGAAATCGC
     CAGAACTCAA
1551 TGTCGACCTG GCCGCCGCCG ATATCAAGCC GGATGGAAAA
     CGCCATGCCG
1601 TCATCAGCGG TTCCGTCCTT TACAACCAAG CCGAGAAAGG
     CAGTTACTCC
1651 CTCGGTATCT TTGGCGGAAA AGCCCAGGAA GTTGCCGGCA
     GCGCGGAAGT
1701 GAAAACCGTA AACGGCATAC GCCATATCGG CCTTGCCGCC
     AAGCAACTCG
1751 AGCACCACCA CCACCACCAC TGA
   1 MATNDDDVKK AATVAIAAAY NNGQEINGFK AGETIYDIDE
     DGTITKKDAT
  51 AADVEADDFK GLGLKKVVTN LTKTVNENKQ NVDAKVKAAE
     SEIEKLTTKL
 101 ADTDAALADT DAALDATTNA LNKLGENITT FAEETKTNIV
     KIDEKLEAVA
 151 DTVDKHAEAF NDIADSLDET NTKADEAVKT ANEAKQTAEE
     TKQNVDAKVK
 201 AAETAAGKAE AAAGTANTAA DKAEAVAAKV TDIKADIATN
     KDNIAKKANS
 251 ADVYTREESD SKFVRIDGLN ATTEKLDTRL ASAEKSIADH
     DTRLNGLDKT
 301 VSDLRKETRQ GLAEQAALSG LFQPYNVGGS GGGGVAADIG
     AGLADALTAP
 351 LDHKDKGLQS LTLDQSVRKN EKLKLAAQGA EKTYGNGDSL
     NTGKLKNDKV
 401 SRFDFIRQIE VDGQLITLES GEFQVYKQSH SALTAFQTEQ
     IQDSEHSGKM
 451 VAKRQFRIGD IAGEHTSFDK LPEGGRATYR GTAFGSDDAG
     GKLTYTIDFA
 501 AKQGNGKIEH LKSPELNVDL AAADIKPDGK RHAVISGSVL
     YNQAEKGSYS
 551 LGIFGGKAQE VAGSAEVKTV NGIRHIGLAA KQLEHHHHHH
     *

961c-983
                        (SEQ ID NOS: 156 and 157)
   1 ATGGCCACAA ACGACGACGA TGTTAAAAAA GCTGCCACTG
     TGGCCATTGC
  51 TGCTGCCTAC AACAATGGCC AAGAAATCAA CGGTTTCAAA
     GCTGGAGAGA
 101 CCATCTACGA CATTGATGAA GACGGCACAA TTACCAAAAA
     AGACGCAACT
 151 GCAGCCGATG TTGAAGCCGA CGACTTTAAA GGTCTGGGTC
     TGAAAAAAGT
 201 CGTGACTAAC CTGACCAAAA CCGTCAATGA AAACAAACAA
     AACGTCGATG
 251 CCAAAGTAAA AGCTGCAGAA TCTGAAATAG AAAAGTTAAC
     AACCAAGTTA
 301 GCAGACACTG ATGCCGCTTT AGCAGATACT GATGCCGCTC
     TGGATGCAAC
 351 CACCAACGCC TTGAATAAAT TGGGAGAAAA TATAACGACA
     TTTGCTGAAG
 401 AGACTAAGAC AAATATCGTA AAAATTGATG AAAAATTAGA
     AGCCGTGGCT
 451 GATACCGTCG ACAAGCATGC CGAAGCATTC AACGATATCG
     CCGATTCATT
 501 GGATGAAACC AACACTAAGG CAGACGAAGC CGTCAAAACC
     GCCAATGAAG
 551 CCAAACAGAC GGCCGAAGAA ACCAAACAAA ACGTCGATGC
     CAAAGTAAAA
 601 GCTGCAGAAA CTGCAGCAGG CAAAGCCGAA GCTGCCGCTG
     GCACAGCTAA
 651 TACTGCAGCC GACAAGGCCG AAGCTGTCGC TGCAAAAGTT
     ACCGACATCA
 701 AAGCTGATAT CGCTACGAAC AAAGATAATA TTGCTAAAAA
     AGCAAACAGT
 751 GCCGACGTGT ACACCAGAGA AGAGTCTGAC AGCAAATTTG
     TCAGAATTGA
 801 TGGTCTGAAC GCTACTACCG AAAAATTGGA CACACGCTTG
     GCTTCTGCTG
```

-continued

```
 851 AAAAATCCAT TGCCGATCAC GATACTCGCC TGAACGGTTT
     GGATAAAACA
 901 GTGTCAGACC TGCGCAAAGA AACCCGCCAA GGCCTTGCAG
     AACAAGCCGC
 951 GCTCTCCGGT CTGTTCCAAC CTTACAACGT GGGTGGATCC
     GGCGGAGGCG
1001 GCACTTCTGC GCCCGACTTC AATGCAGGCG GTACCGGTAT
     CGGCAGCAAC
1051 AGCAGAGCAA CAACAGCGAA ATCAGCAGCA GTATCTTACG
     CCGGTATCAA
1101 GAACGAAATG TGCAAAGACA GAAGCATGCT CTGTGCCGGT
     CGGGATGACG
1151 TTGCGGTTAC AGACAGGGAT GCCAAAATCA ATGCCCCCCC
     CCCGAATCTG
1201 CATACCGGAG ACTTTCCAAA CCCAAATGAC GCATACAAGA
     ATTTGATCAA
1251 CCTCAAACCT GCAATTGAAG CAGGCTATAC AGGACGCGGG
     GTAGAGGTAG
1301 GTATCGTCGA CACAGGCGAA TCCGTCGGCA GCATATCCTT
     TCCCGAACTG
1351 TATGGCAGAA AAGAACACGG CTATAACGAA AATTACAAAA
     ACTATACGGC
1401 GTATATGCGG AAGGAAGCGC CTGAAGACGG AGGCGGTAAA
     GACATTGAAG
1451 CTTCTTTCGA CGATGAGGCC GTTATAGAGA CTGAAGCAAA
     GCCGACGGAT
1501 ATCCGCCACG TAAAAGAAAT CGGACACATC GATTTGGTCT
     CCCATATTAT
1551 TGGCGGGCGT TCCGTGGACG GCAGACCTGC AGGCGGTATT
     GCGCCCGATG
1601 CGACGCTACA CATAATGAAT ACGAATGATG AAACCAAGAA
     CGAAATGATG
1651 GTTGCAGCCA TCCGCAATGC ATGGGTCAAG CTGGGCGAAC
     GTGGCGTGCG
1701 CATCGTCAAT AACAGTTTTG GAACAACATC GAGGGCAGGC
     ACTGCCGACC
1751 TTTTCCAAAT AGCCAATTCG GAGGAGCAGT ACCGCCAAGC
     GTTGCTCGAC
1801 TATTCCGGCG GTGATAAAAC AGACGAGGGT ATCCGCCTGA
     TGCAACAGAG
1851 CGATTACGGC AACCTGTCCT ACCACATCCG TAATAAAAAC
     ATGCTTTTCA
1901 TCTTTTCGAC AGGCAATGAC GCACAAGCTC AGCCCAACAC
     ATATGCCCTA
1951 TTGCCATTTT ATGAAAAAGA CGCTCAAAAA GGCATTATCA
     CAGTCGCAGG
2001 CGTAGACCGC AGTGGAGAAA AGTTCAAACG GGAAATGTAT
     GGAGAACCGG
2051 GTACAGAACC GCTTGAGTAT GGCTCCAACC ATTGCGGAAT
     TACTGCCATG
2101 TGGTGCCTGT CGGCACCCTA TGAAGCAAGC GTCCGTTTCA
     CCCGTACAAA
2151 CCCGATTCAA ATTGCCGGAA CATCCTTTTC CGCACCCATC
     GTAACCGGCA
2201 CGGCGGCTCT GCTGCTGCAG AAATACCCGT GGATGAGCAA
     CGACAACCTG
2251 CGTACCACGT TGCTGACGAC GGCTCAGGAC ATCGGTGCAG
     TCGGCGTGGA
2301 CAGCAAGTTC GGCTGGGGAC TGCTGGATGC GGGTAAGGCC
     ATGAACGGAC
2351 CCGCGTCCTT TCCGTTCGGC GACTTTACCG CCGATACGAA
     AGGTACATCC
2401 GATATTGCCT ACTCCTTCCG TAACGACATT TCAGGCACGG
     GCGGCCTGAT
2451 CAAAAAGGC GGCAGCCAAC TGCAACTGCA CGGCAACAAC
     ACCTATACGG
2501 GCAAACCAT TATCGAAGGC GGTTCGCTGG TGTTGTACGG
     CAACAACAAA
2551 TCGGATATGC GCGTCGAAAC CAAAGGTGCG CTGATTTATA
     ACGGGGCGGC
2601 ATCCGGCGGC AGCCTGAACA GCGACGGCAT TGTCTATCTG
     GCAGATACCG
2651 ACCAATCCGG CGCAAACGAA ACCGTACACA TCAAAGGCAG
     TCTGCAGCTG
2701 GACGGCAAAG GTACGCTGTA CACACGTTTG GGCAAACTGC
     TGAAAGTGGA
2751 CGGTACGGCG ATTATCGGCG GCAAGCTGTA CATGTCGGCA
     CGCGGCAAGG
2801 GGGCAGGCTA TCTCAACAGT ACCGGACGAC GTGTTCCCTT
     CCTGAGTGCC
2851 GCCAAAATCG GCAGGATTA TTCTTTCTTC ACAAACATCG
     AAACCGACGG
2901 CGGCCTGCTG GCTTCCCTCG ACAGCGTCGA AAAAACAGCG
     GGCAGTGAAG
2951 GCGACACGCT GTCCTATTAT GTCCGTCGCG GCAATGCGGC
     ACGGACTGCT
3001 TCGGCAGCGG CACATTCCGC GCCCGCCGGT CTGAAACACG
     CCGTAGAACA
3051 GGGCGGCAGC AATCTGGAAA ACCTGATGGT CGAACTGGAT
     GCCTCCGAAT
3101 CATCCGCAAC ACCCGAGACG GTTGAAACTG CGGCAGCCGA
     CCGCACAGAT
3151 ATGCCGGGCA TCCGCCCCTA CGGCGCAACT TTCCGCGCAG
     CGGCAGCCGT
3201 ACAGCATGCG AATGCCGCCG ACGGTGTACG CATCTTCAAC
     AGTCTCGCCG
3251 CTACCGTCTA TGCCGACAGT ACCGCCGCCC ATGCCGATAT
     GCAGGGACGC
3301 CGCCTGAAAG CCGTATCGGA CGGGTTGGAC CACAACGGCA
     CGGGTCTGCG
3351 CGTCATCGCG CAAACCCAAC AGGACGGTGG AACGTGGGAA
     CAGGGCGGTG
3401 TTGAAGGCAA AATGCGCGGC AGTACCCAAA CCGTCGGCAT
     TGCCGCGAAA
3451 ACCGGCGAAA ATACGACAGC AGCCGCCACA CTGGGCATGG
     GACGCAGCAC
3501 ATGGAGCGAA AACAGTGCAA ATGCAAAAAC CGACAGCATT
     AGTCTGTTTG
```

```
3551 CAGGCATACG GCACGATGCG GGCGATATCG GCTATCTCAA
     AGGCCTGTTC

3601 TCCTACGGAC GCTACAAAAA CAGCATCAGC CGCAGCACCG
     GTGCGGACGA

3651 ACATGCGAA GGCAGCGTCA ACGGCACGCT GATGCAGCTG
     GGCGCACTGG

3701 GCGGTGTCAA CGTTCCGTTT GCCGCAACGG GAGATTTGAC
     GGTCGAAGGC

3751 GGTCTGCGCT ACGACCTGCT CAAACAGGAT GCATTCGCCG
     AAAAAGGCAG

3801 TGCTTTGGGC TGGAGCGGCA ACAGCCTCAC TGAAGGCACG
     CTGGTCGGAC

3851 TCGCGGGTCT GAAGCTGTCG CAACCCTTGA GCGATAAAGC
     CGTCCTGTTT

3901 GCAACGGCGG GCGTGGAACG CGACCTGAAC GGACGCGACT
     ACACGGTAAC

3951 GGGCGGCTTT ACCGGCGCGA CTGCAGCAAC CGGCAAGACG
     GGGGCACGCA

4001 ATATGCCGCA CACCCGTCTG GTTGCCGGCC TGGGCGCGGA
     TGTCGAATTC

4051 GGCAACGGCT GGAACGGCTT GGCACGTTAC AGCTACGCCG
     GTTCCAAACA

4101 GTACGGCAAC CACAGCGGAC GAGTCGGCGT AGGCTACCGG
     TTCCTCGAGC

4151 ACCACCACCA CCACCACTGA

1 MATNDDDVKK AATVAIAAAY NNGQEINGFK AGETIYDIDE
    DGTITKKDAT

51 AADVEADDFK GLGLKKVVTN LTKTVNENKQ NVDAKVKAAE
    SEIEKLTTKL

101 ADTDAALADT DAALDATTNA LNKLGENITT FAEETKTNIV
    KIDEKLEAVA

151 DTVDKHAEAF NDIADSLDET NTKADEAVKT ANEAKQTAEE
    TKQNVDAKVK

201 AAETAAGKAE AAAGTANTAA DKAEAVAAKV TDIKADIATN
    KDNIAKKANS

251 ADVYTREESD SKFVRIDGLN ATTEKLDTRL ASAEKSIADH
    DTRLNGLDKT

301 VSDLRKETRQ GLAEQAALSG LFQPYNVGGS GGGGTSAPDF
    NAGGTGIGSN

351 SRATTAKSAA VSYAGIKNEM CKDRSMLCAG RDDVAVTDRD
    AKINAPPPNL

401 HTGDFPNPND AYKNLINLKP AIEAGYTGRG VEVGIVDTGE
    SVGSISFPEL

451 YGRKEHGYNE NYKNYTAYMR KEAPEDGGGK DIEASFDDEA
    VIETEAKPTD

501 IRHVKEIGHI DLVSHIIGGR SVDGRPAGGI APDATLHIMN
    TNDETKNEMM

551 VAAIRNAWVK LGERGVRIVN NSFGTTSRAG TADLFQIANS
    EEQYRQALLD

601 YSGGDKTDEG IRLMQQSDYG NLSYHIRNKN MLFIFSTGND
    AQAQPNTYAL

651 LPFYEKDAQK GIITVAGVDR SGEKFKREMY GEPGTEPLEY
    GSNHCGITAM

701 WCLSAPYEAS VRFTRTNPIQ IAGTSFSAPI VTGTAALLLQ
    KYPWMSNDNL

751 RTTLLTTAQD IGAVGVDSKF GWGLLDAGKA MNGPASFPFG
    DFTADTKGTS

801 DIAYSFRNDI SGTGGLIKKG GSQLQLHGNN TYTGKTIIEG
    GSLVLYGNNK

851 SDMRVETKGA LIYNGAASGG SLNSDGIVYL ADTDQSGANE
    TVHIKGSLQL

901 DGKGTLYTRL GKLLKVDGTA IIGGKLYMSA RGKGAGYLNS
    TGRRVPFLSA

951 AKIGQDYSFF TNIETDGGLL ASLDSVEKTA GSEGDTLSYY
    VRRGNAARTA

1001 SAAAHSAPAG LKHAVEQGGS NLENLMVELD ASESSATPET
     VETAAADRTD

1051 MPGIRPYGAT FRAAAAVQHA NAADGVRIFN SLAATVYADS
     TAAHADMQGR

1101 RLKAVSDGLD HNGTGLRVIA QTQQDGGTWE QGGVEGKMRG
     STQTVGIAAK

1151 TGENTTAAAT LGMGRSTWSE NSANAKTDSI SLFAGIRHDA
     GDIGYLKGLF

1201 SYGRYKNSIS RSTGADEHAE GSVNGTLMQL GALGGVNVPF
     AATGDLTVEG

1251 GLRYDLLKQD AFAEKGSALG WSGNSLTEGT LVGLAGLKLS
     QPLSDKAVLF

1301 ATAGVERDLN GRDYTVTGGF TGATAATGKT GARNMPHTRL
     VAGLGADVEF

1351 GNGWNGLARY SYAGSKQYGN HSGRVGVGYR FLEHHHHHH*

961cL-ORF46.1
                    (SEQ ID NOS: 158 and 159)
   1 ATGAAACACT TTCCATCCAA AGTACTGACC ACAGCCATCC
     TTGCCACTTT

51 CTGTAGCGGC GCACTGGCAG CCACAAACGA CGACGATGTT
     AAAAAAGCTG

101 CCACTGTGGC CATTGCTGCT GCCTACAACA ATGGCCAAGA
     AATCAACGGT

151 TTCAAAGCTG GAGAGACCAT CTACGACATT GATGAAGACG
     GCACAATTAC

201 CAAAAAAGAC GCAACTGCAG CCGATGTTGA AGCCGACGAC
     TTTAAAGGTC

251 TGGGTCTGAA AAAAGTCGTG ACTAACCTGA CCAAAACCGT
     CAATGAAAAC

301 AAACAAAACG TCGATGCCAA AGTAAAAGCT GCAGAATCTG
     AAATAGAAAA

351 GTTAACAACC AAGTTAGCAG ACACTGATGC CGCTTTAGCA
     GATACTGATG

401 CCGCTCTGGA TGCAACCACC AACGCCTTGA ATAAATTGGG
     AGAAAATATA

451 ACGACATTTG CTGAAGAGAC TAAGACAAAT ATCGTAAAAA
     TTGATGAAAA

501 ATTAGAAGCC GTGGCTGATA CCGTCGACAA GCATGCCGAA
     GCATTCAACG

551 ATATCGCCGA TTCATTGGAT GAAACCAACA CTAAGGCAGA
     CGAAGCCGTC
```

-continued

```
 601 AAAACCGCCA ATGAAGCCAA ACAGACGGCC GAAGAAACCA
     AACAAAACGT

651 CGATGCCAAA GTAAAAGCTG CAGAAACTGC AGCAGGCAAA
     GCCGAAGCTG

701 CCGCTGGCAC AGCTAATACT GCAGCCGACA AGGCCGAAGC
     TGTCGCTGCA

751 AAAGTTACCG ACATCAAAGC TGATATCGCT ACGAACAAAG
     ATAATATTGC

801 TAAAAAAGCA AACAGTGCCG ACGTGTACAC CAGAGAAGAG
     TCTGACAGCA

851 AATTTGTCAG AATTGATGGT CTGAACGCTA CTACCGAAAA
     ATTGGACACA

901 CGCTTGGCTT CTGCTGAAAA ATCCATTGCC GATCACGATA
     CTCGCCTGAA

951 CGGTTTGGAT AAAACAGTGT CAGACCTGCG CAAAGAAACC
     CGCCAAGGCC

1001 TTGCAGAACA AGCCGCGCTC TCCGGTCTGT TCCAACCTTA
     CAACGTGGGT

1051 GGATCCGGAG GAGGAGGATC AGATTTGGCA AACGATTCTT
     TTATCCGGCA

1101 GGTTCTCGAC CGTCAGCATT TCGAACCCGA CGGGAAATAC
     CACCTATTCG

1151 GCAGCAGGGG GGAACTTGCC GAGCGCAGCG GCCATATCGG
     ATTGGGAAAA

1201 ATACAAAGCC ATCAGTTGGG CAACCTGATG ATTCAACAGG
     CGGCCATTAA

1251 AGGAAATATC GGCTACATTG TCCGCTTTTC CGATCACGGG
     CACGAAGTCC

1301 ATTCCCCCTT CGACAACCAT GCCTCACATT CCGATTCTGA
     TGAAGCCGGT

1351 AGTCCCGTTG ACGGATTTAG CCTTTACCGC ATCCATTGGG
     ACGGATACGA

1401 ACACCATCCC GCCGACGGCT ATGACGGGCC ACAGGGCGGC
     GGCTATCCCG

1451 CTCCCAAAGG CGCGAGGGAT ATATACAGCT ACGACATAAA
     AGGCGTTGCC

1501 CAAAATATCC GCCTCAACCT GACCGACAAC CGCAGCACCG
     GACAACGGCT

1551 TGCCGACCGT TTCCACAATG CCGGTAGTAT GCTGACGCAA
     GGAGTAGGCG

1601 ACGGATTCAA ACGCGCCACC CGATACAGCC CCGAGCTGGA
     CAGATCGGGC

1651 AATGCCGCCG AAGCCTTCAA CGGCACTGCA GATATCGTTA
     AAAACATCAT

1701 CGGCGCGGCA GGAGAAATTG TCGGCGCAGG CGATGCCGTG
     CAGGGCATAA

1751 GCGAAGGCTC AAACATTGCT GTCATGCACG GCTTGGGTCT
     GCTTTCCACC

1801 GAAAACAAGA TGGCGCGCAT CAACGATTTG GCAGATATGG
     CGCAACTCAA

1851 AGACTATGCC GCAGCAGCCA TCCGCGATTG GCAGTCCAA
     AACCCCAATG

1901 CCGCACAAGG CATAGAAGCC GTCAGCAATA TCTTTATGGC
     AGCCATCCCC
```

```
1951 ATCAAAGGGA TTGGAGCTGT TCGGGGAAAA TACGGCTTGG
     GCGGCATCAC

2001 GGCACATCCT ATCAAGCGGT CGCAGATGGG CGCGATCGCA
     TTGCCGAAAG

2051 GGAAATCCGC CGTCAGCGAC AATTTTGCCG ATGCGGCATA
     CGCCAAATAC

2101 CCGTCCCCTT ACCATTCCCG AAATATCCGT TCAAACTTGG
     AGCAGCGTTA

2151 CGGCAAAGAA AACATCACCT CCTCAACCGT GCCGCCGTCA
     AACGGCAAAA

2201 ATGTCAAACT GGCAGACCAA CGCCACCCGA AGACAGGCGT
     ACCGTTTGAC

2251 GGTAAAGGGT TTCCGAATTT TGAGAAGCAC GTGAAATATG
     ATACGTAACT

2301 CGAG
```

```
   1 MKHFPSKVLT TAILATFCSG ALAATNDDDV KKAATVAIAA
     AYNNGQEING

51 FKAGETIYDI DEDGTITKKD ATAADVEADD FKGLGLKKVV
     TNLTKTVNEN

101 KQNVDAKVKA AESEIEKLTT KLADTDAALA DTDAALDATT
     NALNKLGENI

151 TTFAEETKTN IVKIDEKLEA VADTVDKHAE AFNDIADSLD
     ETNTKADEAV

201 KTANEAKQTA EETKQNVDAK VKAAETAAGK AEAAAGTANT
     AADKAEAVAA

251 KVTDIKADIA TNKDNIAKKA NSADVYTREE SDSKFVRIDG
     LNATTEKLDT

301 RLASAEKSIA DHDTRLNGLD KTVSDLRKET RQGLAEQAAL
     SGLFQPYNVG

351 GSGGGGSDLA NDSFIRQVLD RQHFEPDGKY HLFGSRGELA
     ERSGHIGLGK

401 IQSHQLGNLM IQQAAIKGNI GYIVRFSDHG HEVHSPFDNH
     ASHSDSDEAG

451 SPVDGFSLYR IHWDGYEHHP ADGYDGPQGG GYPAPKGARD
     IYSYDIKGVA

501 QNIRLNLTDN RSTGQRLADR FHNAGSMLTQ GVGDGFKRAT
     RYSPELDRSG

551 NAAEAFNGTA DIVKNIIGAA GEIVGAGDAV QGISEGSNIA
     VMHGLGLLST

601 ENKMARINDL ADMAQLKDYA AAAIRDWAVQ NPNAAQGIEA
     VSNIFMAAIP

651 IKGIGAVRGK YGLGGITAHP IKRSQMGAIA LPKGKSAVSD
     NFADAAYAKY

701 PSPYHSRNIR SNLEQRYGKE NITSSTVPPS NGKNVKLADQ
     RHPKTGVPFD

751 GKGFPNFEKH VKYDT*
```

961cL-741
(SEQ ID NOS: 160 and 161)

```
   1 ATGAAACACT TTCCATCCAA AGTACTGACC ACAGCCATCC
     TTGCCACTTT

51 CTGTAGCGGC GCACTGGCAG CCACAAACGA CGACGATGTT
     AAAAAAGCTG

101 CCACTGTGGC CATTGCTGCT GCCTACAACA ATGGCCAAGA
     AATCAACGGT
```

-continued

```
 151 TTCAAAGCTG GAGAGACCAT CTACGACATT GATGAAGACG
     GCACAATTAC

201 CAAAAAAGAC GCAACTGCAG CCGATGTTGA AGCCGACGAC
     TTTAAAGGTC

251 TGGGTCTGAA AAAAGTCGTG ACTAACCTGA CCAAAACCGT
     CAATGAAAAC

301 AAACAAAACG TCGATGCCAA AGTAAAAGCT GCAGAATCTG
     AAATAGAAAA

351 GTTAACAACC AAGTTAGCAG ACACTGATGC CGCTTTAGCA
     GATACTGATG

401 CCGCTCTGGA TGCAACCACC AACGCCTTGA ATAAATTGGG
     AGAAAATATA

451 ACGACATTTG CTGAAGAGAC TAAGACAAAT ATCGTAAAAA
     TTGATGAAAA

501 ATTAGAAGCC GTGGCTGATA CCGTCGACAA GCATGCCGAA
     GCATTCAACG

551 ATATCGCCGA TTCATTGGAT GAAACCAACA CTAAGGCAGA
     CGAAGCCGTC

601 AAAACCGCCA ATGAAGCCAA ACAGACGGCC GAAGAAACCA
     AACAAAACGT

651 CGATGCCAAA GTAAAAGCTG CAGAAACTGC AGCAGGCAAA
     GCCGAAGCTG

701 CCGCTGGCAC AGCTAATACT GCAGCCGACA AGGCCGAAGC
     TGTCGCTGCA

751 AAAGTTACCG ACATCAAAGC TGATATCGCT ACGAACAAAG
     ATAATATTGC

801 TAAAAAAGCA AACAGTGCCG ACGTGTACAC CAGAGAAGAG
     TCTGACAGCA

851 AATTTGTCAG AATTGATGGT CTGAACGCTA CTACCGAAAA
     ATTGGACACA

901 CGCTTGGCTT CTGCTGAAAA ATCCATTGCC GATCACGATA
     CTCGCCTGAA

951 CGGTTTGGAT AAAACAGTGT CAGACCTGCG CAAAGAAACC
     CGCCAAGGCC

1001 TTGCAGAACA AGCCGCGCTC TCCGGTCTGT TCCAACCTTA
     CAACGTGGGT

1051 GGATCCGGAG GGGGTGGTGT CGCCGCCGAC ATCGGTGCGG
     GGCTTGCCGA

1101 TGCACTAACC GCACCGCTCG ACCATAAAGA CAAAGGTTTG
     CAGTCTTTGA

1151 CGCTGGATCA GTCCGTCAGG AAAAACGAGA AACTGAAGCT
     GGCGGCACAA

1201 GGTGCGGAAA AAACTTATGG AAACGGTGAC AGCCTCAATA
     CGGGCAAATT

1251 GAAGAACGAC AAGGTCAGCC GTTTCGACTT TATCCGCCAA
     ATCGAAGTGG

1301 ACGGGCAGCT CATTACCTTG GAGAGTGGAG AGTTCCAAGT
     ATACAAACAA

1351 AGCCATTCCG CCTTAACCGC CTTTCAGACC GAGCAAATAC
     AAGATTCGGA

1401 GCATTCCGGG AAGATGGTTG CGAAACGCCA GTTCAGAATC
     GGCGACATAG

1451 CGGGCGAACA TACATCTTTT GACAAGCTTC CCGAAGGCGG
     CAGGGCGACA
```

-continued

```
1501 TATCGCGGGA CGGCGTTCGG TTCAGACGAT GCCGGCGGAA
     AACTGACCTA

1551 CACCATAGAT TTCGCCGCCA AGCAGGGAAA CGGCAAAATC
     GAACATTTGA

1601 AATCGCCAGA ACTCAATGTC GACCTGGCCG CCGCCGATAT
     CAAGCCGGAT

1651 GGAAAACGCC ATGCCGTCAT CAGCGGTTCC GTCCTTTACA
     ACCAAGCCGA

1701 GAAAGGCAGT TACTCCCTCG GTATCTTTGG CGGAAAAGCC
     CAGGAAGTTG

1751 CCGGCAGCGC GGAAGTGAAA ACCGTAAACG GCATACGCCA
     TATCGGCCTT

1801 GCCGCCAAGC AACTCGAGCA CCACCACCAC CACCACTGA

1 MKHFPSKVLT TAILATFCSG ALAATNDDDV KKAATVAIAA
     AYNNGQEING

51 FKAGETIYDI DEDGTITKKD ATAADVEADD FKGLGLKKVV
     TNLTKTVNEN

101 KQNVDAKVKA AESEIEKLTT KLADTDAALA DTDAALDATT
     NALNKLGENI

151 TTFAEETKTN IVKIDEKLEA VADTVDKHAE AFNDIADSLD
     ETNTKADEAV

201 KTANEAKQTA EETKQNVDAK VKAAETAAGK AEAAAGTANT
     AADKAEAVAA

251 KVTDIKADIA TNKDNIAKKA NSADVYTREE SDSKFVRIDG
     LNATTEKLDT

301 RLASAEKSIA DHDTRLNGLD KTVSDLRKET RQGLAEQAAL
     SGLFQPYNVG

351 GSGGGGVAAD IGAGLADALT APLDHKDKGL QSLTLDQSVR
     KNEKLKLAAQ

401 GAEKTYGNGD SLNTGKLKND KVSRFDFIRQ IEVDGQLITL
     ESGEFQVYKQ

451 SHSALTAFQT EQIQDSEHSG KMVAKRQFRI GDIAGEHTSF
     DKLPEGGRAT

501 YRGTAFGSDD AGGKLTYTID FAAKQGNGKI EHLKSPELNV
     DLAAADIKPD

551 GKRHAVISGS VLYNQAEKGS YSLGIFGGKA QEVAGSAEVK
     TVNGIRHIGL

601 AAKQLEHHHH HH*

961cL-98 3
                               (SEQ ID NOS: 164 and 163)
   1 ATGAAACACT TTCCATCCAA AGTACTGACC ACAGCCATCC
     TTGCCACTTT

51 CTGTAGCGGC GCACTGGCAG CCACAAACGA CGACGATGTT
     AAAAAAGCTG

101 CCACTGTGGC CATTGCTGCT GCCTACAACA ATGGCCAAGA
     AATCAACGG

151 TTCAAAGCTG GAGAGACCAT CTACGACATT GATGAAGACG
     GCACAATTAC

201 CAAAAAAGAC GCAACTGCAG CCGATGTTGA AGCCGACGAC
     TTTAAAGGTC

251 TGGGTCTGAA AAAAGTCGTG ACTAACCTGA CCAAAACCGT
     CAATGAAAAC

301 AAACAAAACG TCGATGCCAA AGTAAAAGCT GCAGAATCTG
     AAATAGAAAA
```

-continued

```
 351 GTTAACAACC AAGTTAGCAG ACACTGATGC CGCTTTAGCA
     GATACTGATG
 401 CCGCTCTGGA TGCAACCACC AACGCCTTGA ATAAATTGGG
     AGAAAATATA
 451 ACGACATTTG CTGAAGAGAC TAAGACAAAT ATCGTAAAAA
     TTGATGAAAA
 501 ATTAGAAGCC GTGGCTGATA CCGTCGACAA GCATGCCGAA
     GCATTCAACG
 551 ATATCGCCGA TTCATTGGAT GAAACCAACA CTAAGGCAGA
     CGAAGCCGTC
 601 AAAACCGCCA ATGAAGCCAA ACAGACGGCC GAAGAAACCA
     AACAAAACGT
 651 CGATGCCAAA GTAAAAGCTG CAGAAACTGC AGCAGGCAAA
     GCCGAAGCTG
 701 CCGCTGGCAC AGCTAATACT GCAGCCGACA AGGCCGAAGC
     TGTCGCTGCA
 751 AAAGTTACCG ACATCAAAGC TGATATCGCT ACGAACAAAG
     ATAATATTGC
 801 TAAAAAAGCA AACAGTGCCG ACGTGTACAC CAGAGAAGAG
     TCTGACAGCA
 851 AATTTGTCAG AATTGATGGT CTGAACGCTA CTACCGAAAA
     ATTGGACACA
 901 CGCTTGGCTT CTGCTGAAAA ATCCATTGCC GATCACGATA
     CTCGCCTGAA
 951 CGGTTTGGAT AAAACAGTGT CAGACCTGCG CAAAGAAACC
     CGCCAAGGCC
1001 TTGCAGAACA AGCCGCGCTC TCCGGTCTGT TCCAACCTTA
     CAACGTGGGT
1051 GGATCCGGCG GAGGCGGCAC TTCTGCGCCC GACTTCAATG
     CAGGCGGTAC
1101 CGGTATCGGC AGCAACAGCA GAGCAACAAC AGCGAAATCA
     GCAGCAGTAT
1151 CTTACGCCGG TATCAAGAAC GAAATGTGCA AAGACAGAAG
     CATGCTCTGT
1201 GCCGGTCGGG ATGACGTTGC GGTTACAGAC AGGGATGCCA
     AAATCAATGC
1251 CCCCCCCCCG AATCTGCATA CCGGAGACTT TCCAAACCCA
     AATGACGCAT
1301 ACAAGAATTT GATCAACCTC AAACCTGCAA TTGAAGCAGG
     CTATACAGGA
1351 CGCGGGGTAG AGGTAGGTAT CGTCGACACA GGCGAATCCG
     TCGGCAGCAT
1401 ATCCTTTCCC GAACTGTATG GCAGAAAAGA ACACGGCTAT
     AACGAAAATT
1451 ACAAAAACTA TACGGCGTAT ATGCGGAAGG AAGCGCCTGA
     AGACGGAGGC
1501 GGTAAAGACA TTGAAGCTTC TTTCGACGAT GAGGCCGTTA
     TAGAGACTGA
1551 AGCAAAGCCG ACGGATATCC GCCACGTAAA GAAATCGGA
     CACATCGATT
1601 TGGTCTCCCA TATTATTGGC GGGCGTTCCG TGGACGGCAG
     ACCTGCAGGC
1651 GGTATTGCGC CCGATGCGAC GCTACACATA ATGAATACGA
     ATGATGAAAC
1701 CAAGAACGAA ATGATGGTTG CAGCCATCCG CAATGCATGG
     GTCAAGCTGG
1751 GCGAACGTGG CGTGCGCATC GTCAATAACA GTTTTGGAAC
     AACATCGAGG
1801 GCAGGCACTG CCGACCTTTT CCAAATAGCC AATTCGGAGG
     AGCAGTACCG
1851 CCAAGCGTTG CTCGACTATT CCGGCGGTGA TAAAACAGAC
     GAGGGTATCC
1901 GCCTGATGCA ACAGAGCGAT TACGGCAACC TGTCCTACCA
     CATCCGTAAT
1951 AAAAACATGC TTTTCATCTT TTCGACAGGC AATGACGCAC
     AAGCTCAGCC
2001 CAACACATAT GCCCTATTGC CATTTTATGA AAAAGACGCT
     CAAAAAGGCA
2051 TTATCACAGT CGCAGGCGTA GACCGCAGTG GAGAAAAGTT
     CAAACGGGAA
2101 ATGTATGGAG AACCGGGTAC AGAACCGCTT GAGTATGGCT
     CCAACCATTG
2151 CGGAATTACT GCCATGTGGT GCCTGTCGGC ACCCTATGAA
     GCAAGCGTCC
2201 GTTTCACCCG TACAAACCCG ATTCAAATTG CCGGAACATC
     CTTTTCCGCA
2251 CCCATCGTAA CCGGCACGGC GGCTCTGCTG CTGCAGAAAT
     ACCCGTGGAT
2301 GAGCAACGAC AACCTGCGTA CCACGTTGCT GACGACGGCT
     CAGGACATCG
2351 GTGCAGTCGG CGTGGACAGC AAGTTCGGCT GGGGACTGCT
     GGATGCGGGT
2401 AAGGCCATGA ACGGACCCGC GTCCTTTCCG TTCGGCGACT
     TTACCGCCGA
2451 TACGAAAGGT ACATCCGATA TTGCCTACTC CTTCCGTAAC
     GACATTTCAG
2501 GCACGGGCGG CCTGATCAAA AAAGGCGGCA GCCAACTGCA
     ACTGCACGGC
2551 AACAACACCT ATACGGGCAA AACCATTATC GAAGGCGGTT
     CGCTGGTGTT
2601 GTACGGCAAC AACAAATCGG ATATGCGCGT CGAAACCAAA
     GGTGCGCTGA
2651 TTTATAACGG GGCGGCATCC GGCGGCAGCC TGAACAGCGA
     CGGCATTGTC
2701 TATCTGGCAG ATACCGACCA ATCCGGCGCA AACGAAACCG
     TACACATCAA
2751 AGGCAGTCTG CAGCTGGACG GCAAAGGTAC GCTGTACACA
     CGTTTGGGCA
2801 AACTGCTGAA AGTGGACGGT ACGGCGATTA TCGGCGGCAA
     GCTGTACATG
2851 TCGGCACGCG GCAAGGGGGC AGGCTATCTC AACAGTACCG
     GACGACGTGT
2901 TCCCTTCCTG AGTGCCGCCA AAATCGGGCA GGATTATTCT
     TTCTTCACAA
2951 ACATCGAAAC CGACGGCGGC CTGCTGGCTT CCCTCGACAG
     CGTCGAAAAA
3001 ACAGCGGGCA GTGAAGGCGA CACGCTGTCC TATTATGTCC
     GTCGCGGCAA
```

-continued

```
3051 TGCGGCACGG ACTGCTTCGG CAGCGGCACA TTCCGCGCCC
     GCCGGTCTGA

3101 AACACGCCGT AGAACAGGGC GGCAGCAATC TGGAAAACCT
     GATGGTCGAA

3151 CTGGATGCCT CCGAATCATC CGCAACACCC GAGACGGTTG
     AAACTGCGGC

3201 AGCCGACCGC ACAGATATGC CGGGCATCCG CCCCTACGGC
     GCAACTTTCC

3251 GCGCAGCGGC AGCCGTACAG CATGCGAATG CCGCCGACGG
     TGTACGCATC

3301 TTCAACAGTC TCGCCGCTAC CGTCTATGCC GACAGTACCG
     CCGCCCATGC

3351 CGATATGCAG GGACGCCGCC TGAAAGCCGT ATCGGACGGG
     TTGGACCACA

3401 ACGGCACGGG TCTGCGCGTC ATCGCGCAAA CCCAACAGGA
     CGGTGGAACG

3451 TGGGAACAGG GCGGTGTTGA AGGCAAAATG CGCGGCAGTA
     CCCAAACCGT

3501 CGGCATTGCC GCGAAAACCG GCGAAAATAC GACAGCAGCC
     GCCACACTGG

3551 GCATGGGACG CAGCACATGG AGCGAAAACA GTGCAAATGC
     AAAAACCGAC

3601 AGCATTAGTC TGTTTGCAGG CATACGGCAC GATGCGGGCG
     ATATCGGCTA

3651 TCTCAAAGGC CTGTTCTCCT ACGGACGCTA CAAAAACAGC
     ATCAGCCGCA

3701 GCACCGGTGC GGACGAACAT GCGGAAGGCA GCGTCAACGG
     CACGCTGATG

3751 CAGCTGGGCG CACTGGGCGG TGTCAACGTT CCGTTTGCCG
     CAACGGGAGA

3801 TTTGACGGTC GAAGGCGGTC TGCGCTACGA CCTGCTCAAA
     CAGGATGCAT

3851 TCGCCGAAAA AGGCAGTGCT TTGGGCTGGA GCGGCAACAG
     CCTCACTGAA

3901 GGCACGCTGG TCGGACTCGC GGGTCTGAAG CTGTCGCAAC
     CCTTGAGCGA

3951 TAAAGCCGTC CTGTTTGCAA CGGCGGGCGT GGAACGCGAC
     CTGAACGGAC

4001 GCGACTACAC GGTAACGGGG GGCTTTACCG GCGCGACTGC
     AGCAACCGGC

4051 AAGACGGGGG CACGCAATAT GCCGCACACC CGTCTGGTTG
     CCGGCCTGGG

4101 CGCGGATGTC GAATTCGGCA ACGGCTGGAA CGGCTTGGCA
     CGTTACAGCT

4151 ACGCCGGTTC CAAACAGTAC GGCAACCACA GCGGACGAGT
     CGGCGTAGGC

4201 TACCGGTTCT GACTCGAG

1 MKHFPSKVLT TAILATFCSG ALAATNDDDV KKAATVAIAA
     AYNNGQEING

51 FKAGETIYDI DEDGTITKKD ATAADVEADD FKGLGLKKVV
     TNLTKTVNEN

101 KQNVDAKVKA AESEIEKLTT KLADTDAALA DTDAALDATT
     NALNKLGENI
```

-continued

```
 151 TTFAEETKTN IVKIDEKLEA VADTVDKHAE AFNDIADSLD
     ETNTKADEAV

201 KTANEAKQTA EETKQNVDAK VKAAETAAGK AEAAAGTANT
     AADKAEAVAA

251 KVTDIKADIA TNKDNIAKKA NSADVYTREE SDSKFVRIDG
     LNATTEKLDT

301 RLASAEKSIA DHDTRLNGLD KTVSDLRKET RQGLAEQAAL
     SGLFQPYNVG

351 GSGGGGTSAP DFNAGGTGIG SNSRATTAKS AAVSYAGIKN
     EMCKDRSMLC

401 AGRDDVAVTD RDAKINAPPP NLHTGDFPNP NDAYKNLINL
     KPAIEAGYTG

451 RGVEVGIVDT GESVGSISFP ELYGRKEHGY NENYKNYTAY
     MRKEAPEDGG

501 GKDIEASFDD EAVIETEAKP TDIRHVKEIG HIDLVSHIIG
     GRSVDGRPAG

551 GIAPDATLHI MNTNDETKNE MMVAAIRNAW VKLGERGVRI
     VNNSFGTTSR

601 AGTADLFQIA NSEEQYRQAL LDYSGGDKTD EGIRLMQQSD
     YGNLSYHIRN

651 KNMLFIFSTG NDAQAQPNTY ALLPFYEKDA QKGIITVAGV
     DRSGEKFKRE

701 MYGEPGTEPL EYGSNHCGIT AMWCLSAPYE ASVRFTRTNP
     IQIAGTSFSA

751 PIVTGTAALL LQKYPWMSND NLRTTLLTTA QDIGAVGVDS
     KFGWGLLDAG

801 KAMNGPASFP FGDFTADTKG TSDIAYSFRN DISGTGGLIK
     KGGSQLQLHG

851 NNTYTGKTII EGGSLVLYGN NKSDMRVETK GALIYNGAAS
     GGSLNSDGIV

901 YLADTDQSGA NETVHIKGSL QLDGKGTLYT RLGKLLKVDG
     TAIIGGKLYM

951 SARGKGAGYL NSTGRRVPFL SAAKIGQDYS FFTNIETDGG
     LLASLDSVEK

1001 TAGSEGDTLS YYVRRGNAAR TASAAAHSAP AGLKHAVEQG
     GSNLENLMVE

1051 LDASESSATP ETVETAAADR TDMPGIRPYG ATFRAAAAVQ
     HANAADGVRI

1101 FNSLAATVYA DSTAAHADMQ GRRLKAVSDG LDHNGTGLRV
     IAQTQQDGGT

1151 WEQGGVEGKM RGSTQTVGIA AKTGENTTAA ATLGMGRSTW
     SENSANAKTD

1201 SISLFAGIRH DAGDIGYLKG LFSYGRYKNS ISRSTGADEH
     AEGSVNGTLM

1251 QLGALGGVNV PFAATGDLTV EGGLRYDLLK QDAFAEKGSA
     LGWSGNSLTE

1301 GTLVGLAGLK LSQPLSDKAV LFATAGVERD LNGRDYTVTG
     GFTGATAATG

1351 KTGARNMPHT RLVAGLGADV EFGNGWNGLA RYSYAGSKQY
     GNHSGRVGVG

1401 YRF*
```

It will be understood that the invention has been described by way of example only and modifications may be made whilst remaining within the scope and spirit of the invention. For instance, the use of proteins from other strains is envisaged [e.g. see WO00/66741 for polymorphic sequences for ORF4, ORF40, ORF46, 225, 235, 287, 519, 726, 919 and 953].

Experimental Details

FPLC Protein Purification

The following table summarises the FPLC protein purification that was used:

| Protein | PI | Column | Buffer | pH | Protocol |
|---|---|---|---|---|---|
| 121.1$^{untagged}$ | 6.23 | Mono Q | Tris | 8.0 | A |
| 128.1$^{untagged}$ | 5.04 | Mono Q | Bis-Tris propane | 6.5 | A |
| 406.1L | 7.75 | Mono Q | Diethanolamine | 9.0 | B |
| 576.1L | 5.63 | Mono Q | Tris | 7.5 | B |
| 593$^{untagged}$ | 8.79 | Mono S | Hepes | 7.4 | A |
| 726$^{untagged}$ | 4.95 | Hi-trap S | Bis-Tris | 6.0 | A |
| 919$^{untagged}$ | 10.5(-leader) | Mono S | Bicine | 8.5 | C |
| 919Lorf4 | 10.4(-leader) | Mono S | Tris | 8.0 | B |
| 920L | 6.92(-leader) | Mono Q | Diethanolamine | 8.5 | A |
| 953L | 7.56(-leader) | Mono S | MES | 6.6 | D |
| 982$^{untagged}$ | 4.73 | Mono Q | Bis-Tris propane | 6.5 | A |
| 919-287 | 6.58 | Hi-trap Q | Tris | 8.0 | A |
| 953-287 | 4.92 | Mono Q | Bis-Tris propane | 6.2 | A |

Buffer solutions included 20-120 mM NaCl, 5.0 mg/ml CHAPS and 10% v/v glycerol. The dialysate was centrifuged at 13000 g for 20 min and applied to either a mono Q or mono S FPLC ion-exchange resin. Buffer and ion exchange resins were chosen according to the pI of the protein of interest and the recommendations of the FPLC protocol manual [Pharmacia: *FPLC Ion Exchange and Chromatofocussing; Principles and Methods*. Pharmacia Publication]. Proteins were eluted using a step-wise NaCl gradient. Purification was analysed by SDS-PAGE and protein concentration determined by the Bradford method.

The letter in the 'protocol' column refers to the following: FPLC-A: Clones 121.1, 128.1, 593, 726, 982, periplasmic protein 920L and hybrid proteins 919-287, 953-287 were purified from the soluble fraction of *E. coli* obtained after disruption of the cells. Single colonies harbouring the plasmid of interest were grown overnight at 37° C. in 20 ml of LB/Amp (100 µg/ml) liquid culture. Bacteria were diluted 1:30 in 1.0 L of fresh medium and grown at either 30° C. or 37° C. until the OD$_{550}$ reached 0.6-08. Expression of recombinant protein was induced with IPTG at a final concentration of 1.0 mM. After incubation for 3 hours, bacteria were harvested by centrifugation at 8000 g for 15 minutes at 4° C. When necessary cells were stored at −20° C. All subsequent procedures were performed on ice or at 4° C. For cytosolic proteins (121.1, 128.1, 593, 726 and 982) and periplasmic protein 920L, bacteria were resuspended in 25 ml of PBS containing complete protease inhibitor (Boehringer-Mannheim). Cells were lysed by sonication using a Branson Sonifier® 450 (ultrasonic cell disruption/homogenizer). Disrupted cells were centrifuged at 8000 g for 30 min to sediment unbroken cells and inclusion bodies and the supernatant taken to 35% v/v saturation by the addition of 3.9 M $(NH_4)_2SO_4$. The precipitate was sedimented at 8000 g for 30 minutes. The supernatant was taken to 70% v/v saturation by the addition of 3.9 M $(NH_4)_2SO_4$ and the precipitate collected as above. Pellets containing the protein of interest were identified by SDS-PAGE and dialysed against the appropriate ion-exchange buffer (see below) for 6 hours or overnight. The periplasmic fraction from *E. coli* expressing 953L was prepared according to the protocol of Evans et. al. [*Infect. Immun.* (1974) 10:1010-1017] and dialysed against the appropriate ion-exchange buffer. Buffer and ion exchange resin were chosen according to the pI of the protein of interest and the recommendations of the FPLC protocol manual (Pharmacia). Buffer solutions included 20 mM NaCl, and 10% (v/v) glycerol. The dialysate was centrifuged at 13000 g for 20 min and applied to either a mono Q or mono S FPLC ion-exchange resin. Buffer and ion exchange resin were chosen according to the pI of the protein of interest and the recommendations of the FPLC protocol manual (Pharmacia). Proteins were eluted from the ion-exchange resin using either step-wise or continuous NaCl gradients. Purification was analysed by SDS-PAGE and protein concentration determined by Bradford method. Cleavage of the leader peptide of periplasmic proteins was demonstrated by sequencing the $NH_2$-terminus (see below).

FPLC-B: These proteins were purified from the membrane fraction of *E. coli*. Single colonies harbouring the plasmid of interest were grown overnight at 37° C. in 20 ml of LB/Amp (100 µg/ml) liquid culture. Bacteria were diluted 1:30 in 1.0 L of fresh medium. Clones 406.1L and 919LOrf4 were grown at 30° C. and Orf25L and 576.1L at 37° C. until the OD$_{550}$ reached 0.6-0.8. In the case of 919LOrf4, growth at 30° C. was essential since expression of recombinant protein at 37° C. resulted in lysis of the cells. Expression of recombinant protein was induced with IPTG at a final concentration of 1.0 mM. After incubation for 3 hours, bacteria were harvested by centrifugation at 8000 g for 15 minutes at 4° C. When necessary cells were stored at −20° C. All subsequent procedures were performed at 4° C. Bacteria were resuspended in 25 ml of PBS containing complete protease inhibitor (Boehringer-Mannheim) and lysed by osmotic shock with 2-3 passages through a French Press. Unbroken cells were removed by centrifugation at 5000 g for 15 min and membranes precipitated by centrifugation at 100000 g (Beckman Ti50, 38000 rpm) for 45 minutes. A Dounce homogenizer was used to re-suspend the membrane pellet in 7.5 ml of 20 mM Tris-HCl (pH 8.0), 1.0 M NaCl and complete protease inhibitor. The suspension was mixed for 2-4 hours, centrifuged at 100000 g for 45 min and the pellet resuspended in 7.5 ml of 20 mM Tris-HCl (pH 8.0), 1.0M NaCl, 5.0 mg/ml CHAPS, 10% (v/v) glycerol and complete protease inhibitor. The solution was mixed overnight, centrifuged at 100000 g for 45 minutes and the supernatant dialysed for 6 hours against an appropriately selected buffer. In the case of Orf25.L, the pellet obtained after CHAPS extraction was found to contain the recombinant protein. This fraction, without further purification, was used to immunise mice.

FPLC-C: Identical to FPLC-A, but purification was from the soluble fraction obtained after permeabilising *E. coli* with polymyxin B, rather than after cell disruption.

FPLC-D: A single colony harbouring the plasmid of interest was grown overnight at 37° C. in 20 ml of LB/Amp (100 µg/ml) liquid culture. Bacteria were diluted 1:30 in 1.0 L of fresh medium and grown at 30° C. until the OD$_{550}$ reached 0.6-0.8. Expression of recombinant protein was induced with IPTG at a final concentration of 1.0 mM. After incubation for 3 hours, bacteria were harvested by centrifugation at 8000 g for 15 minutes at 4° C. When necessary cells were stored at −20° C. All subsequent procedures were performed on ice or at 4° C. Cells were resuspended in 20 mM Bicine (pH 8.5), 20 mM NaCl, 10% (v/v) glycerol, complete protease inhibitor (Boehringer-Mannheim) and disrupted using a Branson Sonifier® 450 (ultrasonic cell disruption/homogenizer). The sonicate was centrifuged at 8000 g for 30 mM to sediment unbroken cells and inclusion bodies. The recombinant protein was precipitated from solution between 35% v/v and 70% v/v saturation by the addition of 3.9M $(NH_4)_2SO_4$. The precipitate was sedimented at 8000 g for 30 minutes, resuspended in 20 mM Bicine (pH 8.5), 20 mM NaCl, 10% (v/v) glycerol and dialysed against this buffer for 6 hours or overnight. The dialysate was centrifuged at 13000 g for 20 min and applied to the FPLC resin. The protein was eluted from the column using a step-wise NaCl gradients. Purification was analysed by SDS-PAGE and protein concentration determined by Bradford method.

Cloning Strategy and Oligonucleotide Design

Genes coding for antigens of interest were amplified by PCR, using oligonucleotides designed on the basis of the genomic sequence of *N. meningitidis* B MC58. Genomic DNA from strain 2996 was always used as a template in PCR reactions, unless otherwise specified, and the amplified fragments were cloned in the expression vector pET21b+ (Novagen) to express the protein as C-terminal His-tagged product, or in pET-24b+(Novagen) to express the protein in 'untagged' form (e.g. ΔG 287K).

Where a protein was expressed without a fusion partner and with its own leader peptide (if present), amplification of the open reading frame (ATG to STOP codons) was performed.

Where a protein was expressed in 'untagged' form, the leader peptide was omitted by designing the 5'-end amplification primer downstream from the predicted leader sequence.

The melting temperature of the primers used in PCR depended on the number and type of hybridising nucleotides in the whole primer, and was determined using the formulae:

$$T_{m1} = 4(G+C) + 2(A+T) \text{(tail excluded)}$$

$$T_{m2} = 64.9 + 0.41(\% \ GC) - 600/N \text{(whole primer)}$$

The melting temperatures of the selected oligonucleotides were usually 65-70° C. for the whole oligo and 50-60° C. for the hybridising region alone.

Oligonucleotides were synthesised using a Perkin Elmer 394 DNA/RNA Synthesizer, eluted from the columns in 2.0 ml $NH_4OH$, and deprotected by 5 hours incubation at 56° C. The oligos were precipitated by addition of 0.3M Na-Acetate and 2 volumes ethanol. The samples were centrifuged and the pellets resuspended in water.

| | | Sequences | SEQ ID NO | Restriction site |
|---|---|---|---|---|
| Orf1L | Fwd | CGCGGATCCGCTAGC-AAAACAACCGACAAACGG | 164 | NheI |
| | Rev | CCCGCTCGAG-TTACCAGCGGTAGCCTA | 165 | XhoI |
| Orf1 | Fwd | CTAGCTAGC-GGACACACTTATTTCGGCATC | 166 | NheI |
| | Rev | CCCGCTCGAG-TTACCAGCGGTAGCCTAATTTG | 167 | XhoI |
| Orf1LOmpA | Fwd | | | NdeI-(NheI) |
| | Rev | CCCGCTCGAG- | 168 | XhoI |
| Orf4L | Fwd | CGCGGATCCCATATG-AAAACCTTCTTCAAAACC | 169 | NdeI |
| | Rev | CCCGCTCGAG-TTATTTGGCTGCGCCTTC | 170 | XhoI |
| Orf7-1L | Fwd | GCGGCATTAAT-ATGTTGAGAAAATTGTTGAAATGG | 171 | AseI |
| | Rev | GCGGCCTCGAG-TTATTTTTTCAAAATATATTTGC | 172 | XhoI |
| Orf9-1L | Fwd | GCGGCCATATG-TTACCTAACCGTTTCAAAATGT | 173 | NdeI |
| | Rev | GCGGCCTCGAG-TTATTTCCGAGGTTTTCGGG | 174 | XhoI |
| Orf23L | Fwd | CGCGGATCCCATATG-ACACGCTTCAAATATTC | 175 | NdeI |
| | Rev | CCCGCTCGAG-TTATTTAAACCGATAGGTAAA | 176 | XhoI |
| Orf25-1 His | Fwd | CGCGGATCCCATATG-GGCAGGGAAGAACCGC | 177 | NdeI |
| | Rev | GCCCAAGCTT-ATCGATGGAATAGCCGCG | 178 | HindIII |
| Orf29-1 b-His (MC58) | Fwd | CGCGGATCCGCTAGC-AACGGTTTGGATGCCCG | 179 | NheI |
| | Rev | CCCGCTCGAG-TTTGTCTAAGTTCCTGATAT | 180 | XhoI |
| | | CCCGCTCGAG-ATTCCCACCTGCCATC | 181 | |
| Orf29-1 b-L (MC58) | Fwd | CGCGGATCCGCTAGC-ATGAATTTGCCTATTCAAAAAT | 182 | NheI |
| | Rev | CCCGCTCGAG-TTAATTCCCACCTGCCATC | 183 | XhoI |
| Orf29-1 c-His (MC58) | Fwd | CGCGGATCCGCTAGC-ATGAATTTGCCTATTCAAAAAT | 184 | NheI |
| | Rev | CCCGCTCGAG-TTGGACGATGCCCGCGA | 185 | XhoI |
| Orf29-1 c-L (MC58) | Fwd | CGCGGATCCGCTAGC-ATGAATTTGCCTATTCAAAAAT | 186 | NheI |
| | Rev | CCCGCTCGAG-TTATTGGACGATGCCCGC | 187 | XhoI |
| Orf25L | Fwd | CGCGGATCCCATATG-TATCGCAAACTGATTGC | 188 | NdeI |
| | Rev | CCCGCTCGAG-CTAATCGATGGAATAGCC | 189 | XhoI |
| Orf37L | Fwd | CGCGGATCCCATATG-AAACAGACAGTCAAATG | 190 | NdeI |
| | Rev | CCCGCTCGAG-TCAATAACCCGCCTTCAG | 191 | XhoI |

-continued

| | | Sequences | SEQ ID NO | Restriction site |
|---|---|---|---|---|
| Orf38L | Fwd | CGCGGATCCCATATG-TTACGTTTGACTGCTTTAGCCGTATGCACC | 192 | NdeI |
| | Rev | CCCGCTCGAG-TTATTTTGCCGCGTTAAAAGCGTCGGCAAC | 193 | XhoI |
| Orf40L | Fwd | CGCGGATCCCATATG-AACAAAATATACCGCAT | 194 | NdeI |
| | Rev | CCCGCTCGAG-TTACCACTGATAACCGAC | 195 | XhoI |
| Orf40.2-His | Fwd | CGCGGATCCCATATG-ACCGATGACGACGATTTAT | 196 | NdeI |
| | Rev | GCCCAAGCTT-CCACTGATAACCGACAGA | 197 | HindIII |
| Orf40.2L | Fwd | CGCGGATCCCATATG-AACAAAATATACCGCAT | 198 | NdeI |
| | Rev | GCCCAAGCTT-TTACCACTGATAACCGAC | 199 | HindIII |
| Orf46-2L | Fwd | GGGAATTCCATATG-GGCATTTCCCGCAAAATATC | 200 | NdeI |
| | Rev | CCCGCTCGAG-TTATTTACTCCTATAACGAGGTCTCTTAAC | 201 | XhoI |
| Orf46-2 | Fwd | GGGAATTCCATATG-TCAGATTTGGCAAACGATTCTT | 202 | NdeI |
| | Rev | CCCGCTCGAG-TTATTTACTCCTATAACGAGGTCTCTTAAC | 203 | XhoI |
| Orf46.1L | Fwd | GGGAATTCCATATG-GGCATTTCCCGCAAAATATC | 204 | NdeI |
| | Rev | CCCGCTCGAG-TTACGTATCATATTTCACGTGC | 205 | XhoI |
| orf46. (His-GST) | Fwd | GGGAATTCCATATGCACGTGAAATATGATACGAAG | 206 | BamHI-NdeI |
| | Rev | CCCGCTCGAGTTTACTCCTATAACGAGGTCTCTTAAC | 207 | XhoI |
| orf46.1-His | Fwd | GGGAATTCCATATGTCAGATTTGGCAAACGATTCTT | 208 | NdeI |
| | Rev | CCCGCTCGAGCGTATCATATTTCACGTGC | 209 | XhoI |
| orf46.2-His | Fwd | GGGAATTCCATATGTCAGATTTGGCAAACGATTCTT | 210 | NdeI |
| | Rev | CCCGCTCGAGTTTACTCCTATAACGAGGTCTCTTAAC | 211 | XhoI |
| Orf65-1-(His/GST) (MC58) | Fwd | CGCGGATCCCATATG-CAAAATGCGTTCAAAATCCC | 212 | BamHI-NdeI |
| | Rev | CGCGGATCCCATATG-AACAAAATATACCGCAT CCCGCTCGAG-TTTGCTTTCGATAGAACGG | 213 214 | XhoI |
| Orf72-1L | Fwd | GCGGCCATATG-GTCATAAAATATACAAATTTGAA | 215 | NdeI |
| | Rev | GCGGCCTCGAG-TTAGCCTGAGACCTTTGCAAATT | 216 | XhoI |
| Orf76-1L | Fwd | GCGGCCATATG-AAACAGAAAAAAACCGCTG | 217 | NdeI |
| | Rev | GCGGCCTCGAG-TTACGGTTTGACACCGTTTTC | 218 | XhoI |
| Orf83.1L | Fwd | CGCGGATCCCATATG-AAAACCCTGCTCCTC | 219 | NdeI |
| | Rev | CCCGCTCGAG-TTATCCTCCTTTGCGGC | 220 | XhoI |
| Orf85-2L | Fwd | GCGGCCATATG-GCAAAAATGATGAAATGGG | 221 | NdeI |
| | Rev | GCGGCCTCGAG-TTATCGGCGCGGCGGGCC | 222 | XhoI |
| Orf91L (MC58) | Fwd | GCGGCCATATGAAAAAATCCTCCCTCATCA | 223 | NdeI |
| | Rev | GCGGCCTCGAGTTATTTGCCGCCGTTTTTGGC | 224 | XhoI |
| Orf91-His(MC58) | Fwd | GCGGCCATATGGCCCCTGCCGACGCGGTAAG | 225 | NdeI |
| | Rev | GCGGCCTCGAGTTTGCCGCCGTTTTTGGCTTTC | 226 | XhoI |
| Orf97-1L | Fwd | GCGGCCATATG-AAACACATACTCCCCCTGA | 227 | NdeI |
| | Rev | GCGGCCTCGAG-TTATTCGCCTACGGTTTTTTG | 228 | XhoI |
| Orf119L (MC58) | Fwd | GCGGCCATATGATTTACATCGTACTGTTTC | 229 | NdeI |
| | Rev | GCGGCCTCGAGTTAGGAGAACAGGCGCAATGC | 230 | XhoI |
| Orf119-His(MC58) | Fwd | GCGGCCATATGTACAACATGTATCAGGAAAC | 231 | NdeI |
| | Rev | GCGGCCTCGAGGGAGAACAGGCGCAATGCGG | 232 | XhoI |
| Orf137.1 (His-GST) (MC58) | Fwd | CGCGGATCCGCTAGCTGCGGCACGGCGGG | 233 | BamHI-NheI |
| | Rec | CCCGCTCGAGATAACGGTATGCCGCCAG | 234 | XhoI |
| Orf143-1L | Fwd | CGCGGATCCCATATG-GAATCAACACTTTCAC | 235 | NdeI |
| | Rev | CCCGCTCGAG-TTACACGCGGTTGCTGT | 236 | XhoI |

-continued

|  |  | Sequences | SEQ ID NO | Restriction site |
|---|---|---|---|---|
| 008 | Fwd | CGCGGATCCCATATG-AACAACAGACATTTTG | 237 | NdeI |
|  | Rev | CCCGCTCGAG-TTACCTGTCCGGTAAAAG | 238 | XhoI |
| 050-1(48) | Fwd | CGCGGATCCGCTAGC-ACCGTCATCAAACAGGAA | 239 | NheI |
|  | Rev | CCCGCTCGAG-TCAAGATTCGACGGGGA | 240 | XhoI |
| 105 | Fwd | CGCGGATCCCATATG-TCCGCAAACGAATACG | 241 | NdeI |
|  | Rev | CCCGCTCGAG-TCAGTGTTCTGCCAGTTT | 242 | XhoI |
| 111L | Fwd | CGCGGATCCCATATG-CCGTCTGAAACACG | 243 | NdeI |
|  | Rev | CCCGCTCGAG-TTAGCGGAGCAGTTTTTC | 244 | XhoI |
| 117-1 | Fwd | CGCGGATCCCATATG-ACCGCCATCAGCC | 245 | NdeI |
|  | Rev | CCCGCTCGAG-TTAAAGCCGGGTAACGC | 246 | XhoI |
| 121-1 | Fwd | GCGGCCATATG-GAAACACAGCTTTACATCGG | 247 | NdeI |
|  | Rev | GCGGCCTCGAG-TCAATAATAATATCCCGCG | 248 | XhoI |
| 122-1 | Fwd | GCGGCCATATG-ATTAAAATCCGCAATATCC | 249 | NdeI |
|  | Rev | GCGGCCTCGAG-TTAAATCTTGGTAGATTGGATTTGG | 250 | XhoI |
| 128-1 | Fwd | GCGGCCATATG-ACTGACAACGCACTGCTCC | 251 | NdeI |
|  | Rev | GCGGCCTCGAG-TCAGACCGCGTTGTCGAAAC | 252 | XhoI |
| 148 | Fwd | CGCGGATCCCATATG-GCGTTAAAAACATCAAA | 253 | NdeI |
|  | Rev | CCCGCTCGAG-TCAGCCCTTCATACAGC | 254 | XhoI |
| 149.1L (MC58) | Fwd | GCGGCATTAATGGCACAAACTACACTCAAACC | 255 | AseI |
|  | Rev | GCGGCCTCGAGTTAAAACTTCACGTTCACGCCG | 256 | XhoI |
| 149.1-His(MC58) | Fwd | GCGGCATTAATGCATGAAACTGAGCAATCGGTGG | 257 | AseI |
|  | Rev | GCGGCCTCGAGAAACTTCACGTTCACGCCGCCGGTAAA | 258 | XhoI |
| 205 (His-GST) (MC58) | Fwd | CGCGGATCCCATATGGGCAAATCCGAAAATACG | 259 | BamHI-NdeI |
|  | Rev | CCCGCTCGAGATAATGGCGGCGGCGG | 260 | XhoI |
| 206L | Fwd | CGCGGATCCCATATG-TTTCCCCCCGACAA | 261 | NdeI |
|  | Rev | CCCGCTCGAG-TCATTCTGTAAAAAAGTATG | 262 | XhoI |
| 214 (His-GST) (MC58) | Fwd | CGCGGATCCCATATGCTTCAAAGCGACAGCAG | 263 | BamHI-NdeI |
|  | Rev | CCCGCTCGAGTTCGGATTTTTGCGTACTC | 264 | XhoI |
| 216 | Fwd | CGCGGATCCCATATG-GCAATGGCAGAAAACG | 265 | NdeI |
|  | Rev | CCCGCTCGAG-CTATACAATCCGTGCCG | 266 | XhoI |
| 225-1L | Fwd | CGCGGATCCCATATG-GATTCTTTTTCAAACC | 267 | NdeI |
|  | Rev | CCCGCTCGAG-TCAGTTCAGAAAGCGGG | 268 | XhoI |
| 235L | Fwd | CGCGGATCCCATATG-AAACCTTTGATTTTAGG | 269 | NdeI |
|  | Rev | CCCGCTCGAG-TTATTTGGGCTGCTCTTC | 270 | XhoI |
| 243 | Fwd | CGCGGATCCCATATG-GTAATCGTCTGGTTG | 271 | NdeI |
|  | Rev | CCCGCTCGAG-CTACGACTTGGTTACCG | 272 | XhoI |
| 247-1L | Fwd | GCGGCCATATG-AGACGTAAAATGCTAAAGCTAC | 273 | NdeI |
|  | Rev | GCGGCCTCGAG-TCAAAGTGTTCTGTTTGCGC | 274 | XhoI |
| 264-His | Fwd | GCCGCCATATG-TTGACTTTAACCCGAAAAA | 275 | NdeI |
|  | Rev | GCCGCCTCGAG-GCCGGCGGTCAATACCGCCCGAA | 276 | XhoI |
| 270 (His-GST) (MC58) | Fwd | CGCGGATCCCATATGGCGCAATGCGATTTGAC | 277 | BamHI-NdeI |
|  | Rev | CCCGCTCGAGTTCGGCGGTAAATGCCG | 278 | XhoI |
| 274L | Fwd | GCGGCCATATG-GCGGGGCCGATTTTTGT | 279 | NdeI |
|  | Rev | GCGGCCTCGAG-TTATTTGCTTTCAGTATTATTG | 280 | XhoI |
| 283L | Fwd | GCGGCCATATG-AACTTTGCTTTATCCGTCA | 281 | NdeI |
|  | Rev | GCGGCCTCGAG-TTAACGGCAGTATTTGTTTAC | 282 | XhoI |

-continued

| | | Sequences | SEQ ID NO | Restriction site |
|---|---|---|---|---|
| 285-His | Fwd | CGCGGATCCCATATGGGTTTGCGCTTCGGGC | 283 | BamHI |
| | Rev | GCCCAAGCTTTTTTCCTTTGCCGTTTCCG | 284 | HindIII |
| 286-His (MC58) | Fwd | CGCGGATCCCATATG-GCCGACCTTTCCGAAAA | 285 | NdeI |
| | Rev | CCCGCTCGAG-GAAGCGCGTTCCCAAGC | 286 | XhoI |
| 286L (MC58) | Fwd | CGCGGATCCCATATG-CACGACACCCGTAC | 287 | NdeI |
| | Rev | CCCGCTCGAG-TTAGAAGCGCGTTCCCAA | 288 | XhoI |
| 287L | Fwd | CTAGCTAGC-TTTAAACGCAGCGTAATCGCAATGG | 289 | NheI |
| | Rev | CCCGCTCGAG-TCAATCCTGCTCTTTTTTGCC | 290 | XhoI |
| 287 | Fwd | CTAGCTAGC-GGGGGCGGCGGTGGCG | 291 | NheI |
| | Rev | CCCGCTCGAG-TCAATCCTGCTCTTTTTTGCC | 292 | XhoI |
| 287LOrf4 | Fwd | CTAGCTAGCGCTCATCCTCGCCGCC-TGCGGGGGCGGCGGT | 293 | NheI |
| | Rev | CCCGCTCGAG-TCAATCCTGCTCTTTTTTGCC | 294 | XhoI |
| 287-fu | Fwd | CGGGGATCC-GGGGGCGGCGGTGGCG | 295 | BamHI |
| | Rev | CCCGCTCGAG-TCAATCCTGCTCTTTTTTGCC | 296 | XhoI |
| 287-His | Fwd | CTAGCTAGC-GGGGGCGGCGGTGGCG | 297 | NheI |
| | Rev | CCCGCTCGAG-ATCCTGCTCTTTTTTGCC* | 298 | XhoI |
| 287-His(2996) | Fwd | CTAGCTAGC-TGCGGGGGCGGCGGTGGCG | 299 | NheI |
| | Rev | CCCGCTCGAG-ATCCTGCTCTTTTTTGCC | 300 | XhoI |
| Δ1 287-His | Fwd | CGCGGATCCGCTAGC-CCCGATGTTAAATCGGC§ | 301 | NheI |
| Δ2 287-His | Fwd | CGCGGATCCGCTAGC-CAAGATATGGCGGCAGT§ | 302 | NheI |
| Δ3 287-His | Fwd | CGCGGATCCGCTAGC-GCCGAATCCGCAAATCA§ | 303 | NheI |
| Δ4 287-Hlσ | Fwd | CGCGCTAGC-GGAAGGGTTGATTTGGCTAATGG§ | 304 | NheI |
| Δ4 287MC58-His | Fwd | CGCGCTAGC-GGAAGGGTTGATTTGGCTAATGG§ | 305 | NheI |
| 287a-His | Fwd | CGCCATATG-TTTAAACGCAGCGTAATCGC | 306 | NdeI |
| | Rev | CCCGCTCGAG-AAAATTGCTACCGCCATTCGCAGG | 307 | XhoI |
| 287b-His | Fwd | CGCCATATG-GGAAGGGTTGATTTGGCTAATGG | 308 | NdeI |
| 287b-2996-His | Rev | CCCGCTCGAG-CTTGTCTTTATAAATGATGACATATTTG | 309 | XhoI |
| 287b-MC58-His | Rev | CCCGCTCGAG-TTTATAAAGATAATATATTGATTGATTCC | 310 | XhoI |
| 287c-2996-His | Fwd | CGCGCTAGC-ATGCCGCTGATTCCCGTCAATC§ | 311 | NheI |
| '287$^{untagged}$' (2996) | Fwd | CTAGCTAGC-GGGGGCGGCGGTGGCG | 312 | NheI |
| | Rev | CCCGCTCGAG-TCAATCCTGCTCTTTTTTGCC | 313 | XhoI |
| ΔG287-His* | Fwd | CGCGGATCCGCTAGC-CCCGATGTTAAATCGGC | 314 | NheI |
| | Rev | CCCGCTCGAG-ATCCTGCTCTTTTTTGCC | 315 | XhoI |
| ΔG287K(2996) | Fwd | CGCGGATCCGCTAGC-CCCGATGTTAAATCGGC | 316 | NheI |
| | Rev | CCCGCTCGAG-TCAATCCTGCTCTTTTTTGCC | 317 | XhoI |
| ΔG 287-L | Fwd | CGCGGATCCGCTAGC-TTTGAACGCAGTGTGATTGCAATGGCTTGTATTTTTGCCCTTTCAGCCTGTTCGCCCGATGTTAAATCGGCG | 318 | NheI |
| | Rev | CCCGCTCGAG-TCAATCCTGCTCTTTTTTGCC | 319 | XhoI |
| ΔG 287-Orf4L | Fwd | CGCGGATCCGCTAGC-AAAACCTTCTTCAAAACCCTTTCCGCCGCCGCACTCGCGCTCATCCTCGCCGCCTGCTCGCCCGATGTTAAATCG | 320 | NheI |
| | Rev | CCCGCTCGAG-TCAATCCTGCTCTTTTTTGCC | 321 | XhoI |
| 292L | Fwd | CGCGGATCCCATATG-AAAACCAAGTTAATCAAA | 322 | NdeI |
| | Rev | CCCGCTCGAG-TTATTGATTTTGCGGATGA | 323 | XhoI |

-continued

| | | Sequences | SEQ ID NO | Restriction site |
|---|---|---|---|---|
| 308-1 | Fwd | CGCGGATCC<u>CATATG</u>-TTAAATCGGGTATTTTATC | 324 | NdeI |
| | Rev | CCCG<u>CTCGAG</u>-TTAATCCGCCATTCCCTG | 325 | XhoI |
| 401L | Fwd | GCGG<u>CCATATG</u>-AAATTACAACAATTGGCTG | 326 | NdeI |
| | Rev | GCGG<u>CCTCGAG</u>-TTACCTTACGTTTTTCAAAG | 327 | XhoI |
| 406L | Fwd | CGCGGATCC<u>CATATG</u>-CAAGCACGGCTGCT | 328 | NdeI |
| | Rev | CCCG<u>CTCGAG</u>-TCAAGGTTGTCCTTGTCTA | 329 | XhoI |
| 502-1L | Fwd | CGCGGATCC<u>CATATG</u>-ATGAAACCGCACAAC | 330 | NdeI |
| | Rev | CCCG<u>CTCGAG</u>-TCAGTTGCTCAACACGTC | 331 | XhoI |
| 502-A (His-GST) | Fwd | CGCG<u>GATCCCATATG</u>GTAGACGCGCTTAAGCA | 332 | BamHI-NdeI |
| | Rev | CCCG<u>CTCGAG</u>AGCTGCATGGCGGCG | 333 | XhoI |
| 503-1L | Fwd | CGCGGATCC<u>CATATG</u>-GCACGGTCGTTATAC | 334 | NdeI |
| | Rev | CCCG<u>CTCGAG</u>-CTACCGCGCATTCCTG | 335 | XhoI |
| 519-1L | Fwd | GCGG<u>CCATATG</u>-GAATTTTTCATTATCTTGTT | 336 | NdeI |
| | Rev | GCGG<u>CCTCGAG</u>-TTATTTGGCGGTTTTGCTGC | 337 | XhoI |
| 525-1L | Fwd | GCGG<u>CCATATG</u>-AAGTATGTCCGGTTATTTTC | 338 | NdeI |
| | Rev | GCGG<u>CCTCGAG</u>-TTATCGGCTTGTGCAACGG | 339 | XhoI |
| 529-(His/GST) (MC58) | Fwd | CGC<u>GGATCCGCTAGC</u>-TCCGGCAGCAAAACCGA | 340 | BamHI-NheI |
| | Rev | GCCC<u>AAGCTT</u>-ACGCAGTTCGGAATGGAG | 341 | HindIII |
| 552L | Fwd | GCCGCCATATGTTGAATATTAAACTGAAAACCTTG | 342 | NdeI |
| | Rev | GCCGCCTCGAGTTATTTCTGATGCCTTTTCCC | 343 | XhoI |
| 556L | Fwd | GCCGCCATATGGACAATAAGACCAAACTG | 344 | NdeI |
| | Rev | GCCGCCTCGAGTTAACGGTGCGGACGTTTC | 345 | XhoI |
| 557L | Fwd | CGCGGATCC<u>CATATG</u>-AACAAACTGTTTCTTAC | 346 | NdeI |
| | Rev | CCCG<u>CTCGAG</u>-TCATTCCGCCTTCAGAAA | 347 | XhoI |
| 564ab-(His/GST) (MC58) | Fwd | CGC<u>GGATCCCATATG</u>-CAAGGTATCGTTGCCGACAAATCCGCACCT | 348 | BamHI-NdeI |
| | Rev | CCCG<u>CTCGAG</u>-AGCTAATTGTGCTTGGTTTGCAGATAGGAGTT | 349 | XhoI |
| 564abL (MC58) | Fwd | CGCGGATCC<u>CATATG</u>-AACCGCACCCTGTACAAAGTTGTATTTAACAAACATC | 350 | NdeI |
| | Rev | CCCG<u>CTCGAG</u>-TTAAGCTAATTGTGCTTGGTTTGCAGATAGGAGTT | 351 | XhoI |
| 564b-(His/GST)(MC58) | Fwd | CGC<u>GGATCCCATATG</u>-ACGGGAGAAAATCATGCGGTTTCACTTCATG | 352 | BamHI-NdeI |
| | Rev | CCCG<u>CTCGAG</u>-AGCTAATTGTGCTTGGTTTGCAGATAGGAGTT | 353 | XhoI |
| 564c-(His/GST)(MC58) | Fwd | CGC<u>GGATCCCATATG</u>-GTTTCAGACGGCCTATACAACCAACATGGTGAATT | 354 | BamHI-NdeI |
| | Rev | CCCG<u>CTCGAG</u>-GCGGTAACTGCCGCTTGCACTGAATCCGTAA | 355 | XhoI |
| 564bc-(His/GST)(MC58) | Fwd | CGC<u>GGATCCCATATG</u>-ACGGGAGAAAATCATGCGGTTTCACTTCATG | 356 | BamHI-NdeI |
| | Rev | CCCG<u>CTCGAG</u>-GCGGTAACTGCCGCTTGCACTGAATCCGTAA | 357 | XhoI |
| 564d-(His/GST)(MC58) | Fwd | CGC<u>GGATCCCATATG</u>-CAAAGCAAAGTCAAAGCAGACCATGCCTCCGTAA | 358 | BamHI-NdeI |
| | Rev | CCCG<u>CTCGAG</u>-TCTTTTCCTTTCAATTATAACTTTAGTAGGTTCAATTTTGGTCCCC | 359 | XhoI |
| 564cd-(His/GST)(MC58) | Fwd | CGC<u>GGATCCCATATG</u>-GTTTCAGACGGCCTATACAACCAACATGGTGAATT | 360 | BamHI-NdeI |
| | Rev | CCCG<u>CTCGAG</u>-TCTTTTCCTTTCAATTATAACTTTAGTAGGTTCAATTTTGGTCCCC | 361 | XhoI |

-continued

| | | Sequences | SEQ ID NO | Restriction site |
|---|---|---|---|---|
| 570L | Fwd | GCGGCCATATG-ACCCGTTTGACCCGCG | 362 | NdeI |
| | Rev | GCGGCCTCGAG-TCAGCGGGCGTTCATTTCTT | 363 | XhoI |
| 576-1L | Fwd | CGCGGATCCCATATG-AACACCATTTTCAAAATC | 364 | NdeI |
| | Rev | CCCGCTCGAG-TTAATTTACTTTTTTGATGTCG | 365 | XhoI |
| 580L | Fwd | GCGGCCATATG-GATTCGCCCAAGGTCGG | 366 | NdeI |
| | Rev | GCGGCCTCGAG-CTACACTTCCCCCGAAGTGG | 367 | XhoI |
| 583L | Fwd | CGCGGATCCCATATG-ATAGTTGACCAAAGCC | 368 | NdeI |
| | Rev | CCCGCTCGAG-TTATTTTTCCGATTTTTCGG | 369 | XhoI |
| 593 | Fwd | GCGGCCATATG-CTTGAACTGAACGGACT | 370 | NdeI |
| | Rev | GCGGCCTCGAG-TCAGCGGAAGCGGACGATT | 371 | XhoI |
| 650 (His-GST) (MC58) | Fwd | CGCGGATCCCATATGTCCAAACTCAAAACCATCG | 372 | BamHI-NdeI |
| | Rev | CCCGCTCGAGGCTTCCAATCAGTTTGACC | 373 | XhoI |
| 652 | Fwd | GCGGCCATATG-AGCGCAATCGTTGATATTTTC | 374 | NdeI |
| | Rev | GCGGCCTCGAG-TTATTTGCCCAGTTGGTAGAATG | 375 | XhoI |
| 664L | Fwd | GCGGCCATATG-GTGATACATCCGCACTACTTC | 376 | NdeI |
| | Rev | GCGGCCTCGAG-TCAAAATCGAGTTTTACACCA | 377 | XhoI |
| 726 | Fwd | GCGGCCATATG-ACCATCTATTTCAAAAACGG | 378 | NdeI |
| | Rev | GCGGCCTCGAG-TCAGCCGATGTTTAGCGTCCATT | 379 | XhoI |
| 741-His(MC58) | Fwd | CGCGGATCCCATATG-AGCAGCGGAGGGGGTG | 380 | NdeI |
| | Rev | CCCGCTCGAG-TTGCTTGGCGGCAAGGC | 381 | XhoI |
| ΔG741-His(MC58) | Fwd | CGCGGATCCCATATG-GTCGCCGCCGACATCG | 382 | NdeI |
| | Rev | CCCGCTCGAG-TTGCTTGGCGGCAAGGC | 383 | XhoI |
| 686-2-(His/GST) (MC58) | Fwd | CGCGGATCCCATATG-GGCGGTTCGGAAGGCG | 384 | BamHI-NdeI |
| | Rev | CCCGCTCGAG-TTGAACACTGATGTCTTTTCCGA | 385 | XhoI |
| 719-(His/GST) (MC58) | Fwd | CGCGGATCCGCTAGC-AAACTGTCGTTGGTGTTAAC | 386 | BamHI-NheI |
| | Rev | CCCGCTCGAG-TTGACCCGCTCCACGG | 387 | XhoI |
| 730-His (MC58) | Fwd | GCCGCCATATGGCGGACTTGGCGCAAGACCC | 388 | NdeI |
| | Rev | GCCGCCTCGAGATCTCCTAAACCTGTTTTAACAATGCCG | 389 | XhoI |
| 730A-His (MC58) | Fwd | GCCGCCATATGGCGGACTTGGCGCAAGACCC | 390 | NdeI |
| | Rev | GCGGCCTCGAGCTCCATGCTGTTGCCCCAGC | 391 | XhoI |
| 730B-His (MC58) | Fwd | GCCGCCATATGGCGGACTTGGCGCAAGACCC | 392 | NdeI |
| | Rev | GCGGCCTCGAGAAAATCCCCGCTAACCGCAG | 393 | XhoI |
| 741-His (MC58) | Fwd | CGCGGATCCCATATG-AGCAGCGGAGGGGGTG | 394 | NdeI |
| | Rev | CCCGCTCGAG-TTGCTTGGCGGCAAGGC | 395 | XhoI |
| ΔG741-His (MC58) | Fwd | CGCGGATCCCATATG-GTCGCCGCCGACATCG | 396 | NdeI |
| | Rev | CCCGCTCGAG-TTGCTTGGCGGCAAGGC | 397 | XhoI |
| 743 (His-GST) | Fwd | CGCGGATCCCATATGGACGGTGTTGTGCCTGTT | 398 | BamHI-NdeI |
| | Rev | CCCGCTCGAGCTTACGGATCAAATTGACG | 399 | XhoI |
| 757 (His-GST) (MC58) | Fwd | CGCGGATCCCATATGGGCAGCCAATCTGAAGAA | 400 | BamHI-NdeI |
| | Rev | CCCGCTCGAGCTCAGCTTTTGCCGTCAA | 401 | XhoI |
| 759-His/GST (MC58) | Fwd | CGCGGATCCGCTAGC-TACTCATCCATTGTCCGC | 402 | BamHI-NheI |
| | Rev | CCCGCTCGAG-CCAGTTGTAGCCTATTTTG | 403 | XhoI |
| 759L (MC58) | Fwd | CGCGGATCCGCTAGC-ATGCGCTTCACACACAC | 404 | NheI |
| | Rev | CCCGCTCGAG-TTACCAGTTGTAGCCTATTT | 405 | XhoI |

-continued

| | | Sequences | SEQ ID NO | Restriction site |
|---|---|---|---|---|
| 760-His | Fwd | GCCGCCATATGGCACAAACGGAAGGTTTGGAA | 406 | NdeI |
| | Rev | GCCGCCTCGAGAAAACTGTAACGCAGGTTTGCCGTC | 407 | XhoI |
| 769-His (MC58) | Fwd | GCGGCCATATGGAAGAAACACCGCGCGAACCG | 408 | NdeI |
| | Rev | GCGGCCTCGAGGAACGTTTTATTAAACTCGAC | 409 | XhoI |
| 907L | Fwd | GCGGC<u>CATATG</u>-AGAAAACCGACCGATACCCTA | 410 | NdeI |
| | Rev | GCGGC<u>CTCGAG</u>-TCAACGCCACTGCCAGCGGTTG | 411 | XhoI |
| 911L | Fwd | CGCGGATCC<u>CATATG</u>-AAGAAGAACATATTGGAATTTTGGGTCGGACTG | 412 | NdeI |
| | Rev | CCCG<u>CTCGAG</u>-TTATTCGGCGGCTTTTTCCGCATTGCCG | 413 | XhoI |
| 911LOmpA | Fwd | GGGAATTC<u>CATATG</u>AAAAAGACAGCTATCGCGATTGCAGTGGCACTGGCTGGTTTCGCTACCGTAGCGCAGGCC<u>GCTAGC</u>-GCTTTCCGCGTGGCCGGCGGTGC | 414 | NdeI-(NheI) |
| | Rev | CCCG<u>CTCGAG</u>-TTATTCGGCGGCTTTTTCCGCATTGCCG | 415 | XhoI |
| 911LPelB | Fwd | CATG<u>CCATGG</u>-CTTTCCGCGTGGCCGGCGGTGC | 416 | NcoI |
| | Rev | CCCG<u>CTCGAG</u>-TTATTCGGCGGCTTTTTCCGCATTGCCG | 417 | XhoI |
| 913-His/GST (MC58) | Fwd | CGC<u>GGATCCCATATG</u>-TTTGCCGAAACCCGCC | 418 | BamHI-NdeI |
| | Rev | CCCG<u>CTCGAG</u>-AGGTTGTGTTCCAGGTTG | 419 | XhoI |
| 913L (MC58) | Fwd | CGCGGATCC<u>CATATG</u>-AAAAAAACCGCCTATG | 420 | NdeI |
| | Rev | CCCG<u>CTCGAG</u>-TTAAGGTTGTGTTCCAGG | 421 | XhoI |
| 919L | Fwd | CGCGGATCC<u>CATATG</u>-AAAAAATACCTATTCGC | 422 | NdeI |
| | Rev | CCCG<u>CTCGAG</u>-TTACGGGCGGTATTCGG | 423 | XhoI |
| 919 | Fwd | CGCGGATCC<u>CATATG</u>-CAAAGCAAGAGCATCCAAA | 424 | NdeI |
| | Rev | CCCG<u>CTCGAG</u>-TTACGGGCGGTATTCGG | 425 | XhoI |
| 919L Orf4 | Fwd | GGGAATTC<u>CATATG</u>AAAACCTTCTTCAAACCCTTTCCGCCGCCGC<u>GCTAGC</u>GCTCATCCTCGCCGCC-TGCCAAAGCAAGAGCATC | 426 | NdeI-(NheI) |
| | Rev | CCCG<u>CTCGAG</u>-TTACGGGCGGTATTCGGGCTTCATACCG | 427 | XhoI |
| (919)-287fusion | Fwd | CGCGGATCC<u>GTCGAC</u>-TGTGGGGCGGCGGTGGC | 428 | SalI |
| | Rev | CCCG<u>CTCGAG</u>-TCAATCCTGCTCTTTTTTGCC | 429 | XhoI |
| 920-1L | Fwd | GCGGC<u>CATATG</u>-AAGAAAACATTGACACTGC | 430 | NdeI |
| | Rev | GCGGC<u>CTCGAG</u>-TTAATGGTGCGAATGACCGAT | 431 | XhoI |
| 925-His/GST (MC58)<sup>GATE</sup> | Fwd | ggggacaagtttgtacaaaaaagcaggctTGCGGCAAGGATGCCGG | 432 | attB1 |
| | Rev | ggggaccactttgtacaagaaagctgggtCTAAAGCAACAATGCCGG | 433 | attB2 |
| 926L | Fwd | CGCGGATCC<u>CATATG</u>-AAACACACCGTATCC | 434 | NdeI |
| | Rev | CCCG<u>CTCGAG</u>-TTATCTCGTGCGCGCC | 435 | XhoI |
| 927-2-(His/GST) (MC58) | Fwd | CGC<u>GGATCCCATATG</u>-AGCCCCGCGCCGATT | 436 | BamHI-NdeI |
| | Rev | CCCG<u>CTCGAG</u>-TTTTTGTGCGGTCAGGCG | 437 | XhoI |
| 932-His/GST (MC58)<sup>GATE</sup> | Fwd | ggggacaagtttgtacaaaaaagcaggctTGTTCGTTTGGGGGATTTAAACCAAACCAAATC | 438 | attB1 |
| 935 (His-GST) (MC58) | For | CGC<u>GGATCCCATATG</u>GCGGATGCGCCCGCG | 439 | BamHI-NdeI |
| | Rev | CCCG<u>CTCGAG</u>AAACCGCCAATCCGCC | 440 | XhoI |
| 936-1L | Rev | ggggaccactttgtacaagaaagctgggtTCATTTTGTTTTTCCTTCTTCTCGAGGCCATT | 441 | attB2 |
| | Fwd | CGCGGATCC<u>CATATG</u>-AAACCCAAACCGCAC | 442 | NdeI |
| | Rev | CCCG<u>CTCGAG</u>-TCAGCGTTGGACGTAGT | 443 | XhoI |
| 953L | Fwd | GGGAATTC<u>CATATG</u>-AAAAAAATCATCTTCGCCG | 444 | NdeI |
| | Rev | CCCG<u>CTCGAG</u>-TTATTGTTTGGCTGCCTCGAT | 445 | XhoI |

| | | Sequences | SEQ ID NO | Restriction site |
|---|---|---|---|---|
| 953-fu | Fwd | GGGAATTCCCATATG-GCCACCTACAAAGTGGACG | 446 | NdeI |
| | Rev | CGGGGGATCC-TTGTTTGGCTGCCTCGATTTG | 447 | BamHI |
| 954 (His-GST) (MC58) | Fwd | CGCGGATCCCATATGCAAGAACAATCGCAGAAAG | 448 | BamHI-NdeI |
| | Rev | CCCGCTCGAGTTTTTTCGGCAAATTGGCTT | 449 | XhoI |
| 958-His/GST (MC58)$^{GATE}$ | Fwd | ggggacaagtttgtacaaaaaagcaggctGCCGATGCCGTTGCGG | 450 | attB1 |
| | Rev | ggggaccactttgtacaagaaagctgggtTCAGGGTCGTTTGTTGCG | 451 | attB2 |
| 961L | Fwd | CGCGGATCCCATATG-AAACACTTTCCATCC | 452 | NdeI |
| | Rev | CCCGCTCGAG-TTACCACTCGTAATTGAC | 453 | XhoI |
| 961 | Fwd | CGCGGATCCCATATG-GCCACAAGCGACGAC | 454 | NdeI |
| | Rev | CCCGCTCGAG-TTACCACTCGTAATTGAC | 455 | XhoI |
| 961 c (His/GST) | Fwd | CGCGGATCCCATATG-GCCACAAACGACG | 456 | BamHI-NdeI |
| | Rev | CCCGCTCGAG-ACCCACGTTGTAAGGTTG | 457 | XhoI |
| 961 c-(His/GST) (MC58) | Fwd | CGCGGATCCCATATG-GCCACAAGCGACGACGA | 458 | BamHI-NdeI |
| | Rev | CCCGCTCGAG-ACCCACGTTGTAAGGTTG | 459 | XhoI |
| 961 c-L | Fwd | CGCGGATCCCATATG-ATGAAACACTTTCCATCC | 460 | NdeI |
| | Rev | CCCGCTCGAG-TTAACCCACGTTGTAAGGT | 461 | XhoI |
| 961 c-L (MC58) | Fwd | CGCGGATCCCATATG-ATGAAACACTTTCCATCC | 462 | NdeI |
| | Rev | CCCGCTCGAG-TTAACCCACGTTGTAAGGT | 463 | XhoI |
| 961 d (His/GST) | Fwd | CGCGGATCCCATATG-GCCACAAACGACG | 464 | BamHI-NdeI |
| | Rev | CCCGCTCGAG-GTCTGACACTGTTTTATCC | 465 | XhoI |
| 961 Δ1-L | Fwd | CGCGGATCCCATATG-ATGAAACACTTTCCATCC | 466 | NdeI |
| | Rev | CCCGCTCGAG-TTATGCTTTGGCGGCAAAG | 467 | XhoI |
| fu 961-... | Fwd | CGCGGATCCCATATG-GCCACAAACGACGAC | 468 | NdeI |
| | Rev | CGCGGATCC-CCACTCGTAATTGACGCC | 469 | BamHI |
| fu 961-... (MC58) | Fwd | CGCGGATCCCATATG-GCCACAAGCGACGAC | 470 | NdeI |
| | Rev | CGCGGATCC-CCACTCGTAATTGACGCC | 471 | BamHI |
| fu 961 c-... | Fwd | CGCGGATCCCATATG-GCCACAAACGACGAC | 472 | NdeI |
| | Rev | CGCGGATCC-ACCCACGTTGTAAGGTTG | 473 | BamHI |
| fu 961 c-L-... | Fwd | CGCGGATCCCATATG-ATGAAACACTTTCCATCC | 474 | NdeI |
| | Rev | CGCGGATCC-ACCCACGTTGTAAGGTTG | 475 | BamHI |
| fu (961)-741(MC58)-His | Fwd | CGCGGATCC-GGAGGGGGTGGTGTCG | 476 | BamHI |
| | Rev | CCCGCTCGAG-TTGCTTGGCGGCAAGGC | 477 | XhoI |
| fu (961)-983-His | Fwd | CGCGGATCC-GGCGGAGGCGGCACTT | 478 | BamHI |
| | Rev | CCCGCTCGAG-GAACCGGTAGCCTACG | 479 | XhoI |
| fu (961)-Orf46.1-His | Fwd | CGCGGATCCGGTGGTGGTGGT-TCAGATTTGGCAAACGATTC | 480 | BamHI |
| | Rev | CCCGCTCGAG-CGTATCATATTTCACGTGC | 481 | XhoI |
| fu (961 c-L)-741(MC58) | Fwd | CGCGGATCC-GGAGGGGGTGGTGTCG | 482 | BamHI |
| | Rev | CCCGCTCGAG-TTATTGCTTGGCGGCAAG | 483 | XhoI |
| fu (961c-L)-983 | Fwd | CGCGGATCC-GGCGGAGGCGGCACTT | 484 | BamHI |
| | Rev | CCCGCTCGAG-TCAGAACCGGTAGCCTAC | 485 | XhoI |
| fu (961c-L)-Orf46.1 | Fwd | CGCGGATCCGGTGGTGGTGGT-TCAGATTTGGCAAACGATTC | 486 | BamHI |
| | Rev | CCCGCTCGAG-TTCGTATCATATTTCACGTGC | 487 | XhoI |
| 961-(His/GST) (MC58) | Fwd | CGCGGATCCCATATG-GCCACAAGCGACGACG | 488 | BamHI-NdeI |
| | Rev | CCCGCTCGAG-CCACTCGTAATTGACGCC | 489 | XhoI |
| 961 Δ1-His | Fwd | CGCGGATCCCATATG-GCCACAAACGACGAC | 490 | NdeI |
| | Rev | CCCGCTCGAG-TGCTTTGGCGGCAAAGTT | 491 | XhoI |

-continued

| | | Sequences | SEQ ID NO | Restriction site |
|---|---|---|---|---|
| 961a-(His/GST) | Fwd | CGCGGATCC<u>CATATG</u>-GCCACAAACGACGAC | 492 | BamHI-NdeI |
| | Rev | CCCG<u>CTCGAG</u>-TTTAGCAATATTATCTTTGTTCGTAGC | 493 | XhoI |
| 961b-(His/GST) | Fwd | CGCGGATCC<u>CATATG</u>-AAAGCAAACCGTGCCGA | 494 | BamHI-NdeI |
| | Rev | CCCG<u>CTCGAG</u>-CCACTCGTAATTGACGCC | 495 | XhoI |
| 961-His/GST<sup>GATE</sup> | Fwd | ggggacaagtttgtacaaaaaagcaggctGCAGCCACAAACGACGACGATGTTAAAAAGC | 496 | attB1 |
| | Rev | ggggaccactttgtacaagaaagctgggtTTACCACTCGTAATTGACGCCGACATGGTAGG | 497 | attB2 |
| 982 | Fwd | GCGGC<u>CATATG</u>-GCAGCAAAAGACGTACAGTT | 498 | NdeI |
| | Rev | GCGGC<u>CTCGAG</u>-TTACATCATGCCGCCCATACCA | 499 | XhoI |
| 983-His (2996) | Fwd | CGCGGATCC<u>GCTAGC</u>-TTAGGCGGCGGCGGAG | 500 | NheI |
| | Rev | CCCG<u>CTCGAG</u>-GAACCGGTAGCCTACG | 501 | XhoI |
| ΔG983-His (2996) | Fwd | CCCCTA<u>GCTAGC</u>-ACTTCTGCGCCCGACTT | 502 | NheI |
| | Rev | CCCG<u>CTCGAG</u>-GAACCGGTAGCCTACG | 503 | XhoI |
| 983-His | Fwd | CGCGGATCC<u>GCTAGC</u>-TTAGGCGGCGGCGGAG | 504 | NheI |
| | Rev | CCCG<u>CTCGAG</u>-GAACCGGTAGCCTACG | 505 | XhoI |
| ΔG983-His | Fwd | CGCGGATCC<u>GCTAGC</u>-ACTTCTGCGCCCGACTT | 506 | NheI |
| | Rev | CCCG<u>CTCGAG</u>-GAACCGGTAGCCTACG | 507 | XhoI |
| 983L | Fwd | CGCGGATCC<u>GCTAGC</u>-CGAACGACCCCAACCTTCCCTACAAAAACTTTCAA | 508 | NheI |
| | Rev | CCCG<u>CTCGAG</u>-TCAGAACCGACGTGCCAAGCCGTTC | 509 | XhoI |
| 987-His (MC58) | Fwd | GCCGC<u>CATATG</u>-CCCCCACTGGAAGAACGGACG | 510 | NdeI |
| | Rev | GCCGC<u>CTCGAG</u>-TAATAAACCTTCTATGGGCAGCAG | 511 | XhoI |
| 989-(His/GST) (MC58) | Fwd | CGC<u>GGATCCCATATG</u>-TCCGTCCACGCATCCG | 512 | BamHI-NdeI |
| | Rev | CCCG<u>CTCGAG</u>-TTTGAATTTGTAGGTGTATTG | 513 | XhoI |
| 989L (MC58) | Fwd | CGCGGATCC<u>CATATG</u>-ACCCCTTCCGCACT | 514 | NdeI |
| | Rev | CCCG<u>CTCGAG</u>-TTATTTGAATTTGTAGGTGTAT | 515 | XhoI |
| CrgA-His (MC58) | Fwd | CGCGGATCC<u>CATATG</u>-AAAACCAATTCAGAAGAA | 513 | NdeI |
| | Rev | CCCG<u>CTCGAG</u>-TCCACAGAGATTGTTTCC | 517 | XhoI |
| PilC1-ES (MC58) | Fwd | GATGCCCGAAGGGCGGG | 518 | |
| | Rev | GCCC<u>AAGCTT</u>-TCAGAAGAAGACTTCACGC | 519 | |
| PilC1-His (MC58) | Fwd | CGCGGATCC<u>CATATG</u>-CAAACCCATAAATACGCTATT | 520 | NdeI |
| | Rev | GCCC<u>AAGCTT</u>-GAAGAAGACTTCACGCCAG | 521 | HindIII |
| Δ1PilC1-His (MC58) | Fwd | CGCGGATCC<u>CATATG</u>-GTCTTTTTCGACAATACCGA | 522 | NdeI |
| | Rev | GCCC<u>AAGCTT</u>- | 523 | HindIII |
| PilC1L (MC58) | Fwd | CGCGGATCC<u>CATATG</u>-AATAAAACTTTAAAAAGGCGG | 524 | NdeI |
| | Rev | GCCC<u>AAGCTT</u>-TCAGAAGAAGACTTCACGC | 525 | HindIII |
| ΔGTbp2-His (MC58) | Fwd | CGCGAATCC<u>CATATG</u>-TTCGATCTTGATTCTGTCGA | 526 | NdeI |
| | Rev | CCCG<u>CTCGAG</u>-TCGCACAGGCTGTTGGCG | 527 | XhoI |
| Tbp2-His (MC58) | Fwd | CGCGAATCC<u>CATATG</u>-TTGGGCGGAGGCGGCAG | 528 | NdeI |
| | Rev | CCCG<u>CTCGAG</u>-TCGCACAGGCTGTTGGCG | 529 | XhoI |
| Tbp2-His(MC58) | Fwd | CGCGAATCC<u>CATATG</u>-TTGGGCGGAGGCGGCAG | 530 | NdeI |
| | Rev | CCCG<u>CTCGAG</u>-TCGCACAGGCTGTTGGCG | 531 | XhoI |

-continued

| | | Sequences | SEQ ID NO | Restriction site |
|---|---|---|---|---|
| NMB0109-(His/GST) (MC58) | Fwd | CGC<u>GGATCCCATATG</u>-GCAAATTTGGAGGTGCGC | 532 | BamHI-NdeI |
| | Rev | CCCG<u>CTCGAG</u>-TTCGGAGCGGTTGAAGC | 533 | XhoI |
| NMB0109L (MC58) | Fwd | CGCGGATCC<u>CATATG</u>-CAACGTCGTATTATAACCC | 534 | NdeI |
| | Rev | CCCG<u>CTCGAG</u>-TTATTCGGAGCGGTTGAAG | 535 | XhoI |
| NMB0207-(His/GST) (MC58) | Fwd | CGC<u>GGATCCCATATG</u>-GGCATCAAAGTCGCCATCAACGGCTAC | 536 | BamHI-NdeI |
| | Rev | CCCG<u>CTCGAG</u>-TTTGAGCGGGCGCACTTCAAGTCCG | 537 | XhoI |
| NMB0462-(His/GST) (MC58) | Fwd | CGC<u>GGATCCCATATG</u>-GGCGGCAGCGAAAAAAAC | 538 | BamHI-NdeI |
| | Rev | CCCG<u>CTCGAG</u>-GTTGGTGCCGACTTTGAT | 539 | XhoI |
| NMB0623-(His/GST) (MC58) | Fwd | CGC<u>GGATCCCATATG</u>-GGCGGCGGAAGCGATA | 540 | BamHI-NdeI |
| | Rev | CCCG<u>CTCGAG</u>-TTTGCCCGCTTTGAGCC | 541 | XhoI |
| NMB0625 (His-GST) (MC58) | Fwd | CGC<u>GGATCCCATATG</u>GGCAAATCCGAAAATACG | 542 | BamHI-NdeI |
| | Rev | CCCG<u>CTCGAG</u>CATCCCGTACTGTTTCG | 543 | XhoI |
| NMB0634 (His/GST)(MC58) | Fwd | ggggacaagtttgtacaaaaaagcaggctCCGACATTACCGTGTACAACGGCCAACAAAGAA | 544 | attB1 |
| | Rev | ggggaccactttgtacaagaaagctgggtCTTATTTCATACCGGCTTGCTCAAGCAGCCGG | 545 | attB2 |
| NMB0776-His/GST (MC58)<sup>GATE</sup> | Fwd | ggggacaagtttgtacaaaaaagcaggctGATACGGTGTTTTCCTGTAAAACGGACAACAA | 546 | attB1 |
| | Rev | ggggaccactttgtacaagaaagctgggtCTAGGAAAAATCGTCATCGTTGAAATTCGCC | 547 | attB2 |
| NMB1115-His/GST (MC58)<sup>GATE</sup> | Fwd | ggggacaagtttgtacaaaaaagcaggctATGCACCCCATCGAAACC | 548 | attB1 |
| | Rev | ggggaccactttgtacaagaaagctgggtCTAGTCTTGCAGTGCCTC | 549 | attB2 |
| NMB1343-(His/GST) (MC58) | Fwd | CGC<u>GGATCCCATATG</u>-GGAAATTTCTTATATAGAGGCATTAG | 550 | BamHI-NdeI |
| | Rev | CCCG<u>CTCGAG</u>-GTTAATTTCTATCAACTCTTTAGCAATAAT | 551 | XhoI |
| NMB1369 (His-GST (MC58) | Fwd | CGC<u>GGATCCCATATG</u>GCCTGCCAAGACGACA | 552 | BamHI-NdeI |
| | Rev | CCCG<u>CTCGAG</u>CCGCCTCCTGCCGAAA | 553 | XhoI |
| NMB1551 (His-GST) (MC58) | Fwd | CGC<u>GGATCCCATATG</u>GCAGAGATCTGTTTGATAA | 554 | BamHI-NdeI |
| | Rev | CCCG<u>CTCGAG</u>CGGTTTTCCGCCCAATG | 555 | XhoI |
| NMB1899 (His-GST) (MC58) | Fwd | CGC<u>GGATCCCATATG</u>CAGCCGGATACGGTC | 556 | BamHI-NdeI |
| | Rev | CCCG<u>CTCGAG</u>AATCACTTCCAACACAAAAT | 557 | XhoI |
| NMB2050-(His/GST) (MC58) | Fwd | CGC<u>GGATCCCATATG</u>-TGGTTGCTGATGAAGGGC | 558 | BamHI-NdeI |
| | Rev | CCCG<u>CTCGAG</u>-GACTGCTTCATCTTCTGC | 559 | XhoI |
| NMB2050L (MC58) | Fwd | CGCGGATCC<u>CATATG</u>-GAACTGATGACTGTTTTGC | 560 | NdeI |
| | Rev | CCCG<u>CTCGAG</u>-TCAGACTGCTTCATCTTCT | 561 | XhoI |
| NMB2159-(His/GST) (MC58) | Fwd | CGC<u>GGATCCCATATG</u>-AGCATTAAAGTAGCGATTAACGGTTTCGGC | 562 | BamHI-NdeI |
| | Rev | CCCG<u>CTCGAG</u>-GATTTTGCCTGCGAAGTATTCCAAAGTGCG | 563 | XhoI |
| fu-ΔG287...-His | Fwd | CGCGGATCC<u>GCTAGC</u>-CCCGATGTTAAATCGGC | 564 | NheI |
| | Rev | CGG<u>GGATCC</u>-ATCCTGCTCTTTTTTGCCGG | 565 | BamHI |
| fu-(ΔG287)-919-His | Fwd | CGC<u>GGATCC</u>GGTGGTGGTGGT-CAAAGCAAGAGCATCCAAACC | 566 | BamHI |
| | Rev | CCC<u>AAGCTT</u>-TTCGGGCGGTATTCGGGCTTC | 567 | HindIII |

-continued

| | | Sequences | SEQ ID NO | Restriction site |
|---|---|---|---|---|
| fu-(ΔG287)-953-His | Fwd | CGC<u>GGATCC</u>GGTGGTGGTGGT-GCCACCTACAAAGTGGAC | 568 | BamHI |
| | Rev | GCCC<u>AAGCTT</u>-TTGTTTGGCTGCCTCGAT | 569 | HindIII |
| fu-(ΔG287)-961-His | Fwd | CGC<u>GGATCC</u>GGTGGTGGTGGT-ACAAGCGACGACG | 570 | BamHI |
| | Rev | GCCC<u>AAGCTT</u>-CCACTCGTAATTGACGCC | 571 | HindIII |
| fu-(ΔG287)-Orf46.1-His | Fwd | CGC<u>GGATCC</u>GGTGGTGGTGGT-TCAGATTTGGCAAACGATTC | 572 | BamHI |
| | Rev | CCC<u>AAGCTT</u>-CGTATCATATTTCACGTGC | 573 | HindIII |
| fu-(ΔG287-919)-Orf46.1-His | Fwd | CCC<u>AAGCTT</u>GGTGGTGGTGGT-TCAGATTTGGCAAACGATTC | 574 | HindIII |
| | Rev | CCC<u>GCTCGAG</u>-CGTATCATATTTCACGTGC | 575 | XhoI |
| fu-(ΔG287-Orf46.1)-919-His | Fwd | CCC<u>AAGCTT</u>GGTGGTGGTGGT-CAAAGCAAGAGCATCCAAACC | 576 | HindIII |
| | Rev | CCC<u>GCTCGAG</u>-CGGGCGGTATTCGGGCTT | 577 | XhoI |
| fu ΔG287(394.98)-... | Fwd | CGC<u>GGATCC</u><u>GCTAGC</u>-CCCGATGTTAAATCGGC | 578 | NheI |
| | Rev | CGG<u>GGATCC</u>-ATCCTGCTCTTTTTTGCCGG | 579 | BamHI |
| fu Orf1-(Orf46.1)-His | Fwd | CGC<u>GGATCC</u><u>GCTAGC</u>-GGACACACTTATTTCGGCATC | 580 | NheI |
| | Rev | CGC<u>GGATCC</u>-CCAGCGGTAGCCTAATTGAT | 581 | |
| fu (Orf1)-Orf46.1-His | Fwd | CGC<u>GGATCC</u>GGTGGTGGTGGT-TCAGATTTGGCAAACGATTC | 582 | BamHI |
| | Rev | CCC<u>AAGCTT</u>-CGTATCATATTTCACGTGC | 583 | HindIII |
| fu (919)-Orf46.1-His | Fwd1 | GCGGC<u>GTCGAC</u>GGTGGCGGAGGCACTGGATCCTCAG | 584 | SalI |
| | Fwd2 | GGAGGCACTGGATCCTCAGATTTGGCAAACGATTC | 585 | |
| | Rev | CCC<u>GCTCGAG</u>-CGTATCATATTTCACGTGC | 586 | XhoI |
| Fu orf46-... | Fwd | GGAATTC<u>CATATG</u>TCAGATTTGGCAAACGATTC | 587 | NdeI |
| | Rev | CGC<u>GGATCC</u>CGTATCATATTTCACGTGC | 588 | BamHI |
| Fu (orf46)-287-His | Fwd | CGGG<u>GATCC</u>GGGGCGGCGGTGGCG | 589 | BamHI |
| | Rev | CCC<u>AAGCTT</u>ATCCTGCTCTTTTTTGCCGGC | 590 | HindIII |
| Fu (orf46)-919-His | Fwd | CGC<u>GGATCC</u>GGTGGTGGTGGTCAAAGCAAGAGCATCCAAACC | 591 | BamHI |
| | Rev | CCC<u>AAGCTT</u>CGGGCGGTATTCGGGCTTC | 592 | HindIII |
| Fu (orf46-919)-287-His | Fwd | CCCC<u>AAGCTT</u>GGGGGCGGCGGTGGCG | 593 | HindIII |
| | Rev | CCC<u>GCTCGAG</u>ATCCTGCTCTTTTTTGCCGGC | 594 | XhoI |
| Fu (orf46-287)-919-His | Fwd | CCC<u>AAGCTT</u>GGTGGTGGTGGTGGTCAAAGCAAGAGCATCCAAACC | 595 | HindIII |
| | Rev | CCC<u>GCTCGAG</u>CGGGCGGTATTCGGGCTT | 596 | XhoI |
| (ΔG741)-961c-His | Fwd1 | GGAGGCACTGGATCCGCAGCCACAAACGACGACGA | 597 | XhoI |
| | Fwd2 | GCGGC<u>CTCGAG</u>-GGTGGCGGAGGCACTGGATCCGCAG | 598 | |
| | Rev | CCC<u>GCTCGAG</u>-ACCCAGCTTGTAAGGTTG | 599 | XhoI |
| (ΔG741)-961-His | Fwd1 | GGAGGCACTGGATCCGCAGCCACAAACGACGACGA | 600 | XhoI |
| | Fwd2 | GCGGC<u>CTCGAG</u>-GGTGGCGGAGGCACTGGATCCGCAG | 601 | |
| | Rev | CCC<u>GCTCGAG</u>-CCACTCGTAATTGACGCC | 602 | XhoI |
| (ΔG741)-983-His | Fwd | GCGGC<u>CTCGAG</u>-GGATCCGGCGGAGGCACTTCTGCG | 603 | XhoI |
| | Rev | CCC<u>GCTCGAG</u>-GAACCGGTAGCCTACG | 604 | XhoI |
| (ΔG741)-orf46.1-His | Fwd1 | GGAGGCACTGGATCCTCAGATTTGGCAAACGATTC | 605 | SalI |
| | Fwd2 | GCGGC<u>GTCGAC</u>GGTGGCGGAGGCACTGGATCCTCAGA | 606 | |
| | Rev | CCC<u>GCTCGAG</u>-CGTATCATATTTCACGTGC | 607 | XhoI |
| (ΔG983)-741(MC58)-His | Fwd | GCGGC<u>CTCGAG</u>-GGATCCGGAGGGGGTGGTGTCGCC | 608 | XhoI |
| | Rev | CCCG<u>CTCGAG</u>-TTGCTTGGCGGCAAG | 609 | XhoI |

| Sequences | | | SEQ ID NO | Restriction site |
|---|---|---|---|---|
| (ΔG983)-961c-His | Fwd1 | GGAGGCACTGGATCCGCAGCCACAAACGACGACGA | 610 | XhoI |
| | Fwd2 | GCGGC<u>CTCGAG</u>-GGTGGCGGAGGCACTGGATCCGCAG | 611 | |
| | Rev | CCCG<u>CTCGAG</u>-ACCCAGCTTGTAAGGTTG | 612 | XhoI |
| (ΔG983)-961-His | Fwd1 | GGAGGCACTGGATCCGCAGCCACAAACGACGACG | 613 | XhoI |
| | Fwd2 | A GCGGC<u>CTCGAG</u>-GGTGGCGGAGGCACTGGATCCGCAG | 614 | |
| | Rev | CCCG<u>CTCGAG</u>-CCACTCGTAATTGACGCC | 615 | XhoI |
| (ΔG983)-Orf46.1-His | Fwd1 | GGAGGCACTGGATCCTCAGATTTGGCAAACGATTC | 616 | SalI |
| | Fwd2 | GCGGC<u>GTCGAC</u>GGTGGCGGAGGCACTGGATCCTCAGA | 617 | |
| | Rev | CCCG<u>CTCGAG</u>-CGTATCATATTTCACGTGC | 618 | XhoI |

*This primer was used as a Reverse primer for all the C terminal fusions of 287 to the His-tag.
$Forward primers used in combination with the 287-His Reverse primer.
NB - All PCR reactions use strain 2996 unless otherwise specified (e.g. strain MC58)

In all constructs starting with an ATG not followed by a unique NheI site, the ATG codon is part of the NdeI site used for cloning. The constructs made using NheI as a cloning site at the 5' end (e.g. all those containing 287 at the N-terminus) have two additional codons (GCT AGC) fused to the coding sequence of the antigen.

Preparation of Chromosomal DNA Templates

N. meningitidis strains 2996, MC58, 394.98, 1000 and BZ232 (and others) were grown to exponential phase in 100 ml of GC medium, harvested by centrifugation, and resuspended in 5 ml buffer (20% w/v sucrose, 50 mM Tris-HCl, 50 mM EDTA, pH8). After 10 minutes incubation on ice, the bacteria were lysed by adding 10 ml of lysis solution (50 mM NaCl, 1% Na-Sarkosyl, 50 μg/ml Proteinase K), and the suspension incubated at 37° C. for 2 hours. Two phenol extractions (equilibrated to pH 8) and one $CHCl_3$/isoamylalcohol (24:1) extraction were performed. DNA was precipitated by addition of 0.3M sodium acetate and 2 volumes of ethanol, and collected by centrifugation. The pellet was washed once with 70% (v/v) ethanol and redissolved in 4.0 ml TE buffer (10 mM Tris-HCl, 1 mM EDTA, pH 8.0). The DNA concentration was measured by reading $OD_{260}$.

PCR Amplification

The standard PCR protocol was as follows: 200 ng of genomic DNA from 2996, MC581000, or BZ232 strains or 10 ng of plasmid DNA preparation of recombinant clones were used as template in the presence of 40 μM of each oligonucleotide primer, 400-800 μM dNTPs solution, 1×PCR buffer (including 1.5 mM $MgCl_2$), 2.5 units TaqI DNA polymerase (using Perkin-Elmer AmpliTaQ® DNA Polymerase kit, Boerhingher Mannheim Expand™ Long Template).

After a preliminary 3 minute incubation of the whole mix at 95° C., each sample underwent a two-step amplification: the first 5 cycles were performed using the hybridisation temperature that excluded the restriction enzyme tail of the primer ($T_{m1}$). This was followed by 30 cycles according to the hybridisation temperature calculated for the whole length oligos ($T_{m2}$). Elongation times, performed at 68° C. or 72° C., varied according to the length of the Orf to be amplified. In the case of Orf1 the elongation time, starting from 3 minutes, was increased by 15 seconds each cycle. The cycles were completed with a 10 minute extension step at 72° C.

The amplified DNA was either loaded directly on a 1% agarose gel. The DNA fragment corresponding to the band of correct size was purified from the gel using the Qiagen Gel Extraction Kit, following the manufacturer's protocol.

Digestion of PCR Fragments and of the Cloning Vectors

The purified DNA corresponding to the amplified fragment was digested with the appropriate restriction enzymes for cloning into pET-21b+, pET22b+ or pET-24b+. Digested fragments were purified using the QIAquick PCR purification kit (following the manufacturer's instructions) and eluted with either $H_2O$ or 10 mM Tris, pH 8.5. Plasmid vectors were digested with the appropriate restriction enzymes, loaded onto a 1.0% agarose gel and the band corresponding to the digested vector purified using the Qiagen QIAquick Gel Extraction Kit.

Cloning

The fragments corresponding to each gene, previously digested and purified, were ligated into pET21b+, pET22b+ or pET-24b+. A molar ratio of 3:1 fragment/vector was used with T4 DNA ligase in the ligation buffer supplied by the manufacturer.

Recombinant plasmid was transformed into competent E. coli DH5 or HB101 by incubating the ligase reaction solution and bacteria for 40 minutes on ice, then at 37° C. for 3 minutes. This was followed by the addition of 800 μl LB broth and incubation at 37° C. for 20 minutes. The cells were centrifuged at maximum speed in an Eppendorf microfuge, resuspended in approximately 200 μl of the supernatant and plated onto LB ampicillin (100 mg/ml) agar. Screening for recombinant clones was performed by growing randomly selected colonies overnight at 37° C. in 4.0 ml of LB broth+ 100 μg/ml ampicillin Cells were pelleted and plasmid DNA extracted using the Qiagen QIAprep Spin Miniprep Kit, following the manufacturer's instructions. Approximately 1 μg of each individual miniprep was digested with the appropriate restriction enzymes and the digest loaded onto a 1-1.5% agarose gel (depending on the expected insert size), in parallel with the molecular weight marker (1 kb DNA Ladder, GIBCO®). Positive clones were selected on the basis of the size of insert.

Expression

After cloning each gene into the expression vector, recombinant plasmids were transformed into E. coli strains suitable for expression of the recombinant protein. 1 μl of each construct was used to transform E. coli BL21-DE3 as described above. Single recombinant colonies were inoculated into 2 ml LB+Amp (100 μg/ml), incubated at 37° C. overnight, then diluted 1:30 in 20 ml of LB+Amp (100 μg/ml) in 100 ml flasks, to give an $OD_{600}$ between 0.1 and 0.2. The flasks were incubated at 30° C. or at 37° C. in a gyratory water bath shaker until OD$_{600}$ indicated exponential growth suitable for induction of expression (0.4-0.8 OD). Protein expression was induced by addition of 1.0 mM IPTG. After 3 hours incubation at 30° C. or 37° C. the OD$_{600}$ was measured and expression examined. 1.0 ml of each sample was centrifuged in a microfuge, the pellet resuspended in PBS and analysed by SDS-PAGE and Coomassie Blue staining.

Gateway Cloning and Expression

Sequences labelled GATE were cloned and expressed using the GATEWAY Cloning Technology (GIBCO®-BRL). Recombinational cloning (RC) is based on the recombination reactions that mediate the integration and excision of phage into and from the *E. coli* genome, respectively. The integration involves recombination of the attP site of the phage DNA within the attB site located in the bacterial genome (BP reaction) and generates an integrated phage genome flanked by attL and attR sites. The excision recombines attL and attR sites back to attP and attB sites (LR reaction). The integration reaction requires two enzymes [the phage protein Integrase (Int) and the bacterial protein integration host factor (IHF)] (BP clonase). The excision reaction requires Int, IHF, and an additional phage enzyme, Excisionase (Xis) (LR clonase). Artificial derivatives of the 25-bp bacterial attB recombination site, referred to as B1 and B2, were added to the 5' end of the primers used in PCR reactions to amplify Neisserial ORFs. The resulting products were BP cloned into a "Donor vector" containing complementary derivatives of the phage attP recombination site (P1 and P2) using BP clonase. The resulting "Entry clones" contain ORFs flanked by derivatives of the attL site (L1 and L2) and were subcloned into expression "destination vectors" which contain derivatives of the attL-compatible attR sites (R1 and R2) using LR clonase. This resulted in "expression clones" in which ORFs are flanked by B1 and B2 and fused in frame to the GST or H is N terminal tags.

The *E. coli* strain used for GATEWAY expression is BL21-SI. Cells of this strain are induced for expression of the T7 RNA polymerase by growth in medium containing salt (0.3 M NaCl).

Note that this system gives N-terminus His tags.

Preparation of Membrane Proteins.

Fractions composed principally of either inner, outer or total membrane were isolated in order to obtain recombinant proteins expressed with membrane-localisation leader sequences. The method for preparation of membrane fractions, enriched for recombinant proteins, was adapted from Filip et. al. [*J. Bact.* (1973) 115:717-722] and Davies et. al. [*J. Immunol. Meth.* (1990) 143:215-225]. Single colonies harbouring the plasmid of interest were grown overnight at 37° C. in 20 ml of LB/Amp (100 µg/ml) liquid culture. Bacteria were diluted 1:30 in 1.0 L of fresh medium and grown at either 30° C. or 37° C. until the OD$_{550}$ reached 0.6-0.8. Expression of recombinant protein was induced with IPTG at a final concentration of 1.0 mM. After incubation for 3 hours, bacteria were harvested by centrifugation at 8000 g for 15 minutes at 4° C. and resuspended in 20 ml of 20 mM Tris-HCl (pH 7.5) and complete protease inhibitors (Boehringer-Mannheim). All subsequent procedures were performed at 4° C. or on ice.

Cells were disrupted by sonication using a Branson Sonifier® 450 (ultrasonic cell disruption/homogenizer) and centrifuged at 5000 g for 20 min to sediment unbroken cells and inclusion bodies. The supernatant, containing membranes and cellular debris, was centrifuged at 50000 g (Beckman Ti50, 29000 rpm) for 75 min, washed with 20 mM Bis-tris propane (pH 6.5), 1.0 M NaCl, 10% (v/v) glycerol and sedimented again at 50000 g for 75 minutes. The pellet was resuspended in 20 mM Tris-HCl (pH 7.5), 2.0% (v/v) Sarkosyl, complete protease inhibitor (1.0 mM EDTA, final concentration) and incubated for 20 minutes to dissolve inner membrane. Cellular debris was pelleted by centrifugation at 5000 g for 10 min and the supernatant centrifuged at 75000 g for 75 minutes (Beckman Ti50, 33000 rpm). Proteins 008L and 519L were found in the supernatant suggesting inner membrane localisation. For these proteins both inner and total membrane fractions (washed with NaCl as above) were used to immunise mice. Outer membrane vesicles obtained from the 75000 g pellet were washed with 20 mM Tris-HCl (pH 7.5) and centrifuged at 75000 g for 75 minutes or overnight. The OMV was finally resuspended in 500 µl of 20 mM Tris-HCl (pH 7.5), 10% v/v glycerol. Orf1L and Orf40L were both localised and enriched in the outer membrane fraction which was used to immunise mice. Protein concentration was estimated by standard Bradford Assay (Bio-Rad), while protein concentration of inner membrane fraction was determined with the DC protein assay (Bio-Rad). Various fractions from the isolation procedure were assayed by SDS-PAGE.

Purification of His-Tagged Proteins

Various forms of 287 were cloned from strains 2996 and MC58. They were constructed with a C-terminus His-tagged fusion and included a mature form (aa 18-427), constructs with deletions (Δ1, Δ2, Δ3 and Δ4) and clones composed of either B or C domains. For each clone purified as a His-fusion, a single colony was streaked and grown overnight at 37° C. on a LB/Amp (100 µg/ml) agar plate. An isolated colony from this plate was inoculated into 20 ml of LB/Amp (100 µg/ml) liquid medium and grown overnight at 37° C. with shaking. The overnight culture was diluted 1:30 into 1.0 L LB/Amp (100 µg/ml) liquid medium and allowed to grow at the optimal temperature (30 or 37° C.) until the OD$_{550}$ reached 0.6-0.8. Expression of recombinant protein was induced by addition of IPTG (final concentration 1.0 mM) and the culture incubated for a further 3 hours. Bacteria were harvested by centrifugation at 8000 g for 15 min at 4° C. The bacterial pellet was resuspended in 7.5 ml of either (i) cold buffer A (300 mM NaCl, 50 mM phosphate buffer, 10 mM imidazole, pH 8.0) for soluble proteins or (ii) buffer B (10 mM Tris-HCl, 100 mM phosphate buffer, pH 8.8 and, optionally, 8M urea) for insoluble proteins. Proteins purified in a soluble form included 287-His, Δ1, Δ2, Δ3 and Δ4287-His, Δ4287MC58-His, 287c-His and 287cMC58-His. Protein 287bMC58-His was insoluble and purified accordingly. Cells were disrupted by sonication on ice four times for 30 sec at 40 W using a Branson Sonifier® 450 (ultrasonic cell disruption/homogenizer) and centrifuged at 13000×g for 30 min at 4° C. For insoluble proteins, pellets were resuspended in 2.0 ml buffer C (6 M guanidine hydrochloride, 100 mM phosphate buffer, 10 mM Tris-HCl, pH 7.5 and treated with 10 passes of a Dounce homogenizer. The homogenate was centrifuged at 13000 g for 30 min and the supernatant retained. Supernatants for both soluble and insoluble preparations were mixed with 150 µl Ni$^{2+}$-resin (previously equilibrated with either buffer A or buffer B, as appropriate) and incubated at room temperature with gentle agitation for 30 min. The resin was Chelating Sepharose™ Fast Flow (IMAC medium, Pharmacia), prepared according to the manufacturer's protocol. The batch-wise preparation was centrifuged at 700 g for 5 min at 4° C. and the supernatant discarded. The resin was washed twice (batch-wise) with 10 ml buffer A or B for 10 min, resuspended in 1.0 ml buffer A or B and loaded onto a disposable column. The resin continued to be washed with either (i) buffer A at 4° C. or (ii) buffer B at room temperature, until the OD$_{280}$ of the flow-through reached 0.02-0.01. The resin was further washed with either (i) cold buffer C (300 mM NaCl, 50 mM phosphate buffer, 20 mM imidazole, pH 8.0) or (ii) buffer D (10 mM Tris-HCl, 100 mM phosphate buffer, pH 6.3 and, optionally, 8M urea) until $OD_{280}$ of the flow-through reached 0.02-0.01. The His-fusion protein was eluted by addition of 700 µl of either (i) cold elution buffer A (300 mM NaCl, 50 mM phosphate buffer, 250 mM imidazole, pH 8.0) or (ii) elution buffer B (10 mM Tris-HCl, 100 mM phosphate buffer, pH 4.5 and, optionally, 8M urea) and fractions collected until the $OD_{280}$ indicated all the recombinant protein was obtained. 20 µl aliquots of each elution fraction were analysed by SDS-PAGE. Protein concentrations were estimated using the Bradford assay.

Renaturation of Denatured His Fusion Proteins.

Denaturation was required to solubilize 287bMC8, so a renaturation step was employed prior to immunisation. Glycerol was added to the denatured fractions obtained above to give a final concentration of 10% v/v. The proteins were diluted to 200 µg/ml using dialysis buffer I (10% v/v glycerol, 0.5M arginine, 50 mM phosphate buffer, 5.0 mM reduced glutathione, 0.5 mM oxidised glutathione, 2.0M urea, pH 8.8) and dialysed against the same buffer for 12-14 hours at 4° C. Further dialysis was performed with buffer II (10% v/v glycerol, 0.5M arginine, 50 mM phosphate buffer, 5.0 mM reduced glutathione, 0.5 mM oxidised glutathione, pH 8.8) for 12-14 hours at 4° C. Protein concentration was estimated using the formula:

$$\text{Protein(mg/ml)} = (1.55 \times OD_{280}) - (0.76 \times OD_{260})$$

Amino Acid Sequence Analysis.

Automated sequence analysis of the $NH_2$-terminus of proteins was performed on a Beckman sequencer (LF 3000) equipped with an on-line phenylthiohydantoin-amino acid analyser (System Gold) according to the manufacturer's recommendations.

Immunization

Balb/C mice were immunized with antigens on days 0, 21 and 35 and sera analyzed at day 49.

Sera Analysis—ELISA

The acapsulated MenB M7 and the capsulated strains were plated on chocolate agar plates and incubated overnight at 37° C. with 5% $CO_2$. Bacterial colonies were collected from the agar plates using a sterile dracon swab and inoculated into Mueller-Hinton Broth (Difco) containing 0.25% glucose. Bacterial growth was monitored every 30 minutes by following $OD_{620}$. The bacteria were let to grow until the OD reached the value of 0.4-0.5. The culture was centrifuged for 10 minutes at 4000 rpm. The supernatant was discarded and bacteria were washed twice with PBS, resuspended in PBS containing 0.025% formaldehyde, and incubated for 1 hour at 37° C. and then overnight at 4° C. with stirring. 100 µl bacterial cells were added to each well of a 96 well Greiner plate and incubated overnight at 4° C. The wells were then washed three times with PBT washing buffer (0.1% Tween®-20 (Polysorbate 20, Sigma Aldrich) in PBS). 200 µl of saturation buffer (2.7% polyvinylpyrrolidone 10 in water) was added to each well and the plates incubated for 2 hours at 37° C. Wells were washed three times with PBT. 200 µl of diluted sera (Dilution buffer: 1% BSA, 0.1% Tween®-20 (Polysorbate 20, Sigma Aldrich), 0.1% $NaN_3$ in PBS) were added to each well and the plates incubated for 2 hours at 37° C. Wells were washed three times with PBT. 100 µl of HRP-conjugated rabbit anti-mouse (Dako) serum diluted 1:2000 in dilution buffer were added to each well and the plates were incubated for 90 minutes at 37° C. Wells were washed three times with PBT buffer. 100 µl of substrate buffer for HRP (25 ml of citrate buffer pH5, 10 mg of O-phenildiamine and 10 µl of $H_2O_2$) were added to each well and the plates were left at room temperature for 20 minutes. 100 µl 12.5% $H_2S_4$ was added to each well and $OD_{490}$ was followed. The ELISA titers were calculated abitrarely as the dilution of sera which gave an $OD_{490}$ value of 0.4 above the level of preimmune sera. The ELISA was considered positive when the dilution of sera with $OD_{490}$ of 0.4 was higher than 1:400.

Sera Analysis—FACS Scan Bacteria Binding Assay

The acapsulated MenB M7 strain was plated on chocolate agar plates and incubated overnight at 37° C. with 5% $CO_2$. Bacterial colonies were collected from the agar plates using a sterile dracon swab and inoculated into 4 tubes containing 8 ml each Mueller-Hinton Broth (Difco) containing 0.25% glucose. Bacterial growth was monitored every 30 minutes by following $OD_{620}$. The bacteria were let to grow until the OD reached the value of 0.35-0.5. The culture was centrifuged for 10 minutes at 4000 rpm. The supernatant was discarded and the pellet was resuspended in blocking buffer (1% BSA in PBS, 0.4% $NaN_3$) and centrifuged for 5 minutes at 4000 rpm. Cells were resuspended in blocking buffer to reach $OD_{620}$ of 0.05. 100 µl bacterial cells were added to each well of a Costar® 96 well plate. 100 µl of diluted (1:100, 1:200, 1:400) sera (in blocking buffer) were added to each well and plates incubated for 2 hours at 4° C. Cells were centrifuged for 5 minutes at 4000 rpm, the supernatant aspirated and cells washed by addition of 200 µl/well of blocking buffer in each well. 100 µl of R-Phicoerytrin conjugated $F(ab)_2$ goat anti-mouse, diluted 1:100, was added to each well and plates incubated for 1 hour at 4° C. Cells were spun down by centrifugation at 4000 rpm for 5 minutes and washed by addition of 200 µl/well of blocking buffer. The supernatant was aspirated and cells resuspended in 200 µl/well of PBS, 0.25% formaldehyde. Samples were transferred to FACScan tubes and read. The condition for FACScan (Laser Power 15 mW) setting were: FL2 on; FSC—H threshold:92; FSC PMT Voltage: E 01; SSC PMT: 474; Amp. Gains 6.1; FL-2 PMT: 586; compensation values: 0.

Sera Analysis—Bactericidal Assay

N. meningitidis strain 2996 was grown overnight at 37° C. on chocolate agar plates (starting from a frozen stock) with 5% $CO_2$. Colonies were collected and used to inoculate 7 ml Mueller-Hinton broth, containing 0.25% glucose to reach an $OD_{620}$ of 0.05-0.08. The culture was incubated for approximately 1.5 hours at 37 degrees with shacking until the $OD_{620}$ reached the value of 0.23-0.24. Bacteria were diluted in 50 mM Phosphate buffer pH 7.2 containing 10 mM $MgCl_2$, 10 mM $CaCl_2$ and 0.5% (w/v) BSA (assay buffer) at the working dilution of $10^5$ CFU/ml. The total volume of the final reaction mixture was 50 µl with 25 µl of serial two fold dilution of test serum, 12.5 µl of bacteria at the working dilution, 12.5 µl of baby rabbit complement (final concentration 25%).

Controls included bacteria incubated with complement serum, immune sera incubated with bacteria and with complement inactivated by heating at 56° C. for 30' Immediately after the addition of the baby rabbit complement, 10 µl of the controls were plated on Mueller-Hinton agar plates using the tilt method (time 0). The 96-wells plate was incubated for 1 hour at 37° C. with rotation. 7 µl of each sample were plated on Mueller-Hinton agar plates as spots, whereas 10 µl of the controls were plated on Mueller-Hinton agar plates using the tilt method (time 1). Agar plates were incubated for 18 hours at 37 degrees and the colonies corresponding to time 0 and time 1 were counted.

Sera Analysis—Western Blots

Purified proteins (500 ng/lane), outer membrane vesicles (5 µg) and total cell extracts (25 µg) derived from MenB strain 2996 were loaded onto a 12% SDS-polyacrylamide gel and transferred to a nitrocellulose membrane. The transfer was performed for 2 hours at 150 mA at 4° C., using transfer buffer (0.3% Tris base, 1.44% glycine, 20% (v/v) methanol). The membrane was saturated by overnight incubation at 4° C. in saturation buffer (10% skimmed milk, 0.1% Triton X100 in PBS). The membrane was washed twice with washing buffer (3% skimmed milk, 0.1% Triton X100 in PBS) and incubated for 2 hours at 37° C. with mice sera diluted 1:200 in washing buffer. The membrane was washed twice and incubated for 90 minutes with a 1:2000 dilution of horseradish peroxidase labelled anti-mouse Ig. The membrane was washed twice with 0.1% Triton X100 in PBS and developed with the Opti-4CN Substrate Kit (Bio-Rad). The reaction was stopped by adding water.

The OMVs were prepared as follows: *N. meningitidis* strain 2996 was grown overnight at 37 degrees with 5% $CO_2$ on 5 GC plates, harvested with a loop and resuspended in 10 ml of 20 mM Tris-HCl pH 7.5, 2 mM EDTA. Heat inactivation was performed at 56° C. for 45 minutes and the bacteria disrupted by sonication for 5 minutes on ice (50% duty cycle, 50% output, Branson Sonifier® 3 mm microtip). Unbroken cells were removed by centrifugation at 5000 g for 10 minutes, the supernatant containing the total cell envelope fraction recovered and further centrifuged overnight at 50000 g at the temperature of 4° C. The pellet containing the membranes was resuspended in 2% sarkosyl, 20 mM Tris-HCl pH 7.5, 2 mM EDTA and incubated at room temperature for 20 minutes to solubilise the inner membranes. The suspension was centrifuged at 10000 g for 10 minutes to remove aggregates, the supernatant was further centrifuged at 50000 g for 3 hours. The pellet, containing the outer membranes was washed in PBS and resuspended in the same buffer. Protein concentration was measured by the D.C. Bio-Rad Protein assay (Modified Lowry method), using BSA as a standard.

Total cell extracts were prepared as follows: *N. meningitidis* strain 2996 was grown overnight on a GC plate, harvested with a loop and resuspended in 1 ml of 20 mM Tris-HCl. Heat inactivation was performed at 56° C. for 30 minutes.

961 Domain Studies
Cellular Fractions Preparation

Total lysate, periplasm, supernatant and OMV of *E. coli* clones expressing different domains of 961 were prepared using bacteria from over-night cultures or after 3 hours induction with IPTG. Briefly, the periplasm were obtained suspending bacteria in saccarose 25% and Tris 50 mM (pH 8) with polimixine 100 μg/ml. After 1 hr at room temperature bacteria were centrifuged at 13000 rpm for 15 min and the supernatant were collected. The culture supernatant were filtered with 0.2 μm and precipitated with TCA 50% in ice for two hours. After centrifugation (30 min at 13000 rp) pellets were rinsed twice with ethanol 70% and suspended in PBS. The OMV preparation was performed as previously described. Each cellular fraction were analyzed in SDS-PAGE or in Western Blot using the polyclonal anti-serum raised against GST-961.

Adhesion Assay

Chang epithelial cells (Wong-Kilbourne derivative, clone 1-5c-4, human conjunctiva) were maintained in DMEM GIBCO® supplemented with 10% heat-inactivated FCS, 15 mM L-glutamine and antibiotics.

For the adherence assay, sub-confluent culture of Chang epithelial cells were rinsed with PBS and treated with trypsin-EDTA GIBCO®, to release them from the plastic support. The cells were then suspended in PBS, counted and dilute in PBS to $5 \times 10^5$ cells/ml.

Bacteria from over-night cultures or after induction with IPTG, were pelleted and washed twice with PBS by centrifuging at 13000 for 5 min. Approximately $2-3 \times 10^8$ (cfu) were incubated with 0.5 mg/ml FITC (Sigma) in 1 ml buffer containing 50 mM $NaHCO_3$ and 100 mM NaCl pH 8, for 30 min at room temperature in the dark. FITC-labeled bacteria were wash 2-3 times and suspended in PBS at $1-1.5 \times 10^9$/ml. 200 μl of this suspension ($2-3 \times 10^8$) were incubated with 200 μl ($1 \times 10^5$) epithelial cells for 30 min a 37° C. Cells were than centrifuged at 2000 rpm for 5 min to remove non-adherent bacteria, suspended in 200 μl of PBS, transferred to FACScan tubes and read

---

What is claimed is:

1. A composition comprising a hybrid protein comprising a Neisserial 287 protein and a Neisserial 953 protein, wherein the hybrid protein comprises an amino acid sequence having at least eighty percent identity to SEQ ID NO: 91 or SEQ ID NO: 97.

2. The composition of claim 1, wherein the Neisserial 287 protein and a Neisserial 953 protein are joined by a linker peptide.

3. The composition of claim 2, wherein the linker peptide is a poly-glycine linker.

4. The composition of claim 1, wherein the Neisserial 287 protein is a ΔG form.

5. The composition of claim 1, further comprising a pharmaceutically acceptable carrier.

* * * * *

SEQUENCE LISTING

<160> NUMBER OF SEQ ID NOS: 633

<210> SEQ ID NO 1
<211> LENGTH: 441
<212> TYPE: PRT
<213> ORGANISM: Neisseria meningitidis

<400> SEQUENCE: 1

```
Met Lys Lys Tyr Leu Phe Arg Ala Ala Leu Tyr Gly Ile Ala Ala Ala
1               5                   10                  15

Ile Leu Ala Ala Cys Gln Ser Lys Ser Ile Gln Thr Phe Pro Gln Pro
            20                  25                  30

Asp Thr Ser Val Ile Asn Gly Pro Asp Arg Pro Val Gly Ile Pro Asp
        35                  40                  45

Pro Ala Gly Thr Thr Val Gly Gly Gly Gly Ala Val Tyr Thr Val Val
    50                  55                  60

Pro His Leu Ser Leu Pro His Trp Ala Ala Gln Asp Phe Ala Lys Ser
65                  70                  75                  80

Leu Gln Ser Phe Arg Leu Gly Cys Ala Asn Leu Lys Asn Arg Gln Gly
                85                  90                  95

Trp Gln Asp Val Cys Ala Gln Ala Phe Gln Thr Pro Val His Ser Phe
            100                 105                 110
```

```
Gln Ala Lys Gln Phe Phe Glu Arg Tyr Phe Thr Pro Trp Gln Val Ala
            115                 120                 125
Gly Asn Gly Ser Leu Ala Gly Thr Val Thr Gly Tyr Tyr Glu Pro Val
        130                 135                 140
Leu Lys Gly Asp Asp Arg Arg Thr Ala Gln Ala Arg Phe Pro Ile Tyr
145                 150                 155                 160
Gly Ile Pro Asp Asp Phe Ile Ser Val Pro Leu Pro Ala Gly Leu Arg
                165                 170                 175
Ser Gly Lys Ala Leu Val Arg Ile Arg Gln Thr Gly Lys Asn Ser Gly
            180                 185                 190
Thr Ile Asp Asn Thr Gly Gly Thr His Thr Ala Asp Leu Ser Arg Phe
        195                 200                 205
Pro Ile Thr Ala Arg Thr Thr Ala Ile Lys Gly Arg Phe Glu Gly Ser
    210                 215                 220
Arg Phe Leu Pro Tyr His Thr Arg Asn Gln Ile Asn Gly Gly Ala Leu
225                 230                 235                 240
Asp Gly Lys Ala Pro Ile Leu Gly Tyr Ala Glu Asp Pro Val Glu Leu
                245                 250                 255
Phe Phe Met His Ile Gln Gly Ser Gly Arg Leu Lys Thr Pro Ser Gly
            260                 265                 270
Lys Tyr Ile Arg Ile Gly Tyr Ala Asp Lys Asn Glu His Pro Tyr Val
        275                 280                 285
Ser Ile Gly Arg Tyr Met Ala Asp Lys Gly Tyr Leu Lys Leu Gly Gln
    290                 295                 300
Thr Ser Met Gln Gly Ile Lys Ala Tyr Met Arg Gln Asn Pro Gln Arg
305                 310                 315                 320
Leu Ala Glu Val Leu Gly Gln Asn Pro Ser Tyr Ile Phe Phe Arg Glu
                325                 330                 335
Leu Ala Gly Ser Ser Asn Asp Gly Pro Val Gly Ala Leu Gly Thr Pro
            340                 345                 350
Leu Met Gly Glu Tyr Ala Gly Ala Val Asp Arg His Tyr Ile Thr Leu
        355                 360                 365
Gly Ala Pro Leu Phe Val Ala Thr Ala His Pro Val Thr Arg Lys Ala
    370                 375                 380
Leu Asn Arg Leu Ile Met Ala Gln Asp Thr Gly Ser Ala Ile Lys Gly
385                 390                 395                 400
Ala Val Arg Val Asp Tyr Phe Trp Gly Tyr Gly Asp Glu Ala Gly Glu
                405                 410                 415
Leu Ala Gly Lys Gln Lys Thr Thr Gly Tyr Val Trp Gln Leu Leu Pro
            420                 425                 430
Asn Gly Met Lys Pro Glu Tyr Arg Pro
            435                 440

<210> SEQ ID NO 2
<211> LENGTH: 420
<212> TYPE: PRT
<213> ORGANISM: Neisseria meningitidis

<400> SEQUENCE: 2

Gln Ser Lys Ser Ile Gln Thr Phe Pro Gln Pro Asp Thr Ser Val Ile
1               5                   10                  15
Asn Gly Pro Asp Arg Pro Val Gly Ile Pro Asp Pro Ala Gly Thr Thr
            20                  25                  30
Val Gly Gly Gly Ala Val Tyr Thr Val Pro His Leu Ser Leu
        35                  40                  45
```

```
Pro His Trp Ala Ala Gln Asp Phe Ala Lys Ser Leu Gln Ser Phe Arg
    50                  55                  60

Leu Gly Cys Ala Asn Leu Lys Asn Arg Gln Gly Trp Gln Asp Val Cys
 65                  70                  75                  80

Ala Gln Ala Phe Gln Thr Pro Val His Ser Phe Gln Ala Lys Gln Phe
                 85                  90                  95

Phe Glu Arg Tyr Phe Thr Pro Trp Gln Val Ala Gly Asn Gly Ser Leu
            100                 105                 110

Ala Gly Thr Val Thr Gly Tyr Tyr Glu Pro Val Leu Lys Gly Asp Asp
            115                 120                 125

Arg Arg Thr Ala Gln Ala Arg Phe Pro Ile Tyr Gly Ile Pro Asp Asp
    130                 135                 140

Phe Ile Ser Val Pro Leu Pro Ala Gly Leu Arg Ser Gly Lys Ala Leu
145                 150                 155                 160

Val Arg Ile Arg Gln Thr Gly Lys Asn Ser Gly Thr Ile Asp Asn Thr
                165                 170                 175

Gly Gly Thr His Thr Ala Asp Leu Ser Arg Phe Pro Ile Thr Ala Arg
            180                 185                 190

Thr Thr Ala Ile Lys Gly Arg Phe Glu Gly Ser Arg Phe Leu Pro Tyr
    195                 200                 205

His Thr Arg Asn Gln Ile Asn Gly Gly Ala Leu Asp Gly Lys Ala Pro
210                 215                 220

Ile Leu Gly Tyr Ala Glu Asp Pro Val Glu Leu Phe Phe Met His Ile
225                 230                 235                 240

Gln Gly Ser Gly Arg Leu Lys Thr Pro Ser Gly Lys Tyr Ile Arg Ile
                245                 250                 255

Gly Tyr Ala Asp Lys Asn Glu His Pro Tyr Val Ser Ile Gly Arg Tyr
            260                 265                 270

Met Ala Asp Lys Gly Tyr Leu Lys Leu Gly Gln Thr Ser Met Gln Gly
    275                 280                 285

Ile Lys Ala Tyr Met Arg Gln Asn Pro Gln Arg Leu Ala Glu Val Leu
    290                 295                 300

Gly Gln Asn Pro Ser Tyr Ile Phe Phe Arg Glu Leu Ala Gly Ser Ser
305                 310                 315                 320

Asn Asp Gly Pro Val Gly Ala Leu Gly Thr Pro Leu Met Gly Glu Tyr
                325                 330                 335

Ala Gly Ala Val Asp Arg His Tyr Ile Thr Leu Gly Ala Pro Leu Phe
            340                 345                 350

Val Ala Thr Ala His Pro Val Thr Arg Lys Ala Leu Asn Arg Leu Ile
    355                 360                 365

Met Ala Gln Asp Thr Gly Ser Ala Ile Lys Gly Ala Val Arg Val Asp
    370                 375                 380

Tyr Phe Trp Gly Tyr Gly Asp Glu Ala Gly Glu Leu Ala Gly Lys Gln
385                 390                 395                 400

Lys Thr Thr Gly Tyr Val Trp Gln Leu Leu Pro Asn Gly Met Lys Pro
                405                 410                 415

Glu Tyr Arg Pro
            420

<210> SEQ ID NO 3
<211> LENGTH: 440
<212> TYPE: PRT
<213> ORGANISM: Artificial Sequence
<220> FEATURE:
<223> OTHER INFORMATION: Synthetic construct
```

<400> SEQUENCE: 3

```
Met Lys Thr Phe Phe Lys Thr Leu Ser Ala Ala Leu Ala Leu Ile
1               5                   10                  15

Leu Ala Ala Cys Gln Ser Lys Ser Ile Gln Thr Phe Pro Gln Pro Asp
            20                  25                  30

Thr Ser Val Ile Asn Gly Pro Asp Arg Pro Val Gly Ile Pro Asp Pro
        35                  40                  45

Ala Gly Thr Thr Val Gly Gly Gly Ala Val Tyr Thr Val Val Pro
    50                  55                  60

His Leu Ser Leu Pro His Trp Ala Ala Gln Asp Phe Ala Lys Ser Leu
65                  70                  75                  80

Gln Ser Phe Arg Leu Gly Cys Ala Asn Leu Lys Asn Arg Gln Gly Trp
                85                  90                  95

Gln Asp Val Cys Ala Gln Ala Phe Gln Thr Pro Val His Ser Phe Gln
            100                 105                 110

Ala Lys Gln Phe Phe Glu Arg Tyr Phe Thr Pro Trp Gln Val Ala Gly
        115                 120                 125

Asn Gly Ser Leu Ala Gly Thr Val Thr Gly Tyr Tyr Glu Pro Val Leu
130                 135                 140

Lys Gly Asp Asp Arg Arg Thr Ala Gln Ala Arg Phe Pro Ile Tyr Gly
145                 150                 155                 160

Ile Pro Asp Asp Phe Ile Ser Val Pro Leu Pro Ala Gly Leu Arg Ser
                165                 170                 175

Gly Lys Ala Leu Val Arg Ile Arg Gln Thr Gly Lys Asn Ser Gly Thr
            180                 185                 190

Ile Asp Asn Thr Gly Gly Thr His Thr Ala Asp Leu Ser Arg Phe Pro
        195                 200                 205

Ile Thr Ala Arg Thr Thr Ala Ile Lys Gly Arg Phe Glu Gly Ser Arg
    210                 215                 220

Phe Leu Pro Tyr His Thr Arg Asn Gln Ile Asn Gly Gly Ala Leu Asp
225                 230                 235                 240

Gly Lys Ala Pro Ile Leu Gly Tyr Ala Glu Asp Pro Val Glu Leu Phe
                245                 250                 255

Phe Met His Ile Gln Gly Ser Gly Arg Leu Lys Thr Pro Ser Gly Lys
            260                 265                 270

Tyr Ile Arg Ile Gly Tyr Ala Asp Lys Asn Glu His Pro Tyr Val Ser
        275                 280                 285

Ile Gly Arg Tyr Met Ala Asp Lys Gly Tyr Leu Lys Leu Gly Gln Thr
    290                 295                 300

Ser Met Gln Gly Ile Lys Ser Tyr Met Arg Gln Asn Pro Gln Arg Leu
305                 310                 315                 320

Ala Glu Val Leu Gly Gln Asn Pro Ser Tyr Ile Phe Phe Arg Glu Leu
                325                 330                 335

Ala Gly Ser Ser Asn Asp Gly Pro Val Gly Ala Leu Gly Thr Pro Leu
            340                 345                 350

Met Gly Glu Tyr Ala Gly Ala Val Asp Arg His Tyr Ile Thr Leu Gly
        355                 360                 365

Ala Pro Leu Phe Val Ala Thr Ala His Pro Val Thr Arg Lys Ala Leu
    370                 375                 380

Asn Arg Leu Ile Met Ala Gln Asp Thr Gly Ser Ala Ile Lys Gly Ala
385                 390                 395                 400

Val Arg Val Asp Tyr Phe Trp Gly Tyr Gly Asp Glu Ala Gly Glu Leu
                405                 410                 415
```

```
Ala Gly Lys Gln Lys Thr Thr Gly Tyr Val Trp Gln Leu Leu Pro Asn
            420                 425                 430

Gly Met Lys Pro Glu Tyr Arg Pro
        435                 440

<210> SEQ ID NO 4
<211> LENGTH: 58
<212> TYPE: PRT
<213> ORGANISM: Artificial Sequence
<220> FEATURE:
<223> OTHER INFORMATION: Neisseria meningitidis

<400> SEQUENCE: 4

Glu Arg Arg Arg Leu Leu Val Asn Ile Gln Tyr Glu Ser Ser Arg Ala
1               5                   10                  15

Gly Leu Asp Thr Gln Ile Val Leu Gly Leu Ile Glu Val Glu Ser Ala
            20                  25                  30

Phe Arg Gln Tyr Ala Ile Ser Gly Val Gly Ala Arg Gly Leu Met Gln
        35                  40                  45

Val Met Pro Phe Trp Lys Asn Tyr Ile Gly
    50                  55

<210> SEQ ID NO 5
<211> LENGTH: 60
<212> TYPE: PRT
<213> ORGANISM: Artificial Sequence
<220> FEATURE:
<223> OTHER INFORMATION: Escherichia coli

<400> SEQUENCE: 5

Glu Arg Phe Pro Leu Ala Tyr Asn Asp Leu Phe Lys Arg Tyr Thr Ser
1               5                   10                  15

Gly Lys Glu Ile Pro Gln Ser Tyr Ala Met Ala Ile Ala Arg Gln Glu
            20                  25                  30

Ser Ala Trp Asn Pro Lys Val Lys Ser Pro Val Gly Ala Ser Gly Leu
        35                  40                  45

Met Gln Ile Met Pro Gly Thr Ala Thr His Thr Val
    50                  55                  60

<210> SEQ ID NO 6
<211> LENGTH: 120
<212> TYPE: PRT
<213> ORGANISM: Artificial Sequence
<220> FEATURE:
<223> OTHER INFORMATION: Neisseria meningitidis

<400> SEQUENCE: 6

Val Ala Gln Lys Tyr Gly Val Pro Ala Glu Leu Ile Val Ala Val Ile
1               5                   10                  15

Gly Ile Glu Thr Asn Tyr Gly Lys Asn Thr Gly Ser Phe Arg Val Ala
            20                  25                  30

Asp Ala Leu Ala Thr Leu Gly Phe Asp Tyr Pro Arg Arg Ala Gly Phe
        35                  40                  45

Phe Gln Lys Glu Leu Val Glu Leu Leu Lys Leu Ala Lys Glu Glu Gly
    50                  55                  60

Gly Asp Val Phe Ala Phe Lys Gly Ser Tyr Ala Gly Ala Met Gly Met
65                  70                  75                  80

Pro Gln Phe Met Pro Ser Ser Tyr Arg Lys Trp Ala Val Asp Tyr Asp
                85                  90                  95

Gly Asp Gly His Arg Asp Ile Trp Gly Asn Val Gly Asp Val Ala Ala
```

```
                         100                 105                 110

Ser Val Ala Asn Tyr Met Lys Gln
            115                 120

<210> SEQ ID NO 7
<211> LENGTH: 119
<212> TYPE: PRT
<213> ORGANISM: Artificial Sequence
<220> FEATURE:
<223> OTHER INFORMATION: Escherichia coli

<400> SEQUENCE: 7

Ala Trp Gln Val Tyr Gly Val Pro Pro Glu Ile Ile Val Gly Ile Ile
1               5                   10                  15

Gly Val Glu Thr Arg Trp Gly Arg Val Met Gly Lys Thr Arg Ile Leu
            20                  25                  30

Asp Ala Leu Ala Thr Leu Ser Phe Asn Tyr Pro Arg Arg Ala Glu Tyr
        35                  40                  45

Phe Ser Gly Glu Leu Glu Thr Phe Leu Leu Met Ala Arg Asp Glu Gln
    50                  55                  60

Asp Asp Pro Leu Asn Leu Lys Gly Ser Phe Ala Gly Ala Met Gly Tyr
65                  70                  75                  80

Gly Gln Phe Met Pro Ser Ser Tyr Lys Gln Tyr Ala Val Asp Phe Ser
                85                  90                  95

Gly Asp Gly His Ile Asn Leu Trp Asp Pro Val Asp Ala Ile Gly Ser
            100                 105                 110

Val Ala Asn Tyr Phe Lys Ala
        115

<210> SEQ ID NO 8
<211> LENGTH: 194
<212> TYPE: PRT
<213> ORGANISM: Artificial Sequence
<220> FEATURE:
<223> OTHER INFORMATION: Neisseria meningitidis

<400> SEQUENCE: 8

Ala Leu Asp Gly Lys Ala Pro Ile Leu Gly Tyr Ala Glu Asp Pro Val
1               5                   10                  15

Glu Leu Phe Phe Met His Ile Gln Gly Ser Gly Arg Leu Lys Thr Pro
            20                  25                  30

Ser Gly Lys Tyr Ile Arg Ile Gly Tyr Ala Asp Lys Asn Glu His Pro
        35                  40                  45

Tyr Val Ser Ile Gly Arg Tyr Met Ala Asp Lys Gly Tyr Leu Lys Leu
    50                  55                  60

Gly Gln Thr Ser Met Gln Gly Ile Lys Ser Tyr Met Arg Gln Asn Pro
65                  70                  75                  80

Gln Arg Leu Ala Glu Val Leu Gly Gln Asn Pro Ser Tyr Ile Phe Phe
                85                  90                  95

Arg Glu Leu Ala Gly Ser Ser Asn Asp Gly Pro Val Gly Ala Leu Gly
            100                 105                 110

Thr Pro Leu Met Gly Glu Tyr Ala Gly Ala Val Asp Arg His Tyr Ile
        115                 120                 125

Thr Leu Gly Ala Pro Leu Phe Val Ala Thr Ala His Pro Val Thr Arg
    130                 135                 140

Lys Ala Leu Asn Arg Leu Ile Met Ala Gln Asp Thr Gly Ser Ala Ile
145                 150                 155                 160

Lys Gly Ala Val Arg Val Asp Tyr Phe Trp Gly Tyr Gly Asp Glu Ala
```

```
                    165                 170                 175
Gly Glu Leu Ala Gly Lys Gln Lys Thr Thr Gly Tyr Val Trp Gln Leu
            180                 185                 190

Leu Pro

<210> SEQ ID NO 9
<211> LENGTH: 196
<212> TYPE: PRT
<213> ORGANISM: Escherichia coli

<400> SEQUENCE: 9

Ala Leu Ser Asp Lys Tyr Ile Leu Ala Tyr Ser Asn Ser Leu Met Asp
1               5                   10                  15

Asn Phe Ile Met Asp Val Gln Gly Ser Gly Tyr Ile Asp Phe Gly Asp
            20                  25                  30

Gly Ser Pro Leu Asn Phe Phe Ser Tyr Ala Gly Lys Asn Gly His Ala
        35                  40                  45

Tyr Arg Ser Ile Gly Lys Val Leu Ile Asp Arg Gly Glu Val Lys Lys
    50                  55                  60

Glu Asp Met Ser Met Gln Ala Ile Arg His Trp Gly Glu Thr His Ser
65                  70                  75                  80

Glu Ala Glu Val Arg Glu Leu Leu Glu Gln Asn Pro Ser Phe Val Phe
                85                  90                  95

Phe Lys Pro Gln Ser Phe Ala Pro Val Lys Gly Ala Ser Ala Val Pro
            100                 105                 110

Leu Val Gly Arg Ala Ser Val Ala Ser Asp Arg Ser Ile Ile Pro Pro
        115                 120                 125

Gly Thr Thr Leu Leu Ala Glu Val Pro Leu Leu Asp Asn Asn Gly Lys
    130                 135                 140

Phe Asn Gly Gln Tyr Glu Leu Arg Leu Met Val Ala Leu Asp Val Gly
145                 150                 155                 160

Gly Ala Ile Lys Gly Gln His Phe Asp Ile Tyr Gln Gly Ile Gly Pro
                165                 170                 175

Glu Ala Gly His Arg Ala Gly Trp Tyr Asn His Tyr Gly Arg Val Trp
            180                 185                 190

Val Leu Lys Thr
        195

<210> SEQ ID NO 10
<211> LENGTH: 28
<212> TYPE: DNA
<213> ORGANISM: Artificial Sequence
<220> FEATURE:
<223> OTHER INFORMATION: Synthetic construct

<400> SEQUENCE: 10
cgaagacccc gtcggtcttt ttttatg                                    28

<210> SEQ ID NO 11
<211> LENGTH: 28
<212> TYPE: DNA
<213> ORGANISM: Artificial Sequence
<220> FEATURE:
<223> OTHER INFORMATION: Synthetic construct

<400> SEQUENCE: 11
gtgcataaaa aaaagaccga cggggtct                                   28

<210> SEQ ID NO 12
```

```
<211> LENGTH: 25
<212> TYPE: DNA
<213> ORGANISM: Artificial Sequence
<220> FEATURE:
<223> OTHER INFORMATION: Synthetic construct

<400> SEQUENCE: 12
aacgcctcgc cggtgttttg ggtca                                         25

<210> SEQ ID NO 13
<211> LENGTH: 25
<212> TYPE: DNA
<213> ORGANISM: Artificial Sequence
<220> FEATURE:
<223> OTHER INFORMATION: Synthetic construct

<400> SEQUENCE: 13
tttgacccaa acaccggcg aggcg                                          25

<210> SEQ ID NO 14
<211> LENGTH: 26
<212> TYPE: DNA
<213> ORGANISM: Artificial Sequence
<220> FEATURE:
<223> OTHER INFORMATION: Synthetic construct

<400> SEQUENCE: 14
tgccggcgca gtcggtcggc actaca                                        26

<210> SEQ ID NO 15
<211> LENGTH: 26
<212> TYPE: DNA
<213> ORGANISM: Artificial Sequence
<220> FEATURE:
<223> OTHER INFORMATION: Synthetic construct

<400> SEQUENCE: 15
taatgtagtg ccgaccgact gcgccg                                        26

<210> SEQ ID NO 16
<211> LENGTH: 25
<212> TYPE: DNA
<213> ORGANISM: Artificial Sequence
<220> FEATURE:
<223> OTHER INFORMATION: Synthetic construct

<400> SEQUENCE: 16
tgattgaggt gggtagcgcg ttccg                                         25

<210> SEQ ID NO 17
<211> LENGTH: 25
<212> TYPE: DNA
<213> ORGANISM: Artificial Sequence
<220> FEATURE:
<223> OTHER INFORMATION: Synthetic construct

<400> SEQUENCE: 17
ggcggaacgc gctacccacc tcaat                                         25

<210> SEQ ID NO 18
<211> LENGTH: 34
<212> TYPE: DNA
<213> ORGANISM: Artificial Sequence
<220> FEATURE:
<223> OTHER INFORMATION: Synthetic construct

<400> SEQUENCE: 18
```

```
ccggaattct tatgaaaaaa atcatcttcg ccgc                                    34

<210> SEQ ID NO 19
<211> LENGTH: 32
<212> TYPE: DNA
<213> ORGANISM: Artificial Sequence
<220> FEATURE:
<223> OTHER INFORMATION: Synthetic construct

<400> SEQUENCE: 19
gcccaagctt ttattgtttg gctgcctcga tt                                      32

<210> SEQ ID NO 20
<211> LENGTH: 37
<212> TYPE: DNA
<213> ORGANISM: Artificial Sequence
<220> FEATURE:
<223> OTHER INFORMATION: Synthetic construct

<400> SEQUENCE: 20
ccggaattct tatgtcgccc gatgttaaat cggcgga                                 37

<210> SEQ ID NO 21
<211> LENGTH: 32
<212> TYPE: DNA
<213> ORGANISM: Artificial Sequence
<220> FEATURE:
<223> OTHER INFORMATION: Synthetic construct

<400> SEQUENCE: 21
gcccaagctt tcaatcctgc tcttttttgc cg                                      32

<210> SEQ ID NO 22
<211> LENGTH: 34
<212> TYPE: DNA
<213> ORGANISM: Artificial Sequence
<220> FEATURE:
<223> OTHER INFORMATION: Synthetic construct

<400> SEQUENCE: 22
ccggaattct tatgagccaa gatatggcgg cagt                                    34

<210> SEQ ID NO 23
<211> LENGTH: 32
<212> TYPE: DNA
<213> ORGANISM: Artificial Sequence
<220> FEATURE:
<223> OTHER INFORMATION: Synthetic construct

<400> SEQUENCE: 23
gcccaagctt tcaatcctgc tcttttttgc cg                                      32

<210> SEQ ID NO 24
<211> LENGTH: 34
<212> TYPE: DNA
<213> ORGANISM: Artificial Sequence
<220> FEATURE:
<223> OTHER INFORMATION: Synthetic construct

<400> SEQUENCE: 24
ccggaattct tatgtccgcc gaatccgcaa atca                                    34

<210> SEQ ID NO 25
<211> LENGTH: 32
<212> TYPE: DNA
<213> ORGANISM: Artificial Sequence
<220> FEATURE:
```

<223> OTHER INFORMATION: Synthetic construct

<400> SEQUENCE: 25
gcccaagctt tcaatcctgc tctttttgc cg                              32

<210> SEQ ID NO 26
<211> LENGTH: 36
<212> TYPE: DNA
<213> ORGANISM: Artificial Sequence
<220> FEATURE:
<223> OTHER INFORMATION: Synthetic construct

<400> SEQUENCE: 26
ccggaattct tatgggaagg gttgatttgg ctaatg                         36

<210> SEQ ID NO 27
<211> LENGTH: 32
<212> TYPE: DNA
<213> ORGANISM: Artificial Sequence
<220> FEATURE:
<223> OTHER INFORMATION: Synthetic construct

<400> SEQUENCE: 27
gcccaagctt tcaatcctgc tctttttgc cg                              32

<210> SEQ ID NO 28
<211> LENGTH: 36
<212> TYPE: DNA
<213> ORGANISM: Artificial Sequence
<220> FEATURE:
<223> OTHER INFORMATION: Synthetic construct

<400> SEQUENCE: 28
ccggaattct tatgtcagat ttggcaaacg attctt                         36

<210> SEQ ID NO 29
<211> LENGTH: 35
<212> TYPE: DNA
<213> ORGANISM: Artificial Sequence
<220> FEATURE:
<223> OTHER INFORMATION: Synthetic construct

<400> SEQUENCE: 29
gcccaagctt ttacgtatca tatttcacgt gcttc                          35

<210> SEQ ID NO 30
<211> LENGTH: 37
<212> TYPE: DNA
<213> ORGANISM: Artificial Sequence
<220> FEATURE:
<223> OTHER INFORMATION: Synthetic construct

<400> SEQUENCE: 30
ccggaattct tatgtcgccc gatgttaaat cggcgga                        37

<210> SEQ ID NO 31
<211> LENGTH: 35
<212> TYPE: DNA
<213> ORGANISM: Artificial Sequence
<220> FEATURE:
<223> OTHER INFORMATION: Synthetic construct

<400> SEQUENCE: 31
gcccaagctt ttacgtatca tatttcacgt gcttc                          35

<210> SEQ ID NO 32

```
<211> LENGTH: 36
<212> TYPE: DNA
<213> ORGANISM: Artificial Sequence
<220> FEATURE:
<223> OTHER INFORMATION: Synthetic construct

<400> SEQUENCE: 32
ccggaattct tatgcaaagc aagagcatcc aaacct                              36

<210> SEQ ID NO 33
<211> LENGTH: 30
<212> TYPE: DNA
<213> ORGANISM: Artificial Sequence
<220> FEATURE:
<223> OTHER INFORMATION: Synthetic construct

<400> SEQUENCE: 33
gcccaagctt ttacgggcgg tattcgggct                                     30

<210> SEQ ID NO 34
<211> LENGTH: 29
<212> TYPE: DNA
<213> ORGANISM: Artificial Sequence
<220> FEATURE:
<223> OTHER INFORMATION: Synthetic construct

<400> SEQUENCE: 34
ccggaattca tatgaaacac tttccatcc                                      29

<210> SEQ ID NO 35
<211> LENGTH: 28
<212> TYPE: DNA
<213> ORGANISM: Artificial Sequence
<220> FEATURE:
<223> OTHER INFORMATION: Synthetic construct

<400> SEQUENCE: 35
gcccaagctt ttaccactcg taattgac                                       28

<210> SEQ ID NO 36
<211> LENGTH: 29
<212> TYPE: DNA
<213> ORGANISM: Artificial Sequence
<220> FEATURE:
<223> OTHER INFORMATION: Synthetic construct

<400> SEQUENCE: 36
ccggaattca tatggccaca agcgacgac                                      29

<210> SEQ ID NO 37
<211> LENGTH: 28
<212> TYPE: DNA
<213> ORGANISM: Artificial Sequence
<220> FEATURE:
<223> OTHER INFORMATION: Synthetic construct

<400> SEQUENCE: 37
gcccaagctt ttaccactcg taattgac                                       28

<210> SEQ ID NO 38
<211> LENGTH: 29
<212> TYPE: DNA
<213> ORGANISM: Artificial Sequence
<220> FEATURE:
<223> OTHER INFORMATION: Synthetic construct

<400> SEQUENCE: 38
```

```
ccggaattct tatgaaacac tttccatcc                                    29
```

<210> SEQ ID NO 39
<211> LENGTH: 31
<212> TYPE: DNA
<213> ORGANISM: Artificial Sequence
<220> FEATURE:
<223> OTHER INFORMATION: Synthetic construct

<400> SEQUENCE: 39

```
gcccaagctt tcaacccacg ttgtaaggtt g                                 31
```

<210> SEQ ID NO 40
<211> LENGTH: 30
<212> TYPE: DNA
<213> ORGANISM: Artificial Sequence
<220> FEATURE:
<223> OTHER INFORMATION: Synthetic construct

<400> SEQUENCE: 40

```
ccggaattct tatggccaca aacgacgacg                                   30
```

<210> SEQ ID NO 41
<211> LENGTH: 31
<212> TYPE: DNA
<213> ORGANISM: Artificial Sequence
<220> FEATURE:
<223> OTHER INFORMATION: Synthetic construct

<400> SEQUENCE: 41

```
gcccaagctt tcaacccacg ttgtaaggtt g                                 31
```

<210> SEQ ID NO 42
<211> LENGTH: 34
<212> TYPE: DNA
<213> ORGANISM: Artificial Sequence
<220> FEATURE:
<223> OTHER INFORMATION: Synthetic construct

<400> SEQUENCE: 42

```
ccggaattct tatggccacc tacaaagtgg acga                              34
```

<210> SEQ ID NO 43
<211> LENGTH: 32
<212> TYPE: DNA
<213> ORGANISM: Artificial Sequence
<220> FEATURE:
<223> OTHER INFORMATION: Synthetic construct

<400> SEQUENCE: 43

```
gcccaagctt ttattgtttg gctgcctcga tt                                32
```

<210> SEQ ID NO 44
<211> LENGTH: 32
<212> TYPE: DNA
<213> ORGANISM: Artificial Sequence
<220> FEATURE:
<223> OTHER INFORMATION: Synthetic construct

<400> SEQUENCE: 44

```
cgcggatccg ctagccccga tgttaaatcg gc                                32
```

<210> SEQ ID NO 45
<211> LENGTH: 31
<212> TYPE: DNA
<213> ORGANISM: Artificial Sequence
<220> FEATURE:

<223> OTHER INFORMATION: Synthetic construct

<400> SEQUENCE: 45
cccgctcgag tcaatcctgc tctttttgc c                                31

<210> SEQ ID NO 46
<211> LENGTH: 32
<212> TYPE: DNA
<213> ORGANISM: Artificial Sequence
<220> FEATURE:
<223> OTHER INFORMATION: Synthetic construct

<400> SEQUENCE: 46
cgcggatccg ctagccaaga tatggcggca gt                              32

<210> SEQ ID NO 47
<211> LENGTH: 32
<212> TYPE: DNA
<213> ORGANISM: Artificial Sequence
<220> FEATURE:
<223> OTHER INFORMATION: Synthetic construct

<400> SEQUENCE: 47
cgcggatccg ctagcgccga atccgcaaat ca                              32

<210> SEQ ID NO 48
<211> LENGTH: 32
<212> TYPE: DNA
<213> ORGANISM: Artificial Sequence
<220> FEATURE:
<223> OTHER INFORMATION: Synthetic construct

<400> SEQUENCE: 48
cgcgctagcg gaagggttga tttggctaat gg                              32

<210> SEQ ID NO 49
<211> LENGTH: 34
<212> TYPE: DNA
<213> ORGANISM: Artificial Sequence
<220> FEATURE:
<223> OTHER INFORMATION: Synthetic construct

<400> SEQUENCE: 49
gggaattcca tatgggcatt tcccgcaaaa tatc                            34

<210> SEQ ID NO 50
<211> LENGTH: 32
<212> TYPE: DNA
<213> ORGANISM: Artificial Sequence
<220> FEATURE:
<223> OTHER INFORMATION: Synthetic construct

<400> SEQUENCE: 50
cccgctcgag ttacgtatca tatttcacgt gc                              32

<210> SEQ ID NO 51
<211> LENGTH: 34
<212> TYPE: DNA
<213> ORGANISM: Artificial Sequence
<220> FEATURE:
<223> OTHER INFORMATION: Synthetic construct

<400> SEQUENCE: 51
gggaattcca tatgggcatt tcccgcaaaa tatc                            34

<210> SEQ ID NO 52

<211> LENGTH: 33
<212> TYPE: DNA
<213> ORGANISM: Artificial Sequence
<220> FEATURE:
<223> OTHER INFORMATION: Synthetic construct

<400> SEQUENCE: 52
cccgctcgag ttattctatg ccttgtgcgg cat    33

<210> SEQ ID NO 53
<211> LENGTH: 32
<212> TYPE: DNA
<213> ORGANISM: Artificial Sequence
<220> FEATURE:
<223> OTHER INFORMATION: Synthetic construct

<400> SEQUENCE: 53
cgcggatccc atatggccac aagcgacgac ga    32

<210> SEQ ID NO 54
<211> LENGTH: 28
<212> TYPE: DNA
<213> ORGANISM: Artificial Sequence
<220> FEATURE:
<223> OTHER INFORMATION: Synthetic construct

<400> SEQUENCE: 54
cccgctcgag ttaccactcg taattgac    28

<210> SEQ ID NO 55
<211> LENGTH: 28
<212> TYPE: DNA
<213> ORGANISM: Artificial Sequence
<220> FEATURE:
<223> OTHER INFORMATION: Synthetic construct

<400> SEQUENCE: 55
cgcggatccc atatggccac aaacgacg    28

<210> SEQ ID NO 56
<211> LENGTH: 35
<212> TYPE: DNA
<213> ORGANISM: Artificial Sequence
<220> FEATURE:
<223> OTHER INFORMATION: Synthetic construct

<400> SEQUENCE: 56
cccgctcgag tcatttagca atattatctt tgttc    35

<210> SEQ ID NO 57
<211> LENGTH: 33
<212> TYPE: DNA
<213> ORGANISM: Artificial Sequence
<220> FEATURE:
<223> OTHER INFORMATION: Synthetic construct

<400> SEQUENCE: 57
cgcggatccc atatgaaagc aaacagtgcc gac    33

<210> SEQ ID NO 58
<211> LENGTH: 28
<212> TYPE: DNA
<213> ORGANISM: Artificial Sequence
<220> FEATURE:
<223> OTHER INFORMATION: Synthetic construct

<400> SEQUENCE: 58

```
cccgctcgag ttaccactcg taattgac                                           28

<210> SEQ ID NO 59
<211> LENGTH: 28
<212> TYPE: DNA
<213> ORGANISM: Artificial Sequence
<220> FEATURE:
<223> OTHER INFORMATION: Synthetic construct

<400> SEQUENCE: 59
cgcggatccc atatggccac aaacgacg                                           28

<210> SEQ ID NO 60
<211> LENGTH: 29
<212> TYPE: DNA
<213> ORGANISM: Artificial Sequence
<220> FEATURE:
<223> OTHER INFORMATION: Synthetic construct

<400> SEQUENCE: 60
cccgctcgag ttaacccacg ttgtaaggt                                          29

<210> SEQ ID NO 61
<211> LENGTH: 33
<212> TYPE: DNA
<213> ORGANISM: Artificial Sequence
<220> FEATURE:
<223> OTHER INFORMATION: Synthetic construct

<400> SEQUENCE: 61
cgcggatccc atatgatgaa acactttcca tcc                                     33

<210> SEQ ID NO 62
<211> LENGTH: 29
<212> TYPE: DNA
<213> ORGANISM: Artificial Sequence
<220> FEATURE:
<223> OTHER INFORMATION: Synthetic construct

<400> SEQUENCE: 62
cccgctcgag ttaacccacg ttgtaaggt                                          29

<210> SEQ ID NO 63
<211> LENGTH: 28
<212> TYPE: DNA
<213> ORGANISM: Artificial Sequence
<220> FEATURE:
<223> OTHER INFORMATION: Synthetic construct

<400> SEQUENCE: 63
cgcggatccc atatggccac aaacgacg                                           28

<210> SEQ ID NO 64
<211> LENGTH: 32
<212> TYPE: DNA
<213> ORGANISM: Artificial Sequence
<220> FEATURE:
<223> OTHER INFORMATION: Synthetic construct

<400> SEQUENCE: 64
cccgctcgag tcagtctgac actgttttat cc                                      32

<210> SEQ ID NO 65
<211> LENGTH: 32
<212> TYPE: DNA
<213> ORGANISM: Artificial Sequence
<220> FEATURE:
```

<223> OTHER INFORMATION: Synthetic construct

<400> SEQUENCE: 65
cgcggatccg ctagccccga tgttaaatcg gc        32

<210> SEQ ID NO 66
<211> LENGTH: 27
<212> TYPE: DNA
<213> ORGANISM: Artificial Sequence
<220> FEATURE:
<223> OTHER INFORMATION: Synthetic construct

<400> SEQUENCE: 66
cccgctcgag ttacgggcgg tattcgg        27

<210> SEQ ID NO 67
<211> LENGTH: 32
<212> TYPE: DNA
<213> ORGANISM: Artificial Sequence
<220> FEATURE:
<223> OTHER INFORMATION: Synthetic construct

<400> SEQUENCE: 67
cgcggatccg ctagccccga tgttaaatcg gc        32

<210> SEQ ID NO 68
<211> LENGTH: 32
<212> TYPE: DNA
<213> ORGANISM: Artificial Sequence
<220> FEATURE:
<223> OTHER INFORMATION: Synthetic construct

<400> SEQUENCE: 68
cccgctcgag ttacgtatca tatttcacgt gc        32

<210> SEQ ID NO 69
<211> LENGTH: 32
<212> TYPE: DNA
<213> ORGANISM: Artificial Sequence
<220> FEATURE:
<223> OTHER INFORMATION: Synthetic construct

<400> SEQUENCE: 69
cgcggatccg ctagccccga tgttaaatcg gc        32

<210> SEQ ID NO 70
<211> LENGTH: 28
<212> TYPE: DNA
<213> ORGANISM: Artificial Sequence
<220> FEATURE:
<223> OTHER INFORMATION: Synthetic construct

<400> SEQUENCE: 70
cccgctcgag ttaccactcg taattgac        28

<210> SEQ ID NO 71
<211> LENGTH: 1457
<212> TYPE: PRT
<213> ORGANISM: Neisseria meningitidis

<400> SEQUENCE: 71

Met Lys Thr Thr Asp Lys Arg Thr Thr Glu Thr His Arg Lys Ala Pro
1               5                   10                  15

Lys Thr Gly Arg Ile Arg Phe Ser Pro Ala Tyr Leu Ala Ile Cys Leu
            20                  25                  30

```
Ser Phe Gly Ile Leu Pro Gln Ala Trp Ala Gly His Thr Tyr Phe Gly
    35                  40                  45

Ile Asn Tyr Gln Tyr Tyr Arg Asp Phe Ala Glu Asn Lys Gly Lys Phe
50                  55                  60

Ala Val Gly Ala Lys Asp Ile Glu Val Tyr Asn Lys Lys Gly Glu Leu
65                  70                  75                  80

Val Gly Lys Ser Met Thr Lys Ala Pro Met Ile Asp Phe Ser Val Val
                85                  90                  95

Ser Arg Asn Gly Val Ala Ala Leu Val Gly Asp Gln Tyr Ile Val Ser
                100                 105                 110

Val Ala His Asn Gly Gly Tyr Asn Asn Val Asp Phe Gly Ala Glu Gly
            115                 120                 125

Arg Asn Pro Asp Gln His Arg Phe Thr Tyr Lys Ile Val Lys Arg Asn
130                 135                 140

Asn Tyr Lys Ala Gly Thr Lys Gly His Pro Tyr Gly Gly Asp Tyr His
145                 150                 155                 160

Met Pro Arg Leu His Lys Phe Val Thr Asp Ala Glu Pro Val Glu Met
                165                 170                 175

Thr Ser Tyr Met Asp Gly Arg Lys Tyr Ile Asp Gln Asn Asn Tyr Pro
            180                 185                 190

Asp Arg Val Arg Ile Gly Ala Gly Arg Gln Tyr Trp Arg Ser Asp Glu
            195                 200                 205

Asp Glu Pro Asn Asn Arg Glu Ser Ser Tyr His Ile Ala Ser Ala Tyr
210                 215                 220

Ser Trp Leu Val Gly Gly Asn Thr Phe Ala Gln Asn Gly Ser Gly Gly
225                 230                 235                 240

Gly Thr Val Asn Leu Gly Ser Glu Lys Ile Lys His Ser Pro Tyr Gly
                245                 250                 255

Phe Leu Pro Thr Gly Gly Ser Phe Gly Asp Ser Gly Ser Pro Met Phe
            260                 265                 270

Ile Tyr Asp Ala Gln Lys Gln Lys Trp Leu Ile Asn Gly Val Leu Gln
            275                 280                 285

Thr Gly Asn Pro Tyr Ile Gly Lys Ser Asn Gly Phe Gln Leu Val Arg
290                 295                 300

Lys Asp Trp Phe Tyr Asp Glu Ile Phe Ala Gly Asp Thr His Ser Val
305                 310                 315                 320

Phe Tyr Glu Pro Arg Gln Asn Gly Lys Tyr Ser Phe Asn Asp Asp Asn
                325                 330                 335

Asn Gly Thr Gly Lys Ile Asn Ala Lys His Glu His Asn Ser Leu Pro
            340                 345                 350

Asn Arg Leu Lys Thr Arg Thr Val Gln Leu Phe Asn Val Ser Leu Ser
            355                 360                 365

Glu Thr Ala Arg Glu Pro Val Tyr His Ala Ala Gly Val Asn Ser
370                 375                 380

Tyr Arg Pro Arg Leu Asn Asn Gly Glu Asn Ile Ser Phe Ile Asp Glu
385                 390                 395                 400

Gly Lys Gly Glu Leu Ile Leu Thr Ser Asn Ile Asn Gln Gly Ala Gly
                405                 410                 415

Gly Leu Tyr Phe Gln Gly Asp Phe Thr Val Ser Pro Glu Asn Asn Glu
            420                 425                 430

Thr Trp Gln Gly Ala Gly Val His Ile Ser Glu Asp Ser Thr Val Thr
            435                 440                 445

Trp Lys Val Asn Gly Val Ala Asn Asp Arg Leu Ser Lys Ile Gly Lys
450                 455                 460
```

-continued

```
Gly Thr Leu His Val Gln Ala Lys Gly Glu Asn Gln Gly Ser Ile Ser
465                 470                 475                 480

Val Gly Asp Gly Thr Val Ile Leu Asp Gln Gln Ala Asp Asp Lys Gly
                485                 490                 495

Lys Lys Gln Ala Phe Ser Glu Ile Gly Leu Val Ser Gly Arg Gly Thr
                500                 505                 510

Val Gln Leu Asn Ala Asp Asn Gln Phe Asn Pro Asp Lys Leu Tyr Phe
                515                 520                 525

Gly Phe Arg Gly Gly Arg Leu Asp Leu Asn Gly His Ser Leu Ser Phe
                530                 535                 540

His Arg Ile Gln Asn Thr Asp Glu Gly Ala Met Ile Val Asn His Asn
545                 550                 555                 560

Gln Asp Lys Glu Ser Thr Val Thr Ile Thr Gly Asn Lys Asp Ile Ala
                565                 570                 575

Thr Thr Gly Asn Asn Asn Ser Leu Asp Ser Lys Lys Glu Ile Ala Tyr
                580                 585                 590

Asn Gly Trp Phe Gly Glu Lys Asp Thr Thr Lys Thr Asn Gly Arg Leu
                595                 600                 605

Asn Leu Val Tyr Gln Pro Ala Ala Glu Asp Arg Thr Leu Leu Leu Ser
                610                 615                 620

Gly Gly Thr Asn Leu Asn Gly Asn Ile Thr Gln Thr Asn Gly Lys Leu
625                 630                 635                 640

Phe Phe Ser Gly Arg Pro Thr Pro His Ala Tyr Asn His Leu Asn Asp
                645                 650                 655

His Trp Ser Gln Lys Glu Gly Ile Pro Arg Gly Glu Ile Val Trp Asp
                660                 665                 670

Asn Asp Trp Ile Asn Arg Thr Phe Lys Ala Glu Asn Phe Gln Ile Lys
                675                 680                 685

Gly Gly Gln Ala Val Val Ser Arg Asn Val Ala Lys Val Lys Gly Asp
                690                 695                 700

Trp His Leu Ser Asn His Ala Gln Ala Val Phe Gly Val Ala Pro His
705                 710                 715                 720

Gln Ser His Thr Ile Cys Thr Arg Ser Asp Trp Thr Gly Leu Thr Asn
                725                 730                 735

Cys Val Glu Lys Thr Ile Thr Asp Lys Val Ile Ala Ser Leu Thr
                740                 745                 750

Lys Thr Asp Ile Ser Gly Asn Val Asp Leu Ala Asp His Ala His Leu
                755                 760                 765

Asn Leu Thr Gly Leu Ala Thr Leu Asn Gly Asn Leu Ser Ala Asn Gly
                770                 775                 780

Asp Thr Arg Tyr Thr Val Ser His Asn Ala Thr Gln Asn Gly Asn Leu
785                 790                 795                 800

Ser Leu Val Gly Asn Ala Gln Ala Thr Phe Asn Gln Ala Thr Leu Asn
                805                 810                 815

Gly Asn Thr Ser Ala Ser Gly Asn Ala Ser Phe Asn Leu Ser Asp His
                820                 825                 830

Ala Val Gln Asn Gly Ser Leu Thr Leu Ser Gly Asn Ala Lys Ala Asn
                835                 840                 845

Val Ser His Ser Ala Leu Asn Gly Asn Val Ser Leu Ala Asp Lys Ala
                850                 855                 860

Val Phe His Phe Glu Ser Ser Arg Phe Thr Gly Gln Ile Ser Gly Gly
865                 870                 875                 880

Lys Asp Thr Ala Leu His Leu Lys Asp Ser Glu Trp Thr Leu Pro Ser
```

```
                        885                 890                 895
Gly Thr Glu Leu Gly Asn Leu Asn Leu Asp Asn Ala Thr Ile Thr Leu
                    900                 905                 910

Asn Ser Ala Tyr Arg His Asp Ala Ala Gly Ala Gln Thr Gly Ser Ala
                915                 920                 925

Thr Asp Ala Pro Arg Arg Arg Ser Arg Ser Arg Arg Ser Leu Leu
        930                 935                 940

Ser Val Thr Pro Pro Thr Ser Val Glu Ser Arg Phe Asn Thr Leu Thr
945                 950                 955                 960

Val Asn Gly Lys Leu Asn Gly Gln Gly Thr Phe Arg Phe Met Ser Glu
                965                 970                 975

Leu Phe Gly Tyr Arg Ser Asp Lys Leu Lys Leu Ala Glu Ser Ser Glu
                980                 985                 990

Gly Thr Tyr Thr Leu Ala Val Asn Asn Thr Gly Asn Glu Pro Ala Ser
                995                 1000                1005

Leu Glu Gln Leu Thr Val Val Glu Gly Lys Asp Asn Lys Pro Leu Ser
            1010                1015                1020

Glu Asn Leu Asn Phe Thr Leu Gln Asn Glu His Val Asp Ala Gly Ala
1025                1030                1035                1040

Trp Arg Tyr Gln Leu Ile Arg Lys Asp Gly Glu Phe Arg Leu His Asn
                1045                1050                1055

Pro Val Lys Glu Gln Glu Leu Ser Asp Lys Leu Gly Lys Ala Glu Ala
            1060                1065                1070

Lys Lys Gln Ala Glu Lys Asp Asn Ala Gln Ser Leu Asp Ala Leu Ile
                1075                1080                1085

Ala Ala Gly Arg Asp Ala Val Glu Lys Thr Glu Ser Val Ala Glu Pro
        1090                1095                1100

Ala Arg Gln Ala Gly Gly Glu Asn Val Gly Ile Met Gln Ala Glu Glu
1105                1110                1115                1120

Glu Lys Lys Arg Val Gln Ala Asp Lys Asp Thr Ala Leu Ala Lys Gln
                1125                1130                1135

Arg Glu Ala Glu Thr Arg Pro Ala Thr Thr Ala Phe Pro Arg Ala Arg
            1140                1145                1150

Arg Ala Arg Arg Asp Leu Pro Gln Leu Gln Pro Gln Pro Gln
            1155                1160                1165

Pro Gln Arg Asp Leu Ile Ser Arg Tyr Ala Asn Ser Gly Leu Ser Glu
        1170                1175                1180

Phe Ser Ala Thr Leu Asn Ser Val Phe Ala Val Gln Asp Glu Leu Asp
1185                1190                1195                1200

Arg Val Phe Ala Glu Asp Arg Arg Asn Ala Val Trp Thr Ser Gly Ile
            1205                1210                1215

Arg Asp Thr Lys His Tyr Arg Ser Gln Asp Phe Arg Ala Tyr Arg Gln
        1220                1225                1230

Gln Thr Asp Leu Arg Gln Ile Gly Met Gln Lys Asn Leu Gly Ser Gly
            1235                1240                1245

Arg Val Gly Ile Leu Phe Ser His Asn Arg Thr Glu Asn Thr Phe Asp
        1250                1255                1260

Asp Gly Ile Gly Asn Ser Ala Arg Leu Ala His Gly Ala Val Phe Gly
1265                1270                1275                1280

Gln Tyr Gly Ile Asp Arg Phe Tyr Ile Gly Ile Ser Ala Gly Ala Gly
            1285                1290                1295

Phe Ser Ser Gly Ser Leu Ser Asp Gly Ile Gly Gly Lys Ile Arg Arg
            1300                1305                1310
```

```
Arg Val Leu His Tyr Gly Ile Gln Ala Arg Tyr Arg Ala Gly Phe Gly
        1315                1320                1325

Gly Phe Gly Ile Glu Pro His Ile Gly Ala Thr Arg Tyr Phe Val Gln
    1330                1335                1340

Lys Ala Asp Tyr Arg Tyr Glu Asn Val Asn Ile Ala Thr Pro Gly Leu
1345                1350                1355                1360

Ala Phe Asn Arg Tyr Arg Ala Gly Ile Lys Asp Tyr Ser Phe Lys
                1365                1370                1375

Pro Ala Gln His Ile Ser Ile Thr Pro Tyr Leu Ser Leu Ser Tyr Thr
                1380                1385                1390

Asp Ala Ala Ser Gly Lys Val Arg Thr Arg Val Asn Thr Ala Val Leu
                1395                1400                1405

Ala Gln Asp Phe Gly Lys Thr Arg Ser Ala Glu Trp Gly Val Asn Ala
                1410                1415                1420

Glu Ile Lys Gly Phe Thr Leu Ser Leu His Ala Ala Ala Lys Gly
1425                1430                1435                1440

Pro Gln Leu Glu Ala Gln His Ser Ala Gly Ile Lys Leu Gly Tyr Arg
                1445                1450                1455

Trp

<210> SEQ ID NO 72
<211> LENGTH: 21
<212> TYPE: PRT
<213> ORGANISM: Escherichia coli

<400> SEQUENCE: 72

Met Lys Lys Thr Ala Ile Ala Ile Ala Val Ala Leu Ala Gly Phe Ala
1               5                   10                  15

Thr Val Ala Gln Ala
            20

<210> SEQ ID NO 73
<211> LENGTH: 1439
<212> TYPE: PRT
<213> ORGANISM: Artificial Sequence
<220> FEATURE:
<223> OTHER INFORMATION: Synthetic construct

<400> SEQUENCE: 73

Met Lys Lys Thr Ala Ile Ala Ile Ala Val Ala Leu Ala Gly Phe Ala
1               5                   10                  15

Thr Val Ala Gln Ala Ala Ser Ala Gly His Thr Tyr Phe Gly Ile Asn
            20                  25                  30

Tyr Gln Tyr Tyr Arg Asp Phe Ala Glu Asn Lys Gly Lys Phe Ala Val
                35                  40                  45

Gly Ala Lys Asp Ile Glu Val Tyr Asn Lys Lys Gly Glu Leu Val Gly
        50                  55                  60

Lys Ser Met Thr Lys Ala Pro Met Ile Asp Phe Ser Val Ser Arg
65                  70                  75                  80

Asn Gly Val Ala Ala Leu Val Gly Asp Gln Tyr Ile Val Ser Val Ala
                85                  90                  95

His Asn Gly Gly Tyr Asn Asn Val Asp Phe Gly Ala Glu Gly Arg Asn
            100                 105                 110

Pro Asp Gln His Arg Phe Thr Tyr Lys Ile Val Lys Arg Asn Asn Tyr
                115                 120                 125

Lys Ala Gly Thr Lys Gly His Pro Tyr Gly Gly Asp Tyr His Met Pro
        130                 135                 140
```

```
Arg Leu His Lys Phe Val Thr Asp Ala Glu Pro Val Glu Met Thr Ser
145                 150                 155                 160

Tyr Met Asp Gly Arg Lys Tyr Ile Asp Gln Asn Asn Tyr Pro Asp Arg
                165                 170                 175

Val Arg Ile Gly Ala Gly Arg Gln Tyr Trp Arg Ser Asp Glu Asp Glu
            180                 185                 190

Pro Asn Asn Arg Glu Ser Ser Tyr His Ile Ala Ser Ala Tyr Ser Trp
        195                 200                 205

Leu Val Gly Gly Asn Thr Phe Ala Gln Asn Gly Ser Gly Gly Gly Thr
    210                 215                 220

Val Asn Leu Gly Ser Glu Lys Ile Lys His Ser Pro Tyr Gly Phe Leu
225                 230                 235                 240

Pro Thr Gly Gly Ser Phe Gly Asp Ser Gly Ser Pro Met Phe Ile Tyr
                245                 250                 255

Asp Ala Gln Lys Gln Lys Trp Leu Ile Asn Gly Val Leu Gln Thr Gly
                260                 265                 270

Asn Pro Tyr Ile Gly Lys Ser Asn Gly Phe Gln Leu Val Arg Lys Asp
            275                 280                 285

Trp Phe Tyr Asp Glu Ile Phe Ala Gly Asp Thr His Ser Val Phe Tyr
        290                 295                 300

Glu Pro Arg Gln Asn Gly Lys Tyr Ser Phe Asn Asp Asp Asn Asn Gly
305                 310                 315                 320

Thr Gly Lys Ile Asn Ala Lys His Glu His Asn Ser Leu Pro Asn Arg
                325                 330                 335

Leu Lys Thr Arg Thr Val Gln Leu Phe Asn Val Ser Leu Ser Glu Thr
            340                 345                 350

Ala Arg Glu Pro Val Tyr His Ala Ala Gly Gly Val Asn Ser Tyr Arg
        355                 360                 365

Pro Arg Leu Asn Asn Gly Glu Asn Ile Ser Phe Ile Asp Glu Gly Lys
    370                 375                 380

Gly Glu Leu Ile Leu Thr Ser Asn Ile Asn Gln Gly Ala Gly Gly Leu
385                 390                 395                 400

Tyr Phe Gln Gly Asp Phe Thr Val Ser Pro Glu Asn Asn Glu Thr Trp
                405                 410                 415

Gln Gly Ala Gly Val His Ile Ser Glu Asp Ser Thr Val Thr Trp Lys
                420                 425                 430

Val Asn Gly Val Ala Asn Asp Arg Leu Ser Lys Ile Gly Lys Gly Thr
            435                 440                 445

Leu His Val Gln Ala Lys Gly Glu Asn Gln Gly Ser Ile Ser Val Gly
        450                 455                 460

Asp Gly Thr Val Ile Leu Asp Gln Gln Ala Asp Asp Lys Gly Lys Lys
465                 470                 475                 480

Gln Ala Phe Ser Glu Ile Gly Leu Val Ser Gly Arg Gly Thr Val Gln
                485                 490                 495

Leu Asn Ala Asp Asn Gln Phe Asn Pro Asp Lys Leu Tyr Phe Gly Phe
                500                 505                 510

Arg Gly Gly Arg Leu Asp Leu Asn Gly His Ser Leu Ser Phe His Arg
            515                 520                 525

Ile Gln Asn Thr Asp Glu Gly Ala Met Ile Val Asn His Asn Gln Asp
        530                 535                 540

Lys Glu Ser Thr Val Thr Ile Thr Gly Asn Lys Asp Ile Ala Thr Thr
545                 550                 555                 560

Gly Asn Asn Asn Ser Leu Asp Ser Lys Lys Glu Ile Ala Tyr Asn Gly
                565                 570                 575
```

-continued

Trp Phe Gly Glu Lys Asp Thr Thr Lys Thr Asn Gly Arg Leu Asn Leu
              580                 585                 590

Val Tyr Gln Pro Ala Ala Glu Asp Arg Thr Leu Leu Leu Ser Gly Gly
        595                 600                 605

Thr Asn Leu Asn Gly Asn Ile Thr Gln Thr Asn Gly Lys Leu Phe Phe
        610                 615                 620

Ser Gly Arg Pro Thr Pro His Ala Tyr Asn His Leu Asn Asp His Trp
625                 630                 635                 640

Ser Gln Lys Glu Gly Ile Pro Arg Gly Glu Ile Val Trp Asp Asn Asp
                645                 650                 655

Trp Ile Asn Arg Thr Phe Lys Ala Glu Asn Phe Gln Ile Lys Gly Gly
                660                 665                 670

Gln Ala Val Val Ser Arg Asn Val Ala Lys Val Lys Gly Asp Trp His
                675                 680                 685

Leu Ser Asn His Ala Gln Ala Val Phe Gly Val Ala Pro His Gln Ser
            690                 695                 700

His Thr Ile Cys Thr Arg Ser Asp Trp Thr Gly Leu Thr Asn Cys Val
705                 710                 715                 720

Glu Lys Thr Ile Thr Asp Asp Lys Val Ile Ala Ser Leu Thr Lys Thr
                    725                 730                 735

Asp Ile Ser Gly Asn Val Asp Leu Ala Asp His Ala His Leu Asn Leu
                740                 745                 750

Thr Gly Leu Ala Thr Leu Asn Gly Asn Leu Ser Ala Asn Gly Asp Thr
            755                 760                 765

Arg Tyr Thr Val Ser His Asn Ala Thr Gln Asn Gly Asn Leu Ser Leu
        770                 775                 780

Val Gly Asn Ala Gln Ala Thr Phe Asn Gln Ala Thr Leu Asn Gly Asn
785                 790                 795                 800

Thr Ser Ala Ser Gly Asn Ala Ser Phe Asn Leu Ser Asp His Ala Val
                805                 810                 815

Gln Asn Gly Ser Leu Thr Leu Ser Gly Asn Ala Lys Ala Asn Val Ser
                820                 825                 830

His Ser Ala Leu Asn Gly Asn Val Ser Leu Ala Asp Lys Ala Val Phe
            835                 840                 845

His Phe Glu Ser Ser Arg Phe Thr Gly Gln Ile Ser Gly Gly Lys Asp
850                 855                 860

Thr Ala Leu His Leu Lys Asp Ser Glu Trp Thr Leu Pro Ser Gly Thr
865                 870                 875                 880

Glu Leu Gly Asn Leu Asn Leu Asp Asn Ala Thr Ile Thr Leu Asn Ser
                    885                 890                 895

Ala Tyr Arg His Asp Ala Ala Gly Ala Gln Thr Gly Ser Ala Thr Asp
                900                 905                 910

Ala Pro Arg Arg Arg Ser Arg Arg Ser Arg Arg Ser Leu Leu Ser Val
            915                 920                 925

Thr Pro Pro Thr Ser Val Glu Ser Arg Phe Asn Thr Leu Thr Val Asn
        930                 935                 940

Gly Lys Leu Asn Gly Gln Gly Thr Phe Arg Phe Met Ser Glu Leu Phe
945                 950                 955                 960

Gly Tyr Arg Ser Asp Lys Leu Leu Ala Glu Ser Glu Gly Thr
                965                 970                 975

Tyr Thr Leu Ala Val Asn Asn Thr Gly Asn Glu Pro Ala Ser Leu Glu
            980                 985                 990

Gln Leu Thr Val Val Glu Gly Lys Asp Asn Lys Pro Leu Ser Glu Asn

```
                995                1000               1005
Leu Asn Phe Thr Leu Gln Asn Glu His Val Asp Ala Gly Ala Trp Arg
1010                1015               1020
Tyr Gln Leu Ile Arg Lys Asp Gly Glu Phe Arg Leu His Asn Pro Val
1025                1030               1035               1040
Lys Glu Gln Glu Leu Ser Asp Lys Leu Gly Lys Ala Glu Ala Lys Lys
                1045               1050               1055
Gln Ala Glu Lys Asp Asn Ala Gln Ser Leu Asp Ala Leu Ile Ala Ala
                1060               1065               1070
Gly Arg Asp Ala Val Glu Lys Thr Glu Ser Val Ala Glu Pro Ala Arg
            1075               1080               1085
Gln Ala Gly Gly Glu Asn Val Gly Ile Met Gln Ala Glu Glu Glu Lys
            1090               1095               1100
Lys Arg Val Gln Ala Asp Lys Asp Thr Ala Leu Ala Lys Gln Arg Glu
1105                1110               1115               1120
Ala Glu Thr Arg Pro Ala Thr Thr Ala Phe Pro Arg Ala Arg Arg Ala
                1125               1130               1135
Arg Arg Asp Leu Pro Gln Leu Gln Pro Gln Pro Gln Pro Gln Pro Gln
            1140               1145               1150
Arg Asp Leu Ile Ser Arg Tyr Ala Asn Ser Gly Leu Ser Glu Phe Ser
            1155               1160               1165
Ala Thr Leu Asn Ser Val Phe Ala Val Gln Asp Glu Leu Asp Arg Val
            1170               1175               1180
Phe Ala Glu Asp Arg Arg Asn Ala Val Trp Thr Ser Gly Ile Arg Asp
1185                1190               1195               1200
Thr Lys His Tyr Arg Ser Gln Asp Phe Arg Ala Tyr Arg Gln Gln Thr
                1205               1210               1215
Asp Leu Arg Gln Ile Gly Met Gln Lys Asn Leu Gly Ser Gly Arg Val
            1220               1225               1230
Gly Ile Leu Phe Ser His Asn Arg Thr Glu Asn Thr Phe Asp Asp Gly
            1235               1240               1245
Ile Gly Asn Ser Ala Arg Leu Ala His Gly Ala Val Phe Gly Gln Tyr
            1250               1255               1260
Gly Ile Asp Arg Phe Tyr Ile Gly Ile Ser Ala Gly Ala Gly Phe Ser
1265                1270               1275               1280
Ser Gly Ser Leu Ser Asp Gly Ile Gly Gly Lys Ile Arg Arg Arg Val
                1285               1290               1295
Leu His Tyr Gly Ile Gln Ala Arg Tyr Arg Ala Gly Phe Gly Gly Phe
            1300               1305               1310
Gly Ile Glu Pro His Ile Gly Ala Thr Arg Tyr Phe Val Gln Lys Ala
            1315               1320               1325
Asp Tyr Arg Tyr Glu Asn Val Asn Ile Ala Thr Pro Gly Leu Ala Phe
            1330               1335               1340
Asn Arg Tyr Arg Ala Gly Ile Lys Ala Asp Tyr Ser Phe Lys Pro Ala
1345                1350               1355               1360
Gln His Ile Ser Ile Thr Pro Tyr Leu Ser Leu Ser Tyr Thr Asp Ala
                1365               1370               1375
Ala Ser Gly Lys Val Arg Thr Arg Val Asn Thr Ala Val Leu Ala Gln
                1380               1385               1390
Asp Phe Gly Lys Thr Arg Ser Ala Glu Trp Gly Val Asn Ala Glu Ile
            1395               1400               1405
Lys Gly Phe Thr Leu Ser Leu His Ala Ala Ala Lys Gly Pro Gln
            1410               1415               1420
```

-continued

```
Leu Glu Ala Gln His Ser Ala Gly Ile Lys Leu Gly Tyr Arg Trp
1425                1430                1435

<210> SEQ ID NO 74
<211> LENGTH: 164
<212> TYPE: PRT
<213> ORGANISM: Neisseria meningitidis

<400> SEQUENCE: 74

Met Lys Lys Asn Ile Leu Glu Phe Trp Val Gly Leu Phe Val Leu Ile
1               5                   10                  15

Gly Ala Ala Ala Val Ala Phe Leu Ala Phe Arg Val Ala Gly Gly Ala
                20                  25                  30

Ala Phe Gly Gly Ser Asp Lys Thr Tyr Ala Val Tyr Ala Asp Phe Gly
            35                  40                  45

Asp Ile Gly Gly Leu Lys Val Asn Ala Pro Val Lys Ser Ala Gly Val
        50                  55                  60

Leu Val Gly Arg Val Gly Ala Ile Gly Leu Asp Pro Lys Ser Tyr Gln
65                  70                  75                  80

Ala Arg Val Arg Leu Asp Leu Asp Gly Lys Tyr Gln Phe Ser Ser Asp
                85                  90                  95

Val Ser Ala Gln Ile Leu Thr Ser Gly Leu Leu Gly Glu Gln Tyr Ile
            100                 105                 110

Gly Leu Gln Gln Gly Gly Asp Thr Glu Asn Leu Ala Ala Gly Asp Thr
        115                 120                 125

Ile Ser Val Thr Ser Ser Ala Met Val Leu Asn Leu Ile Gly Lys
    130                 135                 140

Phe Met Thr Ser Phe Ala Glu Lys Asn Ala Asp Gly Gly Asn Ala Glu
145                 150                 155                 160

Lys Ala Ala Glu

<210> SEQ ID NO 75
<211> LENGTH: 21
<212> TYPE: PRT
<213> ORGANISM: Erwinia carotovora

<400> SEQUENCE: 75

Met Lys Tyr Leu Leu Pro Thr Ala Ala Ala Gly Leu Leu Leu Ala Ala
1               5                   10                  15

Gln Pro Ala Met Ala
            20

<210> SEQ ID NO 76
<211> LENGTH: 608
<212> TYPE: PRT
<213> ORGANISM: Neisseria meningitidis

<400> SEQUENCE: 76

Leu Gly Ile Ser Arg Lys Ile Ser Leu Ile Leu Ser Ile Leu Ala Val
1               5                   10                  15

Cys Leu Pro Met His Ala His Ala Ser Asp Leu Ala Asn Asp Ser Phe
                20                  25                  30

Ile Arg Gln Val Leu Asp Arg Gln His Phe Glu Pro Asp Gly Lys Tyr
            35                  40                  45

His Leu Phe Gly Ser Arg Gly Glu Leu Ala Glu Arg Ser Gly His Ile
        50                  55                  60

Gly Leu Gly Lys Ile Gln Ser His Gln Leu Gly Asn Leu Met Ile Gln
65                  70                  75                  80
```

-continued

```
Gln Ala Ala Ile Lys Gly Asn Ile Gly Tyr Ile Val Arg Phe Ser Asp
                 85                  90                  95

His Gly His Glu Val His Ser Pro Phe Asp Asn His Ala Ser His Ser
            100                 105                 110

Asp Ser Asp Glu Ala Gly Ser Pro Val Asp Gly Phe Ser Leu Tyr Arg
        115                 120                 125

Ile His Trp Asp Gly Tyr Glu His His Pro Ala Asp Gly Tyr Asp Gly
    130                 135                 140

Pro Gln Gly Gly Gly Tyr Pro Ala Pro Lys Gly Ala Arg Asp Ile Tyr
145                 150                 155                 160

Ser Tyr Asp Ile Lys Gly Val Ala Gln Asn Ile Arg Leu Asn Leu Thr
                165                 170                 175

Asp Asn Arg Ser Thr Gly Gln Arg Leu Ala Asp Arg Phe His Asn Ala
            180                 185                 190

Gly Ser Met Leu Thr Gln Gly Val Gly Asp Gly Phe Lys Arg Ala Thr
        195                 200                 205

Arg Tyr Ser Pro Glu Leu Asp Arg Ser Gly Asn Ala Ala Glu Ala Phe
    210                 215                 220

Asn Gly Thr Ala Asp Ile Val Lys Asn Ile Gly Ala Ala Gly Glu
225                 230                 235                 240

Ile Val Gly Ala Gly Asp Ala Val Gln Gly Ile Ser Glu Gly Ser Asn
                245                 250                 255

Ile Ala Val Met His Gly Leu Gly Leu Leu Ser Thr Glu Asn Lys Met
            260                 265                 270

Ala Arg Ile Asn Asp Leu Ala Asp Met Ala Gln Leu Lys Asp Tyr Ala
        275                 280                 285

Ala Ala Ala Ile Arg Asp Trp Ala Val Gln Asn Pro Asn Ala Ala Gln
    290                 295                 300

Gly Ile Glu Ala Val Ser Asn Ile Phe Met Ala Ala Ile Pro Ile Lys
305                 310                 315                 320

Gly Ile Gly Ala Val Arg Gly Lys Tyr Gly Leu Gly Ile Thr Ala
                325                 330                 335

His Pro Ile Lys Arg Ser Gln Met Gly Ala Ile Ala Leu Pro Lys Gly
            340                 345                 350

Lys Ser Ala Val Ser Asp Asn Phe Ala Asp Ala Ala Tyr Ala Lys Tyr
        355                 360                 365

Pro Ser Pro Tyr His Ser Arg Asn Ile Arg Ser Asn Leu Glu Gln Arg
    370                 375                 380

Tyr Gly Lys Glu Asn Ile Thr Ser Ser Thr Val Pro Pro Ser Asn Gly
385                 390                 395                 400

Lys Asn Val Lys Leu Ala Asp Gln Arg His Pro Lys Thr Gly Val Pro
                405                 410                 415

Phe Asp Gly Lys Gly Phe Pro Asn Phe Glu Lys His Val Lys Tyr Asp
            420                 425                 430

Thr Lys Leu Asp Ile Gln Glu Leu Ser Gly Gly Ile Pro Lys Ala
        435                 440                 445

Lys Pro Val Ser Asp Ala Lys Pro Arg Trp Glu Val Asp Arg Lys Leu
    450                 455                 460

Asn Lys Leu Thr Thr Arg Glu Gln Val Glu Lys Asn Val Gln Glu Ile
465                 470                 475                 480

Arg Asn Gly Asn Lys Asn Ser Asn Phe Ser Gln His Ala Gln Leu Glu
                485                 490                 495

Arg Glu Ile Asn Lys Leu Lys Ser Ala Asp Glu Ile Asn Phe Ala Asp
            500                 505                 510
```

```
Gly Met Gly Lys Phe Thr Asp Ser Met Asn Asp Lys Ala Phe Ser Arg
            515                 520                 525

Leu Val Lys Ser Val Lys Glu Asn Gly Phe Thr Asn Pro Val Val Glu
        530                 535                 540

Tyr Val Glu Ile Asn Gly Lys Ala Tyr Ile Val Arg Gly Asn Asn Arg
545                 550                 555                 560

Val Phe Ala Ala Glu Tyr Leu Gly Arg Ile His Glu Leu Lys Phe Lys
                565                 570                 575

Lys Val Asp Phe Pro Val Pro Asn Thr Ser Trp Lys Asn Pro Thr Asp
            580                 585                 590

Val Leu Asn Glu Ser Gly Asn Val Lys Arg Pro Arg Tyr Arg Ser Lys
        595                 600                 605

<210> SEQ ID NO 77
<211> LENGTH: 584
<212> TYPE: PRT
<213> ORGANISM: Artificial Sequence
<220> FEATURE:
<223> OTHER INFORMATION: Neisseria meningitidis

<400> SEQUENCE: 77

Ser Asp Leu Ala Asn Asp Ser Phe Ile Arg Gln Val Leu Asp Arg Gln
1               5                   10                  15

His Phe Glu Pro Asp Gly Lys Tyr His Leu Phe Gly Ser Arg Gly Glu
            20                  25                  30

Leu Ala Glu Arg Ser Gly His Ile Gly Leu Gly Lys Ile Gln Ser His
        35                  40                  45

Gln Leu Gly Asn Leu Met Ile Gln Gln Ala Ala Ile Lys Gly Asn Ile
    50                  55                  60

Gly Tyr Ile Val Arg Phe Ser Asp His Gly His Glu Val His Ser Pro
65                  70                  75                  80

Phe Asp Asn His Ala Ser His Ser Asp Ser Glu Ala Gly Ser Pro
                85                  90                  95

Val Asp Gly Phe Ser Leu Tyr Arg Ile His Trp Asp Gly Tyr Glu His
            100                 105                 110

His Pro Ala Asp Gly Tyr Asp Gly Pro Gln Gly Gly Tyr Pro Ala
        115                 120                 125

Pro Lys Gly Ala Arg Asp Ile Tyr Ser Tyr Asp Ile Lys Gly Val Ala
    130                 135                 140

Gln Asn Ile Arg Leu Asn Leu Thr Asp Asn Arg Ser Thr Gly Gln Arg
145                 150                 155                 160

Leu Ala Asp Arg Phe His Asn Ala Gly Ser Met Leu Thr Gln Gly Val
                165                 170                 175

Gly Asp Gly Phe Lys Arg Ala Thr Arg Tyr Ser Pro Glu Leu Asp Arg
            180                 185                 190

Ser Gly Asn Ala Ala Glu Ala Phe Asn Gly Thr Ala Asp Ile Val Lys
        195                 200                 205

Asn Ile Ile Gly Ala Ala Gly Glu Ile Val Gly Ala Gly Asp Ala Val
    210                 215                 220

Gln Gly Ile Ser Glu Gly Ser Asn Ile Ala Val Met His Gly Leu Gly
225                 230                 235                 240

Leu Leu Ser Thr Glu Asn Lys Met Ala Arg Ile Asn Asp Leu Ala Asp
                245                 250                 255

Met Ala Gln Leu Lys Asp Tyr Ala Ala Ala Ile Arg Asp Trp Ala
            260                 265                 270
```

```
Val Gln Asn Pro Asn Ala Ala Gln Gly Ile Glu Ala Val Ser Asn Ile
        275                 280                 285

Phe Met Ala Ala Ile Pro Ile Lys Gly Ile Gly Ala Val Arg Gly Lys
    290                 295                 300

Tyr Gly Leu Gly Gly Ile Thr Ala His Pro Ile Lys Arg Ser Gln Met
305                 310                 315                 320

Gly Ala Ile Ala Leu Pro Lys Gly Lys Ser Ala Val Ser Asp Asn Phe
                325                 330                 335

Ala Asp Ala Ala Tyr Ala Lys Tyr Pro Ser Pro Tyr His Ser Arg Asn
            340                 345                 350

Ile Arg Ser Asn Leu Glu Gln Arg Tyr Gly Lys Glu Asn Ile Thr Ser
        355                 360                 365

Ser Thr Val Pro Pro Ser Asn Gly Lys Asn Val Lys Leu Ala Asp Gln
    370                 375                 380

Arg His Pro Lys Thr Gly Val Pro Phe Asp Gly Lys Gly Phe Pro Asn
385                 390                 395                 400

Phe Glu Lys His Val Lys Tyr Asp Thr Lys Leu Asp Ile Gln Glu Leu
                405                 410                 415

Ser Gly Gly Gly Ile Pro Lys Ala Lys Pro Val Ser Asp Ala Lys Pro
            420                 425                 430

Arg Trp Glu Val Asp Arg Lys Leu Asn Lys Leu Thr Thr Arg Glu Gln
        435                 440                 445

Val Glu Lys Asn Val Gln Glu Ile Arg Asn Gly Asn Lys Asn Ser Asn
    450                 455                 460

Phe Ser Gln His Ala Gln Leu Glu Arg Glu Ile Asn Lys Leu Lys Ser
465                 470                 475                 480

Ala Asp Glu Ile Asn Phe Ala Asp Gly Met Gly Lys Phe Thr Asp Ser
                485                 490                 495

Met Asn Asp Lys Ala Phe Ser Arg Leu Val Lys Ser Val Lys Glu Asn
            500                 505                 510

Gly Phe Thr Asn Pro Val Val Glu Tyr Val Glu Ile Asn Gly Lys Ala
        515                 520                 525

Tyr Ile Val Arg Gly Asn Asn Arg Val Phe Ala Ala Glu Tyr Leu Gly
    530                 535                 540

Arg Ile His Glu Leu Lys Phe Lys Lys Val Asp Phe Pro Val Pro Asn
545                 550                 555                 560

Thr Ser Trp Lys Asn Pro Thr Asp Val Leu Asn Glu Ser Gly Asn Val
                565                 570                 575

Lys Arg Pro Arg Tyr Arg Ser Lys
            580

<210> SEQ ID NO 78
<211> LENGTH: 364
<212> TYPE: PRT
<213> ORGANISM: Neisseria meningitidis

<400> SEQUENCE: 78

Met Ser Met Lys His Phe Pro Ala Lys Val Leu Thr Thr Ala Ile Leu
1               5                   10                  15

Ala Thr Phe Cys Ser Gly Ala Leu Ala Ala Thr Ser Asp Asp Asp Val
                20                  25                  30

Lys Lys Ala Ala Thr Val Ala Ile Val Ala Ala Tyr Asn Asn Gly Gln
            35                  40                  45

Glu Ile Asn Gly Phe Lys Ala Gly Glu Thr Ile Tyr Asp Ile Gly Glu
        50                  55                  60
```

```
Asp Gly Thr Ile Thr Gln Lys Asp Ala Thr Ala Ala Asp Val Glu Ala
 65                  70                  75                  80

Asp Asp Phe Lys Gly Leu Gly Leu Lys Lys Val Val Thr Asn Leu Thr
                 85                  90                  95

Lys Thr Val Asn Glu Asn Lys Gln Asn Val Asp Ala Lys Val Lys Ala
            100                 105                 110

Ala Glu Ser Glu Ile Glu Lys Leu Thr Thr Lys Leu Ala Asp Thr Asp
        115                 120                 125

Ala Ala Leu Ala Asp Thr Asp Ala Ala Leu Asp Glu Thr Thr Asn Ala
    130                 135                 140

Leu Asn Lys Leu Gly Glu Asn Ile Thr Thr Phe Ala Glu Glu Thr Lys
145                 150                 155                 160

Thr Asn Ile Val Lys Ile Asp Glu Lys Leu Glu Ala Val Ala Asp Thr
                165                 170                 175

Val Asp Lys His Ala Glu Ala Phe Asn Asp Ile Ala Asp Ser Leu Asp
            180                 185                 190

Glu Thr Asn Thr Lys Ala Asp Glu Ala Val Lys Thr Ala Asn Glu Ala
        195                 200                 205

Lys Gln Thr Ala Glu Thr Lys Gln Asn Val Asp Ala Lys Val Lys
    210                 215                 220

Ala Ala Glu Thr Ala Ala Gly Lys Ala Glu Ala Ala Gly Thr Ala
225                 230                 235                 240

Asn Thr Ala Ala Asp Lys Ala Glu Ala Val Ala Lys Val Thr Asp
                245                 250                 255

Ile Lys Ala Asp Ile Ala Thr Asn Lys Ala Asp Ile Ala Lys Asn Ser
            260                 265                 270

Ala Arg Ile Asp Ser Leu Asp Lys Asn Val Ala Asn Leu Arg Lys Glu
        275                 280                 285

Thr Arg Gln Gly Leu Ala Glu Gln Ala Ala Leu Ser Gly Leu Phe Gln
    290                 295                 300

Pro Tyr Asn Val Gly Arg Phe Asn Val Thr Ala Ala Val Gly Gly Tyr
305                 310                 315                 320

Lys Ser Glu Ser Ala Val Ala Ile Gly Thr Gly Phe Arg Phe Thr Glu
                325                 330                 335

Asn Phe Ala Ala Lys Ala Gly Val Ala Val Gly Thr Ser Ser Gly Ser
            340                 345                 350

Ser Ala Ala Tyr His Val Gly Val Asn Tyr Glu Trp
        355                 360

<210> SEQ ID NO 79
<211> LENGTH: 427
<212> TYPE: PRT
<213> ORGANISM: Neisseria meningitidis

<400> SEQUENCE: 79

Met Phe Glu Arg Ser Val Ile Ala Met Ala Cys Ile Phe Ala Leu Ser
  1               5                  10                  15

Ala Cys Gly Gly Gly Gly Gly Gly Ser Pro Asp Val Lys Ser Ala Asp
             20                  25                  30

Thr Leu Ser Lys Pro Ala Ala Pro Val Val Ala Glu Lys Glu Thr Glu
         35                  40                  45

Val Lys Glu Asp Ala Pro Gln Ala Gly Ser Gln Gly Gln Gly Ala Pro
     50                  55                  60

Ser Thr Gln Gly Ser Gln Asp Met Ala Ala Val Ser Ala Glu Asn Thr
 65                  70                  75                  80
```

```
Gly Asn Gly Gly Ala Thr Thr Asp Lys Pro Lys Asn Glu Asp Glu
                85                  90                  95

Gly Pro Gln Asn Asp Met Pro Gln Asn Ser Ala Glu Ser Ala Asn Gln
            100                 105                 110

Thr Gly Asn Asn Gln Pro Ala Asp Ser Ser Asp Ser Ala Pro Ala Ser
            115                 120                 125

Asn Pro Ala Pro Ala Asn Gly Gly Ser Asn Phe Gly Arg Val Asp Leu
            130                 135                 140

Ala Asn Gly Val Leu Ile Asp Gly Pro Ser Gln Asn Ile Thr Leu Thr
145                 150                 155                 160

His Cys Lys Gly Asp Ser Cys Asn Gly Asp Asn Leu Leu Asp Glu Glu
                165                 170                 175

Ala Pro Ser Lys Ser Glu Phe Glu Asn Leu Asn Glu Ser Glu Arg Ile
            180                 185                 190

Glu Lys Tyr Lys Lys Asp Gly Lys Ser Asp Lys Phe Thr Asn Leu Val
            195                 200                 205

Ala Thr Ala Val Gln Ala Asn Gly Thr Asn Lys Tyr Val Ile Ile Tyr
210                 215                 220

Lys Asp Lys Ser Ala Ser Ser Ser Ala Arg Phe Arg Arg Ser Ala
225                 230                 235                 240

Arg Ser Arg Arg Ser Leu Pro Ala Glu Met Pro Leu Ile Pro Val Asn
                245                 250                 255

Gln Ala Asp Thr Leu Ile Val Asp Gly Glu Ala Val Ser Leu Thr Gly
            260                 265                 270

His Ser Gly Asn Ile Phe Ala Pro Glu Gly Asn Tyr Arg Tyr Leu Thr
            275                 280                 285

Tyr Gly Ala Glu Lys Leu Pro Gly Gly Ser Tyr Ala Leu Arg Val Gln
290                 295                 300

Gly Glu Pro Ala Lys Gly Glu Met Leu Ala Gly Thr Ala Val Tyr Asn
305                 310                 315                 320

Gly Glu Val Leu His Phe His Thr Glu Asn Gly Arg Pro Tyr Pro Thr
                325                 330                 335

Arg Gly Arg Phe Ala Ala Lys Val Asp Phe Gly Ser Lys Ser Val Asp
            340                 345                 350

Gly Ile Ile Asp Ser Gly Asp Asp Leu His Met Gly Thr Gln Lys Phe
            355                 360                 365

Lys Ala Ala Ile Asp Gly Asn Gly Phe Lys Gly Thr Trp Thr Glu Asn
370                 375                 380

Gly Gly Gly Asp Val Ser Gly Arg Phe Tyr Gly Pro Ala Gly Glu Glu
385                 390                 395                 400

Val Ala Gly Lys Tyr Ser Tyr Arg Pro Thr Asp Ala Glu Lys Gly Gly
                405                 410                 415

Phe Gly Val Phe Ala Gly Lys Lys Glu Gln Asp
            420                 425

<210> SEQ ID NO 80
<211> LENGTH: 410
<212> TYPE: PRT
<213> ORGANISM: Artificial Sequence
<220> FEATURE:
<223> OTHER INFORMATION: Neisseria meningitidis

<400> SEQUENCE: 80

Cys Gly Gly Gly Gly Gly Ser Pro Asp Val Lys Ser Ala Asp Thr
1               5                   10                  15

Leu Ser Lys Pro Ala Ala Pro Val Val Ala Glu Lys Glu Thr Glu Val
```

```
                    20                  25                  30
Lys Glu Asp Ala Pro Gln Ala Gly Ser Gln Gly Gln Gly Ala Pro Ser
            35                  40                  45

Thr Gln Gly Ser Gln Asp Met Ala Ala Val Ser Ala Glu Asn Thr Gly
    50                  55                  60

Asn Gly Gly Ala Ala Thr Thr Asp Lys Pro Lys Asn Glu Asp Glu Gly
65                  70                  75                  80

Pro Gln Asn Asp Met Pro Gln Asn Ser Ala Glu Ser Ala Asn Gln Thr
                85                  90                  95

Gly Asn Asn Gln Pro Ala Asp Ser Ser Asp Ser Ala Pro Ala Ser Asn
            100                 105                 110

Pro Ala Pro Ala Asn Gly Gly Ser Asn Phe Gly Arg Val Asp Leu Ala
        115                 120                 125

Asn Gly Val Leu Ile Asp Gly Pro Ser Gln Asn Ile Thr Leu Thr His
    130                 135                 140

Cys Lys Gly Asp Ser Cys Asn Gly Asp Asn Leu Leu Asp Glu Ala
145                 150                 155                 160

Pro Ser Lys Ser Glu Phe Glu Asn Leu Asn Glu Ser Glu Arg Ile Glu
                165                 170                 175

Lys Tyr Lys Lys Asp Gly Lys Ser Asp Lys Phe Thr Asn Leu Val Ala
            180                 185                 190

Thr Ala Val Gln Ala Asn Gly Thr Asn Lys Tyr Val Ile Ile Tyr Lys
        195                 200                 205

Asp Lys Ser Ala Ser Ser Ser Ala Arg Phe Arg Arg Ser Ala Arg
    210                 215                 220

Ser Arg Arg Ser Leu Pro Ala Glu Met Pro Leu Ile Pro Val Asn Gln
225                 230                 235                 240

Ala Asp Thr Leu Ile Val Asp Gly Glu Ala Val Ser Leu Thr Gly His
                245                 250                 255

Ser Gly Asn Ile Phe Ala Pro Gly Gly Asn Tyr Arg Tyr Leu Thr Tyr
            260                 265                 270

Gly Ala Glu Lys Leu Pro Gly Gly Ser Tyr Ala Leu Arg Val Gln Gly
        275                 280                 285

Glu Pro Ala Lys Gly Glu Met Leu Ala Gly Thr Ala Val Tyr Asn Gly
    290                 295                 300

Glu Val Leu His Phe His Thr Glu Asn Gly Arg Pro Tyr Pro Thr Arg
305                 310                 315                 320

Gly Arg Phe Ala Ala Lys Val Asp Phe Gly Ser Lys Ser Val Asp Gly
                325                 330                 335

Ile Ile Asp Ser Gly Asp Asp Leu His Met Gly Thr Gln Lys Phe Lys
            340                 345                 350

Ala Ala Ile Asp Gly Asn Gly Phe Lys Gly Thr Trp Thr Glu Asn Gly
        355                 360                 365

Gly Gly Asp Val Ser Gly Arg Phe Tyr Gly Pro Ala Gly Glu Glu Val
    370                 375                 380

Ala Gly Lys Tyr Ser Tyr Arg Pro Thr Asp Ala Glu Lys Gly Gly Phe
385                 390                 395                 400

Gly Val Phe Ala Gly Lys Lys Glu Gln Asp
                405                 410

<210> SEQ ID NO 81
<211> LENGTH: 9
<212> TYPE: PRT
<213> ORGANISM: Artificial Sequence
<220> FEATURE:
```

<223> OTHER INFORMATION: Neisseria meningitidis

<400> SEQUENCE: 81

His Arg Val Trp Val Glu Thr Ala His
1               5

<210> SEQ ID NO 82
<211> LENGTH: 16
<212> TYPE: PRT
<213> ORGANISM: Artificial Sequence
<220> FEATURE:
<223> OTHER INFORMATION: Neisseria meningitidis

<400> SEQUENCE: 82

Ala Thr Tyr Lys Val Asp Glu Tyr His Ala Asn Ala Arg Phe Ala Phe
1               5                   10                  15

<210> SEQ ID NO 83
<211> LENGTH: 9
<212> TYPE: PRT
<213> ORGANISM: Artificial Sequence
<220> FEATURE:
<223> OTHER INFORMATION: Neisseria meningitidis

<400> SEQUENCE: 83

Met Glu Phe Phe Ile Ile Leu Leu Ala
1               5

<210> SEQ ID NO 84
<211> LENGTH: 488
<212> TYPE: PRT
<213> ORGANISM: Artificial Sequence
<220> FEATURE:
<223> OTHER INFORMATION: Neisseria meningitidis

<400> SEQUENCE: 84

Met Phe Lys Arg Ser Val Ile Ala Met Ala Cys Ile Phe Ala Leu Ser
1               5                   10                  15

Ala Cys Gly Gly Gly Gly Gly Ser Pro Asp Val Lys Ser Ala Asp
            20                  25                  30

Thr Leu Ser Lys Pro Ala Ala Pro Val Val Ser Glu Lys Glu Thr Glu
        35                  40                  45

Ala Lys Glu Asp Ala Pro Gln Ala Gly Ser Gln Gly Gln Gly Ala Pro
    50                  55                  60

Ser Ala Gln Gly Ser Gln Asp Met Ala Ala Val Ser Glu Glu Asn Thr
65                  70                  75                  80

Gly Asn Gly Gly Ala Val Thr Ala Asp Asn Pro Lys Asn Glu Asp Glu
                85                  90                  95

Val Ala Gln Asn Asp Met Pro Gln Asn Ala Ala Gly Thr Asp Ser Ser
            100                 105                 110

Thr Pro Asn His Thr Pro Asp Pro Asn Met Leu Ala Gly Asn Met Glu
        115                 120                 125

Asn Gln Ala Thr Asp Ala Gly Glu Ser Ser Gln Pro Ala Asn Gln Pro
    130                 135                 140

Asp Met Ala Asn Ala Ala Asp Gly Met Gln Gly Asp Asp Pro Ser Ala
145                 150                 155                 160

Gly Gly Gln Asn Ala Gly Asn Thr Ala Ala Gln Gly Ala Asn Gln Ala
                165                 170                 175

Gly Asn Asn Gln Ala Ala Gly Ser Ser Asp Pro Ile Pro Ala Ser Asn
            180                 185                 190

Pro Ala Pro Ala Asn Gly Gly Ser Asn Phe Gly Arg Val Asp Leu Ala

-continued

```
              195                 200                 205
Asn Gly Val Leu Ile Asp Gly Pro Ser Gln Asn Ile Thr Leu Thr His
210                 215                 220

Cys Lys Gly Asp Ser Cys Ser Gly Asn Asn Phe Leu Asp Glu Glu Val
225                 230                 235                 240

Gln Leu Lys Ser Glu Phe Glu Lys Leu Ser Asp Ala Asp Lys Ile Ser
                245                 250                 255

Asn Tyr Lys Lys Asp Gly Lys Asn Asp Lys Phe Val Gly Leu Val Ala
                260                 265                 270

Asp Ser Val Gln Met Lys Gly Ile Asn Gln Tyr Ile Ile Phe Tyr Lys
            275                 280                 285

Pro Lys Pro Thr Ser Phe Ala Arg Phe Arg Arg Ser Ala Arg Ser Arg
290                 295                 300

Arg Ser Leu Pro Ala Glu Met Pro Leu Ile Pro Val Asn Gln Ala Asp
305                 310                 315                 320

Thr Leu Ile Val Asp Gly Glu Ala Val Ser Leu Thr Gly His Ser Gly
                325                 330                 335

Asn Ile Phe Ala Pro Glu Gly Asn Tyr Arg Tyr Leu Thr Tyr Gly Ala
                340                 345                 350

Glu Lys Leu Pro Gly Gly Ser Tyr Ala Leu Arg Val Gln Gly Glu Pro
            355                 360                 365

Ala Lys Gly Glu Met Leu Ala Gly Ala Ala Val Tyr Asn Gly Glu Val
            370                 375                 380

Leu His Phe His Thr Glu Asn Gly Arg Pro Tyr Pro Thr Arg Gly Arg
385                 390                 395                 400

Phe Ala Ala Lys Val Asp Phe Gly Ser Lys Ser Val Asp Gly Ile Ile
                405                 410                 415

Asp Ser Gly Asp Asp Leu His Met Gly Thr Gln Lys Phe Lys Ala Ala
                420                 425                 430

Ile Asp Gly Asn Gly Phe Lys Gly Thr Trp Thr Glu Asn Gly Ser Gly
            435                 440                 445

Asp Val Ser Gly Lys Phe Tyr Gly Pro Ala Gly Glu Glu Val Ala Gly
            450                 455                 460

Lys Tyr Ser Tyr Arg Pro Thr Asp Ala Glu Lys Gly Gly Phe Gly Val
465                 470                 475                 480

Phe Ala Gly Lys Lys Glu Gln Asp
                485
```

<210> SEQ ID NO 85
<211> LENGTH: 712
<212> TYPE: PRT
<213> ORGANISM: Artificial Sequence
<220> FEATURE:
<223> OTHER INFORMATION: Neisseria meningitidis

<400> SEQUENCE: 85

```
Met Asn Asn Pro Leu Val Asn Gln Ala Ala Met Val Leu Pro Val Phe
1               5                   10                  15

Leu Leu Ser Ala Cys Leu Gly Gly Gly Gly Ser Phe Asp Leu Asp Ser
                20                  25                  30

Val Asp Thr Glu Ala Pro Arg Pro Ala Pro Lys Tyr Gln Asp Val Phe
            35                  40                  45

Ser Glu Lys Pro Gln Ala Gln Lys Asp Gln Gly Gly Tyr Gly Phe Ala
        50                  55                  60

Met Arg Leu Lys Arg Arg Asn Trp Tyr Pro Gln Ala Lys Glu Asp Glu
65                  70                  75                  80
```

-continued

Val Lys Leu Asp Glu Ser Asp Trp Glu Ala Thr Gly Leu Pro Asp Glu
            85                  90                  95

Pro Lys Glu Leu Pro Lys Arg Gln Lys Ser Val Ile Glu Lys Val Glu
            100                 105                 110

Thr Asp Ser Asp Asn Asn Ile Tyr Ser Ser Pro Tyr Leu Lys Pro Ser
            115                 120                 125

Asn His Gln Asn Gly Asn Thr Gly Asn Gly Ile Asn Gln Pro Lys Asn
            130                 135                 140

Gln Ala Lys Asp Tyr Glu Asn Phe Lys Tyr Val Tyr Ser Gly Trp Phe
145                 150                 155                 160

Tyr Lys His Ala Lys Arg Glu Phe Asn Leu Lys Val Glu Pro Lys Ser
            165                 170                 175

Ala Lys Asn Gly Asp Asp Gly Tyr Ile Phe Tyr His Gly Lys Glu Pro
            180                 185                 190

Ser Arg Gln Leu Pro Ala Ser Gly Lys Ile Thr Tyr Lys Gly Val Trp
            195                 200                 205

His Phe Ala Thr Asp Thr Lys Lys Gly Gln Lys Phe Arg Glu Ile Ile
            210                 215                 220

Gln Pro Ser Lys Ser Gln Gly Asp Arg Tyr Ser Gly Phe Ser Gly Asp
225                 230                 235                 240

Asp Gly Glu Glu Tyr Ser Asn Lys Asn Lys Ser Thr Leu Thr Asp Gly
            245                 250                 255

Gln Glu Gly Tyr Gly Phe Thr Ser Asn Leu Glu Val Asp Phe His Asn
            260                 265                 270

Lys Lys Leu Thr Gly Lys Leu Ile Arg Asn Asn Ala Asn Thr Asp Asn
            275                 280                 285

Asn Gln Ala Thr Thr Thr Gln Tyr Tyr Ser Leu Glu Ala Gln Val Thr
            290                 295                 300

Gly Asn Arg Phe Asn Gly Lys Ala Thr Ala Thr Asp Lys Pro Gln Gln
305                 310                 315                 320

Asn Ser Glu Thr Lys Glu His Pro Phe Val Ser Asp Ser Ser Leu
            325                 330                 335

Ser Gly Gly Phe Phe Gly Pro Gln Gly Glu Leu Gly Phe Arg Phe
            340                 345                 350

Leu Ser Asp Asp Gln Lys Val Ala Val Val Gly Ser Ala Lys Thr Lys
            355                 360                 365

Asp Lys Pro Ala Asn Gly Asn Thr Ala Ala Ser Gly Gly Thr Asp
            370                 375                 380

Ala Ala Ala Ser Asn Gly Ala Ala Gly Thr Ser Ser Glu Asn Gly Lys
385                 390                 395                 400

Leu Thr Thr Val Leu Asp Ala Val Glu Leu Lys Leu Gly Asp Lys Glu
            405                 410                 415

Val Gln Lys Leu Asp Asn Phe Ser Asn Ala Ala Gln Leu Val Val Asp
            420                 425                 430

Gly Ile Met Ile Pro Leu Leu Pro Glu Ala Ser Glu Ser Gly Asn Asn
            435                 440                 445

Gln Ala Asn Gln Gly Thr Asn Gly Gly Thr Ala Phe Thr Arg Lys Phe
            450                 455                 460

Asp His Thr Pro Glu Ser Asp Lys Lys Asp Ala Gln Ala Gly Thr Gln
465                 470                 475                 480

Thr Asn Gly Ala Gln Thr Ala Ser Asn Thr Ala Gly Asp Thr Asn Gly
            485                 490                 495

Lys Thr Lys Thr Tyr Glu Val Glu Val Cys Cys Ser Asn Leu Asn Tyr

```
                     500                 505                 510
Leu Lys Tyr Gly Met Leu Thr Arg Lys Asn Ser Lys Ser Ala Met Gln
            515                 520                 525

Ala Gly Glu Ser Ser Gln Ala Asp Ala Lys Thr Glu Gln Val Glu
        530                 535                 540

Gln Ser Met Phe Leu Gln Gly Glu Arg Thr Asp Lys Glu Ile Pro
545                 550                 555                 560

Ser Glu Gln Asn Ile Val Tyr Arg Gly Ser Trp Tyr Gly Tyr Ile Ala
                565                 570                 575

Asn Asp Lys Ser Thr Ser Trp Ser Gly Asn Ala Ser Asn Ala Thr Ser
            580                 585                 590

Gly Asn Arg Ala Glu Phe Thr Val Asn Phe Ala Asp Lys Lys Ile Thr
        595                 600                 605

Gly Thr Leu Thr Ala Asp Asn Arg Gln Glu Ala Thr Phe Thr Ile Asp
    610                 615                 620

Gly Asn Ile Lys Asp Asn Gly Phe Glu Gly Thr Ala Lys Thr Ala Glu
625                 630                 635                 640

Ser Gly Phe Asp Leu Asp Gln Ser Asn Thr Thr Arg Thr Pro Lys Ala
                645                 650                 655

Tyr Ile Thr Asp Ala Lys Val Gln Gly Gly Phe Tyr Gly Pro Lys Ala
            660                 665                 670

Glu Glu Leu Gly Gly Trp Phe Ala Tyr Pro Gly Asp Lys Gln Thr Lys
        675                 680                 685

Asn Ala Thr Asn Ala Ser Gly Asn Ser Ser Ala Thr Val Val Phe Gly
    690                 695                 700

Ala Lys Arg Gln Gln Pro Val Arg
705                 710

<210> SEQ ID NO 86
<211> LENGTH: 274
<212> TYPE: PRT
<213> ORGANISM: Artificial Sequence
<220> FEATURE:
<223> OTHER INFORMATION: Neisseria meningitidis

<400> SEQUENCE: 86

Val Asn Arg Thr Ala Phe Cys Cys Leu Ser Leu Thr Thr Ala Leu Ile
1               5                  10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Gly Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Val Tyr Lys Gln Ser His Ser Ala Leu Thr Ala Phe
        115                 120                 125

Gln Thr Glu Gln Ile Gln Asp Ser Glu His Ser Gly Lys Met Val Ala
    130                 135                 140

Lys Arg Gln Phe Arg Ile Gly Asp Ile Ala Gly Glu His Thr Ser Phe
145                 150                 155                 160
```

```
Asp Lys Leu Pro Glu Gly Gly Arg Ala Thr Tyr Arg Gly Thr Ala Phe
                165                 170                 175

Gly Ser Asp Asp Ala Gly Gly Lys Leu Thr Tyr Thr Ile Asp Phe Ala
            180                 185                 190

Ala Lys Gln Gly Asn Gly Lys Ile Glu His Leu Lys Ser Pro Glu Leu
        195                 200                 205

Asn Val Asp Leu Ala Ala Ala Asp Ile Lys Pro Asp Gly Lys Arg His
    210                 215                 220

Ala Val Ile Ser Gly Ser Val Leu Tyr Asn Gln Ala Glu Lys Gly Ser
225                 230                 235                 240

Tyr Ser Leu Gly Ile Phe Gly Gly Lys Ala Gln Glu Val Ala Gly Ser
                245                 250                 255

Ala Glu Val Lys Thr Val Asn Gly Ile Arg His Ile Gly Leu Ala Ala
            260                 265                 270

Lys Gln

<210> SEQ ID NO 87
<211> LENGTH: 1082
<212> TYPE: PRT
<213> ORGANISM: Artificial Sequence
<220> FEATURE:
<223> OTHER INFORMATION: Neisseria meningitidis

<400> SEQUENCE: 87

Met Arg Thr Thr Pro Thr Phe Pro Thr Lys Thr Phe Lys Pro Thr Ala
1               5                   10                  15

Met Ala Leu Ala Val Ala Thr Thr Leu Ser Ala Cys Leu Gly Gly Gly
            20                  25                  30

Gly Gly Gly Thr Ser Ala Pro Asp Phe Asn Ala Gly Gly Thr Gly Ile
        35                  40                  45

Gly Ser Asn Ser Arg Ala Thr Thr Ala Lys Ser Ala Ala Val Ser Tyr
    50                  55                  60

Ala Gly Ile Lys Asn Glu Met Cys Lys Asp Arg Ser Met Leu Cys Ala
65                  70                  75                  80

Gly Arg Asp Asp Val Ala Val Thr Asp Arg Asp Ala Lys Ile Asn Ala
                85                  90                  95

Pro Pro Pro Asn Leu His Thr Gly Asp Phe Pro Asn Pro Asn Asp Ala
            100                 105                 110

Tyr Lys Asn Leu Ile Asn Leu Lys Pro Ala Ile Glu Ala Gly Tyr Thr
        115                 120                 125

Gly Arg Gly Val Glu Val Gly Ile Val Asp Thr Gly Glu Ser Val Gly
    130                 135                 140

Ser Ile Ser Phe Pro Glu Leu Tyr Gly Arg Lys Glu His Gly Tyr Asn
145                 150                 155                 160

Glu Asn Tyr Lys Asn Tyr Thr Ala Tyr Met Arg Lys Glu Ala Pro Glu
                165                 170                 175

Asp Gly Gly Lys Asp Ile Glu Ala Ser Phe Asp Asp Ala Val
            180                 185                 190

Ile Glu Thr Glu Ala Lys Pro Thr Asp Ile Arg His Val Lys Glu Ile
        195                 200                 205

Gly His Ile Asp Leu Val Ser His Ile Gly Gly Arg Ser Val Asp
    210                 215                 220

Gly Arg Pro Ala Gly Gly Ile Ala Pro Asp Ala Thr Leu His Ile Met
225                 230                 235                 240

Asn Thr Asn Asp Glu Thr Lys Asn Glu Met Met Val Ala Ala Ile Arg
```

-continued

```
                245                 250                 255
Asn Ala Trp Val Lys Leu Gly Glu Arg Gly Val Arg Ile Val Asn Asn
                260                 265                 270

Ser Phe Gly Thr Thr Ser Arg Ala Gly Thr Ala Asp Leu Phe Gln Ile
                275                 280                 285

Ala Asn Ser Glu Glu Gln Tyr Arg Gln Ala Leu Leu Asp Tyr Ser Gly
                290                 295                 300

Gly Asp Lys Thr Asp Glu Gly Ile Arg Leu Met Gln Gln Ser Asp Tyr
305                 310                 315                 320

Gly Asn Leu Ser Tyr His Ile Arg Asn Lys Asn Met Leu Phe Ile Phe
                325                 330                 335

Ser Thr Gly Asn Asp Ala Gln Ala Gln Pro Asn Thr Tyr Ala Leu Leu
                340                 345                 350

Pro Phe Tyr Glu Lys Asp Ala Gln Lys Gly Ile Ile Thr Val Ala Gly
                355                 360                 365

Val Asp Arg Ser Gly Glu Lys Phe Lys Arg Glu Met Tyr Gly Glu Pro
                370                 375                 380

Gly Thr Glu Pro Leu Glu Tyr Gly Ser Asn His Cys Gly Ile Thr Ala
385                 390                 395                 400

Met Trp Cys Leu Ser Ala Pro Tyr Glu Ala Ser Val Arg Phe Thr Arg
                405                 410                 415

Thr Asn Pro Ile Gln Ile Ala Gly Thr Ser Phe Ser Ala Pro Ile Val
                420                 425                 430

Thr Gly Thr Ala Ala Leu Leu Leu Gln Lys Tyr Pro Trp Met Ser Asn
                435                 440                 445

Asp Asn Leu Arg Thr Thr Leu Leu Thr Thr Ala Gln Asp Ile Gly Ala
                450                 455                 460

Val Gly Val Asp Ser Lys Phe Gly Trp Gly Leu Leu Asp Ala Gly Lys
465                 470                 475                 480

Ala Met Asn Gly Pro Ala Ser Phe Pro Phe Gly Asp Phe Thr Ala Asp
                485                 490                 495

Thr Lys Gly Thr Ser Asp Ile Ala Tyr Ser Phe Arg Asn Asp Ile Ser
                500                 505                 510

Gly Thr Gly Gly Leu Ile Lys Lys Gly Gly Ser Gln Leu Gln Leu His
                515                 520                 525

Gly Asn Asn Thr Tyr Thr Gly Lys Thr Ile Ile Glu Gly Gly Ser Leu
                530                 535                 540

Val Leu Tyr Gly Asn Asn Lys Ser Asp Met Arg Val Glu Thr Lys Gly
545                 550                 555                 560

Ala Leu Ile Tyr Asn Gly Ala Ala Ser Gly Gly Ser Leu Asn Ser Asp
                565                 570                 575

Gly Ile Val Tyr Leu Ala Asp Thr Asp Gln Ser Gly Ala Asn Glu Thr
                580                 585                 590

Val His Ile Lys Gly Ser Leu Gln Leu Asp Gly Lys Gly Thr Leu Tyr
                595                 600                 605

Thr Arg Leu Gly Lys Leu Leu Lys Val Asp Gly Thr Ala Ile Ile Gly
                610                 615                 620

Gly Lys Leu Tyr Met Ser Ala Arg Gly Lys Gly Ala Gly Tyr Leu Asn
625                 630                 635                 640

Ser Thr Gly Arg Arg Val Pro Phe Leu Ser Ala Ala Lys Ile Gly Gln
                645                 650                 655

Asp Tyr Ser Phe Phe Thr Asn Ile Glu Thr Asp Gly Gly Leu Leu Ala
                660                 665                 670
```

```
Ser Leu Asp Ser Val Glu Lys Thr Ala Gly Ser Glu Gly Asp Thr Leu
        675                 680                 685

Ser Tyr Tyr Val Arg Arg Gly Asn Ala Ala Arg Thr Ala Ser Ala Ala
    690                 695                 700

Ala His Ser Ala Pro Ala Gly Leu Lys His Ala Val Glu Gln Gly Gly
705                 710                 715                 720

Ser Asn Leu Glu Asn Leu Met Val Glu Leu Asp Ala Ser Glu Ser Ser
            725                 730                 735

Ala Thr Pro Glu Thr Val Glu Thr Ala Ala Ala Asp Arg Thr Asp Met
            740                 745                 750

Pro Gly Ile Arg Pro Tyr Gly Ala Thr Phe Arg Ala Ala Ala Ala Val
        755                 760                 765

Gln His Ala Asn Ala Ala Asp Gly Val Arg Ile Phe Asn Ser Leu Ala
    770                 775                 780

Ala Thr Val Tyr Ala Asp Ser Thr Ala Ala His Ala Asp Met Gln Gly
785                 790                 795                 800

Arg Arg Leu Lys Ala Val Ser Asp Gly Leu Asp His Asn Gly Thr Gly
            805                 810                 815

Leu Arg Val Ile Ala Gln Thr Gln Gln Asp Gly Gly Thr Trp Glu Gln
            820                 825                 830

Gly Gly Val Glu Gly Lys Met Arg Gly Ser Thr Gln Thr Val Gly Ile
        835                 840                 845

Ala Ala Lys Thr Gly Glu Asn Thr Thr Ala Ala Thr Leu Gly Met
    850                 855                 860

Gly Arg Ser Thr Trp Ser Glu Asn Ser Ala Asn Ala Lys Thr Asp Ser
865                 870                 875                 880

Ile Ser Leu Phe Ala Gly Ile Arg His Asp Ala Gly Asp Ile Gly Tyr
            885                 890                 895

Leu Lys Gly Leu Phe Ser Tyr Gly Arg Tyr Lys Asn Ser Ile Ser Arg
            900                 905                 910

Ser Thr Gly Ala Asp Glu His Ala Glu Gly Ser Val Asn Gly Thr Leu
        915                 920                 925

Met Gln Leu Gly Ala Leu Gly Gly Val Asn Val Pro Phe Ala Ala Thr
    930                 935                 940

Gly Asp Leu Thr Val Glu Gly Gly Leu Arg Tyr Asp Leu Leu Lys Gln
945                 950                 955                 960

Asp Ala Phe Ala Glu Lys Gly Ser Ala Leu Gly Trp Ser Gly Asn Ser
            965                 970                 975

Leu Thr Glu Gly Thr Leu Val Gly Leu Ala Gly Leu Lys Leu Ser Gln
            980                 985                 990

Pro Leu Ser Asp Lys Ala Val Leu Phe Ala Thr Ala Gly Val Glu Arg
        995                 1000                1005

Asp Leu Asn Gly Arg Asp Tyr Thr Val Thr Gly Gly Phe Thr Gly Ala
    1010                1015                1020

Thr Ala Ala Thr Gly Lys Thr Gly Ala Arg Asn Met Pro His Thr Arg
1025                1030                1035                1040

Leu Val Ala Gly Leu Gly Ala Asp Val Glu Phe Gly Asn Gly Trp Asn
            1045                1050                1055

Gly Leu Ala Arg Tyr Ser Tyr Ala Gly Ser Lys Gln Tyr Gly Asn His
            1060                1065                1070

Ser Gly Arg Val Gly Val Gly Tyr Arg Phe
        1075                1080
```

<210> SEQ ID NO 88

<211> LENGTH: 2505
<212> TYPE: DNA
<213> ORGANISM: Artificial Sequence
<220> FEATURE:
<223> OTHER INFORMATION: Synthetic construct

<400> SEQUENCE: 88

```
atggctagcc ccgatgttaa atcggcggac acgctgtcaa aaccggccgc tcctgttgtt      60
gctgaaaaag agacagaggt aaaagaagat gcgccacagg caggttctca aggacagggc     120
gcgccatcca cacaaggcag ccaagatatg gcggcagttt cggcagaaaa tacaggcaat     180
ggcggtgcgg caacaacgga caaacccaaa aatgaagacg agggaccgca aaatgatatg     240
ccgcaaaatt ccgccgaatc cgcaaatcaa acagggaaca accaaccgc cgattcttca      300
gattccgccc ccgcgtcaaa ccctgcacct gcgaatggcg gtagcaattt tggaagggtt     360
gatttggcta atggcgtttt gattgatggg ccgtcgcaaa atataacgtt gacccactgt     420
aaaggcgatt cttgtaatgg tgataattta ttggatgaag aagcaccgtc aaaatcagaa     480
tttgaaaatt taaatgagtc tgaacgaatt gagaaatata agaaagatgg gaaaagcgat     540
aaatttacta atttggttgc gacagcagtt caagctaatg aactaacaa atatgtcatc     600
atttataaag acaagtccgc ttcatcttca tctgcgcgat tcaggcgttc tgcacggtcg     660
aggaggtcgc ttcctgccga gatgccgcta atccccgtca atcaggcgga tacgctgatt     720
gtcgatgggg aagcggtcag cctgacgggg cattccggca atatcttcgc gcccgaaggg     780
aattaccggt atctgactta cggggcgaa aaattgcccg gcggatcgta tgccctccgt      840
gtgcaaggcg aaccggcaaa aggcgaaatg cttgctggca cggccgtgta caacggcgaa     900
gtgctgcatt ttcatacgga aaacggccgt ccgtacccga ctagaggcag gtttgccgca     960
aaagtcgatt tcggcagcaa atctgtggac ggcattatcg acagcggcga tgatttgcat    1020
atgggtacgc aaaaattcaa agccgccatc gatggaaacg gctttaaggg gacttggacg    1080
gaaaatggcg gcggggatgt ttccggaagg ttttacggcc cggccggcga ggaagtggcg    1140
ggaaaataca gctatcgccc gacagatgcg gaaaagggcg gattcggcgt gtttgccggc    1200
aaaaaagagc aggatggatc cggaggagga ggatgccaaa gcaagagcat ccaaaccttt    1260
ccgcaacccg acacatccgt catcaacggc ccggaccggc cggtcggcat ccccgacccc    1320
gccgaaacga cggtcggcgg cggcgggcc gtctataccg ttgtaccgca cctgtccctg     1380
ccccactggg cggcgcagga tttcgccaaa agcctgcaat ccttccgcct cggctgcgcc    1440
aatttgaaaa accgccaagg ctggcaggat gtgtgcgccc aagcctttca aaccccgtc     1500
cattcctttc aggcaaaaca gtttttgaa cgctatttca cgccgtggca ggttgcaggc    1560
aacgaagcc ttgccggtac ggttaccggc tattacgagc cggtgctgaa gggcgacgac     1620
aggcggacgg cacaagcccg cttcccgatt tacggtattc ccgacgattt tatctccgtc    1680
ccctgcctg ccggtttgcg gagcggaaaa gcccttgtcc gcatcaggca gacgggaaaa     1740
aacagcggca aatcgacaa taccggcggc acacataccg ccgacctctc ccgattcccc    1800
atcaccgcgc gcacaacggc aatcaaaggc aggtttgaag aagccgctt cctcccctac     1860
cacacgcgca accaaatcaa cggcggcgcg cttgacggca agccccgat actcggttac    1920
gccgaagacc ccgtcgaact ttttttatg cacatccaag gctcgggccg tctgaaaacc    1980
ccgtccggca aatacatccg catcggctat gccgacaaaa acgaacatcc ctacgtttcc    2040
atcggacgct atatgcgga caaaggctac ctcaagctcg gcagacctc gatgcagggc    2100
atcaaagcct atatgcggca aaatccgcaa cgcctcgccg aagttttggg tcaaaacccc    2160
```

-continued

```
agctatatct ttttccgcga gcttgccgga agcagcaatg acggtcccgt cggcgcactg    2220
ggcacgccgt tgatggggga atatgccggc gcagtcgacc ggcactacat taccttgggc    2280
gcgcccttat ttgtcgccac cgcccatccg gttacccgca aagccctcaa ccgcctgatt    2340
atggcgcagg ataccggcag cgcgattaaa ggcgcggtgc gcgtggatta ttttgggga    2400 tacggcgacg aagccggcga acttgccggc aaacagaaaa ccacggggtta cgtctggcag    2460 ctcctaccca acggtatgaa gcccgaatac cgcccgtaac tcgag                   2505
```

<210> SEQ ID NO 89
<211> LENGTH: 832
<212> TYPE: PRT
<213> ORGANISM: Artificial Sequence
<220> FEATURE:
<223> OTHER INFORMATION: Synthetic construct

<400> SEQUENCE: 89

```
Met Ala Ser Pro Asp Val Lys Ser Ala Asp Thr Leu Ser Lys Pro Ala
1               5                   10                  15

Ala Pro Val Val Ala Glu Lys Glu Thr Glu Val Lys Glu Asp Ala Pro
            20                  25                  30

Gln Ala Gly Ser Gln Gly Gln Gly Ala Pro Ser Thr Gln Gly Ser Gln
        35                  40                  45

Asp Met Ala Ala Val Ser Ala Glu Asn Thr Gly Asn Gly Gly Ala Ala
    50                  55                  60

Thr Thr Asp Lys Pro Lys Asn Glu Asp Glu Gly Pro Gln Asn Asp Met
65                  70                  75                  80

Pro Gln Asn Ser Ala Glu Ser Ala Asn Gln Thr Gly Asn Asn Gln Pro
                85                  90                  95

Ala Asp Ser Ser Asp Ser Ala Pro Ala Ser Asn Pro Ala Pro Ala Asn
            100                 105                 110

Gly Gly Ser Asn Phe Gly Arg Val Asp Leu Ala Asn Gly Val Leu Ile
        115                 120                 125

Asp Gly Pro Ser Gln Asn Ile Thr Leu Thr His Cys Lys Gly Asp Ser
    130                 135                 140

Cys Asn Gly Asp Asn Leu Leu Asp Glu Glu Ala Pro Ser Lys Ser Glu
145                 150                 155                 160

Phe Glu Asn Leu Asn Glu Ser Glu Arg Ile Glu Lys Tyr Lys Lys Asp
                165                 170                 175

Gly Lys Ser Asp Lys Phe Thr Asn Leu Val Ala Thr Ala Val Gln Ala
            180                 185                 190

Asn Gly Thr Asn Lys Tyr Val Ile Ile Tyr Lys Asp Lys Ser Ala Ser
        195                 200                 205

Ser Ser Ser Ala Arg Phe Arg Arg Ser Ala Arg Ser Arg Arg Ser Leu
    210                 215                 220

Pro Ala Glu Met Pro Leu Ile Pro Val Asn Gln Ala Asp Thr Leu Ile
225                 230                 235                 240

Val Asp Gly Glu Ala Val Ser Leu Thr Gly His Ser Gly Asn Ile Phe
                245                 250                 255

Ala Pro Glu Gly Asn Tyr Arg Tyr Leu Thr Tyr Gly Ala Glu Lys Leu
            260                 265                 270

Pro Gly Gly Ser Tyr Ala Leu Arg Val Gln Gly Glu Pro Ala Lys Gly
        275                 280                 285

Glu Met Leu Ala Gly Thr Ala Val Tyr Asn Gly Glu Val Leu His Phe
    290                 295                 300

His Thr Glu Asn Gly Arg Pro Tyr Pro Thr Arg Gly Arg Phe Ala Ala
```

```
              305                 310                 315                 320
Lys Val Asp Phe Gly Ser Lys Ser Val Asp Gly Ile Ile Asp Ser Gly
                325                 330                 335

Asp Asp Leu His Met Gly Thr Gln Lys Phe Lys Ala Ala Ile Asp Gly
                340                 345                 350

Asn Gly Phe Lys Gly Thr Trp Thr Glu Asn Gly Gly Asp Val Ser
                355                 360                 365

Gly Arg Phe Tyr Gly Pro Ala Gly Glu Val Ala Gly Lys Tyr Ser
            370                 375                 380

Tyr Arg Pro Thr Asp Ala Glu Lys Gly Phe Gly Val Phe Ala Gly
385                 390                 395                 400

Lys Lys Glu Gln Asp Gly Ser Gly Gly Gly Cys Gln Ser Lys Ser
                405                 410                 415

Ile Gln Thr Phe Pro Gln Pro Asp Thr Ser Val Ile Asn Gly Pro Asp
                420                 425                 430

Arg Pro Val Gly Ile Pro Asp Pro Ala Gly Thr Thr Val Gly Gly Gly
                435                 440                 445

Gly Ala Val Tyr Thr Val Val Pro His Leu Ser Leu Pro His Trp Ala
            450                 455                 460

Ala Gln Asp Phe Ala Lys Ser Leu Gln Ser Phe Arg Leu Gly Cys Ala
465                 470                 475                 480

Asn Leu Lys Asn Arg Gln Gly Trp Gln Asp Val Cys Ala Gln Ala Phe
                485                 490                 495

Gln Thr Pro Val His Ser Phe Gln Ala Lys Gln Phe Phe Glu Arg Tyr
                500                 505                 510

Phe Thr Pro Trp Gln Val Ala Gly Asn Gly Ser Leu Ala Gly Thr Val
                515                 520                 525

Thr Gly Tyr Tyr Glu Pro Val Leu Lys Gly Asp Asp Arg Arg Thr Ala
            530                 535                 540

Gln Ala Arg Phe Pro Ile Tyr Gly Ile Pro Asp Asp Phe Ile Ser Val
545                 550                 555                 560

Pro Leu Pro Ala Gly Leu Arg Ser Gly Lys Ala Leu Val Arg Ile Arg
                565                 570                 575

Gln Thr Gly Lys Asn Ser Gly Thr Ile Asp Asn Thr Gly Gly Thr His
                580                 585                 590

Thr Ala Asp Leu Ser Arg Phe Pro Ile Thr Ala Arg Thr Ala Ile
                595                 600                 605

Lys Gly Arg Phe Glu Gly Ser Arg Phe Leu Pro Tyr His Thr Arg Asn
                610                 615                 620

Gln Ile Asn Gly Gly Ala Leu Asp Gly Lys Ala Pro Ile Leu Gly Tyr
625                 630                 635                 640

Ala Glu Asp Pro Val Glu Leu Phe Phe Met His Ile Gln Gly Ser Gly
                645                 650                 655

Arg Leu Lys Thr Pro Ser Gly Lys Tyr Ile Arg Ile Gly Tyr Ala Asp
                660                 665                 670

Lys Asn Glu His Pro Tyr Val Ser Ile Gly Arg Tyr Met Ala Asp Lys
                675                 680                 685

Gly Tyr Leu Lys Leu Gly Gln Thr Ser Met Gln Gly Ile Lys Ala Tyr
            690                 695                 700

Met Arg Gln Asn Pro Gln Arg Leu Ala Glu Val Leu Gly Gln Asn Pro
705                 710                 715                 720

Ser Tyr Ile Phe Phe Arg Glu Leu Ala Gly Ser Ser Asn Asp Gly Pro
                725                 730                 735
```

```
Val Gly Ala Leu Gly Thr Pro Leu Met Gly Glu Tyr Ala Gly Ala Val
            740                 745                 750

Asp Arg His Tyr Ile Thr Leu Gly Ala Pro Leu Phe Val Ala Thr Ala
            755                 760                 765

His Pro Val Thr Arg Lys Ala Leu Asn Arg Leu Ile Met Ala Gln Asp
    770                 775                 780

Thr Gly Ser Ala Ile Lys Gly Ala Val Arg Val Asp Tyr Phe Trp Gly
785                 790                 795                 800

Tyr Gly Asp Glu Ala Gly Glu Leu Ala Gly Lys Gln Lys Thr Thr Gly
                805                 810                 815

Tyr Val Trp Gln Leu Leu Pro Asn Gly Met Lys Pro Glu Tyr Arg Pro
            820                 825                 830

<210> SEQ ID NO 90
<211> LENGTH: 1746
<212> TYPE: DNA
<213> ORGANISM: Artificial Sequence
<220> FEATURE:
<223> OTHER INFORMATION: Synthetic construct

<400> SEQUENCE: 90
atggctagcc ccgatgttaa atcggcggac acgctgtcaa aaccggccgc tcctgttgtt      60
gctgaaaaag agacagaggt aaaagaagat gcgccacagg caggttctca aggacagggc     120
gcgccatcca cacaaggcag ccaagatatg gcggcagttt cggcagaaaa tacaggcaat     180
ggcggtgcgg caacaacgga caaacccaaa aatgaagacg agggaccgca aaatgatatg     240
ccgcaaaatt ccgccgaatc cgcaaatcaa acagggaaca accaaccgc cgattcttca      300 gattccgccc ccgcgtcaaa ccctgcacct gcgaatggcg gtagcaattt tggaagggtt     360
gatttggcta atggcgtttt gattgatggg ccgtcgcaaa atataacgtt gacccactgt     420
aaaggcgatt cttgtaatgg tgataattta ttggatgaag aagcaccgtc aaaatcagaa     480
tttgaaaatt taaatgagtc tgaacgaatt gagaaatata gaaagatgg gaaaagcgat      540 aaatttacta atttggttgc gacagcagtt caagctaatg gaactaacaa atatgtcatc     600
atttataaag acaagtccgc ttcatcttca tctgcgcgat tcaggcgttc tgcacggtcg     660
aggaggtcgc ttcctgccga gatgccgcta atcccgtca atcaggcgga tacgctgatt      720
gtcgatgggg aagcggtcag cctgacgggg cattccggca atatcttcgc gcccgaaggg     780
aattaccggt atctgactta cggggcggaa aaattgcccg gcggatcgta tgccctccgt     840
gtgcaaggcg aaccggcaaa aggcgaaatg cttgctggca cggccgtgta caacggcgaa     900
gtgctgcatt tcatacgga aaacggccgt ccgtacccga ctagaggcag gtttgccgca      960
aaagtcgatt tcggcagcaa atctgtggac ggcattatcg acagcggcga tgatttgcat    1020
atgggtacgc aaaaattcaa agccgccatc gatggaaacg gctttaaggg gacttggacg    1080
gaaaatggcg gcggggatgt tccggaagg ttttacggcc cggccggcga ggaagtggcg     1140
ggaaaataca gctatcgccc gacagatgcg gaaaagggcg gattcggcgt gtttgccggc    1200 aaaaagagc aggatggatc cggaggagga ggagccacct acaaagtgga cgaatatcac     1260
gccaacgccc gtttcgccat cgaccatttc aacaccagca ccaacgtcgg cggtttttac    1320
ggtctgaccg gttccgtcga gttcgaccaa gcaaaacgcg acggtaaaat cgacatcacc    1380 atcccgttg ccaacctgca aagcggttcg caacacttta ccgaccacct gaaatcagcc     1440
gacatcttcg atgccgccca atatccggac atccgctttg tttccaccaa attcaacttc    1500
aacggcaaaa aactggtttc cgttgacggc aacctgacca tgcacggcaa aaccgccccc    1560
```

-continued

```
gtcaaactca aagccgaaaa attcaactgc taccaaagcc cgatggcgaa aaccgaagtt    1620
tgcggcggcg acttcagcac caccatcgac cgcaccaaat ggggcgtgga ctacctcgtt    1680
aacgttggta tgaccaaaag cgtccgcatc gacatccaaa tcgaggcagc caaacaataa    1740
ctcgag                                                               1746
```

<210> SEQ ID NO 91
<211> LENGTH: 579
<212> TYPE: PRT
<213> ORGANISM: Artificial Sequence
<220> FEATURE:
<223> OTHER INFORMATION: Synthetic construct

<400> SEQUENCE: 91

```
Met Ala Ser Pro Asp Val Lys Ser Ala Asp Thr Leu Ser Lys Pro Ala
1               5                   10                  15

Ala Pro Val Val Ala Glu Lys Glu Thr Glu Val Lys Glu Asp Ala Pro
                20                  25                  30

Gln Ala Gly Ser Gln Gly Gln Gly Ala Pro Ser Thr Gln Gly Ser Gln
            35                  40                  45

Asp Met Ala Ala Val Ser Ala Glu Asn Thr Gly Asn Gly Gly Ala Ala
        50                  55                  60

Thr Thr Asp Lys Pro Lys Asn Glu Asp Glu Gly Pro Gln Asn Asp Met
65                  70                  75                  80

Pro Gln Asn Ser Ala Glu Ser Ala Asn Gln Thr Gly Asn Asn Gln Pro
                85                  90                  95

Ala Asp Ser Ser Asp Ser Ala Pro Ala Ser Asn Pro Ala Pro Ala Asn
            100                 105                 110

Gly Gly Ser Asn Phe Gly Arg Val Asp Leu Ala Asn Gly Val Leu Ile
        115                 120                 125

Asp Gly Pro Ser Gln Asn Ile Thr Leu Thr His Cys Lys Gly Asp Ser
130                 135                 140

Cys Asn Gly Asp Asn Leu Leu Asp Glu Glu Ala Pro Ser Lys Ser Glu
145                 150                 155                 160

Phe Glu Asn Leu Asn Glu Ser Glu Arg Ile Glu Lys Tyr Lys Lys Asp
                165                 170                 175

Gly Lys Ser Asp Lys Phe Thr Asn Leu Val Ala Thr Ala Val Gln Ala
            180                 185                 190

Asn Gly Thr Asn Lys Tyr Val Ile Ile Tyr Lys Asp Lys Ser Ala Ser
        195                 200                 205

Ser Ser Ser Ala Arg Phe Arg Arg Ser Ala Arg Ser Arg Arg Ser Leu
    210                 215                 220

Pro Ala Glu Met Pro Leu Ile Pro Val Asn Gln Ala Asp Thr Leu Ile
225                 230                 235                 240

Val Asp Gly Glu Ala Val Ser Leu Thr Gly His Ser Gly Asn Ile Phe
                245                 250                 255

Ala Pro Glu Gly Asn Tyr Arg Tyr Leu Thr Tyr Gly Ala Glu Lys Leu
            260                 265                 270

Pro Gly Gly Ser Tyr Ala Leu Arg Val Gln Gly Glu Pro Ala Lys Gly
        275                 280                 285

Glu Met Leu Ala Gly Thr Ala Val Tyr Asn Gly Glu Val Leu His Phe
    290                 295                 300

His Thr Glu Asn Gly Arg Pro Tyr Pro Thr Arg Gly Arg Phe Ala Ala
305                 310                 315                 320

Lys Val Asp Phe Gly Ser Lys Ser Val Asp Gly Ile Ile Asp Ser Gly
                325                 330                 335
```

Asp Asp Leu His Met Gly Thr Gln Lys Phe Lys Ala Ala Ile Asp Gly
        340                 345                 350

Asn Gly Phe Lys Gly Thr Trp Thr Glu Asn Gly Gly Asp Val Ser
            355                 360                 365

Gly Arg Phe Tyr Gly Pro Ala Gly Glu Glu Val Ala Gly Lys Tyr Ser
        370                 375                 380

Tyr Arg Pro Thr Asp Ala Glu Lys Gly Gly Phe Gly Val Phe Ala Gly
385                 390                 395                 400

Lys Lys Glu Gln Asp Gly Ser Gly Gly Gly Ala Thr Tyr Lys Val
            405                 410                 415

Asp Glu Tyr His Ala Asn Ala Arg Phe Ala Ile Asp His Phe Asn Thr
        420                 425                 430

Ser Thr Asn Val Gly Gly Phe Tyr Gly Leu Thr Gly Ser Val Glu Phe
        435                 440                 445

Asp Gln Ala Lys Arg Asp Gly Lys Ile Asp Ile Thr Ile Pro Val Ala
450                 455                 460

Asn Leu Gln Ser Gly Ser Gln His Phe Thr Asp His Leu Lys Ser Ala
465                 470                 475                 480

Asp Ile Phe Asp Ala Ala Gln Tyr Pro Asp Ile Arg Phe Val Ser Thr
            485                 490                 495

Lys Phe Asn Phe Asn Gly Lys Lys Leu Val Ser Val Asp Gly Asn Leu
        500                 505                 510

Thr Met His Gly Lys Thr Ala Pro Val Lys Leu Lys Ala Glu Lys Phe
        515                 520                 525

Asn Cys Tyr Gln Ser Pro Met Ala Lys Thr Glu Val Cys Gly Gly Asp
        530                 535                 540

Phe Ser Thr Thr Ile Asp Arg Thr Lys Trp Gly Val Asp Tyr Leu Val
545                 550                 555                 560

Asn Val Gly Met Thr Lys Ser Val Arg Ile Asp Ile Gln Ile Glu Ala
            565                 570                 575

Ala Lys Gln

<210> SEQ ID NO 92
<211> LENGTH: 2388
<212> TYPE: DNA
<213> ORGANISM: Artificial Sequence
<220> FEATURE:
<223> OTHER INFORMATION: Synthetic construct

<400> SEQUENCE: 92

```
atggctagcc ccgatgttaa atcggcggac acgctgtcaa aaccggccgc tcctgttgtt      60
gctgaaaaag agacagaggt aaaagaagat gcgccacagg caggttctca aggacagggc     120
gcgccatcca cacaaggcag ccaagatatg gcggcagttt cggcagaaaa tacaggcaat     180
ggcggtgcgg caacaacgga caaacccaaa aatgaagacg agggaccgca aaatgatatg     240
ccgcaaaatt ccgccgaatc cgcaaatcaa acagggaaca accaaccgc cgattcttca      300
gattccgccc ccgcgtcaaa ccctgcacct gcgaatggcg gtagcaattt tggaagggtt     360
gatttggcta atggcgtttt gattgatggg ccgtcgcaaa atataacgtt gacccactgt     420
aaaggcgatt cttgtaatgg tgataattta ttggatgaag aagcaccgtc aaaatcagaa     480
tttgaaaatt taaatgagtc tgaacgaatt gagaaatata agaaagatgg aaaagcgat      540
aaatttacta atttggttgc gacagcagtt caagctaatg aactaacaa atatgtcatc      600
atttataaag acaagtccgc ttcatcttca tctgcgcgat tcaggcgttc tgcacggtcg     660
```

-continued

| | |
|---|---|
| aggaggtcgc ttcctgccga gatgccgcta atccccgtca atcaggcgga tacgctgatt | 720 |
| gtcgatgggg aagcggtcag cctgacgggg cattccggca atatcttcgc gcccgaaggg | 780 |
| aattaccggt atctgactta cggggcggaa aaattgcccg gcggatcgta tgccctccgt | 840 |
| gtgcaaggcg aaccggcaaa aggcgaaatg cttgctggca cggccgtgta caacggcgaa | 900 |
| gtgctgcatt ttcatacgga aaacggccgt ccgtacccga ctagaggcag gtttgccgca | 960 |
| aaagtcgatt tcggcagcaa atctgtggac ggcattatcg acagcggcga tgatttgcat | 1020 |
| atgggtacgc aaaaattcaa agccgccatc gatggaaacg ctttaaggg gacttggacg | 1080 |
| gaaaatggcg gcggggatgt ttccggaagg ttttacggcc cggccggcga ggaagtggcg | 1140 |
| ggaaaataca gctatcgccc gacagatgcg gaaaagggcg gattcggcgt gtttgccggc | 1200 |
| aaaaaagagc aggatggatc cggaggagga ggagccacaa cgacgacga tgttaaaaaa | 1260 |
| gctgccactg tggccattgc tgctgcctac aacaatggcc aagaaatcaa cggtttcaaa | 1320 |
| gctggagaga ccatctacga cattgatgaa acggcacaa ttaccaaaaa agacgcaact | 1380 |
| gcagccgatg ttgaagccga cgactttaaa ggtctgggtc tgaaaaaagt cgtgactaac | 1440 |
| ctgaccaaaa ccgtcaatga aaacaaacaa aacgtcgatg ccaaagtaaa agctgcagaa | 1500 |
| tctgaaatag aaaagttaac aaccaagtta gcagacactg atgccgcttt agcagatact | 1560 |
| gatgccgctc tggatgcaac caccaacgcc ttgaataaat gggagaaaaa tataacgaca | 1620 |
| tttgctgaag agactaagac aaatatcgta aaaattgatg aaaaattaga gccgtggct | 1680 |
| gataccgtcg acaagcatgc cgaagcattc aacgatatcg ccgattcatt ggatgaaacc | 1740 |
| aacactaagg cagacgaagc cgtcaaaacc gccaatgaag ccaaacagac ggccgaagaa | 1800 |
| accaaacaaa acgtcgatgc caaagtaaaa gctgcagaaa ctgcagcagg caaagccgaa | 1860 |
| gctgccgctg gcacagctaa tactgcagcc gacaaggccg aagctgtcgc tgcaaaagtt | 1920 |
| accgacatca agctgatat cgctacgaac aaagataata ttgctaaaaa agcaaacagt | 1980 |
| gccgacgtgt acaccagaga agagtctgac agcaaatttg tcagaattga tggtctgaac | 2040 |
| gctactaccg aaaaattgga cacacgcttg gcttctgctg aaaaatccat gccgatcac | 2100 |
| gatactcgcc tgaacggttt ggataaaaca gtgtcagacc tgcgcaaaga aacccgccaa | 2160 |
| ggccttgcag aacaagccgc gctctccggt ctgttccaac cttacaacgt gggtcggttc | 2220 |
| aatgtaacgc tgcagtcgg cggctacaaa tccgaatcgg cagtcgccat cggtaccggc | 2280 |
| ttccgcttta ccgaaaactt tgccgccaaa gcaggcgtgg cagtcggcac ttcgtccggt | 2340 |
| tcttccgcag cctaccatgt cggcgtcaat tacgagtggt aactcgag | 2388 |

<210> SEQ ID NO 93
<211> LENGTH: 793
<212> TYPE: PRT
<213> ORGANISM: Artificial Sequence
<220> FEATURE:
<223> OTHER INFORMATION: Synthetic construct

<400> SEQUENCE: 93

Met Ala Ser Pro Asp Val Lys Ser Ala Asp Thr Leu Ser Lys Pro Ala
1               5                   10                  15

Ala Pro Val Val Ala Glu Lys Glu Thr Glu Val Lys Glu Asp Ala Pro
            20                  25                  30

Gln Ala Gly Ser Gln Gly Gln Gly Ala Pro Ser Thr Gln Gly Ser Gln
        35                  40                  45

Asp Met Ala Ala Val Ser Ala Glu Asn Thr Gly Asn Gly Gly Ala Ala
    50                  55                  60

```
Thr Thr Asp Lys Pro Lys Asn Glu Asp Glu Gly Pro Gln Asn Asp Met
 65                  70                  75                  80

Pro Gln Asn Ser Ala Glu Ser Ala Asn Gln Thr Gly Asn Asn Gln Pro
                 85                  90                  95

Ala Asp Ser Ser Asp Ser Ala Pro Ala Ser Asn Pro Ala Pro Ala Asn
            100                 105                 110

Gly Gly Ser Asn Phe Gly Arg Val Asp Leu Ala Asn Gly Val Leu Ile
        115                 120                 125

Asp Gly Pro Ser Gln Asn Ile Thr Leu Thr His Cys Lys Gly Asp Ser
    130                 135                 140

Cys Asn Gly Asp Asn Leu Leu Asp Glu Glu Ala Pro Ser Lys Ser Glu
145                 150                 155                 160

Phe Glu Asn Leu Asn Glu Ser Glu Arg Ile Glu Lys Tyr Lys Lys Asp
                165                 170                 175

Gly Lys Ser Asp Lys Phe Thr Asn Leu Val Ala Thr Ala Val Gln Ala
            180                 185                 190

Asn Gly Thr Asn Lys Tyr Val Ile Ile Tyr Lys Asp Lys Ser Ala Ser
        195                 200                 205

Ser Ser Ser Ala Arg Phe Arg Arg Ser Ala Arg Ser Arg Arg Ser Leu
    210                 215                 220

Pro Ala Glu Met Pro Leu Ile Pro Val Asn Gln Ala Asp Thr Leu Ile
225                 230                 235                 240

Val Asp Gly Glu Ala Val Ser Leu Thr Gly His Ser Gly Asn Ile Phe
                245                 250                 255

Ala Pro Glu Gly Asn Tyr Arg Tyr Leu Thr Tyr Gly Ala Glu Lys Leu
            260                 265                 270

Pro Gly Gly Ser Tyr Ala Leu Arg Val Gln Gly Glu Pro Ala Lys Gly
        275                 280                 285

Glu Met Leu Ala Gly Thr Ala Val Tyr Asn Gly Glu Val Leu His Phe
    290                 295                 300

His Thr Glu Asn Gly Arg Pro Tyr Pro Thr Arg Gly Arg Phe Ala Ala
305                 310                 315                 320

Lys Val Asp Phe Gly Ser Lys Ser Val Asp Gly Ile Ile Asp Ser Gly
                325                 330                 335

Asp Asp Leu His Met Gly Thr Gln Lys Phe Lys Ala Ala Ile Asp Gly
            340                 345                 350

Asn Gly Phe Lys Gly Thr Trp Thr Glu Asn Gly Gly Asp Val Ser
        355                 360                 365

Gly Arg Phe Tyr Gly Pro Ala Gly Glu Glu Val Ala Gly Lys Tyr Ser
    370                 375                 380

Tyr Arg Pro Thr Asp Ala Glu Lys Gly Gly Phe Gly Val Phe Ala Gly
385                 390                 395                 400

Lys Lys Glu Gln Asp Gly Ser Gly Gly Gly Ala Thr Asn Asp Asp
                405                 410                 415

Asp Val Lys Lys Ala Ala Thr Val Ala Ile Ala Ala Ala Tyr Asn Asn
            420                 425                 430

Gly Gln Glu Ile Asn Gly Phe Lys Ala Gly Glu Thr Ile Tyr Asp Ile
        435                 440                 445

Asp Glu Asp Gly Thr Ile Thr Lys Lys Asp Ala Thr Ala Ala Asp Val
    450                 455                 460

Glu Ala Asp Asp Phe Lys Gly Leu Gly Leu Lys Lys Val Val Thr Asn
465                 470                 475                 480

Leu Thr Lys Thr Val Asn Glu Asn Lys Gln Asn Val Asp Ala Lys Val
                485                 490                 495
```

```
Lys Ala Ala Glu Ser Glu Ile Glu Lys Leu Thr Thr Lys Leu Ala Asp
                500                 505                 510
Thr Asp Ala Ala Leu Ala Asp Thr Asp Ala Ala Leu Asp Ala Thr Thr
            515                 520                 525
Asn Ala Leu Asn Lys Leu Gly Glu Asn Ile Thr Thr Phe Ala Glu Glu
        530                 535                 540
Thr Lys Thr Asn Ile Val Lys Ile Asp Glu Lys Leu Glu Ala Val Ala
545                 550                 555                 560
Asp Thr Val Asp Lys His Ala Glu Ala Phe Asn Asp Ile Ala Asp Ser
                565                 570                 575
Leu Asp Glu Thr Asn Thr Lys Ala Asp Glu Ala Val Lys Thr Ala Asn
            580                 585                 590
Glu Ala Lys Gln Thr Ala Glu Glu Thr Lys Gln Asn Val Asp Ala Lys
        595                 600                 605
Val Lys Ala Ala Glu Thr Ala Ala Gly Lys Ala Glu Ala Ala Ala Gly
610                 615                 620
Thr Ala Asn Thr Ala Ala Asp Lys Ala Glu Ala Val Ala Ala Lys Val
625                 630                 635                 640
Thr Asp Ile Lys Ala Asp Ile Ala Thr Asn Lys Asp Asn Ile Ala Lys
                645                 650                 655
Lys Ala Asn Ser Ala Asp Val Tyr Thr Arg Glu Glu Ser Asp Ser Lys
            660                 665                 670
Phe Val Arg Ile Asp Gly Leu Asn Ala Thr Thr Glu Lys Leu Asp Thr
        675                 680                 685
Arg Leu Ala Ser Ala Glu Lys Ser Ile Ala Asp His Asp Thr Arg Leu
690                 695                 700
Asn Gly Leu Asp Lys Thr Val Ser Asp Leu Arg Lys Glu Thr Arg Gln
705                 710                 715                 720
Gly Leu Ala Glu Gln Ala Ala Leu Ser Gly Leu Phe Gln Pro Tyr Asn
                725                 730                 735
Val Gly Arg Phe Asn Val Thr Ala Ala Val Gly Gly Tyr Lys Ser Glu
            740                 745                 750
Ser Ala Val Ala Ile Gly Thr Gly Phe Arg Phe Thr Glu Asn Phe Ala
        755                 760                 765
Ala Lys Ala Gly Val Ala Val Gly Thr Ser Ser Gly Ser Ser Ala Ala
770                 775                 780
Tyr His Val Gly Val Asn Tyr Glu Trp
785                 790

<210> SEQ ID NO 94
<211> LENGTH: 2700
<212> TYPE: DNA
<213> ORGANISM: Artificial Sequence
<220> FEATURE:
<223> OTHER INFORMATION: Synthetic construct

<400> SEQUENCE: 94
atggctagcc ccgatgtcaa gtcggcggac acgctgtcaa aacctgccgc ccctgttgtt      60
tctgaaaaag agacagaggc aaaggaagat gcgccacagg caggttctca aggacagggc     120
gcgccatccg cacaaggcgg tcaagatatg cggcgggttt cggaagaaaa tacaggcaat     180
ggcggtgcgg cagcaacgga caaacccaaa aatgaagacg agggggcgca aaatgatatg     240
ccgcaaaatg ccgccgatac agatagtttg acaccgaatc acaccccggc ttcgaatatg     300
ccggccggaa atatggaaaa ccaagcaccg gatgccgggg aatcggagca gccggcaaac     360
```

```
caaccggata tggcaaatac ggcggacgga atgcagggtg acgatccgtc ggcaggcggg    420
gaaaatgccg gcaatacggc tgcccaaggt acaaatcaag ccgaaaacaa tcaaaccgcc    480
ggttctcaaa atcctgcctc ttcaaccaat cctagcgcca cgaatagcgg tggtgatttt    540
ggaaggacga acgtgggcaa ttctgttgtg attgacgggc cgtcgcaaaa tataacgttg    600
acccactgta aaggcgattc ttgtagtggc aataatttct tggatgaaga agtacagcta    660
aaatcagaat ttgaaaaatt aagtgatgca gacaaaataa gtaattacaa gaaagatggg    720
aagaatgacg ggaagaatga taaatttgtc ggtttggttg ccgatagtgt gcagatgaag    780
ggaatcaatc aatatattat cttttataaa cctaaaccca cttcatttgc gcgatttagg    840
cgttctgcac ggtcgaggcg gtcgcttccg gccgagatgc cgctgattcc cgtcaatcag    900
gcggatacgg tgattgtcga tggggaagcg gtcagcctga cggggcattc cggcaatatc    960
ttcgcgcccg aagggaatta ccggtatctg acttacgggg cggaaaaatt gcccggcgga   1020
tcgtatgccc tccgtgttca aggcgaacct tcaaaaggcg aaatgctcgc gggcacggca   1080
gtgtacaacg gcgaagtgct gcattttcat acggaaaacg gccgtccgtc cccgtccaga   1140
ggcaggtttg ccgcaaaagt cgatttcggc agcaaatctg tggacggcat tatcgacagc   1200
ggcgatggtt tgcatatggg tacgcaaaaa ttcaaagccg ccatcgatgg aaacggcttt   1260
aaggggactt ggacggaaaa tggcggcggg gatgtttccg gaaagtttta cggcccggcc   1320
ggcgaggaag tggcgggaaa atacagctat cgcccaacag atgcggaaaa gggcggattc   1380
ggcgtgtttg ccggcaaaaa agagcaggat ggatccggag gaggaggatg ccaaagcaag   1440
agcatccaaa cctttccgca acccgacaca tccgtcatca acggcccgga ccggccggtc   1500
ggcatccccg accccgccgg aacgacggtc ggcggcggcg gggccgtcta taccgttgta   1560
ccgcacctgt ccctgcccca ctgggcggcg caggatttcg ccaaaagcct gcaatccttc   1620
cgcctcggct gcgccaattt gaaaaaccgc caaggctggc aggatgtgtg cgcccaagcc   1680
tttcaaaccc ccgtccattc ctttcaggca aaacagtttt ttgaacgcta tttcacgccg   1740
tggcaggttg caggcaacgg aagccttgcc ggtacggtta ccggctatta cgagccggtg   1800
ctgaagggcg acgacaggcg gacggcacaa gcccgcttcc cgatttacgg tattcccgac   1860
gattttatct ccgtcccccct gcctgccggt ttgcggagcg aaaagccct tgtccgcatc   1920 aggcagacgg gaaaaaacag cggcacaatc gacaataccg gcggcacaca taccgccgac   1980
ctctcccgat tccccatcac cgcgcgcaca acggcaatca aaggcaggtt tgaaggaagc   2040
cgcttcctcc cctaccacac gcgcaaccaa atcaacggcg cgcgcttgac ggcaaagcc    2100 ccgatactcg gttacgccga agaccccgtc gaactttttt ttatgcacat ccaaggctcg   2160
ggccgtctga aacccccgtc cggcaaatac atccgcatcg gctatgccga caaaaacgaa   2220
catccctacg tttccatcgg acgctatatg gcggacaaag gctacctcaa gctcgggcag   2280
acctcgatgc agggcatcaa agcctatatg cggcaaaatc cgcaacgcct cgccgaagtt   2340
ttgggtcaaa accccagcta tatcttttttc cgcgagcttg ccggaagcag caatgacggt   2400
cccgtcggcg cactgggcac gccgttgatg ggggaatatg ccggcgcagt cgaccggcac   2460
tacattacct tgggcgcgcc cttatttgtc gccaccgccc atccggttac ccgcaaagcc   2520
ctcaaccgcc tgattatggc gcaggatacc ggcagcgcga ttaaaggcgc ggtgcgcgtg   2580
gattattttt ggggatacgg cgacgaagcc ggcgaacttg ccggcaaaca gaaaaccacg   2640
ggttacgtct ggcagctcct acccaacggt atgaagcccg aataccgccc gtaaaagctt   2700
```

<210> SEQ ID NO 95

```
<211> LENGTH: 897
<212> TYPE: PRT
<213> ORGANISM: Artificial Sequence
<220> FEATURE:
<223> OTHER INFORMATION: Synthetic construct

<400> SEQUENCE: 95
```

| | | | | | | | | | | | | | | |
|---|---|---|---|---|---|---|---|---|---|---|---|---|---|---|
| Met | Ala | Ser | Pro | Asp | Val | Lys | Ser | Ala | Asp | Thr | Leu | Ser | Lys | Pro | Ala |
| 1 | | | | 5 | | | | | 10 | | | | | 15 | |
| Ala | Pro | Val | Val | Ser | Glu | Lys | Glu | Thr | Glu | Ala | Lys | Glu | Asp | Ala | Pro |
| | | | 20 | | | | | 25 | | | | | 30 | | |
| Gln | Ala | Gly | Ser | Gln | Gly | Gln | Gly | Ala | Pro | Ser | Ala | Gln | Gly | Gly | Gln |
| | | 35 | | | | | 40 | | | | | 45 | | | |
| Asp | Met | Ala | Ala | Val | Ser | Glu | Glu | Asn | Thr | Gly | Asn | Gly | Gly | Ala | Ala |
| | 50 | | | | | 55 | | | | | 60 | | | | |
| Ala | Thr | Asp | Lys | Pro | Lys | Asn | Glu | Asp | Glu | Gly | Ala | Gln | Asn | Asp | Met |
| 65 | | | | | 70 | | | | | 75 | | | | | 80 |
| Pro | Gln | Asn | Ala | Ala | Asp | Thr | Asp | Ser | Leu | Thr | Pro | Asn | His | Thr | Pro |
| | | | | 85 | | | | | 90 | | | | | 95 | |
| Ala | Ser | Asn | Met | Pro | Ala | Gly | Asn | Met | Glu | Asn | Gln | Ala | Pro | Asp | Ala |
| | | | 100 | | | | | 105 | | | | | 110 | | |
| Gly | Glu | Ser | Glu | Gln | Pro | Ala | Asn | Gln | Pro | Asp | Met | Ala | Asn | Thr | Ala |
| | | 115 | | | | | 120 | | | | | 125 | | | |
| Asp | Gly | Met | Gln | Gly | Asp | Pro | Ser | Ala | Gly | Gly | Asn | Ala | Gly | | |
| | 130 | | | | | 135 | | | | | 140 | | | | |
| Asn | Thr | Ala | Ala | Gln | Gly | Thr | Asn | Gln | Ala | Glu | Asn | Asn | Gln | Thr | Ala |
| 145 | | | | | 150 | | | | | 155 | | | | | 160 |
| Gly | Ser | Gln | Asn | Pro | Ala | Ser | Ser | Thr | Asn | Pro | Ser | Ala | Thr | Asn | Ser |
| | | | | 165 | | | | | 170 | | | | | 175 | |
| Gly | Gly | Asp | Phe | Gly | Arg | Thr | Asn | Val | Gly | Asn | Ser | Val | Val | Ile | Asp |
| | | | 180 | | | | | 185 | | | | | 190 | | |
| Gly | Pro | Ser | Gln | Asn | Ile | Thr | Leu | Thr | His | Cys | Lys | Gly | Asp | Ser | Cys |
| | | 195 | | | | | 200 | | | | | 205 | | | |
| Ser | Gly | Asn | Asn | Phe | Leu | Asp | Glu | Glu | Val | Gln | Leu | Lys | Ser | Glu | Phe |
| | 210 | | | | | 215 | | | | | 220 | | | | |
| Glu | Lys | Leu | Ser | Asp | Ala | Asp | Lys | Ile | Ser | Asn | Tyr | Lys | Lys | Asp | Gly |
| 225 | | | | | 230 | | | | | 235 | | | | | 240 |
| Lys | Asn | Asp | Gly | Lys | Asn | Asp | Lys | Phe | Val | Gly | Leu | Val | Ala | Asp | Ser |
| | | | | 245 | | | | | 250 | | | | | 255 | |
| Val | Gln | Met | Lys | Gly | Ile | Asn | Gln | Tyr | Ile | Ile | Phe | Tyr | Lys | Pro | Lys |
| | | | 260 | | | | | 265 | | | | | 270 | | |
| Pro | Thr | Ser | Phe | Ala | Arg | Phe | Arg | Arg | Ser | Ala | Arg | Ser | Arg | Arg | Ser |
| | | 275 | | | | | 280 | | | | | 285 | | | |
| Leu | Pro | Ala | Glu | Met | Pro | Leu | Ile | Pro | Val | Asn | Gln | Ala | Asp | Thr | Leu |
| | 290 | | | | | 295 | | | | | 300 | | | | |
| Ile | Val | Asp | Gly | Glu | Ala | Val | Ser | Leu | Thr | Gly | His | Ser | Gly | Asn | Ile |
| 305 | | | | | 310 | | | | | 315 | | | | | 320 |
| Phe | Ala | Pro | Glu | Gly | Asn | Tyr | Arg | Tyr | Leu | Thr | Tyr | Gly | Ala | Glu | Lys |
| | | | | 325 | | | | | 330 | | | | | 335 | |
| Leu | Pro | Gly | Gly | Ser | Tyr | Ala | Leu | Arg | Val | Gln | Gly | Glu | Pro | Ser | Lys |
| | | | 340 | | | | | 345 | | | | | 350 | | |
| Gly | Glu | Met | Leu | Ala | Gly | Thr | Ala | Val | Tyr | Asn | Gly | Glu | Val | Leu | His |
| | | 355 | | | | | 360 | | | | | 365 | | | |
| Phe | His | Thr | Glu | Asn | Gly | Arg | Pro | Ser | Pro | Ser | Arg | Gly | Arg | Phe | Ala |
| | 370 | | | | | 375 | | | | | 380 | | | | |

```
Ala Lys Val Asp Phe Gly Ser Lys Ser Val Asp Gly Ile Ile Asp Ser
385                 390                 395                 400

Gly Asp Gly Leu His Met Gly Thr Gln Lys Phe Lys Ala Ala Ile Asp
                    405                 410                 415

Gly Asn Gly Phe Lys Gly Thr Trp Thr Glu Asn Gly Gly Gly Asp Val
                420                 425                 430

Ser Gly Lys Phe Tyr Gly Pro Ala Gly Glu Val Ala Gly Lys Tyr
            435                 440                 445

Ser Tyr Arg Pro Thr Asp Ala Glu Lys Gly Gly Phe Gly Val Phe Ala
        450                 455                 460

Gly Lys Lys Glu Gln Asp Gly Ser Gly Gly Gly Cys Gln Ser Lys
465                 470                 475                 480

Ser Ile Gln Thr Phe Pro Gln Pro Asp Thr Ser Val Ile Asn Gly Pro
                485                 490                 495

Asp Arg Pro Val Gly Ile Pro Asp Pro Ala Gly Thr Thr Val Gly Gly
            500                 505                 510

Gly Gly Ala Val Tyr Thr Val Val Pro His Leu Ser Leu Pro His Trp
            515                 520                 525

Ala Ala Gln Asp Phe Ala Lys Ser Leu Gln Ser Phe Arg Leu Gly Cys
530                 535                 540

Ala Asn Leu Lys Asn Arg Gln Gly Trp Gln Asp Val Cys Ala Gln Ala
545                 550                 555                 560

Phe Gln Thr Pro Val His Ser Phe Gln Ala Lys Gln Phe Phe Glu Arg
                565                 570                 575

Tyr Phe Thr Pro Trp Gln Val Ala Gly Asn Gly Ser Leu Ala Gly Thr
            580                 585                 590

Val Thr Gly Tyr Tyr Glu Pro Val Leu Lys Gly Asp Asp Arg Arg Thr
        595                 600                 605

Ala Gln Ala Arg Phe Pro Ile Tyr Gly Ile Pro Asp Asp Phe Ile Ser
        610                 615                 620

Val Pro Leu Pro Ala Gly Leu Arg Ser Gly Lys Ala Leu Val Arg Ile
625                 630                 635                 640

Arg Gln Thr Gly Lys Asn Ser Gly Thr Ile Asp Asn Thr Gly Gly Thr
                645                 650                 655

His Thr Ala Asp Leu Ser Arg Phe Pro Ile Thr Ala Arg Thr Thr Ala
                660                 665                 670

Ile Lys Gly Arg Phe Glu Gly Ser Arg Phe Leu Pro Tyr His Thr Arg
            675                 680                 685

Asn Gln Ile Asn Gly Gly Ala Leu Asp Gly Lys Ala Pro Ile Leu Gly
            690                 695                 700

Tyr Ala Glu Asp Pro Val Glu Leu Phe Phe Met His Ile Gln Gly Ser
705                 710                 715                 720

Gly Arg Leu Lys Thr Pro Ser Gly Lys Tyr Ile Arg Ile Gly Tyr Ala
                725                 730                 735

Asp Lys Asn Glu His Pro Tyr Val Ser Ile Gly Arg Tyr Met Ala Asp
                740                 745                 750

Lys Gly Tyr Leu Lys Leu Gly Gln Thr Ser Met Gln Gly Ile Lys Ala
            755                 760                 765

Tyr Met Arg Gln Asn Pro Gln Arg Leu Ala Glu Val Leu Gly Gln Asn
770                 775                 780

Pro Ser Tyr Ile Phe Phe Arg Glu Leu Ala Gly Ser Ser Asn Asp Gly
785                 790                 795                 800

Pro Val Gly Ala Leu Gly Thr Pro Leu Met Gly Glu Tyr Ala Gly Ala
                805                 810                 815
```

```
Val Asp Arg His Tyr Ile Thr Leu Gly Ala Pro Leu Phe Val Ala Thr
        820                 825                 830

Ala His Pro Val Thr Arg Lys Ala Leu Asn Arg Leu Ile Met Ala Gln
        835                 840                 845

Asp Thr Gly Ser Ala Ile Lys Gly Ala Val Arg Val Asp Tyr Phe Trp
        850                 855                 860

Gly Tyr Gly Asp Glu Ala Gly Glu Leu Ala Gly Lys Gln Lys Thr Thr
865                 870                 875                 880

Gly Tyr Val Trp Gln Leu Leu Pro Asn Gly Met Lys Pro Glu Tyr Arg
                885                 890                 895

Pro

<210> SEQ ID NO 96
<211> LENGTH: 1941
<212> TYPE: DNA
<213> ORGANISM: Artificial Sequence
<220> FEATURE:
<223> OTHER INFORMATION: Synthetic construct

<400> SEQUENCE: 96
```

| | | | | | |
|---|---|---|---|---|---|
| atggctagcc | ccgatgtcaa | gtcggcggac | acgctgtcaa | aacctgccgc | ccctgttgtt | 60 |
| tctgaaaaag | agacagaggc | aaaggaagat | gcgccacagg | caggttctca | aggacagggc | 120 |
| gcgccatccg | cacaaggcgg | tcaagatatg | gcggcggttt | cggaagaaaa | tacaggcaat | 180 |
| ggcggtgcgg | cagcaacgga | caaacccaaa | aatgaagacg | aggggcgca | aaatgatatg | 240 |
| ccgcaaaatg | ccgccgatac | agatagtttg | acaccgaatc | acaccccggc | ttcgaatatg | 300 |
| ccggccggaa | atatggaaaa | ccaagcaccg | gatgccgggg | aatcggagca | gccggcaaac | 360 |
| caaccggata | tggcaaatac | ggcggacgga | atgcaggtg | acgatccgtc | ggcaggcggg | 420 |
| gaaaatgccg | gcaataccgc | tgcccaaggt | acaaatcaag | ccgaaaacaa | tcaaaccgcc | 480 |
| ggttctcaaa | atcctgcctc | ttcaaccaat | cctagcgcca | cgaatagcgg | tggtgatttt | 540 |
| ggaaggacga | acgtgggcaa | ttctgttgtg | attgacgggc | cgtcgcaaaa | tataacgttg | 600 |
| acccactgta | aaggcgattc | ttgtagtggc | aataatttct | ggatgaaga | agtacagcta | 660 |
| aaatcagaat | ttgaaaaatt | aagtgatgca | gacaaaataa | gtaattacaa | gaaagatggg | 720 |
| aagaatgacg | ggaagaatga | taaatttgtc | ggtttggttg | ccgatagtgt | gcagatgaag | 780 |
| ggaatcaatc | aatatattat | ctttttataaa | cctaaaccca | cttcatttgc | gcgatttagg | 840 |
| cgttctgcac | ggtcgaggcg | gtcgcttccg | gccgagatgc | cgctgattcc | cgtcaatcag | 900 |
| gcggatacgc | tgattgtcga | tggggaagcg | gtcagcctga | cggggcattc | cggcaatatc | 960 |
| ttcgcgcccg | aagggaatta | ccggtatctg | acttacgggg | cggaaaaatt | gcccggcgga | 1020 |
| tcgtatgccc | tccgtgttca | aggcgaacct | tcaaaaggcg | aaatgctcgc | gggcacggca | 1080 |
| gtgtacaacg | gcgaagtgct | gcattttcat | acggaaaacg | gccgtccgtc | ccgtccaga | 1140 |
| ggcaggtttg | ccgcaaaagt | cgatttcggc | agcaaatctg | tggacggcat | tatcgacagc | 1200 |
| ggcgatggtt | tgcatatggg | tacgcaaaaa | ttcaaagccg | ccatcgatgg | aaacggcttt | 1260 |
| aagggggactt | ggacggaaaa | tggcggcggg | gatgtttccg | gaaagtttta | cggcccggcc | 1320 |
| ggcgaggaag | tggcgggaaa | atacagctat | cgcccaacag | atgcggaaaa | gggcggattc | 1380 |
| ggcgtgtttg | ccggcaaaaa | agagcaggat | ggatccggag | gaggaggagc | cacctacaaa | 1440 |
| gtggacgaat | atcacgccaa | cgcccgtttc | gccatcgacc | atttcaacac | cagcaccaac | 1500 |
| gtcggcggtt | tttacggtct | gaccggttcc | gtcgagttcg | accaagcaaa | acgcgacggt | 1560 |

-continued

```
aaaatcgaca tcaccatccc cgttgccaac ctgcaaagcg gttcgcaaca ctttaccgac    1620
cacctgaaat cagccgacat cttcgatgcc gcccaatatc cggacatccg ctttgtttcc    1680
accaaattca acttcaacgg caaaaaactg gtttccgttg acggcaacct gaccatgcac    1740
ggcaaaaccg cccccgtcaa actcaaagcc gaaaaattca actgctacca aagcccgatg    1800
gcgaaaaccg aagtttgcgg cggcgacttc agcaccacca tcgaccgcac caaatggggc    1860
gtggactacc tcgttaacgt tggtatgacc aaaagcgtcc gcatcgacat ccaaatcgag    1920
gcagccaaac aataaaagct t                                              1941
```

<210> SEQ ID NO 97
<211> LENGTH: 644
<212> TYPE: PRT
<213> ORGANISM: Artificial Sequence
<220> FEATURE:
<223> OTHER INFORMATION: Synthetic construct

<400> SEQUENCE: 97

```
Met Ala Ser Pro Asp Val Lys Ser Ala Asp Thr Leu Ser Lys Pro Ala
1               5                   10                  15

Ala Pro Val Val Ser Glu Lys Glu Thr Glu Ala Lys Glu Asp Ala Pro
            20                  25                  30

Gln Ala Gly Ser Gln Gly Gln Gly Ala Pro Ser Ala Gln Gly Gly Gln
        35                  40                  45

Asp Met Ala Ala Val Ser Glu Glu Asn Thr Gly Asn Gly Gly Ala Ala
    50                  55                  60

Ala Thr Asp Lys Pro Lys Asn Glu Asp Glu Gly Ala Gln Asn Asp Met
65                  70                  75                  80

Pro Gln Asn Ala Ala Asp Thr Asp Ser Leu Thr Pro Asn His Thr Pro
                85                  90                  95

Ala Ser Asn Met Pro Ala Gly Asn Met Glu Asn Gln Ala Pro Asp Ala
            100                 105                 110

Gly Glu Ser Glu Gln Pro Ala Asn Gln Pro Asp Met Ala Asn Thr Ala
        115                 120                 125

Asp Gly Met Gln Gly Asp Pro Ser Ala Gly Gly Glu Asn Ala Gly
    130                 135                 140

Asn Thr Ala Ala Gln Gly Thr Asn Gln Ala Glu Asn Asn Gln Thr Ala
145                 150                 155                 160

Gly Ser Gln Asn Pro Ala Ser Ser Thr Asn Pro Ser Ala Thr Asn Ser
                165                 170                 175

Gly Gly Asp Phe Gly Arg Thr Asn Val Gly Asn Ser Val Val Ile Asp
            180                 185                 190

Gly Pro Ser Gln Asn Ile Thr Leu Thr His Cys Lys Gly Asp Ser Cys
        195                 200                 205

Ser Gly Asn Asn Phe Leu Asp Glu Glu Val Gln Leu Lys Ser Glu Phe
    210                 215                 220

Glu Lys Leu Ser Asp Ala Asp Lys Ile Ser Asn Tyr Lys Lys Asp Gly
225                 230                 235                 240

Lys Asn Asp Gly Lys Asn Asp Lys Phe Val Gly Leu Val Ala Asp Ser
                245                 250                 255

Val Gln Met Lys Gly Ile Asn Gln Tyr Ile Ile Phe Tyr Lys Pro Lys
            260                 265                 270

Pro Thr Ser Phe Ala Arg Phe Arg Arg Ser Ala Arg Ser Arg Arg Ser
        275                 280                 285

Leu Pro Ala Glu Met Pro Leu Ile Pro Val Asn Gln Ala Asp Thr Leu
    290                 295                 300
```

```
Ile Val Asp Gly Glu Ala Val Ser Leu Thr Gly His Ser Gly Asn Ile
305                 310                 315                 320

Phe Ala Pro Glu Gly Asn Tyr Arg Tyr Leu Thr Tyr Gly Ala Glu Lys
            325                 330                 335

Leu Pro Gly Gly Ser Tyr Ala Leu Arg Val Gln Gly Glu Pro Ser Lys
        340                 345                 350

Gly Glu Met Leu Ala Gly Thr Ala Val Tyr Asn Gly Glu Val Leu His
    355                 360                 365

Phe His Thr Glu Asn Gly Arg Pro Ser Pro Ser Arg Gly Arg Phe Ala
370                 375                 380

Ala Lys Val Asp Phe Gly Ser Lys Ser Val Asp Gly Ile Ile Asp Ser
385                 390                 395                 400

Gly Asp Gly Leu His Met Gly Thr Gln Lys Phe Lys Ala Ala Ile Asp
                405                 410                 415

Gly Asn Gly Phe Lys Gly Thr Trp Thr Glu Asn Gly Gly Asp Val
            420                 425                 430

Ser Gly Lys Phe Tyr Gly Pro Ala Gly Glu Glu Val Ala Gly Lys Tyr
        435                 440                 445

Ser Tyr Arg Pro Thr Asp Ala Glu Lys Gly Gly Phe Gly Val Phe Ala
450                 455                 460

Gly Lys Lys Glu Gln Asp Gly Ser Gly Gly Gly Ala Thr Tyr Lys
465                 470                 475                 480

Val Asp Glu Tyr His Ala Asn Ala Arg Phe Ala Ile Asp His Phe Asn
                485                 490                 495

Thr Ser Thr Asn Val Gly Gly Phe Tyr Gly Leu Thr Gly Ser Val Glu
            500                 505                 510

Phe Asp Gln Ala Lys Arg Asp Gly Lys Ile Asp Ile Thr Ile Pro Val
        515                 520                 525

Ala Asn Leu Gln Ser Gly Ser Gln His Phe Thr Asp His Leu Lys Ser
530                 535                 540

Ala Asp Ile Phe Asp Ala Ala Gln Tyr Pro Asp Ile Arg Phe Val Ser
545                 550                 555                 560

Thr Lys Phe Asn Phe Asn Gly Lys Lys Leu Val Ser Val Asp Gly Asn
                565                 570                 575

Leu Thr Met His Gly Lys Thr Ala Pro Val Lys Leu Lys Ala Glu Lys
            580                 585                 590

Phe Asn Cys Tyr Gln Ser Pro Met Ala Lys Thr Glu Val Cys Gly Gly
        595                 600                 605

Asp Phe Ser Thr Thr Ile Asp Arg Thr Lys Trp Gly Val Asp Tyr Leu
610                 615                 620

Val Asn Val Gly Met Thr Lys Ser Val Arg Ile Asp Ile Gln Ile Glu
625                 630                 635                 640

Ala Ala Lys Gln

<210> SEQ ID NO 98
<211> LENGTH: 2583
<212> TYPE: DNA
<213> ORGANISM: Artificial Sequence
<220> FEATURE:
<223> OTHER INFORMATION: Synthetic construct

<400> SEQUENCE: 98
atggctagcc ccgatgtcaa gtcggcggac acgctgtcaa aacctgccgc ccctgttgtt      60
tctgaaaaag agacagaggc aaaggaagat gcgccacagg caggttctca aggacagggc     120
```

```
gcgccatccg cacaaggcgg tcaagatatg gcggcggttt cggaagaaaa tacaggcaat    180
ggcggtgcgg cagcaacgga caaacccaaa aatgaagacg aggggggcgca aaatgatatg   240
ccgcaaaatg ccgccgatac agatagtttg acaccgaatc acaccccggc ttcgaatatg    300
ccggccggaa atatggaaaa ccaagcaccg gatgccgggg aatcggagca gccggcaaac    360
caaccggata tggcaaatac ggcggacgga atgcagggtg acgatccgtc ggcaggcggg    420
gaaaatgccg gcaatacggc tgcccaaggt acaaatcaag ccgaaaacaa tcaaaccgcc    480
ggttctcaaa atcctgcctc ttcaaccaat cctagcgcca cgaatagcgg tggtgatttt    540
ggaaggacga acgtgggcaa ttctgttgtg attgacgggc cgtcgcaaaa tataacgttg    600
acccactgta aaggcgattc ttgtagtggc aataatttct tggatgaaga agtacagcta    660
aaatcagaat ttgaaaaatt aagtgatgca gacaaaataa gtaattacaa gaaagatggg    720
aagaatgacg ggaagaatga taaatttgtc ggtttggttg ccgatagtgt gcagatgaag    780
ggaatcaatc aatatattat cttttataaa cctaaaccca cttcatttgc gcgatttagg    840
cgttctgcac ggtcgaggcg gtcgcttccg gccgagatgc cgctgattcc cgtcaatcag    900
gcggatacgt gattgtcga tgggggaagcg gtcagcctga cggggcattc cggcaatatc    960
ttcgcgcccg aagggaatta ccggtatctg acttacgggg cggaaaaatt gcccggcgga   1020
tcgtatgccc tccgtgttca aggcgaacct tcaaaaggcg aaatgctcgc gggcacggca   1080
gtgtacaacg gcgaagtgct gcattttcat acggaaaacg gccgtccgtc cccgtccaga   1140
ggcaggtttg ccgcaaaagt cgatttcggc agcaaatctg tggacggcat tatcgacagc   1200
ggcgatggtt tgcatatggg tacgcaaaaa ttcaaagccg ccatcgatgg aaacggcttt   1260
aaggggactt ggacggaaaa tggcggcggg gatgttccg gaaagtttta cggcccggcc    1320
ggcgaggaag tggcgggaaa atacagctat cgcccaacag atgcggaaaa gggcggattc   1380
ggcgtgtttg ccggcaaaaa agagcaggat ggatccggag gaggaggagc cacaaacgac   1440
gacgatgtta aaaaagctgc cactgtggcc attgctgctg cctacaacaa tggccaagaa   1500
atcaacggtt tcaaagctgg agagaccatc tacgacattg atgaagacgg cacaattacc   1560
aaaaaagacg caactgcagc cgatgttgaa gccgacgact ttaaaggtct gggtctgaaa   1620
aaagtcgtga ctaacctgac caaaaccgtc aatgaaaaca acaaaacgt cgatgccaaa    1680
gtaaaagctg cagaatctga aatagaaaag ttaacaacca agttagcaga cactgatgcc   1740
gctttagcag atactgatgc cgctctggat gcaaccacca acgccttgaa taaattggga   1800
gaaaatataa cgacatttgc tgaagagact aagacaaata tcgtaaaaat tgatgaaaaa   1860
ttagaagccg tggctgatac cgtcgacaag catgccgaag cattcaacga tatcgccgat   1920
tcattggatg aaaccaacac taaggcagac gaagccgtca aaccgccaa tgaagccaaa    1980
cagacggccg aagaaccaa acaaaacgtc gatgccaaag taaaagctgc agaaactgca   2040
gcaggcaaag ccgaagctgc cgctggcaca gctaatactg cagccgacaa ggccgaagct   2100
gtcgctgcaa aagttaccga catcaaagct gatatcgcta cgaacaaaga taatattgct   2160
aaaaaagcaa acagtgccga cgtgtacacc agagaagagt ctgacagcaa atttgtcaga   2220
attgatggtc tgaacgctac taccgaaaaa ttggacacac gcttggcttc tgctgaaaaa   2280
tccattgccg atcacgatac tcgcctgaac ggttttggata aacagtgtc agacctgcgc   2340
aaagaaaccc gccaaggcct tgcagaacaa gccgcgctct ccggtctgtt ccaaccttac   2400
aacgtgggtc ggttcaatgt aacggctgca gtcggcggct acaaatccga atcggcagtc   2460
gccatcggta ccggcttccg ctttaccgaa aactttgccg ccaaagcagg cgtggcagtc   2520
```

```
ggcacttcgt ccggttcttc cgcagcctac catgtcggcg tcaattacga gtggtaaaag   2580
ctt                                                                 2583
```

<210> SEQ ID NO 99
<211> LENGTH: 858
<212> TYPE: PRT
<213> ORGANISM: Artificial Sequence
<220> FEATURE:
<223> OTHER INFORMATION: Synthetic construct

<400> SEQUENCE: 99

```
Met Ala Ser Pro Asp Val Lys Ser Ala Asp Thr Leu Ser Lys Pro Ala
1               5                   10                  15

Ala Pro Val Val Ser Glu Lys Glu Thr Glu Ala Lys Glu Asp Ala Pro
            20                  25                  30

Gln Ala Gly Ser Gln Gly Gln Gly Ala Pro Ser Ala Gln Gly Gly Gln
        35                  40                  45

Asp Met Ala Ala Val Ser Glu Glu Asn Thr Gly Asn Gly Gly Ala Ala
    50                  55                  60

Ala Thr Asp Lys Pro Lys Asn Glu Asp Glu Gly Ala Gln Asn Asp Met
65                  70                  75                  80

Pro Gln Asn Ala Ala Asp Thr Asp Ser Leu Thr Pro Asn His Thr Pro
                85                  90                  95

Ala Ser Asn Met Pro Ala Gly Asn Met Glu Asn Gln Ala Pro Asp Ala
            100                 105                 110

Gly Glu Ser Glu Gln Pro Ala Asn Gln Pro Asp Met Ala Asn Thr Ala
        115                 120                 125

Asp Gly Met Gln Gly Asp Asp Pro Ser Ala Gly Gly Glu Asn Ala Gly
    130                 135                 140

Asn Thr Ala Ala Gln Gly Thr Asn Gln Ala Glu Asn Asn Gln Thr Ala
145                 150                 155                 160

Gly Ser Gln Asn Pro Ala Ser Ser Thr Asn Pro Ser Ala Thr Asn Ser
                165                 170                 175

Gly Gly Asp Phe Gly Arg Thr Asn Val Gly Asn Ser Val Val Ile Asp
            180                 185                 190

Gly Pro Ser Gln Asn Ile Thr Leu Thr His Cys Lys Gly Asp Ser Cys
        195                 200                 205

Ser Gly Asn Asn Phe Leu Asp Glu Glu Val Gln Leu Lys Ser Glu Phe
    210                 215                 220

Glu Lys Leu Ser Asp Ala Asp Lys Ile Ser Asn Tyr Lys Lys Asp Gly
225                 230                 235                 240

Lys Asn Asp Gly Lys Asn Asp Lys Phe Val Gly Leu Val Ala Asp Ser
                245                 250                 255

Val Gln Met Lys Gly Ile Asn Gln Tyr Ile Ile Phe Tyr Lys Pro Lys
            260                 265                 270

Pro Thr Ser Phe Ala Arg Phe Arg Arg Ser Ala Arg Ser Arg Arg Ser
        275                 280                 285

Leu Pro Ala Glu Met Pro Leu Ile Pro Val Asn Gln Ala Asp Thr Leu
    290                 295                 300

Ile Val Asp Gly Glu Ala Val Ser Leu Thr Gly His Ser Gly Asn Ile
305                 310                 315                 320

Phe Ala Pro Glu Gly Asn Tyr Arg Tyr Leu Thr Tyr Gly Ala Glu Lys
                325                 330                 335

Leu Pro Gly Gly Ser Tyr Ala Leu Arg Val Gln Gly Glu Pro Ser Lys
            340                 345                 350
```

```
Gly Glu Met Leu Ala Gly Thr Ala Val Tyr Asn Gly Glu Val Leu His
            355                 360                 365
Phe His Thr Glu Asn Gly Arg Pro Ser Pro Ser Arg Gly Arg Phe Ala
    370                 375                 380
Ala Lys Val Asp Phe Gly Ser Lys Ser Val Asp Gly Ile Ile Asp Ser
385                 390                 395                 400
Gly Asp Gly Leu His Met Gly Thr Gln Lys Phe Lys Ala Ala Ile Asp
                405                 410                 415
Gly Asn Gly Phe Lys Gly Thr Trp Thr Glu Asn Gly Gly Asp Val
                420                 425                 430
Ser Gly Lys Phe Tyr Gly Pro Ala Gly Glu Val Ala Gly Lys Tyr
            435                 440                 445
Ser Tyr Arg Pro Thr Asp Ala Glu Lys Gly Phe Gly Val Phe Ala
    450                 455                 460
Gly Lys Lys Glu Gln Asp Gly Ser Gly Gly Gly Ala Thr Asn Asp
465                 470                 475                 480
Asp Asp Val Lys Lys Ala Ala Thr Val Ala Ile Ala Ala Tyr Asn
                485                 490                 495
Asn Gly Gln Glu Ile Asn Gly Phe Lys Ala Gly Glu Thr Ile Tyr Asp
                500                 505                 510
Ile Asp Glu Asp Gly Thr Ile Thr Lys Lys Asp Ala Thr Ala Ala Asp
                515                 520                 525
Val Glu Ala Asp Asp Phe Lys Gly Leu Gly Leu Lys Lys Val Val Thr
            530                 535                 540
Asn Leu Thr Lys Thr Val Asn Glu Asn Lys Gln Asn Val Asp Ala Lys
545                 550                 555                 560
Val Lys Ala Ala Glu Ser Glu Ile Glu Lys Leu Thr Thr Lys Leu Ala
                565                 570                 575
Asp Thr Asp Ala Ala Leu Ala Asp Thr Ala Ala Leu Asp Ala Thr
            580                 585                 590
Thr Asn Ala Leu Asn Lys Leu Gly Glu Asn Ile Thr Thr Phe Ala Glu
            595                 600                 605
Glu Thr Lys Thr Asn Ile Val Lys Ile Asp Glu Lys Leu Glu Ala Val
            610                 615                 620
Ala Asp Thr Val Asp Lys His Ala Glu Ala Phe Asn Asp Ile Ala Asp
625                 630                 635                 640
Ser Leu Asp Glu Thr Asn Thr Lys Ala Asp Glu Ala Val Lys Thr Ala
                645                 650                 655
Asn Glu Ala Lys Gln Thr Ala Glu Glu Thr Lys Gln Asn Val Asp Ala
                660                 665                 670
Lys Val Lys Ala Ala Glu Thr Ala Ala Gly Lys Ala Glu Ala Ala Ala
            675                 680                 685
Gly Thr Ala Asn Thr Ala Ala Asp Lys Ala Glu Ala Val Ala Ala Lys
            690                 695                 700
Val Thr Asp Ile Lys Ala Asp Ile Ala Thr Asn Lys Asp Asn Ile Ala
705                 710                 715                 720
Lys Lys Ala Asn Ser Ala Asp Val Tyr Thr Arg Glu Glu Ser Asp Ser
                725                 730                 735
Lys Phe Val Arg Ile Asp Gly Leu Asn Ala Thr Thr Glu Lys Leu Asp
                740                 745                 750
Thr Arg Leu Ala Ser Ala Glu Lys Ser Ile Ala Asp His Asp Thr Arg
            755                 760                 765
Leu Asn Gly Leu Asp Lys Thr Val Ser Asp Leu Arg Lys Glu Thr Arg
            770                 775                 780
```

```
Gln Gly Leu Ala Glu Gln Ala Ala Leu Ser Gly Leu Phe Gln Pro Tyr
785                 790                 795                 800

Asn Val Gly Arg Phe Asn Val Thr Ala Ala Val Gly Gly Tyr Lys Ser
            805                 810                 815

Glu Ser Ala Val Ala Ile Gly Thr Gly Phe Arg Phe Thr Glu Asn Phe
        820                 825                 830

Ala Ala Lys Ala Gly Val Ala Val Gly Thr Ser Ser Gly Ser Ser Ala
    835                 840                 845

Ala Tyr His Val Gly Val Asn Tyr Glu Trp
    850                 855

<210> SEQ ID NO 100
<211> LENGTH: 4425
<212> TYPE: DNA
<213> ORGANISM: Artificial Sequence
<220> FEATURE:
<223> OTHER INFORMATION: Synthetic construct

<400> SEQUENCE: 100
atgacttctg cgcccgactt caatgcaggc ggtaccggta tcggcagcaa cagcagagca      60
acaacagcga aatcagcagc agtatcttac gccggtatca agaacgaaat gtgcaaagac     120
agaagcatgc tctgtgccgg tcgggatgac gttgcggtta cagacaggga tgccaaaatc     180 aatgccccc ccccgaatct gcataccgga gactttccaa acccaaatga cgcatacaag     240
aatttgatca acctcaaacc tgcaattgaa gcaggctata caggacgcgg ggtagaggta     300
ggtatcgtcg acacaggcga atccgtcggc agcatatcct ttcccgaact gtatggcaga     360
aaagaacacg gctataacga aaattacaaa actatacgg cgtatatgcg gaaggaagcg     420
cctgaagacg gaggcggtaa agacattgaa gcttctttcg acgatgaggc cgttatagag     480
actgaagcaa agccgacgga tatccgccac gtaaaagaaa tcggacacat cgatttggtc     540
tcccatatta ttggcgggcg ttccgtgac ggcagacctg caggcggtat tgcgcccgat     600
gcgacgctac acataatgaa tacgaatgat gaaaccaaga cgaaatgat ggttgcagcc     660 atccgcaatg catgggtcaa gctgggcgaa cgtggcgtgc gcatcgtcaa taacagtttt     720
ggaacaacat cgagggcagg cactgccgac cttttccaaa tagccaattc ggaggagcag     780
taccgccaag cgttgctcga ctattccggc ggtgataaaa cagacgaggg tatccgcctg     840
atgcaacaga gcgattacgg caacctgtcc taccacatcc gtaataaaaa catgcttttc     900
atcttttcga caggcaatga cgcacaagct cagcccaaca catatgccct attgccattt     960
tatgaaaaag acgctcaaaa aggcattatc acagtcgcag gcgtagaccg cagtggagaa    1020
aagttcaaac gggaaatgta tggagaaccg ggtacagaac cgcttgagta tggctccaac    1080
cattgcggaa ttactgccat gtggtgcctg tcggcaccct atgaagcaag cgtccgtttc    1140
acccgtacaa acccgattca aattgccgga acatcctttt ccgcacccat cgtaaccggc    1200
acggcggctc tgctgctgca gaaatacccg tggatgagca acgacaacct gcgtaccacg    1260
ttgctgacga cggctcagga catcggtgca gtcggcgtgg acagcaagtt cggctggga    1320 ctgctggatg cgggtaaggc catgaacgga cccgcgtcct ttccgttcgg cgactttacc    1380
gccgatacga aagtacatc cgatattgcc tactccttcc gtaacgacat ttcaggcacg    1440
ggcggcctga tcaaaaaagg cggcagccaa ctgcaactgc acggcaacaa cacctatacg    1500
ggcaaaacca ttatcgaagg cggttcgctg gtgttgtacg gcaacaacaa atcggatatg    1560
cgcgtcgaaa ccaaaggtgc gctgattat aacggggcgg catccggcgg cagccctgaac    1620
```

| | |
|---|---|
| agcgacggca ttgtctatct ggcagatacc gaccaatccg gcgcaaacga aaccgtacac | 1680 |
| atcaaaggca gtctgcagct ggacggcaaa ggtacgctgt acacacgttt gggcaaactg | 1740 |
| ctgaaagtgg acggtacggc gattatcggc ggcaagctgt acatgtcggc acgcggcaag | 1800 |
| ggggcaggct atctcaacag taccggacga cgtgttccct tcctgagtgc cgccaaaatc | 1860 |
| gggcaggatt attctttctt cacaaacatc gaaaccgacg gcggcctgct ggcttccctc | 1920 |
| gacagcgtcg aaaaaacagc gggcagtgaa ggcgacacgc tgtcctatta tgtccgtcgc | 1980 |
| ggcaatgcgg cacggactgc ttcggcagcg gcacattccg cgcccgccgg tctgaaacac | 2040 |
| gccgtagaac agggcggcag caatctggaa aacctgatgg tcgaactgga tgcctccgaa | 2100 |
| tcatccgcaa cacccgagac ggttgaaact gcggcagccg accgcacaga tatgccgggc | 2160 |
| atccgcccct acgcgcaac tttccgcgca gcggcagccg tacagcatgc gaatgccgcc | 2220 |
| gacggtgtac gcatcttcaa cagtctcgcc gctaccgtct atgccgacag taccgccgcc | 2280 |
| catgccgata tgcagggacg ccgcctgaaa gccgtatcgg acgggttgga ccacaacggc | 2340 |
| acgggtctgc gcgtcatcgc gcaaacccaa caggacggtg aacgtgggga acagggcggt | 2400 |
| gttgaaggca aaatgcgcgg cagtacccaa accgtcggca ttgccgcgaa aaccggcgaa | 2460 |
| aatacgacag cagccgccac actgggcatg ggacgcagca catggagcga aaacagtgca | 2520 |
| aatgcaaaaa ccgacagcat tagtctgttt gcaggcatac ggcacgatgc gggcgatatc | 2580 |
| ggctatctca aaggcctgtt ctcctacgga cgctacaaaa acagcatcag ccgcagcacc | 2640 |
| ggtgcggacg aacatgcgga aggcagcgtc aacggcacgc tgatgcagct gggcgcactg | 2700 |
| ggcggtgtca acgttccgtt tgccgcaacg ggagatttga cggtcgaagg cggtctgcgc | 2760 |
| tacgacctgc tcaaacagga tgcattcgcc gaaaaaggca gtgctttggg ctggagcggc | 2820 |
| aacagcctca ctgaaggcac gctggtcgga ctcgcgggtc tgaagctgtc gcaacccttg | 2880 |
| agcgataaag ccgtcctgtt tgcaacggcg ggcgtggaac gcgacctgaa cggacgcgac | 2940 |
| tacacggtaa cgggcggctt taccggcgcg actgcagcaa ccggcaagac gggggcacgc | 3000 |
| aatatgccgc acacccgtct ggttgccggc ctgggcgcgg atgtcgaatt cggcaacggc | 3060 |
| tggaacggct tggcacgtta cagctacgcc ggttccaaac agtacggcaa ccacagcgga | 3120 |
| cgagtcggcg taggctaccg gttcctcgac ggtggcggag gcactggatc ctcagatttg | 3180 |
| gcaaacgatt cttttatccg gcaggttctc gaccgtcagc atttcgaacc cgacgggaaa | 3240 |
| taccacctat tcggcagcag gggggaactt gccgagcgca gcggccatat cggattggga | 3300 |
| aaaatacaaa gccatcagtt gggcaacctg atgattcaac aggcggccat taaggaaat | 3360 |
| atcggctaca ttgtccgctt ttccgatcac gggcacgaag tccattcccc cttcgacaac | 3420 |
| catgcctcac attccgattc tgatgaagcc ggtagtcccg ttgacggatt tagcctttac | 3480 |
| cgcatccatt gggacggata cgaacaccat cccgccgacg gctatgacgg gccacagggc | 3540 |
| ggcggctatc ccgctcccaa aggcgcgagg gatatataca gctacgacat aaaaggcgtt | 3600 |
| gcccaaaata tccgcctcaa cctgaccgac aaccgcagca ccggacaacg gcttgccgac | 3660 |
| cgtttccaca atgccggtag tatgctgacg caaggagtag gcgacggatt caaacgcgcc | 3720 |
| acccgataca gccccgagct ggacagatcg ggcaatgccg ccgaagcctt caacggcact | 3780 |
| gcagatatcg ttaaaaacat catcggcgcg gcaggagaaa ttgtcggcgc aggcgatgcc | 3840 |
| gtgcagggca taagcgaagg ctcaaacatt gctgtcatgc acggcttggg tctgctttcc | 3900 |
| accgaaaaca agatggcgcg catcaacgat ttggcagata tggcgcaact caaagactat | 3960 |
| gccgcagcag ccatccgcga ttgggcagtc caaaaccccca atgccgcaca aggcatagaa | 4020 |

-continued

```
gccgtcagca atatctttat ggcagccatc cccatcaaag ggattggagc tgttcgggga    4080
aaatacggct tgggcggcat cacggcacat cctatcaagc ggtcgcagat gggcgcgatc    4140
gcattgccga aagggaaatc cgccgtcagc gacaattttg ccgatgcggc atacgccaaa    4200
tacccgtccc cttaccattc ccgaaatatc cgttcaaact tggagcagcg ttacggcaaa    4260
gaaaacatca cctcctcaac cgtgccgccg tcaaacggca aaaatgtcaa actggcagac    4320
caacgccacc cgaagacagg cgtaccgttt gacggtaaag ggtttccgaa ttttgagaag    4380
cacgtgaaat atgatacgct cgagcaccac caccaccacc actga                   4425
```

<210> SEQ ID NO 101
<211> LENGTH: 1474
<212> TYPE: PRT
<213> ORGANISM: Artificial Sequence
<220> FEATURE:
<223> OTHER INFORMATION: Synthetic construct

<400> SEQUENCE: 101

```
Met Thr Ser Ala Pro Asp Phe Asn Ala Gly Gly Thr Gly Ile Gly Ser
1               5                   10                  15

Asn Ser Arg Ala Thr Thr Ala Lys Ser Ala Ala Val Ser Tyr Ala Gly
            20                  25                  30

Ile Lys Asn Glu Met Cys Lys Asp Arg Ser Met Leu Cys Ala Gly Arg
        35                  40                  45

Asp Asp Val Ala Val Thr Arg Asp Ala Lys Ile Asn Ala Pro Pro
    50                  55                  60

Pro Asn Leu His Thr Gly Asp Phe Pro Asn Pro Asn Ala Tyr Lys
65                  70                  75                  80

Asn Leu Ile Asn Leu Lys Pro Ala Ile Glu Ala Gly Tyr Thr Gly Arg
                85                  90                  95

Gly Val Glu Val Gly Ile Val Asp Thr Gly Glu Ser Val Gly Ser Ile
            100                 105                 110

Ser Phe Pro Glu Leu Tyr Gly Arg Lys Glu His Gly Tyr Asn Glu Asn
        115                 120                 125

Tyr Lys Asn Tyr Thr Ala Tyr Met Arg Lys Glu Ala Pro Glu Asp Gly
    130                 135                 140

Gly Gly Lys Asp Ile Glu Ala Ser Phe Asp Asp Glu Ala Val Ile Glu
145                 150                 155                 160

Thr Glu Ala Lys Pro Thr Asp Ile Arg His Val Lys Glu Ile Gly His
                165                 170                 175

Ile Asp Leu Val Ser His Ile Ile Gly Gly Arg Ser Val Asp Gly Arg
            180                 185                 190

Pro Ala Gly Gly Ile Ala Pro Asp Ala Thr Leu His Ile Met Asn Thr
        195                 200                 205

Asn Asp Glu Thr Lys Asn Glu Met Met Val Ala Ala Ile Arg Asn Ala
    210                 215                 220

Trp Val Lys Leu Gly Glu Arg Gly Val Arg Ile Val Asn Asn Ser Phe
225                 230                 235                 240

Gly Thr Thr Ser Arg Ala Gly Thr Ala Asp Leu Phe Gln Ile Ala Asn
                245                 250                 255

Ser Glu Glu Gln Tyr Arg Gln Ala Leu Leu Asp Tyr Ser Gly Gly Asp
            260                 265                 270

Lys Thr Asp Glu Gly Ile Arg Leu Met Gln Gln Ser Asp Tyr Gly Asn
        275                 280                 285

Leu Ser Tyr His Ile Arg Asn Lys Asn Met Leu Phe Ile Phe Ser Thr
    290                 295                 300
```

-continued

```
Gly Asn Asp Ala Gln Ala Gln Pro Asn Thr Tyr Ala Leu Leu Pro Phe
305                 310                 315                 320

Tyr Glu Lys Asp Ala Gln Lys Gly Ile Ile Thr Val Ala Gly Val Asp
                325                 330                 335

Arg Ser Gly Glu Lys Phe Lys Arg Glu Met Tyr Gly Glu Pro Gly Thr
            340                 345                 350

Glu Pro Leu Glu Tyr Gly Ser Asn His Cys Gly Ile Thr Ala Met Trp
        355                 360                 365

Cys Leu Ser Ala Pro Tyr Glu Ala Ser Val Arg Phe Thr Arg Thr Asn
    370                 375                 380

Pro Ile Gln Ile Ala Gly Thr Ser Phe Ser Ala Pro Ile Val Thr Gly
385                 390                 395                 400

Thr Ala Ala Leu Leu Leu Gln Lys Tyr Pro Trp Met Ser Asn Asp Asn
                405                 410                 415

Leu Arg Thr Thr Leu Leu Thr Thr Ala Gln Asp Ile Gly Ala Val Gly
            420                 425                 430

Val Asp Ser Lys Phe Gly Trp Gly Leu Leu Asp Ala Gly Lys Ala Met
        435                 440                 445

Asn Gly Pro Ala Ser Phe Pro Phe Gly Asp Phe Thr Ala Asp Thr Lys
    450                 455                 460

Gly Thr Ser Asp Ile Ala Tyr Ser Phe Arg Asn Asp Ile Ser Gly Thr
465                 470                 475                 480

Gly Gly Leu Ile Lys Lys Gly Gly Ser Gln Leu Gln Leu His Gly Asn
                485                 490                 495

Asn Thr Tyr Thr Gly Lys Thr Ile Ile Glu Gly Gly Ser Leu Val Leu
            500                 505                 510

Tyr Gly Asn Asn Lys Ser Asp Met Arg Val Glu Thr Lys Gly Ala Leu
        515                 520                 525

Ile Tyr Asn Gly Ala Ala Ser Gly Gly Ser Leu Asn Ser Asp Gly Ile
    530                 535                 540

Val Tyr Leu Ala Asp Thr Asp Gln Ser Gly Ala Asn Glu Thr Val His
545                 550                 555                 560

Ile Lys Gly Ser Leu Gln Leu Asp Gly Lys Gly Thr Leu Tyr Thr Arg
                565                 570                 575

Leu Gly Lys Leu Leu Lys Val Asp Gly Thr Ala Ile Ile Gly Gly Lys
            580                 585                 590

Leu Tyr Met Ser Ala Arg Gly Lys Gly Ala Gly Tyr Leu Asn Ser Thr
        595                 600                 605

Gly Arg Arg Val Pro Phe Leu Ser Ala Ala Lys Ile Gly Gln Asp Tyr
    610                 615                 620

Ser Phe Phe Thr Asn Ile Glu Thr Asp Gly Gly Leu Leu Ala Ser Leu
625                 630                 635                 640

Asp Ser Val Glu Lys Thr Ala Gly Ser Glu Gly Asp Thr Leu Ser Tyr
                645                 650                 655

Tyr Val Arg Arg Gly Asn Ala Ala Arg Thr Ala Ser Ala Ala Ala His
            660                 665                 670

Ser Ala Pro Ala Gly Leu Lys His Ala Val Glu Gln Gly Gly Ser Asn
        675                 680                 685

Leu Glu Asn Leu Met Val Glu Leu Asp Ala Ser Glu Ser Ser Ala Thr
    690                 695                 700

Pro Glu Thr Val Glu Thr Ala Ala Ala Asp Arg Thr Asp Met Pro Gly
705                 710                 715                 720

Ile Arg Pro Tyr Gly Ala Thr Phe Arg Ala Ala Ala Ala Val Gln His
```

```
                    725                 730                 735
Ala Asn Ala Ala Asp Gly Val Arg Ile Phe Asn Ser Leu Ala Ala Thr
                740                 745                 750

Val Tyr Ala Asp Ser Thr Ala Ala His Ala Asp Met Gln Gly Arg Arg
                755                 760                 765

Leu Lys Ala Val Ser Asp Gly Leu Asp His Asn Gly Thr Gly Leu Arg
                770                 775                 780

Val Ile Ala Gln Thr Gln Asp Gly Gly Thr Trp Glu Gln Gly Gly
785                 790                 795                 800

Val Glu Gly Lys Met Arg Gly Ser Thr Gln Thr Val Gly Ile Ala Ala
                805                 810                 815

Lys Thr Gly Glu Asn Thr Thr Ala Ala Ala Thr Leu Gly Met Gly Arg
                820                 825                 830

Ser Thr Trp Ser Glu Asn Ser Ala Asn Ala Lys Thr Asp Ser Ile Ser
                835                 840                 845

Leu Phe Ala Gly Ile Arg His Asp Ala Gly Asp Ile Gly Tyr Leu Lys
                850                 855                 860

Gly Leu Phe Ser Tyr Gly Arg Tyr Lys Asn Ser Ile Ser Arg Ser Thr
865                 870                 875                 880

Gly Ala Asp Glu His Ala Glu Gly Ser Val Asn Gly Thr Leu Met Gln
                885                 890                 895

Leu Gly Ala Leu Gly Gly Val Asn Val Pro Phe Ala Ala Thr Gly Asp
                900                 905                 910

Leu Thr Val Glu Gly Gly Leu Arg Tyr Asp Leu Leu Lys Gln Asp Ala
                915                 920                 925

Phe Ala Glu Lys Gly Ser Ala Leu Gly Trp Ser Gly Asn Ser Leu Thr
                930                 935                 940

Glu Gly Thr Leu Val Gly Leu Ala Gly Leu Lys Leu Ser Gln Pro Leu
945                 950                 955                 960

Ser Asp Lys Ala Val Leu Phe Ala Thr Ala Gly Val Glu Arg Asp Leu
                965                 970                 975

Asn Gly Arg Asp Tyr Thr Val Thr Gly Gly Phe Thr Gly Ala Thr Ala
                980                 985                 990

Ala Thr Gly Lys Thr Gly Ala Arg Asn Met Pro His Thr Arg Leu Val
                995                 1000                1005

Ala Gly Leu Gly Ala Asp Val Glu Phe Gly Asn Gly Trp Asn Gly Leu
                1010                1015                1020

Ala Arg Tyr Ser Tyr Ala Gly Ser Lys Gln Tyr Gly Asn His Ser Gly
1025                1030                1035                1040

Arg Val Gly Val Gly Tyr Arg Phe Leu Asp Gly Gly Gly Thr Gly
                1045                1050                1055

Ser Ser Asp Leu Ala Asn Asp Ser Phe Ile Arg Gln Val Leu Asp Arg
                1060                1065                1070

Gln His Phe Glu Pro Asp Gly Lys Tyr His Leu Phe Gly Ser Arg Gly
                1075                1080                1085

Glu Leu Ala Glu Arg Ser Gly His Ile Gly Leu Gly Lys Ile Gln Ser
                1090                1095                1100

His Gln Leu Gly Asn Leu Met Ile Gln Gln Ala Ala Ile Lys Gly Asn
1105                1110                1115                1120

Ile Gly Tyr Ile Val Arg Phe Ser Asp His Gly His Glu Val His Ser
                1125                1130                1135

Pro Phe Asp Asn His Ala Ser His Ser Asp Ser Asp Glu Ala Gly Ser
                1140                1145                1150
```

-continued

Pro Val Asp Gly Phe Ser Leu Tyr Arg Ile His Trp Asp Gly Tyr Glu
        1155                1160                1165
His His Pro Ala Asp Gly Tyr Asp Gly Pro Gln Gly Gly Tyr Pro
    1170                1175                1180
Ala Pro Lys Gly Ala Arg Asp Ile Tyr Ser Tyr Asp Ile Lys Gly Val
1185                1190                1195                1200
Ala Gln Asn Ile Arg Leu Asn Leu Thr Asp Asn Arg Ser Thr Gly Gln
        1205                1210                1215
Arg Leu Ala Asp Arg Phe His Asn Ala Gly Ser Met Leu Thr Gln Gly
            1220                1225                1230
Val Gly Asp Gly Phe Lys Arg Ala Thr Arg Tyr Ser Pro Glu Leu Asp
        1235                1240                1245
Arg Ser Gly Asn Ala Ala Glu Ala Phe Asn Gly Thr Ala Asp Ile Val
    1250                1255                1260
Lys Asn Ile Ile Gly Ala Ala Gly Glu Ile Gly Ala Gly Asp Ala
1265                1270                1275                1280
Val Gln Gly Ile Ser Glu Gly Ser Asn Ile Ala Val Met His Gly Leu
        1285                1290                1295
Gly Leu Leu Ser Thr Glu Asn Lys Met Ala Arg Ile Asn Asp Leu Ala
    1300                1305                1310
Asp Met Ala Gln Leu Lys Asp Tyr Ala Ala Ala Ile Arg Asp Trp
        1315                1320                1325
Ala Val Gln Asn Pro Asn Ala Ala Gln Gly Ile Glu Ala Val Ser Asn
    1330                1335                1340
Ile Phe Met Ala Ala Ile Pro Ile Lys Gly Ile Gly Ala Val Arg Gly
1345                1350                1355                1360
Lys Tyr Gly Leu Gly Gly Ile Thr Ala His Pro Ile Lys Arg Ser Gln
        1365                1370                1375
Met Gly Ala Ile Ala Leu Pro Lys Gly Lys Ser Ala Val Ser Asp Asn
    1380                1385                1390
Phe Ala Asp Ala Ala Tyr Ala Lys Tyr Pro Ser Pro Tyr His Ser Arg
        1395                1400                1405
Asn Ile Arg Ser Asn Leu Glu Gln Arg Tyr Gly Lys Glu Asn Ile Thr
    1410                1415                1420
Ser Ser Thr Val Pro Pro Ser Asn Gly Lys Asn Val Lys Leu Ala Asp
1425                1430                1435                1440
Gln Arg His Pro Lys Thr Gly Val Pro Phe Asp Gly Lys Gly Phe Pro
        1445                1450                1455
Asn Phe Glu Lys His Val Lys Tyr Asp Thr Leu Glu His His His His
    1460                1465                1470
His His

<210> SEQ ID NO 102
<211> LENGTH: 3939
<212> TYPE: DNA
<213> ORGANISM: Artificial Sequence
<220> FEATURE:
<223> OTHER INFORMATION: Synthetic construct

<400> SEQUENCE: 102
atgacttctg cgcccgactt caatgcaggc ggtaccggta tcggcagcaa cagcagagca      60
acaacagcga aatcagcagc agtatcttac gccggtatca agaacgaaat gtgcaaagac     120
agaagcatgc tctgtgccgg tcgggatgac gttgcggtta cagacaggga tgccaaaatc     180 aatgccccc ccccgaatct gcataccgga gactttccaa acccaaatga cgcatacaag     240

```
aatttgatca acctcaaacc tgcaattgaa gcaggctata caggacgcgg ggtagaggta    300
ggtatcgtcg acacaggcga atccgtcggc agcatatcct ttcccgaact gtatggcaga    360
aaagaacacg gctataacga aaattacaaa aactatacgg cgtatatgcg gaaggaagcg    420
cctgaagacg gaggcggtaa agacattgaa gcttctttcg acgatgaggc cgttatagag    480
actgaagcaa agccgacgga tatccgccac gtaaaagaaa tcggacacat cgatttggtc    540
tcccatatta ttggcgggcg ttccgtggac ggcagacctg caggcggtat tgcgcccgat    600
gcgacgctac acataatgaa tacgaatgat gaaaccaaga acgaaatgat ggttgcagcc    660
atccgcaatg catgggtcaa gctgggcgaa cgtggcgtgc gcatcgtcaa taacagtttt    720
ggaacaacat cgagggcagg cactgccgac cttttccaaa tagccaattc ggaggagcag    780
taccgccaag cgttgctcga ctattccggc ggtgataaaa cagacgaggg tatccgcctg    840
atgcaacaga gcgattacgg caacctgtcc taccacatcc gtaataaaaa catgcttttc    900
atcttttcga caggcaatga cgcacaagct cagcccaaca catatgccct attgccattt    960
tatgaaaaag acgctcaaaa aggcattatc acagtcgcag gcgtagaccg cagtggagaa   1020
aagttcaaac gggaaatgta tggagaaccg ggtacagaac cgcttgagta tggctccaac   1080
cattgcggaa ttactgccat gtggtgcctg tcggcaccct atgaagcaag cgtccgtttc   1140
acccgtacaa acccgattca aattgccgga acatcctttt ccgcacccat cgtaaccggc   1200
acggcggctc tgctgctgca gaaatacccg tggatgagca cgacaacct gcgtaccacg   1260
ttgctgacga cggctcagga catcggtgca gtcggcgtgg acagcaagtt cggctgggga   1320
ctgctggatg cgggtaaggc catgaacgga cccgcgtcct ttccgttcgg cgactttacc   1380
gccgatacga aaggtacatc cgatattgcc tactccttcc gtaacgacat ttcaggcacg   1440
ggcggcctga tcaaaaaagg cggcagccaa ctgcaactgc acggcaacaa cacctatacg   1500
ggcaaaacca ttatcgaagg cggttcgctg gtgttgtacg gcaacaacaa atcggatatg   1560
cgcgtcgaaa ccaaaggtgc gctgatttat aacggggcgg catccggcgg cagcctgaac   1620
agcgacggca ttgtctatct ggcagatacc gaccaatccg gcgcaaacga aaccgtacac   1680
atcaaaggca gtctgcagct ggacggcaaa ggtacgctgt acacacgttt gggcaaactg   1740
ctgaaagtgg acggtacggc gattatcggc ggcaagctgt acatgtcggc acgcggcaag   1800
ggggcaggct atctcaacag taccggacga cgtgttccct tcctgagtgc cgccaaaatc   1860
gggcaggatt attctttctt cacaaacatc gaaaccgacg gcggcctgct ggcttccctc   1920
gacagcgtcg aaaaaacagc gggcagtgaa ggcgacacgc tgtcctatta tgtccgtcgc   1980
ggcaatgcgg cacggactgc ttcggcagcg gcacattccg cgcccgccgg tctgaaacac   2040
gccgtagaac agggcggcag caatctggaa aacctgatgg tcgaactgga tgcctccgaa   2100
tcatccgcaa caccgagac ggttgaaact gcggcagccg accgcacaga tatgccgggc   2160
atccgcccct acgcgcaac tttccgcgca gcggcagccg tacagcatgc gaatgccgcc   2220
gacggtgtac gcatcttcaa cagtctcgcc gctaccgtct atgccgacag taccgccgcc   2280
catgccgata tgcagggacg ccgcctgaaa gccgtatcgg acgggttgga ccacaacggc   2340
acgggtctgc gcgtcatcgc gcaaacccaa caggacggtg gaacgtggga cagggcggt   2400
gttgaaggca aaatgcgcgg cagtacccaa accgtcggca ttgccgcgaa accggcgaa   2460
aatacgacag cagccgccac actgggcatg ggacgcagca catggagcga aaacagtgca   2520
aatgcaaaaa ccgacagcat tagtctgttt gcaggcatac ggcacgatgc gggcgatatc   2580
ggctatctca aaggcctgtt ctcctacgga cgctacaaaa acagcatcag ccgcagcacc   2640
```

| | |
|---|---|
| ggtgcggacg aacatgcgga aggcagcgtc aacggcacgc tgatgcagct gggcgcactg | 2700 |
| ggcggtgtca acgttccgtt tgccgcaacg ggagatttga cggtcgaagg cggtctgcgc | 2760 |
| tacgacctgc tcaaacagga tgcattcgcc gaaaaaggca gtgctttggg ctggagcggc | 2820 |
| aacagcctca ctgaaggcac gctggtcgga ctcgcgggtc tgaagctgtc gcaacccttg | 2880 |
| agcgataaag ccgtcctgtt tgcaacggcg ggcgtggaac gcgacctgaa cggacgcgac | 2940 |
| tacacggtaa cgggcggctt taccggcgcg actgcagcaa ccggcaagac gggggcacgc | 3000 |
| aatatgccgc acaccegtct ggttgccggc ctgggcgcgg atgtcgaatt cggcaacggc | 3060 |
| tggaacggct tggcacgtta cagctacgcc ggttccaaac agtacggcaa ccacagcgga | 3120 |
| cgagtcggcg taggctaccg gttcctcgag ggatccggag ggggtggtgt cgccgccgac | 3180 |
| atcggtgcgg ggcttgccga tgcactaacc gcaccgctcg accataaaga caaaggtttg | 3240 |
| cagtctttga cgctggatca gtccgtcagg aaaaacgaga aactgaagct ggcggcacaa | 3300 |
| ggtgcggaaa aaacttatgg aaacggtgac agcctcaata cggcaaaatt gaagaacgac | 3360 |
| aaggtcagcc gtttcgactt tatccgccaa atcgaagtgg acgggcagct cattaccttg | 3420 |
| gagagtggag agttccaagt atacaaacaa agccattccg ccttaaccgc ctttcagacc | 3480 |
| gagcaaatac aagattcgga gcattccggg aagatggttg cgaaacgcca gttcagaatc | 3540 |
| ggcgacatag cgggcgaaca tacatctttt gacaagcttc ccgaaggcgg cagggcgaca | 3600 |
| tatcgcggga cggcgttcgg ttcagacgat gccggcggaa aactgaccta caccatagat | 3660 |
| ttcgccgcca gcagggaaa cggcaaaatc gaacatttga atcgccaga actcaatgtc | 3720 |
| gacctggccg ccgccgatat caagccggat ggaaaacgcc atgccgtcat cagcggttcc | 3780 |
| gtcctttaca accaagccga gaaggcagt tactccctcg gtatctttgg cggaaaagcc | 3840 |
| caggaagttg ccggcagcgc ggaagtgaaa accgtaaacg gcatacgcca tatcggcctt | 3900 |
| gccgccaagc aactcgagca ccaccaccac caccactga | 3939 |

<210> SEQ ID NO 103
<211> LENGTH: 1312
<212> TYPE: PRT
<213> ORGANISM: Artificial Sequence
<220> FEATURE:
<223> OTHER INFORMATION: Synthetic construct

<400> SEQUENCE: 103

```
Met Thr Ser Ala Pro Asp Phe Asn Ala Gly Gly Thr Gly Ile Gly Ser
1               5                   10                  15

Asn Ser Arg Ala Thr Thr Ala Lys Ser Ala Ala Val Ser Tyr Ala Gly
            20                  25                  30

Ile Lys Asn Glu Met Cys Lys Asp Arg Ser Met Leu Cys Ala Gly Arg
        35                  40                  45

Asp Asp Val Ala Val Thr Asp Arg Asp Ala Lys Ile Asn Ala Pro Pro
    50                  55                  60

Pro Asn Leu His Thr Gly Asp Phe Pro Asn Pro Asn Asp Ala Tyr Lys
65                  70                  75                  80

Asn Leu Ile Asn Leu Lys Pro Ala Ile Glu Ala Gly Tyr Thr Gly Arg
                85                  90                  95

Gly Val Glu Val Gly Ile Val Asp Thr Gly Glu Ser Val Gly Ser Ile
            100                 105                 110

Ser Phe Pro Glu Leu Tyr Gly Arg Lys Glu His Gly Tyr Asn Glu Asn
        115                 120                 125

Tyr Lys Asn Tyr Thr Ala Tyr Met Arg Lys Glu Ala Pro Glu Asp Gly
    130                 135                 140
```

-continued

```
Gly Gly Lys Asp Ile Glu Ala Ser Phe Asp Asp Glu Ala Val Ile Glu
145                 150                 155                 160
Thr Glu Ala Lys Pro Thr Asp Ile Arg His Val Lys Glu Ile Gly His
                165                 170                 175
Ile Asp Leu Val Ser His Ile Ile Gly Gly Arg Ser Val Asp Gly Arg
            180                 185                 190
Pro Ala Gly Gly Ile Ala Pro Asp Ala Thr Leu His Ile Met Asn Thr
        195                 200                 205
Asn Asp Glu Thr Lys Asn Glu Met Met Val Ala Ala Ile Arg Asn Ala
    210                 215                 220
Trp Val Lys Leu Gly Glu Arg Gly Val Arg Ile Val Asn Asn Ser Phe
225                 230                 235                 240
Gly Thr Thr Ser Arg Ala Gly Thr Ala Asp Leu Phe Gln Ile Ala Asn
                245                 250                 255
Ser Glu Glu Gln Tyr Arg Gln Ala Leu Leu Asp Tyr Ser Gly Gly Asp
            260                 265                 270
Lys Thr Asp Glu Gly Ile Arg Leu Met Gln Gln Ser Asp Tyr Gly Asn
        275                 280                 285
Leu Ser Tyr His Ile Arg Asn Lys Asn Met Leu Phe Ile Phe Ser Thr
    290                 295                 300
Gly Asn Asp Ala Gln Ala Gln Pro Asn Thr Tyr Ala Leu Leu Pro Phe
305                 310                 315                 320
Tyr Glu Lys Asp Ala Gln Lys Gly Ile Ile Thr Val Ala Gly Val Asp
                325                 330                 335
Arg Ser Gly Glu Lys Phe Lys Arg Glu Met Tyr Gly Glu Pro Gly Thr
            340                 345                 350
Glu Pro Leu Glu Tyr Gly Ser Asn His Cys Gly Ile Thr Ala Met Trp
        355                 360                 365
Cys Leu Ser Ala Pro Tyr Glu Ala Ser Val Arg Phe Thr Arg Thr Asn
    370                 375                 380
Pro Ile Gln Ile Ala Gly Thr Ser Phe Ser Ala Pro Ile Val Thr Gly
385                 390                 395                 400
Thr Ala Ala Leu Leu Leu Gln Lys Tyr Pro Trp Met Ser Asn Asp Asn
                405                 410                 415
Leu Arg Thr Thr Leu Leu Thr Thr Ala Gln Asp Ile Gly Ala Val Gly
            420                 425                 430
Val Asp Ser Lys Phe Gly Trp Gly Leu Leu Asp Ala Gly Lys Ala Met
        435                 440                 445
Asn Gly Pro Ala Ser Phe Pro Phe Gly Asp Phe Thr Ala Asp Thr Lys
    450                 455                 460
Gly Thr Ser Asp Ile Ala Tyr Ser Phe Arg Asn Asp Ile Ser Gly Thr
465                 470                 475                 480
Gly Gly Leu Ile Lys Lys Gly Gly Ser Gln Leu Gln Leu His Gly Asn
                485                 490                 495
Asn Thr Tyr Thr Gly Lys Thr Ile Ile Glu Gly Gly Ser Leu Val Leu
            500                 505                 510
Tyr Gly Asn Asn Lys Ser Asp Met Arg Val Glu Thr Lys Gly Ala Leu
        515                 520                 525
Ile Tyr Asn Gly Ala Ala Ser Gly Gly Ser Leu Asn Ser Asp Gly Ile
    530                 535                 540
Val Tyr Leu Ala Asp Thr Asp Gln Ser Gly Ala Asn Glu Thr Val His
545                 550                 555                 560
Ile Lys Gly Ser Leu Gln Leu Asp Gly Lys Gly Thr Leu Tyr Thr Arg
```

```
                565                 570                 575
Leu Gly Lys Leu Leu Lys Val Asp Gly Thr Ala Ile Ile Gly Gly Lys
            580                 585                 590

Leu Tyr Met Ser Ala Arg Gly Lys Gly Ala Gly Tyr Leu Asn Ser Thr
            595                 600                 605

Gly Arg Arg Val Pro Phe Leu Ser Ala Lys Ile Gly Gln Asp Tyr
            610                 615                 620

Ser Phe Phe Thr Asn Ile Glu Thr Asp Gly Gly Leu Leu Ala Ser Leu
625                 630                 635                 640

Asp Ser Val Glu Lys Thr Ala Gly Ser Glu Gly Asp Thr Leu Ser Tyr
            645                 650                 655

Tyr Val Arg Arg Gly Asn Ala Ala Arg Thr Ala Ser Ala Ala His
            660                 665                 670

Ser Ala Pro Ala Gly Leu Lys His Ala Val Glu Gln Gly Gly Ser Asn
            675                 680                 685

Leu Glu Asn Leu Met Val Glu Leu Asp Ala Ser Glu Ser Ser Ala Thr
            690                 695                 700

Pro Glu Thr Val Glu Thr Ala Ala Asp Arg Thr Asp Met Pro Gly
705                 710                 715                 720

Ile Arg Pro Tyr Gly Ala Thr Phe Arg Ala Ala Ala Val Gln His
            725                 730                 735

Ala Asn Ala Ala Asp Gly Val Arg Ile Phe Asn Ser Leu Ala Ala Thr
            740                 745                 750

Val Tyr Ala Asp Ser Thr Ala Ala His Ala Asp Met Gln Gly Arg Arg
            755                 760                 765

Leu Lys Ala Val Ser Asp Gly Leu Asp His Asn Gly Thr Gly Leu Arg
            770                 775                 780

Val Ile Ala Gln Thr Gln Gln Asp Gly Gly Thr Trp Glu Gln Gly Gly
785                 790                 795                 800

Val Glu Gly Lys Met Arg Gly Ser Thr Gln Thr Val Gly Ile Ala Ala
            805                 810                 815

Lys Thr Gly Glu Asn Thr Thr Ala Ala Ala Thr Leu Gly Met Gly Arg
            820                 825                 830

Ser Thr Trp Ser Glu Asn Ser Ala Asn Ala Lys Thr Asp Ser Ile Ser
            835                 840                 845

Leu Phe Ala Gly Ile Arg His Asp Ala Gly Asp Ile Gly Tyr Leu Lys
            850                 855                 860

Gly Leu Phe Ser Tyr Gly Arg Tyr Lys Asn Ser Ile Ser Arg Ser Thr
865                 870                 875                 880

Gly Ala Asp Glu His Ala Glu Gly Ser Val Asn Gly Thr Leu Met Gln
            885                 890                 895

Leu Gly Ala Leu Gly Gly Val Asn Val Pro Phe Ala Ala Thr Gly Asp
            900                 905                 910

Leu Thr Val Glu Gly Gly Leu Arg Tyr Asp Leu Leu Lys Gln Asp Ala
            915                 920                 925

Phe Ala Glu Lys Gly Ser Ala Leu Gly Trp Ser Gly Asn Ser Leu Thr
            930                 935                 940

Glu Gly Thr Leu Val Gly Leu Ala Gly Leu Lys Leu Ser Gln Pro Leu
945                 950                 955                 960

Ser Asp Lys Ala Val Leu Phe Ala Thr Ala Gly Val Glu Arg Asp Leu
            965                 970                 975

Asn Gly Arg Asp Tyr Thr Val Thr Gly Gly Phe Thr Gly Ala Thr Ala
            980                 985                 990
```

```
Ala Thr Gly Lys Thr Gly Ala Arg Asn Met Pro His Thr Arg Leu Val
        995                 1000                1005

Ala Gly Leu Gly Ala Asp Val Glu Phe Gly Asn Gly Trp Asn Gly Leu
    1010                1015                1020

Ala Arg Tyr Ser Tyr Ala Gly Ser Lys Gln Tyr Gly Asn His Ser Gly
1025                1030                1035                1040

Arg Val Gly Val Gly Tyr Arg Phe Leu Glu Gly Ser Gly Gly Gly
                1045                1050                1055

Val Ala Ala Asp Ile Gly Ala Gly Leu Ala Asp Ala Leu Thr Ala Pro
            1060                1065                1070

Leu Asp His Lys Asp Lys Gly Leu Gln Ser Leu Thr Leu Asp Gln Ser
        1075                1080                1085

Val Arg Lys Asn Glu Lys Leu Lys Leu Ala Ala Gln Gly Ala Glu Lys
    1090                1095                1100

Thr Tyr Gly Asn Gly Asp Ser Leu Asn Thr Gly Lys Leu Lys Asn Asp
1105                1110                1115                1120

Lys Val Ser Arg Phe Asp Phe Ile Arg Gln Ile Glu Val Asp Gly Gln
                1125                1130                1135

Leu Ile Thr Leu Glu Ser Gly Glu Phe Gln Val Tyr Lys Gln Ser His
            1140                1145                1150

Ser Ala Leu Thr Ala Phe Gln Thr Glu Gln Ile Gln Asp Ser Glu His
        1155                1160                1165

Ser Gly Lys Met Val Ala Lys Arg Gln Phe Arg Ile Gly Asp Ile Ala
    1170                1175                1180

Gly Glu His Thr Ser Phe Asp Lys Leu Pro Gly Gly Arg Ala Thr
1185                1190                1195                1200

Tyr Arg Gly Thr Ala Phe Gly Ser Asp Asp Ala Gly Gly Lys Leu Thr
                1205                1210                1215

Tyr Thr Ile Asp Phe Ala Ala Lys Gln Gly Asn Gly Lys Ile Glu His
            1220                1225                1230

Leu Lys Ser Pro Glu Leu Asn Val Asp Leu Ala Ala Ala Asp Ile Lys
        1235                1240                1245

Pro Asp Gly Lys Arg His Ala Val Ile Ser Gly Ser Val Leu Tyr Asn
    1250                1255                1260

Gln Ala Glu Lys Gly Ser Tyr Ser Leu Gly Ile Phe Gly Gly Lys Ala
1265                1270                1275                1280

Gln Glu Val Ala Gly Ser Ala Glu Val Lys Thr Val Asn Gly Ile Arg
                1285                1290                1295

His Ile Gly Leu Ala Ala Lys Gln Leu Glu His His His His His
            1300                1305                1310

<210> SEQ ID NO 104
<211> LENGTH: 4344
<212> TYPE: DNA
<213> ORGANISM: Artificial Sequence
<220> FEATURE:
<223> OTHER INFORMATION: Synthetic construct

<400> SEQUENCE: 104
atgacttctg cgcccgactt caatgcaggc ggtaccggta tcggcagcaa cagcagagca      60
acaacagcga atcagcagc agtatcttac gccggtatca agaacgaaat gtgcaaagac     120
agaagcatgc tctgtgccgg tcgggatgac gttgcggtta cagacaggga tgccaaaatc     180 aatgccccc cccgaatct gcataccgga gactttccaa acccaaatga cgcatacaag     240
aatttgatca acctcaaacc tgcaattgaa gcaggctata caggacgcgg ggtagaggta     300
```

```
ggtatcgtcg acacaggcga atccgtcggc agcatatcct ttcccgaact gtatggcaga    360
aaagaacacg gctataacga aaattacaaa aactatacgg cgtatatgcg aaggaagcg     420
cctgaagacg gaggcggtaa agacattgaa gcttctttcg acgatgaggc cgttatagag    480
actgaagcaa agccgacgga tatccgccac gtaaaagaaa tcggacacat cgatttggtc    540
tcccatatta ttggcgggcg ttccgtggac ggcagacctg caggcggtat tgcgcccgat    600
gcgacgctac acataatgaa tacgaatgat gaaaccaaga acgaaatgat ggttgcagcc    660
atccgcaatg catgggtcaa gctgggcgaa cgtggcgtgc gcatcgtcaa taacagtttt    720
ggaacaacat cgagggcagg cactgccgac cttttccaaa tagccaattc ggaggagcag    780
taccgccaag cgttgctcga ctattccggc ggtgataaaa cagacgaggg tatccgcctg    840
atgcaacaga gcgattacgg caacctgtcc taccacatcc gtaataaaaa catgcttttc    900
atcttttcga caggcaatga cgcacaagct cagcccaaca catatgccct attgccattt    960
tatgaaaaag acgctcaaaa aggcattatc acagtcgcag cgtagaccg cagtggagaa    1020
aagttcaaac gggaaatgta tggagaaccg ggtacagaac cgcttgagta tggctccaac    1080
cattgcggaa ttactgccat gtggtgcctg tcggcaccct atgaagcaag cgtccgtttc    1140
acccgtacaa acccgattca aattgccgga acatcctttt ccgcacccat cgtaaccggc    1200
acggcggctc tgctgctgca gaaatacccg tggatgagca acgacaacct gcgtaccacg    1260
ttgctgacga cggctcagga catcggtgca gtcggcgtgg acagcaagtt cggctgggga    1320
ctgctggatg cgggtaaggc catgaacgga cccgcgtcct ttccgttcgg cgactttacc    1380
gccgatacga aggtacatc cgatattgcc tactccttcc gtaacgacat ttcaggcacg    1440
ggcggcctga tcaaaaaagg cggcagccaa ctgcaactgc acggcaacaa cacctatacg    1500
ggcaaaacca ttatcgaagg cggttcgctg gtgttgtacg gcaacaacaa atcggatatg    1560
cgcgtcgaaa ccaaaggtgc gctgatttat aacggggcgg catccggcgg cagcctgaac    1620
agcgacggca ttgtctatct ggcagatacc gaccaatccg gcgcaaacga aaccgtacac    1680
atcaaaggca gtctgcagct ggacggcaaa ggtacgctgt acacacgttt gggcaaactg    1740
ctgaaagtgg acggtacggc gattatcggc ggcaagctgt acatgtcggc acgcggcaag    1800
ggggcaggct atctcaacag taccggacga cgtgttccct tcctgagtgc cgccaaaatc    1860
gggcaggatt attcttttctt cacaaacatc gaaaccgacg cgcggcctgct ggcttccctc    1920
gacagcgtcg aaaaaacagc gggcagtgaa ggcgacacgc tgtcctatta tgtccgtcgc    1980
ggcaatgcgg cacggactgc ttcggcagcg gcacattccg cgcccgccgg tctgaaacac    2040
gccgtagaac agggcggcag caatctggaa aacctgatgg tcgaactgga tgcctccgaa    2100
tcatccgcaa caccgagac ggttgaaact gcggcagccg accgcacaga tatgccgggc    2160
atccgcccct acggcgcaac tttccgcgca gcggcagccg tacagcatgc gaatgccgcc    2220
gacggtgtac gcatcttcaa cagtctcgcc gctaccgtct atgccgacag taccgccgcc    2280
catgccgata tgcagggacg ccgcctgaaa gccgtatcgg acgggttgga ccacaacggc    2340
acgggtctgc gcgtcatcgc gcaaacccaa caggacggtg aacgtgggga cagggcggt    2400
gttgaaggca aaatgcgcgg cagtacccaa accgtcggca ttgccgcgaa aaccggcgaa    2460
aatacgacag cagccgccac actgggcatg gacgcagca catggagcga aaacagtgca    2520
aatgcaaaaa ccgacagcat tagtctgttt gcaggcatac ggcacgatgc gggcgatatc    2580
ggctatctca aaggcctgtt ctcctacgga cgctacaaaa acagcatcag ccgcagcacc    2640
ggtgcggacg aacatgcgga aggcagcgtc aacggcacgc tgatgcagct gggcgcactg    2700
```

```
ggcggtgtca acgttccgtt tgccgcaacg ggagatttga cggtcgaagg cggtctgcgc    2760
tacgacctgc tcaaacagga tgcattcgcc gaaaaaggca gtgctttggg ctggagcggc    2820
aacagcctca ctgaaggcac gctggtcgga ctcgcgggtc tgaagctgtc gcaacccttg    2880
agcgataaag ccgtcctgtt tgcaacggcg ggcgtggaac gcgacctgaa cggacgcgac    2940
tacacggtaa cgggcggctt taccggcgcg actgcagcaa ccggcaagac ggggcacgc     3000
aatatgccgc acacccgtct ggttgccggc ctgggcgcgg atgtcgaatt cggcaacggc    3060
tggaacggct tggcacgtta cagctacgcc ggttccaaac agtacggcaa ccacagcgga    3120
cgagtcggcg taggctaccg gttcctcgag ggtggcggag gcactggatc cgccacaaac    3180
gacgacgatg ttaaaaaagc tgccactgtg gccattgctg ctgcctacaa caatggccaa    3240
gaaatcaacg gtttcaaagc tggagagacc atctacgaca ttgatgaaga cggcacaatt    3300
accaaaaaag acgcaactgc agccgatgtt gaagccgacg actttaaagg tctgggtctg    3360
aaaaaagtcg tgactaacct gaccaaaacc gtcaatgaaa acaaacaaaa cgtcgatgcc    3420
aaagtaaaag ctgcagaatc tgaaatagaa aagttaacaa ccaagttagc agacactgat    3480
gccgctttag cagatactga tgccgctctg gatgcaacca ccaacgcctt gaataaattg    3540
ggagaaaata taacgacatt tgctgaagag actaagacaa atatcgtaaa aattgatgaa    3600
aaattagaag ccgtggctga taccgtcgac aagcatgccg aagcattcaa cgatatcgcc    3660
gattcattgg atgaaaccaa cactaaggca gacgaagccg tcaaaccgc caatgaagcc     3720
aaacagacgg ccgaagaaac caaacaaac gtcgatgcca agtaaaagc tgcagaaact       3780
gcagcaggca agccgaagc tgccgctggc acagctaata ctgcagccga caaggccgaa      3840
gctgtcgctg caaagttac cgacatcaaa gctgatatcg ctacgaacaa agataatatt       3900
gctaaaaaag caaacagtgc cgacgtgtac accagagaag agtctgacag caaatttgtc      3960
agaattgatg gtctgaacgc tactaccgaa aaattggaca cacgcttggc ttctgctgaa      4020
aaatccattg ccgatcacga tactcgcctg aacggtttgg ataaaacagt gtcagacctg      4080
cgcaaagaaa cccgccaagg ccttgcagaa caagccgcgc tctccggtct gttccaacct      4140
tacaacgtgg tcggttcaa tgtaacggct gcagtcggcg gctacaaatc cgaatcggca      4200
gtcgccatcg gtaccggctt ccgctttacc gaaaactttg ccgccaaagc aggcgtggca      4260
gtcggcactt cgtccggttc ttccgcagcc taccatgtcg gcgtcaatta cgagtggctc      4320
gagcaccacc accaccacca ctga                                                           4344
```

<210> SEQ ID NO 105
<211> LENGTH: 1447
<212> TYPE: PRT
<213> ORGANISM: Artificial Sequence
<220> FEATURE:
<223> OTHER INFORMATION: Synthetic construct

<400> SEQUENCE: 105

```
Met Thr Ser Ala Pro Asp Phe Asn Ala Gly Gly Thr Gly Ile Gly Ser
1               5                   10                  15

Asn Ser Arg Ala Thr Thr Ala Lys Ser Ala Ala Val Ser Tyr Ala Gly
            20                  25                  30

Ile Lys Asn Glu Met Cys Lys Asp Arg Ser Met Leu Cys Ala Gly Arg
        35                  40                  45

Asp Asp Val Ala Val Thr Asp Arg Asp Ala Lys Ile Asn Ala Pro Pro
    50                  55                  60

Pro Asn Leu His Thr Gly Asp Phe Pro Asn Pro Asn Asp Ala Tyr Lys
65                  70                  75                  80
```

```
Asn Leu Ile Asn Leu Lys Pro Ala Ile Glu Ala Gly Tyr Thr Gly Arg
                85                  90                  95
Gly Val Glu Val Gly Ile Val Asp Thr Gly Glu Ser Val Gly Ser Ile
            100                 105                 110
Ser Phe Pro Glu Leu Tyr Gly Arg Lys Glu His Gly Tyr Asn Glu Asn
        115                 120                 125
Tyr Lys Asn Tyr Thr Ala Tyr Met Arg Lys Glu Ala Pro Glu Asp Gly
    130                 135                 140
Gly Gly Lys Asp Ile Glu Ala Ser Phe Asp Asp Glu Ala Val Ile Glu
145                 150                 155                 160
Thr Glu Ala Lys Pro Thr Asp Ile Arg His Val Lys Glu Ile Gly His
                165                 170                 175
Ile Asp Leu Val Ser His Ile Ile Gly Gly Arg Ser Val Asp Gly Arg
            180                 185                 190
Pro Ala Gly Gly Ile Ala Pro Asp Ala Thr Leu His Ile Met Asn Thr
        195                 200                 205
Asn Asp Glu Thr Lys Asn Glu Met Met Val Ala Ala Ile Arg Asn Ala
    210                 215                 220
Trp Val Lys Leu Gly Glu Arg Gly Val Arg Ile Val Asn Asn Ser Phe
225                 230                 235                 240
Gly Thr Thr Ser Arg Ala Gly Thr Ala Asp Leu Phe Gln Ile Ala Asn
                245                 250                 255
Ser Glu Glu Gln Tyr Arg Gln Ala Leu Leu Asp Tyr Ser Gly Gly Asp
            260                 265                 270
Lys Thr Asp Glu Gly Ile Arg Leu Met Gln Gln Ser Asp Tyr Gly Asn
        275                 280                 285
Leu Ser Tyr His Ile Arg Asn Lys Asn Met Leu Phe Ile Phe Ser Thr
    290                 295                 300
Gly Asn Asp Ala Gln Ala Gln Pro Asn Thr Tyr Ala Leu Leu Pro Phe
305                 310                 315                 320
Tyr Glu Lys Asp Ala Gln Lys Gly Ile Ile Thr Val Ala Gly Val Asp
                325                 330                 335
Arg Ser Gly Glu Lys Phe Lys Arg Glu Met Tyr Gly Glu Pro Gly Thr
            340                 345                 350
Glu Pro Leu Glu Tyr Gly Ser Asn His Cys Gly Ile Thr Ala Met Trp
        355                 360                 365
Cys Leu Ser Ala Pro Tyr Glu Ala Ser Val Arg Phe Thr Arg Thr Asn
    370                 375                 380
Pro Ile Gln Ile Ala Gly Thr Ser Phe Ser Ala Pro Ile Val Thr Gly
385                 390                 395                 400
Thr Ala Leu Leu Leu Gln Lys Tyr Pro Trp Met Ser Asn Asp Asn
                405                 410                 415
Leu Arg Thr Thr Leu Leu Thr Thr Ala Gln Asp Ile Gly Ala Val Gly
            420                 425                 430
Val Asp Ser Lys Phe Gly Trp Gly Leu Leu Asp Ala Gly Lys Ala Met
        435                 440                 445
Asn Gly Pro Ala Ser Phe Pro Phe Gly Asp Phe Thr Ala Asp Thr Lys
    450                 455                 460
Gly Thr Ser Asp Ile Ala Tyr Ser Phe Arg Asn Asp Ile Ser Gly Thr
465                 470                 475                 480
Gly Gly Leu Ile Lys Lys Gly Ser Gln Leu Gln Leu His Gly Asn
                485                 490                 495
Asn Thr Tyr Thr Gly Lys Thr Ile Ile Glu Gly Gly Ser Leu Val Leu
```

```
                500             505             510
Tyr Gly Asn Asn Lys Ser Asp Met Arg Val Glu Thr Lys Gly Ala Leu
            515                 520                 525
Ile Tyr Asn Gly Ala Ala Ser Gly Gly Ser Leu Asn Ser Asp Gly Ile
        530                 535                 540
Val Tyr Leu Ala Asp Thr Asp Gln Ser Gly Ala Asn Glu Thr Val His
545                 550                 555                 560
Ile Lys Gly Ser Leu Gln Leu Asp Gly Lys Gly Thr Leu Tyr Thr Arg
                565                 570                 575
Leu Gly Lys Leu Leu Lys Val Asp Gly Thr Ala Ile Ile Gly Gly Lys
            580                 585                 590
Leu Tyr Met Ser Ala Arg Gly Lys Gly Ala Gly Tyr Leu Asn Ser Thr
        595                 600                 605
Gly Arg Arg Val Pro Phe Leu Ser Ala Ala Lys Ile Gly Gln Asp Tyr
    610                 615                 620
Ser Phe Phe Thr Asn Ile Glu Thr Asp Gly Gly Leu Leu Ala Ser Leu
625                 630                 635                 640
Asp Ser Val Glu Lys Thr Ala Gly Ser Glu Gly Asp Thr Leu Ser Tyr
                645                 650                 655
Tyr Val Arg Arg Gly Asn Ala Ala Arg Thr Ala Ser Ala Ala Ala His
            660                 665                 670
Ser Ala Pro Ala Gly Leu Lys His Ala Val Glu Gln Gly Gly Ser Asn
        675                 680                 685
Leu Glu Asn Leu Met Val Glu Leu Asp Ala Ser Glu Ser Ser Ala Thr
    690                 695                 700
Pro Glu Thr Val Glu Thr Ala Ala Asp Arg Thr Asp Met Pro Gly
705                 710                 715                 720
Ile Arg Pro Tyr Gly Ala Thr Phe Arg Ala Ala Ala Val Gln His
                725                 730                 735
Ala Asn Ala Ala Asp Gly Val Arg Ile Phe Asn Ser Leu Ala Ala Thr
            740                 745                 750
Val Tyr Ala Asp Ser Thr Ala Ala His Ala Asp Met Gln Gly Arg Arg
        755                 760                 765
Leu Lys Ala Val Ser Asp Gly Leu Asp His Asn Gly Thr Gly Leu Arg
    770                 775                 780
Val Ile Ala Gln Thr Gln Gln Asp Gly Gly Thr Trp Glu Gln Gly Gly
785                 790                 795                 800
Val Glu Gly Lys Met Arg Gly Ser Thr Gln Thr Val Gly Ile Ala Ala
                805                 810                 815
Lys Thr Gly Glu Asn Thr Thr Ala Ala Ala Thr Leu Gly Met Gly Arg
            820                 825                 830
Ser Thr Trp Ser Glu Asn Ser Ala Asn Ala Lys Thr Asp Ser Ile Ser
        835                 840                 845
Leu Phe Ala Gly Ile Arg His Asp Ala Gly Asp Ile Gly Tyr Leu Lys
    850                 855                 860
Gly Leu Phe Ser Tyr Gly Arg Tyr Lys Asn Ser Ile Ser Arg Ser Thr
865                 870                 875                 880
Gly Ala Asp Glu His Ala Glu Gly Ser Val Asn Gly Thr Leu Met Gln
                885                 890                 895
Leu Gly Ala Leu Gly Gly Val Asn Val Pro Phe Ala Ala Thr Gly Asp
            900                 905                 910
Leu Thr Val Glu Gly Gly Leu Arg Tyr Asp Leu Leu Lys Gln Asp Ala
        915                 920                 925
```

```
Phe Ala Glu Lys Gly Ser Ala Leu Gly Trp Ser Gly Asn Ser Leu Thr
        930                 935                 940

Glu Gly Thr Leu Val Gly Leu Ala Gly Leu Lys Leu Ser Gln Pro Leu
945                 950                 955                 960

Ser Asp Lys Ala Val Leu Phe Ala Thr Ala Gly Val Glu Arg Asp Leu
                965                 970                 975

Asn Gly Arg Asp Tyr Thr Val Thr Gly Gly Phe Thr Gly Ala Thr Ala
            980                 985                 990

Ala Thr Gly Lys Thr Gly Ala Arg Asn Met Pro His Thr Arg Leu Val
        995                 1000                1005

Ala Gly Leu Gly Ala Asp Val Glu Phe Gly Asn Gly Trp Asn Gly Leu
    1010                1015                1020

Ala Arg Tyr Ser Tyr Ala Gly Ser Lys Gln Tyr Gly Asn His Ser Gly
1025                1030                1035                1040

Arg Val Gly Val Gly Tyr Arg Phe Leu Glu Gly Gly Gly Thr Gly
                1045                1050                1055

Ser Ala Thr Asn Asp Asp Val Lys Lys Ala Ala Thr Val Ala Ile
            1060                1065                1070

Ala Ala Ala Tyr Asn Asn Gly Gln Glu Ile Asn Gly Phe Lys Ala Gly
            1075                1080                1085

Glu Thr Ile Tyr Asp Ile Asp Glu Asp Gly Thr Ile Thr Lys Lys Asp
    1090                1095                1100

Ala Thr Ala Ala Asp Val Glu Ala Asp Phe Lys Gly Leu Gly Leu
1105                1110                1115                1120

Lys Lys Val Val Thr Asn Leu Lys Thr Val Asn Glu Asn Lys Gln
            1125                1130                1135

Asn Val Asp Ala Lys Val Lys Ala Ala Glu Ser Glu Ile Glu Lys Leu
            1140                1145                1150

Thr Thr Lys Leu Ala Asp Thr Asp Ala Ala Leu Ala Asp Thr Asp Ala
            1155                1160                1165

Ala Leu Asp Ala Thr Thr Asn Ala Leu Asn Lys Leu Gly Glu Asn Ile
    1170                1175                1180

Thr Thr Phe Ala Glu Glu Thr Lys Thr Asn Ile Val Lys Ile Asp Glu
1185                1190                1195                1200

Lys Leu Glu Ala Val Ala Asp Thr Val Asp Lys His Ala Glu Ala Phe
            1205                1210                1215

Asn Asp Ile Ala Asp Ser Leu Asp Glu Thr Asn Thr Lys Ala Asp Glu
            1220                1225                1230

Ala Val Lys Thr Ala Asn Glu Ala Lys Gln Thr Ala Glu Glu Thr Lys
            1235                1240                1245

Gln Asn Val Asp Ala Lys Val Lys Ala Ala Glu Thr Ala Ala Gly Lys
    1250                1255                1260

Ala Glu Ala Ala Ala Gly Thr Ala Asn Thr Ala Ala Asp Lys Ala Glu
1265                1270                1275                1280

Ala Val Ala Ala Lys Val Thr Asp Ile Lys Ala Asp Ile Ala Thr Asn
            1285                1290                1295

Lys Asp Asn Ile Ala Lys Lys Ala Asn Ser Ala Asp Val Tyr Thr Arg
            1300                1305                1310

Glu Glu Ser Asp Ser Lys Phe Val Arg Ile Asp Gly Leu Asn Ala Thr
            1315                1320                1325

Thr Glu Lys Leu Asp Thr Arg Leu Ala Ser Ala Glu Lys Ser Ile Ala
    1330                1335                1340

Asp His Asp Thr Arg Leu Asn Gly Leu Asp Lys Thr Val Ser Asp Leu
1345                1350                1355                1360
```

Arg Lys Glu Thr Arg Gln Gly Leu Ala Glu Gln Ala Ala Leu Ser Gly
            1365                1370                1375

Leu Phe Gln Pro Tyr Asn Val Gly Arg Phe Asn Val Thr Ala Ala Val
        1380                1385                1390

Gly Gly Tyr Lys Ser Glu Ser Ala Val Ala Ile Gly Thr Gly Phe Arg
    1395                1400                1405

Phe Thr Glu Asn Phe Ala Ala Lys Ala Gly Val Ala Val Gly Thr Ser
    1410                1415                1420

Ser Gly Ser Ser Ala Ala Tyr His Val Gly Val Asn Tyr Glu Trp Leu
1425                1430                1435                1440

Glu His His His His His His
            1445

<210> SEQ ID NO 106
<211> LENGTH: 4179
<212> TYPE: DNA
<213> ORGANISM: Artificial Sequence
<220> FEATURE:
<223> OTHER INFORMATION: Synthetic construct

<400> SEQUENCE: 106
atgacttctg cgcccgactt caatgcaggc ggtaccggta tcggcagcaa cagcagagca      60
acaacagcga aatcagcagc agtatcttac gccgtatca agaacgaaat gtgcaaagac      120
agaagcatgc tctgtgccgg tcgggatgac gttgcggtta cagacaggga tgccaaaatc      180
aatgccccc ccccgaatct gcataccgga gactttccaa acccaaatga cgcatacaag      240
aatttgatca acctcaaacc tgcaattgaa gcaggctata caggacgcgg ggtagaggta      300
ggtatcgtcg acacaggcga atccgtcggc agcatatcct ttcccgaact gtatggcaga      360
aaagaacacg gctataacga aaattacaaa aactatacgg cgtatatgcg aaggaagcg      420
cctgaagacg gaggcggtaa agacattgaa gcttctttcg acgatgaggc cgttatagag      480
actgaagcaa agccgacgga tatccgccac gtaaaagaaa tcggacacat cgatttggtc      540
tcccatatta ttggcgggcg ttccgtggac ggcagacctg caggcggtat tgcgcccgat      600
gcgacgctac acataatgaa tacgaatgat gaaaccaaga acgaaatgat ggttgcagcc      660
atccgcaatg catgggtcaa gctgggcgaa cgtggcgtgc gcatcgtcaa taacagtttt      720
ggaacaacat cgagggcagg cactgccgac ctttttccaaa tagccaattc ggaggagcag      780
taccgccaag cgttgctcga ctattccggc ggtgataaaa cagacgaggg tatccgcctg      840
atgcaacaga gcgattacgg caacctgtcc taccacatcc gtaataaaaa catgcttttc      900
atcttttcga caggcaatga cgcacaagct cagcccaaca catatgccct attgccattt      960
tatgaaaaag acgctcaaaa aggcattatc acagtcgcag gcgtagaccg cagtggagaa      1020
aagttcaaac gggaaatgta tggagaaccg gtacagaac cgcttgagta tggctccaac      1080
cattgcggaa ttactgccat gtggtgcctg tcggcaccct atgaagcaag cgtccgtttc      1140
acccgtacaa acccgattca aattgccgga acatcctttt ccgcacccat cgtaaccggc      1200
acggcggctc tgctgctgca gaaataccg tggatgagca cgacaacct gcgtaccacg      1260
ttgctgacga cggctcagga catcggtgca gtcggcgtgg acagcaagtt cggctgggga      1320
ctgctggatg cgggtaaggc catgaacgga cccgcgtcct ttccgttcgg cgactttacc      1380
gccgatacga aggtacatc cgatattgcc tactccttcc gtaacgacat ttcaggcacg      1440
ggcggcctga tcaaaaaagg cggcagccaa ctgcaactgc acggcaacaa cacctatacg      1500
ggcaaaacca ttatcgaagg cggttcgctg gtgttgtacg gcaacaacaa atcggatatg      1560

```
cgcgtcgaaa ccaaaggtgc gctgatttat aacggggcgg catccggcgg cagcctgaac    1620
agcgacggca ttgtctatct ggcagatacc gaccaatccg gcgcaaacga aaccgtacac    1680
atcaaaggca gtctgcagct ggacggcaaa ggtacgctgt acacacgttt gggcaaactg    1740
ctgaaagtgg acggtacggc gattatcggc ggcaagctgt acatgtcggc acgcggcaag    1800
ggggcaggct atctcaacag taccggacga cgtgttccct tcctgagtgc cgccaaaatc    1860
gggcaggatt attctttctt cacaaacatc gaaaccgacg gcggcctgct ggcttccctc    1920
gacagcgtcg aaaaaacagc gggcagtgaa ggcgacacgc tgtcctatta tgtccgtcgc    1980
ggcaatgcgg cacggactgc ttcggcagcg gcacattccg cgcccgccgg tctgaaacac    2040
gccgtagaac agggcggcag caatctggaa aacctgatgg tcgaactgga tgcctccgaa    2100
tcatccgcaa cacccgagac ggttgaaact gcggcagccg accgcacaga tatgccgggc    2160
atccgcccct acggcgcaac tttccgcgca gcggcagccg tacagcatgc gaatgccgcc    2220
gacggtgtac gcatcttcaa cagtctcgcc gctaccgtct atgccgacag taccgccgcc    2280
catgccgata tgcagggacg ccgcctgaaa gccgtatcgg acgggttgga ccacaacggc    2340
acgggtctgc gcgtcatcgc gcaaacccaa caggacggtg aacgtgggga cagggcggt     2400 gttgaaggca aaatgcgcgg cagtacccaa accgtcggca ttgccgcgaa accggcgaa     2460 aatacgacag cagccgccac actgggcatg ggacgcagca catggagcga aaacagtgca    2520
aatgcaaaaa ccgacagcat tagtctgttt gcaggcatac ggcacgatgc gggcgatatc    2580
ggctatctca aaggcctgtt ctcctacgga cgctacaaaa acagcatcag ccgcagcacc    2640
ggtgcggacg aacatgcgga aggcagcgtc aacggcacgc tgatgcagct gggcgcactg    2700
ggcggtgtca acgttccgtt tgccgcaacg ggagatttga cggtcgaagg cggtctgcgc    2760
tacgacctgc tcaaacagga tgcattcgcc gaaaaaggca gtgctttggg ctggagcggc    2820
aacagcctca ctgaaggcac gctggtcgga ctcgcgggtc tgaagctgtc gcaacccttg    2880
agcgataaag ccgtcctgtt tgcaacggcg ggcgtggaac gcgacctgaa cggacgcgac    2940
tacacggtaa cgggcggctt taccggcgcg actgcagcaa ccggcaagac gggggcacgc    3000
aatatgccgc acaccgtct ggttgccggc ctgggcgcgg atgtcgaatt cggcaacggc     3060
tggaacggct tggcacgtta cagctaccgc ggttccaaac agtacggcaa ccacagcgga    3120
cgagtcggcg taggctaccg gttcctcgag ggtggcggag gcactggatc cgccacaaac    3180
gacgacgatg ttaaaaaagc tgccactgtg gccattgctg ctgcctacaa caatggccaa    3240
gaaatcaacg gtttcaaagc tggagagacc atctacgaca ttgatgaaga cggcacaatt    3300
accaaaaaag acgcaactgc agccgatgtt gaagccgacg actttaaagg tctgggtctg    3360
aaaaaagtcg tgactaacct gaccaaaacc gtcaatgaaa acaaacaaaa cgtcgatgcc    3420
aaagtaaaag ctgcagaatc tgaaatagaa aagttaacaa ccaagttagc agacactgat    3480
gccgctttag cagatactga tgccgctctg gatgcaacca ccaacgcctt gaataaattg    3540
ggagaaaata taacgacatt tgctgaagag actaagacaa atatcgtaaa aattgatgaa    3600
aaattagaag ccgtggctga taccgtcgac aagcatgcca agcattcaa cgatatcgcc     3660 gattcattgg atgaaaccaa cactaaggca gacgaagccg tcaaaccgc caatgaagcc     3720 aaacagacgg ccgaagaaac caaacaaaac gtcgatgcca agtaaaagc tgcagaaact    3780 gcagcaggca aagccgaagc tgccgctggc acagctaata ctgcagccga caggccgaa    3840 gctgtcgctg caaaagttac cgacatcaaa gctgatatcg ctacgaacaa agataatatt    3900
gctaaaaaag caaacagtgc cgacgtgtac accagagaag agtctgacag caaatttgtc    3960
```

```
agaattgatg gtctgaacgc tactaccgaa aaattggaca cacgcttggc ttctgctgaa    4020
aaatccattg ccgatcacga tactcgcctg aacggtttgg ataaaacagt gtcagacctg    4080
cgcaaagaaa cccgccaagg ccttgcagaa caagccgcgc tctccggtct gttccaacct    4140
tacaacgtgg gtctcgagca ccaccaccac caccactga                           4179
```

```
<210> SEQ ID NO 107
<211> LENGTH: 1392
<212> TYPE: PRT
<213> ORGANISM: Artificial Sequence
<220> FEATURE:
<223> OTHER INFORMATION: Synthetic construct

<400> SEQUENCE: 107
```

```
Met Thr Ser Ala Pro Asp Phe Asn Ala Gly Gly Thr Gly Ile Gly Ser
1               5                   10                  15

Asn Ser Arg Ala Thr Thr Ala Lys Ser Ala Ala Val Ser Tyr Ala Gly
            20                  25                  30

Ile Lys Asn Glu Met Cys Lys Asp Arg Ser Met Leu Cys Ala Gly Arg
        35                  40                  45

Asp Asp Val Ala Val Thr Arg Asp Ala Lys Ile Asn Ala Pro Pro
    50                  55                  60

Pro Asn Leu His Thr Gly Asp Phe Pro Asn Pro Asn Asp Ala Tyr Lys
65                  70                  75                  80

Asn Leu Ile Asn Leu Lys Pro Ala Ile Glu Ala Gly Tyr Thr Gly Arg
                85                  90                  95

Gly Val Glu Val Gly Ile Val Asp Thr Gly Glu Ser Val Gly Ser Ile
            100                 105                 110

Ser Phe Pro Glu Leu Tyr Gly Arg Lys Glu His Gly Tyr Asn Glu Asn
        115                 120                 125

Tyr Lys Asn Tyr Thr Ala Tyr Met Arg Lys Glu Ala Pro Glu Asp Gly
    130                 135                 140

Gly Gly Lys Asp Ile Glu Ala Ser Phe Asp Asp Glu Ala Val Ile Glu
145                 150                 155                 160

Thr Glu Ala Lys Pro Thr Asp Ile Arg His Val Lys Glu Ile Gly His
                165                 170                 175

Ile Asp Leu Val Ser His Ile Ile Gly Gly Arg Ser Val Asp Gly Arg
            180                 185                 190

Pro Ala Gly Gly Ile Ala Pro Asp Ala Thr Leu His Ile Met Asn Thr
        195                 200                 205

Asn Asp Glu Thr Lys Asn Glu Met Met Val Ala Ala Ile Arg Asn Ala
    210                 215                 220

Trp Val Lys Leu Gly Glu Arg Gly Val Arg Ile Val Asn Asn Ser Phe
225                 230                 235                 240

Gly Thr Thr Ser Arg Ala Gly Thr Ala Asp Leu Phe Gln Ile Ala Asn
                245                 250                 255

Ser Glu Glu Gln Tyr Arg Gln Ala Leu Leu Asp Tyr Ser Gly Gly Asp
            260                 265                 270

Lys Thr Asp Glu Gly Ile Arg Leu Met Gln Gln Ser Asp Tyr Gly Asn
        275                 280                 285

Leu Ser Tyr His Ile Arg Asn Lys Asn Met Leu Phe Ile Phe Ser Thr
    290                 295                 300

Gly Asn Asp Ala Gln Ala Gln Pro Asn Thr Tyr Ala Leu Leu Pro Phe
305                 310                 315                 320

Tyr Glu Lys Asp Ala Gln Lys Gly Ile Ile Thr Val Ala Gly Val Asp
```

```
                   325                 330                 335
Arg Ser Gly Glu Lys Phe Lys Arg Glu Met Tyr Gly Glu Pro Gly Thr
                340                 345                 350
Glu Pro Leu Glu Tyr Gly Ser Asn His Cys Gly Ile Thr Ala Met Trp
            355                 360                 365
Cys Leu Ser Ala Pro Tyr Glu Ala Ser Val Arg Phe Thr Arg Thr Asn
        370                 375                 380
Pro Ile Gln Ile Ala Gly Thr Ser Phe Ser Ala Pro Ile Val Thr Gly
385                 390                 395                 400
Thr Ala Ala Leu Leu Leu Gln Lys Tyr Pro Trp Met Ser Asn Asp Asn
                405                 410                 415
Leu Arg Thr Thr Leu Leu Thr Thr Ala Gln Asp Ile Gly Ala Val Gly
            420                 425                 430
Val Asp Ser Lys Phe Gly Trp Gly Leu Leu Asp Ala Gly Lys Ala Met
        435                 440                 445
Asn Gly Pro Ala Ser Phe Pro Phe Gly Asp Phe Thr Ala Asp Thr Lys
    450                 455                 460
Gly Thr Ser Asp Ile Ala Tyr Ser Phe Arg Asn Asp Ile Ser Gly Thr
465                 470                 475                 480
Gly Gly Leu Ile Lys Lys Gly Gly Ser Gln Leu Gln Leu His Gly Asn
                485                 490                 495
Asn Thr Tyr Thr Gly Lys Thr Ile Ile Glu Gly Gly Ser Leu Val Leu
            500                 505                 510
Tyr Gly Asn Asn Lys Ser Asp Met Arg Val Glu Thr Lys Gly Ala Leu
        515                 520                 525
Ile Tyr Asn Gly Ala Ala Ser Gly Gly Ser Leu Asn Ser Asp Gly Ile
    530                 535                 540
Val Tyr Leu Ala Asp Thr Asp Gln Ser Gly Ala Asn Glu Thr Val His
545                 550                 555                 560
Ile Lys Gly Ser Leu Gln Leu Asp Gly Lys Gly Thr Leu Tyr Thr Arg
                565                 570                 575
Leu Gly Lys Leu Leu Lys Val Asp Gly Thr Ala Ile Ile Gly Gly Lys
            580                 585                 590
Leu Tyr Met Ser Ala Arg Gly Lys Gly Ala Gly Tyr Leu Asn Ser Thr
        595                 600                 605
Gly Arg Arg Val Pro Phe Leu Ser Ala Ala Lys Ile Gly Gln Asp Tyr
    610                 615                 620
Ser Phe Phe Thr Asn Ile Glu Thr Asp Gly Gly Leu Leu Ala Ser Leu
625                 630                 635                 640
Asp Ser Val Glu Lys Thr Ala Gly Ser Glu Gly Asp Thr Leu Ser Tyr
                645                 650                 655
Tyr Val Arg Arg Gly Asn Ala Ala Arg Thr Ala Ser Ala Ala Ala His
            660                 665                 670
Ser Ala Pro Ala Gly Leu Lys His Ala Val Glu Gln Gly Gly Ser Asn
        675                 680                 685
Leu Glu Asn Leu Met Val Glu Leu Asp Ala Ser Glu Ser Ser Ala Thr
    690                 695                 700
Pro Glu Thr Val Glu Thr Ala Ala Ala Asp Arg Thr Asp Met Pro Gly
705                 710                 715                 720
Ile Arg Pro Tyr Gly Ala Thr Phe Arg Ala Ala Ala Val Gln His
                725                 730                 735
Ala Asn Ala Ala Asp Gly Val Arg Ile Phe Asn Ser Leu Ala Ala Thr
            740                 745                 750
```

-continued

```
Val Tyr Ala Asp Ser Thr Ala His Ala Asp Met Gln Gly Arg Arg
    755                 760                 765

Leu Lys Ala Val Ser Asp Gly Leu Asp His Asn Gly Thr Gly Leu Arg
    770                 775                 780

Val Ile Ala Gln Thr Gln Gln Asp Gly Gly Thr Trp Glu Gln Gly Gly
785                 790                 795                 800

Val Glu Gly Lys Met Arg Gly Ser Thr Gln Thr Val Gly Ile Ala Ala
                805                 810                 815

Lys Thr Gly Glu Asn Thr Thr Ala Ala Thr Leu Gly Met Gly Arg
    820                 825                 830

Ser Thr Trp Ser Glu Asn Ser Ala Asn Ala Lys Thr Asp Ser Ile Ser
            835                 840                 845

Leu Phe Ala Gly Ile Arg His Asp Ala Gly Asp Ile Gly Tyr Leu Lys
    850                 855                 860

Gly Leu Phe Ser Tyr Gly Arg Tyr Lys Asn Ser Ile Ser Arg Ser Thr
865                 870                 875                 880

Gly Ala Asp Glu His Ala Glu Gly Ser Val Asn Gly Thr Leu Met Gln
                885                 890                 895

Leu Gly Ala Leu Gly Gly Val Asn Val Pro Phe Ala Ala Thr Gly Asp
            900                 905                 910

Leu Thr Val Glu Gly Gly Leu Arg Tyr Asp Leu Leu Lys Gln Asp Ala
    915                 920                 925

Phe Ala Glu Lys Gly Ser Ala Leu Gly Trp Ser Gly Asn Ser Leu Thr
930                 935                 940

Glu Gly Thr Leu Val Gly Leu Ala Gly Leu Lys Leu Ser Gln Pro Leu
945                 950                 955                 960

Ser Asp Lys Ala Val Leu Phe Ala Thr Ala Gly Val Glu Arg Asp Leu
                965                 970                 975

Asn Gly Arg Asp Tyr Thr Val Thr Gly Gly Phe Thr Gly Ala Thr Ala
            980                 985                 990

Ala Thr Gly Lys Thr Gly Ala Arg Asn Met Pro His Thr Arg Leu Val
    995                 1000                1005

Ala Gly Leu Gly Ala Asp Val Glu Phe Gly Asn Gly Trp Asn Gly Leu
    1010                1015                1020

Ala Arg Tyr Ser Tyr Ala Gly Ser Lys Gln Tyr Gly Asn His Ser Gly
1025                1030                1035                1040

Arg Val Gly Val Gly Tyr Arg Phe Leu Glu Gly Gly Gly Thr Gly
                1045                1050                1055

Ser Ala Thr Asn Asp Asp Val Lys Lys Ala Ala Thr Val Ala Ile
            1060                1065                1070

Ala Ala Ala Tyr Asn Asn Gly Gln Glu Ile Asn Gly Phe Lys Ala Gly
    1075                1080                1085

Glu Thr Ile Tyr Asp Ile Asp Glu Asp Gly Thr Ile Thr Lys Lys Asp
    1090                1095                1100

Ala Thr Ala Ala Asp Val Glu Ala Asp Phe Lys Gly Leu Gly Leu
1105                1110                1115                1120

Lys Lys Val Val Thr Asn Leu Thr Lys Thr Val Asn Glu Asn Lys Gln
                1125                1130                1135

Asn Val Asp Ala Lys Val Lys Ala Ala Glu Ser Glu Ile Glu Lys Leu
            1140                1145                1150

Thr Thr Lys Leu Ala Asp Thr Asp Ala Ala Leu Ala Asp Thr Asp Ala
    1155                1160                1165

Ala Leu Asp Ala Thr Thr Asn Ala Leu Asn Lys Leu Gly Glu Asn Ile
    1170                1175                1180
```

```
Thr Thr Phe Ala Glu Glu Thr Lys Thr Asn Ile Val Lys Ile Asp Glu
1185                1190                1195                1200

Lys Leu Glu Ala Val Ala Asp Thr Val Asp Lys His Ala Glu Ala Phe
            1205                1210                1215

Asn Asp Ile Ala Asp Ser Leu Asp Glu Thr Asn Thr Lys Ala Asp Glu
        1220                1225                1230

Ala Val Lys Thr Ala Asn Glu Ala Lys Gln Thr Ala Glu Glu Thr Lys
    1235                1240                1245

Gln Asn Val Asp Ala Lys Val Lys Ala Ala Glu Thr Ala Ala Gly Lys
        1250                1255                1260

Ala Glu Ala Ala Ala Gly Thr Ala Asn Thr Ala Ala Asp Lys Ala Glu
1265                1270                1275                1280

Ala Val Ala Ala Lys Val Thr Asp Ile Lys Ala Asp Ile Ala Thr Asn
            1285                1290                1295

Lys Asp Asn Ile Ala Lys Lys Ala Asn Ser Ala Asp Val Tyr Thr Arg
        1300                1305                1310

Glu Glu Ser Asp Ser Lys Phe Val Arg Ile Asp Gly Leu Asn Ala Thr
    1315                1320                1325

Thr Glu Lys Leu Asp Thr Arg Leu Ala Ser Ala Glu Lys Ser Ile Ala
        1330                1335                1340

Asp His Asp Thr Arg Leu Asn Gly Leu Asp Lys Thr Val Ser Asp Leu
1345                1350                1355                1360

Arg Lys Glu Thr Arg Gln Gly Leu Ala Glu Gln Ala Ala Leu Ser Gly
            1365                1370                1375

Leu Phe Gln Pro Tyr Asn Val Gly Leu Glu His His His His His His
        1380                1385                1390

<210> SEQ ID NO 108
<211> LENGTH: 1947
<212> TYPE: DNA
<213> ORGANISM: Artificial Sequence
<220> FEATURE:
<223> OTHER INFORMATION: Synthetic construct

<400> SEQUENCE: 108
atggtcgccg ccgacatcgg tgcggggctt gccgatgcac taaccgcacc gctcgaccat      60
aaagacaaag gtttgcagtc tttgacgctg gatcagtccg tcaggaaaaa cgagaaactg     120
aagctggcgg cacaaggtgc ggaaaaaact tatggaaacg gtgacagcct caatacgggc     180
aaattgaaga cgacaaggt cagccgtttc gactttatcc gccaaatcga agtgacgggg      240
cagctcatta ccttggagag tggagagttc aagtataca aacaaagcca ttccgcctta     300
accgcctttc agaccgagca aatacaagat tcggagcatt ccgggaagat ggttgcgaaa     360
cgccagttca gaatcggcga catagcgggc gaacatacat cttttgacaa gcttcccgaa     420
ggcggcaggg cgacatatcg cgggacggcg ttcggttcag acgatgccgg cggaaaactg     480
acctacacca tagatttcgc cgccaagcag ggaaacggca aaatcgaaca tttgaaatcg     540
ccagaactca atgtcgacct ggccgccgcc gatatcaagc cggatggaaa acgccatgcc     600
gtcatcagcg gttccgtcct ttacaaccaa gccgagaaag gcagttactc cctcggtatc     660
tttggcggaa aagcccagga agttgccggc agcgcggaag tgaaaaccgt aaacggcata     720
cgccatatcg gccttgccgc caagcaactc gagggtggcg gaggcactgg atccgccaca     780
aacgacgacg atgttaaaaa agctgccact gtggccattg ctgctgccta acaatggc      840 caagaaatca acggtttcaa agctggagag accatctacg acattgatga agacggcaca     900
```

```
attaccaaaa aagacgcaac tgcagccgat gttgaagccg acgactttaa aggtctgggt    960
ctgaaaaaag tcgtgactaa cctgaccaaa accgtcaatg aaaacaaaca aaacgtcgat   1020
gccaaagtaa aagctgcaga atctgaaata gaaaagttaa caaccaagtt agcagacact   1080
gatgccgctt tagcagatac tgatgccgct ctggatgcaa ccaccaacgc cttgaataaa   1140
ttgggagaaa atataacgac atttgctgaa gagactaaga caaatatcgt aaaaattgat   1200
gaaaaattag aagccgtggc tgataccgtc gacaagcatg ccgaagcatt caacgatatc   1260
gccgattcat ggatgaaaac caacactaag gcagacgaag ccgtcaaaac cgccaatgaa   1320
gccaaacaga cggccgaaga aaccaaacaa aacgtcgatg ccaaagtaaa agctgcagaa   1380
actgcagcag gcaaagccga agctgccgct ggcacagcta atactgcagc cgacaaggcc   1440
gaagctgtcg ctgcaaaagt taccgacatc aaagctgata tcgctacgaa caagataat   1500 attgctaaaa aagcaaacag tgccgacgtg tacaccagag aagagtctga cagcaaattt   1560
gtcagaattg atggtctgaa cgctactacc gaaaaattgg acacacgctt ggcttctgct   1620
gaaaaatcca ttgccgatca cgatactcgc ctgaacggtt tggataaaac agtgtcagac   1680
ctgcgcaaag aaacccgcca aggccttgca gaacaagccg cgctctccgg tctgttccaa   1740
ccttacaacg tgggtcggtt caatgtaacg gctgcagtcg gcggctacaa atccgaatcg   1800
gcagtcgcca tcgtaccgg cttccgcttt accgaaaaact tgccgccaa agcaggcgtg   1860 gcagtcggca cttcgtccgg ttcttccgca gcctaccatg tcggcgtcaa ttacgagtgg   1920
ctcgagcacc accaccacca ccactga                                       1947
```

<210> SEQ ID NO 109
<211> LENGTH: 648
<212> TYPE: PRT
<213> ORGANISM: Artificial Sequence
<220> FEATURE:
<223> OTHER INFORMATION: Synthetic construct

<400> SEQUENCE: 109

```
Met Val Ala Ala Asp Ile Gly Ala Gly Leu Ala Asp Ala Leu Thr Ala
1               5                   10                  15

Pro Leu Asp His Lys Asp Lys Gly Leu Gln Ser Leu Thr Leu Asp Gln
            20                  25                  30

Ser Val Arg Lys Asn Glu Lys Leu Lys Leu Ala Gln Gly Ala Glu
        35                  40                  45

Lys Thr Tyr Gly Asn Gly Asp Ser Leu Asn Thr Gly Lys Leu Lys Asn
50                  55                  60

Asp Lys Val Ser Arg Phe Asp Phe Ile Arg Gln Ile Glu Val Asp Gly
65                  70                  75                  80

Gln Leu Ile Thr Leu Glu Ser Gly Glu Phe Gln Val Tyr Lys Gln Ser
                85                  90                  95

His Ser Ala Leu Thr Ala Phe Gln Thr Glu Gln Ile Gln Asp Ser Glu
            100                 105                 110

His Ser Gly Lys Met Val Ala Lys Arg Gln Phe Arg Ile Gly Asp Ile
        115                 120                 125

Ala Gly Glu His Thr Ser Phe Asp Lys Leu Pro Glu Gly Gly Arg Ala
    130                 135                 140

Thr Tyr Arg Gly Thr Ala Phe Gly Ser Asp Asp Ala Gly Gly Lys Leu
145                 150                 155                 160

Thr Tyr Thr Ile Asp Phe Ala Ala Lys Gln Gly Asn Gly Lys Ile Glu
                165                 170                 175

His Leu Lys Ser Pro Glu Leu Asn Val Asp Leu Ala Ala Ala Asp Ile
```

-continued

```
                180             185                 190
Lys Pro Asp Gly Lys Arg His Ala Val Ile Ser Gly Ser Val Leu Tyr
            195                 200             205

Asn Gln Ala Glu Lys Gly Ser Tyr Ser Leu Gly Ile Phe Gly Gly Lys
        210                 215             220

Ala Gln Glu Val Ala Gly Ser Ala Glu Val Lys Thr Val Asn Gly Ile
225                 230              235                 240

Arg His Ile Gly Leu Ala Ala Lys Gln Leu Glu Gly Gly Gly Gly Thr
                245                 250                 255

Gly Ser Ala Thr Asn Asp Asp Val Lys Lys Ala Ala Thr Val Ala
                260                 265             270

Ile Ala Ala Ala Tyr Asn Asn Gly Gln Glu Ile Asn Gly Phe Lys Ala
                275             280                 285

Gly Glu Thr Ile Tyr Asp Ile Asp Glu Asp Gly Thr Ile Thr Lys Lys
            290             295             300

Asp Ala Thr Ala Ala Asp Val Glu Ala Asp Phe Lys Gly Leu Gly
305             310                 315                 320

Leu Lys Lys Val Val Thr Asn Leu Thr Lys Thr Val Asn Glu Asn Lys
                325                 330                 335

Gln Asn Val Asp Ala Lys Val Lys Ala Glu Ser Glu Ile Glu Lys
            340             345                 350

Leu Thr Thr Lys Leu Ala Asp Thr Asp Ala Ala Leu Ala Asp Thr Asp
                355                 360                 365

Ala Ala Leu Asp Ala Thr Thr Asn Ala Leu Asn Lys Leu Gly Glu Asn
370                 375                 380

Ile Thr Thr Phe Ala Glu Glu Thr Lys Thr Asn Ile Val Lys Ile Asp
385                 390                 395                 400

Glu Lys Leu Glu Ala Val Ala Asp Thr Val Asp Lys His Ala Glu Ala
                405                 410                 415

Phe Asn Asp Ile Ala Asp Ser Leu Asp Glu Thr Asn Thr Lys Ala Asp
                420                 425                 430

Glu Ala Val Lys Thr Ala Asn Glu Ala Lys Gln Thr Ala Glu Glu Thr
                435                 440                 445

Lys Gln Asn Val Asp Ala Lys Val Lys Ala Glu Thr Ala Ala Gly
            450                 455             460

Lys Ala Glu Ala Ala Ala Gly Thr Ala Asn Thr Ala Ala Asp Lys Ala
465                 470                 475                 480

Glu Ala Val Ala Ala Lys Val Thr Asp Ile Lys Ala Asp Ile Ala Thr
                485                 490                 495

Asn Lys Asp Asn Ile Ala Lys Lys Ala Asn Ser Ala Asp Val Tyr Thr
            500                 505             510

Arg Glu Glu Ser Asp Ser Lys Phe Val Arg Ile Asp Gly Leu Asn Ala
            515                 520             525

Thr Thr Glu Lys Leu Asp Thr Arg Leu Ala Ser Ala Glu Lys Ser Ile
            530                 535             540

Ala Asp His Asp Thr Arg Leu Asn Gly Leu Asp Lys Thr Val Ser Asp
545                 550                 555                 560

Leu Arg Lys Glu Thr Arg Gln Gly Leu Ala Glu Gln Ala Ala Leu Ser
                565                 570                 575

Gly Leu Phe Gln Pro Tyr Asn Val Gly Arg Phe Asn Val Thr Ala Ala
                580                 585                 590

Val Gly Gly Tyr Lys Ser Glu Ser Ala Val Ala Ile Gly Thr Gly Phe
                595                 600                 605
```

```
Arg Phe Thr Glu Asn Phe Ala Ala Lys Ala Gly Val Ala Val Gly Thr
            610                 615                 620

Ser Ser Gly Ser Ser Ala Ala Tyr His Val Gly Val Asn Tyr Glu Trp
625                 630                 635                 640

Leu Glu His His His His His His
                645

<210> SEQ ID NO 110
<211> LENGTH: 1782
<212> TYPE: DNA
<213> ORGANISM: Artificial Sequence
<220> FEATURE:
<223> OTHER INFORMATION: Synthetic construct

<400> SEQUENCE: 110
```

| | |
|---|---|
| atggtcgccg ccgacatcgg tgcggggctt gccgatgcac taaccgcacc gctcgaccat | 60 |
| aaagacaaag gtttgcagtc tttgacgctg gatcagtccg tcaggaaaaa cgagaaactg | 120 |
| aagctggcgg cacaaggtgc ggaaaaaact tatggaaacg gtgacagcct caatacgggc | 180 |
| aaattgaaga acgacaaggt cagccgtttc gactttatcc gccaaatcga agtggacggg | 240 |
| cagctcatta ccttggagag tggagagttc aagtatataa acaaagcca ttccgcctta | 300 |
| accgcctttc agaccgagca aatacaagat tcggagcatt ccgggaagat ggttgcgaaa | 360 |
| cgccagttca gaatcggcga catagcgggc gaacatatac tttttgacaa gcttcccgaa | 420 |
| ggcggcaggg cgacatatcg cgggacggcg ttcggttcag acgatgccgg cggaaaactg | 480 |
| acctacacca tagatttcgc cgccaagcag ggaaacggca aaatcgaaca tttgaaatcg | 540 |
| ccagaactca atgtcgacct ggccgccgcc gatatcaagc cggatggaaa acgccatgcc | 600 |
| gtcatcagcg gttccgtcct ttacaaccaa gccgagaaag gcagttactc cctcggtatc | 660 |
| tttggcggaa agcccagga gttgccggc agcgcggaag tgaaaaccgt aaacggcata | 720 |
| cgccatatcg gccttgccgc caagcaactc gagggtggcg aggcactgg atccgccaca | 780 |
| aacgacgacg atgttaaaaa agctgccact gtggccattg ctgctgccta acaatggc | 840 |
| caagaaatca acggtttcaa agctggagag accatctacg acattgatga agacggcaca | 900 |
| attaccaaaa aagacgcaac tgcagccgat gttgaagccg acgactttaa aggtctgggt | 960 |
| ctgaaaaaag tcgtgactaa cctgaccaaa accgtcaatg aaaacaaaca aaacgtcgat | 1020 |
| gccaaagtaa aagctgcaga atctgaaata gaaaagttaa caaccaagtt agcagacact | 1080 |
| gatgccgctt tagcagatac tgatgccgct ctggatgcaa ccaccaacgc cttgaataaa | 1140 |
| ttgggagaaa atataacgac atttgctgaa gagactaaga caaatatcgt aaaaattgat | 1200 |
| gaaaaattag aagccgtggc tgataccgtc gacaagcatg ccgaagcatt caacgatatc | 1260 |
| gccgattcat tggatgaaac caacactaag gcagacgaag ccgtcaaaac cgccaatgaa | 1320 |
| gccaaacaga cggccgaaga aaccaaacaa aacgtcgatg ccaaagtaaa agctgcagaa | 1380 |
| actgcagcag gcaaagccga agctgccgct ggcacagcta atactgcagc cgacaaggcc | 1440 |
| gaagctgtcg ctgcaaaagt taccgacatc aaagctgata tcgctacgaa caaagataat | 1500 |
| attgctaaaa aagcaaacag tgccgacgtg tacaccagag aagagtctga cagcaaattt | 1560 |
| gtcagaattg atggtctgaa cgctactacc gaaaaattgg acacacgctt ggcttctgct | 1620 |
| gaaaaatcca ttgccgatca cgatactcgc ctgaacggtt tggataaaac agtgtcagac | 1680 |
| ctgcgcaaag aaacccgcca aggccttgca gaacaagccg cgctctccgg tctgttccaa | 1740 |
| ccttacaacg tgggtctcga gcaccaccac caccaccact ga | 1782 |

```
<210> SEQ ID NO 111
<211> LENGTH: 593
<212> TYPE: PRT
<213> ORGANISM: Artificial Sequence
<220> FEATURE:
<223> OTHER INFORMATION: Synthetic construct

<400> SEQUENCE: 111
```

| | | | | | | | | | | | | | | | |
|---|---|---|---|---|---|---|---|---|---|---|---|---|---|---|---|
| Met | Val | Ala | Ala | Asp | Ile | Gly | Ala | Gly | Leu | Ala | Asp | Ala | Leu | Thr | Ala |
| 1 | | | | 5 | | | | | 10 | | | | | 15 | |
| Pro | Leu | Asp | His | Lys | Asp | Lys | Gly | Leu | Gln | Ser | Leu | Thr | Leu | Asp | Gln |
| | | | 20 | | | | | 25 | | | | | 30 | | |
| Ser | Val | Arg | Lys | Asn | Glu | Lys | Leu | Lys | Leu | Ala | Ala | Gln | Gly | Ala | Glu |
| | | 35 | | | | | 40 | | | | | 45 | | | |
| Lys | Thr | Tyr | Gly | Asn | Gly | Asp | Ser | Leu | Asn | Thr | Gly | Lys | Leu | Lys | Asn |
| | 50 | | | | | 55 | | | | | 60 | | | | |
| Asp | Lys | Val | Ser | Arg | Phe | Asp | Phe | Ile | Arg | Gln | Ile | Glu | Val | Asp | Gly |
| 65 | | | | | 70 | | | | | 75 | | | | | 80 |
| Gln | Leu | Ile | Thr | Leu | Glu | Ser | Gly | Glu | Phe | Gln | Val | Tyr | Lys | Gln | Ser |
| | | | | 85 | | | | | 90 | | | | | 95 | |
| His | Ser | Ala | Leu | Thr | Ala | Phe | Gln | Thr | Glu | Gln | Ile | Gln | Asp | Ser | Glu |
| | | | 100 | | | | | 105 | | | | | 110 | | |
| His | Ser | Gly | Lys | Met | Val | Ala | Lys | Arg | Gln | Phe | Arg | Ile | Gly | Asp | Ile |
| | | 115 | | | | | 120 | | | | | 125 | | | |
| Ala | Gly | Glu | His | Thr | Ser | Phe | Asp | Lys | Leu | Pro | Glu | Gly | Gly | Arg | Ala |
| 130 | | | | | 135 | | | | | 140 | | | | | |
| Thr | Tyr | Arg | Gly | Thr | Ala | Phe | Gly | Ser | Asp | Asp | Ala | Gly | Gly | Lys | Leu |
| 145 | | | | | 150 | | | | | 155 | | | | | 160 |
| Thr | Tyr | Thr | Ile | Asp | Phe | Ala | Ala | Lys | Gln | Gly | Asn | Gly | Lys | Ile | Glu |
| | | | | 165 | | | | | 170 | | | | | 175 | |
| His | Leu | Lys | Ser | Pro | Glu | Leu | Asn | Val | Asp | Leu | Ala | Ala | Ala | Asp | Ile |
| | | | 180 | | | | | 185 | | | | | 190 | | |
| Lys | Pro | Asp | Gly | Lys | Arg | His | Ala | Val | Ile | Ser | Gly | Ser | Val | Leu | Tyr |
| | | 195 | | | | | 200 | | | | | 205 | | | |
| Asn | Gln | Ala | Glu | Lys | Gly | Ser | Tyr | Ser | Leu | Gly | Ile | Phe | Gly | Gly | Lys |
| 210 | | | | | 215 | | | | | 220 | | | | | |
| Ala | Gln | Glu | Val | Ala | Gly | Ser | Ala | Glu | Val | Lys | Thr | Val | Asn | Gly | Ile |
| 225 | | | | | 230 | | | | | 235 | | | | | 240 |
| Arg | His | Ile | Gly | Leu | Ala | Ala | Lys | Gln | Leu | Glu | Gly | Gly | Gly | Gly | Thr |
| | | | | 245 | | | | | 250 | | | | | 255 | |
| Gly | Ser | Ala | Thr | Asn | Asp | Asp | Val | Lys | Lys | Ala | Ala | Thr | Val | Ala | |
| | | | 260 | | | | | 265 | | | | | 270 | | |
| Ile | Ala | Ala | Ala | Tyr | Asn | Asn | Gly | Gln | Glu | Ile | Asn | Gly | Phe | Lys | Ala |
| | | | 275 | | | | | 280 | | | | | 285 | | |
| Gly | Glu | Thr | Ile | Tyr | Asp | Ile | Asp | Glu | Asp | Gly | Thr | Ile | Thr | Lys | Lys |
| | | 290 | | | | | 295 | | | | | 300 | | | |
| Asp | Ala | Thr | Ala | Ala | Asp | Val | Glu | Ala | Asp | Phe | Lys | Gly | Leu | Gly | |
| 305 | | | | | 310 | | | | | 315 | | | | | 320 |
| Leu | Lys | Lys | Val | Val | Thr | Asn | Leu | Thr | Lys | Thr | Val | Asn | Glu | Asn | Lys |
| | | | | 325 | | | | | 330 | | | | | 335 | |
| Gln | Asn | Val | Asp | Ala | Lys | Val | Lys | Ala | Ala | Glu | Ser | Glu | Ile | Glu | Lys |
| | | | 340 | | | | | 345 | | | | | 350 | | |
| Leu | Thr | Thr | Lys | Leu | Ala | Asp | Thr | Asp | Ala | Ala | Leu | Ala | Asp | Thr | Asp |
| | | | 355 | | | | | 360 | | | | | 365 | | |
| Ala | Ala | Leu | Asp | Ala | Thr | Thr | Asn | Ala | Leu | Asn | Lys | Leu | Gly | Glu | Asn |
| | | 370 | | | | | 375 | | | | | 380 | | | |

```
Ile Thr Thr Phe Ala Glu Glu Thr Lys Thr Asn Ile Val Lys Ile Asp
385                 390                 395                 400

Glu Lys Leu Glu Ala Val Ala Asp Thr Val Asp Lys His Ala Glu Ala
            405                 410                 415

Phe Asn Asp Ile Ala Asp Ser Leu Asp Glu Thr Asn Thr Lys Ala Asp
            420                 425                 430

Glu Ala Val Lys Thr Ala Asn Glu Ala Lys Gln Thr Ala Glu Glu Thr
            435                 440                 445

Lys Gln Asn Val Asp Ala Lys Val Lys Ala Ala Glu Thr Ala Ala Gly
            450                 455                 460

Lys Ala Glu Ala Ala Ala Gly Thr Ala Asn Thr Ala Ala Asp Lys Ala
465                 470                 475                 480

Glu Ala Val Ala Ala Lys Val Thr Asp Ile Lys Ala Asp Ile Ala Thr
            485                 490                 495

Asn Lys Asp Asn Ile Ala Lys Lys Ala Asn Ser Ala Asp Val Tyr Thr
            500                 505                 510

Arg Glu Glu Ser Asp Ser Lys Phe Val Arg Ile Asp Gly Leu Asn Ala
            515                 520                 525

Thr Thr Glu Lys Leu Asp Thr Arg Leu Ala Ser Ala Glu Lys Ser Ile
            530                 535                 540

Ala Asp His Asp Thr Arg Leu Asn Gly Leu Asp Lys Thr Val Ser Asp
545                 550                 555                 560

Leu Arg Lys Glu Thr Arg Gln Gly Leu Ala Glu Gln Ala Ala Leu Ser
            565                 570                 575

Gly Leu Phe Gln Pro Tyr Asn Val Gly Leu Glu His His His His
            580                 585                 590

His
```

<210> SEQ ID NO 112
<211> LENGTH: 3939
<212> TYPE: DNA
<213> ORGANISM: Artificial Sequence
<220> FEATURE:
<223> OTHER INFORMATION: Synthetic construct

<400> SEQUENCE: 112

```
atggtcgccg ccgacatcgg tgcggggctt gccgatgcac taaccgcacc gctcgaccat    60
aaagacaaag gtttgcagtc tttgacgctg gatcagtccg tcaggaaaaa cgagaaactg   120
aagctggcgg cacaaggtgc ggaaaaaact tatggaaacg gtgacagcct caatacgggc   180
aaattgaaga cgacaaggt cagccgtttc gactttatcc gccaaatcga agtggacggg   240
cagctcatta ccttggagag tggagagttc aagtataca aacaaagcca ttccgcctta   300
accgcctttc agaccgagca aatacaagat tcggagcatt ccgggaagat ggttgcgaaa   360
cgccagttca gaatcggcga catagcgggc gaacatacat cttttgacaa gcttcccgaa   420
ggcggcaggg cgacatatcg cgggacggcg ttcggttcag acgatgccgg cggaaaactg   480
acctacacca tagatttcgc cgccaagcag ggaaacggca aaatcgaaca tttgaaatcg   540
ccagaactca atgtcgacct ggccgccgcc gatatcaagc cggatggaaa acgccatgcc   600
gtcatcagcg gttccgtcct ttacaaccaa gccgagaaag gcagttactc cctcggtatc   660
tttggcggaa aagcccagga agttgccggc agcgcggaag tgaaaaccgt aaacggcata   720
cgccatatcg gccttgccgc caagcaactc gagggatccg gcgaggcgg cacttctgcg   780
cccgacttca tgcaggcgg taccggtatc ggcagcaaca gcagagcaac aacagcgaaa   840
```

```
tcagcagcag tatcttacgc cggtatcaag aacgaaatgt gcaaagacag aagcatgctc    900
tgtgccggtc gggatgacgt tgcggttaca gacaggatgg ccaaaatcaa tgccccccccc   960
ccgaatctgc ataccggaga cttttccaaac ccaaatgacg catacaagaa tttgatcaac   1020
ctcaaacctg caattgaagc aggctataca ggacgcgggg tagaggtagg tatcgtcgac   1080
acaggcgaat ccgtcggcag catatccttt cccgaactgt atggcagaaa agaacacggc   1140
tataacgaaa attacaaaaa ctatacgcg tatatgcgga aggaagcgcc tgaagacgga    1200
ggcggtaaag acattgaagc ttctttcgac gatgaggccg ttatagagac tgaagcaaag   1260
ccgacggata tccgccacgt aaaagaaatc ggacacatcg atttggtctc ccatattatt   1320
ggcgggcgtt ccgtggacgg cagacctgca ggcggtattg cgcccgatgc gacgctacac   1380
ataatgaata cgaatgatga aaccaagaac gaaatgatgg ttgcagccat ccgcaatgca   1440
tgggtcaagc tgggcgaacg tggcgtgcgc atcgtcaata acagttttgg aacaacatcg   1500
agggcaggca ctgccgacct tttccaaata gccaattcgg aggagcagta ccgccaagcg   1560
ttgctcgact attccggcgg tgataaaaca gacgagggta tccgcctgat gcaacagagc   1620
gattacggca acctgtccta ccacatccgt aataaaaaca tgcttttcat cttttcgaca   1680
ggcaatgacg cacaagctca gcccaacaca tatgccctat tgccatttta tgaaaaagac   1740
gctcaaaaag gcattatcac agtcgcaggc gtagaccgca gtggagaaaa gttcaaacgg   1800
gaaatgtatg agaaccgggg tacagaaccg cttgagtatg gctccaacca ttgcggaatt   1860
actgccatgt ggtgcctgtc ggcaccctat gaagcaagcg tccgtttcac ccgtacaaac   1920
ccgattcaaa ttgccggaac atccttttcc gcacccatcg taaccggcac ggcggctctg   1980
ctgctgcaga ataccccgtg gatgagcaac gacaacctgc gtaccacgtt gctgacgacg   2040
gctcaggaca tcggtgcagt cggcgtggac agcaagttcg gctggggact gctggatgcg   2100
ggtaaggcca tgaacggacc cgcgtccttt ccgttcggcg actttaccgc cgatacgaaa   2160
ggtacatccg atattgccta ctccttccgt aacgacattt caggcacggg cggcctgatc   2220
aaaaaaggcg gcagccaact gcaactgcac ggcaacaaca cctatacggg caaaaccatt   2280
atcgaaggcg gttcgctggt gttgtacggc aacaacaaat cggatatgcg cgtcgaaacc   2340
aaaggtgcgc tgatttataa cggggcggca tccggcggca gcctgaacag cgacggcatt   2400
gtctatctgg cagataccga ccaatccggc gcaaacgaaa ccgtacacat caaaggcagt   2460
ctgcagctgg acggcaaagg tacgctgtac acacgtttgg gcaaactgct gaaagtggac   2520
ggtacggcga ttatcggcgg caagctgtac atgtcggcac gcggcaaggg ggcaggctat   2580
ctcaacagta ccggacgacg tgttcccttc ctgagtgccg ccaaaatcgg gcaggattat   2640
tcttctcttca caaacatcga aaccgacggc ggcctgctgg cttccctcga cagcgtcgaa   2700
aaaacagcgg gcagtgaagg cgacacgctg tcctattatg tccgtcgcgg caatgcggca   2760
cggactgctt cggcagcggc acattccgcg cccgccggtc tgaaacacgc cgtagaacag   2820
ggcggcagca atctggaaaa cctgatggtc gaactggatg cctccgaatc atccgcaaca   2880
cccgagacgt ttgaaactgc ggcagccgac cgcacagata tgccgggcat ccgcccctac   2940
ggcgcaactt tccgcgcagc ggcagccgta cagcatgcga atgccgccga cggtgtacgc   3000
atcttcaaca gtctcgccgc taccgtctat gccgacagta ccgccgccca tgccgatatg   3060
cagggacgcc gcctgaaagc cgtatcggac gggttggacc acaacggcac gggtctgcgc   3120
gtcatcgcgc aaacccaaca ggacggtgga acgtgggaac agggcggtgt tgaaggcaaa   3180
atgcgcggca gtacccaaac cgtcggcatt gccgcgaaaa ccggcgaaaa tacgacagca   3240
```

```
gccgccacac tgggcatggg acgcagcaca tggagcgaaa acagtgcaaa tgcaaaaacc    3300
gacagcatta gtctgtttgc aggcatacgg cacgatgcgg gcgatatcgg ctatctcaaa    3360
ggcctgttct cctacggacg ctacaaaaac agcatcagcc gcagcaccgg tgcggacgaa    3420
catgcggaag gcagcgtcaa cggcacgctg atgcagctgg gcgcactggg cggtgtcaac    3480
gttccgtttg ccgcaacggg agatttgacg gtcgaaggcg gtctgcgcta cgacctgctc    3540
aaacaggatg cattcgccga aaaaggcagt gctttgggct ggagcggcaa cagcctcact    3600
gaaggcacgc tggtcggact cgcgggtctg aagctgtcgc aacccttgag cgataaagcc    3660
gtcctgtttg caacggcggg cgtggaacgc gacctgaacg gacgcgacta cacggtaacg    3720
ggcggcttta ccggcgcgac tgcagcaacc ggcaagacgg gggcacgcaa tatgccgcac    3780
acccgtctgg ttgccggcct gggcgcggat gtcgaattcg caacggctg gaacggcttg    3840 gcacgttaca gctacgccgg ttccaaacag tacggcaacc acagcggacg agtcggcgta    3900
ggctaccggt tcctcgagca ccaccaccac caccactga                          3939
```

```
<210> SEQ ID NO 113
<211> LENGTH: 1312
<212> TYPE: PRT
<213> ORGANISM: Artificial Sequence
<220> FEATURE:
<223> OTHER INFORMATION: Synthetic construct

<400> SEQUENCE: 113

Met Val Ala Ala Asp Ile Gly Ala Gly Leu Ala Asp Ala Leu Thr Ala
1               5                   10                  15

Pro Leu Asp His Lys Asp Lys Gly Leu Gln Ser Leu Thr Leu Asp Gln
                20                  25                  30

Ser Val Arg Lys Asn Glu Lys Leu Lys Leu Ala Ala Gln Gly Ala Glu
            35                  40                  45

Lys Thr Tyr Gly Asn Gly Asp Ser Leu Asn Thr Gly Lys Leu Lys Asn
        50                  55                  60

Asp Lys Val Ser Arg Phe Asp Phe Ile Arg Gln Ile Glu Val Asp Gly
65                  70                  75                  80

Gln Leu Ile Thr Leu Glu Ser Gly Glu Phe Gln Val Tyr Lys Gln Ser
                85                  90                  95

His Ser Ala Leu Thr Ala Phe Gln Thr Glu Gln Ile Gln Asp Ser Glu
            100                 105                 110

His Ser Gly Lys Met Val Ala Lys Arg Gln Phe Arg Ile Gly Asp Ile
        115                 120                 125

Ala Gly Glu His Thr Ser Phe Asp Lys Leu Pro Glu Gly Gly Arg Ala
    130                 135                 140

Thr Tyr Arg Gly Thr Ala Phe Gly Ser Asp Asp Ala Gly Gly Lys Leu
145                 150                 155                 160

Thr Tyr Thr Ile Asp Phe Ala Ala Lys Gln Gly Asn Gly Lys Ile Glu
                165                 170                 175

His Leu Lys Ser Pro Glu Leu Asn Val Asp Leu Ala Ala Ala Asp Ile
            180                 185                 190

Lys Pro Asp Gly Lys Arg His Ala Val Ile Ser Gly Ser Val Leu Tyr
        195                 200                 205

Asn Gln Ala Glu Lys Gly Ser Tyr Ser Leu Gly Ile Phe Gly Gly Lys
    210                 215                 220

Ala Gln Glu Val Ala Gly Ser Ala Glu Val Lys Thr Val Asn Gly Ile
225                 230                 235                 240

Arg His Ile Gly Leu Ala Ala Lys Gln Leu Glu Gly Ser Gly Gly Gly
```

```
                245                 250                 255
Gly Thr Ser Ala Pro Asp Phe Asn Ala Gly Thr Gly Ile Gly Ser
            260                 265                 270

Asn Ser Arg Ala Thr Thr Ala Lys Ser Ala Ala Val Ser Tyr Ala Gly
        275                 280                 285

Ile Lys Asn Glu Met Cys Lys Asp Arg Ser Met Leu Cys Ala Gly Arg
        290                 295                 300

Asp Asp Val Ala Val Thr Asp Arg Asp Ala Lys Ile Asn Ala Pro Pro
305                 310                 315                 320

Pro Asn Leu His Thr Gly Asp Phe Pro Asn Pro Asn Asp Ala Tyr Lys
                325                 330                 335

Asn Leu Ile Asn Leu Lys Pro Ala Ile Glu Ala Gly Tyr Thr Gly Arg
            340                 345                 350

Gly Val Glu Val Gly Ile Val Asp Thr Gly Glu Ser Val Gly Ser Ile
        355                 360                 365

Ser Phe Pro Glu Leu Tyr Gly Arg Lys Glu His Gly Tyr Asn Glu Asn
    370                 375                 380

Tyr Lys Asn Tyr Thr Ala Tyr Met Arg Lys Glu Ala Pro Glu Asp Gly
385                 390                 395                 400

Gly Gly Lys Asp Ile Glu Ala Ser Phe Asp Asp Glu Ala Val Ile Glu
                405                 410                 415

Thr Glu Ala Lys Pro Thr Asp Ile Arg His Val Lys Glu Ile Gly His
            420                 425                 430

Ile Asp Leu Val Ser His Ile Ile Gly Gly Arg Ser Val Asp Gly Arg
        435                 440                 445

Pro Ala Gly Gly Ile Ala Pro Asp Ala Thr Leu His Ile Met Asn Thr
    450                 455                 460

Asn Asp Glu Thr Lys Asn Glu Met Met Val Ala Ala Ile Arg Asn Ala
465                 470                 475                 480

Trp Val Lys Leu Gly Glu Arg Gly Val Arg Ile Val Asn Asn Ser Phe
                485                 490                 495

Gly Thr Thr Ser Arg Ala Gly Thr Ala Asp Leu Phe Gln Ile Ala Asn
            500                 505                 510

Ser Glu Glu Gln Tyr Arg Gln Ala Leu Leu Asp Tyr Ser Gly Gly Asp
        515                 520                 525

Lys Thr Asp Glu Gly Ile Arg Leu Met Gln Gln Ser Asp Tyr Gly Asn
    530                 535                 540

Leu Ser Tyr His Ile Arg Asn Lys Asn Met Leu Phe Ile Phe Ser Thr
545                 550                 555                 560

Gly Asn Asp Ala Gln Ala Gln Pro Asn Thr Tyr Ala Leu Leu Pro Phe
                565                 570                 575

Tyr Glu Lys Asp Ala Gln Lys Gly Ile Ile Thr Val Ala Gly Val Asp
            580                 585                 590

Arg Ser Gly Glu Lys Phe Lys Arg Glu Met Tyr Gly Glu Pro Gly Thr
        595                 600                 605

Glu Pro Leu Glu Tyr Gly Ser Asn His Cys Gly Ile Thr Ala Met Trp
    610                 615                 620

Cys Leu Ser Ala Pro Tyr Glu Ala Ser Val Arg Phe Thr Arg Thr Asn
625                 630                 635                 640

Pro Ile Gln Ile Ala Gly Thr Ser Phe Ser Ala Pro Ile Val Thr Gly
                645                 650                 655

Thr Ala Ala Leu Leu Leu Gln Lys Tyr Pro Trp Met Ser Asn Asp Asn
            660                 665                 670
```

-continued

```
Leu Arg Thr Thr Leu Leu Thr Thr Ala Gln Asp Ile Gly Ala Val Gly
            675                 680                 685

Val Asp Ser Lys Phe Gly Trp Gly Leu Leu Asp Ala Gly Lys Ala Met
        690                 695                 700

Asn Gly Pro Ala Ser Phe Pro Phe Gly Asp Phe Thr Ala Asp Thr Lys
705                 710                 715                 720

Gly Thr Ser Asp Ile Ala Tyr Ser Phe Arg Asn Asp Ile Ser Gly Thr
                725                 730                 735

Gly Gly Leu Ile Lys Lys Gly Ser Gln Leu Gln Leu His Gly Asn
                740                 745                 750

Asn Thr Tyr Thr Gly Lys Thr Ile Ile Glu Gly Gly Ser Leu Val Leu
        755                 760                 765

Tyr Gly Asn Asn Lys Ser Asp Met Arg Val Glu Thr Lys Gly Ala Leu
770                 775                 780

Ile Tyr Asn Gly Ala Ala Ser Gly Gly Ser Leu Asn Ser Asp Gly Ile
785                 790                 795                 800

Val Tyr Leu Ala Asp Thr Asp Gln Ser Gly Ala Asn Glu Thr Val His
                805                 810                 815

Ile Lys Gly Ser Leu Gln Leu Asp Gly Lys Gly Thr Leu Tyr Thr Arg
        820                 825                 830

Leu Gly Lys Leu Leu Lys Val Asp Gly Thr Ala Ile Ile Gly Gly Lys
        835                 840                 845

Leu Tyr Met Ser Ala Arg Gly Lys Gly Ala Gly Tyr Leu Asn Ser Thr
    850                 855                 860

Gly Arg Arg Val Pro Phe Leu Ser Ala Ala Lys Ile Gly Gln Asp Tyr
865                 870                 875                 880

Ser Phe Phe Thr Asn Ile Glu Thr Asp Gly Gly Leu Leu Ala Ser Leu
                885                 890                 895

Asp Ser Val Glu Lys Thr Ala Gly Ser Glu Gly Asp Thr Leu Ser Tyr
            900                 905                 910

Tyr Val Arg Arg Gly Asn Ala Ala Arg Thr Ala Ser Ala Ala Ala His
        915                 920                 925

Ser Ala Pro Ala Gly Leu Lys His Ala Val Glu Gln Gly Gly Ser Asn
    930                 935                 940

Leu Glu Asn Leu Met Val Glu Leu Asp Ala Ser Glu Ser Ser Ala Thr
945                 950                 955                 960

Pro Glu Thr Val Glu Thr Ala Ala Ala Asp Arg Thr Asp Met Pro Gly
                965                 970                 975

Ile Arg Pro Tyr Gly Ala Thr Phe Arg Ala Ala Ala Val Gln His
            980                 985                 990

Ala Asn Ala Ala Asp Gly Val Arg Ile Phe Asn Ser Leu Ala Ala Thr
        995                1000                1005

Val Tyr Ala Asp Ser Thr Ala Ala His Ala Asp Met Gln Gly Arg Arg
    1010                1015                1020

Leu Lys Ala Val Ser Asp Gly Leu Asp His Asn Gly Thr Gly Leu Arg
1025                1030                1035                1040

Val Ile Ala Gln Thr Gln Gln Asp Gly Gly Thr Trp Glu Gln Gly Gly
                1045                1050                1055

Val Glu Gly Lys Met Arg Gly Ser Thr Gln Thr Val Gly Ile Ala Ala
            1060                1065                1070

Lys Thr Gly Glu Asn Thr Thr Ala Ala Ala Thr Leu Gly Met Gly Arg
        1075                1080                1085

Ser Thr Trp Ser Glu Asn Ser Ala Asn Ala Lys Thr Asp Ser Ile Ser
    1090                1095                1100
```

```
Leu Phe Ala Gly Ile Arg His Asp Ala Gly Asp Ile Gly Tyr Leu Lys
1105                1110                1115                1120

Gly Leu Phe Ser Tyr Gly Arg Tyr Lys Asn Ser Ile Ser Arg Ser Thr
            1125                1130                1135

Gly Ala Asp Glu His Ala Glu Ser Val Asn Gly Thr Leu Met Gln
        1140                1145                1150

Leu Gly Ala Leu Gly Gly Val Asn Val Pro Phe Ala Ala Thr Gly Asp
            1155                1160                1165

Leu Thr Val Glu Gly Gly Leu Arg Tyr Asp Leu Leu Lys Gln Asp Ala
        1170                1175                1180

Phe Ala Glu Lys Gly Ser Ala Leu Gly Trp Ser Gly Asn Ser Leu Thr
1185                1190                1195                1200

Glu Gly Thr Leu Val Gly Leu Ala Gly Leu Lys Leu Ser Gln Pro Leu
            1205                1210                1215

Ser Asp Lys Ala Val Leu Phe Ala Thr Ala Gly Val Glu Arg Asp Leu
        1220                1225                1230

Asn Gly Arg Asp Tyr Thr Val Thr Gly Gly Phe Thr Gly Ala Thr Ala
            1235                1240                1245

Ala Thr Gly Lys Thr Gly Ala Arg Asn Met Pro His Thr Arg Leu Val
        1250                1255                1260

Ala Gly Leu Gly Ala Asp Val Glu Phe Gly Asn Gly Trp Asn Gly Leu
1265                1270                1275                1280

Ala Arg Tyr Ser Tyr Ala Gly Ser Lys Gln Tyr Gly Asn His Ser Gly
            1285                1290                1295

Arg Val Gly Val Gly Tyr Arg Phe Leu Glu His His His His His His
        1300                1305                1310

<210> SEQ ID NO 114
<211> LENGTH: 2028
<212> TYPE: DNA
<213> ORGANISM: Artificial Sequence
<220> FEATURE:
<223> OTHER INFORMATION: Synthetic construct

<400> SEQUENCE: 114
atggtcgccg ccgacatcgg tgcggggctt gccgatgcac taaccgcacc gctcgaccat      60
aaagacaaag gtttgcagtc tttgacgctg gatcagtccg tcaggaaaaa cgagaaactg     120
aagctggcgg cacaaggtgc ggaaaaaact tatggaaacg gtgacagcct caatacgggc     180
aaattgaaga acgacaaggt cagccgtttc gactttatcc gccaaatcga agtgacgggg     240
cagctcatta ccttggagag tggagagttc caagtataca acaaagccat tccgccttta     300
accgcctttc agaccgagca atacaagatt cggagcattt cgggaagatg gttgcgaaa     360
cgccagttca gaatcggcga catagcgggc gaacatacat cttttgacaa gcttcccgaa     420
ggcggcaggg cgacatatcg cgggacggcg ttcggttcag acgatgccgg cggaaaactg     480
acctacacca tagatttcgc cgccaagcag ggaaacggca aaatcgaaca tttgaaatcg     540
ccagaactca atgtcgacct ggccgccgcc gatatcaagc cggatggaaa acgccatgcc     600
gtcatcagcg gttccgtcct ttacaaccaa gccgagaaag gcagttactc cctcggtatc     660
tttggcggaa aagcccagga agttgccggc agcgcgaagt gaaaaccgt aaacggcata     720
cgccatatcg gccttgccgc caagcaactc gacggtggcg gaggcactgg atcctcagat     780
ttggcaaacg attctttat ccggcaggtt ctcgaccgtc agcatttcga acccgacggg     840
aaataccacc tattcggcag caggggggaa cttgccgagc gcagcggcca tatcggattg     900
```

```
ggaaaaatac aaagccatca gttgggcaac ctgatgattc aacaggcggc cattaaagga    960
aatatcggct acattgtccg cttttccgat cacgggcacg aagtccattc cccttcgac   1020 aaccatgcct cacattccga ttctgatgaa gccggtagtc ccgttgacgg atttagcctt   1080
taccgcatcc attgggacgg atacgaacac catcccgccg acggctatga cgggccacag   1140
ggcggcggct atcccgctcc caaaggcgcg agggatatat acagctacga cataaaaggc   1200
gttgcccaaa atatccgcct caacctgacc gacaaccgca gcaccggaca acggcttgcc   1260
gaccgtttcc acaatgccgg tagtatgctg acgcaaggag taggcgacgg attcaaacgc   1320
gccacccgat acagccccga gctggacaga tcgggcaatg ccgccgaagc cttcaacggc   1380
actgcagata tcgttaaaaa catcatcggc gcggcaggag aaattgtcgg cgcaggcgat   1440
gccgtgcagg gcataagcga aggctcaaac attgctgtca tgcacggctt gggtctgctt   1500
tccaccgaaa acaagatggc gcgcatcaac gatttggcag atatggcgca actcaaagac   1560
tatgccgcag cagccatccg cgattgggca gtccaaaacc ccaatgccgc acaaggcata   1620
gaagccgtca gcaatatctt tatggcagcc atccccatca aagggattgg agctgttcgg   1680
ggaaaatacg gcttgggcgg catcacggca catcctatca gcggtcgca gatgggcgcg   1740 atcgcattgc cgaaagggaa atccgccgtc agcgacaatt ttgccgatgc ggcatacgcc   1800
aaatacccgt ccccttacca ttcccgaaat atccgttcaa acttggagca gcgttacggc   1860
aaagaaaaca tcacctcctc aaccgtgccg ccgtcaaacg gcaaaaatgt caaactggca   1920
gaccaacgcc acccgaagac aggcgtaccg tttgacggta aagggtttcc gaattttgag   1980
aagcacgtga aatatgatac gctcgagcac caccaccacc accactga              2028
```

<210> SEQ ID NO 115
<211> LENGTH: 675
<212> TYPE: PRT
<213> ORGANISM: Artificial Sequence
<220> FEATURE:
<223> OTHER INFORMATION: Synthetic construct

<400> SEQUENCE: 115

```
Met Val Ala Ala Asp Ile Gly Ala Gly Leu Ala Asp Ala Leu Thr Ala
1               5                  10                  15

Pro Leu Asp His Lys Asp Lys Gly Leu Gln Ser Leu Thr Leu Asp Gln
            20                  25                  30

Ser Val Arg Lys Asn Glu Lys Leu Lys Leu Ala Ala Gln Gly Ala Glu
        35                  40                  45

Lys Thr Tyr Gly Asn Gly Asp Ser Leu Asn Thr Gly Lys Leu Lys Asn
    50                  55                  60

Asp Lys Val Ser Arg Phe Asp Phe Ile Arg Gln Ile Glu Val Asp Gly
65                  70                  75                  80

Gln Leu Ile Thr Leu Glu Ser Gly Glu Phe Gln Val Tyr Lys Gln Ser
                85                  90                  95

His Ser Ala Leu Thr Ala Phe Gln Thr Glu Gln Ile Gln Asp Ser Glu
            100                 105                 110

His Ser Gly Lys Met Val Ala Lys Arg Gln Phe Arg Ile Gly Asp Ile
        115                 120                 125

Ala Gly Glu His Thr Ser Phe Asp Lys Leu Pro Glu Gly Gly Arg Ala
    130                 135                 140

Thr Tyr Arg Gly Thr Ala Phe Gly Ser Asp Asp Ala Gly Gly Lys Leu
145                 150                 155                 160

Thr Tyr Thr Ile Asp Phe Ala Ala Lys Gln Gly Asn Gly Lys Ile Glu
                165                 170                 175
```

```
His Leu Lys Ser Pro Glu Leu Asn Val Asp Leu Ala Ala Asp Ile
            180                 185                 190

Lys Pro Asp Gly Lys Arg His Ala Val Ile Ser Gly Ser Val Leu Tyr
            195                 200                 205

Asn Gln Ala Glu Lys Gly Ser Tyr Ser Leu Gly Ile Phe Gly Gly Lys
210                 215                 220

Ala Gln Glu Val Ala Gly Ser Ala Glu Val Lys Thr Val Asn Gly Ile
225                 230                 235                 240

Arg His Ile Gly Leu Ala Ala Lys Gln Leu Asp Gly Gly Gly Thr
            245                 250                 255

Gly Ser Ser Asp Leu Ala Asn Asp Ser Phe Ile Arg Gln Val Leu Asp
            260                 265                 270

Arg Gln His Phe Glu Pro Asp Gly Lys Tyr His Leu Phe Gly Ser Arg
            275                 280                 285

Gly Glu Leu Ala Glu Arg Ser Gly His Ile Gly Leu Gly Lys Ile Gln
            290                 295                 300

Ser His Gln Leu Gly Asn Leu Met Ile Gln Gln Ala Ala Ile Lys Gly
305                 310                 315                 320

Asn Ile Gly Tyr Ile Val Arg Phe Ser Asp His Gly His Glu Val His
            325                 330                 335

Ser Pro Phe Asp Asn His Ala Ser His Ser Asp Ser Asp Glu Ala Gly
            340                 345                 350

Ser Pro Val Asp Gly Phe Ser Leu Tyr Arg Ile His Trp Asp Gly Tyr
            355                 360                 365

Glu His His Pro Ala Asp Gly Tyr Asp Gly Pro Gln Gly Gly Gly Tyr
            370                 375                 380

Pro Ala Pro Lys Gly Ala Arg Asp Ile Tyr Ser Tyr Asp Ile Lys Gly
385                 390                 395                 400

Val Ala Gln Asn Ile Arg Leu Asn Leu Thr Asp Asn Arg Ser Thr Gly
            405                 410                 415

Gln Arg Leu Ala Asp Arg Phe His Asn Ala Gly Ser Met Leu Thr Gln
            420                 425                 430

Gly Val Gly Asp Gly Phe Lys Arg Ala Thr Arg Tyr Ser Pro Glu Leu
            435                 440                 445

Asp Arg Ser Gly Asn Ala Ala Glu Ala Phe Asn Gly Thr Ala Asp Ile
450                 455                 460

Val Lys Asn Ile Ile Gly Ala Ala Gly Glu Ile Val Gly Ala Gly Asp
465                 470                 475                 480

Ala Val Gln Gly Ile Ser Glu Gly Ser Asn Ile Ala Val Met His Gly
            485                 490                 495

Leu Gly Leu Leu Ser Thr Glu Asn Lys Met Ala Arg Ile Asn Asp Leu
            500                 505                 510

Ala Asp Met Ala Gln Leu Lys Asp Tyr Ala Ala Ala Ile Arg Asp
            515                 520                 525

Trp Ala Val Gln Asn Pro Asn Ala Ala Gln Gly Ile Glu Ala Val Ser
            530                 535                 540

Asn Ile Phe Met Ala Ala Ile Pro Ile Lys Gly Ile Gly Ala Val Arg
545                 550                 555                 560

Gly Lys Tyr Gly Leu Gly Gly Ile Thr Ala His Pro Ile Lys Arg Ser
            565                 570                 575

Gln Met Gly Ala Ile Ala Leu Pro Lys Gly Lys Ser Ala Val Ser Asp
            580                 585                 590

Asn Phe Ala Asp Ala Ala Tyr Ala Lys Tyr Pro Ser Pro Tyr His Ser
```

```
                595                 600                 605
Arg Asn Ile Arg Ser Asn Leu Glu Gln Arg Tyr Gly Lys Glu Asn Ile
        610                 615                 620

Thr Ser Ser Thr Val Pro Ser Asn Gly Lys Asn Val Lys Leu Ala
625                 630                 635                 640

Asp Gln Arg His Pro Lys Thr Gly Val Pro Phe Asp Gly Lys Gly Phe
                645                 650                 655

Pro Asn Phe Glu Lys His Val Lys Tyr Asp Thr Leu Glu His His His
            660                 665                 670

His His His
        675

<210> SEQ ID NO 116
<211> LENGTH: 249
<212> TYPE: PRT
<213> ORGANISM: Artificial Sequence
<220> FEATURE:
<223> OTHER INFORMATION: Synthetic construct

<400> SEQUENCE: 116

Met Lys Lys Tyr Leu Phe Arg Ala Ala Leu Tyr Gly Ile Ala Ala Ala
1               5                   10                  15

Ile Leu Ala Ala Ala Ile Pro Ala Gly Asn Asp Ala Thr Thr Lys Pro
            20                  25                  30

Asp Leu Tyr Tyr Leu Lys Asn Glu Gln Ala Ile Asp Ser Leu Lys Leu
        35                  40                  45

Leu Pro Pro Pro Glu Val Gly Ser Ile Gln Phe Leu Asn Asp Gln
    50                  55                  60

Ala Met Tyr Glu Lys Gly Arg Met Leu Arg Asn Thr Glu Arg Gly Lys
65                  70                  75                  80

Gln Ala Gln Ala Asp Ala Asp Leu Ala Ala Gly Gly Val Ala Thr Ala
                85                  90                  95

Phe Ser Gly Ala Phe Gly Tyr Pro Ile Thr Glu Lys Asp Ser Pro Glu
            100                 105                 110

Leu Tyr Lys Leu Leu Thr Asn Met Ile Glu Asp Ala Gly Asp Leu Ala
        115                 120                 125

Thr Arg Ser Ala Lys Glu His Tyr Met Arg Ile Arg Pro Phe Ala Phe
    130                 135                 140

Tyr Gly Thr Glu Thr Cys Asn Thr Lys Asp Gln Lys Lys Leu Ser Thr
145                 150                 155                 160

Asn Gly Ser Tyr Pro Ser Gly His Thr Ser Ile Gly Trp Ala Thr Ala
                165                 170                 175

Leu Val Leu Ala Glu Val Asn Pro Ala Asn Gln Asp Ala Ile Leu Glu
            180                 185                 190

Arg Gly Tyr Gln Leu Gly Gln Ser Arg Val Ile Cys Gly Tyr His Trp
        195                 200                 205

Gln Ser Asp Val Asp Ala Ala Arg Ile Val Gly Ser Ala Ala Val Ala
    210                 215                 220

Thr Leu His Ser Asp Pro Ala Phe Gln Ala Gln Leu Ala Lys Ala Lys
225                 230                 235                 240

Gln Glu Phe Ala Gln Lys Ser Gln Lys
                245

<210> SEQ ID NO 117
<211> LENGTH: 66
<212> TYPE: DNA
<213> ORGANISM: Artificial Sequence
```

```
<220> FEATURE:
<223> OTHER INFORMATION: Synthetic construct
<220> FEATURE:
<221> NAME/KEY: misc_feature
<222> LOCATION: (1)...(66)
<223> OTHER INFORMATION: n = A, T/U, G or C

<400> SEQUENCE: 117
tatgaartay ytnttymgcg ccgccctgta cggcatcgcc gccgccatcc tcgccgccgc    60
gatccc                                                              66

<210> SEQ ID NO 118
<211> LENGTH: 69
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)...(69)
<223> OTHER INFORMATION: n = A, T/U, G or C

<400> SEQUENCE: 118
tatgaaaaaa tacctattcc grgcngcnyt rtayggsatc gccgccgcca tcctcgccgc    60
cgcgatccc                                                           69

<210> SEQ ID NO 119
<211> LENGTH: 27
<212> TYPE: DNA
<213> ORGANISM: Artificial Sequence
<220> FEATURE:
<223> OTHER INFORMATION: Synthetic construct

<400> SEQUENCE: 119
atgaagaagt accttttcag cgccgcc                                       27

<210> SEQ ID NO 120
<211> LENGTH: 27
<212> TYPE: DNA
<213> ORGANISM: Artificial Sequence
<220> FEATURE:
<223> OTHER INFORMATION: Synthetic construct

<400> SEQUENCE: 120
atgaaaaaat acttttccg cgccgcc                                        27

<210> SEQ ID NO 121
<211> LENGTH: 27
<212> TYPE: DNA
<213> ORGANISM: Artificial Sequence
<220> FEATURE:
<223> OTHER INFORMATION: Synthetic construct

<400> SEQUENCE: 121
atgaaaaaat acttttccg cgccgcc                                        27

<210> SEQ ID NO 122
<211> LENGTH: 60
<212> TYPE: DNA
<213> ORGANISM: Artificial Sequence
<220> FEATURE:
<223> OTHER INFORMATION: Synthetic construct

<400> SEQUENCE: 122
atgaaaaaat atctctttag cgccgccctg tacggcatcg ccgccgccat cctcgccgcc    60
```

<210> SEQ ID NO 123
<211> LENGTH: 60
<212> TYPE: DNA
<213> ORGANISM: Artificial Sequence
<220> FEATURE:
<223> OTHER INFORMATION: Synthetic construct

<400> SEQUENCE: 123
atgaaaaaat acctattccg cgccgccctg tacggcatcg ccgccgccat cctcgccgcc      60

<210> SEQ ID NO 124
<211> LENGTH: 9
<212> TYPE: PRT
<213> ORGANISM: Artificial Sequence
<220> FEATURE:
<223> OTHER INFORMATION: Synthetic construct

<400> SEQUENCE: 124

Met Lys Lys Tyr Leu Phe Ser Ala Ala
1               5

<210> SEQ ID NO 125
<211> LENGTH: 9
<212> TYPE: PRT
<213> ORGANISM: Artificial Sequence
<220> FEATURE:
<223> OTHER INFORMATION: Synthetic construct

<400> SEQUENCE: 125

Met Lys Lys Tyr Phe Phe Arg Ala Ala
1               5

<210> SEQ ID NO 126
<211> LENGTH: 9
<212> TYPE: PRT
<213> ORGANISM: Artificial Sequence
<220> FEATURE:
<223> OTHER INFORMATION: Synthetic construct

<400> SEQUENCE: 126

Met Lys Lys Tyr Phe Phe Arg Ala Ala
1               5

<210> SEQ ID NO 127
<211> LENGTH: 20
<212> TYPE: PRT
<213> ORGANISM: Artificial Sequence
<220> FEATURE:
<223> OTHER INFORMATION: Synthetic construct

<400> SEQUENCE: 127

Met Lys Lys Tyr Leu Phe Ser Ala Ala Leu Tyr Gly Ile Ala Ala Ala
1               5                   10                  15

Ile Leu Ala Ala
            20

<210> SEQ ID NO 128
<211> LENGTH: 20
<212> TYPE: PRT
<213> ORGANISM: Artificial Sequence
<220> FEATURE:
<223> OTHER INFORMATION: Synthetic construct

<400> SEQUENCE: 128

Met Lys Lys Tyr Leu Phe Arg Ala Ala Leu Tyr Gly Ile Ala Ala Ala
1               5                   10                  15

Ile Leu Ala Ala

<210> SEQ ID NO 129
<211> LENGTH: 42
<212> TYPE: DNA
<213> ORGANISM: Artificial Sequence
<220> FEATURE:
<223> OTHER INFORMATION: Synthetic construct

<400> SEQUENCE: 129
atgaaaaaat acctattcat cgccgccgcc atcctcgccg cc            42

<210> SEQ ID NO 130
<211> LENGTH: 60
<212> TYPE: DNA
<213> ORGANISM: Artificial Sequence
<220> FEATURE:
<223> OTHER INFORMATION: Synthetic construct

<400> SEQUENCE: 130
atgaaaaaat acctattccg agctgcccaa tacggcatcg ccgccgccat cctcgccgcc    60

<210> SEQ ID NO 131
<211> LENGTH: 60
<212> TYPE: DNA
<213> ORGANISM: Artificial Sequence
<220> FEATURE:
<223> OTHER INFORMATION: Synthetic construct

<400> SEQUENCE: 131
atgaaaaaat acctattccg ggccgcccaa tacggcatcg ccgccgccat cctcgccgcc    60

<210> SEQ ID NO 132
<211> LENGTH: 60
<212> TYPE: DNA
<213> ORGANISM: Artificial Sequence
<220> FEATURE:
<223> OTHER INFORMATION: Synthetic construct

<400> SEQUENCE: 132
atgaaaaaat acctattccg ggcggctttg tacgggatcg ccgccgccat cctcgccgcc    60

<210> SEQ ID NO 133
<211> LENGTH: 14
<212> TYPE: PRT
<213> ORGANISM: Artificial Sequence
<220> FEATURE:
<223> OTHER INFORMATION: Synthetic construct

<400> SEQUENCE: 133

Met Lys Lys Tyr Leu Phe Ile Ala Ala Ala Ile Leu Ala Ala
1               5                   10

<210> SEQ ID NO 134
<211> LENGTH: 20
<212> TYPE: PRT
<213> ORGANISM: Artificial Sequence
<220> FEATURE:
<223> OTHER INFORMATION: Synthetic construct

<400> SEQUENCE: 134

Met Lys Lys Tyr Leu Phe Arg Ala Ala Gln Tyr Gly Ile Ala Ala Ala
1               5                   10                  15

Ile Leu Ala Ala
            20

```
<210> SEQ ID NO 135
<211> LENGTH: 20
<212> TYPE: PRT
<213> ORGANISM: Artificial Sequence
<220> FEATURE:
<223> OTHER INFORMATION: Synthetic construct

<400> SEQUENCE: 135

Met Lys Lys Tyr Leu Phe Arg Ala Ala Gln Tyr Gly Ile Ala Ala Ala
1               5                   10                  15

Ile Leu Ala Ala
            20

<210> SEQ ID NO 136
<211> LENGTH: 20
<212> TYPE: PRT
<213> ORGANISM: Artificial Sequence
<220> FEATURE:
<223> OTHER INFORMATION: Synthetic construct

<400> SEQUENCE: 136

Met Lys Lys Tyr Leu Phe Arg Ala Ala Leu Tyr Gly Ile Ala Ala Ala
1               5                   10                  15

Ile Leu Ala Ala
            20

<210> SEQ ID NO 137
<211> LENGTH: 467
<212> TYPE: PRT
<213> ORGANISM: Artificial Sequence
<220> FEATURE:
<223> OTHER INFORMATION: Neisseria meningitidis

<400> SEQUENCE: 137

Val Lys Pro Leu Arg Arg Leu Thr Asn Leu Leu Ala Ala Cys Ala Val
1               5                   10                  15

Ala Ala Ala Ala Leu Ile Gln Pro Ala Leu Ala Ala Asp Leu Ala Gln
                20                  25                  30

Asp Pro Phe Ile Thr Asp Asn Ala Gln Arg Gln His Tyr Glu Pro Gly
            35                  40                  45

Gly Lys Tyr His Leu Phe Gly Asp Pro Arg Gly Ser Val Ser Asp Arg
        50                  55                  60

Thr Gly Lys Ile Asn Val Ile Gln Asp Tyr Thr His Gln Met Gly Asn
65                  70                  75                  80

Leu Leu Ile Gln Gln Ala Asn Ile Asn Gly Thr Ile Gly Tyr His Thr
                85                  90                  95

Arg Phe Ser Gly His Gly His Glu Glu His Ala Pro Phe Asp Asn His
            100                 105                 110

Ala Ala Asp Ser Ala Ser Glu Glu Lys Gly Asn Val Asp Glu Gly Phe
        115                 120                 125

Thr Val Tyr Arg Leu Asn Trp Glu Gly His Glu His Pro Ala Asp
        130                 135                 140

Ala Tyr Asp Gly Pro Lys Gly Gly Asn Tyr Pro Lys Pro Thr Gly Ala
145                 150                 155                 160

Arg Asp Glu Tyr Thr Tyr His Val Asn Gly Thr Ala Arg Ser Ile Lys
                165                 170                 175

Leu Asn Pro Thr Asp Thr Arg Ser Ile Arg Gln Arg Ile Ser Asp Asn
            180                 185                 190

Tyr Ser Asn Leu Gly Ser Asn Phe Ser Asp Arg Ala Asp Glu Ala Asn
        195                 200                 205
```

Arg Lys Met Phe Glu His Asn Ala Lys Leu Asp Arg Trp Gly Asn Ser
210                 215                 220

Met Glu Phe Ile Asn Gly Val Ala Ala Gly Ala Leu Asn Pro Phe Ile
225                 230                 235                 240

Ser Ala Gly Glu Ala Leu Gly Ile Gly Asp Ile Leu Tyr Gly Thr Arg
            245                 250                 255

Tyr Ala Ile Asp Lys Ala Ala Met Arg Asn Ile Ala Pro Leu Pro Ala
            260                 265                 270

Glu Gly Lys Phe Ala Val Ile Gly Gly Leu Gly Ser Val Ala Gly Phe
            275                 280                 285

Glu Lys Asn Thr Arg Glu Ala Val Asp Arg Trp Ile Gln Glu Asn Pro
290                 295                 300

Asn Ala Ala Glu Thr Val Glu Ala Val Phe Asn Val Ala Ala Ala Ala
305                 310                 315                 320

Lys Val Ala Lys Leu Ala Lys Ala Ala Lys Pro Gly Lys Ala Ala Val
            325                 330                 335

Ser Gly Asp Phe Ala Asp Ser Tyr Lys Lys Leu Ala Leu Ser Asp
            340                 345                 350

Ser Ala Arg Gln Leu Tyr Gln Asn Ala Lys Tyr Arg Glu Ala Leu Asp
            355                 360                 365

Ile His Tyr Glu Asp Leu Ile Arg Arg Lys Thr Asp Gly Ser Ser Lys
370                 375                 380

Phe Ile Asn Gly Arg Glu Ile Asp Ala Val Thr Asn Asp Ala Leu Ile
385                 390                 395                 400

Gln Ala Lys Arg Thr Ile Ser Ala Ile Asp Lys Pro Lys Asn Phe Leu
            405                 410                 415

Asn Gln Lys Asn Arg Lys Gln Ile Lys Ala Thr Ile Glu Ala Ala Asn
            420                 425                 430

Gln Gln Gly Lys Arg Ala Glu Phe Trp Phe Lys Tyr Gly Val His Ser
            435                 440                 445

Gln Val Lys Ser Tyr Ile Glu Ser Lys Gly Gly Ile Val Lys Thr Gly
            450                 455                 460

Leu Gly Asp
465

<210> SEQ ID NO 138
<211> LENGTH: 377
<212> TYPE: PRT
<213> ORGANISM: Artificial Sequence
<220> FEATURE:
<223> OTHER INFORMATION: Synthetic construct

<400> SEQUENCE: 138

Met Ala Asp Leu Ala Gln Asp Pro Phe Ile Thr Asp Asn Ala Gln Arg
1               5                   10                  15

Gln His Tyr Glu Pro Gly Gly Lys Tyr His Leu Phe Gly Asp Pro Arg
            20                  25                  30

Gly Ser Val Ser Asp Arg Thr Gly Lys Ile Asn Val Ile Gln Asp Tyr
            35                  40                  45

Thr His Gln Met Gly Asn Leu Leu Ile Gln Gln Ala Asn Ile Asn Gly
        50                  55                  60

Thr Ile Gly Tyr His Thr Arg Phe Ser Gly His Gly His Glu Glu His
65                  70                  75                  80

Ala Pro Phe Asp Asn His Ala Ala Asp Ser Ala Ser Glu Glu Lys Gly
            85                  90                  95

Asn Val Asp Glu Gly Phe Thr Val Tyr Arg Leu Asn Trp Glu Gly His

```
                    100                 105                 110
Glu His His Pro Ala Asp Ala Tyr Asp Gly Pro Lys Gly Gly Asn Tyr
                115                 120                 125
Pro Lys Pro Thr Gly Ala Arg Asp Glu Tyr Thr Tyr His Val Asn Gly
            130                 135                 140
Thr Ala Arg Ser Ile Lys Leu Asn Pro Thr Asp Thr Arg Ser Ile Arg
145                 150                 155                 160
Gln Arg Ile Ser Asp Asn Tyr Ser Asn Leu Gly Ser Asn Phe Ser Asp
                165                 170                 175
Arg Ala Asp Glu Ala Asn Arg Lys Met Phe Glu His Asn Ala Lys Leu
            180                 185                 190
Asp Arg Trp Gly Asn Ser Met Glu Phe Ile Asn Gly Val Ala Ala Gly
            195                 200                 205
Ala Leu Asn Pro Phe Ile Ser Ala Gly Glu Ala Leu Gly Ile Gly Asp
        210                 215                 220
Ile Leu Tyr Gly Thr Arg Tyr Ala Ile Asp Lys Ala Ala Met Arg Asn
225                 230                 235                 240
Ile Ala Pro Leu Pro Ala Glu Gly Lys Phe Ala Val Ile Gly Gly Leu
                245                 250                 255
Gly Ser Val Ala Gly Phe Glu Lys Asn Thr Arg Glu Ala Val Asp Arg
            260                 265                 270
Trp Ile Gln Glu Asn Pro Asn Ala Glu Thr Val Glu Ala Val Phe
            275                 280                 285
Asn Val Ala Ala Ala Lys Val Ala Lys Leu Ala Lys Ala Ala Lys
            290                 295                 300
Pro Gly Lys Ala Ala Val Ser Gly Asp Phe Ala Asp Ser Tyr Lys Lys
305                 310                 315                 320
Lys Leu Ala Leu Ser Asp Ser Ala Arg Gln Leu Tyr Gln Asn Ala Lys
                325                 330                 335
Tyr Arg Glu Ala Leu Asp Ile His Tyr Glu Asp Leu Ile Arg Arg Lys
            340                 345                 350
Thr Asp Gly Ser Ser Lys Phe Ile Asn Gly Arg Glu Ile Asp Ala Val
            355                 360                 365
Thr Asn Asp Ala Leu Ile Gln Ala Arg
        370                 375

<210> SEQ ID NO 139
<211> LENGTH: 353
<212> TYPE: PRT
<213> ORGANISM: Artificial Sequence
<220> FEATURE:
<223> OTHER INFORMATION: Synthetic construct

<400> SEQUENCE: 139

Met Ala Asp Leu Ala Gln Asp Pro Phe Ile Thr Asp Asn Ala Gln Arg
1               5                   10                  15
Gln His Tyr Glu Pro Gly Gly Lys Tyr His Leu Phe Gly Asp Pro Arg
                20                  25                  30
Gly Ser Val Ser Asp Arg Thr Gly Lys Ile Asn Val Ile Gln Asp Tyr
            35                  40                  45
Thr His Gln Met Gly Asn Leu Leu Ile Gln Gln Ala Asn Ile Asn Gly
        50                  55                  60
Thr Ile Gly Tyr His Thr Arg Phe Ser Gly His Gly His Glu Glu His
65                  70                  75                  80
Ala Pro Phe Asp Asn His Ala Ala Asp Ser Ala Ser Glu Glu Lys Gly
                85                  90                  95
```

Asn Val Asp Glu Gly Phe Thr Val Tyr Arg Leu Asn Trp Glu Gly His
            100                 105                 110

Glu His His Pro Ala Asp Ala Tyr Asp Gly Pro Lys Gly Gly Asn Tyr
        115                 120                 125

Pro Lys Pro Thr Gly Ala Arg Asp Glu Tyr Thr Tyr His Val Asn Gly
130                 135                 140

Thr Ala Arg Ser Ile Lys Leu Asn Pro Thr Asp Thr Arg Ser Ile Arg
145                 150                 155                 160

Gln Arg Ile Ser Asp Asn Tyr Ser Asn Leu Gly Ser Asn Phe Ser Asp
                165                 170                 175

Arg Ala Asp Glu Ala Asn Arg Lys Met Phe Glu His Asn Ala Lys Leu
            180                 185                 190

Asp Arg Trp Gly Asn Ser Met Glu Phe Ile Asn Gly Val Ala Ala Gly
        195                 200                 205

Ala Leu Asn Pro Phe Ile Ser Ala Gly Glu Ala Leu Gly Ile Gly Asp
    210                 215                 220

Ile Leu Tyr Gly Thr Arg Tyr Ala Ile Asp Lys Ala Ala Met Arg Asn
225                 230                 235                 240

Ile Ala Pro Leu Pro Ala Glu Gly Lys Phe Ala Val Ile Gly Gly Leu
                245                 250                 255

Gly Ser Val Ala Gly Phe Glu Lys Asn Thr Arg Glu Ala Val Asp Arg
            260                 265                 270

Trp Ile Gln Glu Asn Pro Asn Ala Ala Glu Thr Val Glu Ala Val Phe
        275                 280                 285

Asn Val Ala Ala Ala Lys Val Ala Lys Leu Ala Lys Ala Ala Lys
    290                 295                 300

Pro Gly Lys Ala Ala Val Ser Gly Asp Phe Ala Asp Ser Tyr Lys Lys
305                 310                 315                 320

Lys Leu Ala Leu Ser Asp Ser Ala Arg Gln Leu Tyr Gln Asn Ala Lys
                325                 330                 335

Tyr Arg Glu Ala Leu Gly Lys Val Arg Ile Ser Gly Glu Ile Leu Leu
            340                 345                 350

Gly

<210> SEQ ID NO 140
<211> LENGTH: 2019
<212> TYPE: DNA
<213> ORGANISM: Artificial Sequence
<220> FEATURE:
<223> OTHER INFORMATION: Synthetic construct

<400> SEQUENCE: 140
atgtcagatt tggcaaacga ttcttttatc cggcaggttc tcgaccgtca gcatttcgaa      60
cccgacggga ataccacct attcggcagc agggggaac ttgccgagcg cagcggccat       120
atcggattgg gaaaaataca agccatcag ttgggcaacc tgatgattca acaggcggcc      180
attaaaggaa atatcggcta cattgtccgc ttttccgatc acgggcacga agtccattcc      240
cccttcgaca accatgcctc acattccgat tctgatgaag ccggtagtcc cgttgacgga      300
tttagccttt accgcatcca ttgggacgga tacgaacacc atcccgccga cggctatgac      360
gggccacagg gcggcggcta tcccgctccc aaaggcgcga gggatatata cagctacgac      420
ataaaaggcg ttgcccaaaa tatccgcctc aacctgaccg acaaccgcag caccggacaa      480
cggcttgccg accgttttcca caatgccggt agtatgctga cgcaaggagt aggcgacgga      540
ttcaaacgcg ccacccgata cagccccgag ctggacagat cgggcaatgc cgccgaagcc      600

-continued

```
ttcaacggca ctgcagatat cgttaaaaac atcatcggcg cggcaggaga aattgtcggc      660
gcaggcgatg ccgtgcaggg cataagcgaa ggctcaaaca ttgctgtcat gcacggcttg      720
ggtctgcttt ccaccgaaaa caagatggcg cgcatcaacg atttggcaga tatggcgcaa      780
ctcaaagact atgccgcagc agccatccgc gattgggcag tccaaaaccc caatgccgca      840
caaggcatag aagccgtcag caatatcttt atggcagcca tccccatcaa agggattgga      900
gctgttcggg gaaaatacgg cttgggcggc atcacggcac atcctatcaa gcggtcgcag      960
atgggcgcga tcgcattgcc gaaagggaaa tccgccgtca gcgacaattt tgccgatgcg     1020
gcatacgcca ataccccgtc cccttaccat tcccgaaata tccgttcaaa cttggagcag     1080
cgttacggca agaaaaacat cacctcctca accgtgccgc cgtcaaacgg caaaaatgtc     1140
aaactggcag accaacgcca cccgaagaca ggcgtaccgt ttgacggtaa agggtttccg     1200
aattttgaga agcacgtgaa atatgatacg ggatccggag ggggtggtgt cgccgccgac     1260
atcggtgcgg ggcttgccga tgcactaacc gcaccgctcg accataaaga caaaggtttg     1320
cagtctttga cgctggatca gtccgtcagg aaaaacgaga aactgaagct ggcggcacaa     1380
ggtgcggaaa aaacttatgg aaacggtgac agcctcaata cgggcaaatt gaagaacgac     1440
aaggtcagcc gtttcgactt tatccgccaa atcgaagtgg acgggcagct cattaccttg     1500
gagagtggag agttccaagt atacaaacaa agccattccg ccttaaccgc ctttcagacc     1560
gagcaaatac aagattcgga gcattccggg aagatggttg cgaaacgcca gttcagaatc     1620
ggcgacatag cgggcgaaca tacatctttt gacaagcttc ccgaaggcgg cagggcgaca     1680
tatcgcggga cggcgttcgg ttcagacgat gccggcggaa aactgaccta caccatagat     1740
ttcgccgcca gcagggaaa cggcaaaatc gaacatttga atcgccaga actcaatgtc       1800 gacctggccg ccgccgatat caagccggat ggaaaacgcc atgccgtcat cagcggttcc     1860
gtcctttaca accaagccga aaaggcagt tactccctcg gtatctttgg cggaaaagcc      1920
caggaagttg ccggcagcgc ggaagtgaaa accgtaaacg gcatacgcca tatcggcctt     1980
gccgccaagc aactcgagca ccaccaccac caccactga                            2019
```

<210> SEQ ID NO 141
<211> LENGTH: 672
<212> TYPE: PRT
<213> ORGANISM: Artificial Sequence
<220> FEATURE:
<223> OTHER INFORMATION: Synthetic construct

<400> SEQUENCE: 141

```
Met Ser Asp Leu Ala Asn Asp Ser Phe Ile Arg Gln Val Leu Asp Arg
1               5                   10                  15

Gln His Phe Glu Pro Asp Gly Lys Tyr His Leu Phe Gly Ser Arg Gly
            20                  25                  30

Glu Leu Ala Glu Arg Ser Gly His Ile Gly Leu Gly Lys Ile Gln Ser
        35                  40                  45

His Gln Leu Gly Asn Leu Met Ile Gln Gln Ala Ile Lys Gly Asn
    50                  55                  60

Ile Gly Tyr Ile Val Arg Phe Ser Asp His Gly His Glu Val His Ser
65                  70                  75                  80

Pro Phe Asp Asn His Ala Ser His Ser Asp Ser Asp Glu Ala Gly Ser
                85                  90                  95

Pro Val Asp Gly Phe Ser Leu Tyr Arg Ile His Trp Asp Gly Tyr Glu
            100                 105                 110
```

```
His His Pro Ala Asp Gly Tyr Asp Gly Pro Gln Gly Gly Gly Tyr Pro
    115                 120                 125

Ala Pro Lys Gly Ala Arg Asp Ile Tyr Ser Tyr Asp Ile Lys Gly Val
130                 135                 140

Ala Gln Asn Ile Arg Leu Asn Leu Thr Asp Asn Arg Ser Thr Gly Gln
145                 150                 155                 160

Arg Leu Ala Asp Arg Phe His Asn Ala Gly Ser Met Leu Thr Gln Gly
                165                 170                 175

Val Gly Asp Gly Phe Lys Arg Ala Thr Arg Tyr Ser Pro Glu Leu Asp
            180                 185                 190

Arg Ser Gly Asn Ala Ala Glu Ala Phe Asn Gly Thr Ala Asp Ile Val
        195                 200                 205

Lys Asn Ile Ile Gly Ala Ala Gly Glu Ile Val Gly Ala Gly Asp Ala
    210                 215                 220

Val Gln Gly Ile Ser Glu Gly Ser Asn Ile Ala Val Met His Gly Leu
225                 230                 235                 240

Gly Leu Leu Ser Thr Glu Asn Lys Met Ala Arg Ile Asn Asp Leu Ala
                245                 250                 255

Asp Met Ala Gln Leu Lys Asp Tyr Ala Ala Ala Ile Arg Asp Trp
            260                 265                 270

Ala Val Gln Asn Pro Asn Ala Ala Gln Gly Ile Glu Ala Val Ser Asn
        275                 280                 285

Ile Phe Met Ala Ala Ile Pro Ile Lys Gly Ile Gly Ala Val Arg Gly
    290                 295                 300

Lys Tyr Gly Leu Gly Gly Ile Thr Ala His Pro Ile Lys Arg Ser Gln
305                 310                 315                 320

Met Gly Ala Ile Ala Leu Pro Lys Gly Lys Ser Ala Val Ser Asp Asn
                325                 330                 335

Phe Ala Asp Ala Ala Tyr Ala Lys Tyr Pro Ser Pro Tyr His Ser Arg
            340                 345                 350

Asn Ile Arg Ser Asn Leu Glu Gln Arg Tyr Gly Lys Glu Asn Ile Thr
        355                 360                 365

Ser Ser Thr Val Pro Pro Ser Asn Gly Lys Asn Val Lys Leu Ala Asp
    370                 375                 380

Gln Arg His Pro Lys Thr Gly Val Pro Phe Asp Gly Lys Gly Phe Pro
385                 390                 395                 400

Asn Phe Glu Lys His Val Lys Tyr Asp Thr Gly Ser Gly Gly Gly
                405                 410                 415

Val Ala Ala Asp Ile Gly Ala Gly Leu Ala Asp Ala Leu Thr Ala Pro
            420                 425                 430

Leu Asp His Lys Asp Lys Gly Leu Gln Ser Leu Thr Leu Asp Gln Ser
        435                 440                 445

Val Arg Lys Asn Glu Lys Leu Lys Leu Ala Ala Gln Gly Ala Glu Lys
    450                 455                 460

Thr Tyr Gly Asn Gly Asp Ser Leu Asn Thr Gly Lys Leu Lys Asn Asp
465                 470                 475                 480

Lys Val Ser Arg Phe Asp Phe Ile Arg Gln Ile Glu Val Asp Gly Gln
                485                 490                 495

Leu Ile Thr Leu Glu Ser Gly Glu Phe Gln Val Tyr Lys Gln Ser His
            500                 505                 510

Ser Ala Leu Thr Ala Phe Gln Thr Glu Gln Ile Gln Asp Ser Glu His
        515                 520                 525

Ser Gly Lys Met Val Ala Lys Arg Gln Phe Arg Ile Gly Asp Ile Ala
    530                 535                 540
```

```
Gly Glu His Thr Ser Phe Asp Lys Leu Pro Glu Gly Gly Arg Ala Thr
545                 550                 555                 560

Tyr Arg Gly Thr Ala Phe Gly Ser Asp Asp Ala Gly Gly Lys Leu Thr
                565                 570                 575

Tyr Thr Ile Asp Phe Ala Ala Lys Gln Gly Asn Gly Lys Ile Glu His
            580                 585                 590

Leu Lys Ser Pro Glu Leu Asn Val Asp Leu Ala Ala Ala Asp Ile Lys
        595                 600                 605

Pro Asp Gly Lys Arg His Ala Val Ile Ser Gly Ser Val Leu Tyr Asn
    610                 615                 620

Gln Ala Glu Lys Gly Ser Tyr Ser Leu Gly Ile Phe Gly Gly Lys Ala
625                 630                 635                 640

Gln Glu Val Ala Gly Ser Ala Glu Val Lys Thr Val Asn Gly Ile Arg
                645                 650                 655

His Ile Gly Leu Ala Ala Lys Gln Leu Glu His His His His His His
            660                 665                 670
```

<210> SEQ ID NO 142
<211> LENGTH: 2421
<212> TYPE: DNA
<213> ORGANISM: Artificial Sequence
<220> FEATURE:
<223> OTHER INFORMATION: Synthetic construct

<400> SEQUENCE: 142

```
atgtcagatt tggcaaacga ttctttatc cggcaggttc tcgaccgtca gcatttcgaa      60
cccgacggga ataccaccct attcggcagc aggggggaac ttgccgagcg cagcggccat     120
atcggattgg gaaaatacaa agccatcag ttgggcaacc tgatgattca acaggcggcc     180
attaaaggaa atatcggcta cattgtccgc ttttccgatc acgggcacga agtccattcc     240
cccttcgaca accatgcctc acattccgat tctgatgaag ccgtagtcc cgttgacgga     300
tttagccttt accgcatcca ttgggacgga tacgaacacc atcccgccga cggctatgac     360
gggccacagg gcggcggcta tcccgctccc aaaggcgcga gggatatata cagctacgac     420
ataaaaggcg ttgcccaaaa tatccgcctc aacctgaccg acaaccgcag caccggacaa     480
cggcttgccg accgtttcca caatgccggt agtatgctga cgcaaggagt aggcgacgga     540
ttcaaacgcg ccacccgata cagccccgag ctggacagat cgggcaatgc cgccgaagcc     600
ttcaacggca ctgcagatat cgttaaaaac atcatcggcg cggcaggaga aattgtcggc     660
gcaggcgatg ccgtgcaggg cataagcgaa ggctcaaaca ttgctgtcat gcacggcttg     720
ggtctgcttt ccaccgaaaa caagatggcg cgcatcaacg atttggcaga tatggcgcaa     780
ctcaaagact atgccgcagc agccatccgc gattgggcag tccaaaaccc caatgccgca     840
caaggcatag aagccgtcag caatatcttt atggcagcca tccccatcaa agggattgga     900
gctgttcggg gaaaatacgg cttgggcggc atcacggcac atcctatcaa gcggtcgcag     960
atgggcgcga tcgcattgcc gaaagggaaa tccgccgtca gcgacaattt tgccgatgcg    1020
gcatacgcca ataccgtc ccttaccat tcccgaaata ccgttcaaa cttggagcag    1080
cgttacggca agaaaacat cacctcctca accgtgccgc cgtcaaacgg caaaaatgtc    1140
aaactggcag ccaacgcca cccgaagaca ggcgtaccgt ttgacggtaa agggtttccg    1200
aattttgaga gcacgtgaa atatgatacg ggatccggag gaggggagc cacaaacgac    1260
gacgatgtta aaaagctgc cactgtggcc attgctgctg cctacaacaa tggccaagaa    1320
atcaacggtt tcaaagctgg agagaccatc tacgacattg atgaagacgg cacaattacc    1380
```

-continued

```
aaaaaagacg caactgcagc cgatgttgaa gccgacgact ttaaaggtct gggtctgaaa    1440
aaagtcgtga ctaacctgac caaaaccgtc aatgaaaaca acaaaacgt cgatgccaaa     1500 gtaaaagctg cagaatctga aatagaaaag ttaacaacca agttagcaga cactgatgcc    1560
gctttagcag atactgatgc cgctctggat gcaaccacca acgccttgaa taaattggga    1620
gaaaatataa cgacatttgc tgaagagact aagacaaata tcgtaaaaat tgatgaaaaa    1680
ttagaagccg tggctgatac cgtcgacaag catgccgaag cattcaacga tatcgccgat    1740
tcattggatg aaaccaacac taaggcagac gaagccgtca aaaccgccaa tgaagccaaa    1800
cagacggccg aagaaaccaa acaaaacgtc gatgccaaag taaaagctgc agaaactgca    1860
gcaggcaaag ccgaagctgc cgctggcaca gctaatactg cagccgacaa ggccgaagct    1920
gtcgctgcaa aagttaccga catcaaagct gatatcgcta cgaacaaaga taatattgct    1980
aaaaaagcaa acagtgccga cgtgtacacc agagaagagt ctgacagcaa atttgtcaga    2040
attgatggtc tgaacgctac taccgaaaaa ttggacacac gcttggcttc tgctgaaaaa    2100
tccattgccg atcacgatac tcgcctgaac ggtttggata aacagtgtc agacctgcgc    2160 aaagaaaccc gccaaggcct tgcagaacaa gccgcgctct ccggtctgtt ccaaccttac    2220
aacgtgggtc ggttcaatgt aacggctgca gtcggcggct acaaatccga atcggcagtc    2280
gccatcggta ccggcttccg ctttaccgaa aactttgccg ccaaagcagg cgtggcagtc    2340
ggcacttcgt ccggttcttc cgcagcctac catgtcggcg tcaattacga gtggctcgag    2400
caccaccacc accaccactg a                                              2421
```

<210> SEQ ID NO 143
<211> LENGTH: 806
<212> TYPE: PRT
<213> ORGANISM: Artificial Sequence
<220> FEATURE:
<223> OTHER INFORMATION: Synthetic construct

<400> SEQUENCE: 143

```
Met Ser Asp Leu Ala Asn Asp Ser Phe Ile Arg Gln Val Leu Asp Arg
1               5                   10                  15

Gln His Phe Glu Pro Asp Gly Lys Tyr His Leu Phe Gly Ser Arg Gly
            20                  25                  30

Glu Leu Ala Glu Arg Ser Gly His Ile Gly Leu Gly Lys Ile Gln Ser
        35                  40                  45

His Gln Leu Gly Asn Leu Met Ile Gln Gln Ala Ile Lys Gly Asn
    50                  55                  60

Ile Gly Tyr Ile Val Arg Phe Ser Asp His Gly His Glu Val His Ser
65                  70                  75                  80

Pro Phe Asp Asn His Ala Ser His Ser Asp Ser Asp Glu Ala Gly Ser
                85                  90                  95

Pro Val Asp Gly Phe Ser Leu Tyr Arg Ile His Trp Asp Gly Tyr Glu
            100                 105                 110

His His Pro Ala Asp Gly Tyr Asp Gly Pro Gln Gly Gly Tyr Pro
        115                 120                 125

Ala Pro Lys Gly Ala Arg Asp Ile Tyr Ser Tyr Asp Ile Lys Gly Val
    130                 135                 140

Ala Gln Asn Ile Arg Leu Asn Leu Thr Asp Asn Arg Ser Thr Gly Gln
145                 150                 155                 160

Arg Leu Ala Asp Arg Phe His Asn Ala Gly Ser Met Leu Thr Gln Gly
                165                 170                 175
```

```
Val Gly Asp Gly Phe Lys Arg Ala Thr Arg Tyr Ser Pro Glu Leu Asp
            180                 185                 190

Arg Ser Gly Asn Ala Ala Glu Ala Phe Asn Gly Thr Ala Asp Ile Val
        195                 200                 205

Lys Asn Ile Ile Gly Ala Ala Gly Glu Ile Val Gly Ala Gly Asp Ala
    210                 215                 220

Val Gln Gly Ile Ser Glu Gly Ser Asn Ile Ala Val Met His Gly Leu
225                 230                 235                 240

Gly Leu Leu Ser Thr Glu Asn Lys Met Ala Arg Ile Asn Asp Leu Ala
                245                 250                 255

Asp Met Ala Gln Leu Lys Asp Tyr Ala Ala Ala Ile Arg Asp Trp
            260                 265                 270

Ala Val Gln Asn Pro Asn Ala Ala Gln Gly Ile Glu Ala Val Ser Asn
        275                 280                 285

Ile Phe Met Ala Ala Ile Pro Ile Lys Gly Ile Gly Ala Val Arg Gly
    290                 295                 300

Lys Tyr Gly Leu Gly Gly Ile Thr Ala His Pro Ile Lys Arg Ser Gln
305                 310                 315                 320

Met Gly Ala Ile Ala Leu Pro Lys Gly Lys Ser Ala Val Ser Asp Asn
                325                 330                 335

Phe Ala Asp Ala Ala Tyr Ala Lys Tyr Pro Ser Pro Tyr His Ser Arg
            340                 345                 350

Asn Ile Arg Ser Asn Leu Glu Gln Arg Tyr Gly Lys Glu Asn Ile Thr
        355                 360                 365

Ser Ser Thr Val Pro Pro Ser Asn Gly Lys Asn Val Lys Leu Ala Asp
    370                 375                 380

Gln Arg His Pro Lys Thr Gly Val Pro Phe Asp Gly Lys Gly Phe Pro
385                 390                 395                 400

Asn Phe Glu Lys His Val Lys Tyr Asp Thr Gly Ser Gly Gly Gly Gly
                405                 410                 415

Ala Thr Asn Asp Asp Asp Val Lys Lys Ala Ala Thr Val Ala Ile Ala
            420                 425                 430

Ala Ala Tyr Asn Asn Gly Gln Glu Ile Asn Gly Phe Lys Ala Gly Glu
        435                 440                 445

Thr Ile Tyr Asp Ile Asp Glu Asp Gly Thr Ile Thr Lys Lys Asp Ala
    450                 455                 460

Thr Ala Ala Asp Val Glu Ala Asp Asp Phe Lys Gly Leu Gly Leu Lys
465                 470                 475                 480

Lys Val Val Thr Asn Leu Thr Lys Thr Val Asn Glu Asn Lys Gln Asn
                485                 490                 495

Val Asp Ala Lys Val Lys Ala Ala Glu Ser Glu Ile Glu Lys Leu Thr
            500                 505                 510

Thr Lys Leu Ala Asp Thr Asp Ala Ala Leu Ala Asp Thr Asp Ala Ala
        515                 520                 525

Leu Asp Ala Thr Thr Asn Ala Leu Asn Lys Leu Gly Glu Asn Ile Thr
    530                 535                 540

Thr Phe Ala Glu Glu Thr Lys Thr Asn Ile Val Lys Ile Asp Glu Lys
545                 550                 555                 560

Leu Glu Ala Val Ala Asp Thr Val Asp Lys His Ala Glu Ala Phe Asn
                565                 570                 575

Asp Ile Ala Asp Ser Leu Asp Glu Thr Asn Thr Lys Ala Asp Glu Ala
            580                 585                 590

Val Lys Thr Ala Asn Glu Ala Lys Gln Thr Ala Glu Glu Thr Lys Gln
        595                 600                 605
```

```
Asn Val Asp Ala Lys Val Lys Ala Ala Glu Thr Ala Ala Gly Lys Ala
    610                 615                 620

Glu Ala Ala Ala Gly Thr Ala Asn Thr Ala Asp Lys Ala Glu Ala
625                 630                 635                 640

Val Ala Ala Lys Val Thr Asp Ile Lys Ala Asp Ile Ala Thr Asn Lys
                645                 650                 655

Asp Asn Ile Ala Lys Lys Ala Asn Ser Ala Asp Val Tyr Thr Arg Glu
                660                 665                 670

Glu Ser Asp Ser Lys Phe Val Arg Ile Asp Gly Leu Asn Ala Thr Thr
            675                 680                 685

Glu Lys Leu Asp Thr Arg Leu Ala Ser Ala Glu Lys Ser Ile Ala Asp
        690                 695                 700

His Asp Thr Arg Leu Asn Gly Leu Asp Lys Thr Val Ser Asp Leu Arg
705                 710                 715                 720

Lys Glu Thr Arg Gln Gly Leu Ala Glu Gln Ala Ala Leu Ser Gly Leu
                725                 730                 735

Phe Gln Pro Tyr Asn Val Gly Arg Phe Asn Val Thr Ala Ala Val Gly
            740                 745                 750

Gly Tyr Lys Ser Glu Ser Ala Val Ala Ile Gly Thr Gly Phe Arg Phe
        755                 760                 765

Thr Glu Asn Phe Ala Ala Lys Ala Gly Val Ala Val Gly Thr Ser Ser
770                 775                 780

Gly Ser Ser Ala Ala Tyr His Val Gly Val Asn Tyr Glu Trp Leu Glu
785                 790                 795                 800

His His His His His His
            805

<210> SEQ ID NO 144
<211> LENGTH: 2256
<212> TYPE: DNA
<213> ORGANISM: Artificial Sequence
<220> FEATURE:
<223> OTHER INFORMATION: Synthetic construct

<400> SEQUENCE: 144
atgtcagatt tggcaaacga ttcttttatc cggcaggttc tcgaccgtca gcatttcgaa     60
cccgacggga ataccacct attcggcagc aggggggaac ttgccgagcg cagcggccat    120
atcggattgg gaaaaataca aagccatcag ttgggcaacc tgatgattca caggcggcc    180 attaaaggaa atatcggcta cattgtccgc ttttccgatc acgggcacga agtccattcc    240
cccttcgaca accatgcctc acattccgat tctgatgaag ccggtagtcc cgttgacgga    300
tttagccttt accgcatcca ttgggacgga tacgaacacc atcccgccga cggctatgac    360
gggccacagg gcggcggcta tcccgctccc aaaggcgcga gggatatata cagctacgac    420
ataaaaggcg ttgcccaaaa tatccgcctc aacctgaccg caaaccgcag caccggacaa    480
cggcttgccg accgtttcca caatgccggt agtatgctga cgcaaggagt aggcgacgga    540
ttcaaacgcg ccaccgata cagccccgag ctggacagat cggcaatgc cgccgaagcc    600 ttcaacggca ctgcagatat cgttaaaaac atcatcggcg cggcaggaga aattgtcggc    660
gcaggcgatg ccgtgcaggg cataagcgaa ggctcaaaca ttgctgtcat gcacggcttg    720
ggtctgcttt ccaccgaaaa caagatggcg cgcatcaacg atttggcaga tatggcgcaa    780
ctcaaagact atgccgcagc agccatccgc gattgggcag tccaaaaccc caatgccgca    840
caaggcatag aagccgtcag caatatcttt atggcagcca tccccatcaa agggattgga    900
```

-continued

```
gctgttcggg gaaaatacgg cttgggcggc atcacggcac atcctatcaa gcggtcgcag    960
atgggcgcga tcgcattgcc gaaagggaaa tccgccgtca gcgacaattt tgccgatgcg   1020
gcatacgcca atacccgtc cccttaccat tcccgaaata tccgttcaaa cttggagcag   1080
cgttacggca aagaaaacat cacctcctca accgtgccgc cgtcaaacgg caaaaatgtc   1140
aaactggcag accaacgcca cccgaagaca ggcgtaccgt ttgacggtaa agggtttccg   1200
aattttgaga agcacgtgaa atatgatacg ggatccggag gaggaggagc acaaacgac    1260 gacgatgtta aaaaagctgc cactgtggcc attgctgctg cctacaacaa tggccaagaa   1320
atcaacggtt tcaaagctgg agagaccatc tacgacattg atgaagacgg cacaattacc   1380
aaaaaagacg caactgcagc cgatgttgaa gccgacgact ttaaaggtct gggtctgaaa   1440
aaagtcgtga ctaacctgac caaaaccgtc aatgaaaaca acaaaacgt cgatgccaaa    1500 gtaaaagctg cagaatctga aatagaaaag ttaacaacca agttagcaga cactgatgcc   1560
gctttagcag atactgatgc cgctctggat gcaaccacca acgccttgaa taaattggga   1620
gaaaatataa cgacatttgc tgaagagact aagacaaata tcgtaaaaat tgatgaaaaa   1680
ttagaagccg tggctgatac cgtcgacaag catgccgaag cattcaacga tatcgccgat   1740
tcattggatg aaaccaacac taaggcagac gaagccgtca aaccgccaa tgaagccaaa    1800 cagacggccg aagaaaccaa acaaaacgtc gatgccaaag taaaagctgc agaaactgca   1860
gcaggcaaag ccgaagctgc cgctggcaca gctaatactg cagccgacaa ggccgaagct   1920
gtcgctgcaa aagttaccga catcaaagct gatatcgcta cgaacaaaga taatattgct   1980
aaaaaagcaa acagtgccga cgtgtacacc agagaagagt ctgacagcaa atttgtcaga   2040
attgatggtc tgaacgctac taccgaaaaa ttggacacac gcttggcttc tgctgaaaaa   2100
tccattgccg atcacgatac tcgcctgaac ggtttggata aacagtgtc agacctgcgc    2160 aaagaaaccc gccaaggcct tgcagaacaa gccgcgctct ccggtctgtt ccaaccttac   2220
aacgtgggtc tcgagcacca ccaccaccac cactga                             2256
```

<210> SEQ ID NO 145
<211> LENGTH: 751
<212> TYPE: PRT
<213> ORGANISM: Artificial Sequence
<220> FEATURE:
<223> OTHER INFORMATION: Synthetic construct

<400> SEQUENCE: 145

```
Met Ser Asp Leu Ala Asn Asp Ser Phe Ile Arg Gln Val Leu Asp Arg
1               5                   10                  15

Gln His Phe Glu Pro Asp Gly Lys Tyr His Leu Phe Gly Ser Arg Gly
            20                  25                  30

Glu Leu Ala Glu Arg Ser Gly His Ile Gly Leu Gly Lys Ile Gln Ser
        35                  40                  45

His Gln Leu Gly Asn Leu Met Ile Gln Gln Ala Ala Ile Lys Gly Asn
    50                  55                  60

Ile Gly Tyr Ile Val Arg Phe Ser Asp His Gly His Glu Val His Ser
65                  70                  75                  80

Pro Phe Asp Asn His Ala Ser His Ser Asp Ser Asp Glu Ala Gly Ser
                85                  90                  95

Pro Val Asp Gly Phe Ser Leu Tyr Arg Ile His Trp Asp Gly Tyr Glu
            100                 105                 110

His His Pro Ala Asp Gly Tyr Asp Gly Pro Gln Gly Gly Gly Tyr Pro
        115                 120                 125
```

-continued

```
Ala Pro Lys Gly Ala Arg Asp Ile Tyr Ser Tyr Asp Ile Lys Gly Val
    130                 135                 140
Ala Gln Asn Ile Arg Leu Asn Leu Thr Asp Asn Arg Ser Thr Gly Gln
145                 150                 155                 160
Arg Leu Ala Asp Arg Phe His Asn Ala Gly Ser Met Leu Thr Gln Gly
                165                 170                 175
Val Gly Asp Gly Phe Lys Arg Ala Thr Arg Tyr Ser Pro Glu Leu Asp
            180                 185                 190
Arg Ser Gly Asn Ala Ala Glu Ala Phe Asn Gly Thr Ala Asp Ile Val
        195                 200                 205
Lys Asn Ile Ile Gly Ala Ala Gly Glu Ile Val Gly Ala Gly Asp Ala
    210                 215                 220
Val Gln Gly Ile Ser Glu Gly Ser Asn Ile Ala Val Met His Gly Leu
225                 230                 235                 240
Gly Leu Leu Ser Thr Glu Asn Lys Met Ala Arg Ile Asn Asp Leu Ala
                245                 250                 255
Asp Met Ala Gln Leu Lys Asp Tyr Ala Ala Ala Ile Arg Asp Trp
            260                 265                 270
Ala Val Gln Asn Pro Asn Ala Ala Gln Gly Ile Glu Ala Val Ser Asn
        275                 280                 285
Ile Phe Met Ala Ala Ile Pro Ile Lys Gly Ile Gly Ala Val Arg Gly
    290                 295                 300
Lys Tyr Gly Leu Gly Gly Ile Thr Ala His Pro Ile Lys Arg Ser Gln
305                 310                 315                 320
Met Gly Ala Ile Ala Leu Pro Lys Gly Lys Ser Ala Val Ser Asp Asn
                325                 330                 335
Phe Ala Asp Ala Ala Tyr Ala Lys Tyr Pro Ser Pro Tyr His Ser Arg
            340                 345                 350
Asn Ile Arg Ser Asn Leu Glu Gln Arg Tyr Gly Lys Glu Asn Ile Thr
        355                 360                 365
Ser Ser Thr Val Pro Pro Ser Asn Gly Lys Asn Val Lys Leu Ala Asp
    370                 375                 380
Gln Arg His Pro Lys Thr Gly Val Pro Phe Asp Gly Lys Gly Phe Pro
385                 390                 395                 400
Asn Phe Glu Lys His Val Lys Tyr Asp Thr Gly Ser Gly Gly Gly Gly
                405                 410                 415
Ala Thr Asn Asp Asp Asp Val Lys Lys Ala Ala Thr Val Ala Ile Ala
            420                 425                 430
Ala Ala Tyr Asn Asn Gly Gln Glu Ile Asn Gly Phe Lys Ala Gly Glu
        435                 440                 445
Thr Ile Tyr Asp Ile Asp Glu Asp Gly Thr Ile Thr Lys Lys Asp Ala
    450                 455                 460
Thr Ala Ala Asp Val Glu Ala Asp Phe Lys Gly Leu Gly Leu Lys
465                 470                 475                 480
Lys Val Val Thr Asn Leu Thr Lys Thr Val Asn Glu Asn Lys Gln Asn
                485                 490                 495
Val Asp Ala Lys Val Lys Ala Ala Glu Ser Glu Ile Glu Lys Leu Thr
            500                 505                 510
Thr Lys Leu Ala Asp Thr Asp Ala Ala Leu Ala Asp Thr Asp Ala Ala
        515                 520                 525
Leu Asp Ala Thr Thr Asn Ala Leu Asn Lys Leu Gly Glu Asn Ile Thr
    530                 535                 540
Thr Phe Ala Glu Glu Thr Lys Thr Asn Ile Val Lys Ile Asp Glu Lys
545                 550                 555                 560
```

Leu Glu Ala Val Ala Asp Thr Val Asp Lys His Ala Glu Ala Phe Asn
          565                 570                 575

Asp Ile Ala Asp Ser Leu Asp Glu Thr Asn Thr Lys Ala Asp Glu Ala
      580                 585                 590

Val Lys Thr Ala Asn Glu Ala Lys Gln Thr Ala Glu Thr Lys Gln
  595                 600                 605

Asn Val Asp Ala Lys Val Lys Ala Ala Glu Thr Ala Ala Gly Lys Ala
      610                 615                 620

Glu Ala Ala Ala Gly Thr Ala Asn Thr Ala Ala Asp Lys Ala Glu Ala
625                 630                 635                 640

Val Ala Ala Lys Val Thr Asp Ile Lys Ala Asp Ile Ala Thr Asn Lys
              645                 650                 655

Asp Asn Ile Ala Lys Lys Ala Asn Ser Ala Asp Val Tyr Thr Arg Glu
              660                 665                 670

Glu Ser Asp Ser Lys Phe Val Arg Ile Asp Gly Leu Asn Ala Thr Thr
          675                 680                 685

Glu Lys Leu Asp Thr Arg Leu Ala Ser Ala Glu Lys Ser Ile Ala Asp
      690                 695                 700

His Asp Thr Arg Leu Asn Gly Leu Asp Lys Thr Val Ser Asp Leu Arg
705                 710                 715                 720

Lys Glu Thr Arg Gln Gly Leu Ala Glu Gln Ala Ala Leu Ser Gly Leu
              725                 730                 735

Phe Gln Pro Tyr Asn Val Gly Leu Glu His His His His His His
              740                 745                 750

<210> SEQ ID NO 146
<211> LENGTH: 2421
<212> TYPE: DNA
<213> ORGANISM: Artificial Sequence
<220> FEATURE:
<223> OTHER INFORMATION: Synthetic construct

<400> SEQUENCE: 146

| | | | | |
|---|---|---|---|---|
| atggccacaa | acgacgacga | tgttaaaaaa | gctgccactg | tggccattgc  tgctgcctac | 60 |
| aacaatggcc | aagaaatcaa | cggtttcaaa | gctggagaga | ccatctacga  cattgatgaa | 120 |
| gacggcacaa | ttaccaaaaa | agacgcaact | gcagccgatg | ttgaagccga  cgactttaaa | 180 |
| ggtctgggtc | tgaaaaaagt | cgtgactaac | ctgaccaaaa | ccgtcaatga  aaacaaacaa | 240 |
| aacgtcgatg | ccaaagtaaa | agctgcagaa | tctgaaatag | aaagttaac  aaccaagtta | 300 |
| gcagacactg | atgccgcttt | agcagatact | gatgccgctc | tggatgcaac  caccaacgcc | 360 |
| ttgaataaat | ggggagaaaa | tataacgaca | tttgctgaag | agactaagac  aaatatcgta | 420 |
| aaaattgatg | aaaaattaga | agccgtggct | gataccgtcg | acaagcatgc  cgaagcattc | 480 |
| aacgatatcg | ccgattcatt | ggatgaaacc | aacactaagg | cagacgaagc  cgtcaaaacc | 540 |
| gccaatgaag | ccaaacagac | aggccgaagaa | accaaacaaa | acgtcgatgc  caaagtaaaa | 600 |
| gctgcagaaa | ctgcagcagg | caaagccgaa | gctgccgctg | gcacagctaa  tactgcagcc | 660 |
| gacaaggccg | aagctgtcgc | tgcaaaagtt | accgacatca | agctgatat  cgctacgaac | 720 |
| aaagataata | ttgctaaaaa | agcaaacagt | gccgacgtgt | acaccagaga  agagtctgac | 780 |
| agcaaatttg | tcagaattga | tggtctgaac | gctactaccg | aaaaattgga  cacacgcttg | 840 |
| gcttctgctg | aaaaatccat | tgccgatcac | gatactcgcc | tgaacggttt  ggataaaaca | 900 |
| gtgtcagacc | tgcgcaaaga | aacccgccaa | ggccttgcag | aacaagccgc  gctctccggt | 960 |
| ctgttccaac | cttacaacgt | gggtcggttc | aatgtaacgg | ctgcagtcgg  cggctacaaa | 1020 |

```
tccgaatcgg cagtcgccat cggtaccggc ttccgcttta ccgaaaactt tgccgccaaa    1080
gcaggcgtgg cagtcggcac ttcgtccggt tcttccgcag cctaccatgt cggcgtcaat    1140
tacgagtggg gatccggagg aggaggatca gatttggcaa acgattcttt tatccggcag    1200
gttctcgacc gtcagcattt cgaacccgac gggaaatacc acctattcgg cagcaggggg    1260
gaacttgccg agcgcagcgg ccatatcgga ttgggaaaaa tacaaagcca tcagttgggc    1320
aacctgatga ttcaacaggc ggccattaaa ggaaatatcg gctacattgt ccgcttttcc    1380
gatcacgggc acgaagtcca ttccccttc gacaaccatg cctcacattc cgattctgat    1440
gaagccggta gtcccgttga cggatttagc ctttaccgca tccattggga cggatacgaa    1500
caccatcccg ccgacggcta tgacgggcca cagggcggcg gctatcccgc tcccaaaggc    1560
gcgagggata tatacagcta cgacataaaa ggcgttgccc aaaatatccg cctcaacctg    1620
accgacaacc gcagcaccgg acaacggctt gccgaccgtt tccacaatgc cggtagtatg    1680
ctgacgcaag gagtaggcga cggattcaaa cgcgccaccc gatacagccc cgagctggac    1740
agatcgggca atgccgccga agccttcaac ggcactgcag atatcgttaa aaacatcatc    1800
ggcgcggcag gagaaattgt cggcgcaggc gatgccgtgc agggcataag cgaaggctca    1860
aacattgctg tcatgcacgg cttgggtctg cttttccaccg aaaacaagat ggcgcgcatc    1920
aacgatttgg cagatatggc gcaactcaaa gactatgccg cagcagccat ccgcgattgg    1980
gcagtccaaa accccaatgc cgcacaaggc atagaagccg tcagcaatat ctttatggca    2040
gccatcccca tcaagggat tggagctgtt cggggaaaat acggcttggg cggcatcacg    2100
gcacatccta tcaagcggtc gcagatgggc gcgatcgcat tgccgaaagg gaaatccgcc    2160
gtcagcgaca ttttgccga tgcggcatac gccaaatacc cgtcccctta ccattcccga    2220
aatatccgtt caaacttgga gcagcgttac ggcaaagaaa acatcacctc ctcaaccgtg    2280
ccgccgtcaa acggcaaaaa tgtcaaactg cagaccaac gccacccgaa gacaggcgta    2340 ccgttttgacg gtaaagggtt tccgaatttt gagaagcacg tgaaatatga tacgctcgag    2400
caccaccacc accaccactg a                                              2421
```

<210> SEQ ID NO 147
<211> LENGTH: 806
<212> TYPE: PRT
<213> ORGANISM: Artificial Sequence
<220> FEATURE:
<223> OTHER INFORMATION: Synthetic construct

<400> SEQUENCE: 147

```
Met Ala Thr Asn Asp Asp Val Lys Lys Ala Thr Val Ala Ile
1               5                   10                  15

Ala Ala Ala Tyr Asn Asn Gly Gln Glu Ile Asn Gly Phe Lys Ala Gly
                20                  25                  30

Glu Thr Ile Tyr Asp Ile Asp Glu Asp Gly Thr Ile Thr Lys Lys Asp
            35                  40                  45

Ala Thr Ala Ala Asp Val Glu Ala Asp Phe Lys Gly Leu Gly Leu
        50                  55                  60

Lys Lys Val Val Thr Asn Leu Thr Lys Thr Val Asn Glu Asn Lys Gln
65                  70                  75                  80

Asn Val Asp Ala Lys Val Lys Ala Ala Glu Ser Glu Ile Glu Lys Leu
                85                  90                  95

Thr Thr Lys Leu Ala Asp Thr Asp Ala Ala Leu Ala Asp Thr Asp Ala
            100                 105                 110
```

```
Ala Leu Asp Ala Thr Thr Asn Ala Leu Asn Lys Leu Gly Glu Asn Ile
        115                 120                 125

Thr Thr Phe Ala Glu Glu Thr Lys Thr Asn Ile Val Lys Ile Asp Glu
    130                 135                 140

Lys Leu Glu Ala Val Ala Asp Thr Val Asp Lys His Ala Glu Ala Phe
145                 150                 155                 160

Asn Asp Ile Ala Asp Ser Leu Asp Glu Thr Asn Thr Lys Ala Asp Glu
                165                 170                 175

Ala Val Lys Thr Ala Asn Glu Ala Lys Gln Thr Ala Glu Glu Thr Lys
            180                 185                 190

Gln Asn Val Asp Ala Lys Val Lys Ala Glu Thr Ala Ala Gly Lys
        195                 200                 205

Ala Glu Ala Ala Ala Gly Thr Ala Asn Thr Ala Ala Asp Lys Ala Glu
    210                 215                 220

Ala Val Ala Ala Lys Val Thr Asp Ile Lys Ala Asp Ile Ala Thr Asn
225                 230                 235                 240

Lys Asp Asn Ile Ala Lys Lys Ala Asn Ser Ala Asp Val Tyr Thr Arg
                245                 250                 255

Glu Glu Ser Asp Ser Lys Phe Val Arg Ile Asp Gly Leu Asn Ala Thr
            260                 265                 270

Thr Glu Lys Leu Asp Thr Arg Leu Ala Ser Ala Glu Lys Ser Ile Ala
    275                 280                 285

Asp His Asp Thr Arg Leu Asn Gly Leu Asp Lys Thr Val Ser Asp Leu
    290                 295                 300

Arg Lys Glu Thr Arg Gln Gly Leu Ala Glu Gln Ala Ala Leu Ser Gly
305                 310                 315                 320

Leu Phe Gln Pro Tyr Asn Val Gly Arg Phe Asn Val Thr Ala Ala Val
                325                 330                 335

Gly Gly Tyr Lys Ser Glu Ser Ala Val Ala Ile Gly Thr Gly Phe Arg
            340                 345                 350

Phe Thr Glu Asn Phe Ala Ala Lys Ala Gly Val Ala Val Gly Thr Ser
    355                 360                 365

Ser Gly Ser Ser Ala Ala Tyr His Val Gly Val Asn Tyr Glu Trp Gly
    370                 375                 380

Ser Gly Gly Gly Ser Asp Leu Ala Asn Asp Ser Phe Ile Arg Gln
385                 390                 395                 400

Val Leu Asp Arg Gln His Phe Glu Pro Asp Gly Lys Tyr His Leu Phe
                405                 410                 415

Gly Ser Arg Gly Glu Leu Ala Glu Arg Ser Gly His Ile Gly Leu Gly
            420                 425                 430

Lys Ile Gln Ser His Gln Leu Gly Asn Leu Met Ile Gln Gln Ala Ala
    435                 440                 445

Ile Lys Gly Asn Ile Gly Tyr Ile Val Arg Phe Ser Asp His Gly His
    450                 455                 460

Glu Val His Ser Pro Phe Asp Asn His Ala Ser His Ser Asp Ser Asp
465                 470                 475                 480

Glu Ala Gly Ser Pro Val Asp Gly Phe Ser Leu Tyr Arg Ile His Trp
                485                 490                 495

Asp Gly Tyr Glu His His Pro Ala Asp Gly Tyr Asp Gly Pro Gln Gly
            500                 505                 510

Gly Gly Tyr Pro Ala Pro Lys Gly Ala Arg Asp Ile Tyr Ser Tyr Asp
    515                 520                 525

Ile Lys Gly Val Ala Gln Asn Ile Arg Leu Asn Leu Thr Asp Asn Arg
    530                 535                 540
```

```
Ser Thr Gly Gln Arg Leu Ala Asp Arg Phe His Asn Ala Gly Ser Met
545                 550                 555                 560

Leu Thr Gln Gly Val Gly Asp Gly Phe Lys Arg Ala Thr Arg Tyr Ser
                565                 570                 575

Pro Glu Leu Asp Arg Ser Gly Asn Ala Ala Ala Phe Asn Gly Thr
                580                 585                 590

Ala Asp Ile Val Lys Asn Ile Ile Gly Ala Ala Gly Glu Ile Val Gly
                595                 600                 605

Ala Gly Asp Ala Val Gln Gly Ile Ser Glu Gly Ser Asn Ile Ala Val
                610                 615                 620

Met His Gly Leu Gly Leu Leu Ser Thr Glu Asn Lys Met Ala Arg Ile
625                 630                 635                 640

Asn Asp Leu Ala Asp Met Ala Gln Leu Lys Asp Tyr Ala Ala Ala Ala
                645                 650                 655

Ile Arg Asp Trp Ala Val Gln Asn Pro Asn Ala Ala Gln Gly Ile Glu
                660                 665                 670

Ala Val Ser Asn Ile Phe Met Ala Ala Ile Pro Ile Lys Gly Ile Gly
                675                 680                 685

Ala Val Arg Gly Lys Tyr Gly Leu Gly Gly Ile Thr Ala His Pro Ile
                690                 695                 700

Lys Arg Ser Gln Met Gly Ala Ile Ala Leu Pro Lys Gly Lys Ser Ala
705                 710                 715                 720

Val Ser Asp Asn Phe Ala Asp Ala Ala Tyr Ala Lys Tyr Pro Ser Pro
                725                 730                 735

Tyr His Ser Arg Asn Ile Arg Ser Asn Leu Glu Gln Arg Tyr Gly Lys
                740                 745                 750

Glu Asn Ile Thr Ser Ser Thr Val Pro Pro Ser Asn Gly Lys Asn Val
                755                 760                 765

Lys Leu Ala Asp Gln Arg His Pro Lys Thr Gly Val Pro Phe Asp Gly
                770                 775                 780

Lys Gly Phe Pro Asn Phe Glu Lys His Val Lys Tyr Asp Thr Leu Glu
785                 790                 795                 800

His His His His His His
                805

<210> SEQ ID NO 148
<211> LENGTH: 1938
<212> TYPE: DNA
<213> ORGANISM: Artificial Sequence
<220> FEATURE:
<223> OTHER INFORMATION: Synthetic construct

<400> SEQUENCE: 148
atggccacaa acgacgacga tgttaaaaaa gctgccactg tggccattgc tgctgcctac      60
aacaatggcc aagaaatcaa cggttttcaaa gctggagaga ccatctacga cattgatgaa     120
gacggcacaa ttaccaaaaa agacgcaact gcagccgatg ttgaagccga cgactttaaa     180
ggtctgggtc tgaaaaaagt cgtgactaac ctgaccaaaa ccgtcaatga aacaaacaa      240 aacgtcgatg ccaaagtaaa agctgcagaa tctgaaatag aaaagttaac aaccaagtta     300
gcagacactg atgccgcttt agcagatact gatgccgctc tggatgcaac caccaacgcc     360
ttgaataaat tgggagaaaa tataacgaca tttgctgaag agactaagac aaatatcgta     420
aaaattgatg aaaaattaga agccgtggct gataccgtcg acaagcatgc cgaagcattc     480
aacgatatcg ccgattcatt ggatgaaacc aacactaagg cagacgaagc cgtcaaaacc     540
```

```
gccaatgaag ccaaacagac ggccgaagaa accaaacaaa acgtcgatgc caaagtaaaa      600
gctgcagaaa ctgcagcagg caaagccgaa gctgccgctg cacagctaa tactgcagcc       660
gacaaggccg aagctgtcgc tgcaaaagtt accgacatca agctgatat cgctacgaac       720
aaagataata ttgctaaaaa agcaaacagt gccgacgtgt acaccagaga agagtctgac      780
agcaaatttg tcagaattga tggtctgaac gctactaccg aaaaattgga cacacgcttg      840
gcttctgctg aaaaatccat tgccgatcac gatactcgcc tgaacggttt ggataaaaca      900
gtgtcagacc tgcgcaaaga aacccgccaa ggccttgcag aacaagccgc gctctccggt      960
ctgttccaac cttacaacgt gggtcggttc aatgtaacgg ctgcagtcgg cggctacaaa     1020
tccgaatcgg cagtcgccat cggtaccggc ttccgcttta ccgaaaactt tgccgccaaa     1080
gcaggcgtgg cagtcggcac ttcgtccggt tcttccgcag cctaccatgt cggcgtcaat     1140
tacgagtggg atccggaggg ggtggtgtc gccgccgaca tcggtgcggg gcttgccgat     1200
gcactaaccg caccgctcga ccataaagac aaaggtttgc agtctttgac gctggatcag    1260
tccgtcagga aaacgagaa actgaagctg gcggcacaag gtgcggaaaa aacttatgga     1320
aacggtgaca gcctcaatac gggcaaattg aagaacgaca aggtcagccg tttcgacttt    1380
atccgccaaa tcgaagtgga cgggcagctc attaccttgg agagtggaga gttccaagta    1440
tacaaacaaa gccattccgc cttaaccgcc tttcagaccg agcaaataca agattcggag    1500
cattccggga agatggttgc gaaacgccag ttcagaatcg gcgacatagc gggcgaacat    1560
acatcttttg acaagcttcc cgaaggcggc agggcgacat atcgcgggac ggcgttcggt    1620
tcagacgatg ccggcggaaa actgacctac accatagatt tcgccgccaa gcagggaaac    1680
ggcaaaatcg aacatttgaa atcgccagaa ctcaatgtcg acctggccgc cgccgatatc    1740
aagccggatg gaaaacgcca tgccgtcatc agcggttccg tcctttacaa ccaagccgag    1800
aaaggcagtt actccctcgg tatctttggc ggaaaagccc aggaagttgc cggcagcgcg    1860
gaagtgaaaa ccgtaaacgg catacgccat atcggccttg ccgccaagca actcgagcac    1920
caccaccacc accactga                                                   1938
```

<210> SEQ ID NO 149
<211> LENGTH: 645
<212> TYPE: PRT
<213> ORGANISM: Artificial Sequence
<220> FEATURE:
<223> OTHER INFORMATION: Synthetic construct

<400> SEQUENCE: 149

```
Met Ala Thr Asn Asp Asp Val Lys Lys Ala Ala Thr Val Ala Ile
1               5                   10                  15

Ala Ala Ala Tyr Asn Asn Gly Gln Glu Ile Asn Gly Phe Lys Ala Gly
            20                  25                  30

Glu Thr Ile Tyr Asp Ile Asp Glu Asp Gly Thr Ile Thr Lys Lys Asp
        35                  40                  45

Ala Thr Ala Ala Asp Val Glu Ala Asp Phe Lys Gly Leu Gly Leu
    50                  55                  60

Lys Lys Val Val Thr Asn Leu Thr Lys Thr Val Asn Glu Asn Lys Gln
65                  70                  75                  80

Asn Val Asp Ala Lys Val Lys Ala Ala Glu Ser Glu Ile Glu Lys Leu
                85                  90                  95

Thr Thr Lys Leu Ala Asp Thr Asp Ala Ala Leu Ala Asp Thr Asp Ala
            100                 105                 110

Ala Leu Asp Ala Thr Thr Asn Ala Leu Asn Lys Leu Gly Glu Asn Ile
```

```
                  115                 120                      125
Thr Thr Phe Ala Glu Glu Thr Lys Thr Asn Ile Val Lys Ile Asp Glu
        130                 135                 140
Lys Leu Glu Ala Val Ala Asp Thr Val Asp Lys His Ala Glu Ala Phe
145                 150                 155                 160
Asn Asp Ile Ala Asp Ser Leu Asp Glu Thr Asn Thr Lys Ala Asp Glu
                165                 170                 175
Ala Val Lys Thr Ala Asn Glu Ala Lys Gln Thr Ala Glu Thr Lys
            180                 185                 190
Gln Asn Val Asp Ala Lys Val Lys Ala Ala Glu Thr Ala Ala Gly Lys
        195                 200                 205
Ala Glu Ala Ala Ala Gly Thr Ala Asn Thr Ala Ala Asp Lys Ala Glu
    210                 215                 220
Ala Val Ala Ala Lys Val Thr Asp Ile Lys Ala Asp Ile Ala Thr Asn
225                 230                 235                 240
Lys Asp Asn Ile Ala Lys Lys Ala Asn Ser Ala Asp Val Tyr Thr Arg
                245                 250                 255
Glu Glu Ser Asp Ser Lys Phe Val Arg Ile Asp Gly Leu Asn Ala Thr
            260                 265                 270
Thr Glu Lys Leu Asp Thr Arg Leu Ala Ser Ala Glu Lys Ser Ile Ala
    275                 280                 285
Asp His Asp Thr Arg Leu Asn Gly Leu Asp Lys Thr Val Ser Asp Leu
    290                 295                 300
Arg Lys Glu Thr Arg Gln Gly Leu Ala Glu Gln Ala Ala Leu Ser Gly
305                 310                 315                 320
Leu Phe Gln Pro Tyr Asn Val Gly Arg Phe Asn Val Thr Ala Ala Val
                325                 330                 335
Gly Gly Tyr Lys Ser Glu Ser Ala Val Ala Ile Gly Thr Gly Phe Arg
            340                 345                 350
Phe Thr Glu Asn Phe Ala Ala Lys Ala Gly Val Ala Val Gly Thr Ser
        355                 360                 365
Ser Gly Ser Ser Ala Ala Tyr His Val Gly Val Asn Tyr Glu Trp Gly
    370                 375                 380
Ser Gly Gly Gly Val Ala Ala Asp Ile Gly Ala Gly Leu Ala Asp
385                 390                 395                 400
Ala Leu Thr Ala Pro Leu Asp His Lys Asp Lys Gly Leu Gln Ser Leu
                405                 410                 415
Thr Leu Asp Gln Ser Val Arg Lys Asn Glu Lys Leu Lys Leu Ala Ala
            420                 425                 430
Gln Gly Ala Glu Lys Thr Tyr Gly Asn Gly Asp Ser Leu Asn Thr Gly
        435                 440                 445
Lys Leu Lys Asn Asp Lys Val Ser Arg Phe Asp Phe Ile Arg Gln Ile
    450                 455                 460
Glu Val Asp Gly Gln Leu Ile Thr Leu Glu Ser Gly Glu Phe Gln Val
465                 470                 475                 480
Tyr Lys Gln Ser His Ser Ala Leu Thr Ala Phe Gln Thr Glu Gln Ile
                485                 490                 495
Gln Asp Ser Glu His Ser Gly Lys Met Val Ala Lys Arg Gln Phe Arg
            500                 505                 510
Ile Gly Asp Ile Ala Gly Glu His Thr Ser Phe Asp Lys Leu Pro Glu
        515                 520                 525
Gly Gly Arg Ala Thr Tyr Arg Gly Thr Ala Phe Gly Ser Asp Asp Ala
    530                 535                 540
```

```
Gly Gly Lys Leu Thr Tyr Thr Ile Asp Phe Ala Ala Lys Gln Gly Asn
545                 550                 555                 560

Gly Lys Ile Glu His Leu Lys Ser Pro Glu Leu Asn Val Asp Leu Ala
            565                 570                 575

Ala Ala Asp Ile Lys Pro Asp Gly Lys Arg His Ala Val Ile Ser Gly
        580                 585                 590

Ser Val Leu Tyr Asn Gln Ala Glu Lys Gly Ser Tyr Ser Leu Gly Ile
    595                 600                 605

Phe Gly Gly Lys Ala Gln Glu Val Ala Gly Ser Ala Glu Val Lys Thr
610                 615                 620

Val Asn Gly Ile Arg His Ile Gly Leu Ala Ala Lys Gln Leu Glu His
625                 630                 635                 640

His His His His His
            645

<210> SEQ ID NO 150
<211> LENGTH: 4335
<212> TYPE: DNA
<213> ORGANISM: Artificial Sequence
<220> FEATURE:
<223> OTHER INFORMATION: Synthetic construct

<400> SEQUENCE: 150
atggccacaa acgacgacga tgttaaaaaa gctgccactg tggccattgc tgctgcctac      60
aacaatggcc aagaaatcaa cggtttcaaa gctggagaga ccatctacga cattgatgaa     120
gacggcacaa ttaccaaaaa agacgcaact gcagccgatg ttgaagccga cgactttaaa     180
ggtctgggtc tgaaaaaagt cgtgactaac ctgaccaaaa ccgtcaatga aacaaacaa      240 aacgtcgatg ccaaagtaaa agctgcagaa tctgaaatag aaaagttaac aaccaagtta     300
gcagacactg atgccgcttt agcagatact gatgccgctc tggatgcaac caccaacgcc     360
ttgaataaat gggagaaaaa tataacgaca tttgctgaag agactaagac aaatatcgta     420
aaaattgatg aaaaattaga gccgtggct gataccgtcg acaagcatgc cgaagcattc     480
aacgatatcg ccgattcatt ggatgaaacc aacactaagg cagacgaagc cgtcaaaacc     540
gccaatgaag ccaaacagac ggccgaagaa accaaacaaa acgtcgatgc caaagtaaaa     600
gctgcagaaa ctgcagcagg caaagccgaa gctgccgctg gcacagctaa tactgcagcc     660
gacaaggccg aagctgtcgc tgcaaaagtt accgacatca agctgatat cgctacgaac     720 aaagataata ttgctaaaaa agcaaacagt gccgacgtgt acaccagaga gagtctgac     780 agcaaatttg tcagaattga tggtctgaac gctactaccg aaaaattgga cacacgcttg     840
gcttctgctg aaaaatccat tgccgatcac gatactcgcc tgaacggttt ggataaaaca     900
gtgtcagacc tgcgcaaaga aacccgccaa ggccttgcag acaagccgc gctctccggt     960 ctgttccaac cttacaacgt gggtcggttc aatgtaacgg ctgcagtcgg cggctacaaa    1020
tccgaatcgg cagtcgccat cggtaccggc ttccgcttta ccgaaaactt tgccgccaaa    1080
gcaggcgtgg cagtcggcac ttcgtccggt tcttccgcag cctaccatgt cggcgtcaat    1140
tacgagtggg gatccggcgg aggcggcact tctgcgcccg acttcaatgc aggcggtacc    1200
ggtatcggca gcaacagcag agcaacaaca gcgaaatcag cagcagtatc ttacgccggt    1260
atcaagaacg aaatgtgcaa agacagaagc atgctctgtg ccggtcggga tgacgttgcg    1320
gttacagaca gggatgccaa aatcaatgcc ccccccccga atctgcatac cggagacttt    1380
ccaaacccaa atgacgcata caagaatttg atcaacctca aacctgcaat tgaagcaggc    1440
tatacaggac gcggggtaga ggtaggtatc gtcgacacag gcgaatccgt cggcagcata    1500
```

```
tcctttcccg aactgtatgg cagaaaagaa cacggctata acgaaaatta caaaaactat    1560
acggcgtata tgcggaagga agcgcctgaa gacggaggcg gtaaagacat tgaagcttct    1620
ttcgacgatg aggccgttat agagactgaa gcaaagccga cggatatccg ccacgtaaaa    1680
gaaatcggac acatcgattt ggtctcccat attattggcg ggcgttccgt ggacggcaga    1740
cctgcaggcg gtattgcgcc cgatgcgacg ctacacataa tgaatacgaa tgatgaaacc    1800
aagaacgaaa tgatggttgc agccatccgc aatgcatggg tcaagctggg cgaacgtggc    1860
gtgcgcatcg tcaataacag ttttggaaca acatcgaggg caggcactgc cgacttttc    1920
caaatagcca attcggagga gcagtaccgc caagcgttgc tcgactattc cggcggtgat    1980
aaaacgacg agggtatccg cctgatgcaa cagagcgatt acggcaacct gtcctaccac    2040
atccgtaata aaacatgct tttcatcttt tcgacaggca atgacgcaca agctcagccc    2100
aacacatatg ccctattgcc attttatgaa aaagacgctc aaaaaggcat tatcacagtc    2160
gcaggcgtag accgcagtgg agaaaagttc aaacgggaaa tgtatggaga accgggtaca    2220
gaaccgcttg agtatggctc caaccattgc ggaattactg ccatgtggtg cctgtcggca    2280
ccctatgaag caagcgtccg tttcacccgt acaaacccga ttcaaattgc cggaacatcc    2340
ttttccgcac ccatcgtaac cggcacggcg gctctgctgc tgcagaaata cccgtggatg    2400
agcaacgaca acctgcgtac cacgttgctg acgacggctc aggacatcgg tgcagtcggc    2460
gtggacagca agttcggctg gggactgctg gatgcgggta aggccatgaa cggacccgcg    2520
tcctttccgt tcggcgactt taccgccgat acgaaaggta catccgatat tgcctactcc    2580
ttccgtaacg acatttcagg cacgggcggc ctgatcaaaa aaggcggcag ccaactgcaa    2640
ctgcacggca caacaccta cgggcaaa accattatcg aaggcggttc gctggtgttg    2700
tacggcaaca caaatcgga tatgcgcgtc gaaaccaaag gtgcgctgat ttataacggg    2760
gcggcatccg gcggcagcct gaacagcgac ggcattgtct atctggcaga taccgaccaa    2820
tccggcgcaa acgaaaccgt acacatcaaa ggcagtctgc agctggacgg caaaggtacg    2880
ctgtacacac gtttgggcaa actgctgaaa gtggacggta cggcgattat cggcggcaag    2940
ctgtacatgt cggcacgcgg caaggggca ggctatctca acagtaccgg acgacgtgtt    3000
cccttcctga gtgccgccaa aatcgggcag gattattctt tcttcacaaa catcgaaacc    3060
gacggcggcc tgctggcttc cctcgacagc gtcgaaaaaa cagcgggcag tgaaggcgac    3120
acgctgtcct attatgtccg tcgcggcaat gcggcacgga ctgcttcggc agcggcacat    3180
tccgcgcccg ccggtctgaa acacgccgta gaacagggcg gcagcaatct ggaaaacctg    3240
atggtcgaac tggatgcctc cgaatcatcc gcaacacccg agacggttga aactgcggca    3300
gccgaccgca cagatatgcc gggcatccgc ccctacggcg caactttccg cgcagcggca    3360
gccgtacagc atgcgaatgc cgccgacggt gtacgcatct tcaacagtct cgccgctacc    3420
gtctatgccg acagtaccgc cgcccatgcc gatatgcagg gacgccgcct gaaagccgta    3480
tcggacgggt tggaccacaa cggcacgggt ctgcgcgtca tcgcgcaaac ccaacaggac    3540
ggtggaacgt gggaacaggg cggtgttgaa ggcaaaatgc gcggcagtac ccaaaccgtc    3600
ggcattgccg cgaaaaccgg cgaaaatacg acagcagccg ccacactggg catgggacgc    3660
agcacatgga gcgaaaacag tgcaaatgca aaaaccgaca gcattagtct gtttgcaggc    3720
atacggcacg atgcgggcga tatcggctat ctcaaaggcc tgttctccta cggacgctac    3780
aaaaacagca tcagccgcag caccggtgcg gacgaacatg cggaaggcag cgtcaacggc    3840
acgctgatgc agctgggcgc actgggcggt gtcaacgttc cgtttgccgc aacgggagat    3900
```

```
ttgacggtcg aaggcggtct gcgctacgac ctgctcaaac aggatgcatt cgccgaaaaa    3960
ggcagtgctt tgggctggag cggcaacagc ctcactgaag gcacgctggt cggactcgcg    4020
ggtctgaagc tgtcgcaacc cttgagcgat aaagccgtcc tgtttgcaac ggcgggcgtg    4080
gaacgcgacc tgaacggacg cgactacacg gtaacgggcg gctttaccgg cgcgactgca    4140
gcaaccggca agacggggc acgcaatatg ccgcacaccc gtctggttgc cggcctgggc    4200
gcggatgtcg aattcggcaa cggctggaac ggcttggcac gttacagcta cgccggttcc    4260
aaacagtacg gcaaccacag cggacgagtc ggcgtaggct accggttcct cgagcaccac    4320
caccaccacc actga                                                     4335
```

<210> SEQ ID NO 151
<211> LENGTH: 1444
<212> TYPE: PRT
<213> ORGANISM: Artificial Sequence
<220> FEATURE:
<223> OTHER INFORMATION: Synthetic construct

<400> SEQUENCE: 151

```
Met Ala Thr Asn Asp Asp Val Lys Lys Ala Ala Thr Val Ala Ile
 1               5                  10                  15

Ala Ala Ala Tyr Asn Asn Gly Gln Glu Ile Asn Gly Phe Lys Ala Gly
            20                  25                  30

Glu Thr Ile Tyr Asp Ile Asp Glu Asp Gly Thr Ile Thr Lys Lys Asp
        35                  40                  45

Ala Thr Ala Ala Asp Val Glu Ala Asp Asp Phe Lys Gly Leu Gly Leu
    50                  55                  60

Lys Lys Val Val Thr Asn Leu Thr Lys Thr Val Asn Glu Asn Lys Gln
65                  70                  75                  80

Asn Val Asp Ala Lys Val Lys Ala Ala Glu Ser Glu Ile Glu Lys Leu
                85                  90                  95

Thr Thr Lys Leu Ala Asp Thr Asp Ala Ala Leu Ala Asp Thr Asp Ala
            100                 105                 110

Ala Leu Asp Ala Thr Thr Asn Ala Leu Asn Lys Leu Gly Glu Asn Ile
        115                 120                 125

Thr Thr Phe Ala Glu Glu Thr Lys Thr Asn Ile Val Lys Ile Asp Glu
    130                 135                 140

Lys Leu Glu Ala Val Ala Asp Thr Val Asp Lys His Ala Glu Ala Phe
145                 150                 155                 160

Asn Asp Ile Ala Asp Ser Leu Asp Glu Thr Asn Thr Lys Ala Asp Glu
                165                 170                 175

Ala Val Lys Thr Ala Asn Glu Ala Lys Gln Thr Ala Glu Glu Thr Lys
            180                 185                 190

Gln Asn Val Asp Ala Lys Val Lys Ala Ala Glu Thr Ala Ala Gly Lys
        195                 200                 205

Ala Glu Ala Ala Ala Gly Thr Ala Asn Thr Ala Ala Asp Lys Ala Glu
    210                 215                 220

Ala Val Ala Ala Lys Val Thr Asp Ile Lys Ala Asp Ile Ala Thr Asn
225                 230                 235                 240

Lys Asp Asn Ile Ala Lys Lys Ala Asn Ser Ala Asp Val Tyr Thr Arg
                245                 250                 255

Glu Glu Ser Asp Ser Lys Phe Val Arg Ile Asp Gly Leu Asn Ala Thr
            260                 265                 270

Thr Glu Lys Leu Asp Thr Arg Leu Ala Ser Ala Glu Lys Ser Ile Ala
        275                 280                 285
```

-continued

Asp His Asp Thr Arg Leu Asn Gly Leu Asp Lys Thr Val Ser Asp Leu
    290                 295                 300

Arg Lys Glu Thr Arg Gln Gly Leu Ala Glu Gln Ala Ala Leu Ser Gly
305                 310                 315                 320

Leu Phe Gln Pro Tyr Asn Val Gly Arg Phe Asn Val Thr Ala Ala Val
                325                 330                 335

Gly Gly Tyr Lys Ser Glu Ser Ala Val Ala Ile Gly Thr Gly Phe Arg
            340                 345                 350

Phe Thr Glu Asn Phe Ala Ala Lys Ala Gly Val Ala Val Gly Thr Ser
                355                 360                 365

Ser Gly Ser Ser Ala Ala Tyr His Val Gly Val Asn Tyr Glu Trp Gly
370                 375                 380

Ser Gly Gly Gly Thr Ser Ala Pro Asp Phe Asn Ala Gly Gly Thr
385                 390                 395                 400

Gly Ile Gly Ser Asn Ser Arg Ala Thr Thr Ala Lys Ser Ala Ala Val
                405                 410                 415

Ser Tyr Ala Gly Ile Lys Asn Glu Met Cys Lys Asp Arg Ser Met Leu
            420                 425                 430

Cys Ala Gly Arg Asp Asp Val Ala Val Thr Asp Arg Asp Ala Lys Ile
                435                 440                 445

Asn Ala Pro Pro Pro Asn Leu His Thr Gly Asp Phe Pro Asn Pro Asn
450                 455                 460

Asp Ala Tyr Lys Asn Leu Ile Asn Leu Lys Pro Ala Ile Glu Ala Gly
465                 470                 475                 480

Tyr Thr Gly Arg Gly Val Glu Val Gly Ile Val Asp Thr Gly Glu Ser
                485                 490                 495

Val Gly Ser Ile Ser Phe Pro Glu Leu Tyr Arg Lys Glu His Gly
            500                 505                 510

Tyr Asn Glu Asn Tyr Lys Asn Tyr Thr Ala Tyr Met Arg Lys Glu Ala
            515                 520                 525

Pro Glu Asp Gly Gly Gly Lys Asp Ile Glu Ala Ser Phe Asp Asp Glu
    530                 535                 540

Ala Val Ile Glu Thr Glu Ala Lys Pro Thr Asp Ile Arg His Val Lys
545                 550                 555                 560

Glu Ile Gly His Ile Asp Leu Val Ser His Ile Ile Gly Gly Arg Ser
                565                 570                 575

Val Asp Gly Arg Pro Ala Gly Gly Ile Ala Pro Asp Ala Thr Leu His
            580                 585                 590

Ile Met Asn Thr Asn Asp Glu Thr Lys Asn Glu Met Met Val Ala Ala
    595                 600                 605

Ile Arg Asn Ala Trp Val Lys Leu Gly Glu Arg Gly Val Arg Ile Val
    610                 615                 620

Asn Asn Ser Phe Gly Thr Thr Ser Arg Ala Gly Thr Ala Asp Leu Phe
625                 630                 635                 640

Gln Ile Ala Asn Ser Glu Glu Gln Tyr Arg Gln Ala Leu Leu Asp Tyr
                645                 650                 655

Ser Gly Gly Asp Lys Thr Asp Glu Gly Ile Arg Leu Met Gln Gln Ser
            660                 665                 670

Asp Tyr Gly Asn Leu Ser Tyr His Ile Arg Asn Lys Asn Met Leu Phe
            675                 680                 685

Ile Phe Ser Thr Gly Asn Asp Ala Gln Ala Gln Pro Asn Thr Tyr Ala
    690                 695                 700

Leu Leu Pro Phe Tyr Glu Lys Asp Ala Gln Lys Gly Ile Ile Thr Val

```
            705                 710                 715                 720
Ala Gly Val Asp Arg Ser Gly Glu Lys Phe Lys Arg Glu Met Tyr Gly
                    725                 730                 735

Glu Pro Gly Thr Glu Pro Leu Glu Tyr Gly Ser Asn His Cys Gly Ile
                740                 745                 750

Thr Ala Met Trp Cys Leu Ser Ala Pro Tyr Glu Ala Ser Val Arg Phe
            755                 760                 765

Thr Arg Thr Asn Pro Ile Gln Ile Ala Gly Thr Ser Phe Ser Ala Pro
        770                 775                 780

Ile Val Thr Gly Thr Ala Ala Leu Leu Leu Gln Lys Tyr Pro Trp Met
785                 790                 795                 800

Ser Asn Asp Asn Leu Arg Thr Thr Leu Leu Thr Thr Ala Gln Asp Ile
                805                 810                 815

Gly Ala Val Gly Val Asp Ser Lys Phe Gly Trp Gly Leu Leu Asp Ala
            820                 825                 830

Gly Lys Ala Met Asn Gly Pro Ala Ser Phe Pro Phe Gly Asp Phe Thr
        835                 840                 845

Ala Asp Thr Lys Gly Thr Ser Asp Ile Ala Tyr Ser Phe Arg Asn Asp
    850                 855                 860

Ile Ser Gly Thr Gly Gly Leu Ile Lys Lys Gly Ser Gln Leu Gln
865                 870                 875                 880

Leu His Gly Asn Asn Thr Tyr Thr Gly Lys Thr Ile Ile Glu Gly Gly
                885                 890                 895

Ser Leu Val Leu Tyr Gly Asn Asn Lys Ser Asp Met Arg Val Glu Thr
            900                 905                 910

Lys Gly Ala Leu Ile Tyr Asn Gly Ala Ala Ser Gly Gly Ser Leu Asn
        915                 920                 925

Ser Asp Gly Ile Val Tyr Leu Ala Asp Thr Asp Gln Ser Gly Ala Asn
    930                 935                 940

Glu Thr Val His Ile Lys Gly Ser Leu Gln Leu Asp Gly Lys Gly Thr
945                 950                 955                 960

Leu Tyr Thr Arg Leu Gly Lys Leu Leu Lys Val Asp Gly Thr Ala Ile
                965                 970                 975

Ile Gly Gly Lys Leu Tyr Met Ser Ala Arg Gly Lys Gly Ala Gly Tyr
            980                 985                 990

Leu Asn Ser Thr Gly Arg Arg Val Pro Phe Leu Ser Ala Ala Lys Ile
        995                 1000                1005

Gly Gln Asp Tyr Ser Phe Phe Thr Asn Ile Glu Thr Asp Gly Gly Leu
    1010                1015                1020

Leu Ala Ser Leu Asp Ser Val Glu Lys Thr Ala Gly Ser Glu Gly Asp
1025                1030                1035                1040

Thr Leu Ser Tyr Tyr Val Arg Arg Gly Asn Ala Ala Arg Thr Ala Ser
                1045                1050                1055

Ala Ala Ala His Ser Ala Pro Ala Gly Leu Lys His Ala Val Glu Gln
            1060                1065                1070

Gly Gly Ser Asn Leu Glu Asn Leu Met Val Glu Leu Asp Ala Ser Glu
        1075                1080                1085

Ser Ser Ala Thr Pro Glu Thr Val Glu Thr Ala Ala Ala Asp Arg Thr
    1090                1095                1100

Asp Met Pro Gly Ile Arg Pro Tyr Gly Ala Thr Phe Arg Ala Ala Ala
1105                1110                1115                1120

Ala Val Gln His Ala Asn Ala Ala Asp Gly Val Arg Ile Phe Asn Ser
                1125                1130                1135
```

```
Leu Ala Ala Thr Val Tyr Ala Asp Ser Thr Ala Ala His Ala Asp Met
            1140                1145                1150

Gln Gly Arg Arg Leu Lys Ala Val Ser Asp Gly Leu Asp His Asn Gly
        1155                1160                1165

Thr Gly Leu Arg Val Ile Ala Gln Thr Gln Asp Gly Gly Thr Trp
    1170                1175                1180

Glu Gln Gly Gly Val Glu Gly Lys Met Arg Gly Ser Thr Gln Thr Val
1185                1190                1195                1200

Gly Ile Ala Ala Lys Thr Gly Glu Asn Thr Thr Ala Ala Thr Leu
                1205                1210                1215

Gly Met Gly Arg Ser Thr Trp Ser Glu Asn Ser Ala Asn Ala Lys Thr
        1220                1225                1230

Asp Ser Ile Ser Leu Phe Ala Gly Ile Arg His Asp Ala Gly Asp Ile
            1235                1240                1245

Gly Tyr Leu Lys Gly Leu Phe Ser Tyr Gly Arg Tyr Lys Asn Ser Ile
    1250                1255                1260

Ser Arg Ser Thr Gly Ala Asp Glu His Ala Glu Gly Ser Val Asn Gly
1265                1270                1275                1280

Thr Leu Met Gln Leu Gly Ala Leu Gly Gly Val Asn Val Pro Phe Ala
                1285                1290                1295

Ala Thr Gly Asp Leu Thr Val Glu Gly Gly Leu Arg Tyr Asp Leu Leu
        1300                1305                1310

Lys Gln Asp Ala Phe Ala Glu Lys Gly Ser Ala Leu Gly Trp Ser Gly
            1315                1320                1325

Asn Ser Leu Thr Glu Gly Thr Leu Val Gly Leu Ala Gly Leu Lys Leu
    1330                1335                1340

Ser Gln Pro Leu Ser Asp Lys Ala Val Leu Phe Ala Thr Ala Gly Val
1345                1350                1355                1360

Glu Arg Asp Leu Asn Gly Arg Asp Tyr Thr Val Thr Gly Gly Phe Thr
                1365                1370                1375

Gly Ala Thr Ala Ala Thr Gly Lys Thr Gly Ala Arg Asn Met Pro His
        1380                1385                1390

Thr Arg Leu Val Ala Gly Leu Gly Ala Asp Val Glu Phe Gly Asn Gly
            1395                1400                1405

Trp Asn Gly Leu Ala Arg Tyr Ser Tyr Ala Gly Ser Lys Gln Tyr Gly
    1410                1415                1420

Asn His Ser Gly Arg Val Gly Val Gly Tyr Arg Phe Leu Glu His His
1425                1430                1435                1440

His His His His

<210> SEQ ID NO 152
<211> LENGTH: 2256
<212> TYPE: DNA
<213> ORGANISM: Artificial Sequence
<220> FEATURE:
<223> OTHER INFORMATION: Synthetic construct

<400> SEQUENCE: 152
atggccacaa acgacgacga tgttaaaaaa gctgccactg tggccattgc tgctgcctac      60
aacaatggcc aagaaatcaa cggtttcaaa gctggagaga ccatctacga cattgatgaa     120
gacggcacaa ttaccaaaaa agacgcaact gcagccgatg ttgaagccga cgactttaaa     180
ggtctgggtc tgaaaaaagt cgtgactaac ctgaccaaaa ccgtcaatga aacaaacaa      240 aacgtcgatg ccaaagtaaa agctgcagaa tctgaaatag aaaagttaac aaccaagtta     300
gcagacactg atgccgcttt agcagatact gatgccgctc tggatgcaac caccaacgcc     360
```

```
ttgaataaat tgggagaaaa tataacgaca tttgctgaag agactaagac aaatatcgta    420
aaaattgatg aaaaattaga agccgtggct gataccgtcg acaagcatgc cgaagcattc    480
aacgatatcg ccgattcatt ggatgaaacc aacactaagg cagacgaagc cgtcaaaacc    540
gccaatgaag ccaaacagac ggccgaagaa accaaacaaa acgtcgatgc caaagtaaaa    600
gctgcagaaa ctgcagcagg caaagccgaa gctgccgctg gcacagctaa tactgcagcc    660
gacaaggccg aagctgtcgc tgcaaaagtt accgacatca aagctgatat cgctacgaac    720
aaagataata ttgctaaaaa agcaaacagt gccgacgtgt acaccagaga gagtctgac     780
agcaaatttg tcagaattga tggtctgaac gctactaccg aaaaattgga cacacgcttg    840
gcttctgctg aaaaatccat tgccgatcac gatactcgcc tgaacggttt ggataaaaca    900
gtgtcagacc tgcgcaaaga aacccgccaa ggccttgcag aacaagccgc gctctccggt    960
ctgttccaac cttacaacgt gggtggatcc ggaggaggag gatcagattt ggcaaacgat   1020
tcttttatcc ggcaggttct cgaccgtcag catttcgaac ccgacgggaa ataccaccta   1080
ttcggcagca gggggggaact tgccgagcgc agcggccata tcggattggg aaaaatacaa   1140
agccatcagt tgggcaacct gatgattcaa caggcggcca ttaaaggaaa tatcggctac   1200
attgtccgct tttccgatca cgggcacgaa gtccattccc ccttcgacaa ccatgcctca   1260
cattccgatt ctgatgaagc cggtagtccc gttgacggat ttagccttta ccgcatccat   1320
tgggacggat acgaacacca tcccgccgac ggctatgacg gccacagggc ggcggctat    1380
cccgctccca aggcgcgag ggatatatac agctacgaca taaaaggcgt tgcccaaaat    1440
atccgcctca acctgaccga caaccgcagc accggacaac ggcttgccga ccgtttccac   1500
aatgccggta gtatgctgac gcaaggagta ggcgacggat tcaaacgcgc cacccgatac   1560
agccccgagc tggacagatc gggcaatgcc gccgaagcct tcaacggcac tgcagatatc   1620
gttaaaaaca tcatcggcgc ggcaggagaa attgtcggcg caggcgatgc cgtgcagggc   1680
ataagcgaag gctcaaacat tgctgtcatg cacggcttgg gtctgctttc caccgaaaac   1740
aagatggcgc gcatcaacga tttggcagat atggcgcaac tcaaagacta tgccgcagca   1800
gccatccgcg attgggcagt ccaaaacccc aatgccgcac aaggcataga agccgtcagc   1860
aatatcttta tggcagccat ccccatcaaa gggattggag ctgttcgggg aaaatacgg    1920
ttgggcggca tcacggcaca tcctatcaag cggtcgcaga tgggcgcgat cgcattgccg   1980
aaagggaaat ccgccgtcag cgacaatttt gccgatgcgg catacgccaa atacccgtcc   2040
ccttaccatt cccgaaatat ccgttcaaac ttggagcagc gttacggcaa agaaaacatc   2100
acctcctcaa ccgtgccgcc gtcaaacggc aaaaatgtca aactggcaga ccaacgccac   2160
ccgaagacag gcgtaccgtt tgacggtaaa gggtttccga attttgagaa gcacgtgaaa   2220
tatgatacgc tcgagcacca ccaccaccac cactga                            2256
```

<210> SEQ ID NO 153
<211> LENGTH: 751
<212> TYPE: PRT
<213> ORGANISM: Artificial Sequence
<220> FEATURE:
<223> OTHER INFORMATION: Synthetic construct

<400> SEQUENCE: 153

```
Met Ala Thr Asn Asp Asp Val Lys Lys Ala Ala Thr Val Ala Ile
1               5                   10                  15

Ala Ala Ala Tyr Asn Asn Gly Gln Glu Ile Asn Gly Phe Lys Ala Gly
                20                  25                  30
```

```
Glu Thr Ile Tyr Asp Ile Asp Glu Asp Gly Thr Ile Thr Lys Lys Asp
            35                  40                  45

Ala Thr Ala Ala Asp Val Glu Ala Asp Asp Phe Lys Gly Leu Gly Leu
 50                  55                  60

Lys Lys Val Val Thr Asn Leu Thr Lys Thr Val Asn Glu Asn Lys Gln
 65                  70                  75                  80

Asn Val Asp Ala Lys Val Lys Ala Ala Glu Ser Glu Ile Glu Lys Leu
                 85                  90                  95

Thr Thr Lys Leu Ala Asp Thr Asp Ala Ala Leu Ala Asp Thr Asp Ala
            100                 105                 110

Ala Leu Asp Ala Thr Thr Asn Ala Leu Asn Lys Leu Gly Glu Asn Ile
        115                 120                 125

Thr Thr Phe Ala Glu Glu Thr Lys Thr Asn Ile Val Lys Ile Asp Glu
        130                 135                 140

Lys Leu Glu Ala Val Ala Asp Thr Val Asp Lys His Ala Glu Ala Phe
145                 150                 155                 160

Asn Asp Ile Ala Asp Ser Leu Asp Glu Thr Asn Thr Lys Ala Asp Glu
                165                 170                 175

Ala Val Lys Thr Ala Asn Glu Ala Lys Gln Thr Ala Glu Glu Thr Lys
            180                 185                 190

Gln Asn Val Asp Ala Lys Val Lys Ala Ala Glu Thr Ala Ala Gly Lys
        195                 200                 205

Ala Glu Ala Ala Ala Gly Thr Ala Asn Thr Ala Ala Asp Lys Ala Glu
        210                 215                 220

Ala Val Ala Ala Lys Val Thr Asp Ile Lys Ala Asp Ile Ala Thr Asn
225                 230                 235                 240

Lys Asp Asn Ile Ala Lys Lys Ala Asn Ser Ala Asp Val Tyr Thr Arg
                245                 250                 255

Glu Glu Ser Asp Ser Lys Phe Val Arg Ile Asp Gly Leu Asn Ala Thr
            260                 265                 270

Thr Glu Lys Leu Asp Thr Arg Leu Ala Ser Ala Glu Lys Ser Ile Ala
        275                 280                 285

Asp His Asp Thr Arg Leu Asn Gly Leu Asp Lys Thr Val Ser Asp Leu
        290                 295                 300

Arg Lys Glu Thr Arg Gln Gly Leu Ala Glu Gln Ala Ala Leu Ser Gly
305                 310                 315                 320

Leu Phe Gln Pro Tyr Asn Val Gly Gly Ser Gly Gly Gly Ser Asp
                325                 330                 335

Leu Ala Asn Asp Ser Phe Ile Arg Gln Val Leu Asp Arg Gln His Phe
            340                 345                 350

Glu Pro Asp Gly Lys Tyr His Leu Phe Gly Ser Arg Gly Glu Leu Ala
        355                 360                 365

Glu Arg Ser Gly His Ile Gly Leu Gly Lys Ile Gln Ser His Gln Leu
        370                 375                 380

Gly Asn Leu Met Ile Gln Gln Ala Ala Ile Lys Gly Asn Ile Gly Tyr
385                 390                 395                 400

Ile Val Arg Phe Ser Asp His Gly His Glu Val His Ser Pro Phe Asp
                405                 410                 415

Asn His Ala Ser His Ser Asp Ser Asp Glu Ala Gly Ser Pro Val Asp
            420                 425                 430

Gly Phe Ser Leu Tyr Arg Ile His Trp Asp Gly Tyr Glu His His Pro
        435                 440                 445

Ala Asp Gly Tyr Asp Gly Pro Gln Gly Gly Gly Tyr Pro Ala Pro Lys
```

| | | | | | | | | | | | |
|---|---|---|---|---|---|---|---|---|---|---|---|
| | | 450 | | | 455 | | | 460 | | | |
| Gly | Ala | Arg | Asp | Ile | Tyr | Ser | Tyr | Asp | Ile | Lys | Gly | Val | Ala | Gln | Asn |
| 465 | | | | 470 | | | | 475 | | | | 480 | | | |

Gly Ala Arg Asp Ile Tyr Ser Tyr Asp Ile Lys Gly Val Ala Gln Asn
465                 470                 475                 480

Ile Arg Leu Asn Leu Thr Asp Asn Arg Ser Thr Gly Gln Arg Leu Ala
            485                 490                 495

Asp Arg Phe His Asn Ala Gly Ser Met Leu Thr Gln Gly Val Gly Asp
        500                 505                 510

Gly Phe Lys Arg Ala Thr Arg Tyr Ser Pro Glu Leu Asp Arg Ser Gly
        515                 520                 525

Asn Ala Ala Glu Ala Phe Asn Gly Thr Ala Asp Ile Val Lys Asn Ile
        530                 535                 540

Ile Gly Ala Ala Gly Glu Ile Val Gly Ala Gly Asp Ala Val Gln Gly
545                 550                 555                 560

Ile Ser Glu Gly Ser Asn Ile Ala Val Met His Gly Leu Gly Leu Leu
            565                 570                 575

Ser Thr Glu Asn Lys Met Ala Arg Ile Asn Asp Leu Ala Asp Met Ala
        580                 585                 590

Gln Leu Lys Asp Tyr Ala Ala Ala Ile Arg Asp Trp Ala Val Gln
        595                 600                 605

Asn Pro Asn Ala Ala Gln Gly Ile Glu Ala Val Ser Asn Ile Phe Met
610                 615                 620

Ala Ala Ile Pro Ile Lys Gly Ile Gly Ala Val Arg Gly Lys Tyr Gly
625                 630                 635                 640

Leu Gly Gly Ile Thr Ala His Pro Ile Lys Arg Ser Gln Met Gly Ala
            645                 650                 655

Ile Ala Leu Pro Lys Gly Lys Ser Ala Val Ser Asp Asn Phe Ala Asp
        660                 665                 670

Ala Ala Tyr Ala Lys Tyr Pro Ser Pro Tyr His Ser Arg Asn Ile Arg
        675                 680                 685

Ser Asn Leu Glu Gln Arg Tyr Gly Lys Glu Asn Ile Thr Ser Ser Thr
        690                 695                 700

Val Pro Pro Ser Asn Gly Lys Asn Val Lys Leu Ala Asp Gln Arg His
705                 710                 715                 720

Pro Lys Thr Gly Val Pro Phe Asp Gly Lys Gly Phe Pro Asn Phe Glu
            725                 730                 735

Lys His Val Lys Tyr Asp Thr Leu Glu His His His His His His
        740                 745                 750

<210> SEQ ID NO 154
<211> LENGTH: 1773
<212> TYPE: DNA
<213> ORGANISM: Artificial Sequence
<220> FEATURE:
<223> OTHER INFORMATION: Synthetic construct

<400> SEQUENCE: 154

```
atggccacaa acgacgacga tgttaaaaaa gctgccactg tggccattgc tgctgcctac      60
aacaatggcc aagaaatcaa cggtttcaaa gctggagaga ccatctcacga cattgatgaa    120 gacggcacaa ttaccaaaaa agacgcaact gcagccgatg ttgaagccga cgactttaaa    180
ggtctgggtc tgaaaaaagt cgtgactaac ctgaccaaaa ccgtcaatga aacaaacaa     240 aacgtcgatg ccaaagtaaa agctgcagaa tctgaaatag aaagttaac aaccaagtta    300 gcagacactg atgccgcttt agcagatact gatgccgctc tggatgcaac caccaacgcc    360
ttgaataaat tgggagaaaa atataacgaca tttgctgaag agactaagac aaatatcgta    420
```

```
aaaattgatg aaaaattaga agccgtggct gataccgtcg acaagcatgc cgaagcattc    480
aacgatatcg ccgattcatt ggatgaaacc aacactaagg cagacgaagc cgtcaaaacc    540
gccaatgaag ccaaacagac ggccgaagaa accaaacaaa acgtcgatgc caaagtaaaa    600
gctgcagaaa ctgcagcagg caaagccgaa gctgccgctg cacagctaa tactgcagcc     660 gacaaggccg aagctgtcgc tgcaaaagtt accgacatca agctgatat cgctacgaac     720 aaagataata ttgctaaaaa agcaaacagt gccgacgtgt acaccagaga gagtctgac    780 agcaaatttg tcagaattga tggtctgaac gctactaccg aaaaattgga cacacgcttg    840
gcttctgctg aaaaatccat tgccgatcac gatactcgcc tgaacggttt ggataaaaca    900
gtgtcagacc tgcgcaaaga aacccgccaa ggccttgcag aacaagccgc gctctccggt    960
ctgttccaac cttacaacgt gggtggatcc ggaggggtg tgtcgccgc cgacatcggt     1020 gcggggcttg ccgatgcact aaccgcaccg ctcgaccata agacaaagg tttgcagtct    1080 ttgacgctgg atcagtccgt caggaaaaac gagaaactga agctggcggc acaaggtgcg   1140
gaaaaaactt atggaaacgg tgacagcctc aatacgggca aattgaagaa cgacaaggtc    1200
agccgtttcg actttatccg ccaaatcgaa gtggacgggc agctcattac cttggagagt    1260
ggagagttcc aagtatacaa acaaagccat tccgccttaa ccgcctttca gaccgagcaa    1320
atacaagatt cggagcattc cgggaagatg gttgcgaaac gccagttcag aatcggcgac    1380
atagcgggcg aacatacatc ttttgacaag cttcccgaag gcggcagggc gacatatcgc    1440
gggacggcgt tcggttcaga cgatgccggc ggaaaactga cctacaccat agatttcgcc    1500
gccaagcagg gaaacggcaa aatcgaacat ttgaaatcgc cagaactcaa tgtcgacctg    1560
gccgccgccg atatcaagcc ggatggaaaa cgccatgccg tcatcagcgg ttccgtcctt    1620
tacaaccaag ccgagaaagg cagttactcc ctcggtatct ttggcggaaa agcccaggaa    1680
gttgccggca gcgcggaagt gaaaaccgta acggcatac gccatatcgg ccttgccgcc     1740
aagcaactcg agcaccacca ccaccaccac tga                                  1773
```

<210> SEQ ID NO 155
<211> LENGTH: 590
<212> TYPE: PRT
<213> ORGANISM: Artificial Sequence
<220> FEATURE:
<223> OTHER INFORMATION: Synthetic construct

<400> SEQUENCE: 155

```
Met Ala Thr Asn Asp Asp Val Lys Lys Ala Ala Thr Val Ala Ile
 1               5                  10                  15

Ala Ala Ala Tyr Asn Asn Gly Gln Glu Ile Asn Gly Phe Lys Ala Gly
                20                  25                  30

Glu Thr Ile Tyr Asp Ile Asp Glu Asp Gly Thr Ile Thr Lys Lys Asp
            35                  40                  45

Ala Thr Ala Ala Asp Val Glu Ala Asp Asp Phe Lys Gly Leu Gly Leu
        50                  55                  60

Lys Lys Val Val Thr Asn Leu Thr Lys Thr Val Asn Glu Asn Lys Gln
65                  70                  75                  80

Asn Val Asp Ala Lys Val Lys Ala Ala Glu Ser Glu Ile Glu Lys Leu
                85                  90                  95

Thr Thr Lys Leu Ala Asp Thr Asp Ala Ala Leu Ala Asp Thr Asp Ala
            100                 105                 110

Ala Leu Asp Ala Thr Thr Asn Ala Leu Asn Lys Leu Gly Glu Asn Ile
        115                 120                 125
```

```
Thr Thr Phe Ala Glu Glu Thr Lys Thr Asn Ile Val Lys Ile Asp Glu
    130                 135                 140

Lys Leu Glu Ala Val Ala Asp Thr Val Asp Lys His Ala Glu Ala Phe
145                 150                 155                 160

Asn Asp Ile Ala Asp Ser Leu Asp Glu Thr Asn Thr Lys Ala Asp Glu
                165                 170                 175

Ala Val Lys Thr Ala Asn Glu Ala Lys Gln Thr Ala Glu Glu Thr Lys
                180                 185                 190

Gln Asn Val Asp Ala Lys Val Lys Ala Ala Glu Thr Ala Ala Gly Lys
                195                 200                 205

Ala Glu Ala Ala Ala Gly Thr Ala Asn Thr Ala Ala Asp Lys Ala Glu
    210                 215                 220

Ala Val Ala Ala Lys Val Thr Asp Ile Lys Ala Asp Ile Ala Thr Asn
225                 230                 235                 240

Lys Asp Asn Ile Ala Lys Lys Ala Asn Ser Ala Asp Val Tyr Thr Arg
                245                 250                 255

Glu Glu Ser Asp Ser Lys Phe Val Arg Ile Asp Gly Leu Asn Ala Thr
                260                 265                 270

Thr Glu Lys Leu Asp Thr Arg Leu Ala Ser Ala Glu Lys Ser Ile Ala
    275                 280                 285

Asp His Asp Thr Arg Leu Asn Gly Leu Asp Lys Thr Val Ser Asp Leu
    290                 295                 300

Arg Lys Glu Thr Arg Gln Gly Leu Ala Glu Gln Ala Ala Leu Ser Gly
305                 310                 315                 320

Leu Phe Gln Pro Tyr Asn Val Gly Gly Ser Gly Gly Gly Gly Val Ala
                325                 330                 335

Ala Asp Ile Gly Ala Gly Leu Ala Asp Ala Leu Thr Ala Pro Leu Asp
                340                 345                 350

His Lys Asp Lys Gly Leu Gln Ser Leu Thr Leu Asp Gln Ser Val Arg
                355                 360                 365

Lys Asn Glu Lys Leu Lys Leu Ala Ala Gln Gly Ala Glu Lys Thr Tyr
                370                 375                 380

Gly Asn Gly Asp Ser Leu Asn Thr Gly Lys Leu Lys Asn Asp Lys Val
385                 390                 395                 400

Ser Arg Phe Asp Phe Ile Arg Gln Ile Glu Val Asp Gly Gln Leu Ile
                405                 410                 415

Thr Leu Glu Ser Gly Glu Phe Gln Val Tyr Lys Gln Ser His Ser Ala
                420                 425                 430

Leu Thr Ala Phe Gln Thr Glu Gln Ile Gln Asp Ser Glu His Ser Gly
                435                 440                 445

Lys Met Val Ala Lys Arg Gln Phe Arg Ile Gly Asp Ile Ala Gly Glu
    450                 455                 460

His Thr Ser Phe Asp Lys Leu Pro Glu Gly Gly Arg Ala Thr Tyr Arg
465                 470                 475                 480

Gly Thr Ala Phe Gly Ser Asp Asp Ala Gly Gly Lys Leu Thr Tyr Thr
                485                 490                 495

Ile Asp Phe Ala Ala Lys Gln Gly Asn Gly Lys Ile Glu His Leu Lys
                500                 505                 510

Ser Pro Glu Leu Asn Val Asp Leu Ala Ala Ala Asp Ile Lys Pro Asp
                515                 520                 525

Gly Lys Arg His Ala Val Ile Ser Gly Ser Val Leu Tyr Asn Gln Ala
    530                 535                 540

Glu Lys Gly Ser Tyr Ser Leu Gly Ile Phe Gly Gly Lys Ala Gln Glu
545                 550                 555                 560
```

Val Ala Gly Ser Ala Glu Val Lys Thr Val Asn Gly Ile Arg His Ile
                565                 570                 575

Gly Leu Ala Ala Lys Gln Leu Glu His His His His His His
            580                 585                 590

<210> SEQ ID NO 156
<211> LENGTH: 4170
<212> TYPE: DNA
<213> ORGANISM: Artificial Sequence
<220> FEATURE:
<223> OTHER INFORMATION: Synthetic construct

<400> SEQUENCE: 156

| | | |
|---|---|---|
| atggccacaa acgacgacga tgttaaaaaa gctgccactg tggccattgc tgctgcctac | 60 |
| aacaatggcc aagaaatcaa cggtttcaaa gctggagaga ccatctacga cattgatgaa | 120 |
| gacggcacaa ttaccaaaaa agacgcaact gcagccgatg ttgaagccga cgactttaaa | 180 |
| ggtctgggtc tgaaaaaagt cgtgactaac ctgaccaaaa ccgtcaatga aaacaaacaa | 240 |
| aacgtcgatg ccaaagtaaa agctgcagaa tctgaaatag aaaagttaac aaccaagtta | 300 |
| gcagacactg atgccgcttt agcagatact gatgccgctc tggatgcaac caccaacgcc | 360 |
| ttgaataaat gggagaaaaa tataacgaca tttgctgaag agactaagac aaatatcgta | 420 |
| aaaattgatg aaaaattaga agccgtggct gataccgtcg acaagcatgc cgaagcattc | 480 |
| aacgatatcg ccgattcatt ggatgaaacc aacactaagg cagacgaagc cgtcaaaacc | 540 |
| gccaatgaag ccaaacagac ggccgaagaa accaaacaaa acgtcgatgc caaagtaaaa | 600 |
| gctgcagaaa ctgcagcagg caaagccgaa gctgccgctg cacagctaa tactgcagcc | 660 |
| gacaaggccg aagctgtcgc tgcaaaagtt accgacatca aagctgatat cgctacgaac | 720 |
| aaagataata ttgctaaaaa agcaaacagt gccgacgtgt acaccagaga gagtctgac | 780 |
| agcaaatttg tcagaattga tggtctgaac gctactaccg aaaaattgga cacacgcttg | 840 |
| gcttctgctg aaaaaatccat tgccgatcac gatactcgcc tgaacggttt ggataaaaca | 900 |
| gtgtcagacc tgcgcaaaga aacccgccaa ggccttgcag acaagccgc gctctccggt | 960 |
| ctgttccaac cttacaacgt gggtggatcc ggcggaggcg gcacttctgc gcccgacttc | 1020 |
| aatgcaggcg gtaccggtat cggcagcaac agcagagcaa caacagcgaa atcagcagca | 1080 |
| gtatcttacg ccggtatcaa gaacgaaatg tgcaaagaca gaagcatgct ctgtgccggt | 1140 |
| cgggatgacg ttgcggttac agacagggat gccaaaatca atgcccccc cccgaatctg | 1200 |
| cataccggag actttccaaa cccaaatgac gcatacaaga atttgatcaa cctcaaacct | 1260 |
| gcaattgaag caggctatac aggacgcggg gtagaggtag gtatcgtcga cacaggcgaa | 1320 |
| tccgtcggca gcatatcctt tcccgaactg tatggcagaa aagaacacgg ctataacgaa | 1380 |
| aattacaaaa actatacggc gtatatgcgg aaggaagcgc tgaagacgg aggcggtaaa | 1440 |
| gacattgaag cttctttcga cgatgaggcc gttatagaga ctgaagcaaa gccgacggat | 1500 |
| atccgccacg taaagaaat cggacacatc gatttggtct cccatattat tggcgggcgt | 1560 |
| tccgtggacg gcagacctgc aggcggtatt gcgcccgatg cgacgctaca cataatgaat | 1620 |
| acgaatgatg aaaccaagaa cgaaatgatg gttgcagcca tccgcaatgc atgggtcaag | 1680 |
| ctgggcgaac gtggcgtgcg catcgtcaat aacagttttg aacaacatc gagggcaggc | 1740 |
| actgccgacc ttttccaaat agccaattcg gaggagcagt accgccaagc gttgctcgac | 1800 |
| tattccggcg gtgataaaac agacgagggt atccgcctga tgcaacagag cgattacggc | 1860 |
| aacctgtcct accacatccg taataaaaac atgcttttca tcttttcgac aggcaatgac | 1920 |

```
gcacaagctc agcccaacac atatgcccta ttgccatttt atgaaaaaga cgctcaaaaa    1980
ggcattatca cagtcgcagg cgtagaccgc agtggagaaa agttcaaacg ggaaatgtat    2040
ggagaaccgg gtacagaacc gcttgagtat ggctccaacc attgcggaat tactgccatg    2100
tggtgcctgt cggcacccta tgaagcaagc gtccgtttca cccgtacaaa cccgattcaa    2160
attgccggaa catccttttc cgcacccatc gtaaccggca cggcggctct gctgctgcag    2220
aaatacccgt ggatgagcaa cgacaacctg cgtaccacgt tgctgacgac ggctcaggac    2280
atcggtgcag tcggcgtgga cagcaagttc ggctggggac tgctggatgc gggtaaggcc    2340
atgaacggac ccgcgtcctt tccgttcggc gactttaccg ccgatacgaa aggtacatcc    2400
gatattgcct actccttccg taacgacatt tcaggcacgg gcggcctgat caaaaaaggc    2460
ggcagccaac tgcaactgca cggcaacaac acctatacgg caaaaccat tatcgaaggc     2520 ggttcgctgg tgttgtacgg caacaacaaa tcggatatgc cgtcgaaac caaaggtgcg     2580 ctgatttata cgggcggc atccggcggc agcctgaaca cgacggcat tgtctatctg       2640 gcagataccg accaatccgg cgcaaacgaa accgtacaca tcaaaggcag tctgcagctg    2700
gacggcaaag gtacgctgta cacacgtttg ggcaaactgc tgaaagtgga cggtacggcg    2760
attatcggcg gcaagctgta catgtcggca cgcggcaagg gggcaggcta tctcaacagt    2820 accgacgac gtgttcccct cctgagtgcc gccaaaatcg gcaggatta ttctttcttc      2880 acaaacatcg aaaccgacgg cggcctgctg gcttccctcg acagcgtcga aaaaacagcg    2940
ggcagtgaag gcgacacgct gtcctattat gtccgtcgcg gcaatgcggc acggactgct    3000
tcggcagcgg cacattccgc gcccgccggt ctgaaacacg ccgtagaaca gggcggcagc    3060
aatctggaaa acctgatggt cgaactggat gcctccgaat catccgcaac acccgagacg    3120
gttgaaactg cggcagccga ccgcacagat atgccgggca tccgccccta cggcgcaact    3180
ttccgcgcag cggcagccgt acagcatgcg aatgccgccg acggtgtacg catcttcaac    3240
agtctcgccg ctaccgtcta tgccgacagt accgccgccc atgccgatat gcagggacgc    3300
cgcctgaaag ccgtatcgga cgggttggac cacaacggca cgggtctgcg cgtcatcgcg    3360
caaacccaac aggacggtgg aacgtgggaa cagggcggtg ttgaaggcaa aatgcgcggc    3420
agtacccaaa ccgtcggcat tgccgcgaaa accggcgaaa atacgacagc agccgccaca    3480
ctgggcatgg gacgcagcac atggagcgaa aacagtgcaa atgcaaaaac cgacagcatt    3540
agtctgtttg caggcatacg gcacgatgcg ggcgatatcg gctatctcaa aggcctgttc    3600
tcctacggac gctacaaaaa cagcatcagc cgcagcaccg gtgcggacga acatgcggaa    3660
ggcagcgtca acggcacgct gatgcagctg ggcgcactgg gcggtgtcaa cgttccgttt    3720
gccgcaacgg gagatttgac ggtcgaaggc ggtctgcgct acgacctgct caaacaggat    3780
gcattcgccg aaaaaggcag tgctttgggc tggagcggca acagcctcac tgaaggcacg    3840
ctggtcggac tcgcgggtct gaagctgtcg caacccttga gcgataaagc cgtcctgttt    3900
gcaacggcgg gcgtggaacg cgacctgaac ggacgcgact acacggtaac gggcggcttt    3960
accggcgcga ctgcagcaac cggcaagacg ggggcacgca atatgccgca cacccgtctg    4020
gttgccggcc tgggcgcgga tgtcgaattc ggcaacggct ggaacggctt ggcacgttac    4080
agctacgccg gttccaaaca gtacggcaac cacagcggac gagtcggcgt aggctaccgg    4140
ttcctcgagc accaccacca ccaccactga                                     4170

<210> SEQ ID NO 157
<211> LENGTH: 1389
```

```
<212> TYPE: PRT
<213> ORGANISM: Artificial Sequence
<220> FEATURE:
<223> OTHER INFORMATION: Synthetic construct

<400> SEQUENCE: 157

Met Ala Thr Asn Asp Asp Val Lys Lys Ala Thr Val Ala Ile
1               5                   10                  15

Ala Ala Ala Tyr Asn Asn Gly Gln Glu Ile Asn Gly Phe Lys Ala Gly
            20                  25                  30

Glu Thr Ile Tyr Asp Ile Asp Glu Asp Gly Thr Ile Thr Lys Lys Asp
        35                  40                  45

Ala Thr Ala Ala Asp Val Glu Ala Asp Phe Lys Gly Leu Gly Leu
    50                  55                  60

Lys Lys Val Val Thr Asn Leu Thr Lys Thr Val Asn Glu Asn Lys Gln
65                  70                  75                  80

Asn Val Asp Ala Lys Val Lys Ala Ala Glu Ser Glu Ile Glu Lys Leu
                85                  90                  95

Thr Thr Lys Leu Ala Asp Thr Asp Ala Ala Leu Ala Asp Thr Asp Ala
            100                 105                 110

Ala Leu Asp Ala Thr Thr Asn Ala Leu Asn Lys Leu Gly Glu Asn Ile
            115                 120                 125

Thr Thr Phe Ala Glu Gly Thr Lys Thr Asn Ile Val Lys Ile Asp Glu
    130                 135                 140

Lys Leu Glu Ala Val Ala Asp Thr Val Asp Lys His Ala Glu Ala Phe
145                 150                 155                 160

Asn Asp Ile Ala Asp Ser Leu Asp Glu Thr Asn Thr Lys Ala Asp Glu
                165                 170                 175

Ala Val Lys Thr Ala Asn Glu Ala Lys Gln Thr Ala Glu Glu Thr Lys
            180                 185                 190

Gln Asn Val Asp Ala Lys Val Lys Ala Ala Glu Thr Ala Ala Gly Lys
            195                 200                 205

Ala Glu Ala Ala Ala Gly Thr Ala Asn Thr Ala Ala Asp Lys Ala Glu
    210                 215                 220

Ala Val Ala Ala Lys Val Thr Asp Ile Lys Ala Asp Ile Ala Thr Asn
225                 230                 235                 240

Lys Asp Asn Ile Ala Lys Lys Ala Asn Ser Ala Asp Val Tyr Thr Arg
                245                 250                 255

Glu Glu Ser Asp Ser Lys Phe Val Arg Ile Asp Gly Leu Asn Ala Thr
            260                 265                 270

Thr Glu Lys Leu Asp Thr Arg Leu Ala Ser Ala Glu Lys Ser Ile Ala
    275                 280                 285

Asp His Asp Thr Arg Leu Asn Gly Leu Asp Lys Thr Val Ser Asp Leu
    290                 295                 300

Arg Lys Glu Thr Arg Gln Gly Leu Ala Glu Gln Ala Ala Leu Ser Gly
305                 310                 315                 320

Leu Phe Gln Pro Tyr Asn Val Gly Gly Ser Gly Gly Gly Thr Ser
                325                 330                 335

Ala Pro Asp Phe Asn Ala Gly Gly Thr Gly Ile Gly Ser Asn Ser Arg
            340                 345                 350

Ala Thr Thr Ala Lys Ser Ala Ala Val Ser Tyr Ala Gly Ile Lys Asn
            355                 360                 365

Glu Met Cys Lys Asp Arg Ser Met Leu Cys Ala Gly Arg Asp Asp Val
    370                 375                 380

Ala Val Thr Asp Arg Asp Ala Lys Ile Asn Ala Pro Pro Pro Asn Leu
```

```
385                 390                 395                 400
His Thr Gly Asp Phe Pro Asn Pro Asn Asp Ala Tyr Lys Asn Leu Ile
                    405                 410                 415
Asn Leu Lys Pro Ala Ile Glu Ala Gly Tyr Thr Gly Arg Gly Val Glu
                    420                 425                 430
Val Gly Ile Val Asp Thr Gly Glu Ser Val Gly Ser Ile Ser Phe Pro
                    435                 440                 445
Glu Leu Tyr Gly Arg Lys Glu His Gly Tyr Asn Glu Asn Tyr Lys Asn
                    450                 455                 460
Tyr Thr Ala Tyr Met Arg Lys Glu Ala Pro Glu Asp Gly Gly Lys
465                 470                 475                 480
Asp Ile Glu Ala Ser Phe Asp Asp Glu Ala Val Ile Glu Thr Glu Ala
                    485                 490                 495
Lys Pro Thr Asp Ile Arg His Val Lys Glu Ile Gly His Ile Asp Leu
                    500                 505                 510
Val Ser His Ile Ile Gly Gly Arg Ser Val Asp Gly Arg Pro Ala Gly
                    515                 520                 525
Gly Ile Ala Pro Asp Ala Thr Leu His Ile Met Asn Thr Asn Asp Glu
                    530                 535                 540
Thr Lys Asn Glu Met Met Val Ala Ala Ile Arg Asn Ala Trp Val Lys
545                 550                 555                 560
Leu Gly Glu Arg Gly Val Arg Ile Val Asn Asn Ser Phe Gly Thr Thr
                    565                 570                 575
Ser Arg Ala Gly Thr Ala Asp Leu Phe Gln Ile Ala Asn Ser Glu Glu
                    580                 585                 590
Gln Tyr Arg Gln Ala Leu Leu Asp Tyr Ser Gly Gly Asp Lys Thr Asp
                    595                 600                 605
Glu Gly Ile Arg Leu Met Gln Gln Ser Asp Tyr Gly Asn Leu Ser Tyr
                    610                 615                 620
His Ile Arg Asn Lys Asn Met Leu Phe Ile Phe Ser Thr Gly Asn Asp
625                 630                 635                 640
Ala Gln Ala Gln Pro Asn Thr Tyr Ala Leu Leu Pro Phe Tyr Glu Lys
                    645                 650                 655
Asp Ala Gln Lys Gly Ile Ile Thr Val Ala Gly Val Asp Arg Ser Gly
                    660                 665                 670
Glu Lys Phe Lys Arg Glu Met Tyr Gly Glu Pro Gly Thr Glu Pro Leu
                    675                 680                 685
Glu Tyr Gly Ser Asn His Cys Gly Ile Thr Ala Met Trp Cys Leu Ser
                    690                 695                 700
Ala Pro Tyr Glu Ala Ser Val Arg Phe Thr Arg Thr Asn Pro Ile Gln
705                 710                 715                 720
Ile Ala Gly Thr Ser Phe Ser Ala Pro Ile Val Thr Gly Thr Ala Ala
                    725                 730                 735
Leu Leu Leu Gln Lys Tyr Pro Trp Met Ser Asn Asp Asn Leu Arg Thr
                    740                 745                 750
Thr Leu Leu Thr Thr Ala Gln Asp Ile Gly Ala Val Gly Val Asp Ser
                    755                 760                 765
Lys Phe Gly Trp Gly Leu Leu Asp Ala Gly Lys Ala Met Asn Gly Pro
                    770                 775                 780
Ala Ser Phe Pro Phe Gly Asp Phe Thr Ala Asp Thr Lys Gly Thr Ser
785                 790                 795                 800
Asp Ile Ala Tyr Ser Phe Arg Asn Asp Ile Ser Gly Thr Gly Gly Leu
                    805                 810                 815
```

```
Ile Lys Lys Gly Gly Ser Gln Leu Gln Leu His Gly Asn Asn Thr Tyr
            820                 825                 830

Thr Gly Lys Thr Ile Ile Glu Gly Ser Leu Val Leu Tyr Gly Asn
        835                 840                 845

Asn Lys Ser Asp Met Arg Val Glu Thr Lys Gly Ala Leu Ile Tyr Asn
    850                 855                 860

Gly Ala Ala Ser Gly Gly Ser Leu Asn Ser Asp Gly Ile Val Tyr Leu
865                 870                 875                 880

Ala Asp Thr Asp Gln Ser Gly Ala Asn Glu Thr Val His Ile Lys Gly
                885                 890                 895

Ser Leu Gln Leu Asp Gly Lys Gly Thr Leu Tyr Thr Arg Leu Gly Lys
            900                 905                 910

Leu Leu Lys Val Asp Gly Thr Ala Ile Ile Gly Gly Lys Leu Tyr Met
            915                 920                 925

Ser Ala Arg Gly Lys Gly Ala Gly Tyr Leu Asn Ser Thr Gly Arg Arg
    930                 935                 940

Val Pro Phe Leu Ser Ala Ala Lys Ile Gly Gln Asp Tyr Ser Phe Phe
945                 950                 955                 960

Thr Asn Ile Glu Thr Asp Gly Gly Leu Leu Ala Ser Leu Asp Ser Val
                965                 970                 975

Glu Lys Thr Ala Gly Ser Glu Gly Asp Thr Leu Ser Tyr Tyr Val Arg
            980                 985                 990

Arg Gly Asn Ala Ala Arg Thr Ala Ser Ala Ala Ala His Ser Ala Pro
    995                 1000                1005

Ala Gly Leu Lys His Ala Val Glu Gln Gly Gly Ser Asn Leu Glu Asn
    1010                1015                1020

Leu Met Val Glu Leu Asp Ala Ser Glu Ser Ser Ala Thr Pro Glu Thr
1025                1030                1035                1040

Val Glu Thr Ala Ala Ala Asp Arg Thr Asp Met Pro Gly Ile Arg Pro
                1045                1050                1055

Tyr Gly Ala Thr Phe Arg Ala Ala Ala Val Gln His Ala Asn Ala
                1060                1065                1070

Ala Asp Gly Val Arg Ile Phe Asn Ser Leu Ala Ala Thr Val Tyr Ala
    1075                1080                1085

Asp Ser Thr Ala Ala His Ala Asp Met Gln Gly Arg Arg Leu Lys Ala
    1090                1095                1100

Val Ser Asp Gly Leu Asp His Asn Gly Thr Gly Leu Arg Val Ile Ala
1105                1110                1115                1120

Gln Thr Gln Gln Asp Gly Gly Thr Trp Glu Gln Gly Val Glu Gly
                1125                1130                1135

Lys Met Arg Gly Ser Thr Gln Thr Val Gly Ile Ala Ala Lys Thr Gly
                1140                1145                1150

Glu Asn Thr Thr Ala Ala Ala Thr Leu Gly Met Gly Arg Ser Thr Trp
                1155                1160                1165

Ser Glu Asn Ser Ala Asn Ala Lys Thr Asp Ser Ile Ser Leu Phe Ala
    1170                1175                1180

Gly Ile Arg His Asp Ala Gly Asp Ile Gly Tyr Leu Lys Gly Leu Phe
1185                1190                1195                1200

Ser Tyr Gly Arg Tyr Lys Asn Ser Ile Ser Arg Ser Thr Gly Ala Asp
                1205                1210                1215

Glu His Ala Glu Gly Ser Val Asn Gly Thr Leu Met Gln Leu Gly Ala
            1220                1225                1230

Leu Gly Gly Val Asn Val Pro Phe Ala Ala Thr Gly Asp Leu Thr Val
            1235                1240                1245
```

Glu Gly Gly Leu Arg Tyr Asp Leu Leu Lys Gln Asp Ala Phe Ala Glu
            1250                1255                1260

Lys Gly Ser Ala Leu Gly Trp Ser Gly Asn Ser Leu Thr Glu Gly Thr
1265                1270                1275                1280

Leu Val Gly Leu Ala Gly Leu Lys Leu Ser Gln Pro Leu Ser Asp Lys
                1285                1290                1295

Ala Val Leu Phe Ala Thr Ala Gly Val Glu Arg Asp Leu Asn Gly Arg
            1300                1305                1310

Asp Tyr Thr Val Thr Gly Gly Phe Thr Gly Ala Thr Ala Thr Gly
        1315                1320                1325

Lys Thr Gly Ala Arg Asn Met Pro His Thr Arg Leu Val Ala Gly Leu
            1330                1335                1340

Gly Ala Asp Val Glu Phe Gly Asn Gly Trp Asn Gly Leu Ala Arg Tyr
1345                1350                1355                1360

Ser Tyr Ala Gly Ser Lys Gln Tyr Gly Asn His Ser Gly Arg Val Gly
                1365                1370                1375

Val Gly Tyr Arg Phe Leu Glu His His His His His
            1380                1385

<210> SEQ ID NO 158
<211> LENGTH: 2304
<212> TYPE: DNA
<213> ORGANISM: Artificial Sequence
<220> FEATURE:
<223> OTHER INFORMATION: Synthetic construct

<400> SEQUENCE: 158
atgaaacact tccatccaa gtactgacc acagccatcc ttgccacttt ctgtagcggc      60
gcactggcag ccacaaacga cgacgatgtt aaaaaagctg ccactgtggc cattgctgct    120
gcctacaaca atggccaaga atcaacggt tcaaagctg agagaccat ctacgacatt      180 gatgaagacg gcacaattac caaaaaagac gcaactgcag ccgatgttga agccgacgac    240
tttaaaggtc tgggtctgaa aaagtcgtg actaacctga ccaaaaccgt caatgaaaac    300
aaacaaaacg tcgatgccaa agtaaaagct gcagaatctg aaatagaaaa gttaacaacc    360
aagttagcag acactgatgc cgctttagca gatactgatg ccgctctgga tgcaaccacc    420
aacgccttga ataaattggg agaaaatata acgacatttg ctgaagagac taagacaaat    480
atcgtaaaaa ttgatgaaaa attagaagcc gtggctgata ccgtcgacaa gcatgccgaa    540
gcattcaacg atatcgccga ttcattggat gaaaccaaca ctaaggcaga cgaagccgtc    600
aaaaccgcca atgaagccaa acagacggcc gaagaaacca acaaaacgt cgatgccaaa    660 gtaaaagctg cagaaactgc agcaggcaaa gccgaagctg ccgctggcac agctaatact    720
gcagccgaca aggccgaagc tgtcgctgca aaagttaccg acatcaaagc tgatatcgct    780
acgaacaaag ataatattgc taaaaaagca acagtgccg acgtgtacac cagagaagag    840
tctgacagca aatttgtcag aattgatggt ctgaacgcta ctaccgaaaa attggacaca    900
cgcttggctt ctgctgaaaa atccattgcc gatcacgata ctcgcctgaa cggttttggat   960 aaaacagtgt cagacctgcg caaagaaacc cgccaaggcc ttgcagaaca gccgcgctc   1020 tccggtctgt tccaacctta acgtgggt gatccggag gaggaggatc agatttggca   1080
aacgattctt ttatccggca ggttctcgac cgtcagcatt tcgaacccga cgggaaatac   1140
cacctattcg gcagcagggg ggaacttgcc gagcgcagcg ccatatcgg attgggaaaa   1200 atacaaagcc atcagttggg caacctgatg attcaacagg cggccattaa aggaaatatc   1260

-continued

```
ggctacattg tccgcttttc cgatcacggg cacgaagtcc attccccctt cgacaaccat    1320
gcctcacatt ccgattctga tgaagccggt agtcccgttg acggatttag cctttaccgc    1380
atccattggg acggatacga acaccatccc gccgacggct atgacgggcc acagggcggc    1440
ggctatcccg ctcccaaagg cgcgagggat atatacagct acgacataaa aggcgttgcc    1500
caaaatatcc gcctcaacct gaccgacaac cgcagcaccg gacaacggct tgccgaccgt    1560
ttccacaatg ccggtagtat gctgacgcaa ggagtaggcg acggattcaa acgcgccacc    1620
cgatacagcc ccgagctgga cagatcgggc aatgccgccg aagccttcaa cggcactgca    1680
gatatcgtta aaaacatcat cggcgcggca ggagaaattg tcggcgcagg cgatgccgtg    1740
cagggcataa gcgaaggctc aaacattgct gtcatgcacg gcttgggtct gctttccacc    1800
gaaaacaaga tggcgcgcat caacgatttg gcagatatgg cgcaactcaa agactatgcc    1860
gcagcagcca tccgcgattg ggcagtccaa accccaatg ccgcacaagg catagaagcc    1920
gtcagcaata tctttatggc agccatcccc atcaaaggga ttggagctgt tcggggaaaa    1980
tacggcttgg gcggcatcac ggcacatcct atcaagcggt cgcagatggg cgcgatcgca    2040
ttgccgaaag ggaaatccgc cgtcagcgac aattttgccg atgcggcata cgccaaatac    2100
ccgtcccctt accattcccg aaatatccgt tcaaacttgg agcagcgtta cggcaaagaa    2160
aacatcacct cctcaaccgt gccgccgtca acggcaaaaa atgtcaaact ggcagaccaa    2220
cgccacccga agacaggcgt accgtttgac ggtaaagggt ttccgaattt tgagaagcac    2280
gtgaaatatg atacgtaact cgag                                           2304
```

<210> SEQ ID NO 159
<211> LENGTH: 765
<212> TYPE: PRT
<213> ORGANISM: Artificial Sequence
<220> FEATURE:
<223> OTHER INFORMATION: Synthetic construct

<400> SEQUENCE: 159

```
Met Lys His Phe Pro Ser Lys Val Leu Thr Thr Ala Ile Leu Ala Thr
1               5                   10                  15

Phe Cys Ser Gly Ala Leu Ala Ala Thr Asn Asp Asp Val Lys Lys
            20                  25                  30

Ala Ala Thr Val Ala Ile Ala Ala Tyr Asn Asn Gly Gln Glu Ile
        35                  40                  45

Asn Gly Phe Lys Ala Gly Glu Thr Ile Tyr Asp Ile Asp Glu Asp Gly
    50                  55                  60

Thr Ile Thr Lys Lys Asp Ala Thr Ala Ala Asp Val Glu Ala Asp Asp
65                  70                  75                  80

Phe Lys Gly Leu Gly Leu Lys Lys Val Val Thr Asn Leu Thr Lys Thr
                85                  90                  95

Val Asn Glu Asn Lys Gln Asn Val Asp Ala Lys Val Lys Ala Ala Glu
            100                 105                 110

Ser Glu Ile Glu Lys Leu Thr Thr Lys Leu Ala Asp Thr Asp Ala Ala
        115                 120                 125

Leu Ala Asp Thr Asp Ala Ala Leu Ala Thr Thr Asn Ala Leu Asn
    130                 135                 140

Lys Leu Gly Glu Asn Ile Thr Thr Phe Ala Glu Thr Lys Thr Asn
145                 150                 155                 160

Ile Val Lys Ile Asp Glu Lys Leu Glu Ala Val Ala Asp Thr Val Asp
                165                 170                 175

Lys His Ala Glu Ala Phe Asn Asp Ile Ala Asp Ser Leu Asp Glu Thr
```

-continued

```
            180                 185                 190
Asn Thr Lys Ala Asp Glu Ala Val Lys Thr Ala Asn Glu Ala Lys Gln
            195                 200                 205
Thr Ala Glu Glu Thr Lys Gln Asn Val Asp Ala Lys Val Lys Ala Ala
        210                 215                 220
Glu Thr Ala Ala Gly Lys Ala Glu Ala Ala Gly Thr Ala Asn Thr
225                 230                 235                 240
Ala Ala Asp Lys Ala Glu Ala Val Ala Lys Val Thr Asp Ile Lys
                245                 250                 255
Ala Asp Ile Ala Thr Asn Lys Asp Asn Ile Ala Lys Lys Ala Asn Ser
            260                 265                 270
Ala Asp Val Tyr Thr Arg Glu Glu Ser Asp Ser Lys Phe Val Arg Ile
            275                 280                 285
Asp Gly Leu Asn Ala Thr Thr Glu Lys Leu Asp Thr Arg Leu Ala Ser
        290                 295                 300
Ala Glu Lys Ser Ile Ala Asp His Asp Thr Arg Leu Asn Gly Leu Asp
305                 310                 315                 320
Lys Thr Val Ser Asp Leu Arg Lys Glu Thr Arg Gln Gly Leu Ala Glu
                325                 330                 335
Gln Ala Ala Leu Ser Gly Leu Phe Gln Pro Tyr Asn Val Gly Gly Ser
            340                 345                 350
Gly Gly Gly Gly Ser Asp Leu Ala Asn Asp Ser Phe Ile Arg Gln Val
            355                 360                 365
Leu Asp Arg Gln His Phe Glu Pro Asp Gly Lys Tyr His Leu Phe Gly
        370                 375                 380
Ser Arg Gly Glu Leu Ala Glu Arg Ser Gly His Ile Gly Leu Gly Lys
385                 390                 395                 400
Ile Gln Ser His Gln Leu Gly Asn Leu Met Ile Gln Gln Ala Ala Ile
                405                 410                 415
Lys Gly Asn Ile Gly Tyr Ile Val Arg Phe Ser Asp His Gly His Glu
            420                 425                 430
Val His Ser Pro Phe Asp Asn His Ala Ser His Ser Asp Ser Asp Glu
            435                 440                 445
Ala Gly Ser Pro Val Asp Gly Phe Ser Leu Tyr Arg Ile His Trp Asp
        450                 455                 460
Gly Tyr Glu His His Pro Ala Asp Gly Tyr Asp Gly Pro Gln Gly Gly
465                 470                 475                 480
Gly Tyr Pro Ala Pro Lys Gly Ala Arg Asp Ile Tyr Ser Tyr Asp Ile
                485                 490                 495
Lys Gly Val Ala Gln Asn Ile Arg Leu Asn Leu Thr Asp Asn Arg Ser
            500                 505                 510
Thr Gly Gln Arg Leu Ala Asp Arg Phe His Asn Ala Gly Ser Met Leu
        515                 520                 525
Thr Gln Gly Val Gly Asp Gly Phe Lys Arg Ala Thr Arg Tyr Ser Pro
        530                 535                 540
Glu Leu Asp Arg Ser Gly Asn Ala Ala Glu Ala Phe Asn Gly Thr Ala
545                 550                 555                 560
Asp Ile Val Lys Asn Ile Ile Gly Ala Ala Gly Glu Ile Val Gly Ala
                565                 570                 575
Gly Asp Ala Val Gln Gly Ile Ser Glu Gly Ser Asn Ile Ala Val Met
            580                 585                 590
His Gly Leu Gly Leu Leu Ser Thr Glu Asn Lys Met Ala Arg Ile Asn
            595                 600                 605
```

```
Asp Leu Ala Asp Met Ala Gln Leu Lys Asp Tyr Ala Ala Ala Ile
        610                 615                 620
Arg Asp Trp Ala Val Gln Asn Pro Asn Ala Ala Gln Gly Ile Glu Ala
625                 630                 635                 640
Val Ser Asn Ile Phe Met Ala Ala Ile Pro Ile Lys Gly Ile Gly Ala
            645                 650                 655
Val Arg Gly Lys Tyr Gly Leu Gly Gly Ile Thr Ala His Pro Ile Lys
        660                 665                 670
Arg Ser Gln Met Gly Ala Ile Ala Leu Pro Lys Gly Lys Ser Ala Val
        675                 680                 685
Ser Asp Asn Phe Ala Asp Ala Ala Tyr Ala Lys Tyr Pro Ser Pro Tyr
690                 695                 700
His Ser Arg Asn Ile Arg Ser Asn Leu Glu Gln Arg Tyr Gly Lys Glu
705                 710                 715                 720
Asn Ile Thr Ser Ser Thr Val Pro Pro Ser Asn Gly Lys Asn Val Lys
            725                 730                 735
Leu Ala Asp Gln Arg His Pro Lys Thr Gly Val Pro Phe Asp Gly Lys
        740                 745                 750
Gly Phe Pro Asn Phe Glu Lys His Val Lys Tyr Asp Thr
        755                 760                 765

<210> SEQ ID NO 160
<211> LENGTH: 1839
<212> TYPE: DNA
<213> ORGANISM: Artificial Sequence
<220> FEATURE:
<223> OTHER INFORMATION: Synthetic construct

<400> SEQUENCE: 160
atgaaacact tccatccaa agtactgacc acagccatcc ttgccacttt ctgtagcggc      60
gcactggcag ccacaaacga cgacgatgtt aaaaaagctg ccactgtggc cattgctgct     120
gcctacaaca atggccaaga atcaacggt ttcaaagctg agagaccat ctacgacatt      180 gatgaagacg gcacaattac caaaaaagac gcaactgcag ccgatgttga agccgacgac     240
tttaaaggtc tgggtctgaa aaaagtcgtg actaacctga ccaaaaccgt caatgaaaac     300
aaacaaaacg tcgatgccaa agtaaaagct gcagaatctg aaatagaaaa gttaacaacc     360
aagttagcag acactgatgc cgctttagca gatactgatg ccgctctgga tgcaaccacc     420
aacgccttga taaaattggg agaaaatata cgacatttg ctgaagagac taagacaaat      480
atcgtaaaaa ttgatgaaaa attagaagcc gtggctgata ccgtcgacaa gcatgccgaa     540
gcattcaacg atatcgccga ttcattggat gaaaccaaca ctaaggcaga cgaagccgtc     600 aaaccgcca atgaagccaa acagacggcc gaagaaacca acaaaaacgt cgatgccaaa      660
gtaaaagctg cagaaactgc agcaggcaaa gccgaagctg ccgctggcac agctaatact     720
gcagccgaca aggccgaagc tgtcgctgca aagttaccg acatcaaagc tgatatcgct      780
acgaacaaag ataatattgc taaaaaagca acagtgccg acgtgtacac cagagaagag      840
tctgacagca aatttgtcag aattgatggt ctgaacgcta ctaccgaaaa attggacaca     900
cgcttggctt ctgctgaaaa atccattgcc gatcacgata ctcgcctgaa cggtttggat     960
aaaacagtgt cagacctgcg caaagaaacc cgccaaggcc ttgcagaaca agccgcgctc    1020
tccggtctgt tccaacctta aacgtgggt ggatccggag ggggtggtgt cgccgccgac     1080
atcggtgcgg ggcttgccga tgcactaacc gcaccgctcg accataaaga caaaggtttg    1140
cagtctttga cgctggatca gtccgtcagg aaaaacgaga aactgaagct ggcggcacaa    1200
```

```
ggtgcggaaa aaacttatgg aaacggtgac agcctcaata cgggcaaatt gaagaacgac    1260
aaggtcagcc gtttcgactt tatccgccaa atcgaagtgg acgggcagct cattaccttg    1320
gagagtggag agttccaagt atacaaacaa agccattccg ccttaaccgc ctttcagacc    1380
gagcaaatac aagattcgga gcattccggg aagatggttg cgaaacgcca gttcagaatc    1440
ggcgacatag cgggcgaaca tacatctttt gacaagcttc ccgaaggcgg cagggcgaca    1500
tatcgcggga cggcgttcgg ttcagacgat gccggcggaa aactgaccta caccatagat    1560
ttcgccgcca agcagggaaa cggcaaaatc gaacatttga aatcgccaga actcaatgtc    1620
gacctggccg ccgccgatat caagccggat ggaaaacgcc atgccgtcat cagcggttcc    1680
gtcctttaca accaagccga gaaggcagt tactccctcg gtatctttgg cggaaaagcc    1740
caggaagttg ccggcagcgc ggaagtgaaa accgtaaacg gcatacgcca tatcggcctt    1800
gccgccaagc aactcgagca ccaccaccac caccactga                          1839
```

<210> SEQ ID NO 161
<211> LENGTH: 612
<212> TYPE: PRT
<213> ORGANISM: Artificial Sequence
<220> FEATURE:
<223> OTHER INFORMATION: Synthetic construct

<400> SEQUENCE: 161

```
Met Lys His Phe Pro Ser Lys Val Leu Thr Thr Ala Ile Leu Ala Thr
1               5                   10                  15

Phe Cys Ser Gly Ala Leu Ala Ala Thr Asn Asp Asp Val Lys Lys
            20                  25                  30

Ala Ala Thr Val Ala Ile Ala Ala Ala Tyr Asn Asn Gly Gln Glu Ile
        35                  40                  45

Asn Gly Phe Lys Ala Gly Glu Thr Ile Tyr Asp Ile Asp Glu Asp Gly
    50                  55                  60

Thr Ile Thr Lys Lys Asp Ala Thr Ala Asp Val Glu Ala Asp Asp
65                  70                  75                  80

Phe Lys Gly Leu Gly Leu Lys Lys Val Val Thr Asn Leu Thr Lys Thr
                85                  90                  95

Val Asn Glu Asn Lys Gln Asn Val Asp Ala Lys Val Lys Ala Ala Glu
            100                 105                 110

Ser Glu Ile Glu Lys Leu Thr Thr Lys Leu Ala Asp Thr Asp Ala Ala
        115                 120                 125

Leu Ala Asp Thr Asp Ala Ala Leu Asp Ala Thr Asn Ala Leu Asn
    130                 135                 140

Lys Leu Gly Glu Asn Ile Thr Thr Phe Ala Glu Glu Thr Lys Thr Asn
145                 150                 155                 160

Ile Val Lys Ile Asp Glu Lys Leu Glu Ala Val Ala Asp Thr Val Asp
                165                 170                 175

Lys His Ala Glu Ala Phe Asn Asp Ile Ala Asp Ser Leu Asp Glu Thr
            180                 185                 190

Asn Thr Lys Ala Asp Glu Ala Val Lys Thr Ala Asn Glu Ala Lys Gln
        195                 200                 205

Thr Ala Glu Glu Thr Lys Gln Asn Val Asp Ala Lys Val Lys Ala Ala
    210                 215                 220

Glu Thr Ala Ala Gly Lys Ala Glu Ala Ala Gly Thr Ala Asn Thr
225                 230                 235                 240

Ala Ala Asp Lys Ala Glu Ala Val Ala Ala Lys Val Thr Asp Ile Lys
                245                 250                 255
```

-continued

Ala Asp Ile Ala Thr Asn Lys Asp Asn Ile Ala Lys Lys Ala Asn Ser
            260                 265                 270

Ala Asp Val Tyr Thr Arg Glu Glu Ser Asp Ser Lys Phe Val Arg Ile
            275                 280                 285

Asp Gly Leu Asn Ala Thr Thr Glu Lys Leu Asp Thr Arg Leu Ala Ser
            290                 295                 300

Ala Glu Lys Ser Ile Ala Asp His Asp Thr Arg Leu Asn Gly Leu Asp
305                 310                 315                 320

Lys Thr Val Ser Asp Leu Arg Lys Glu Thr Arg Gln Gly Leu Ala Glu
            325                 330                 335

Gln Ala Ala Leu Ser Gly Leu Phe Gln Pro Tyr Asn Val Gly Gly Ser
            340                 345                 350

Gly Gly Gly Gly Val Ala Ala Asp Ile Gly Ala Gly Leu Ala Asp Ala
            355                 360                 365

Leu Thr Ala Pro Leu Asp His Lys Asp Lys Gly Leu Gln Ser Leu Thr
            370                 375                 380

Leu Asp Gln Ser Val Arg Lys Asn Glu Lys Leu Lys Leu Ala Ala Gln
385                 390                 395                 400

Gly Ala Glu Lys Thr Tyr Gly Asn Gly Asp Ser Leu Asn Thr Gly Lys
            405                 410                 415

Leu Lys Asn Asp Lys Val Ser Arg Phe Asp Phe Ile Arg Gln Ile Glu
            420                 425                 430

Val Asp Gly Gln Leu Ile Thr Leu Glu Ser Gly Glu Phe Gln Val Tyr
            435                 440                 445

Lys Gln Ser His Ser Ala Leu Thr Ala Phe Gln Thr Glu Gln Ile Gln
            450                 455                 460

Asp Ser Glu His Ser Gly Lys Met Val Ala Lys Arg Gln Phe Arg Ile
465                 470                 475                 480

Gly Asp Ile Ala Gly Glu His Thr Ser Phe Asp Lys Leu Pro Glu Gly
            485                 490                 495

Gly Arg Ala Thr Tyr Arg Gly Thr Ala Phe Gly Ser Asp Asp Ala Gly
            500                 505                 510

Gly Lys Leu Thr Tyr Thr Ile Asp Phe Ala Ala Lys Gln Gly Asn Gly
            515                 520                 525

Lys Ile Glu His Leu Lys Ser Pro Glu Leu Asn Val Asp Leu Ala Ala
530                 535                 540

Ala Asp Ile Lys Pro Asp Gly Lys Arg His Ala Val Ile Ser Gly Ser
545                 550                 555                 560

Val Leu Tyr Asn Gln Ala Glu Lys Gly Ser Tyr Ser Leu Gly Ile Phe
            565                 570                 575

Gly Gly Lys Ala Gln Glu Val Ala Gly Ser Ala Glu Val Lys Thr Val
            580                 585                 590

Asn Gly Ile Arg His Ile Gly Leu Ala Ala Lys Gln Leu Glu His His
            595                 600                 605

His His His His
    610

<210> SEQ ID NO 162
<211> LENGTH: 4218
<212> TYPE: DNA
<213> ORGANISM: Artificial Sequence
<220> FEATURE:
<223> OTHER INFORMATION: Synthetic construct

<400> SEQUENCE: 162
atgaaacact tccatccaa agtactgacc acagccatcc ttgccacttt ctgtagcggc      60

```
gcactggcag ccacaaacga cgacgatgtt aaaaaagctg ccactgtggc cattgctgct    120
gcctacaaca atggccaaga aatcaacggt ttcaaagctg gagagaccat ctacgacatt    180
gatgaagacg gcacaattac caaaaaagac gcaactgcag ccgatgttga agccgacgac    240
tttaaaggtc tgggtctgaa aaaagtcgtg actaacctga ccaaaaccgt caatgaaaac    300
aaacaaaacg tcgatgccaa agtaaaagct gcagaatctg aaatagaaaa gttaacaacc    360
aagttagcag acactgatgc cgctttagca gatactgatg ccgctctgga tgcaaccacc    420
aacgccttga ataaattggg agaaaatata cgacatttg  ctgaagagac taagacaaat    480
atcgtaaaaa ttgatgaaaa attagaagcc gtggctgata ccgtcgacaa gcatgccgaa    540
gcattcaacg atatcgccga ttcattggat gaaaccaaca ctaaggcaga cgaagccgtc    600
aaaaccgcca atgaagccaa acagacggcc gaagaaacca acaaaacgt  cgatgccaaa    660 gtaaaagctg cagaaactgc agcaggcaaa gccgaagctg ccgctggcac agctaatact    720
gcagccgaca aggccgaagc tgtcgctgca aaagttaccg acatcaaagc tgatatcgct    780
acgaacaaag ataatattgc taaaaaagca acagtgccg  acgtgtacac cagagaagag    840
tctgacagca aatttgtcag aattgatggt ctgaacgcta ctaccgaaaa attggacaca    900
cgcttggctt ctgctgaaaa atccattgcc gatcacgata ctcgcctgaa cggtttggat    960
aaaacagtgt cagacctgcg caaagaaacc cgccaaggcc ttgcagaaca agccgcgctc   1020
tccggtctgt tccaacctta caacgtgggt ggatccggcg gaggcggcac ttctgcgccc   1080
gacttcaatg caggcggtac cggtatcggc agcaacagca gagcaacaac agcgaaatca   1140
gcagcagtat cttacgccgg tatcaagaac gaaatgtgca agacagaag  catgctctgt   1200 gccggtcggg atgacgttgc ggttacgaca agggatgcca aaatcaatgc cccccccccg   1260
aatctgcata ccggagactt tccaaaccca aatgacgcat acaagaattt gatcaacctc   1320
aaacctgcaa ttgaagcagg ctatacagga cgcggggtag aggtaggtat cgtcgacaca   1380
ggcgaatccg tcggcagcat atcctttccc gaactgtatg cagaaaaga  acacggctat   1440 aacgaaaatt acaaaaacta tacgcgtat  atgcggaagg aagcgcctga agacggaggc   1500
ggtaaagaca ttgaagcttc tttcgacgat gaggccgtta tagagactga agcaaagccg   1560
acggatatcc gccacgtaaa agaaatcgga cacatcgatt tggtctccca tattattggc   1620
gggcgttccg tggacggcag acctgcaggc ggtattgcgc ccgatgcgac gctacacata   1680
atgaatacga atgatgaaac caagaacgaa atgatggttg cagccatccg caatgcatgg   1740
gtcaagctgg gcgaacgtgg cgtgcgcatc gtcaataaca gttttggaac aacatcgagg   1800
gcaggcactg ccgaccttt  ccaaatagcc aattcggagg agcagtaccg ccaagcgttg   1860
ctcgactatt ccggcggtga taaaacagac gagggtatcc gcctgatgca acagagcgat   1920
tacggcaacc tgtcctacca catccgtaat aaaaacatgc ttttcatctt ttcgacaggc   1980
aatgacgcac aagctcagcc caacacatat gccctattgc cattttatga aaaagacgct   2040
caaaaaggca ttatcacagt cgcaggcgta gaccgcagtg gagaaaagtt caaacgggaa   2100
atgtatggag aaccgggtac agaaccgctt gagtatggct ccaaccattg cggaattact   2160
gccatgtggt gcctgtcggc accctatgaa gcaagcgtcc gtttcacccg tacaaacccg   2220
attcaaattg ccggaacatc cttttccgca cccatcgtaa ccggcacggc ggctctgctg   2280
ctgcagaaat acccgtggat gagcaacgac aacctgcgta ccacgttgct gacgacggct   2340
caggacatcg tgcagtcgg  cgtggacagc aagttcggct ggggactgct ggatgcgggt   2400
aaggccatga acggacccgc gtcctttccg ttcggcgact ttaccgccga tacgaaaggt   2460
```

```
acatccgata ttgcctactc cttccgtaac gacatttcag gcacgggcgg cctgatcaaa    2520
aaaggcggca gccaactgca actgcacggc aacaacacct atacgggcaa aaccattatc    2580
gaaggcggtt cgctggtgtt gtacggcaac aacaaatcgg atatgcgcgt cgaaaccaaa    2640
ggtgcgctga tttataacgg ggcggcatcc ggcggcagcc tgaacagcga cggcattgtc    2700
tatctggcag ataccgacca atccggcgca aacgaaaccg tacacatcaa aggcagtctg    2760
cagctggacg gcaaaggtac gctgtacaca cgtttgggca aactgctgaa agtggacggt    2820
acggcgatta tcggcggcaa gctgtacatg tcggcacgcg gcaaggggc aggctatctc    2880 aacagtaccg gacgacgtgt tcccttcctg agtgccgcca aaatcgggca ggattattct    2940
ttcttcacaa acatcgaaac cgacggcggc ctgctggctt ccctcgacag cgtcgaaaaa    3000
acagcgggca gtgaaggcga cacgctgtcc tattatgtcc gtcgcggcaa tgcggcacgg    3060
actgcttcgg cagcggcaca ttccgcgccc gccggtctga aacacgccgt agaacagggc    3120
ggcagcaatc tggaaaacct gatggtcgaa ctggatgcct ccgaatcatc cgcaacaccc    3180
gagacggttg aaactgcggc agccgaccgc acagatatgc cgggcatccg ccctacggc     3240 gcaacttttc cgcgcagcgg cagccgtacag catgcgaatg ccgccgacgg tgtacgcatc    3300
ttcaacagtc tcgccgctac cgtctatgcc gacagtaccg ccgcccatgc cgatatgcag    3360
ggacgccgcc tgaaagccgt atcggacggg ttggaccaca acggcacggg tctgcgcgtc    3420
atcgcgcaaa cccaacagga cggtggaacg tgggaacagg gcggtgttga aggcaaaatg    3480
cgcggcagta cccaaaccgt cggcattgcc gcgaaaccg gcgaaaatac gacagcagcc    3540
gccacactgg gcatgggacg cagcacatgg agcgaaaaca gtgcaaatgc aaaaaccgac    3600
agcattagtc tgtttgcagg catacggcac gatgcgggcg atatcggcta tctcaaaggc    3660
ctgttctcct acggacgcta caaaaacagc atcagccgca gcaccggtgc ggacgaacat    3720
gcggaaggca gcgtcaacgg cacgctgatg cagctgggcg cactgggcgg tgtcaacgtt    3780
ccgtttgccg caacgggaga tttgacggtc gaaggcggtc tgcgctacga cctgctcaaa    3840
caggatgcat cgccgaaaaa aggcagtgct ttgggctgga gcggcaacag cctcactgaa    3900
ggcacgctgg tcggactcgc gggtctgaag ctgtcgcaac ccttgagcga taaagccgtc    3960
ctgtttgcaa cggcgggcgt ggaacgcgac ctgaacggac gcgactacac ggtaacgggc    4020
ggctttaccg gcgcgactgc agcaaccggc aagacggggg cacgcaatat gccgcacacc    4080
cgtctggttg ccggcctggg cgcggatgtc gaattcggca acggctggaa cggcttggca    4140
cgttacagct acgccggttc caaacagtac ggcaaccaca gcggacgagt cggcgtaggc    4200
taccggttct gactcgag                                                  4218
```

<210> SEQ ID NO 163
<211> LENGTH: 1403
<212> TYPE: PRT
<213> ORGANISM: Artificial Sequence
<220> FEATURE:
<223> OTHER INFORMATION: Synthetic construct

<400> SEQUENCE: 163

```
Met Lys His Phe Pro Ser Lys Val Leu Thr Thr Ala Ile Leu Ala Thr
1               5                   10                  15

Phe Cys Ser Gly Ala Leu Ala Ala Thr Asn Asp Asp Val Lys Lys
                20                  25                  30

Ala Ala Thr Val Ala Ile Ala Ala Tyr Asn Asn Gly Gln Glu Ile
        35                  40                  45
```

-continued

```
Asn Gly Phe Lys Ala Gly Glu Thr Ile Tyr Asp Ile Asp Glu Asp Gly
     50                  55                  60
Thr Ile Thr Lys Lys Asp Ala Thr Ala Asp Val Glu Ala Asp Asp
 65                  70                  75                  80
Phe Lys Gly Leu Gly Leu Lys Lys Val Val Thr Asn Leu Thr Lys Thr
                 85                  90                  95
Val Asn Glu Asn Lys Gln Asn Val Asp Ala Lys Val Lys Ala Ala Glu
            100                 105                 110
Ser Glu Ile Glu Lys Leu Thr Thr Lys Leu Ala Asp Thr Asp Ala Ala
        115                 120                 125
Leu Ala Asp Thr Asp Ala Ala Leu Asp Ala Thr Asn Ala Leu Asn
    130                 135                 140
Lys Leu Gly Glu Asn Ile Thr Thr Phe Ala Glu Thr Lys Thr Asn
145                 150                 155                 160
Ile Val Lys Ile Asp Glu Lys Leu Glu Ala Val Ala Asp Thr Val Asp
                165                 170                 175
Lys His Ala Glu Ala Phe Asn Asp Ile Ala Asp Ser Leu Asp Glu Thr
            180                 185                 190
Asn Thr Lys Ala Asp Glu Ala Val Lys Thr Ala Asn Glu Ala Lys Gln
        195                 200                 205
Thr Ala Glu Glu Thr Lys Gln Asn Val Asp Ala Lys Val Lys Ala Ala
    210                 215                 220
Glu Thr Ala Ala Gly Lys Ala Glu Ala Ala Gly Thr Ala Asn Thr
225                 230                 235                 240
Ala Ala Asp Lys Ala Glu Ala Val Ala Ala Lys Val Thr Asp Ile Lys
                245                 250                 255
Ala Asp Ile Ala Thr Asn Lys Asp Asn Ile Ala Lys Lys Ala Asn Ser
            260                 265                 270
Ala Asp Val Tyr Thr Arg Glu Glu Ser Asp Ser Lys Phe Val Arg Ile
        275                 280                 285
Asp Gly Leu Asn Ala Thr Thr Glu Lys Leu Asp Thr Arg Leu Ala Ser
    290                 295                 300
Ala Glu Lys Ser Ile Ala Asp His Asp Thr Arg Leu Asn Gly Leu Asp
305                 310                 315                 320
Lys Thr Val Ser Asp Leu Arg Lys Glu Thr Arg Gln Gly Leu Ala Glu
                325                 330                 335
Gln Ala Ala Leu Ser Gly Leu Phe Gln Pro Tyr Asn Val Gly Gly Ser
            340                 345                 350
Gly Gly Gly Gly Thr Ser Ala Pro Asp Phe Asn Ala Gly Thr Gly
        355                 360                 365
Ile Gly Ser Asn Ser Arg Ala Thr Thr Ala Lys Ser Ala Ala Val Ser
    370                 375                 380
Tyr Ala Gly Ile Lys Asn Glu Met Cys Lys Asp Arg Ser Met Leu Cys
385                 390                 395                 400
Ala Gly Arg Asp Asp Val Ala Val Thr Asp Arg Asp Ala Lys Ile Asn
                405                 410                 415
Ala Pro Pro Asn Leu His Thr Gly Asp Phe Pro Asn Pro Asn Asp
            420                 425                 430
Ala Tyr Lys Asn Leu Ile Asn Leu Lys Pro Ala Ile Glu Ala Gly Tyr
        435                 440                 445
Thr Gly Arg Gly Val Glu Val Gly Ile Val Asp Thr Gly Glu Ser Val
    450                 455                 460
Gly Ser Ile Ser Phe Pro Glu Leu Tyr Gly Arg Lys Glu His Gly Tyr
465                 470                 475                 480
```

```
Asn Glu Asn Tyr Lys Asn Tyr Thr Ala Tyr Met Arg Lys Glu Ala Pro
                485                 490                 495
Glu Asp Gly Gly Gly Lys Asp Ile Glu Ala Ser Phe Asp Asp Glu Ala
            500                 505                 510
Val Ile Glu Thr Glu Ala Lys Pro Thr Asp Ile Arg His Val Lys Glu
        515                 520                 525
Ile Gly His Ile Asp Leu Val Ser His Ile Ile Gly Arg Ser Val
    530                 535                 540
Asp Gly Arg Pro Ala Gly Gly Ile Ala Pro Asp Ala Thr Leu His Ile
545                 550                 555                 560
Met Asn Thr Asn Asp Glu Thr Lys Asn Glu Met Met Val Ala Ala Ile
                565                 570                 575
Arg Asn Ala Trp Val Lys Leu Gly Glu Arg Gly Val Arg Ile Val Asn
            580                 585                 590
Asn Ser Phe Gly Thr Thr Ser Arg Ala Gly Thr Ala Asp Leu Phe Gln
        595                 600                 605
Ile Ala Asn Ser Glu Glu Gln Tyr Arg Gln Ala Leu Leu Asp Tyr Ser
    610                 615                 620
Gly Gly Asp Lys Thr Asp Glu Gly Ile Arg Leu Met Gln Gln Ser Asp
625                 630                 635                 640
Tyr Gly Asn Leu Ser Tyr His Ile Arg Asn Lys Asn Met Leu Phe Ile
                645                 650                 655
Phe Ser Thr Gly Asn Asp Ala Gln Ala Gln Pro Asn Thr Tyr Ala Leu
            660                 665                 670
Leu Pro Phe Tyr Glu Lys Asp Ala Gln Lys Gly Ile Ile Thr Val Ala
        675                 680                 685
Gly Val Asp Arg Ser Gly Glu Lys Phe Lys Arg Glu Met Tyr Gly Glu
    690                 695                 700
Pro Gly Thr Glu Pro Leu Glu Tyr Gly Ser Asn His Cys Gly Ile Thr
705                 710                 715                 720
Ala Met Trp Cys Leu Ser Ala Pro Tyr Glu Ala Ser Val Arg Phe Thr
                725                 730                 735
Arg Thr Asn Pro Ile Gln Ile Ala Gly Thr Ser Phe Ser Ala Pro Ile
            740                 745                 750
Val Thr Gly Thr Ala Ala Leu Leu Leu Gln Lys Tyr Pro Trp Met Ser
        755                 760                 765
Asn Asp Asn Leu Arg Thr Thr Leu Leu Thr Thr Ala Gln Asp Ile Gly
    770                 775                 780
Ala Val Gly Val Asp Ser Lys Phe Gly Trp Gly Leu Leu Asp Ala Gly
785                 790                 795                 800
Lys Ala Met Asn Gly Pro Ala Ser Phe Pro Phe Gly Asp Phe Thr Ala
                805                 810                 815
Asp Thr Lys Gly Thr Ser Asp Ile Ala Tyr Ser Phe Arg Asn Asp Ile
            820                 825                 830
Ser Gly Thr Gly Gly Leu Ile Lys Lys Gly Gly Ser Gln Leu Gln Leu
        835                 840                 845
His Gly Asn Asn Thr Tyr Thr Gly Lys Thr Ile Ile Glu Gly Gly Ser
    850                 855                 860
Leu Val Leu Tyr Gly Asn Asn Lys Ser Asp Met Arg Val Glu Thr Lys
865                 870                 875                 880
Gly Ala Leu Ile Tyr Asn Gly Ala Ala Ser Gly Gly Ser Leu Asn Ser
                885                 890                 895
Asp Gly Ile Val Tyr Leu Ala Asp Thr Asp Gln Ser Gly Ala Asn Glu
```

-continued

```
                900             905             910
Thr Val His Ile Lys Gly Ser Leu Gln Leu Asp Gly Lys Gly Thr Leu
            915                 920             925
Tyr Thr Arg Leu Gly Lys Leu Leu Lys Val Asp Gly Thr Ala Ile Ile
            930                 935             940
Gly Gly Lys Leu Tyr Met Ser Ala Arg Gly Lys Gly Ala Gly Tyr Leu
945                 950                 955                 960
Asn Ser Thr Gly Arg Arg Val Pro Phe Leu Ser Ala Ala Lys Ile Gly
                965                 970             975
Gln Asp Tyr Ser Phe Phe Thr Asn Ile Glu Thr Asp Gly Gly Leu Leu
            980                 985                 990
Ala Ser Leu Asp Ser Val Glu Lys Thr Ala Gly Ser Glu Gly Asp Thr
            995                 1000            1005
Leu Ser Tyr Tyr Val Arg Arg Gly Asn Ala Ala Arg Thr Ala Ser Ala
            1010                1015            1020
Ala Ala His Ser Ala Pro Ala Gly Leu Lys His Ala Val Glu Gln Gly
1025                1030                1035                1040
Gly Ser Asn Leu Glu Asn Leu Met Val Glu Leu Asp Ala Ser Glu Ser
                1045                1050                1055
Ser Ala Thr Pro Glu Thr Val Glu Thr Ala Ala Ala Asp Arg Thr Asp
            1060                1065                1070
Met Pro Gly Ile Arg Pro Tyr Gly Ala Thr Phe Arg Ala Ala Ala Ala
            1075                1080            1085
Val Gln His Ala Asn Ala Ala Asp Gly Val Arg Ile Phe Asn Ser Leu
            1090                1095            1100
Ala Ala Thr Val Tyr Ala Asp Ser Thr Ala His Ala Asp Met Gln
1105                1110                1115                1120
Gly Arg Arg Leu Lys Ala Val Ser Asp Gly Leu Asp His Asn Gly Thr
            1125                1130                1135
Gly Leu Arg Val Ile Ala Gln Thr Gln Gln Asp Gly Gly Thr Trp Glu
            1140                1145                1150
Gln Gly Gly Val Glu Gly Lys Met Arg Gly Ser Thr Gln Thr Val Gly
            1155                1160            1165
Ile Ala Ala Lys Thr Gly Glu Asn Thr Thr Ala Ala Ala Thr Leu Gly
            1170                1175            1180
Met Gly Arg Ser Thr Trp Ser Glu Asn Ser Ala Asn Ala Lys Thr Asp
1185                1190                1195                1200
Ser Ile Ser Leu Phe Ala Gly Ile Arg His Asp Ala Gly Asp Ile Gly
            1205                1210                1215
Tyr Leu Lys Gly Leu Phe Ser Tyr Gly Arg Tyr Lys Asn Ser Ile Ser
            1220                1225            1230
Arg Ser Thr Gly Ala Asp Glu His Ala Glu Gly Ser Val Asn Gly Thr
            1235                1240            1245
Leu Met Gln Leu Gly Ala Leu Gly Gly Val Asn Val Pro Phe Ala Ala
            1250                1255            1260
Thr Gly Asp Leu Thr Val Glu Gly Gly Leu Arg Tyr Asp Leu Leu Lys
1265                1270                1275                1280
Gln Asp Ala Phe Ala Glu Lys Gly Ser Ala Leu Gly Trp Ser Gly Asn
            1285                1290                1295
Ser Leu Thr Glu Gly Thr Leu Val Gly Leu Ala Gly Leu Lys Leu Ser
                1300                1305            1310
Gln Pro Leu Ser Asp Lys Ala Val Leu Phe Ala Thr Ala Gly Val Glu
            1315                1320            1325
```

Arg Asp Leu Asn Gly Arg Asp Tyr Thr Val Thr Gly Gly Phe Thr Gly
            1330                1335                1340

Ala Thr Ala Ala Thr Gly Lys Thr Gly Ala Arg Asn Met Pro His Thr
1345                1350                1355                1360

Arg Leu Val Ala Gly Leu Gly Ala Asp Val Glu Phe Gly Asn Gly Trp
                1365                1370                1375

Asn Gly Leu Ala Arg Tyr Ser Tyr Ala Gly Ser Lys Gln Tyr Gly Asn
            1380                1385                1390

His Ser Gly Arg Val Gly Val Gly Tyr Arg Phe
        1395                1400

<210> SEQ ID NO 164
<211> LENGTH: 33
<212> TYPE: DNA
<213> ORGANISM: Artificial Sequence
<220> FEATURE:
<223> OTHER INFORMATION: Synthetic construct

<400> SEQUENCE: 164
cgcggatccg ctagcaaaac aaccgacaaa cgg                          33

<210> SEQ ID NO 165
<211> LENGTH: 27
<212> TYPE: DNA
<213> ORGANISM: Artificial Sequence
<220> FEATURE:
<223> OTHER INFORMATION: Synthetic construct

<400> SEQUENCE: 165
cccgctcgag ttaccagcgg tagccta                                27

<210> SEQ ID NO 166
<211> LENGTH: 30
<212> TYPE: DNA
<213> ORGANISM: Artificial Sequence
<220> FEATURE:
<223> OTHER INFORMATION: Synthetic construct

<400> SEQUENCE: 166
ctagctagcg gacacactta tttcggcatc                             30

<210> SEQ ID NO 167
<211> LENGTH: 32
<212> TYPE: DNA
<213> ORGANISM: Artificial Sequence
<220> FEATURE:
<223> OTHER INFORMATION: Synthetic construct

<400> SEQUENCE: 167
cccgctcgag ttaccagcgg tagcctaatt tg                          32

<210> SEQ ID NO 168
<211> LENGTH: 10
<212> TYPE: DNA
<213> ORGANISM: Artificial Sequence
<220> FEATURE:
<223> OTHER INFORMATION: Synthetic construct

<400> SEQUENCE: 168
cccgctcgag                                                   10

<210> SEQ ID NO 169
<211> LENGTH: 33
<212> TYPE: DNA
<213> ORGANISM: Artificial Sequence

```
<220> FEATURE:
<223> OTHER INFORMATION: Synthetic construct

<400> SEQUENCE: 169
cgcggatccc atatgaaaac cttcttcaaa acc                                33

<210> SEQ ID NO 170
<211> LENGTH: 28
<212> TYPE: DNA
<213> ORGANISM: Artificial Sequence
<220> FEATURE:
<223> OTHER INFORMATION: Synthetic construct

<400> SEQUENCE: 170
cccgctcgag ttatttggct gcgccttc                                     28

<210> SEQ ID NO 171
<211> LENGTH: 35
<212> TYPE: DNA
<213> ORGANISM: Artificial Sequence
<220> FEATURE:
<223> OTHER INFORMATION: Synthetic construct

<400> SEQUENCE: 171
gcggcattaa tatgttgaga aaattgttga aatgg                             35

<210> SEQ ID NO 172
<211> LENGTH: 34
<212> TYPE: DNA
<213> ORGANISM: Artificial Sequence
<220> FEATURE:
<223> OTHER INFORMATION: Synthetic construct

<400> SEQUENCE: 172
gcggcctcga gttattttttt caaaatatat ttgc                             34

<210> SEQ ID NO 173
<211> LENGTH: 33
<212> TYPE: DNA
<213> ORGANISM: Artificial Sequence
<220> FEATURE:
<223> OTHER INFORMATION: Synthetic construct

<400> SEQUENCE: 173
gcggccatat gttacctaac cgtttcaaaa tgt                               33

<210> SEQ ID NO 174
<211> LENGTH: 31
<212> TYPE: DNA
<213> ORGANISM: Artificial Sequence
<220> FEATURE:
<223> OTHER INFORMATION: Synthetic construct

<400> SEQUENCE: 174
gcggcctcga gttatttccg aggttttcgg g                                 31

<210> SEQ ID NO 175
<211> LENGTH: 32
<212> TYPE: DNA
<213> ORGANISM: Artificial Sequence
<220> FEATURE:
<223> OTHER INFORMATION: Synthetic construct

<400> SEQUENCE: 175
cgcggatccc atatgacacg cttcaaatat tc                                32
```

```
<210> SEQ ID NO 176
<211> LENGTH: 31
<212> TYPE: DNA
<213> ORGANISM: Artificial Sequence
<220> FEATURE:
<223> OTHER INFORMATION: Synthetic construct

<400> SEQUENCE: 176
cccgctcgag ttatttaaac cgataggtaa a                               31

<210> SEQ ID NO 177
<211> LENGTH: 31
<212> TYPE: DNA
<213> ORGANISM: Artificial Sequence
<220> FEATURE:
<223> OTHER INFORMATION: Synthetic construct

<400> SEQUENCE: 177
cgcggatccc atatgggcag ggaagaaccg c                               31

<210> SEQ ID NO 178
<211> LENGTH: 28
<212> TYPE: DNA
<213> ORGANISM: Artificial Sequence
<220> FEATURE:
<223> OTHER INFORMATION: Synthetic construct

<400> SEQUENCE: 178
gcccaagctt atcgatggaa tagccgcg                                   28

<210> SEQ ID NO 179
<211> LENGTH: 32
<212> TYPE: DNA
<213> ORGANISM: Artificial Sequence
<220> FEATURE:
<223> OTHER INFORMATION: Synthetic construct

<400> SEQUENCE: 179
cgcggatccg ctagcaacgg tttggatgcc cg                              32

<210> SEQ ID NO 180
<211> LENGTH: 30
<212> TYPE: DNA
<213> ORGANISM: Artificial Sequence
<220> FEATURE:
<223> OTHER INFORMATION: Synthetic construct

<400> SEQUENCE: 180
cccgctcgag tttgtctaag ttcctgatat                                 30

<210> SEQ ID NO 181
<211> LENGTH: 26
<212> TYPE: DNA
<213> ORGANISM: Artificial Sequence
<220> FEATURE:
<223> OTHER INFORMATION: Synthetic construct

<400> SEQUENCE: 181
cccgctcgag attcccacct gccatc                                     26

<210> SEQ ID NO 182
<211> LENGTH: 37
<212> TYPE: DNA
<213> ORGANISM: Artificial Sequence
<220> FEATURE:
<223> OTHER INFORMATION: Synthetic construct

<400> SEQUENCE: 182
```
cgcggatccg ctagcatgaa tttgcctatt caaaaat                                    37

<210> SEQ ID NO 183
<211> LENGTH: 29
<212> TYPE: DNA
<213> ORGANISM: Artificial Sequence
<220> FEATURE:
<223> OTHER INFORMATION: Synthetic construct

<400> SEQUENCE: 183
cccgctcgag ttaattccca cctgccatc                                              29

<210> SEQ ID NO 184
<211> LENGTH: 37
<212> TYPE: DNA
<213> ORGANISM: Artificial Sequence
<220> FEATURE:
<223> OTHER INFORMATION: Synthetic construct

<400> SEQUENCE: 184
cgcggatccg ctagcatgaa tttgcctatt caaaaat                                    37

<210> SEQ ID NO 185
<211> LENGTH: 27
<212> TYPE: DNA
<213> ORGANISM: Artificial Sequence
<220> FEATURE:
<223> OTHER INFORMATION: Synthetic construct

<400> SEQUENCE: 185
cccgctcgag ttggacgatg cccgcga                                                27

<210> SEQ ID NO 186
<211> LENGTH: 37
<212> TYPE: DNA
<213> ORGANISM: Artificial Sequence
<220> FEATURE:
<223> OTHER INFORMATION: Synthetic construct

<400> SEQUENCE: 186
cgcggatccg ctagcatgaa tttgcctatt caaaaat                                    37

<210> SEQ ID NO 187
<211> LENGTH: 28
<212> TYPE: DNA
<213> ORGANISM: Artificial Sequence
<220> FEATURE:
<223> OTHER INFORMATION: Synthetic construct

<400> SEQUENCE: 187
cccgctcgag ttattggacg atgcccgc                                               28

<210> SEQ ID NO 188
<211> LENGTH: 32
<212> TYPE: DNA
<213> ORGANISM: Artificial Sequence
<220> FEATURE:
<223> OTHER INFORMATION: Synthetic construct

<400> SEQUENCE: 188
cgcggatccc atatgtatcg caaactgatt gc                                          32

<210> SEQ ID NO 189
<211> LENGTH: 28
<212> TYPE: DNA
<213> ORGANISM: Artificial Sequence
<220> FEATURE:
<223> OTHER INFORMATION: Synthetic construct

<400> SEQUENCE: 189
cccgctcgag ctaatcgatg gaatagcc                                    28

<210> SEQ ID NO 190
<211> LENGTH: 32
<212> TYPE: DNA
<213> ORGANISM: Artificial Sequence
<220> FEATURE:
<223> OTHER INFORMATION: Synthetic construct

<400> SEQUENCE: 190
cgcggatccc atatgaaaca gacagtcaaa tg                                32

<210> SEQ ID NO 191
<211> LENGTH: 28
<212> TYPE: DNA
<213> ORGANISM: Artificial Sequence
<220> FEATURE:
<223> OTHER INFORMATION: Synthetic construct

<400> SEQUENCE: 191
cccgctcgag tcaataaccc gccttcag                                    28

<210> SEQ ID NO 192
<211> LENGTH: 45
<212> TYPE: DNA
<213> ORGANISM: Artificial Sequence
<220> FEATURE:
<223> OTHER INFORMATION: Synthetic construct

<400> SEQUENCE: 192
cgcggatccc atatgttacg tttgactgct ttagccgtat gcacc                 45

<210> SEQ ID NO 193
<211> LENGTH: 40
<212> TYPE: DNA
<213> ORGANISM: Artificial Sequence
<220> FEATURE:
<223> OTHER INFORMATION: Synthetic construct

<400> SEQUENCE: 193
cccgctcgag ttattttgcc gcgttaaaag cgtcggcaac                       40

<210> SEQ ID NO 194
<211> LENGTH: 32
<212> TYPE: DNA
<213> ORGANISM: Artificial Sequence
<220> FEATURE:
<223> OTHER INFORMATION: Synthetic construct

<400> SEQUENCE: 194
cgcggatccc atatgaacaa aatataccgc at                               32

<210> SEQ ID NO 195
<211> LENGTH: 28
<212> TYPE: DNA
<213> ORGANISM: Artificial Sequence
<220> FEATURE:
<223> OTHER INFORMATION: Synthetic construct

<400> SEQUENCE: 195
cccgctcgag ttaccactga taaccgac                                    28

<210> SEQ ID NO 196
<211> LENGTH: 34
<212> TYPE: DNA
<213> ORGANISM: Artificial Sequence
<220> FEATURE:
<223> OTHER INFORMATION: Synthetic construct

<400> SEQUENCE: 196
cgcggatccc atatgaccga tgacgacgat ttat                          34

<210> SEQ ID NO 197
<211> LENGTH: 28
<212> TYPE: DNA
<213> ORGANISM: Artificial Sequence
<220> FEATURE:
<223> OTHER INFORMATION: Synthetic construct

<400> SEQUENCE: 197
gcccaagctt ccactgataa ccgacaga                                 28

<210> SEQ ID NO 198
<211> LENGTH: 32
<212> TYPE: DNA
<213> ORGANISM: Artificial Sequence
<220> FEATURE:
<223> OTHER INFORMATION: Synthetic construct

<400> SEQUENCE: 198
cgcggatccc atatgaacaa aatataccgc at                            32

<210> SEQ ID NO 199
<211> LENGTH: 28
<212> TYPE: DNA
<213> ORGANISM: Artificial Sequence
<220> FEATURE:
<223> OTHER INFORMATION: Synthetic construct

<400> SEQUENCE: 199
gcccaagctt ttaccactga taaccgac                                 28

<210> SEQ ID NO 200
<211> LENGTH: 34
<212> TYPE: DNA
<213> ORGANISM: Artificial Sequence
<220> FEATURE:
<223> OTHER INFORMATION: Synthetic construct

<400> SEQUENCE: 200
gggaattcca tatgggcatt tcccgcaaaa tatc                          34

<210> SEQ ID NO 201
<211> LENGTH: 40
<212> TYPE: DNA
<213> ORGANISM: Artificial Sequence
<220> FEATURE:
<223> OTHER INFORMATION: Synthetic construct

<400> SEQUENCE: 201
cccgctcgag ttatttactc ctataacgag gtctcttaac                    40

<210> SEQ ID NO 202
<211> LENGTH: 36
<212> TYPE: DNA
<213> ORGANISM: Artificial Sequence
<220> FEATURE:
<223> OTHER INFORMATION: Synthetic construct

<400> SEQUENCE: 202
gggaattcca tatgtcagat ttggcaaacg attctt                     36

<210> SEQ ID NO 203
<211> LENGTH: 40
<212> TYPE: DNA
<213> ORGANISM: Artificial Sequence
<220> FEATURE:
<223> OTHER INFORMATION: Synthetic construct

<400> SEQUENCE: 203
cccgctcgag ttatttactc ctataacgag gtctcttaac                 40

<210> SEQ ID NO 204
<211> LENGTH: 34
<212> TYPE: DNA
<213> ORGANISM: Artificial Sequence
<220> FEATURE:
<223> OTHER INFORMATION: Synthetic construct

<400> SEQUENCE: 204
gggaattcca tatgggcatt tcccgcaaaa tatc                       34

<210> SEQ ID NO 205
<211> LENGTH: 32
<212> TYPE: DNA
<213> ORGANISM: Artificial Sequence
<220> FEATURE:
<223> OTHER INFORMATION: Synthetic construct

<400> SEQUENCE: 205
cccgctcgag ttacgtatca tatttcacgt gc                         32

<210> SEQ ID NO 206
<211> LENGTH: 35
<212> TYPE: DNA
<213> ORGANISM: Artificial Sequence
<220> FEATURE:
<223> OTHER INFORMATION: Synthetic construct

<400> SEQUENCE: 206
gggaattcca tatgcacgtg aaatatgata cgaag                      35

<210> SEQ ID NO 207
<211> LENGTH: 37
<212> TYPE: DNA
<213> ORGANISM: Artificial Sequence
<220> FEATURE:
<223> OTHER INFORMATION: Synthetic construct

<400> SEQUENCE: 207
cccgctcgag tttactccta taacgaggtc tcttaac                    37

<210> SEQ ID NO 208
<211> LENGTH: 36
<212> TYPE: DNA
<213> ORGANISM: Artificial Sequence
<220> FEATURE:
<223> OTHER INFORMATION: Synthetic construct

<400> SEQUENCE: 208
gggaattcca tatgtcagat ttggcaaacg attctt                     36

<210> SEQ ID NO 209
<211> LENGTH: 29
<212> TYPE: DNA
<213> ORGANISM: Artificial Sequence

```
<220> FEATURE:
<223> OTHER INFORMATION: Synthetic construct

<400> SEQUENCE: 209
cccgctcgag cgtatcatat ttcacgtgc                                29

<210> SEQ ID NO 210
<211> LENGTH: 36
<212> TYPE: DNA
<213> ORGANISM: Artificial Sequence
<220> FEATURE:
<223> OTHER INFORMATION: Synthetic construct

<400> SEQUENCE: 210
gggaattcca tatgtcagat ttggcaaacg attctt                        36

<210> SEQ ID NO 211
<211> LENGTH: 37
<212> TYPE: DNA
<213> ORGANISM: Artificial Sequence
<220> FEATURE:
<223> OTHER INFORMATION: Synthetic construct

<400> SEQUENCE: 211
cccgctcgag tttactccta taacgaggtc tcttaac                       37

<210> SEQ ID NO 212
<211> LENGTH: 35
<212> TYPE: DNA
<213> ORGANISM: Artificial Sequence
<220> FEATURE:
<223> OTHER INFORMATION: Synthetic construct

<400> SEQUENCE: 212
cgcggatccc atatgcaaaa tgcgttcaaa atccc                         35

<210> SEQ ID NO 213
<211> LENGTH: 32
<212> TYPE: DNA
<213> ORGANISM: Artificial Sequence
<220> FEATURE:
<223> OTHER INFORMATION: Synthetic construct

<400> SEQUENCE: 213
cgcggatccc atatgaacaa aatataccgc at                            32

<210> SEQ ID NO 214
<211> LENGTH: 29
<212> TYPE: DNA
<213> ORGANISM: Artificial Sequence
<220> FEATURE:
<223> OTHER INFORMATION: Synthetic construct

<400> SEQUENCE: 214
cccgctcgag tttgctttcg atagaacgg                                29

<210> SEQ ID NO 215
<211> LENGTH: 34
<212> TYPE: DNA
<213> ORGANISM: Artificial Sequence
<220> FEATURE:
<223> OTHER INFORMATION: Synthetic construct

<400> SEQUENCE: 215
gcggccatat ggtcataaaa tatacaaatt tgaa                          34
```

<210> SEQ ID NO 216
<211> LENGTH: 34
<212> TYPE: DNA
<213> ORGANISM: Artificial Sequence
<220> FEATURE:
<223> OTHER INFORMATION: Synthetic construct

<400> SEQUENCE: 216
gcggcctcga gttagcctga gacctttgca aatt        34

<210> SEQ ID NO 217
<211> LENGTH: 30
<212> TYPE: DNA
<213> ORGANISM: Artificial Sequence
<220> FEATURE:
<223> OTHER INFORMATION: Synthetic construct

<400> SEQUENCE: 217
gcggccatat gaaacagaaa aaaaccgctg        30

<210> SEQ ID NO 218
<211> LENGTH: 32
<212> TYPE: DNA
<213> ORGANISM: Artificial Sequence
<220> FEATURE:
<223> OTHER INFORMATION: Synthetic construct

<400> SEQUENCE: 218
gcggcctcga gttacggttt gacaccgttt tc        32

<210> SEQ ID NO 219
<211> LENGTH: 30
<212> TYPE: DNA
<213> ORGANISM: Artificial Sequence
<220> FEATURE:
<223> OTHER INFORMATION: Synthetic construct

<400> SEQUENCE: 219
cgcggatccc atatgaaaac cctgctcctc        30

<210> SEQ ID NO 220
<211> LENGTH: 27
<212> TYPE: DNA
<213> ORGANISM: Artificial Sequence
<220> FEATURE:
<223> OTHER INFORMATION: Synthetic construct

<400> SEQUENCE: 220
cccgctcgag ttatcctcct ttgcggc        27

<210> SEQ ID NO 221
<211> LENGTH: 30
<212> TYPE: DNA
<213> ORGANISM: Artificial Sequence
<220> FEATURE:
<223> OTHER INFORMATION: Synthetic construct

<400> SEQUENCE: 221
gcggccatat ggcaaaaatg atgaaatggg        30

<210> SEQ ID NO 222
<211> LENGTH: 29
<212> TYPE: DNA
<213> ORGANISM: Artificial Sequence
<220> FEATURE:
<223> OTHER INFORMATION: Synthetic construct

<400> SEQUENCE: 222

```
gcggcctcga gttatcggcg cggcgggcc                                      29
```

<210> SEQ ID NO 223
<211> LENGTH: 30
<212> TYPE: DNA
<213> ORGANISM: Artificial Sequence
<220> FEATURE:
<223> OTHER INFORMATION: Synthetic construct

<400> SEQUENCE: 223

```
gcggccatat gaaaaaatcc tccctcatca                                     30
```

<210> SEQ ID NO 224
<211> LENGTH: 32
<212> TYPE: DNA
<213> ORGANISM: Artificial Sequence
<220> FEATURE:
<223> OTHER INFORMATION: Synthetic construct

<400> SEQUENCE: 224

```
gcggcctcga gttatttgcc gccgttttg gc                                   32
```

<210> SEQ ID NO 225
<211> LENGTH: 31
<212> TYPE: DNA
<213> ORGANISM: Artificial Sequence
<220> FEATURE:
<223> OTHER INFORMATION: Synthetic construct

<400> SEQUENCE: 225

```
gcggccatat ggccctgcc gacgcggtaa g                                    31
```

<210> SEQ ID NO 226
<211> LENGTH: 33
<212> TYPE: DNA
<213> ORGANISM: Artificial Sequence
<220> FEATURE:
<223> OTHER INFORMATION: Synthetic construct

<400> SEQUENCE: 226

```
gcggcctcga gtttgccgcc gttttggct ttc                                  33
```

<210> SEQ ID NO 227
<211> LENGTH: 30
<212> TYPE: DNA
<213> ORGANISM: Artificial Sequence
<220> FEATURE:
<223> OTHER INFORMATION: Synthetic construct

<400> SEQUENCE: 227

```
gcggccatat gaaacacata ctccccctga                                     30
```

<210> SEQ ID NO 228
<211> LENGTH: 32
<212> TYPE: DNA
<213> ORGANISM: Artificial Sequence
<220> FEATURE:
<223> OTHER INFORMATION: Synthetic construct

<400> SEQUENCE: 228

```
gcggcctcga gttattcgcc tacggttttt tg                                  32
```

<210> SEQ ID NO 229
<211> LENGTH: 30
<212> TYPE: DNA
<213> ORGANISM: Artificial Sequence -continued
<220> FEATURE:
<223> OTHER INFORMATION: Synthetic construct

<400> SEQUENCE: 229
gcggccatat gatttacatc gtactgtttc          30

<210> SEQ ID NO 230
<211> LENGTH: 32
<212> TYPE: DNA
<213> ORGANISM: Artificial Sequence
<220> FEATURE:
<223> OTHER INFORMATION: Synthetic construct

<400> SEQUENCE: 230
gcggcctcga gttaggagaa caggcgcaat gc          32

<210> SEQ ID NO 231
<211> LENGTH: 32
<212> TYPE: DNA
<213> ORGANISM: Artificial Sequence
<220> FEATURE:
<223> OTHER INFORMATION: Synthetic construct

<400> SEQUENCE: 231
gcggccatat gtacaacatg tatcaggaaa ac          32

<210> SEQ ID NO 232
<211> LENGTH: 31
<212> TYPE: DNA
<213> ORGANISM: Artificial Sequence
<220> FEATURE:
<223> OTHER INFORMATION: Synthetic construct

<400> SEQUENCE: 232
gcggcctcga gggagaacag gcgcaatgcg g          31

<210> SEQ ID NO 233
<211> LENGTH: 29
<212> TYPE: DNA
<213> ORGANISM: Artificial Sequence
<220> FEATURE:
<223> OTHER INFORMATION: Synthetic construct

<400> SEQUENCE: 233
cgcggatccg ctagctgcgg cacggcggg          29

<210> SEQ ID NO 234
<211> LENGTH: 28
<212> TYPE: DNA
<213> ORGANISM: Artificial Sequence
<220> FEATURE:
<223> OTHER INFORMATION: Synthetic construct

<400> SEQUENCE: 234
cccgctcgag ataacggtat gccgccag          28

<210> SEQ ID NO 235
<211> LENGTH: 31
<212> TYPE: DNA
<213> ORGANISM: Artificial Sequence
<220> FEATURE:
<223> OTHER INFORMATION: Synthetic construct

<400> SEQUENCE: 235
cgcggatccc atatggaatc aacactttca c          31

<210> SEQ ID NO 236
<211> LENGTH: 27
<212> TYPE: DNA
<213> ORGANISM: Artificial Sequence
<220> FEATURE:
<223> OTHER INFORMATION: Synthetic construct

<400> SEQUENCE: 236
cccgctcgag ttacacgcgg ttgctgt                                27

<210> SEQ ID NO 237
<211> LENGTH: 31
<212> TYPE: DNA
<213> ORGANISM: Artificial Sequence
<220> FEATURE:
<223> OTHER INFORMATION: Synthetic construct

<400> SEQUENCE: 237
cgcggatccc atatgaacaa cagacatttt g                           31

<210> SEQ ID NO 238
<211> LENGTH: 28
<212> TYPE: DNA
<213> ORGANISM: Artificial Sequence
<220> FEATURE:
<223> OTHER INFORMATION: Synthetic construct

<400> SEQUENCE: 238
cccgctcgag ttacctgtcc ggtaaaag                               28

<210> SEQ ID NO 239
<211> LENGTH: 33
<212> TYPE: DNA
<213> ORGANISM: Artificial Sequence
<220> FEATURE:
<223> OTHER INFORMATION: Synthetic construct

<400> SEQUENCE: 239
cgcggatccg ctagcaccgt catcaaacag gaa                         33

<210> SEQ ID NO 240
<211> LENGTH: 27
<212> TYPE: DNA
<213> ORGANISM: Artificial Sequence
<220> FEATURE:
<223> OTHER INFORMATION: Synthetic construct

<400> SEQUENCE: 240
cccgctcgag tcaagattcg acgggga                                27

<210> SEQ ID NO 241
<211> LENGTH: 31
<212> TYPE: DNA
<213> ORGANISM: Artificial Sequence
<220> FEATURE:
<223> OTHER INFORMATION: Synthetic construct

<400> SEQUENCE: 241
cgcggatccc atatgtccgc aaacgaatac g                           31

<210> SEQ ID NO 242
<211> LENGTH: 28
<212> TYPE: DNA
<213> ORGANISM: Artificial Sequence
<220> FEATURE:
<223> OTHER INFORMATION: Synthetic construct

<400> SEQUENCE: 242

```
cccgctcgag tcagtgttct gccagttt                                28
```

<210> SEQ ID NO 243
<211> LENGTH: 29
<212> TYPE: DNA
<213> ORGANISM: Artificial Sequence
<220> FEATURE:
<223> OTHER INFORMATION: Synthetic construct

<400> SEQUENCE: 243

```
cgcggatccc atatgccgtc tgaaacacg                               29
```

<210> SEQ ID NO 244
<211> LENGTH: 28
<212> TYPE: DNA
<213> ORGANISM: Artificial Sequence
<220> FEATURE:
<223> OTHER INFORMATION: Synthetic construct

<400> SEQUENCE: 244

```
cccgctcgag ttagcggagc agttttc                                 28
```

<210> SEQ ID NO 245
<211> LENGTH: 28
<212> TYPE: DNA
<213> ORGANISM: Artificial Sequence
<220> FEATURE:
<223> OTHER INFORMATION: Synthetic construct

<400> SEQUENCE: 245

```
cgcggatccc atatgaccgc catcagcc                                28
```

<210> SEQ ID NO 246
<211> LENGTH: 27
<212> TYPE: DNA
<213> ORGANISM: Artificial Sequence
<220> FEATURE:
<223> OTHER INFORMATION: Synthetic construct

<400> SEQUENCE: 246

```
cccgctcgag ttaaagccgg gtaacgc                                 27
```

<210> SEQ ID NO 247
<211> LENGTH: 31
<212> TYPE: DNA
<213> ORGANISM: Artificial Sequence
<220> FEATURE:
<223> OTHER INFORMATION: Synthetic construct

<400> SEQUENCE: 247

```
gcggccatat ggaaacacag ctttacatcg g                            31
```

<210> SEQ ID NO 248
<211> LENGTH: 30
<212> TYPE: DNA
<213> ORGANISM: Artificial Sequence
<220> FEATURE:
<223> OTHER INFORMATION: Synthetic construct

<400> SEQUENCE: 248

```
gcggcctcga gtcaataata atatcccgcg                              30
```

<210> SEQ ID NO 249
<211> LENGTH: 30
<212> TYPE: DNA
<213> ORGANISM: Artificial Sequence

```
<220> FEATURE:
<223> OTHER INFORMATION: Synthetic construct

<400> SEQUENCE: 249
gcggccatat gattaaaatc cgcaatatcc                                      30

<210> SEQ ID NO 250
<211> LENGTH: 36
<212> TYPE: DNA
<213> ORGANISM: Artificial Sequence
<220> FEATURE:
<223> OTHER INFORMATION: Synthetic construct

<400> SEQUENCE: 250
gcggcctcga gttaaatctt ggtagattgg atttgg                               36

<210> SEQ ID NO 251
<211> LENGTH: 30
<212> TYPE: DNA
<213> ORGANISM: Artificial Sequence
<220> FEATURE:
<223> OTHER INFORMATION: Synthetic construct

<400> SEQUENCE: 251
gcggccatat gactgacaac gcactgctcc                                      30

<210> SEQ ID NO 252
<211> LENGTH: 31
<212> TYPE: DNA
<213> ORGANISM: Artificial Sequence
<220> FEATURE:
<223> OTHER INFORMATION: Synthetic construct

<400> SEQUENCE: 252
gcggcctcga gtcagaccgc gttgtcgaaa c                                    31

<210> SEQ ID NO 253
<211> LENGTH: 32
<212> TYPE: DNA
<213> ORGANISM: Artificial Sequence
<220> FEATURE:
<223> OTHER INFORMATION: Synthetic construct

<400> SEQUENCE: 253
cgcggatccc atatggcgtt aaaaacatca aa                                   32

<210> SEQ ID NO 254
<211> LENGTH: 27
<212> TYPE: DNA
<213> ORGANISM: Artificial Sequence
<220> FEATURE:
<223> OTHER INFORMATION: Synthetic construct

<400> SEQUENCE: 254
cccgctcgag tcagcccttc atacagc                                         27

<210> SEQ ID NO 255
<211> LENGTH: 32
<212> TYPE: DNA
<213> ORGANISM: Artificial Sequence
<220> FEATURE:
<223> OTHER INFORMATION: Synthetic construct

<400> SEQUENCE: 255
gcggcattaa tggcacaaac tacactcaaa cc                                   32
```

```
<210> SEQ ID NO 256
<211> LENGTH: 33
<212> TYPE: DNA
<213> ORGANISM: Artificial Sequence
<220> FEATURE:
<223> OTHER INFORMATION: Synthetic construct

<400> SEQUENCE: 256
gcggcctcga gttaaaactt cacgttcacg ccg                                    33

<210> SEQ ID NO 257
<211> LENGTH: 34
<212> TYPE: DNA
<213> ORGANISM: Artificial Sequence
<220> FEATURE:
<223> OTHER INFORMATION: Synthetic construct

<400> SEQUENCE: 257
gcggcattaa tgcatgaaac tgagcaatcg gtgg                                   34

<210> SEQ ID NO 258
<211> LENGTH: 38
<212> TYPE: DNA
<213> ORGANISM: Artificial Sequence
<220> FEATURE:
<223> OTHER INFORMATION: Synthetic construct

<400> SEQUENCE: 258
gcggcctcga gaaacttcac gttcacgccg ccggtaaa                               38

<210> SEQ ID NO 259
<211> LENGTH: 33
<212> TYPE: DNA
<213> ORGANISM: Artificial Sequence
<220> FEATURE:
<223> OTHER INFORMATION: Synthetic construct

<400> SEQUENCE: 259
cgcggatccc atatgggcaa atccgaaaat acg                                    33

<210> SEQ ID NO 260
<211> LENGTH: 26
<212> TYPE: DNA
<213> ORGANISM: Artificial Sequence
<220> FEATURE:
<223> OTHER INFORMATION: Synthetic construct

<400> SEQUENCE: 260
cccgctcgag ataatggcgg cggcgg                                            26

<210> SEQ ID NO 261
<211> LENGTH: 29
<212> TYPE: DNA
<213> ORGANISM: Artificial Sequence
<220> FEATURE:
<223> OTHER INFORMATION: Synthetic construct

<400> SEQUENCE: 261
cgcggatccc atatgtttcc ccccgacaa                                         29

<210> SEQ ID NO 262
<211> LENGTH: 31
<212> TYPE: DNA
<213> ORGANISM: Artificial Sequence
<220> FEATURE:
<223> OTHER INFORMATION: Synthetic construct

<400> SEQUENCE: 262
```

```
cccgctcgag tcattctgta aaaaaagtat g                              31
```

<210> SEQ ID NO 263
<211> LENGTH: 32
<212> TYPE: DNA
<213> ORGANISM: Artificial Sequence
<220> FEATURE:
<223> OTHER INFORMATION: Synthetic construct

<400> SEQUENCE: 263

```
cgcggatccc atatgcttca aagcgacagc ag                             32
```

<210> SEQ ID NO 264
<211> LENGTH: 29
<212> TYPE: DNA
<213> ORGANISM: Artificial Sequence
<220> FEATURE:
<223> OTHER INFORMATION: Synthetic construct

<400> SEQUENCE: 264

```
cccgctcgag ttcggatttt tgcgtactc                                 29
```

<210> SEQ ID NO 265
<211> LENGTH: 31
<212> TYPE: DNA
<213> ORGANISM: Artificial Sequence
<220> FEATURE:
<223> OTHER INFORMATION: Synthetic construct

<400> SEQUENCE: 265

```
cgcggatccc atatggcaat ggcagaaaac g                              31
```

<210> SEQ ID NO 266
<211> LENGTH: 27
<212> TYPE: DNA
<213> ORGANISM: Artificial Sequence
<220> FEATURE:
<223> OTHER INFORMATION: Synthetic construct

<400> SEQUENCE: 266

```
cccgctcgag ctatacaatc cgtgccg                                   27
```

<210> SEQ ID NO 267
<211> LENGTH: 32
<212> TYPE: DNA
<213> ORGANISM: Artificial Sequence
<220> FEATURE:
<223> OTHER INFORMATION: Synthetic construct

<400> SEQUENCE: 267

```
cgcggatccc atatggattc tttttttcaaa cc                            32
```

<210> SEQ ID NO 268
<211> LENGTH: 27
<212> TYPE: DNA
<213> ORGANISM: Artificial Sequence
<220> FEATURE:
<223> OTHER INFORMATION: Synthetic construct

<400> SEQUENCE: 268

```
cccgctcgag tcagttcaga aagcggg                                   27
```

<210> SEQ ID NO 269
<211> LENGTH: 32
<212> TYPE: DNA
<213> ORGANISM: Artificial Sequence

```
<220> FEATURE:
<223> OTHER INFORMATION: Synthetic construct

<400> SEQUENCE: 269
cgcggatccc atatgaaacc tttgatttta gg                                      32

<210> SEQ ID NO 270
<211> LENGTH: 28
<212> TYPE: DNA
<213> ORGANISM: Artificial Sequence
<220> FEATURE:
<223> OTHER INFORMATION: Synthetic construct

<400> SEQUENCE: 270
cccgctcgag ttatttgggc tgctcttc                                           28

<210> SEQ ID NO 271
<211> LENGTH: 30
<212> TYPE: DNA
<213> ORGANISM: Artificial Sequence
<220> FEATURE:
<223> OTHER INFORMATION: Synthetic construct

<400> SEQUENCE: 271
cgcggatccc atatggtaat cgtctggttg                                         30

<210> SEQ ID NO 272
<211> LENGTH: 27
<212> TYPE: DNA
<213> ORGANISM: Artificial Sequence
<220> FEATURE:
<223> OTHER INFORMATION: Synthetic construct

<400> SEQUENCE: 272
cccgctcgag ctacgacttg gttaccg                                            27

<210> SEQ ID NO 273
<211> LENGTH: 33
<212> TYPE: DNA
<213> ORGANISM: Artificial Sequence
<220> FEATURE:
<223> OTHER INFORMATION: Synthetic construct

<400> SEQUENCE: 273
gcggccatat gagacgtaaa atgctaaagc tac                                     33

<210> SEQ ID NO 274
<211> LENGTH: 31
<212> TYPE: DNA
<213> ORGANISM: Artificial Sequence
<220> FEATURE:
<223> OTHER INFORMATION: Synthetic construct

<400> SEQUENCE: 274
gcggcctcga gtcaaagtgt tctgtttgcg c                                       31

<210> SEQ ID NO 275
<211> LENGTH: 30
<212> TYPE: DNA
<213> ORGANISM: Artificial Sequence
<220> FEATURE:
<223> OTHER INFORMATION: Synthetic construct

<400> SEQUENCE: 275
gccgccatat gttgacttta acccgaaaaa                                         30
```

```
<210> SEQ ID NO 276
<211> LENGTH: 34
<212> TYPE: DNA
<213> ORGANISM: Artificial Sequence
<220> FEATURE:
<223> OTHER INFORMATION: Synthetic construct

<400> SEQUENCE: 276
gccgcctcga ggccggcggt caataccgcc cgaa                              34

<210> SEQ ID NO 277
<211> LENGTH: 32
<212> TYPE: DNA
<213> ORGANISM: Artificial Sequence
<220> FEATURE:
<223> OTHER INFORMATION: Synthetic construct

<400> SEQUENCE: 277
cgcggatccc atatggcgca atgcgatttg ac                                32

<210> SEQ ID NO 278
<211> LENGTH: 27
<212> TYPE: DNA
<213> ORGANISM: Artificial Sequence
<220> FEATURE:
<223> OTHER INFORMATION: Synthetic construct

<400> SEQUENCE: 278
cccgctcgag ttcggcggta aatgccg                                      27

<210> SEQ ID NO 279
<211> LENGTH: 28
<212> TYPE: DNA
<213> ORGANISM: Artificial Sequence
<220> FEATURE:
<223> OTHER INFORMATION: Synthetic construct

<400> SEQUENCE: 279
gcggccatat ggcggggccg attttttgt                                    28

<210> SEQ ID NO 280
<211> LENGTH: 33
<212> TYPE: DNA
<213> ORGANISM: Artificial Sequence
<220> FEATURE:
<223> OTHER INFORMATION: Synthetic construct

<400> SEQUENCE: 280
gcggcctcga gttatttgct ttcagtatta ttg                               33

<210> SEQ ID NO 281
<211> LENGTH: 30
<212> TYPE: DNA
<213> ORGANISM: Artificial Sequence
<220> FEATURE:
<223> OTHER INFORMATION: Synthetic construct

<400> SEQUENCE: 281
gcggccatat gaactttgct ttatccgtca                                   30

<210> SEQ ID NO 282
<211> LENGTH: 32
<212> TYPE: DNA
<213> ORGANISM: Artificial Sequence
<220> FEATURE:
<223> OTHER INFORMATION: Synthetic construct

<400> SEQUENCE: 282
```
gcggcctcga gttaacggca gtatttgttt ac					32

<210> SEQ ID NO 283
<211> LENGTH: 31
<212> TYPE: DNA
<213> ORGANISM: Artificial Sequence
<220> FEATURE:
<223> OTHER INFORMATION: Synthetic construct

<400> SEQUENCE: 283
cgcggatccc atatgggttt gcgcttcggg c					31

<210> SEQ ID NO 284
<211> LENGTH: 29
<212> TYPE: DNA
<213> ORGANISM: Artificial Sequence
<220> FEATURE:
<223> OTHER INFORMATION: Synthetic construct

<400> SEQUENCE: 284
gcccaagctt ttttcctttg ccgtttccg						29

<210> SEQ ID NO 285
<211> LENGTH: 32
<212> TYPE: DNA
<213> ORGANISM: Artificial Sequence
<220> FEATURE:
<223> OTHER INFORMATION: Synthetic construct

<400> SEQUENCE: 285
cgcggatccc atatggccga cctttccgaa aa					32

<210> SEQ ID NO 286
<211> LENGTH: 27
<212> TYPE: DNA
<213> ORGANISM: Artificial Sequence
<220> FEATURE:
<223> OTHER INFORMATION: Synthetic construct

<400> SEQUENCE: 286
cccgctcgag gaagcgcgtt cccaagc						27

<210> SEQ ID NO 287
<211> LENGTH: 29
<212> TYPE: DNA
<213> ORGANISM: Artificial Sequence
<220> FEATURE:
<223> OTHER INFORMATION: Synthetic construct

<400> SEQUENCE: 287
cgcggatccc atatgcacga cacccgtac						29

<210> SEQ ID NO 288
<211> LENGTH: 28
<212> TYPE: DNA
<213> ORGANISM: Artificial Sequence
<220> FEATURE:
<223> OTHER INFORMATION: Synthetic construct

<400> SEQUENCE: 288
cccgctcgag ttagaagcgc gttcccaa						28

<210> SEQ ID NO 289
<211> LENGTH: 34
<212> TYPE: DNA
<213> ORGANISM: Artificial Sequence

```
<220> FEATURE:
<223> OTHER INFORMATION: Synthetic construct

<400> SEQUENCE: 289
ctagctagct ttaaacgcag cgtaatcgca atgg                         34

<210> SEQ ID NO 290
<211> LENGTH: 31
<212> TYPE: DNA
<213> ORGANISM: Artificial Sequence
<220> FEATURE:
<223> OTHER INFORMATION: Synthetic construct

<400> SEQUENCE: 290
cccgctcgag tcaatcctgc tcttttttgc c                            31

<210> SEQ ID NO 291
<211> LENGTH: 25
<212> TYPE: DNA
<213> ORGANISM: Artificial Sequence
<220> FEATURE:
<223> OTHER INFORMATION: Synthetic construct

<400> SEQUENCE: 291
ctagctagcg ggggcggcgg tggcg                                   25

<210> SEQ ID NO 292
<211> LENGTH: 31
<212> TYPE: DNA
<213> ORGANISM: Artificial Sequence
<220> FEATURE:
<223> OTHER INFORMATION: Synthetic construct

<400> SEQUENCE: 292
cccgctcgag tcaatcctgc tcttttttgc c                            31

<210> SEQ ID NO 293
<211> LENGTH: 40
<212> TYPE: DNA
<213> ORGANISM: Artificial Sequence
<220> FEATURE:
<223> OTHER INFORMATION: Synthetic construct

<400> SEQUENCE: 293
ctagctagcg ctcatcctcg ccgcctgcgg gggcggcggt                   40

<210> SEQ ID NO 294
<211> LENGTH: 31
<212> TYPE: DNA
<213> ORGANISM: Artificial Sequence
<220> FEATURE:
<223> OTHER INFORMATION: Synthetic construct

<400> SEQUENCE: 294
cccgctcgag tcaatcctgc tcttttttgc c                            31

<210> SEQ ID NO 295
<211> LENGTH: 25
<212> TYPE: DNA
<213> ORGANISM: Artificial Sequence
<220> FEATURE:
<223> OTHER INFORMATION: Synthetic construct

<400> SEQUENCE: 295
cggggatccg ggggcggcgg tggcg                                   25
```

```
<210> SEQ ID NO 296
<211> LENGTH: 31
<212> TYPE: DNA
<213> ORGANISM: Artificial Sequence
<220> FEATURE:
<223> OTHER INFORMATION: Synthetic construct

<400> SEQUENCE: 296
cccgctcgag tcaatcctgc tcttttttgc c                              31

<210> SEQ ID NO 297
<211> LENGTH: 25
<212> TYPE: DNA
<213> ORGANISM: Artificial Sequence
<220> FEATURE:
<223> OTHER INFORMATION: Synthetic construct

<400> SEQUENCE: 297
ctagctagcg ggggcggcgg tggcg                                     25

<210> SEQ ID NO 298
<211> LENGTH: 28
<212> TYPE: DNA
<213> ORGANISM: Artificial Sequence
<220> FEATURE:
<223> OTHER INFORMATION: Synthetic construct

<400> SEQUENCE: 298
cccgctcgag atcctgctct tttttgcc                                  28

<210> SEQ ID NO 299
<211> LENGTH: 28
<212> TYPE: DNA
<213> ORGANISM: Artificial Sequence
<220> FEATURE:
<223> OTHER INFORMATION: Synthetic construct

<400> SEQUENCE: 299
ctagctagct gcggggcgg cggtggcg                                   28

<210> SEQ ID NO 300
<211> LENGTH: 28
<212> TYPE: DNA
<213> ORGANISM: Artificial Sequence
<220> FEATURE:
<223> OTHER INFORMATION: Synthetic construct

<400> SEQUENCE: 300
cccgctcgag atcctgctct tttttgcc                                  28

<210> SEQ ID NO 301
<211> LENGTH: 32
<212> TYPE: DNA
<213> ORGANISM: Artificial Sequence
<220> FEATURE:
<223> OTHER INFORMATION: Synthetic construct

<400> SEQUENCE: 301
cgcggatccg ctagccccga tgttaaatcg gc                             32

<210> SEQ ID NO 302
<211> LENGTH: 32
<212> TYPE: DNA
<213> ORGANISM: Artificial Sequence
<220> FEATURE:
<223> OTHER INFORMATION: Synthetic construct

<400> SEQUENCE: 302
```
cgcggatccg ctagccaaga tatggcggca gt                                           32

<210> SEQ ID NO 303
<211> LENGTH: 32
<212> TYPE: DNA
<213> ORGANISM: Artificial Sequence
<220> FEATURE:
<223> OTHER INFORMATION: Synthetic construct

<400> SEQUENCE: 303
cgcggatccg ctagcgccga atccgcaaat ca                                           32

<210> SEQ ID NO 304
<211> LENGTH: 32
<212> TYPE: DNA
<213> ORGANISM: Artificial Sequence
<220> FEATURE:
<223> OTHER INFORMATION: Synthetic construct

<400> SEQUENCE: 304
cgcgctagcg gaagggttga tttggctaat gg                                           32

<210> SEQ ID NO 305
<211> LENGTH: 32
<212> TYPE: DNA
<213> ORGANISM: Artificial Sequence
<220> FEATURE:
<223> OTHER INFORMATION: Synthetic construct

<400> SEQUENCE: 305
cgcgctagcg gaagggttga tttggctaat gg                                           32

<210> SEQ ID NO 306
<211> LENGTH: 29
<212> TYPE: DNA
<213> ORGANISM: Artificial Sequence
<220> FEATURE:
<223> OTHER INFORMATION: Synthetic construct

<400> SEQUENCE: 306
cgccatatgt ttaaacgcag cgtaatcgc                                               29

<210> SEQ ID NO 307
<211> LENGTH: 34
<212> TYPE: DNA
<213> ORGANISM: Artificial Sequence
<220> FEATURE:
<223> OTHER INFORMATION: Synthetic construct

<400> SEQUENCE: 307
cccgctcgag aaaattgcta ccgccattcg cagg                                         34

<210> SEQ ID NO 308
<211> LENGTH: 32
<212> TYPE: DNA
<213> ORGANISM: Artificial Sequence
<220> FEATURE:
<223> OTHER INFORMATION: Synthetic construct

<400> SEQUENCE: 308
cgccatatgg gaagggttga tttggctaat gg                                           32

<210> SEQ ID NO 309
<211> LENGTH: 38
<212> TYPE: DNA
<213> ORGANISM: Artificial Sequence

```
<220> FEATURE:
<223> OTHER INFORMATION: Synthetic construct

<400> SEQUENCE: 309
cccgctcgag cttgtcttta taaatgatga catatttg                               38

<210> SEQ ID NO 310
<211> LENGTH: 40
<212> TYPE: DNA
<213> ORGANISM: Artificial Sequence
<220> FEATURE:
<223> OTHER INFORMATION: Synthetic construct

<400> SEQUENCE: 310
cccgctcgag tttataaaag ataatatatt gattgattcc                             40

<210> SEQ ID NO 311
<211> LENGTH: 31
<212> TYPE: DNA
<213> ORGANISM: Artificial Sequence
<220> FEATURE:
<223> OTHER INFORMATION: Synthetic construct

<400> SEQUENCE: 311
cgcgctagca tgccgctgat tcccgtcaat c                                      31

<210> SEQ ID NO 312
<211> LENGTH: 25
<212> TYPE: DNA
<213> ORGANISM: Artificial Sequence
<220> FEATURE:
<223> OTHER INFORMATION: Synthetic construct

<400> SEQUENCE: 312
ctagctagcg ggggcggcgg tggcg                                             25

<210> SEQ ID NO 313
<211> LENGTH: 31
<212> TYPE: DNA
<213> ORGANISM: Artificial Sequence
<220> FEATURE:
<223> OTHER INFORMATION: Synthetic construct

<400> SEQUENCE: 313
cccgctcgag tcaatcctgc tcttttttgc c                                      31

<210> SEQ ID NO 314
<211> LENGTH: 32
<212> TYPE: DNA
<213> ORGANISM: Artificial Sequence
<220> FEATURE:
<223> OTHER INFORMATION: Synthetic construct

<400> SEQUENCE: 314
cgcggatccg ctagccccga tgttaaatcg gc                                     32

<210> SEQ ID NO 315
<211> LENGTH: 28
<212> TYPE: DNA
<213> ORGANISM: Artificial Sequence
<220> FEATURE:
<223> OTHER INFORMATION: Synthetic construct

<400> SEQUENCE: 315
cccgctcgag atcctgctct tttttgcc                                          28
```

```
<210> SEQ ID NO 316
<211> LENGTH: 32
<212> TYPE: DNA
<213> ORGANISM: Artificial Sequence
<220> FEATURE:
<223> OTHER INFORMATION: Synthetic construct

<400> SEQUENCE: 316
cgcggatccg ctagccccga tgttaaatcg gc                              32

<210> SEQ ID NO 317
<211> LENGTH: 31
<212> TYPE: DNA
<213> ORGANISM: Artificial Sequence
<220> FEATURE:
<223> OTHER INFORMATION: Synthetic construct

<400> SEQUENCE: 317
cccgctcgag tcaatcctgc tcttttttgc c                               31

<210> SEQ ID NO 318
<211> LENGTH: 87
<212> TYPE: DNA
<213> ORGANISM: Artificial Sequence
<220> FEATURE:
<223> OTHER INFORMATION: Synthetic construct

<400> SEQUENCE: 318
cgcggatccg ctagctttga acgcagtgtg attgcaatgg cttgtatttt tgccctttca    60
gcctgttcgc ccgatgttaa atcggcg                                       87

<210> SEQ ID NO 319
<211> LENGTH: 31
<212> TYPE: DNA
<213> ORGANISM: Artificial Sequence
<220> FEATURE:
<223> OTHER INFORMATION: Synthetic construct

<400> SEQUENCE: 319
cccgctcgag tcaatcctgc tcttttttgc c                               31

<210> SEQ ID NO 320
<211> LENGTH: 90
<212> TYPE: DNA
<213> ORGANISM: Artificial Sequence
<220> FEATURE:
<223> OTHER INFORMATION: Synthetic construct

<400> SEQUENCE: 320
cgcggatccg ctagcaaaac cttcttcaaa accctttccg ccgccgcact cgcgctcatc    60
ctcgccgcct gctcgcccga tgttaaatcg                                    90

<210> SEQ ID NO 321
<211> LENGTH: 31
<212> TYPE: DNA
<213> ORGANISM: Artificial Sequence
<220> FEATURE:
<223> OTHER INFORMATION: Synthetic construct

<400> SEQUENCE: 321
cccgctcgag tcaatcctgc tcttttttgc c                               31

<210> SEQ ID NO 322
<211> LENGTH: 33
<212> TYPE: DNA
<213> ORGANISM: Artificial Sequence
```

```
<220> FEATURE:
<223> OTHER INFORMATION: Synthetic construct

<400> SEQUENCE: 322
cgcggatccc atatgaaaac caagttaatc aaa                                33

<210> SEQ ID NO 323
<211> LENGTH: 30
<212> TYPE: DNA
<213> ORGANISM: Artificial Sequence
<220> FEATURE:
<223> OTHER INFORMATION: Synthetic construct

<400> SEQUENCE: 323
cccgctcgag ttattgattt ttgcggatga                                   30

<210> SEQ ID NO 324
<211> LENGTH: 34
<212> TYPE: DNA
<213> ORGANISM: Artificial Sequence
<220> FEATURE:
<223> OTHER INFORMATION: Synthetic construct

<400> SEQUENCE: 324
cgcggatccc atatgttaaa tcgggtattt tatc                              34

<210> SEQ ID NO 325
<211> LENGTH: 28
<212> TYPE: DNA
<213> ORGANISM: Artificial Sequence
<220> FEATURE:
<223> OTHER INFORMATION: Synthetic construct

<400> SEQUENCE: 325
cccgctcgag ttaatccgcc attccctg                                     28

<210> SEQ ID NO 326
<211> LENGTH: 30
<212> TYPE: DNA
<213> ORGANISM: Artificial Sequence
<220> FEATURE:
<223> OTHER INFORMATION: Synthetic construct

<400> SEQUENCE: 326
gcggccatat gaaattacaa caattggctg                                   30

<210> SEQ ID NO 327
<211> LENGTH: 31
<212> TYPE: DNA
<213> ORGANISM: Artificial Sequence
<220> FEATURE:
<223> OTHER INFORMATION: Synthetic construct

<400> SEQUENCE: 327
gcggcctcga gttaccttac gtttttcaaa g                                 31

<210> SEQ ID NO 328
<211> LENGTH: 29
<212> TYPE: DNA
<213> ORGANISM: Artificial Sequence
<220> FEATURE:
<223> OTHER INFORMATION: Synthetic construct

<400> SEQUENCE: 328
cgcggatccc atatgcaagc acggctgct                                    29
```

```
<210> SEQ ID NO 329
<211> LENGTH: 29
<212> TYPE: DNA
<213> ORGANISM: Artificial Sequence
<220> FEATURE:
<223> OTHER INFORMATION: Synthetic construct

<400> SEQUENCE: 329
cccgctcgag tcaaggttgt ccttgtcta                               29

<210> SEQ ID NO 330
<211> LENGTH: 30
<212> TYPE: DNA
<213> ORGANISM: Artificial Sequence
<220> FEATURE:
<223> OTHER INFORMATION: Synthetic construct

<400> SEQUENCE: 330
cgcggatccc atatgatgaa accgcacaac                              30

<210> SEQ ID NO 331
<211> LENGTH: 28
<212> TYPE: DNA
<213> ORGANISM: Artificial Sequence
<220> FEATURE:
<223> OTHER INFORMATION: Synthetic construct

<400> SEQUENCE: 331
cccgctcgag tcagttgctc aacacgtc                                28

<210> SEQ ID NO 332
<211> LENGTH: 32
<212> TYPE: DNA
<213> ORGANISM: Artificial Sequence
<220> FEATURE:
<223> OTHER INFORMATION: Synthetic construct

<400> SEQUENCE: 332
cgcggatccc atatggtaga cgcgcttaag ca                           32

<210> SEQ ID NO 333
<211> LENGTH: 25
<212> TYPE: DNA
<213> ORGANISM: Artificial Sequence
<220> FEATURE:
<223> OTHER INFORMATION: Synthetic construct

<400> SEQUENCE: 333
cccgctcgag agctgcatgg cggcg                                   25

<210> SEQ ID NO 334
<211> LENGTH: 30
<212> TYPE: DNA
<213> ORGANISM: Artificial Sequence
<220> FEATURE:
<223> OTHER INFORMATION: Synthetic construct

<400> SEQUENCE: 334
cgcggatccc atatggcacg gtcgttatac                              30

<210> SEQ ID NO 335
<211> LENGTH: 26
<212> TYPE: DNA
<213> ORGANISM: Artificial Sequence
<220> FEATURE:
<223> OTHER INFORMATION: Synthetic construct

<400> SEQUENCE: 335
```

```
cccgctcgag ctaccgcgca ttcctg                                              26
```

<210> SEQ ID NO 336
<211> LENGTH: 31
<212> TYPE: DNA
<213> ORGANISM: Artificial Sequence
<220> FEATURE:
<223> OTHER INFORMATION: Synthetic construct

<400> SEQUENCE: 336

```
gcggccatat ggaattttc attatcttgt t                                         31
```

<210> SEQ ID NO 337
<211> LENGTH: 31
<212> TYPE: DNA
<213> ORGANISM: Artificial Sequence
<220> FEATURE:
<223> OTHER INFORMATION: Synthetic construct

<400> SEQUENCE: 337

```
gcggcctcga gttatttggc ggttttgctg c                                        31
```

<210> SEQ ID NO 338
<211> LENGTH: 32
<212> TYPE: DNA
<213> ORGANISM: Artificial Sequence
<220> FEATURE:
<223> OTHER INFORMATION: Synthetic construct

<400> SEQUENCE: 338

```
gcggccatat gaagtatgtc cggttatttt tc                                       32
```

<210> SEQ ID NO 339
<211> LENGTH: 30
<212> TYPE: DNA
<213> ORGANISM: Artificial Sequence
<220> FEATURE:
<223> OTHER INFORMATION: Synthetic construct

<400> SEQUENCE: 339

```
gcggcctcga gttatcggct tgtgcaacgg                                          30
```

<210> SEQ ID NO 340
<211> LENGTH: 32
<212> TYPE: DNA
<213> ORGANISM: Artificial Sequence
<220> FEATURE:
<223> OTHER INFORMATION: Synthetic construct

<400> SEQUENCE: 340

```
cgcggatccg ctagctccgg cagcaaaacc ga                                       32
```

<210> SEQ ID NO 341
<211> LENGTH: 28
<212> TYPE: DNA
<213> ORGANISM: Artificial Sequence
<220> FEATURE:
<223> OTHER INFORMATION: Synthetic construct

<400> SEQUENCE: 341

```
gcccaagctt acgcagttcg gaatggag                                            28
```

<210> SEQ ID NO 342
<211> LENGTH: 35
<212> TYPE: DNA
<213> ORGANISM: Artificial Sequence -continued
<220> FEATURE:
<223> OTHER INFORMATION: Synthetic construct

<400> SEQUENCE: 342
gccgccatat gttgaatatt aaactgaaaa ccttg                             35

<210> SEQ ID NO 343
<211> LENGTH: 32
<212> TYPE: DNA
<213> ORGANISM: Artificial Sequence
<220> FEATURE:
<223> OTHER INFORMATION: Synthetic construct

<400> SEQUENCE: 343
gccgcctcga gttatttctg atgccttttc cc                               32

<210> SEQ ID NO 344
<211> LENGTH: 29
<212> TYPE: DNA
<213> ORGANISM: Artificial Sequence
<220> FEATURE:
<223> OTHER INFORMATION: Synthetic construct

<400> SEQUENCE: 344
gccgccatat ggacaataag accaaactg                                   29

<210> SEQ ID NO 345
<211> LENGTH: 30
<212> TYPE: DNA
<213> ORGANISM: Artificial Sequence
<220> FEATURE:
<223> OTHER INFORMATION: Synthetic construct

<400> SEQUENCE: 345
gccgcctcga gttaacggtg cggacgtttc                                  30

<210> SEQ ID NO 346
<211> LENGTH: 32
<212> TYPE: DNA
<213> ORGANISM: Artificial Sequence
<220> FEATURE:
<223> OTHER INFORMATION: Synthetic construct

<400> SEQUENCE: 346
cgcggatccc atatgaacaa actgtttctt ac                               32

<210> SEQ ID NO 347
<211> LENGTH: 28
<212> TYPE: DNA
<213> ORGANISM: Artificial Sequence
<220> FEATURE:
<223> OTHER INFORMATION: Synthetic construct

<400> SEQUENCE: 347
cccgctcgag tcattccgcc ttcagaaa                                    28

<210> SEQ ID NO 348
<211> LENGTH: 45
<212> TYPE: DNA
<213> ORGANISM: Artificial Sequence
<220> FEATURE:
<223> OTHER INFORMATION: Synthetic construct

<400> SEQUENCE: 348
cgcggatccc atatgcaagg tatcgttgcc gacaaatccg cacct                 45

<210> SEQ ID NO 349
<211> LENGTH: 42
<212> TYPE: DNA
<213> ORGANISM: Artificial Sequence
<220> FEATURE:
<223> OTHER INFORMATION: Synthetic construct

<400> SEQUENCE: 349
cccgctcgag agctaattgt gcttggtttg cagataggag tt                     42

<210> SEQ ID NO 350
<211> LENGTH: 52
<212> TYPE: DNA
<213> ORGANISM: Artificial Sequence
<220> FEATURE:
<223> OTHER INFORMATION: Synthetic construct

<400> SEQUENCE: 350
cgcggatccc atatgaaccg caccctgtac aaagttgtat ttaacaaaca tc           52

<210> SEQ ID NO 351
<211> LENGTH: 45
<212> TYPE: DNA
<213> ORGANISM: Artificial Sequence
<220> FEATURE:
<223> OTHER INFORMATION: Synthetic construct

<400> SEQUENCE: 351
cccgctcgag ttaagctaat tgtgcttggt ttgcagatag gagtt                  45

<210> SEQ ID NO 352
<211> LENGTH: 46
<212> TYPE: DNA
<213> ORGANISM: Artificial Sequence
<220> FEATURE:
<223> OTHER INFORMATION: Synthetic construct

<400> SEQUENCE: 352
cgcggatccc atatgacggg agaaaatcat gcggtttcac ttcatg                 46

<210> SEQ ID NO 353
<211> LENGTH: 42
<212> TYPE: DNA
<213> ORGANISM: Artificial Sequence
<220> FEATURE:
<223> OTHER INFORMATION: Synthetic construct

<400> SEQUENCE: 353
cccgctcgag agctaattgt gcttggtttg cagataggag tt                     42

<210> SEQ ID NO 354
<211> LENGTH: 51
<212> TYPE: DNA
<213> ORGANISM: Artificial Sequence
<220> FEATURE:
<223> OTHER INFORMATION: Synthetic construct

<400> SEQUENCE: 354
cgcggatccc atatggtttc agacggccta tacaaccaac atggtgaaat t           51

<210> SEQ ID NO 355
<211> LENGTH: 41
<212> TYPE: DNA
<213> ORGANISM: Artificial Sequence
<220> FEATURE:
<223> OTHER INFORMATION: Synthetic construct

<400> SEQUENCE: 355

```
cccgctcgag gcggtaactg ccgcttgcac tgaatccgta a                         41

<210> SEQ ID NO 356
<211> LENGTH: 46
<212> TYPE: DNA
<213> ORGANISM: Artificial Sequence
<220> FEATURE:
<223> OTHER INFORMATION: Synthetic construct

<400> SEQUENCE: 356
cgcggatccc atatgacggg agaaaatcat gcggtttcac ttcatg                    46

<210> SEQ ID NO 357
<211> LENGTH: 41
<212> TYPE: DNA
<213> ORGANISM: Artificial Sequence
<220> FEATURE:
<223> OTHER INFORMATION: Synthetic construct

<400> SEQUENCE: 357
cccgctcgag gcggtaactg ccgcttgcac tgaatccgta a                         41

<210> SEQ ID NO 358
<211> LENGTH: 49
<212> TYPE: DNA
<213> ORGANISM: Artificial Sequence
<220> FEATURE:
<223> OTHER INFORMATION: Synthetic construct

<400> SEQUENCE: 358
cgcggatccc atatgcaaag caaagtcaaa gcagaccatg cctccgtaa                 49

<210> SEQ ID NO 359
<211> LENGTH: 56
<212> TYPE: DNA
<213> ORGANISM: Artificial Sequence
<220> FEATURE:
<223> OTHER INFORMATION: Synthetic construct

<400> SEQUENCE: 359
cccgctcgag tcttttcctt tcaattataa ctttagtagg ttcaattttg gtcccc         56

<210> SEQ ID NO 360
<211> LENGTH: 51
<212> TYPE: DNA
<213> ORGANISM: Artificial Sequence
<220> FEATURE:
<223> OTHER INFORMATION: Synthetic construct

<400> SEQUENCE: 360
cgcggatccc atatggtttc agacggccta tacaaccaac atggtgaaat t              51

<210> SEQ ID NO 361
<211> LENGTH: 56
<212> TYPE: DNA
<213> ORGANISM: Artificial Sequence
<220> FEATURE:
<223> OTHER INFORMATION: Synthetic construct

<400> SEQUENCE: 361
cccgctcgag tcttttcctt tcaattataa ctttagtagg ttcaattttg gtcccc         56

<210> SEQ ID NO 362
<211> LENGTH: 27
<212> TYPE: DNA
<213> ORGANISM: Artificial Sequence
```

```
<220> FEATURE:
<223> OTHER INFORMATION: Synthetic construct

<400> SEQUENCE: 362
gcggccatat gacccgtttg acccgcg                                              27

<210> SEQ ID NO 363
<211> LENGTH: 31
<212> TYPE: DNA
<213> ORGANISM: Artificial Sequence
<220> FEATURE:
<223> OTHER INFORMATION: Synthetic construct

<400> SEQUENCE: 363
gcggcctcga gtcagcgggc gttcatttct t                                         31

<210> SEQ ID NO 364
<211> LENGTH: 33
<212> TYPE: DNA
<213> ORGANISM: Artificial Sequence
<220> FEATURE:
<223> OTHER INFORMATION: Synthetic construct

<400> SEQUENCE: 364
cgcggatccc atatgaacac cattttcaaa atc                                       33

<210> SEQ ID NO 365
<211> LENGTH: 32
<212> TYPE: DNA
<213> ORGANISM: Artificial Sequence
<220> FEATURE:
<223> OTHER INFORMATION: Synthetic construct

<400> SEQUENCE: 365
cccgctcgag ttaatttact tttttgatgt cg                                        32

<210> SEQ ID NO 366
<211> LENGTH: 28
<212> TYPE: DNA
<213> ORGANISM: Artificial Sequence
<220> FEATURE:
<223> OTHER INFORMATION: Synthetic construct

<400> SEQUENCE: 366
gcggccatat ggattcgccc aaggtcgg                                             28

<210> SEQ ID NO 367
<211> LENGTH: 31
<212> TYPE: DNA
<213> ORGANISM: Artificial Sequence
<220> FEATURE:
<223> OTHER INFORMATION: Synthetic construct

<400> SEQUENCE: 367
gcggcctcga gctacacttc ccccgaagtg g                                         31

<210> SEQ ID NO 368
<211> LENGTH: 31
<212> TYPE: DNA
<213> ORGANISM: Artificial Sequence
<220> FEATURE:
<223> OTHER INFORMATION: Synthetic construct

<400> SEQUENCE: 368
cgcggatccc atatgatagt tgaccaaagc c                                         31
```

<210> SEQ ID NO 369
<211> LENGTH: 30
<212> TYPE: DNA
<213> ORGANISM: Artificial Sequence
<220> FEATURE:
<223> OTHER INFORMATION: Synthetic construct

<400> SEQUENCE: 369
cccgctcgag ttattttcc gatttttcgg                                30

<210> SEQ ID NO 370
<211> LENGTH: 28
<212> TYPE: DNA
<213> ORGANISM: Artificial Sequence
<220> FEATURE:
<223> OTHER INFORMATION: Synthetic construct

<400> SEQUENCE: 370
gcggccatat gcttgaactg aacggact                                 28

<210> SEQ ID NO 371
<211> LENGTH: 30
<212> TYPE: DNA
<213> ORGANISM: Artificial Sequence
<220> FEATURE:
<223> OTHER INFORMATION: Synthetic construct

<400> SEQUENCE: 371
gcggcctcga gtcagcggaa gcggacgatt                               30

<210> SEQ ID NO 372
<211> LENGTH: 34
<212> TYPE: DNA
<213> ORGANISM: Artificial Sequence
<220> FEATURE:
<223> OTHER INFORMATION: Synthetic construct

<400> SEQUENCE: 372
cgcggatccc atatgtccaa actcaaaacc atcg                          34

<210> SEQ ID NO 373
<211> LENGTH: 29
<212> TYPE: DNA
<213> ORGANISM: Artificial Sequence
<220> FEATURE:
<223> OTHER INFORMATION: Synthetic construct

<400> SEQUENCE: 373
cccgctcgag gcttccaatc agtttgacc                                29

<210> SEQ ID NO 374
<211> LENGTH: 32
<212> TYPE: DNA
<213> ORGANISM: Artificial Sequence
<220> FEATURE:
<223> OTHER INFORMATION: Synthetic construct

<400> SEQUENCE: 374
gcggccatat gagcgcaatc gttgatattt tc                            32

<210> SEQ ID NO 375
<211> LENGTH: 34
<212> TYPE: DNA
<213> ORGANISM: Artificial Sequence
<220> FEATURE:
<223> OTHER INFORMATION: Synthetic construct

<400> SEQUENCE: 375

```
gcggcctcga gttatttgcc cagttggtag aatg                          34
```

<210> SEQ ID NO 376
<211> LENGTH: 32
<212> TYPE: DNA
<213> ORGANISM: Artificial Sequence
<220> FEATURE:
<223> OTHER INFORMATION: Synthetic construct

<400> SEQUENCE: 376

```
gcggccatat ggtgatacat ccgcactact tc                            32
```

<210> SEQ ID NO 377
<211> LENGTH: 32
<212> TYPE: DNA
<213> ORGANISM: Artificial Sequence
<220> FEATURE:
<223> OTHER INFORMATION: Synthetic construct

<400> SEQUENCE: 377

```
gcggcctcga gtcaaaatcg agttttacac ca                            32
```

<210> SEQ ID NO 378
<211> LENGTH: 31
<212> TYPE: DNA
<213> ORGANISM: Artificial Sequence
<220> FEATURE:
<223> OTHER INFORMATION: Synthetic construct

<400> SEQUENCE: 378

```
gcggccatat gaccatctat ttcaaaaacg g                             31
```

<210> SEQ ID NO 379
<211> LENGTH: 34
<212> TYPE: DNA
<213> ORGANISM: Artificial Sequence
<220> FEATURE:
<223> OTHER INFORMATION: Synthetic construct

<400> SEQUENCE: 379

```
gcggcctcga gtcagccgat gtttagcgtc catt                          34
```

<210> SEQ ID NO 380
<211> LENGTH: 31
<212> TYPE: DNA
<213> ORGANISM: Artificial Sequence
<220> FEATURE:
<223> OTHER INFORMATION: Synthetic construct

<400> SEQUENCE: 380

```
cgcggatccc atatgagcag cggaggggt g                              31
```

<210> SEQ ID NO 381
<211> LENGTH: 27
<212> TYPE: DNA
<213> ORGANISM: Artificial Sequence
<220> FEATURE:
<223> OTHER INFORMATION: Synthetic construct

<400> SEQUENCE: 381

```
cccgctcgag ttgcttggcg gcaaggc                                  27
```

<210> SEQ ID NO 382
<211> LENGTH: 31
<212> TYPE: DNA
<213> ORGANISM: Artificial Sequence
<220> FEATURE:
<223> OTHER INFORMATION: Synthetic construct

<400> SEQUENCE: 382
cgcggatccc atatggtcgc cgccgacatc g         31

<210> SEQ ID NO 383
<211> LENGTH: 27
<212> TYPE: DNA
<213> ORGANISM: Artificial Sequence
<220> FEATURE:
<223> OTHER INFORMATION: Synthetic construct

<400> SEQUENCE: 383
cccgctcgag ttgcttggcg gcaaggc               27

<210> SEQ ID NO 384
<211> LENGTH: 31
<212> TYPE: DNA
<213> ORGANISM: Artificial Sequence
<220> FEATURE:
<223> OTHER INFORMATION: Synthetic construct

<400> SEQUENCE: 384
cgcggatccc atatgggcgg ttcggaaggc g         31

<210> SEQ ID NO 385
<211> LENGTH: 33
<212> TYPE: DNA
<213> ORGANISM: Artificial Sequence
<220> FEATURE:
<223> OTHER INFORMATION: Synthetic construct

<400> SEQUENCE: 385
cccgctcgag ttgaacactg atgtcttttc cga       33

<210> SEQ ID NO 386
<211> LENGTH: 35
<212> TYPE: DNA
<213> ORGANISM: Artificial Sequence
<220> FEATURE:
<223> OTHER INFORMATION: Synthetic construct

<400> SEQUENCE: 386
cgcggatccg ctagcaaaact gtcgttggtg ttaac    35

<210> SEQ ID NO 387
<211> LENGTH: 26
<212> TYPE: DNA
<213> ORGANISM: Artificial Sequence
<220> FEATURE:
<223> OTHER INFORMATION: Synthetic construct

<400> SEQUENCE: 387
cccgctcgag ttgacccgct ccacgg              26

<210> SEQ ID NO 388
<211> LENGTH: 31
<212> TYPE: DNA
<213> ORGANISM: Artificial Sequence
<220> FEATURE:
<223> OTHER INFORMATION: Synthetic construct

<400> SEQUENCE: 388
gccgccatat ggcggacttg gcgcaagacc c         31

```
<210> SEQ ID NO 389
<211> LENGTH: 39
<212> TYPE: DNA
<213> ORGANISM: Artificial Sequence
<220> FEATURE:
<223> OTHER INFORMATION: Synthetic construct

<400> SEQUENCE: 389
gccgcctcga gatctcctaa acctgtttta acaatgccg                              39

<210> SEQ ID NO 390
<211> LENGTH: 31
<212> TYPE: DNA
<213> ORGANISM: Artificial Sequence
<220> FEATURE:
<223> OTHER INFORMATION: Synthetic construct

<400> SEQUENCE: 390
gccgccatat ggcggacttg gcgcaagacc c                                      31

<210> SEQ ID NO 391
<211> LENGTH: 31
<212> TYPE: DNA
<213> ORGANISM: Artificial Sequence
<220> FEATURE:
<223> OTHER INFORMATION: Synthetic construct

<400> SEQUENCE: 391
gcggcctcga gctccatgct gttgccccag c                                      31

<210> SEQ ID NO 392
<211> LENGTH: 31
<212> TYPE: DNA
<213> ORGANISM: Artificial Sequence
<220> FEATURE:
<223> OTHER INFORMATION: Synthetic construct

<400> SEQUENCE: 392
gccgccatat ggcggacttg gcgcaagacc c                                      31

<210> SEQ ID NO 393
<211> LENGTH: 31
<212> TYPE: DNA
<213> ORGANISM: Artificial Sequence
<220> FEATURE:
<223> OTHER INFORMATION: Synthetic construct

<400> SEQUENCE: 393
gcggcctcga gaaaatcccc gctaaccgca g                                      31

<210> SEQ ID NO 394
<211> LENGTH: 31
<212> TYPE: DNA
<213> ORGANISM: Artificial Sequence
<220> FEATURE:
<223> OTHER INFORMATION: Synthetic construct

<400> SEQUENCE: 394
cgcggatccc atatgagcag cggaggggt g                                       31

<210> SEQ ID NO 395
<211> LENGTH: 27
<212> TYPE: DNA
<213> ORGANISM: Artificial Sequence
<220> FEATURE:
<223> OTHER INFORMATION: Synthetic construct

<400> SEQUENCE: 395
```
cccgctcgag ttgcttggcg gcaaggc                                        27

<210> SEQ ID NO 396
<211> LENGTH: 31
<212> TYPE: DNA
<213> ORGANISM: Artificial Sequence
<220> FEATURE:
<223> OTHER INFORMATION: Synthetic construct

<400> SEQUENCE: 396
cgcggatccc atatggtcgc cgccgacatc g                                   31

<210> SEQ ID NO 397
<211> LENGTH: 27
<212> TYPE: DNA
<213> ORGANISM: Artificial Sequence
<220> FEATURE:
<223> OTHER INFORMATION: Synthetic construct

<400> SEQUENCE: 397
cccgctcgag ttgcttggcg gcaaggc                                        27

<210> SEQ ID NO 398
<211> LENGTH: 33
<212> TYPE: DNA
<213> ORGANISM: Artificial Sequence
<220> FEATURE:
<223> OTHER INFORMATION: Synthetic construct

<400> SEQUENCE: 398
cgcggatccc atatggacgg tgttgtgcct gtt                                 33

<210> SEQ ID NO 399
<211> LENGTH: 29
<212> TYPE: DNA
<213> ORGANISM: Artificial Sequence
<220> FEATURE:
<223> OTHER INFORMATION: Synthetic construct

<400> SEQUENCE: 399
cccgctcgag cttacggatc aaattgacg                                      29

<210> SEQ ID NO 400
<211> LENGTH: 33
<212> TYPE: DNA
<213> ORGANISM: Artificial Sequence
<220> FEATURE:
<223> OTHER INFORMATION: Synthetic construct

<400> SEQUENCE: 400
cgcggatccc atatgggcag ccaatctgaa gaa                                 33

<210> SEQ ID NO 401
<211> LENGTH: 28
<212> TYPE: DNA
<213> ORGANISM: Artificial Sequence
<220> FEATURE:
<223> OTHER INFORMATION: Synthetic construct

<400> SEQUENCE: 401
cccgctcgag ctcagctttt gccgtcaa                                       28

<210> SEQ ID NO 402
<211> LENGTH: 33
<212> TYPE: DNA
<213> ORGANISM: Artificial Sequence

```
<220> FEATURE:
<223> OTHER INFORMATION: Synthetic construct

<400> SEQUENCE: 402
cgcggatccg ctagctactc atccattgtc cgc                                33

<210> SEQ ID NO 403
<211> LENGTH: 29
<212> TYPE: DNA
<213> ORGANISM: Artificial Sequence
<220> FEATURE:
<223> OTHER INFORMATION: Synthetic construct

<400> SEQUENCE: 403
cccgctcgag ccagttgtag cctattttg                                     29

<210> SEQ ID NO 404
<211> LENGTH: 32
<212> TYPE: DNA
<213> ORGANISM: Artificial Sequence
<220> FEATURE:
<223> OTHER INFORMATION: Synthetic construct

<400> SEQUENCE: 404
cgcggatccg ctagcatgcg cttcacacac ac                                 32

<210> SEQ ID NO 405
<211> LENGTH: 30
<212> TYPE: DNA
<213> ORGANISM: Artificial Sequence
<220> FEATURE:
<223> OTHER INFORMATION: Synthetic construct

<400> SEQUENCE: 405
cccgctcgag ttaccagttg tagcctattt                                    30

<210> SEQ ID NO 406
<211> LENGTH: 32
<212> TYPE: DNA
<213> ORGANISM: Artificial Sequence
<220> FEATURE:
<223> OTHER INFORMATION: Synthetic construct

<400> SEQUENCE: 406
gccgccatat ggcacaaacg gaaggtttgg aa                                 32

<210> SEQ ID NO 407
<211> LENGTH: 36
<212> TYPE: DNA
<213> ORGANISM: Artificial Sequence
<220> FEATURE:
<223> OTHER INFORMATION: Synthetic construct

<400> SEQUENCE: 407
gccgcctcga gaaaactgta acgcaggttt gccgtc                             36

<210> SEQ ID NO 408
<211> LENGTH: 32
<212> TYPE: DNA
<213> ORGANISM: Artificial Sequence
<220> FEATURE:
<223> OTHER INFORMATION: Synthetic construct

<400> SEQUENCE: 408
gcggccatat ggaagaaaca ccgcgcgaac cg                                 32
```

```
<210> SEQ ID NO 409
<211> LENGTH: 32
<212> TYPE: DNA
<213> ORGANISM: Artificial Sequence
<220> FEATURE:
<223> OTHER INFORMATION: Synthetic construct

<400> SEQUENCE: 409
gcggcctcga ggaacgtttt attaaactcg ac                                     32

<210> SEQ ID NO 410
<211> LENGTH: 32
<212> TYPE: DNA
<213> ORGANISM: Artificial Sequence
<220> FEATURE:
<223> OTHER INFORMATION: Synthetic construct

<400> SEQUENCE: 410
gcggccatat gagaaaaccg accgataccc ta                                     32

<210> SEQ ID NO 411
<211> LENGTH: 33
<212> TYPE: DNA
<213> ORGANISM: Artificial Sequence
<220> FEATURE:
<223> OTHER INFORMATION: Synthetic construct

<400> SEQUENCE: 411
gcggcctcga gtcaacgcca ctgccagcgg ttg                                    33

<210> SEQ ID NO 412
<211> LENGTH: 48
<212> TYPE: DNA
<213> ORGANISM: Artificial Sequence
<220> FEATURE:
<223> OTHER INFORMATION: Synthetic construct

<400> SEQUENCE: 412
cgcggatccc atatgaagaa gaacatattg gaattttggg tcggactg                    48

<210> SEQ ID NO 413
<211> LENGTH: 38
<212> TYPE: DNA
<213> ORGANISM: Artificial Sequence
<220> FEATURE:
<223> OTHER INFORMATION: Synthetic construct

<400> SEQUENCE: 413
cccgctcgag ttattcggcg gcttttccg cattgccg                                38

<210> SEQ ID NO 414
<211> LENGTH: 103
<212> TYPE: DNA
<213> ORGANISM: Artificial Sequence
<220> FEATURE:
<223> OTHER INFORMATION: Synthetic construct

<400> SEQUENCE: 414
gggaattcca tatgaaaaag acagctatcg cgattgcagt ggcactggct ggtttcgcta       60
ccgtagcgca ggccgctagc gctttccgcg tggccggcgg tgc                        103

<210> SEQ ID NO 415
<211> LENGTH: 38
<212> TYPE: DNA
<213> ORGANISM: Artificial Sequence
<220> FEATURE:
<223> OTHER INFORMATION: Synthetic construct
```

```
<400> SEQUENCE: 415
cccgctcgag ttattcggcg gcttttccg cattgccg                              38

<210> SEQ ID NO 416
<211> LENGTH: 32
<212> TYPE: DNA
<213> ORGANISM: Artificial Sequence
<220> FEATURE:
<223> OTHER INFORMATION: Synthetic construct

<400> SEQUENCE: 416
catgccatgg ctttccgcgt ggccggcggt gc                                   32

<210> SEQ ID NO 417
<211> LENGTH: 38
<212> TYPE: DNA
<213> ORGANISM: Artificial Sequence
<220> FEATURE:
<223> OTHER INFORMATION: Synthetic construct

<400> SEQUENCE: 417
cccgctcgag ttattcggcg gcttttccg cattgccg                              38

<210> SEQ ID NO 418
<211> LENGTH: 31
<212> TYPE: DNA
<213> ORGANISM: Artificial Sequence
<220> FEATURE:
<223> OTHER INFORMATION: Synthetic construct

<400> SEQUENCE: 418
cgcggatccc atatgtttgc cgaaacccgc c                                    31

<210> SEQ ID NO 419
<211> LENGTH: 28
<212> TYPE: DNA
<213> ORGANISM: Artificial Sequence
<220> FEATURE:
<223> OTHER INFORMATION: Synthetic construct

<400> SEQUENCE: 419
cccgctcgag aggttgtgtt ccaggttg                                        28

<210> SEQ ID NO 420
<211> LENGTH: 31
<212> TYPE: DNA
<213> ORGANISM: Artificial Sequence
<220> FEATURE:
<223> OTHER INFORMATION: Synthetic construct

<400> SEQUENCE: 420
cgcggatccc atatgaaaaa aaccgcctat g                                    31

<210> SEQ ID NO 421
<211> LENGTH: 28
<212> TYPE: DNA
<213> ORGANISM: Artificial Sequence
<220> FEATURE:
<223> OTHER INFORMATION: Synthetic construct

<400> SEQUENCE: 421
cccgctcgag ttaaggttgt gttccagg                                        28

<210> SEQ ID NO 422
<211> LENGTH: 33
```

```
<212> TYPE: DNA
<213> ORGANISM: Artificial Sequence
<220> FEATURE:
<223> OTHER INFORMATION: Synthetic construct

<400> SEQUENCE: 422
cgcggatccc atatgaaaaa atacctattc cgc                                    33

<210> SEQ ID NO 423
<211> LENGTH: 27
<212> TYPE: DNA
<213> ORGANISM: Artificial Sequence
<220> FEATURE:
<223> OTHER INFORMATION: Synthetic construct

<400> SEQUENCE: 423
cccgctcgag ttacgggcgg tattcgg                                           27

<210> SEQ ID NO 424
<211> LENGTH: 34
<212> TYPE: DNA
<213> ORGANISM: Artificial Sequence
<220> FEATURE:
<223> OTHER INFORMATION: Synthetic construct

<400> SEQUENCE: 424
cgcggatccc atatgcaaag caagagcatc caaa                                   34

<210> SEQ ID NO 425
<211> LENGTH: 27
<212> TYPE: DNA
<213> ORGANISM: Artificial Sequence
<220> FEATURE:
<223> OTHER INFORMATION: Synthetic construct

<400> SEQUENCE: 425
cccgctcgag ttacgggcgg tattcgg                                           27

<210> SEQ ID NO 426
<211> LENGTH: 86
<212> TYPE: DNA
<213> ORGANISM: Artificial Sequence
<220> FEATURE:
<223> OTHER INFORMATION: Synthetic construct

<400> SEQUENCE: 426
gggaattcca tatgaaaacc ttcttcaaaa ccctttccgc cgccgcgcta gcgctcatcc        60
tcgccgcctg ccaaagcaag agcatc                                            86

<210> SEQ ID NO 427
<211> LENGTH: 38
<212> TYPE: DNA
<213> ORGANISM: Artificial Sequence
<220> FEATURE:
<223> OTHER INFORMATION: Synthetic construct

<400> SEQUENCE: 427
cccgctcgag ttacgggcgg tattcgggct tcataccg                               38

<210> SEQ ID NO 428
<211> LENGTH: 33
<212> TYPE: DNA
<213> ORGANISM: Artificial Sequence
<220> FEATURE:
<223> OTHER INFORMATION: Synthetic construct

<400> SEQUENCE: 428
```
cgcggatccg tcgactgtgg gggcggcggt ggc                          33

<210> SEQ ID NO 429
<211> LENGTH: 31
<212> TYPE: DNA
<213> ORGANISM: Artificial Sequence
<220> FEATURE:
<223> OTHER INFORMATION: Synthetic construct

<400> SEQUENCE: 429
cccgctcgag tcaatcctgc tcttttttgc c                            31

<210> SEQ ID NO 430
<211> LENGTH: 30
<212> TYPE: DNA
<213> ORGANISM: Artificial Sequence
<220> FEATURE:
<223> OTHER INFORMATION: Synthetic construct

<400> SEQUENCE: 430
gcggccatat gaagaaaaca ttgacactgc                              30

<210> SEQ ID NO 431
<211> LENGTH: 32
<212> TYPE: DNA
<213> ORGANISM: Artificial Sequence
<220> FEATURE:
<223> OTHER INFORMATION: Synthetic construct

<400> SEQUENCE: 431
gcggcctcga gttaatggtg cgaatgaccg at                           32

<210> SEQ ID NO 432
<211> LENGTH: 46
<212> TYPE: DNA
<213> ORGANISM: Artificial Sequence
<220> FEATURE:
<223> OTHER INFORMATION: Synthetic construct

<400> SEQUENCE: 432
ggggacaagt ttgtacaaaa aagcaggctt gcggcaagga tgccgg            46

<210> SEQ ID NO 433
<211> LENGTH: 47
<212> TYPE: DNA
<213> ORGANISM: Artificial Sequence
<220> FEATURE:
<223> OTHER INFORMATION: Synthetic construct

<400> SEQUENCE: 433
ggggaccact ttgtacaaga aagctgggtc taaagcaaca atgccgg            47

<210> SEQ ID NO 434
<211> LENGTH: 30
<212> TYPE: DNA
<213> ORGANISM: Artificial Sequence
<220> FEATURE:
<223> OTHER INFORMATION: Synthetic construct

<400> SEQUENCE: 434
cgcggatccc atatgaaaca caccgtatcc                              30

<210> SEQ ID NO 435
<211> LENGTH: 26
<212> TYPE: DNA
<213> ORGANISM: Artificial Sequence

```
<220> FEATURE:
<223> OTHER INFORMATION: Synthetic construct

<400> SEQUENCE: 435
cccgctcgag ttatctcgtg cgcgcc                                          26

<210> SEQ ID NO 436
<211> LENGTH: 30
<212> TYPE: DNA
<213> ORGANISM: Artificial Sequence
<220> FEATURE:
<223> OTHER INFORMATION: Synthetic construct

<400> SEQUENCE: 436
cgcggatccc atatgagccc cgcgccgatt                                      30

<210> SEQ ID NO 437
<211> LENGTH: 28
<212> TYPE: DNA
<213> ORGANISM: Artificial Sequence
<220> FEATURE:
<223> OTHER INFORMATION: Synthetic construct

<400> SEQUENCE: 437
cccgctcgag tttttgtgcg gtcaggcg                                        28

<210> SEQ ID NO 438
<211> LENGTH: 62
<212> TYPE: DNA
<213> ORGANISM: Artificial Sequence
<220> FEATURE:
<223> OTHER INFORMATION: Synthetic construct

<400> SEQUENCE: 438
ggggacaagt ttgtacaaaa aagcaggctt gttcgtttgg gggatttaaa ccaaaccaaa     60
tc                                                                    62

<210> SEQ ID NO 439
<211> LENGTH: 30
<212> TYPE: DNA
<213> ORGANISM: Artificial Sequence
<220> FEATURE:
<223> OTHER INFORMATION: Synthetic construct

<400> SEQUENCE: 439
cgcggatccc atatggcgga tgcgcccgcg                                      30

<210> SEQ ID NO 440
<211> LENGTH: 26
<212> TYPE: DNA
<213> ORGANISM: Artificial Sequence
<220> FEATURE:
<223> OTHER INFORMATION: Synthetic construct

<400> SEQUENCE: 440
cccgctcgag aaaccgccaa tccgcc                                          26

<210> SEQ ID NO 441
<211> LENGTH: 61
<212> TYPE: DNA
<213> ORGANISM: Artificial Sequence
<220> FEATURE:
<223> OTHER INFORMATION: Synthetic construct

<400> SEQUENCE: 441
ggggaccact ttgtacaaga aagctgggtt catttgtttt ttccttcttc tcgaggccat     60
```

```
t                                                             61

<210> SEQ ID NO 442
<211> LENGTH: 30
<212> TYPE: DNA
<213> ORGANISM: Artificial Sequence
<220> FEATURE:
<223> OTHER INFORMATION: Synthetic construct

<400> SEQUENCE: 442
cgcggatccc atatgaaacc caaaccgcac                              30

<210> SEQ ID NO 443
<211> LENGTH: 27
<212> TYPE: DNA
<213> ORGANISM: Artificial Sequence
<220> FEATURE:
<223> OTHER INFORMATION: Synthetic construct

<400> SEQUENCE: 443
cccgctcgag tcagcgttgg acgtagt                                 27

<210> SEQ ID NO 444
<211> LENGTH: 33
<212> TYPE: DNA
<213> ORGANISM: Artificial Sequence
<220> FEATURE:
<223> OTHER INFORMATION: Synthetic construct

<400> SEQUENCE: 444
gggaattcca tatgaaaaaa atcatcttcg ccg                          33

<210> SEQ ID NO 445
<211> LENGTH: 31
<212> TYPE: DNA
<213> ORGANISM: Artificial Sequence
<220> FEATURE:
<223> OTHER INFORMATION: Synthetic construct

<400> SEQUENCE: 445
cccgctcgag ttattgtttg gctgcctcga t                            31

<210> SEQ ID NO 446
<211> LENGTH: 33
<212> TYPE: DNA
<213> ORGANISM: Artificial Sequence
<220> FEATURE:
<223> OTHER INFORMATION: Synthetic construct

<400> SEQUENCE: 446
gggaattcca tatggccacc tacaaagtgg acg                          33

<210> SEQ ID NO 447
<211> LENGTH: 30
<212> TYPE: DNA
<213> ORGANISM: Artificial Sequence
<220> FEATURE:
<223> OTHER INFORMATION: Synthetic construct

<400> SEQUENCE: 447
cggggatcct tgtttggctg cctcgatttg                              30

<210> SEQ ID NO 448
<211> LENGTH: 34
<212> TYPE: DNA
<213> ORGANISM: Artificial Sequence
```

```
<220> FEATURE:
<223> OTHER INFORMATION: Synthetic construct

<400> SEQUENCE: 448
cgcggatccc atatgcaaga acaatcgcag aaag                          34

<210> SEQ ID NO 449
<211> LENGTH: 30
<212> TYPE: DNA
<213> ORGANISM: Artificial Sequence
<220> FEATURE:
<223> OTHER INFORMATION: Synthetic construct

<400> SEQUENCE: 449
cccgctcgag tttttcggc aaattggctt                                30

<210> SEQ ID NO 450
<211> LENGTH: 45
<212> TYPE: DNA
<213> ORGANISM: Artificial Sequence
<220> FEATURE:
<223> OTHER INFORMATION: Synthetic construct

<400> SEQUENCE: 450
ggggacaagt ttgtacaaaa aagcaggctg ccgatgccgt tgcgg              45

<210> SEQ ID NO 451
<211> LENGTH: 47
<212> TYPE: DNA
<213> ORGANISM: Artificial Sequence
<220> FEATURE:
<223> OTHER INFORMATION: Synthetic construct

<400> SEQUENCE: 451
ggggaccact ttgtacaaga aagctgggtt cagggtcgtt tgttgcg            47

<210> SEQ ID NO 452
<211> LENGTH: 30
<212> TYPE: DNA
<213> ORGANISM: Artificial Sequence
<220> FEATURE:
<223> OTHER INFORMATION: Synthetic construct

<400> SEQUENCE: 452
cgcggatccc atatgaaaca ctttccatcc                               30

<210> SEQ ID NO 453
<211> LENGTH: 28
<212> TYPE: DNA
<213> ORGANISM: Artificial Sequence
<220> FEATURE:
<223> OTHER INFORMATION: Synthetic construct

<400> SEQUENCE: 453
cccgctcgag ttaccactcg taattgac                                 28

<210> SEQ ID NO 454
<211> LENGTH: 30
<212> TYPE: DNA
<213> ORGANISM: Artificial Sequence
<220> FEATURE:
<223> OTHER INFORMATION: Synthetic construct

<400> SEQUENCE: 454
cgcggatccc atatggccac aagcgacgac                               30
```

```
<210> SEQ ID NO 455
<211> LENGTH: 28
<212> TYPE: DNA
<213> ORGANISM: Artificial Sequence
<220> FEATURE:
<223> OTHER INFORMATION: Synthetic construct

<400> SEQUENCE: 455
cccgctcgag ttaccactcg taattgac                                    28

<210> SEQ ID NO 456
<211> LENGTH: 28
<212> TYPE: DNA
<213> ORGANISM: Artificial Sequence
<220> FEATURE:
<223> OTHER INFORMATION: Synthetic construct

<400> SEQUENCE: 456
cgcggatccc atatggccac aaacgacg                                    28

<210> SEQ ID NO 457
<211> LENGTH: 28
<212> TYPE: DNA
<213> ORGANISM: Artificial Sequence
<220> FEATURE:
<223> OTHER INFORMATION: Synthetic construct

<400> SEQUENCE: 457
cccgctcgag acccacgttg taaggttg                                    28

<210> SEQ ID NO 458
<211> LENGTH: 32
<212> TYPE: DNA
<213> ORGANISM: Artificial Sequence
<220> FEATURE:
<223> OTHER INFORMATION: Synthetic construct

<400> SEQUENCE: 458
cgcggatccc atatggccac aagcgacgac ga                               32

<210> SEQ ID NO 459
<211> LENGTH: 28
<212> TYPE: DNA
<213> ORGANISM: Artificial Sequence
<220> FEATURE:
<223> OTHER INFORMATION: Synthetic construct

<400> SEQUENCE: 459
cccgctcgag acccacgttg taaggttg                                    28

<210> SEQ ID NO 460
<211> LENGTH: 33
<212> TYPE: DNA
<213> ORGANISM: Artificial Sequence
<220> FEATURE:
<223> OTHER INFORMATION: Synthetic construct

<400> SEQUENCE: 460
cgcggatccc atatgatgaa acactttcca tcc                              33

<210> SEQ ID NO 461
<211> LENGTH: 29
<212> TYPE: DNA
<213> ORGANISM: Artificial Sequence
<220> FEATURE:
<223> OTHER INFORMATION: Synthetic construct

<400> SEQUENCE: 461
```

-continued

```
cccgctcgag ttaacccacg ttgtaaggt                                               29

<210> SEQ ID NO 462
<211> LENGTH: 33
<212> TYPE: DNA
<213> ORGANISM: Artificial Sequence
<220> FEATURE:
<223> OTHER INFORMATION: Synthetic construct

<400> SEQUENCE: 462
cgcggatccc atatgatgaa acactttcca tcc                                          33

<210> SEQ ID NO 463
<211> LENGTH: 29
<212> TYPE: DNA
<213> ORGANISM: Artificial Sequence
<220> FEATURE:
<223> OTHER INFORMATION: Synthetic construct

<400> SEQUENCE: 463
cccgctcgag ttaacccacg ttgtaaggt                                               29

<210> SEQ ID NO 464
<211> LENGTH: 28
<212> TYPE: DNA
<213> ORGANISM: Artificial Sequence
<220> FEATURE:
<223> OTHER INFORMATION: Synthetic construct

<400> SEQUENCE: 464
cgcggatccc atatggccac aaacgacg                                                28

<210> SEQ ID NO 465
<211> LENGTH: 29
<212> TYPE: DNA
<213> ORGANISM: Artificial Sequence
<220> FEATURE:
<223> OTHER INFORMATION: Synthetic construct

<400> SEQUENCE: 465
cccgctcgag gtctgacact gttttatcc                                               29

<210> SEQ ID NO 466
<211> LENGTH: 33
<212> TYPE: DNA
<213> ORGANISM: Artificial Sequence
<220> FEATURE:
<223> OTHER INFORMATION: Synthetic construct

<400> SEQUENCE: 466
cgcggatccc atatgatgaa acactttcca tcc                                          33

<210> SEQ ID NO 467
<211> LENGTH: 29
<212> TYPE: DNA
<213> ORGANISM: Artificial Sequence
<220> FEATURE:
<223> OTHER INFORMATION: Synthetic construct

<400> SEQUENCE: 467
cccgctcgag ttatgctttg gcggcaaag                                               29

<210> SEQ ID NO 468
<211> LENGTH: 30
<212> TYPE: DNA
<213> ORGANISM: Artificial Sequence
```

<220> FEATURE:
<223> OTHER INFORMATION: Synthetic construct

<400> SEQUENCE: 468
cgcggatccc atatggccac aaacgacgac          30

<210> SEQ ID NO 469
<211> LENGTH: 27
<212> TYPE: DNA
<213> ORGANISM: Artificial Sequence
<220> FEATURE:
<223> OTHER INFORMATION: Synthetic construct

<400> SEQUENCE: 469
cgcggatccc cactcgtaat tgacgcc          27

<210> SEQ ID NO 470
<211> LENGTH: 30
<212> TYPE: DNA
<213> ORGANISM: Artificial Sequence
<220> FEATURE:
<223> OTHER INFORMATION: Synthetic construct

<400> SEQUENCE: 470
cgcggatccc atatggccac aagcgacgac          30

<210> SEQ ID NO 471
<211> LENGTH: 27
<212> TYPE: DNA
<213> ORGANISM: Artificial Sequence
<220> FEATURE:
<223> OTHER INFORMATION: Synthetic construct

<400> SEQUENCE: 471
cgcggatccc cactcgtaat tgacgcc          27

<210> SEQ ID NO 472
<211> LENGTH: 30
<212> TYPE: DNA
<213> ORGANISM: Artificial Sequence
<220> FEATURE:
<223> OTHER INFORMATION: Synthetic construct

<400> SEQUENCE: 472
cgcggatccc atatggccac aaacgacgac          30

<210> SEQ ID NO 473
<211> LENGTH: 27
<212> TYPE: DNA
<213> ORGANISM: Artificial Sequence
<220> FEATURE:
<223> OTHER INFORMATION: Synthetic construct

<400> SEQUENCE: 473
cgcggatcca cccacgttgt aaggttg          27

<210> SEQ ID NO 474
<211> LENGTH: 33
<212> TYPE: DNA
<213> ORGANISM: Artificial Sequence
<220> FEATURE:
<223> OTHER INFORMATION: Synthetic construct

<400> SEQUENCE: 474
cgcggatccc atatgatgaa acactttcca tcc          33

```
<210> SEQ ID NO 475
<211> LENGTH: 27
<212> TYPE: DNA
<213> ORGANISM: Artificial Sequence
<220> FEATURE:
<223> OTHER INFORMATION: Synthetic construct

<400> SEQUENCE: 475
cgcggatcca cccacgttgt aaggttg                                27

<210> SEQ ID NO 476
<211> LENGTH: 25
<212> TYPE: DNA
<213> ORGANISM: Artificial Sequence
<220> FEATURE:
<223> OTHER INFORMATION: Synthetic construct

<400> SEQUENCE: 476
cgcggatccg gagggggtgg tgtcg                                  25

<210> SEQ ID NO 477
<211> LENGTH: 27
<212> TYPE: DNA
<213> ORGANISM: Artificial Sequence
<220> FEATURE:
<223> OTHER INFORMATION: Synthetic construct

<400> SEQUENCE: 477
cccgctcgag ttgcttggcg gcaaggc                                27

<210> SEQ ID NO 478
<211> LENGTH: 25
<212> TYPE: DNA
<213> ORGANISM: Artificial Sequence
<220> FEATURE:
<223> OTHER INFORMATION: Synthetic construct

<400> SEQUENCE: 478
cgcggatccg gcggaggcgg cactt                                  25

<210> SEQ ID NO 479
<211> LENGTH: 26
<212> TYPE: DNA
<213> ORGANISM: Artificial Sequence
<220> FEATURE:
<223> OTHER INFORMATION: Synthetic construct

<400> SEQUENCE: 479
cccgctcgag gaaccggtag cctacg                                 26

<210> SEQ ID NO 480
<211> LENGTH: 41
<212> TYPE: DNA
<213> ORGANISM: Artificial Sequence
<220> FEATURE:
<223> OTHER INFORMATION: Synthetic construct

<400> SEQUENCE: 480
cgcggatccg gtggtggtgg ttcagatttg gcaaacgatt c                41

<210> SEQ ID NO 481
<211> LENGTH: 29
<212> TYPE: DNA
<213> ORGANISM: Artificial Sequence
<220> FEATURE:
<223> OTHER INFORMATION: Synthetic construct

<400> SEQUENCE: 481
```

```
cccgctcgag cgtatcatat ttcacgtgc                                          29
```

<210> SEQ ID NO 482
<211> LENGTH: 25
<212> TYPE: DNA
<213> ORGANISM: Artificial Sequence
<220> FEATURE:
<223> OTHER INFORMATION: Synthetic construct

<400> SEQUENCE: 482

```
cgcggatccg gagggggtgg tgtcg                                              25
```

<210> SEQ ID NO 483
<211> LENGTH: 28
<212> TYPE: DNA
<213> ORGANISM: Artificial Sequence
<220> FEATURE:
<223> OTHER INFORMATION: Synthetic construct

<400> SEQUENCE: 483

```
cccgctcgag ttattgcttg gcggcaag                                           28
```

<210> SEQ ID NO 484
<211> LENGTH: 25
<212> TYPE: DNA
<213> ORGANISM: Artificial Sequence
<220> FEATURE:
<223> OTHER INFORMATION: Synthetic construct

<400> SEQUENCE: 484

```
cgcggatccg gcggaggcgg cactt                                              25
```

<210> SEQ ID NO 485
<211> LENGTH: 28
<212> TYPE: DNA
<213> ORGANISM: Artificial Sequence
<220> FEATURE:
<223> OTHER INFORMATION: Synthetic construct

<400> SEQUENCE: 485

```
cccgctcgag tcagaaccgg tagcctac                                           28
```

<210> SEQ ID NO 486
<211> LENGTH: 41
<212> TYPE: DNA
<213> ORGANISM: Artificial Sequence
<220> FEATURE:
<223> OTHER INFORMATION: Synthetic construct

<400> SEQUENCE: 486

```
cgcggatccg gtggtggtgg ttcagatttg gcaaacgatt c                            41
```

<210> SEQ ID NO 487
<211> LENGTH: 32
<212> TYPE: DNA
<213> ORGANISM: Artificial Sequence
<220> FEATURE:
<223> OTHER INFORMATION: Synthetic construct

<400> SEQUENCE: 487

```
cccgctcgag ttacgtatca tatttcacgt gc                                      32
```

<210> SEQ ID NO 488
<211> LENGTH: 31
<212> TYPE: DNA
<213> ORGANISM: Artificial Sequence

```
<220> FEATURE:
<223> OTHER INFORMATION: Synthetic construct

<400> SEQUENCE: 488
cgcggatccc atatggccac aagcgacgac g                          31

<210> SEQ ID NO 489
<211> LENGTH: 28
<212> TYPE: DNA
<213> ORGANISM: Artificial Sequence
<220> FEATURE:
<223> OTHER INFORMATION: Synthetic construct

<400> SEQUENCE: 489
cccgctcgag ccactcgtaa ttgacgcc                              28

<210> SEQ ID NO 490
<211> LENGTH: 30
<212> TYPE: DNA
<213> ORGANISM: Artificial Sequence
<220> FEATURE:
<223> OTHER INFORMATION: Synthetic construct

<400> SEQUENCE: 490
cgcggatccc atatggccac aaacgacgac                            30

<210> SEQ ID NO 491
<211> LENGTH: 28
<212> TYPE: DNA
<213> ORGANISM: Artificial Sequence
<220> FEATURE:
<223> OTHER INFORMATION: Synthetic construct

<400> SEQUENCE: 491
cccgctcgag tgctttggcg gcaaagtt                              28

<210> SEQ ID NO 492
<211> LENGTH: 30
<212> TYPE: DNA
<213> ORGANISM: Artificial Sequence
<220> FEATURE:
<223> OTHER INFORMATION: Synthetic construct

<400> SEQUENCE: 492
cgcggatccc atatggccac aaacgacgac                            30

<210> SEQ ID NO 493
<211> LENGTH: 37
<212> TYPE: DNA
<213> ORGANISM: Artificial Sequence
<220> FEATURE:
<223> OTHER INFORMATION: Synthetic construct

<400> SEQUENCE: 493
cccgctcgag tttagcaata ttatctttgt tcgtagc                    37

<210> SEQ ID NO 494
<211> LENGTH: 32
<212> TYPE: DNA
<213> ORGANISM: Artificial Sequence
<220> FEATURE:
<223> OTHER INFORMATION: Synthetic construct

<400> SEQUENCE: 494
cgcggatccc atatgaaagc aaaccgtgcc ga                         32
```

```
<210> SEQ ID NO 495
<211> LENGTH: 28
<212> TYPE: DNA
<213> ORGANISM: Artificial Sequence
<220> FEATURE:
<223> OTHER INFORMATION: Synthetic construct

<400> SEQUENCE: 495
cccgctcgag ccactcgtaa ttgacgcc                                          28

<210> SEQ ID NO 496
<211> LENGTH: 61
<212> TYPE: DNA
<213> ORGANISM: Artificial Sequence
<220> FEATURE:
<223> OTHER INFORMATION: Synthetic construct

<400> SEQUENCE: 496
ggggacaagt ttgtacaaaa aagcaggctg cagccacaaa cgacgacgat gttaaaaaag       60
c                                                                      61

<210> SEQ ID NO 497
<211> LENGTH: 61
<212> TYPE: DNA
<213> ORGANISM: Artificial Sequence
<220> FEATURE:
<223> OTHER INFORMATION: Synthetic construct

<400> SEQUENCE: 497
ggggaccact ttgtacaaga aagctgggtt taccactcgt aattgacgcc gacatggtag       60
g                                                                      61

<210> SEQ ID NO 498
<211> LENGTH: 31
<212> TYPE: DNA
<213> ORGANISM: Artificial Sequence
<220> FEATURE:
<223> OTHER INFORMATION: Synthetic construct

<400> SEQUENCE: 498
gcggccatat ggcagcaaaa gacgtacagt t                                      31

<210> SEQ ID NO 499
<211> LENGTH: 33
<212> TYPE: DNA
<213> ORGANISM: Artificial Sequence
<220> FEATURE:
<223> OTHER INFORMATION: Synthetic construct

<400> SEQUENCE: 499
gcggcctcga gttacatcat gccgcccata cca                                    33

<210> SEQ ID NO 500
<211> LENGTH: 31
<212> TYPE: DNA
<213> ORGANISM: Artificial Sequence
<220> FEATURE:
<223> OTHER INFORMATION: Synthetic construct

<400> SEQUENCE: 500
cgcggatccg ctagcttagg cggcggcgga g                                      31

<210> SEQ ID NO 501
<211> LENGTH: 26
<212> TYPE: DNA
<213> ORGANISM: Artificial Sequence
```

```
<220> FEATURE:
<223> OTHER INFORMATION: Synthetic construct

<400> SEQUENCE: 501
cccgctcgag gaaccggtag cctacg                                          26

<210> SEQ ID NO 502
<211> LENGTH: 29
<212> TYPE: DNA
<213> ORGANISM: Artificial Sequence
<220> FEATURE:
<223> OTHER INFORMATION: Synthetic construct

<400> SEQUENCE: 502
cccctagcta gcacttctgc gcccgactt                                       29

<210> SEQ ID NO 503
<211> LENGTH: 26
<212> TYPE: DNA
<213> ORGANISM: Artificial Sequence
<220> FEATURE:
<223> OTHER INFORMATION: Synthetic construct

<400> SEQUENCE: 503
cccgctcgag gaaccggtag cctacg                                          26

<210> SEQ ID NO 504
<211> LENGTH: 31
<212> TYPE: DNA
<213> ORGANISM: Artificial Sequence
<220> FEATURE:
<223> OTHER INFORMATION: Synthetic construct

<400> SEQUENCE: 504
cgcggatccg ctagcttagg cggcggcgga g                                    31

<210> SEQ ID NO 505
<211> LENGTH: 26
<212> TYPE: DNA
<213> ORGANISM: Artificial Sequence
<220> FEATURE:
<223> OTHER INFORMATION: Synthetic construct

<400> SEQUENCE: 505
cccgctcgag gaaccggtag cctacg                                          26

<210> SEQ ID NO 506
<211> LENGTH: 32
<212> TYPE: DNA
<213> ORGANISM: Artificial Sequence
<220> FEATURE:
<223> OTHER INFORMATION: Synthetic construct

<400> SEQUENCE: 506
cgcggatccg ctagcacttc tgcgcccgac tt                                   32

<210> SEQ ID NO 507
<211> LENGTH: 26
<212> TYPE: DNA
<213> ORGANISM: Artificial Sequence
<220> FEATURE:
<223> OTHER INFORMATION: Synthetic construct

<400> SEQUENCE: 507
cccgctcgag gaaccggtag cctacg                                          26
```

```
<210> SEQ ID NO 508
<211> LENGTH: 50
<212> TYPE: DNA
<213> ORGANISM: Artificial Sequence
<220> FEATURE:
<223> OTHER INFORMATION: Synthetic construct

<400> SEQUENCE: 508
cgcggatccg ctagccgaac gaccccaacc ttccctacaa aaactttcaa            50

<210> SEQ ID NO 509
<211> LENGTH: 35
<212> TYPE: DNA
<213> ORGANISM: Artificial Sequence
<220> FEATURE:
<223> OTHER INFORMATION: Synthetic construct

<400> SEQUENCE: 509
cccgctcgag tcagaaccga cgtgccaagc cgttc                            35

<210> SEQ ID NO 510
<211> LENGTH: 32
<212> TYPE: DNA
<213> ORGANISM: Artificial Sequence
<220> FEATURE:
<223> OTHER INFORMATION: Synthetic construct

<400> SEQUENCE: 510
gccgccatat gcccccactg gaagaacgga cg                               32

<210> SEQ ID NO 511
<211> LENGTH: 35
<212> TYPE: DNA
<213> ORGANISM: Artificial Sequence
<220> FEATURE:
<223> OTHER INFORMATION: Synthetic construct

<400> SEQUENCE: 511
gccgcctcga gtaataaacc ttctatgggc agcag                            35

<210> SEQ ID NO 512
<211> LENGTH: 31
<212> TYPE: DNA
<213> ORGANISM: Artificial Sequence
<220> FEATURE:
<223> OTHER INFORMATION: Synthetic construct

<400> SEQUENCE: 512
cgcggatccc atatgtccgt ccacgcatcc g                                31

<210> SEQ ID NO 513
<211> LENGTH: 31
<212> TYPE: DNA
<213> ORGANISM: Artificial Sequence
<220> FEATURE:
<223> OTHER INFORMATION: Synthetic construct

<400> SEQUENCE: 513
cccgctcgag tttgaatttg taggtgtatt g                                31

<210> SEQ ID NO 514
<211> LENGTH: 29
<212> TYPE: DNA
<213> ORGANISM: Artificial Sequence
<220> FEATURE:
<223> OTHER INFORMATION: Synthetic construct

<400> SEQUENCE: 514
```
cgcggatccc atatgacccc ttccgcact                                              29

<210> SEQ ID NO 515
<211> LENGTH: 32
<212> TYPE: DNA
<213> ORGANISM: Artificial Sequence
<220> FEATURE:
<223> OTHER INFORMATION: Synthetic construct

<400> SEQUENCE: 515
cccgctcgag ttatttgaat ttgtaggtgt at                                          32

<210> SEQ ID NO 516
<211> LENGTH: 33
<212> TYPE: DNA
<213> ORGANISM: Artificial Sequence
<220> FEATURE:
<223> OTHER INFORMATION: Synthetic construct

<400> SEQUENCE: 516
cgcggatccc atatgaaaac caattcagaa gaa                                         33

<210> SEQ ID NO 517
<211> LENGTH: 28
<212> TYPE: DNA
<213> ORGANISM: Artificial Sequence
<220> FEATURE:
<223> OTHER INFORMATION: Synthetic construct

<400> SEQUENCE: 517
cccgctcgag tccacagaga ttgtttcc                                               28

<210> SEQ ID NO 518
<211> LENGTH: 17
<212> TYPE: DNA
<213> ORGANISM: Artificial Sequence
<220> FEATURE:
<223> OTHER INFORMATION: Synthetic construct

<400> SEQUENCE: 518
gatgcccgaa gggcggg                                                           17

<210> SEQ ID NO 519
<211> LENGTH: 29
<212> TYPE: DNA
<213> ORGANISM: Artificial Sequence
<220> FEATURE:
<223> OTHER INFORMATION: Synthetic construct

<400> SEQUENCE: 519
gcccaagctt tcagaagaag acttcacgc                                              29

<210> SEQ ID NO 520
<211> LENGTH: 36
<212> TYPE: DNA
<213> ORGANISM: Artificial Sequence
<220> FEATURE:
<223> OTHER INFORMATION: Synthetic construct

<400> SEQUENCE: 520
cgcggatccc atatgcaaac ccataaatac gctatt                                      36

<210> SEQ ID NO 521
<211> LENGTH: 29
<212> TYPE: DNA
<213> ORGANISM: Artificial Sequence

```
<220> FEATURE:
<223> OTHER INFORMATION: Synthetic construct

<400> SEQUENCE: 521
gcccaagctt gaagaagact tcacgccag                                29

<210> SEQ ID NO 522
<211> LENGTH: 35
<212> TYPE: DNA
<213> ORGANISM: Artificial Sequence
<220> FEATURE:
<223> OTHER INFORMATION: Synthetic construct

<400> SEQUENCE: 522
cgcggatccc atatggtctt tttcgacaat accga                         35

<210> SEQ ID NO 523
<211> LENGTH: 10
<212> TYPE: DNA
<213> ORGANISM: Artificial Sequence
<220> FEATURE:
<223> OTHER INFORMATION: Synthetic construct

<400> SEQUENCE: 523
gcccaagctt                                                     10

<210> SEQ ID NO 524
<211> LENGTH: 36
<212> TYPE: DNA
<213> ORGANISM: Artificial Sequence
<220> FEATURE:
<223> OTHER INFORMATION: Synthetic construct

<400> SEQUENCE: 524
cgcggatccc atatgaataa aactttaaaa aggcgg                        36

<210> SEQ ID NO 525
<211> LENGTH: 29
<212> TYPE: DNA
<213> ORGANISM: Artificial Sequence
<220> FEATURE:
<223> OTHER INFORMATION: Synthetic construct

<400> SEQUENCE: 525
gcccaagctt tcagaagaag acttcacgc                                29

<210> SEQ ID NO 526
<211> LENGTH: 35
<212> TYPE: DNA
<213> ORGANISM: Artificial Sequence
<220> FEATURE:
<223> OTHER INFORMATION: Synthetic construct

<400> SEQUENCE: 526
cgcgaatccc atatgttcga tcttgattct gtcga                         35

<210> SEQ ID NO 527
<211> LENGTH: 28
<212> TYPE: DNA
<213> ORGANISM: Artificial Sequence
<220> FEATURE:
<223> OTHER INFORMATION: Synthetic construct

<400> SEQUENCE: 527
cccgctcgag tcgcacaggc tgttggcg                                 28
```

<210> SEQ ID NO 528
<211> LENGTH: 32
<212> TYPE: DNA
<213> ORGANISM: Artificial Sequence
<220> FEATURE:
<223> OTHER INFORMATION: Synthetic construct

<400> SEQUENCE: 528
cgcgaatccc atatgttggg cggaggcggc ag            32

<210> SEQ ID NO 529
<211> LENGTH: 28
<212> TYPE: DNA
<213> ORGANISM: Artificial Sequence
<220> FEATURE:
<223> OTHER INFORMATION: Synthetic construct

<400> SEQUENCE: 529
cccgctcgag tcgcacaggc tgttggcg                28

<210> SEQ ID NO 530
<211> LENGTH: 32
<212> TYPE: DNA
<213> ORGANISM: Artificial Sequence
<220> FEATURE:
<223> OTHER INFORMATION: Synthetic construct

<400> SEQUENCE: 530
cgcgaatccc atatgttggg cggaggcggc ag            32

<210> SEQ ID NO 531
<211> LENGTH: 28
<212> TYPE: DNA
<213> ORGANISM: Artificial Sequence
<220> FEATURE:
<223> OTHER INFORMATION: Synthetic construct

<400> SEQUENCE: 531
cccgctcgag tcgcacaggc tgttggcg                28

<210> SEQ ID NO 532
<211> LENGTH: 33
<212> TYPE: DNA
<213> ORGANISM: Artificial Sequence
<220> FEATURE:
<223> OTHER INFORMATION: Synthetic construct

<400> SEQUENCE: 532
cgcggatccc atatggcaaa tttggaggtg cgc           33

<210> SEQ ID NO 533
<211> LENGTH: 27
<212> TYPE: DNA
<213> ORGANISM: Artificial Sequence
<220> FEATURE:
<223> OTHER INFORMATION: Synthetic construct

<400> SEQUENCE: 533
cccgctcgag ttcggagcgg ttgaagc                 27

<210> SEQ ID NO 534
<211> LENGTH: 34
<212> TYPE: DNA
<213> ORGANISM: Artificial Sequence
<220> FEATURE:
<223> OTHER INFORMATION: Synthetic construct

<400> SEQUENCE: 534

```
cgcggatccc atatgcaacg tcgtattata accc                                      34
```

<210> SEQ ID NO 535
<211> LENGTH: 29
<212> TYPE: DNA
<213> ORGANISM: Artificial Sequence
<220> FEATURE:
<223> OTHER INFORMATION: Synthetic construct

<400> SEQUENCE: 535

```
cccgctcgag ttattcggag cggttgaag                                            29
```

<210> SEQ ID NO 536
<211> LENGTH: 42
<212> TYPE: DNA
<213> ORGANISM: Artificial Sequence
<220> FEATURE:
<223> OTHER INFORMATION: Synthetic construct

<400> SEQUENCE: 536

```
cgcggatccc atatgggcat caaagtcgcc atcaacggct ac                             42
```

<210> SEQ ID NO 537
<211> LENGTH: 35
<212> TYPE: DNA
<213> ORGANISM: Artificial Sequence
<220> FEATURE:
<223> OTHER INFORMATION: Synthetic construct

<400> SEQUENCE: 537

```
cccgctcgag tttgagcggg cgcacttcaa gtccg                                     35
```

<210> SEQ ID NO 538
<211> LENGTH: 33
<212> TYPE: DNA
<213> ORGANISM: Artificial Sequence
<220> FEATURE:
<223> OTHER INFORMATION: Synthetic construct

<400> SEQUENCE: 538

```
cgcggatccc atatgggcgg cagcgaaaaa aac                                       33
```

<210> SEQ ID NO 539
<211> LENGTH: 28
<212> TYPE: DNA
<213> ORGANISM: Artificial Sequence
<220> FEATURE:
<223> OTHER INFORMATION: Synthetic construct

<400> SEQUENCE: 539

```
cccgctcgag gttggtgccg actttgat                                             28
```

<210> SEQ ID NO 540
<211> LENGTH: 31
<212> TYPE: DNA
<213> ORGANISM: Artificial Sequence
<220> FEATURE:
<223> OTHER INFORMATION: Synthetic construct

<400> SEQUENCE: 540

```
cgcggatccc atatgggcgg cggaagcgat a                                         31
```

<210> SEQ ID NO 541
<211> LENGTH: 27
<212> TYPE: DNA
<213> ORGANISM: Artificial Sequence

```
<220> FEATURE:
<223> OTHER INFORMATION: Synthetic construct

<400> SEQUENCE: 541
cccgctcgag tttgcccgct ttgagcc                                27

<210> SEQ ID NO 542
<211> LENGTH: 33
<212> TYPE: DNA
<213> ORGANISM: Artificial Sequence
<220> FEATURE:
<223> OTHER INFORMATION: Synthetic construct

<400> SEQUENCE: 542
cgcggatccc atatgggcaa atccgaaaat acg                         33

<210> SEQ ID NO 543
<211> LENGTH: 27
<212> TYPE: DNA
<213> ORGANISM: Artificial Sequence
<220> FEATURE:
<223> OTHER INFORMATION: Synthetic construct

<400> SEQUENCE: 543
cccgctcgag catcccgtac tgtttcg                                27

<210> SEQ ID NO 544
<211> LENGTH: 62
<212> TYPE: DNA
<213> ORGANISM: Artificial Sequence
<220> FEATURE:
<223> OTHER INFORMATION: Synthetic construct

<400> SEQUENCE: 544
ggggacaagt ttgtacaaaa aagcaggctc cgacattacc gtgtacaacg gccaacaaag    60
aa                                                                  62

<210> SEQ ID NO 545
<211> LENGTH: 61
<212> TYPE: DNA
<213> ORGANISM: Artificial Sequence
<220> FEATURE:
<223> OTHER INFORMATION: Synthetic construct

<400> SEQUENCE: 545
ggggaccact ttgtacaaga aagctgggtc ttatttcata ccggcttgct caagcagccg    60
g                                                                   61

<210> SEQ ID NO 546
<211> LENGTH: 61
<212> TYPE: DNA
<213> ORGANISM: Artificial Sequence
<220> FEATURE:
<223> OTHER INFORMATION: Synthetic construct

<400> SEQUENCE: 546
ggggacaagt ttgtacaaaa aagcaggctg atacggtgtt ttcctgtaaa acggacaaca    60
a                                                                   61

<210> SEQ ID NO 547
<211> LENGTH: 60
<212> TYPE: DNA
<213> ORGANISM: Artificial Sequence
<220> FEATURE:
<223> OTHER INFORMATION: Synthetic construct
```

```
<400> SEQUENCE: 547 gggggaccact ttgtacaaga aagctgggtc taggaaaaat cgtcatcgtt gaaattcgcc        60

<210> SEQ ID NO 548
<211> LENGTH: 47
<212> TYPE: DNA
<213> ORGANISM: Artificial Sequence
<220> FEATURE:
<223> OTHER INFORMATION: Synthetic construct

<400> SEQUENCE: 548
ggggacaagt ttgtacaaaa aagcaggcta tgcaccccat cgaaacc                      47

<210> SEQ ID NO 549
<211> LENGTH: 47
<212> TYPE: DNA
<213> ORGANISM: Artificial Sequence
<220> FEATURE:
<223> OTHER INFORMATION: Synthetic construct

<400> SEQUENCE: 549
ggggaccact ttgtacaaga aagctgggtc tagtcttgca gtgcctc                      47

<210> SEQ ID NO 550
<211> LENGTH: 41
<212> TYPE: DNA
<213> ORGANISM: Artificial Sequence
<220> FEATURE:
<223> OTHER INFORMATION: Synthetic construct

<400> SEQUENCE: 550
cgcggatccc atatgggaaa tttcttatat agaggcatta g                            41

<210> SEQ ID NO 551
<211> LENGTH: 40
<212> TYPE: DNA
<213> ORGANISM: Artificial Sequence
<220> FEATURE:
<223> OTHER INFORMATION: Synthetic construct

<400> SEQUENCE: 551
cccgctcgag gttaatttct atcaactctt tagcaataat                              40

<210> SEQ ID NO 552
<211> LENGTH: 31
<212> TYPE: DNA
<213> ORGANISM: Artificial Sequence
<220> FEATURE:
<223> OTHER INFORMATION: Synthetic construct

<400> SEQUENCE: 552
cgcggatccc atatggcctg ccaagacgac a                                       31

<210> SEQ ID NO 553
<211> LENGTH: 26
<212> TYPE: DNA
<213> ORGANISM: Artificial Sequence
<220> FEATURE:
<223> OTHER INFORMATION: Synthetic construct

<400> SEQUENCE: 553
cccgctcgag ccgcctcctg ccgaaa                                             26

<210> SEQ ID NO 554
<211> LENGTH: 34
```

```
<212> TYPE: DNA
<213> ORGANISM: Artificial Sequence
<220> FEATURE:
<223> OTHER INFORMATION: Synthetic construct

<400> SEQUENCE: 554
cgcggatccc atatggcaga gatctgtttg ataa                           34

<210> SEQ ID NO 555
<211> LENGTH: 27
<212> TYPE: DNA
<213> ORGANISM: Artificial Sequence
<220> FEATURE:
<223> OTHER INFORMATION: Synthetic construct

<400> SEQUENCE: 555
cccgctcgag cggttttccg cccaatg                                   27

<210> SEQ ID NO 556
<211> LENGTH: 30
<212> TYPE: DNA
<213> ORGANISM: Artificial Sequence
<220> FEATURE:
<223> OTHER INFORMATION: Synthetic construct

<400> SEQUENCE: 556
cgcggatccc atatgcagcc ggatacggtc                                30

<210> SEQ ID NO 557
<211> LENGTH: 30
<212> TYPE: DNA
<213> ORGANISM: Artificial Sequence
<220> FEATURE:
<223> OTHER INFORMATION: Synthetic construct

<400> SEQUENCE: 557
cccgctcgag aatcacttcc aacacaaaat                                30

<210> SEQ ID NO 558
<211> LENGTH: 33
<212> TYPE: DNA
<213> ORGANISM: Artificial Sequence
<220> FEATURE:
<223> OTHER INFORMATION: Synthetic construct

<400> SEQUENCE: 558
cgcggatccc atatgtggtt gctgatgaag ggc                            33

<210> SEQ ID NO 559
<211> LENGTH: 28
<212> TYPE: DNA
<213> ORGANISM: Artificial Sequence
<220> FEATURE:
<223> OTHER INFORMATION: Synthetic construct

<400> SEQUENCE: 559
cccgctcgag gactgcttca tcttctgc                                  28

<210> SEQ ID NO 560
<211> LENGTH: 34
<212> TYPE: DNA
<213> ORGANISM: Artificial Sequence
<220> FEATURE:
<223> OTHER INFORMATION: Synthetic construct

<400> SEQUENCE: 560
cgcggatccc atatggaact gatgactgtt ttgc                           34
```

<210> SEQ ID NO 561
<211> LENGTH: 29
<212> TYPE: DNA
<213> ORGANISM: Artificial Sequence
<220> FEATURE:
<223> OTHER INFORMATION: Synthetic construct

<400> SEQUENCE: 561
cccgctcgag tcagactgct tcatcttct                                    29

<210> SEQ ID NO 562
<211> LENGTH: 45
<212> TYPE: DNA
<213> ORGANISM: Artificial Sequence
<220> FEATURE:
<223> OTHER INFORMATION: Synthetic construct

<400> SEQUENCE: 562
cgcggatccc atatgagcat taaagtagcg attaacggtt tcggc                  45

<210> SEQ ID NO 563
<211> LENGTH: 40
<212> TYPE: DNA
<213> ORGANISM: Artificial Sequence
<220> FEATURE:
<223> OTHER INFORMATION: Synthetic construct

<400> SEQUENCE: 563
cccgctcgag gattttgcct gcgaagtatt ccaaagtgcg                        40

<210> SEQ ID NO 564
<211> LENGTH: 32
<212> TYPE: DNA
<213> ORGANISM: Artificial Sequence
<220> FEATURE:
<223> OTHER INFORMATION: Synthetic construct

<400> SEQUENCE: 564
cgcggatccg ctagccccga tgttaaatcg gc                                32

<210> SEQ ID NO 565
<211> LENGTH: 29
<212> TYPE: DNA
<213> ORGANISM: Artificial Sequence
<220> FEATURE:
<223> OTHER INFORMATION: Synthetic construct

<400> SEQUENCE: 565
cggggatcca tcctgctctt ttttgccgg                                    29

<210> SEQ ID NO 566
<211> LENGTH: 42
<212> TYPE: DNA
<213> ORGANISM: Artificial Sequence
<220> FEATURE:
<223> OTHER INFORMATION: Synthetic construct

<400> SEQUENCE: 566
cgcggatccg gtggtggtgg tcaaagcaag agcatccaaa cc                     42

<210> SEQ ID NO 567
<211> LENGTH: 30
<212> TYPE: DNA
<213> ORGANISM: Artificial Sequence
<220> FEATURE:
<223> OTHER INFORMATION: Synthetic construct

<400> SEQUENCE: 567
cccaagcttt tcgggcggta ttcgggcttc                       30

<210> SEQ ID NO 568
<211> LENGTH: 39
<212> TYPE: DNA
<213> ORGANISM: Artificial Sequence
<220> FEATURE:
<223> OTHER INFORMATION: Synthetic construct

<400> SEQUENCE: 568
cgcggatccg gtggtggtgg tgccacctac aaagtggac             39

<210> SEQ ID NO 569
<211> LENGTH: 28
<212> TYPE: DNA
<213> ORGANISM: Artificial Sequence
<220> FEATURE:
<223> OTHER INFORMATION: Synthetic construct

<400> SEQUENCE: 569
gcccaagctt ttgtttggct gcctcgat                         28

<210> SEQ ID NO 570
<211> LENGTH: 34
<212> TYPE: DNA
<213> ORGANISM: Artificial Sequence
<220> FEATURE:
<223> OTHER INFORMATION: Synthetic construct

<400> SEQUENCE: 570
cgcggatccg gtggtggtgg tacaagcgac gacg                  34

<210> SEQ ID NO 571
<211> LENGTH: 28
<212> TYPE: DNA
<213> ORGANISM: Artificial Sequence
<220> FEATURE:
<223> OTHER INFORMATION: Synthetic construct

<400> SEQUENCE: 571
gcccaagctt ccactcgtaa ttgacgcc                         28

<210> SEQ ID NO 572
<211> LENGTH: 41
<212> TYPE: DNA
<213> ORGANISM: Artificial Sequence
<220> FEATURE:
<223> OTHER INFORMATION: Synthetic construct

<400> SEQUENCE: 572
cgcggatccg gtggtggtgg ttcagatttg gcaaacgatt c          41

<210> SEQ ID NO 573
<211> LENGTH: 28
<212> TYPE: DNA
<213> ORGANISM: Artificial Sequence
<220> FEATURE:
<223> OTHER INFORMATION: Synthetic construct

<400> SEQUENCE: 573
cccaagcttc gtatcatatt tcacgtgc                         28

<210> SEQ ID NO 574
<211> LENGTH: 44

```
<212> TYPE: DNA
<213> ORGANISM: Artificial Sequence
<220> FEATURE:
<223> OTHER INFORMATION: Synthetic construct

<400> SEQUENCE: 574
cccaagcttg gtggtggtgg tggttcagat ttggcaaacg attc              44

<210> SEQ ID NO 575
<211> LENGTH: 29
<212> TYPE: DNA
<213> ORGANISM: Artificial Sequence
<220> FEATURE:
<223> OTHER INFORMATION: Synthetic construct

<400> SEQUENCE: 575
cccgctcgag cgtatcatat ttcacgtgc                                29

<210> SEQ ID NO 576
<211> LENGTH: 45
<212> TYPE: DNA
<213> ORGANISM: Artificial Sequence
<220> FEATURE:
<223> OTHER INFORMATION: Synthetic construct

<400> SEQUENCE: 576
cccaagcttg gtggtggtgg tggtcaaagc aagagcatcc aaacc              45

<210> SEQ ID NO 577
<211> LENGTH: 28
<212> TYPE: DNA
<213> ORGANISM: Artificial Sequence
<220> FEATURE:
<223> OTHER INFORMATION: Synthetic construct

<400> SEQUENCE: 577
cccgctcgag cgggcggtat tcgggctt                                 28

<210> SEQ ID NO 578
<211> LENGTH: 32
<212> TYPE: DNA
<213> ORGANISM: Artificial Sequence
<220> FEATURE:
<223> OTHER INFORMATION: Synthetic construct

<400> SEQUENCE: 578
cgcggatccg ctagccccga tgttaaatcg gc                            32

<210> SEQ ID NO 579
<211> LENGTH: 29
<212> TYPE: DNA
<213> ORGANISM: Artificial Sequence
<220> FEATURE:
<223> OTHER INFORMATION: Synthetic construct

<400> SEQUENCE: 579
cggggatcca tcctgctctt ttttgccgg                                29

<210> SEQ ID NO 580
<211> LENGTH: 36
<212> TYPE: DNA
<213> ORGANISM: Artificial Sequence
<220> FEATURE:
<223> OTHER INFORMATION: Synthetic construct

<400> SEQUENCE: 580
cgcggatccg ctagcggaca cacttatttc ggcatc                        36
```

<210> SEQ ID NO 581
<211> LENGTH: 30
<212> TYPE: DNA
<213> ORGANISM: Artificial Sequence
<220> FEATURE:
<223> OTHER INFORMATION: Synthetic construct

<400> SEQUENCE: 581
cgcggatccc cagcggtagc ctaatttgat                                         30

<210> SEQ ID NO 582
<211> LENGTH: 41
<212> TYPE: DNA
<213> ORGANISM: Artificial Sequence
<220> FEATURE:
<223> OTHER INFORMATION: Synthetic construct

<400> SEQUENCE: 582
cgcggatccg gtggtggtgg ttcagatttg gcaaacgatt c                            41

<210> SEQ ID NO 583
<211> LENGTH: 28
<212> TYPE: DNA
<213> ORGANISM: Artificial Sequence
<220> FEATURE:
<223> OTHER INFORMATION: Synthetic construct

<400> SEQUENCE: 583
cccaagcttc gtatcatatt tcacgtgc                                           28

<210> SEQ ID NO 584
<211> LENGTH: 36
<212> TYPE: DNA
<213> ORGANISM: Artificial Sequence
<220> FEATURE:
<223> OTHER INFORMATION: Synthetic construct

<400> SEQUENCE: 584
gcggcgtcga cggtggcgga ggcactggat cctcag                                  36

<210> SEQ ID NO 585
<211> LENGTH: 35
<212> TYPE: DNA
<213> ORGANISM: Artificial Sequence
<220> FEATURE:
<223> OTHER INFORMATION: Synthetic construct

<400> SEQUENCE: 585
ggaggcactg gatcctcaga tttggcaaac gattc                                   35

<210> SEQ ID NO 586
<211> LENGTH: 29
<212> TYPE: DNA
<213> ORGANISM: Artificial Sequence
<220> FEATURE:
<223> OTHER INFORMATION: Synthetic construct

<400> SEQUENCE: 586
cccgctcgag cgtatcatat ttcacgtgc                                          29

<210> SEQ ID NO 587
<211> LENGTH: 33
<212> TYPE: DNA
<213> ORGANISM: Artificial Sequence
<220> FEATURE:
<223> OTHER INFORMATION: Synthetic construct

```
<400> SEQUENCE: 587
ggaattccat atgtcagatt tggcaaacga ttc                                    33

<210> SEQ ID NO 588
<211> LENGTH: 28
<212> TYPE: DNA
<213> ORGANISM: Artificial Sequence
<220> FEATURE:
<223> OTHER INFORMATION: Synthetic construct

<400> SEQUENCE: 588
cgcggatccc gtatcatatt tcacgtgc                                          28

<210> SEQ ID NO 589
<211> LENGTH: 25
<212> TYPE: DNA
<213> ORGANISM: Artificial Sequence
<220> FEATURE:
<223> OTHER INFORMATION: Synthetic construct

<400> SEQUENCE: 589
cggggatccg ggggcggcgg tggcg                                             25

<210> SEQ ID NO 590
<211> LENGTH: 30
<212> TYPE: DNA
<213> ORGANISM: Artificial Sequence
<220> FEATURE:
<223> OTHER INFORMATION: Synthetic construct

<400> SEQUENCE: 590
cccaagctta tcctgctctt ttttgccggc                                        30

<210> SEQ ID NO 591
<211> LENGTH: 42
<212> TYPE: DNA
<213> ORGANISM: Artificial Sequence
<220> FEATURE:
<223> OTHER INFORMATION: Synthetic construct

<400> SEQUENCE: 591
cgcggatccg gtggtggtgg tcaaagcaag agcatccaaa cc                          42

<210> SEQ ID NO 592
<211> LENGTH: 28
<212> TYPE: DNA
<213> ORGANISM: Artificial Sequence
<220> FEATURE:
<223> OTHER INFORMATION: Synthetic construct

<400> SEQUENCE: 592
cccaagcttc gggcggtatt cgggcttc                                          28

<210> SEQ ID NO 593
<211> LENGTH: 26
<212> TYPE: DNA
<213> ORGANISM: Artificial Sequence
<220> FEATURE:
<223> OTHER INFORMATION: Synthetic construct

<400> SEQUENCE: 593
ccccaagctt gggggcggcg gtggcg                                            26

<210> SEQ ID NO 594
<211> LENGTH: 31
```

```
<212> TYPE: DNA
<213> ORGANISM: Artificial Sequence
<220> FEATURE:
<223> OTHER INFORMATION: Synthetic construct

<400> SEQUENCE: 594
cccgctcgag atcctgctct tttttgccgg c                              31

<210> SEQ ID NO 595
<211> LENGTH: 45
<212> TYPE: DNA
<213> ORGANISM: Artificial Sequence
<220> FEATURE:
<223> OTHER INFORMATION: Synthetic construct

<400> SEQUENCE: 595
cccaagcttg gtggtggtgg tggtcaaagc aagagcatcc aaacc               45

<210> SEQ ID NO 596
<211> LENGTH: 28
<212> TYPE: DNA
<213> ORGANISM: Artificial Sequence
<220> FEATURE:
<223> OTHER INFORMATION: Synthetic construct

<400> SEQUENCE: 596
cccgctcgag cgggcggtat tcgggctt                                  28

<210> SEQ ID NO 597
<211> LENGTH: 35
<212> TYPE: DNA
<213> ORGANISM: Artificial Sequence
<220> FEATURE:
<223> OTHER INFORMATION: Synthetic construct

<400> SEQUENCE: 597
ggaggcactg gatccgcagc cacaaacgac gacga                          35

<210> SEQ ID NO 598
<211> LENGTH: 36
<212> TYPE: DNA
<213> ORGANISM: Artificial Sequence
<220> FEATURE:
<223> OTHER INFORMATION: Synthetic construct

<400> SEQUENCE: 598
gcggcctcga gggtggcgga ggcactggat ccgcag                         36

<210> SEQ ID NO 599
<211> LENGTH: 28
<212> TYPE: DNA
<213> ORGANISM: Artificial Sequence
<220> FEATURE:
<223> OTHER INFORMATION: Synthetic construct

<400> SEQUENCE: 599
cccgctcgag acccagcttg taaggttg                                  28

<210> SEQ ID NO 600
<211> LENGTH: 35
<212> TYPE: DNA
<213> ORGANISM: Artificial Sequence
<220> FEATURE:
<223> OTHER INFORMATION: Synthetic construct

<400> SEQUENCE: 600
ggaggcactg gatccgcagc cacaaacgac gacga                          35
```

<210> SEQ ID NO 601
<211> LENGTH: 36
<212> TYPE: DNA
<213> ORGANISM: Artificial Sequence
<220> FEATURE:
<223> OTHER INFORMATION: Synthetic construct

<400> SEQUENCE: 601
gcggcctcga gggtggcgga ggcactggat ccgcag                                36

<210> SEQ ID NO 602
<211> LENGTH: 28
<212> TYPE: DNA
<213> ORGANISM: Artificial Sequence
<220> FEATURE:
<223> OTHER INFORMATION: Synthetic construct

<400> SEQUENCE: 602
cccgctcgag ccactcgtaa ttgacgcc                                        28

<210> SEQ ID NO 603
<211> LENGTH: 38
<212> TYPE: DNA
<213> ORGANISM: Artificial Sequence
<220> FEATURE:
<223> OTHER INFORMATION: Synthetic construct

<400> SEQUENCE: 603
gcggcctcga gggatccggc ggaggcggca cttctgcg                              38

<210> SEQ ID NO 604
<211> LENGTH: 26
<212> TYPE: DNA
<213> ORGANISM: Artificial Sequence
<220> FEATURE:
<223> OTHER INFORMATION: Synthetic construct

<400> SEQUENCE: 604
cccgctcgag gaaccggtag cctacg                                          26

<210> SEQ ID NO 605
<211> LENGTH: 35
<212> TYPE: DNA
<213> ORGANISM: Artificial Sequence
<220> FEATURE:
<223> OTHER INFORMATION: Synthetic construct

<400> SEQUENCE: 605
ggaggcactg gatcctcaga tttggcaaac gattc                                35

<210> SEQ ID NO 606
<211> LENGTH: 37
<212> TYPE: DNA
<213> ORGANISM: Artificial Sequence
<220> FEATURE:
<223> OTHER INFORMATION: Synthetic construct

<400> SEQUENCE: 606
gcggcgtcga cggtggcgga ggcactggat cctcaga                              37

<210> SEQ ID NO 607
<211> LENGTH: 29
<212> TYPE: DNA
<213> ORGANISM: Artificial Sequence
<220> FEATURE:
<223> OTHER INFORMATION: Synthetic construct

```
<400> SEQUENCE: 607
cccgctcgag cgtatcatat ttcacgtgc                                    29

<210> SEQ ID NO 608
<211> LENGTH: 35
<212> TYPE: DNA
<213> ORGANISM: Artificial Sequence
<220> FEATURE:
<223> OTHER INFORMATION: Synthetic construct

<400> SEQUENCE: 608
gcggcctcga gggatccgga gggggtggtg tcgcc                             35

<210> SEQ ID NO 609
<211> LENGTH: 25
<212> TYPE: DNA
<213> ORGANISM: Artificial Sequence
<220> FEATURE:
<223> OTHER INFORMATION: Synthetic construct

<400> SEQUENCE: 609
cccgctcgag ttgcttggcg gcaag                                        25

<210> SEQ ID NO 610
<211> LENGTH: 35
<212> TYPE: DNA
<213> ORGANISM: Artificial Sequence
<220> FEATURE:
<223> OTHER INFORMATION: Synthetic construct

<400> SEQUENCE: 610
ggaggcactg gatccgcagc cacaaacgac gacga                             35

<210> SEQ ID NO 611
<211> LENGTH: 36
<212> TYPE: DNA
<213> ORGANISM: Artificial Sequence
<220> FEATURE:
<223> OTHER INFORMATION: Synthetic construct

<400> SEQUENCE: 611
gcggcctcga gggtggcgga ggcactggat ccgcag                            36

<210> SEQ ID NO 612
<211> LENGTH: 28
<212> TYPE: DNA
<213> ORGANISM: Artificial Sequence
<220> FEATURE:
<223> OTHER INFORMATION: Synthetic construct

<400> SEQUENCE: 612
cccgctcgag acccagcttg taaggttg                                     28

<210> SEQ ID NO 613
<211> LENGTH: 35
<212> TYPE: DNA
<213> ORGANISM: Artificial Sequence
<220> FEATURE:
<223> OTHER INFORMATION: Synthetic construct

<400> SEQUENCE: 613
ggaggcactg gatccgcagc cacaaacgac gacga                             35

<210> SEQ ID NO 614
<211> LENGTH: 36
```

-continued

```
<212> TYPE: DNA
<213> ORGANISM: Artificial Sequence
<220> FEATURE:
<223> OTHER INFORMATION: Synthetic construct

<400> SEQUENCE: 614
gcggcctcga gggtggcgga ggcactggat ccgcag                              36

<210> SEQ ID NO 615
<211> LENGTH: 28
<212> TYPE: DNA
<213> ORGANISM: Artificial Sequence
<220> FEATURE:
<223> OTHER INFORMATION: Synthetic construct

<400> SEQUENCE: 615
cccgctcgag ccactcgtaa ttgacgcc                                       28

<210> SEQ ID NO 616
<211> LENGTH: 35
<212> TYPE: DNA
<213> ORGANISM: Artificial Sequence
<220> FEATURE:
<223> OTHER INFORMATION: Synthetic construct

<400> SEQUENCE: 616
ggaggcactg gatcctcaga tttggcaaac gattc                               35

<210> SEQ ID NO 617
<211> LENGTH: 37
<212> TYPE: DNA
<213> ORGANISM: Artificial Sequence
<220> FEATURE:
<223> OTHER INFORMATION: Synthetic construct

<400> SEQUENCE: 617
gcggcgtcga cggtggcgga ggcactggat cctcaga                             37

<210> SEQ ID NO 618
<211> LENGTH: 29
<212> TYPE: DNA
<213> ORGANISM: Artificial Sequence
<220> FEATURE:
<223> OTHER INFORMATION: Synthetic construct

<400> SEQUENCE: 618
cccgctcgag cgtatcatat ttcacgtgc                                      29

<210> SEQ ID NO 619
<211> LENGTH: 488
<212> TYPE: PRT
<213> ORGANISM: Artificial Sequence
<220> FEATURE:
<223> OTHER INFORMATION: Neisseria meningitidis

<400> SEQUENCE: 619
```

Met Phe Lys Arg Ser Val Ile Ala Met Ala Cys Ile Phe Ala Leu Ser
1               5                   10                  15

Ala Cys Gly Gly Gly Gly Gly Ser Pro Asp Val Lys Ser Ala Asp
            20                  25                  30

Thr Leu Ser Lys Pro Ala Ala Pro Val Val Ser Glu Lys Glu Thr Glu
        35                  40                  45

Ala Lys Glu Asp Ala Pro Gln Ala Gly Ser Gln Gly Gln Gly Ala Pro
    50                  55                  60

Ser Ala Gln Gly Ser Gln Asp Met Ala Ala Val Ser Glu Glu Asn Thr

-continued

```
                65                  70                  75                  80
Gly Asn Gly Gly Ala Val Thr Ala Asp Asn Pro Lys Asn Glu Asp Glu
                    85                  90                  95

Val Ala Gln Asn Asp Met Pro Gln Asn Ala Ala Gly Thr Asp Ser Ser
                100                 105                 110

Thr Pro Asn His Thr Pro Asp Pro Asn Met Leu Ala Gly Asn Met Glu
                115                 120                 125

Asn Gln Ala Thr Asp Ala Gly Glu Ser Ser Gln Pro Ala Asn Gln Pro
            130                 135                 140

Asp Met Ala Asn Ala Ala Asp Gly Met Gln Gly Asp Pro Ser Ala
145                 150                 155                 160

Gly Gly Gln Asn Ala Gly Asn Thr Ala Ala Gln Gly Ala Asn Gln Ala
                165                 170                 175

Gly Asn Asn Gln Ala Ala Gly Ser Ser Asp Pro Ile Pro Ala Ser Asn
            180                 185                 190

Pro Ala Pro Ala Asn Gly Gly Ser Asn Phe Gly Arg Val Asp Leu Ala
                195                 200                 205

Asn Gly Val Leu Ile Asp Gly Pro Ser Gln Asn Ile Thr Leu Thr His
            210                 215                 220

Cys Lys Gly Asp Ser Cys Ser Gly Asn Asn Phe Leu Asp Glu Glu Val
225                 230                 235                 240

Gln Leu Lys Ser Glu Phe Glu Lys Leu Ser Asp Ala Asp Lys Ile Ser
                245                 250                 255

Asn Tyr Lys Lys Asp Gly Lys Asn Asp Lys Phe Val Gly Leu Val Ala
                260                 265                 270

Asp Ser Val Gln Met Lys Gly Ile Asn Gln Tyr Ile Ile Phe Tyr Lys
            275                 280                 285

Pro Lys Pro Thr Ser Phe Ala Arg Phe Arg Arg Ser Ala Arg Ser Arg
            290                 295                 300

Arg Ser Leu Pro Ala Glu Met Pro Leu Ile Pro Val Asn Gln Ala Asp
305                 310                 315                 320

Thr Leu Ile Val Asp Gly Glu Ala Val Ser Leu Thr Gly His Ser Gly
                325                 330                 335

Asn Ile Phe Ala Pro Glu Gly Asn Tyr Arg Tyr Leu Thr Tyr Gly Ala
                340                 345                 350

Glu Lys Leu Pro Gly Gly Ser Tyr Ala Leu Arg Val Gln Gly Glu Pro
            355                 360                 365

Ala Lys Gly Glu Met Leu Ala Gly Ala Ala Val Tyr Asn Gly Glu Val
            370                 375                 380

Leu His Phe His Thr Glu Asn Gly Arg Pro Tyr Pro Thr Arg Gly Arg
385                 390                 395                 400

Phe Ala Ala Lys Val Asp Phe Gly Ser Lys Ser Val Asp Gly Ile Ile
                405                 410                 415

Asp Ser Gly Asp Asp Leu His Met Gly Thr Gln Lys Phe Lys Ala Ala
            420                 425                 430

Ile Asp Gly Asn Gly Phe Lys Gly Thr Trp Thr Glu Asn Gly Ser Gly
            435                 440                 445

Asp Val Ser Gly Lys Phe Tyr Gly Pro Ala Gly Glu Glu Val Ala Gly
            450                 455                 460

Lys Tyr Ser Tyr Arg Pro Thr Asp Ala Glu Lys Gly Gly Phe Gly Val
465                 470                 475                 480

Phe Ala Gly Lys Lys Glu Gln Asp
                485
```

<210> SEQ ID NO 620
<211> LENGTH: 427
<212> TYPE: PRT
<213> ORGANISM: Artificial Sequence
<220> FEATURE:
<223> OTHER INFORMATION: Neisseria meningitidis

<400> SEQUENCE: 620

```
Met Phe Glu Arg Ser Val Ile Ala Met Ala Cys Ile Phe Ala Leu Ser
1               5                   10                  15

Ala Cys Gly Gly Gly Gly Gly Ser Pro Asp Val Lys Ser Ala Asp
            20                  25                  30

Thr Leu Ser Lys Pro Ala Ala Pro Val Ala Glu Lys Glu Thr Glu
        35                  40                  45

Val Lys Glu Asp Ala Pro Gln Ala Gly Ser Gln Gly Gln Gly Ala Pro
 50                  55                  60

Ser Thr Gln Gly Ser Gln Asp Met Ala Ala Val Ser Ala Glu Asn Thr
 65                  70                  75                  80

Gly Asn Gly Gly Ala Ala Thr Thr Asp Lys Pro Lys Asn Glu Asp Glu
                85                  90                  95

Gly Pro Gln Asn Asp Met Pro Gln Asn Ser Ala Glu Ser Ala Asn Gln
            100                 105                 110

Thr Gly Asn Asn Gln Pro Ala Asp Ser Ser Asp Ser Ala Pro Ala Ser
        115                 120                 125

Asn Pro Ala Pro Ala Asn Gly Gly Ser Asn Phe Gly Arg Val Asp Leu
130                 135                 140

Ala Asn Gly Val Leu Ile Asp Gly Pro Ser Gln Asn Ile Thr Leu Thr
145                 150                 155                 160

His Cys Lys Gly Asp Ser Cys Asn Gly Asp Asn Leu Leu Asp Glu Glu
                165                 170                 175

Ala Pro Ser Lys Ser Glu Phe Glu Asn Leu Asn Glu Ser Glu Arg Ile
            180                 185                 190

Glu Lys Tyr Lys Lys Asp Gly Lys Ser Asp Lys Phe Thr Asn Leu Val
        195                 200                 205

Ala Thr Ala Val Gln Ala Asn Gly Thr Asn Lys Tyr Val Ile Ile Tyr
210                 215                 220

Lys Asp Lys Ser Ala Ser Ser Ser Ala Arg Phe Arg Ser Ala
225                 230                 235                 240

Arg Ser Arg Arg Ser Leu Pro Ala Glu Met Pro Leu Ile Pro Val Asn
                245                 250                 255

Gln Ala Asp Thr Leu Ile Val Asp Gly Glu Ala Val Ser Leu Thr Gly
            260                 265                 270

His Ser Gly Asn Ile Phe Ala Pro Glu Gly Asn Tyr Arg Tyr Leu Thr
        275                 280                 285

Tyr Gly Ala Glu Lys Leu Pro Gly Gly Ser Tyr Ala Leu Arg Val Gln
290                 295                 300

Gly Glu Pro Ala Lys Gly Glu Met Leu Ala Gly Thr Ala Val Tyr Asn
305                 310                 315                 320

Gly Glu Val Leu His Phe His Thr Glu Asn Gly Arg Pro Tyr Pro Thr
                325                 330                 335

Arg Gly Arg Phe Ala Ala Lys Val Asp Phe Gly Ser Lys Ser Val Asp
            340                 345                 350

Gly Ile Ile Asp Ser Gly Asp Asp Leu His Met Gly Thr Gln Lys Phe
        355                 360                 365

Lys Ala Ala Ile Asp Gly Asn Gly Phe Lys Gly Thr Trp Thr Glu Asn
```

```
                370             375             380
Gly Gly Gly Asp Val Ser Gly Arg Phe Tyr Gly Pro Ala Gly Glu Glu
385             390             395             400

Val Ala Gly Lys Tyr Ser Tyr Arg Pro Thr Asp Ala Glu Lys Gly Gly
                405             410             415

Phe Gly Val Phe Ala Gly Lys Lys Glu Gln Asp
            420             425
```

<210> SEQ ID NO 621
<211> LENGTH: 9
<212> TYPE: PRT
<213> ORGANISM: artificial sequence
<220> FEATURE:
<223> OTHER INFORMATION: Synthetic construct

<400> SEQUENCE: 621

```
Met Lys Lys Tyr Leu Phe Ser Ala Ala
1               5
```

<210> SEQ ID NO 622
<211> LENGTH: 6
<212> TYPE: PRT
<213> ORGANISM: artificial sequence
<220> FEATURE:
<223> OTHER INFORMATION: Synthetic construct

<400> SEQUENCE: 622

```
Cys Gly Gly Gly Gly Ser
1               5
```

<210> SEQ ID NO 623
<211> LENGTH: 5
<212> TYPE: PRT
<213> ORGANISM: artificial sequence
<220> FEATURE:
<223> OTHER INFORMATION: Synthetic construct

<400> SEQUENCE: 623

```
Cys Gly Gly Gly Ser
1               5
```

<210> SEQ ID NO 624
<211> LENGTH: 4
<212> TYPE: PRT
<213> ORGANISM: artificial sequence
<220> FEATURE:
<223> OTHER INFORMATION: Synthetic construct

<400> SEQUENCE: 624

```
Cys Gly Gly Ser
1
```

<210> SEQ ID NO 625
<211> LENGTH: 6
<212> TYPE: PRT
<213> ORGANISM: artificial sequence
<220> FEATURE:
<223> OTHER INFORMATION: Synthetic construct
<220> FEATURE:
<221> NAME/KEY: misc_feature
<222> LOCATION: 3)..(3)
<223> OTHER INFORMATION: Xaa can be any naturally occurring amino acid

<400> SEQUENCE: 625

```
Cys Gly Xaa Gly Gly Ser
1               5
```

```
<210> SEQ ID NO 626
<211> LENGTH: 6
<212> TYPE: PRT
<213> ORGANISM: artificial sequence
<220> FEATURE:
<223> OTHER INFORMATION: Synthetic construct
<220> FEATURE:
<221> NAME/KEY: misc_feature
<222> LOCATION: (3)..(4)
<223> OTHER INFORMATION: Xaa can be any naturally occurring amino acid

<400> SEQUENCE: 626

Cys Gly Xaa Xaa Gly Ser
1               5

<210> SEQ ID NO 627
<211> LENGTH: 6
<212> TYPE: PRT
<213> ORGANISM: artificial sequence
<220> FEATURE:
<223> OTHER INFORMATION: Synthetic construct
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 627

Cys Gly Xaa Gly Xaa Ser
1               5

<210> SEQ ID NO 628
<211> LENGTH: 7
<212> TYPE: PRT
<213> ORGANISM: artificial sequence
<220> FEATURE:
<223> OTHER INFORMATION: Synthetic construct
<220> FEATURE:
<221> NAME/KEY: misc_feature
<222> LOCATION: (4)..(4)
<223> OTHER INFORMATION: Xaa can be any naturally occurring amino acid

<400> SEQUENCE: 628

Cys Gly Gly Xaa Gly Gly Ser
1               5

<210> SEQ ID NO 629
<211> LENGTH: 7
<212> TYPE: PRT
<213> ORGANISM: artificial sequence
<220> FEATURE:
<223> OTHER INFORMATION: Synthetic construct
<220> FEATURE:
<221> NAME/KEY: misc_feature
<222> LOCATION: (3)..(3)
<223> OTHER INFORMATION: Xaa can be any naturally occurring amino acid

<400> SEQUENCE: 629

Cys Gly Xaa Gly Gly Gly Ser
1               5

<210> SEQ ID NO 630
<211> LENGTH: 19
<212> TYPE: PRT
<213> ORGANISM: artificial sequence
<220> FEATURE:
<223> OTHER INFORMATION: Neisseria meningitidis
```

```
<400> SEQUENCE: 630

Met Lys Thr Phe Phe Lys Thr Leu Ser Ala Ala Ala Leu Ala Leu Ile
1               5                   10                  15

Leu Ala Ala

<210> SEQ ID NO 631
<211> LENGTH: 7
<212> TYPE: PRT
<213> ORGANISM: artificial sequence
<220> FEATURE:
<223> OTHER INFORMATION: Neisseria meningitidis

<400> SEQUENCE: 631

Gly Gly Gly Gly Gly Gly Ser
1               5

<210> SEQ ID NO 632
<211> LENGTH: 6
<212> TYPE: PRT
<213> ORGANISM: artificial sequence
<220> FEATURE:
<223> OTHER INFORMATION: Neisseria meningitidis

<400> SEQUENCE: 632

Gly Gly Gly Gly Gly Gly
1               5

<210> SEQ ID NO 633
<211> LENGTH: 20
<212> TYPE: PRT
<213> ORGANISM: artificial sequence
<220> FEATURE:
<223> OTHER INFORMATION: Neisseria meningitidis

<400> SEQUENCE: 633

Met Lys Lys Tyr Leu Phe Arg Ala Ala Leu Tyr Gly Ile Ala Ala Ala
1               5                   10                  15

Ile Leu Ala Ala
            20
```